US011382989B2

(12) United States Patent
Moran et al.

(10) Patent No.: US 11,382,989 B2
(45) Date of Patent: Jul. 12, 2022

(54) ENGINEERED MICROBIAL POPULATION

(71) Applicant: Board of Regents, The University of Texas System, Austin, TX (US)

(72) Inventors: Nancy Moran, Austin, TX (US); Jeffrey Barrick, Austin, TX (US); Sean Leonard, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 179 days.

(21) Appl. No.: 16/029,686

(22) Filed: Jul. 9, 2018

(65) Prior Publication Data

US 2019/0015528 A1 Jan. 17, 2019

Related U.S. Application Data

(60) Provisional application No. 62/529,754, filed on Jul. 7, 2017.

(51) Int. Cl.

| | |
|---|---|
| ***A61K 48/00*** | (2006.01) |
| ***A61K 9/00*** | (2006.01) |
| ***A23K 50/90*** | (2016.01) |
| ***C12N 15/74*** | (2006.01) |
| ***A23K 10/18*** | (2016.01) |
| ***C12N 1/20*** | (2006.01) |

(52) U.S. Cl.

CPC ............ *A61K 48/005* (2013.01); *A23K 10/18* (2016.05); *A23K 50/90* (2016.05); *A61K 9/0053* (2013.01); *C12N 1/20* (2013.01); *C12N 15/746* (2013.01); *A01K 2227/706* (2013.01); *C12N 2310/141* (2013.01); *C12N 2310/20* (2017.05)

(58) Field of Classification Search

CPC .... A61K 48/005; A61K 9/0053; A23K 50/90; C12N 2310/141; A01K 2227/706

See application file for complete search history.

(56) References Cited

U.S. PATENT DOCUMENTS

| | | | |
|---|---|---|---|
| 8,962,584 | B2 | 2/2015 | Sela |
| 9,662,348 | B2 | 5/2017 | Sela |
| 9,932,590 | B2 | 4/2018 | Bowman |
| 10,190,118 | B2 | 1/2019 | Ward |
| 10,557,138 | B2 | 2/2020 | Gleit-Kielmanowicz |
| 10,801,028 | B2 | 10/2020 | Sela |
| 10,888,579 | B2 | 1/2021 | Paldi |
| 10,907,152 | B2 | 2/2021 | Inberg |

OTHER PUBLICATIONS

Whitten et al (Proc. R. Soc. B 283: 20160042, 2016, 9 pages) (Year: 2016).*

Thammasorn et al (Aquacult Int (2017) 25:1679-1692) (Year: 2017).*

Maddaloni et al (Journal of Applied Microbiology 117: 1572-1584, 2014) (Year: 2014).*

Li et al (Applied and Environmental Microbiology 82(22): 6779-6787, 2016) (Year: 2016).*

Vasquez et al (PLoS ONE 7(3): e33188, 9 pages) (Year: 2012).*

Daisley et al (ISME Journal (2020) 14:476-491) (Year: 2020).*

Whitten et al (Proc. R. Soc. B 283: 20160042, 2016, Supplementary Material) (Year: 2016).*

Medina et al (Curr Microbiol (2009) 58:478-482) (Year: 2009).*

Addgene, pDsRed (GB0100), retrieved from https://www.addgene.org/68202/ on May 20, 2021 (Year: 2021).*

Yeast extract, retrieved from https://www.chemicalbook.com/ChemicalProductProperty_EN_CB9440339.htm on May 20, 2021 (Year: 2021).*

Sudhager et al (Journal of Entomology and Zoology Studies (May-Jun. 2017); 5(3): 434-440) (Year: 2017).*

Peloquin et al (Current Microbiology vol. 45 (2002), pp. 41-45) (Year: 2002).*

Furste JP, et al., 1986, "Molecular cloning of the plasmid RP4 primase region in a multi-host-range tacP expression vector," Gene, 48:119-131.

Jain A. et al., 2013, "Broad host range plasmids," FEMS Microbiol Lett., 348:87-96.

Meyer R. et al., 2009, "Replication and conjugative mobilization of broad host-range IncQ plasmids," Plasmid, 62:57-70.

Ferrieres L. et al., 2010, "Silent Mischief: Bacteriophage Mu Insertions Contaminate Products of *Escherichia coli* Random Mutagenesis Performed Using Suicidal Transposon Delivery Plasmids Mobilized by Broad-Host-Range RP4 Conjugative Machinery," J Bacteriol., 192:6418-6427.

Lee ME, 2015, "A Highly Characterized Yeast Toolkit for Modular, Multipart Assembly," ACS Synth Biol., 4:975-986.

Taton A et al., 2014, "Broad-host-range Vector System for Synthetic Biology and Biotechnology in Cyanobacteria," Nucleic Acids Res., 42:gku673-e136.

Clewell DB et al., 1974, "Characterization of three plasmid deoxyribonucleic acid molecules in a strain of *Streptococcus faecalis*: identification of a plasmid determining erythromycin resistance," J Bacteriol., 117:283-289.

Jensen PR et al., 1998, "The sequence of spacers between the consensus sequences modulates the strength of prokaryotic promoters," Appl Environ Microbiol., 64:82-87.

Robinson CJ et al., 2010, "From structure to function: the ecology of host-associated microbial communities," Microbiol Mol Biol Rev., 74:453-476.

Rangberg A et al., 2012, "Paratransgenesis: An Approach to Improve Colony Health and Molecular Insight in Honey Bees (*Apis mellifera*)?," Integr Comp Biol., 52:89-99.

Miyazaki K et al., 2011, ",MEGAWHOP Cloning: A Method of Creating Random Mutagenesis Libraries via Megaprimer PCR of Whole Plasmids" Meth Enz., 498:399-406.

Kwong WK et al., 2014, "Genomics and host specialization of honey bee and bumble bee gut symbionts," Proc Natl Acad Sci USA., 111:11509-11514.

(Continued)

*Primary Examiner* — Richard A Schnizer

(74) *Attorney, Agent, or Firm* — Riverside Law LLP

(57) ABSTRACT

Provided herein are genetically engineered bacteria that are native to a host insect microbiome. Further provided are methods of inducing RNA interference in an insect, such as a bee, by administering the genetically engineered bacteria.

14 Claims, 38 Drawing Sheets

Specification includes a Sequence Listing.

(56) References Cited

OTHER PUBLICATIONS

Powell JE et al., 2014, "Routes of acquisition of the gut microbiota of the honey bee Apis mellifera," Appl Environ Microbiol., 80:7378-7387.
Powell JE et al., 2016, "Genome-wide screen identifies host colonization determinants in a bacterial gut symbiont," Proc Natl Acad Sci USA., 113:13887-13892.
Whitaker WR et al., 2017, "Tunable Expression Tools Enable Single-Cell Strain Distinction in the Gut Microbiome," Cell, 169:538-546.e12.
Bikard D et al., 2013, "Programmable repression and activation of bacterial gene expression using an engineered CRISPR-Cas system," Nucleic Acids Res., 41:7429-7437.
Choi KH et al., 2005, "A Tn 7-based broad-range bacterial cloning and expression system," Nat Meth., 2:443-448.
Barrangou R et al., 2017, "A Decade of Discovery: CRISPR Functions and Applications," Nat Microbiol., 2:1-9.
Martinson VG et al., 2012, "Establishment of characteristic gut bacteria during development of the honeybee worker," Apl Environ Microbiol., 78:2830-2840.
Engel P et al., 2013, "Standard methods for research on Apis mellifera gut symbionts," J of Api Res., 52:1-24.
Raymann K et al., 2017, "Antibiotic exposure perturbs the gut microbiota and elevates mortality in honeybees," PLoS Biol., 15:e2001861, 22 pages.
Burritt NL et al., 2016, "Sepsis and Hemocyte Loss in Honey Bees (*Apis mellifera*) Infected with Serratia marcescens Strain Sicaria," PLoS One., 11:e0167752, 26 pages.
Linke D et al., 2006, "Trimeric Autotransporter Adhesins: Variable Structure, Common Function," Trends Microbiol., 14:264-270.
Ribet D et al., 2015, "How Bacterial Pathogens Colonize Their Hosts and Invade Deeper Tissues," Microbes Infect, 17:173-183.
Tahir El Y et al., 2001, "YadA, the multifaceted Yersinia adhesin," Int J Med Microbiol., 291:209-218.
Scott et al., 2013, "Towards the elements of successful insect RNAi," Journal of Insect Physiology 59:1212-1221.

* cited by examiner

Broad-host-range Plasmid Screen in Bee Gut Bacteria

| **Plasmid** | RP4 | pTD-C_sfYFP | pAKgfp | pBMTBX-3 | pMMB67EH | pBMTBX-2 |
|---|---|---|---|---|---|---|
| **Origin** | RP4 | mini-rp4 | pBBR1 | pBBR1 | RSF1010 | pBBR1 |
| **Antibiotic Marker** | Amp, Kan | Strep, Spec | Amp | Cam | Amp | Kan |
| ***Snodgrassella alvi*** | - | - | + | - | + | + |
| ***Gilliamella apicola*** | - | - | - | - | + | - |

"+" indicates transconjugants were successfully passaged on selective media, and plasmid was re-isolated and able to re-transform *E. coli* DH5alpha cells.

Figure 16

Bacterial Strains

| Species and strain | Source | ID |
|---|---|---|
| *E. coli* MFDpir | [1] | N/A |
| *E. coli* DH5alpha | Thermo-Fisher | CAT# 11319-019 |
| *E. coli* EC100D | Lucigen | CAT# ECP09500 |
| *Snodgrassella alvi* wkB2 | [2] | ATCC BAA-2449 |
| *Snodgrassella alvi* PEB0171 | This study | N/A |
| *Snodgrassella alvi* wkB12 | [2] | N/A |
| *Snodgrassella alvi* Snod 2-1-5 | This study | N/A |
| *Snodgrassella alvi* PENS 2-2-5 | This study | N/A |
| *Gilliamella apicola* wkB7 | [3] | N/A |
| *Gilliamella apicola* PEB0183 | This study | N/A |
| *Bartonella apis* PEB0150 | [4] | N/A |
| *Bartonella apis* PEB0149 | [4] | N/A |
| *Parasaccharibacter apium* wkB6 | This study | N/A |
| *Serratia marcescens* N10A28 | This study | N/A |

Figure 17

| part | type | 5'-site | 3'-site | description | marker | origin | Part Source |
|---|---|---|---|---|---|---|---|
| | | | | **Entry Vector** | | | |
| **pBTK001** | entry vector | | | entry vector for generating new parts | CamR | p15A | 1 |
| | | | | **pYTK001 from Yeast Toolkit is a suitable entry vector** | | | |
| | | | | **Type 1 - Connectors** | | | |
| | | | | **Use Connector sequences from Yeast Toolkit** | | | |
| | | | | **Type 2 - Promoters** | | | |
| | ***Constitutive*** | | | | | | |
| **pBTK102** | promoter | 2 | 2 | T7 + RBS | CamR | ColE1 | 2 |
| **pBTK107** | promoter | 2 | 2 | CP25 + RBS | CamR | ColE1 | 3 |
| **pBTK110** | promoter | 2 | 2 | CP6 + RBS | CamR | ColE1 | 3 |
| **pBTK112** | promoter | 2 | 2 | CP12b + RBS | CamR | ColE1 | 3 |
| **pBTK113** | promoter | 2 | 2 | CP32 + RBS | CamR | ColE1 | 3 |
| **pBTK119** | promoter | 2 | 2 | PA1 + RBS | CamR | p15A | 4 |
| **pBTK120** | promoter | 2 | 2 | PA2 + RBS | CamR | p15A | 4 |
| **pBTK121** | promoter | 2 | 2 | PA3 + RBS | CamR | p15A | 4 |
| | ***Inducible*** | | | | | | |
| **pBTK103** | promoter | 2 | 2 | Lac lacO + RBS | CamR | ColE1 | 6 |
| **pBTK124** | promoter | 2 | 2 | CP25 (lacO) | CamR | ColE1 | |
| **pBTK130** | promoter | 2 | 2 | T7 (lacO) | CamR | ColE1 | |
| | | | | **Type 3 - Coding Sequences** | | | |
| **pBTK200** | coding_sequence | 3 | 3 | T7 RNA Polymerase | CamR | ColE1 | 2 |
| **pBTK203** | coding_sequence | 3 | 3 | LacI repressor | CamR | ColE1 | 6 |
| **pBTK205** | coding_sequence | 3 | 3 | GFP optim-1 | CamR | ColE1 | 7 |
| **pBTK206** | coding_sequence | 3 | 3 | Nanoluc | CamR | ColE1 | 8 |
| **pBTK209** | coding_sequence | 3 | 3 | dCas9 | CamR | ColE1 | 9 |
| **pBTK224** | coding_sequence | 3 | 3 | E2-Crimson | CamR | ColE1 | 10 |
| **pBTK229** | For homologous recombination | 3 | 3 | Kanamycin Resistance | CamR | ColE1 | 1 |
| | | | | **Type 4 - Terminators** | | | |
| **pBTK300** | terminator | 4 | 4 | *rpoC* | CamR | ColE1 | 11 |
| **pBTK301** | terminator | 6 | 7 | BBa_B0015 Terminator | CamR | ColE1 | 12 |
| **pBTK306** | terminator | 4 | 4 | T7 | CamR | ColE1 | 2 |
| | | | | **Type 5 - Connectors** | | | |
| | | | | **Use Connector sequences from Yeast Toolkit** | | | |
| | | | | **Type 6 - Repressors (reverse CDS)** | | | |
| **pBTK211** | | 6 | 6 | LacI Reverse | CamR | ColE1 | 13 |
| | | | | **Type VII - Reverse promoters** | | | |
| **pBTK138** | promoter | 7 | 7 | CP25 + RBS Reverse | CamR | ColE1 | 3 |
| | | | | **Type 8 - Origins and Antibiotics** | | | |
| **pBTK401** | origin_marker | 8 | 8 | mRFP1 dropout | AmpR | RSF1010 | 14 |
| **pBTK402** | origin_marker | 8 | 8 | mRFP1 dropout | KanR | RSF1010 | 14 |
| **pBTK403** | origin_marker | 8 | 8 | mRFP1 dropout | SpecR | RSF1010 | 14 |

Figure 18

| Vectors for Stage 2 Assembly | | | | | | | |
|---|---|---|---|---|---|---|---|
| **pBTK527** | Stage 1 | ConLS' | ConRE' | SPACE | KanR | RSF1010 | |
| **pBTK527α** | Stage 1 | ConLS' | ConRE' | SPACE | SpecR | RSF1010 | |
| **pBTK599** | for homologous recombination | 6 | 8 | R6K-sfGFP | AmpR | R6k | 15 |
| **pBTK599s** | for homologous recombination | 6 | 8 | R6K-sfGFP | SpecR | R6k | 15 |

| Assembled Plasmids | | | | | | |
|---|---|---|---|---|---|---|
| **pBTK501** | Stage 1 | ConLS' | ConRE' | PA1 GFP optim1 | AmpR | RSF1010 |
| **pBTK503** | Stage 1 | ConLS' | ConRE' | CP25 GFP optim1 | AmpR | RSF1010 |
| **pBTK509** | Stage 1 | ConLS' | ConRE' | PA2 GFP optim1 | AmpR | RSF1010 |
| **pBTK510** | Stage 1 | ConLS' | ConRE' | PA3 GFP optim1 | AmpR | RSF1010 |
| **pBTK519** | Stage 1 | ConLS | ConR1 | PA1 GFP optim1 | KanR | RSF1010 |
| **pBTK520** | Stage 1 | ConLS | ConR1 | PA1 GFP optim1 | SpecR | RSF1010 |
| **pBTK549** | Stage 1 | ConLS' | ConRE' | T7 RNAP + CP25 LacI reverse | SpecR | RSF1010 |
| **pBTK541** | Stage 1 | ConLS | ConRE | T7 lacO GFP optim1 | AmpR | RSF1010 |
| **pBTK550d** | Stage 2 | NA | NA | pBTK549 + pBTK541 | SpecR | RSF1010 |
| **pBTK562** | Stage 1 | ConLS | ConR1 | CP25(lacO) inducible GFP | SpecR | RSF1010 |
| **pBTK563** | Stage 1 | ConLS | ConR1 | CP25 NanoLuc luciferase | SpecR | RSF1010 |
| **pBTK564** | Stage 1 | ConLS | ConR1 | PA3 NanoLuc luciferase | SpecR | RSF1010 |
| **pBTK569** | Stage 2 | NA | NA | CP25 E2-crimson | SpecR | RSF1010 |
| **pBTK570** | Stage 2 | NA | NA | PA3 E2-crimson | SpecR | RSF1010 |
| **pBTK601** | Stage 2 | NA | NA | Cas9 (no sgRNA) | SpecR | RSF1010 |
| **pBTK614** | Stage 1 | ConL1 | ConRE | dCas9 (no sgRNA) | AmpR | ColE1 |
| **pBTK615** | Stage 1 | ConLS | ConR1 | sgRNA (gfp) | AmpR | ColE1 |
| **pBTK619** | Stage 1 | ConLS | ConRE | CP12b GFP optim1 | KanR | RSF1010 |
| **pBTK620** | Stage 1 | ConLS | ConRE | CP32 GFP optim1 | KanR | RSF1010 |
| **pBTK621** | Stage 1 | ConLS | ConRE | CP6 GFP optim1 | KanR | RSF1010 |

Figure 18 (Continued)

Oligonucleotides Used in the Study

| ID | Use | Source | Sequence (5' to 3') | |
|---|---|---|---|---|
| wkB2_KO_1 | Validate wkB2Δ*staA* mutant, upstream junction F | This Study | TACCAACAGCGACAGAACCC | SEQ ID NO:13 |
| wkB2_KO_2 | Validate wkB2Δ*staA* mutant, upstream junction R | This Study | CTCAGGCGCAATCACGAATG | SEQ ID NO:14 |
| wkB2_KO_3 | Validate wkB2Δ*staA* mutant, downstream junction F | This Study | AATGCTGTTTTCCCGGGGAT | SEQ ID NO:15 |
| wkB2_KO_4 | Validate wkB2Δ*staA* mutant, downstream junction R | This Study | CTGGAAATTGCTGCTGCCAG | SEQ ID NO:16 |
| wkB7_KO_1 | Validate wkB7Δ*ackA* mutant, upstream junction F | This Study | TCGCTTGTTCACAGCGATAGA | SEQ ID NO:17 |
| wkB7_KO_2 | Validate wkB7Δ*ackA* mutant, upstream junction R | This Study | GCTTTTGCCATTCTCACCGG | SEQ ID NO:18 |
| wkB7_KO_3 | Validate wkB7Δ*ackA* mutant, downstream junction F | This Study | ATTGGCAACGCTACCTTTGC | SEQ ID NO:19 |
| wkB7_KO_4 | Validate wkB7Δ*ackA* mutant, downstream junction R: | This Study | GTCGTGGTATTGTCAGGAGCA | SEQ ID NO:20 |
| 0150_KO_1 | Validate PEB0150Δ*narG* mutant, upstream junction F | This Study | TGTTCAGGACGTCAATACACCTTAT | SEQ ID NO:21 |
| 0150_KO_2 | Validate PEB0150Δ*narG* mutant, upstream junction R | This Study | AAATTGCAGTTTCATTTGATGCTCG | SEQ ID NO:22 |
| 0150_KO_3 | Validate PEB0150Δ*narG* mutant, downstream junction F | This Study | GCGAGCCCATTTATACCCATATAAA | SEQ ID NO:23 |
| 0150_KO_4 | Validate PEB0150Δ*narG* mutant, downstream junction R | This Study | TTCAAGGTTCCATTTGCCTTTTTCA | SEQ ID NO:24 |
| KO_5 | Amplify backbone of suicide plasmid F | This Study | ACCTGTTGATAGTACGTACTAAGCTC | SEQ ID NO:25 |
| KO_6 | Amplify backbone of suicide plasmid R | This Study | TCAAAATTGCTTTGAGAGGCTCTAAG | SEQ ID NO:26 |
| pMMB_F | Validate replication of pMMB67EH / BTK plasmids F | This Study | TCATGTCATCCAGGTCAAACTC | SEQ ID NO:27 |
| pMMB_R | Validate replication of pMMB67EH / BTK plasmids R | This Study | TGAAGAAATCCAGAGGCATCAA | SEQ ID NO:28 |
| Beta-1009-qtF | 16S betaproteobacteria qPCR primer F, Beta-1009-qtF | [12] | CTTAGAGATAGGAGAGTG | SEQ ID NO:29 |
| Beta-1115-qtR | 16S betaproteobacteria qPCR primer R, Beta-1115-qtR | [12] | TAATGATGGCAACTAATGACAA | SEQ ID NO:30 |
| dCas9_sg | sgRNA sequence targeting *gfp* for dCas9 | This Study | CCCAATCCTCGTGGAATTAGACG | SEQ ID NO:31 |
| wkB2_KO_sg | Cas9 sgRNA targeting *S. alvi* wkB2 *staA* | This Study | GAATTCGAAGCATAAGAATT | SEQ ID NO:32 |
| wkB7_KO_sg | Cas9 sgRNA targeting *G. apicola* wkB7 *ackA* | This Study | TTCCACTTAATACGTGCATC | SEQ ID NO:33 |
| 0150_KO_sg | Cas9 sgRNA targeting *B. apis* PEB0150 *narG* | This Study | ACACCATGTCCATGCGAAAA | SEQ ID NO:34 |

*S. alvi* CFU in whole gut 5
10
15

Days after inoculation

Figure 30

ENGINEERED MICROBIAL POPULATION

CROSS REFERENCE TO RELATED APPLICATIONS

This application claims priority to U.S. Provisional Application No. 62/529,754, filed Jul. 7, 2017 which is hereby incorporated by reference herein in its entirety.

STATEMENT REGARDING FEDERALLY SPONSORED RESEARCH OR DEVELOPMENT

This invention was made with government support under Grant No. HR0011-15-C-0095 awarded by the Defense Advanced Research Projects Agency. The government has certain rights in the invention

FIELD OF THE INVENTION

The present invention relates generally to the field of molecular biology. More particularly, it concerns microbiome engineering.

BACKGROUND OF THE INVENTION

Most animals have symbiotic microorganisms living in their bodies. Most often these are bacteria that are specialized to live in particular animal species. Honey bees (*Apis mellifera*) are important agricultural pollinators. Unfortunately, recent years have seen substantial bee colony losses (e.g., Colony Collapse Disorder), due to a myriad of complex causes. Some of the most significant causes are bee viral pathogens and *Varroa* mite infestations.

RNA interference (RNAi) is a powerful technique to specifically downregulate gene expression in many eukaryotes by providing dsRNA with sequence identity to eukaryotic genes. RNAi has been shown to function in honey bees previously, and has been used to knock down bee genes to investigate their function and also improve bee health by lowering pathogen burden (e.g., viral and *Varroa* mite). Injection or feeding of double stranded RNA (dsRNA) has been shown to trigger RNAi in honey bees, leading to molecular cascades that can degrade invading viral RNA and kill pests (e.g., *Varroa* mites). However, production of large quantities of dsRNA in the laboratory is expensive and the dsRNA itself is unstable and rapidly degrades in the environment. Additionally, injecting dsRNA into bees is traumatic and feeding them dsRNA is unreliable. Thus, there is an unmet need for improved methods of inducing RNAi in bees.

SUMMARY OF THE INVENTION

In one embodiment, the invention relates to a microbial composition comprising one or more bacteria genetically engineered to express at least one heterologous nucleic acid, wherein the one or more bacteria are native to the microbiome of a host insect.

In one embodiment, the host insect is selected from the group consisting of a honey bee and a bumble bee.

In one embodiment, the one or more bacteria is *Snodgrassella alvi, Bartonella apis, Gilliamella apicola, Serratia marcescens, Parasaccharibacter apium*, or *Lactobacillus* sp.

In one embodiment, the composition comprises 2, 3, 4, or 5 bacterial species.

In one embodiment, the one or more bacteria express at least two heterologous nucleic acids.

In one embodiment, the heterologous nucleic acid encodes a polypeptide that improves the health of a host insect.

In one embodiment, the heterologous nucleic acid encodes a pesticide degrading polypeptide or a cytochrome.

In one embodiment, the heterologous nucleic acid is an inhibitory nucleic acid. In one embodiment, the inhibitory nucleic acid is selected from the group consisting of an antisense DNA, dsRNA, siRNA, shRNA, sgRNA and a miRNA.

In one embodiment, the heterologous nucleic acid is incorporated into a broad host range plasmid.

In one embodiment, the broad host range plasmid comprises at least one regulatory sequence selected from the group consisting of an RSF1010 origin of replication, a PA1 promoter sequence, a PA2 promoter sequence, a PA3 promoter sequence, a cp25 promoter sequence, and a detectable marker.

In one embodiment, the composition is a bee-ingestible composition.

In one embodiment, the bacteria are present as a live suspension. In one embodiment, the bacteria are present as a lyophilized powder. In one embodiment, the composition is in solid form. In one embodiment, the composition is in liquid form. In one embodiment, the composition comprises protein. In one embodiment, the composition comprises pollen. In one embodiment, the composition is a sucrose solution. In one embodiment, the composition is a corn syrup solution. In one embodiment, the composition comprises a carbohydrate or sugar supplement.

In one embodiment, the invention relates to an insect comprising a microbial composition comprising one or more bacteria genetically engineered to express at least one heterologous nucleic acid, wherein the one or more bacteria are native to the microbiome of a host insect.

In one embodiment, the insect is a bee, a honey bee, a forager, a hive bee, a pupae, an adult bee, and a bee colony parasite.

In one embodiment, the invention relates to a method for producing a microbial composition comprising one or more bacteria genetically engineered to express at least one heterologous nucleic acid, wherein the one or more bacteria are native to the microbiome of a host insect, comprising transfecting said bacterial species with an expression cassette comprising at least one heterologous nucleic acid.

In one embodiment, the invention relates to a method for downregulating expression of a target gene product, comprising administering an effective amount of a microbial composition comprising one or more bacteria genetically engineered to express at least one heterologous nucleic acid, wherein the one or more bacteria are native to the microbiome of a host insect to the host insect, wherein said bacteria express an inhibitor of said target gene product.

In one embodiment, the target gene product is a gene from an organism selected from the group consisting of a pathogen, a parasite, a virus, a mite, Acute Bee Paralysis Virus (ABPV), Kashmir Bee Virus (KBV), Israeli Acute Paralysis Virus (IAPV), *Nosema ceranae*, Deformed Wing Virus, and *Varroa destructor* mite.

In one embodiment, the insect is selected from the group consisting of a bee, a honey bee, a forager, a hive bee, a pupae, an adult bee, and a bee colony parasite.

In one embodiment, the target gene is selected from the group consisting of TOM70, TIM22, TOM40, Imp2, mitochondrial Hsp70, ATM1-ABC transporter proteins, Frataxin, Ferredoxin, ERV1, ferredoxin, NADPH oxido-reductase [FNR], pyruvate dehydrogenase a subunit, pyruvate dehydrogenase β subunit, mitochondrial glycerol-3-phosphate dehydrogenase (mtG3PDH), manganese-containing superoxide dismutase (MnSOD), DNAJ (Hsp70 interacting), Iron Sulfur cluster ISU1, Cystein desulfurase Nsf1, NAR1, RLI1, ATPase subunit A, RNA polymerase I, RNA polymerase III, Inhibitor of apoptosis (IAP), and FAS apoptotic.

In one embodiment, the invention relates to a method for modulating expression of a target gene product in an insect, comprising administering an effective amount of a microbial composition comprising one or more bacteria genetically engineered to express at least one heterologous nucleic acid to said insect.

In one embodiment, the insect is selected from the group consisting of a bee, a honey bee, a forager, a hive bee, a pupae, an adult bee, and a bee colony parasite.

In one embodiment, the invention relates to a method for reducing the susceptibility of a bee to a disease or disorder selected from the group consisting of Colony Collapse Disorder (CCD) and infection, comprising administering an effective amount of a microbial composition comprising one or more bacteria genetically engineered to express at least one heterologous nucleic acid, wherein the one or more bacteria are native to the microbiome of a host insect, to said bee, wherein said bacteria express an inhibitor of a pathogen or parasite specific gene product.

In one embodiment, the pathogen or parasite is selected from the group consisting of Acute Bee Paralysis Virus (ABPV), Kashmir Bee Virus (KBV), Israeli Acute Paralysis Virus (IAPV), *Nosema ceranae, Nosema cerana, Nosema apis*, Deformed Wing Virus, and *Varroa destructor* mite.

In one embodiment, the bacteria express at least two non-contiguous dsRNAs downregulating expression of a pathogen or parasite specific gene product.

In one embodiment, the invention relates to a method for reducing the susceptibility of a bee colony to infestation by the Small Hive Beetle, comprising administering an effective amount of a microbial composition comprising one or more bacteria genetically engineered to express at least one heterologous nucleic acid to hive components, wherein said bacteria express an inhibitor of a Small Hive Beetle specific gene product.

In one embodiment, the bacteria express at least two non-contiguous dsRNAs downregulating expression of a Small Hive Beetle specific gene product.

In one embodiment, the invention relates to a method for expression of a heterologous nucleic acid sequence in a bee, the method comprising administering to the bee at least one modified *Snodgrassella alvi* bacterium comprising an expression plasmid for expression of the heterologous nucleic acid sequence.

In one embodiment, the heterologous nucleic acid sequence encodes a molecule selected from the group consisting of a protein, a peptide, an inhibitory RNA, a dsRNA, a siRNA, a shRNA, a sgRNA and a miRNA.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 9A depicts the BTK designed for Golden Gate assembly according to a scheme with eight-part types compatible with the yeast toolkit (YTK) (Lee M E et al., 2015, ACS Synth Biol., 4:975-986). Parts of each type generated in this study are shown in the top panel. Type 1-5 and Type 8 parts are defined as in the YTK except that Type 3 open reading frames include the stop codon. Type 6 and 7 parts are either replaced with a linker part or used to incorporate a reverse reading frame encoding a transcriptional regulator for inducible expression of the main Type 3 open-reading frame and its promoter, respectively, during Stage 1 assembly, so that costly or toxic genes can be repressed while they are assembled into transcriptional units. FIG. 9B Schematic of Stage 1 (BsaI) assembly. Plasmid parts are shown, but PCR products with appropriate overhangs can be substituted. FIG. 9*c* Schematic Stage 2 (BsmBI) assembly. Compatible Stage 2 connectors are described in the YTK documentation.

FIG. 10A depicts replication of the BTK backbone and the function of three antibiotic resistance cassettes were tested in eight honey bee-associated bacterial strains as described in the Methods. At least one antibiotic resistance cassette functioned in each strain, and the kanamycin cassette functioned in all eight strains. FIG. 10B depicts replication of the BTK backbone and the function of three antibiotic resistance cassettes were tested in three bumble bee-associated bacterial strains. Again, the plasmid with kanamycin resistance was maintained in all three bacteria.

FIG. 11A depicts flow cytometry results of GFP fluorescence from four broad-host-range promoters in each of four honey bee-associated bacterial strains and an *E. coli* control. One representative fluorescence distribution for each promoter is shown, with the medians from three biological replicates plotted as open circles. Spotted grey line indicates maximum detected fluorescence in wildtype cells. Median fluorescent values were calculated from cells more fluorescent than wildtype. FIG. 11B depicts GFP fluorescence from a designed CP25 (lacO) promoter at different levels of IPTG-induction, measured in four BGM strains and an *E. coli* control. All tested species are responsive to IPTG induction, and *G. apicola* shows the highest expression across all strains. FIG. 11C depicts GFP fluorescence from a T7 (lacO) promoter at different levels of IPTG-induction of T7 RNAP expression in the same four BGM strains. Schematics in FIG. 11A through FIG. 11C show the design of tested constructs using Synthetic Biology Open Language (SBOL) standard glyphs (Galdzicki M et al., 2014, Nat Biotechnol., 32:545-550). Error bars are standard deviations (n=3).

FIG. 12A depicts schematic assembly of dCas9 plasmids for gene suppression. FIG. 12B depicts fluorescence from chromosomally integrated GFP in PEB0150 in the presence and absence of dCas9 and sgRNA targeting GFP. Background fluorescence of wild-type PEB0150 was subtracted. GFP fluorescence decreased in presence of dCas9 targeting GFP (p=0.004, Kruskal-Wallis rank sum test). Error bars are 95% confidence intervals (n=4).

FIG. 13A depicts schematic assembly of R6K-based suicide plasmids. Assembly strategy and validation primers are described in FIG. 23. FIG. 13B depicts the two tested approaches for gene disruption. The suicide plasmids were introduced into either wild-type bacteria or bacteria possessing the constitutively active Cas9 (pBTK601). FIG. 13C depicts transconjugation frequency and percent of desired mutants in *B. apis*, in the presence and absence of Cas9. The Cas9 plasmid did not increase the efficiency of genome modification. Numbers above each bar indicate the number of clones evaluated. FIG. 13D depicts transconjugation frequency and proportion of desired mutants in *S. alvi*. *S. alvi* wkB2 showed increased efficiency of genome modification in the presence of the Cas9 plasmid (p=0.0007, Kruskal-Wallis rank sum test). FIG. 13E depicts transconjugation frequency and proportion of desired mutants in *G. apicola*. Each point in FIG. 13C and FIG. 13E is from an independent conjugation experiment. Bars in FIG. 13C and FIG. 13E represent the geometric mean of estimated transconjugation efficiencies.

FIG. 14A depicts intact honey bee worker and dissection of honey bee gut showing brightfield microscopy of midgut, ileum, and rectum. FIG. 14B depicts fluorescent imaging of whole bee (left) and dissected bee (right) 5 days after inoculation with *S. marcescens* N10A28 expressing E2-Crimson (plasmid pBTK570). Control bee is uninoculated. Color corresponds to pixel fluorescence intensity. Engineered *S. marcescens* N10A28 is present in the midgut, ileum, and rectum. FIG. 14C Similar to FIG. 14B, with *S. alvi* wkB2 expressing E2-Crimson as inoculum. Control bee is identical to FIG. 14B, but different fluorescent intensity scales are used for comparison between bees inoculated with *S. alvi* and *S. marcescens*. Engineered *S. alvi* wkB2 is visibly fluorescent in the midgut and ileum. FIG. 14D depicts confocal imaging of partial ileum and rectum in bees inoculated with *S. marcescens* N10A28 expressing E2-Crimson (red). As in FIG. 14B, *S. marcescens* can be seen robustly colonizing throughout the ileum and rectum. FIG. 14E Similar to FIG. 14D, with *S. alvi* wkB2 expressing E2-Crimson (green). *Snodgrassella alvi* wkB2 colonizes the ileum, but not the rectum. Scale bars in FIG. 14D and FIG. 14E are 100 m. Images are representative of multiple bees inspected (n=3-5 per condition) for (FIG. 14B through FIG. 14E). White and black arrows correspond to the ileum-rectum junction across images (FIG. 14A through FIG. 14E).

FIG. 15A depicts the ileum-rectum junction imaged by confocal fluorescence microscopy 5 days after co-inoculating *B. apis* PEB0150 and *S. alvi* wkB2. When co-inoculated, *B. apis* and *S. alvi* are co-located in the ileum, but only *B. apis* colonizes the rectum. FIG. 15B, similar to FIG. 15A, depicts images taken 5 days after co-inoculation of *G. apicola* wkB7 and *S. alvi* wkB2. As in FIG. 15A, *S. alvi* remains restricted to the ileum, while *G. apicola* is present in both ileum and rectum. Scale bars are 100 μm. Images are representative of multiple bees inspected (n=3 per condition). FIG. 15C depicts the number of *S. alvi* 16S ribosomal DNA copies 5 days after inoculating newly emerged worker bees with the *S. alvi* WT or ΔstaA mutant, based on quantitative PCR. Horizontal bars represent means per condition (n=5). The ΔstaA has a significant colonization defect compared to WT ($p=2.7\times10-6$, Kruskall-Wallis rank sum test). FIG. 15D depicts the ileums of bees inoculated with *S. alvi* wkB2ΔstaA expressing E2-Crimson (pBTK570) were imaged 5 days after colonization. Mutants achieved lower colonization levels than did *S. alvi* WT (see FIG. 6E). Localized colonization was typical of multiple ileums inspected (n=3). Scale bar is 100 μm.

FIG. 16 depicts broad-host-range plasmid screen in bee gut bacteria.

FIG. 17 depicts the bacterial strains used in this study.

FIG. 18 depicts BTK plasmids.

FIG. 19 depicts oligonucleotides used in the study.

FIG. 23A depicts schematic assembly of homology donor plasmids using BTK Golden Gate assembly. Type 2, 3, and 4 overhangs are repurposed for the upstream homology, antibiotic resistance, and downstream homology respectively. Combined with parts Type 1, 5, and pYTK095 (Type 6-8), the donor plasmid is then ready for further BsmBI assembly as shown in FIG. 12. FIG. 23B depicts possible outcomes from homologous recombination crossing-over events. Single-crossover mutants are more common and occur with integration of the suicide plasmid backbone. Double-crossover mutants are the desired mutant, where only the antibiotic resistance cassette is retained in the chromosome of the target strain. FIG. 23C depicts sets of PCR primers used to verify mutants.

FIG. 24A depicts schematic of staA disruption in *S. alvi*. FIG. 24B depicts DNA gel with products from the PCR of upstream junctions using primers 1-2. The double-crossover mutant (DC) shows a band at the expected size of 1583 bp, wild type (WT) shows no amplification. FIG. 24C depicts DNA gel with products from the PCR of downstream junctions using primers 3-4. DC shows a band at the expected size of 1587 bp, WT shows no amplification. FIG. 24D depicts DNA gel with products from the PCR of the entire region using primers 1-4. DC shows an increase in size of approximately 880 bp compared to WT. Lanes rearranged from original gel for clarity. FIG. 24E depicts DNA gel with products from the PCR of plasmid backbone. A single crossover mutant (SC) shows expected amplification at 453 bp, DC shows no amplification. Black bars indicate image cropping for clarity.

FIG. 25A depicts schematic of planned ackA disruption in *G. apicola*. FIG. 25B depicts DNA gel showing products from the PCR of upstream junctions using primers 1-2. Forty clones were tested, and two distinct single cross-over events (SC) were observed: a smaller than expected band at ~550 bp and a second, larger band at ~2800 bp (often in the same clone). Neither of these is the expected size of 1501 bp. This may represent a duplication or other complex recombination event. No downstream junctions were effectively amplified using primers 3-4 (data not shown). PCR using primers 1-4 showed no change in size between wild-type (WT) and SC mutants, indicating the SC event likely did not disrupt ackA function (data not shown). FIG. 25C depicts DNA gel showing product from the PCR using primers KO_5 and KO_6. Expected product at 453 bp shows retention of the suicide backbone in the SC mutants.

FIG. 26A depicts schematic of planned narG disruption in *B. apis*. FIG. 26B depicts DNA gel with products from the PCR of upstream junctions using primers 1-2. The double-crossover mutant (DC) shows a band at the expected size of 1169 bp, wild type (WT) shows no amplification. FIG. 26C depicts DNA gel with products from the PCR of downstream junctions using primers 3-4. DC shows a band at the expected size of 1309 bp, WT shows no amplification. FIG. 26D depicts DNA gel with products from the PCR of the entire region using primers 1-4. DC shows an increase in size of approximately 757 bp compared to WT. Lanes rearranged from original gel for clarity. FIG. 26E depicts DNA gel with products from the PCR of plasmid backbone. A single crossover mutant (SC) shows expected amplification at 453 bp, DC shows no amplification. Black bars indicate image cropping for clarity.

FIG. 30: Depicts exemplary experimental results demonstrating the proportion of *S. alvi* CFU persisting in the gut of inoculated bees at different times.

DETAILED DESCRIPTION

Figure 1:
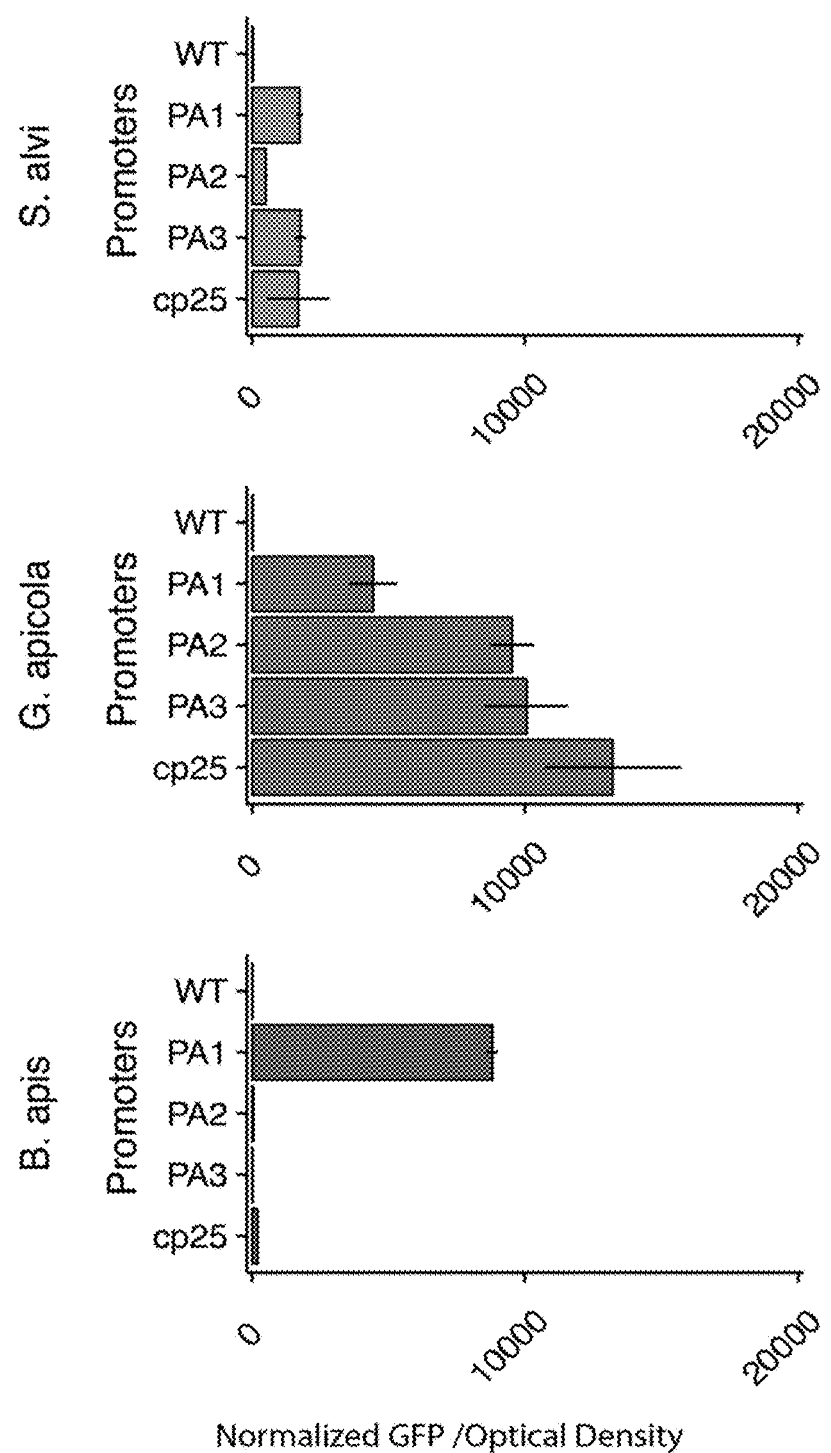
FIG. 1: In vitro fluorescent protein expression in bee gut microbiome bacteria.

In some embodiments, the present disclosure provides methods and compositions concerning microbiome engineering, such as in the gut microbiome of arthropods. In certain embodiments, one or more species of bacteria that are naturally present in the arthropod gut are genetically engineered. These methods may be used to improve arthropod health in a variety of ways. For example, these engineered bacterial species may then be introduced to an insect population, such as a bee population, to directly produce one or more compounds in the insect gut. In some instances, the engineered bacterial species are used to directly express double-stranded RNA (dsRNA) in an insect. In some embodiments, the microbe-produced dsRNA induces RNA interference (RNAi) against a host insect gene product. In some embodiments, the microbe-produced dsRNA induces RNA interference (RNAi) against a gene product of a pathogen or parasite of a host insect.

A broad host range plasmid (e.g., comprising a RSF 1010 origin of replication, such as from the pMMB67EH plasmid) may be used to introduce genes into one or more arthropod gut microbiome strains including, but not limited to, *Snodgrassella alvi, Bartonella apis, Gilliamella apicola, Serratia* sp., *Parasaccharibacter apium*, and *Lactobacillus* sp.

In one embodiment, the invention relates to the use of paired, convergent transcriptional promoters on a plasmid to generate dsRNA constructs against any target gene product or series of targets. In this embodiment, no purification of the dsRNA is required, as the genetically engineered bacteria continually produce the desired dsRNA and the dsRNA is directly taken up through the gut of the arthropod. Because these are modified natural arthropod gut microbiome species, they can be maintained over the arthropod's lifetime. In one embodiment, they may be naturally transferred to newly emerged arthropod (e.g., newly emerged bees in a hive) from adults. Thus, the present methods may reduce the need for frequent and costly reapplication.

The present studies showed the production of dsRNA directly in the bee gut by engineering natural members of their microbiota. By producing dsRNA directly in the honey bee gut, the present methods can provide a continual and cost-effective supply of dsRNA to silence bee or bee-pest genes. In one example, the efficacy of the present methods was demonstrated by using *Snodgrassella alvi* to produce a dsRNA that targets an essential honey bee cytoskeletal gene. Application of this engineered bacterium to bees resulted in increased bee mortality compared to one encoding an off-target dsRNA control. Further aspects may comprise additional methods to increase dsRNA expression, such as knock out of bacterial RNaseII or RNase III or using T7 RNA polymerase to produce dsRNA.

Thus, in one embodiment, the present methods may be used to produce and administer dsRNA by genetically engineering bacteria that are native to the bee gut microbiome. The methods may be useful in reducing bee mortality from RNA viruses (e.g., Israeli acute paralysis virus, Deformed wing virus) and for *Varroa* mite and Small Hive Beetle control as well as other microbial and insect pathogens. As bacterial production can be inexpensive, the present methods be useful to small and large scale apiaries. Further embodiments may concern bumble bee production, an industry that is important in providing pollination for many fruit and vegetable crops.

In some cases, Colony Collapse Disorder (CCD) of honeybees can be due to *Varroa* mite infections. *Varroa* mites are suspected of acting as vectors for a number of honey bee pathogens, including Deformed Wing Virus (DWV), Kashmir Bee Virus (KBV), Acute Bee Paralysis Virus (ABPV) and Black Queen Cell Virus (BQCV), and may weaken the immune systems of their hosts, leaving them vulnerable to infections. Accordingly, certain embodiments of the present disclosure provide methods of reducing the susceptibility of honeybees to Colony Collapse Disorder (CCD). Thus, in some aspects, the dsRNA of the present methods and compositions may target a gene product of picorna-like viruses (e.g., Acute Bee Paralysis Virus (ABPV), Kashmir Bee Virus (KBV), and Israeli Acute Paralysis Virus (IAPV)), *Nosema* parasite, Deformed Wing Virus, and/or a *Varroa destructor* mite, or Small Hive Beetle. The inhibitory nucleic acid molecules (e.g., dsRNA) may be complementary to the mRNA of the target gene product. For example, the inhibitory nucleic acid molecule can be complementary to region of a mRNA comprising at least 10, 15, 20, 21, 22, 23, 24, or 25 contiguous nucleotides. In some aspects, the inhibitory nucleic acid molecule can be complementary to region of a mRNA comprising at least 50, 100, 150, 200, 300 400 or 500 contiguous nucleotides or essentially the entire mRNA. In some aspects a dsRNA comprise at least 10, 15, 20, 21, 22, 23, 24, or 25 complementary nucleotides. For example, the dsRNA produced by the engineered bacteria may comprise a sequence complementary to *Varroa destructor* mite mRNA of and capable of inducing degradation of the *Varroa destructor*-specific mRNA. The target mRNA sequences for use in the present methods include those described in, but are not limited to, U.S. Patent Publication No. 20140371298 or 20150133532; both incorporated herein by reference in their entirety.

In some embodiments, there is provided an expression cassette encoding a dsRNA under the control of one or more broad host range promoters, wherein the dsRNA is complementary to a target gene product of Acute Bee Paralysis Virus (ABPV), Kashmir Bee Virus (KBV), Israeli Acute Paralysis Virus (IAPV), *Nosema* parasite, Deformed Wing Virus, *Varroa destructor* mite, or Small Hive Beetle. The expression cassette may encode for 2, 3, 4, 5, 6, 7, 8, 9, 10 or more inhibitory nucleic acids, such as dsRNAs. In some aspects, the inhibitory nucleic acids may target the same virus, parasite or mite. In other aspects, the inhibitory nucleic acids target mRNAs encoding different gene products, such as a dsRNA to a gene product of the *Varroa destructor* mite.

In further embodiments, there are provided microbial compositions comprising one or more insect microbiome bacteria engineered to express one or more heterologous nucleic acids, such as inhibitory nucleic acids. The inhibitory nucleic acid may be dsRNA, siRNA, shRNA, and/or miRNA. The dsRNAs may also be precursor miRNAs. In some cases, the inhibitory nucleic acids may be at least 15 base pairs in length, such as at 16, 17, 18, 19, 20, 21, 22, 23, 24, 25, 26, 27, 28, 29, or 30 base pairs in length. In further aspects, the inhibitory nucleic acids may be complementary to 50, 100 or more based pairs of a target mRNA. Exemplary insect microbiome species include, but are not limited to, *Snodgrassella alvi, Bartonella apis, Gilliamella apicola, Serratia marcescens, Parasaccharibacter apium* and *Lactobacillus* sp. The microbial composition may comprise 2, 3, 4, or 5 bacterial species. Each engineered bacterium may express 1, 2, 3, 4, 5, or more heterologous nucleic acids. The nucleic acids may be pathogen, pest or parasite-specific, such as parasites which may infect insects, particularly bees. Exemplary pathogens, pests and parasites include, but are not limited to, viruses, microbial pathogens, Acute Bee Paralysis Virus (ABPV), Kashmir Bee Virus (KBV), Israeli Acute Paralysis Virus (IAPV), Deformed Wing Virus, parasites such as *Nosema ceranae*, mites such as the *Varroa destructor* mite and pests such as the Small Hive Beetle (*Aethina tumida*).

The microbial composition may be formulated for insect ingestion, particularly as an ingestible composition (e.g., oral formulations). The composition may be solid or liquid (e.g, a sucrose solution or corn syrup solution). The composition may comprise additives or excipients, such as a carbohydrate or sugar supplement.

The microbial composition may be formulated for application to an insect pest food source, for example bee hive components.

The engineered bacteria or microbial compositions provided herein may be used to reduce insect susceptibility to infections, such as viral infections. They may also be used to down-regulated expression of a target gene product, such as by inducing RNAi in the insect.

In addition, the same bacterial species including *S. alvi* and *G. apicola* live in both honey bees (species in the genus *Apis*) and bumble bees (species in the genus *Bombus*), and the broad host range plasmid replicated in diverse bacterial hosts. Thus, the present methods may be applied to other bees or other species of insects, such as to induce similar RNAi effects. Additionally, the present methods allow for easy targeting of bee-specific genes to silence, and thus may be used for research.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.01%. Most preferred is a composition in which no amount of the specified component can be detected with standard analytical methods. "Genetically engineered bacteria" refers to bacterial cells that replicate a heterologous nucleic acid, or express a polypeptide encoded by a heterologous nucleic acid.

"Heterologous nucleic acid" is one that originates from a source foreign to the particular host cell, or, if from the same source, is modified from its original form.

As used herein, an "instructional material" includes a publication, a recording, a diagram, or any other medium of expression which can be used to communicate the usefulness of a compound, composition, vector, or system of the invention in the kit. Optionally, or alternately, the instructional material can describe one or more methods of modulating expression of a gene product using a compound, composition, vector, or system of the invention in the kit. The instructional material of the kit of the invention can, for example, be affixed to a container which contains the identified compound, composition, vector, or delivery system of the invention or be shipped together with a container which contains the identified compound, composition, vector, or system. Alternatively, the instructional material can be shipped separately from the container with the intention that the instructional material and the kit be used cooperatively by the recipient.

"Promoter" is a nucleic acid sequence that acts as a signal sequence necessary to initiate transcription of a gene.

As used herein, the term "bee" is defined as any of several winged, hairy-bodied, usually stinging insects of the superfamily Apoidea in the order Hymenoptera, including both solitary and social species and characterized by sucking and chewing mouthparts for gathering nectar and pollen. Exemplary bee species include, but are not limited to species in the genera *Apis, Bombus, Trigona, Osmia* and the like. In one embodiment, bees include, but are not limited to bumblebees (*Bombus terrestris, Bombus impatiens*, or other *Bombus* species) and honeybees (*Apis mellifera* or *Apis cerana*).

As used herein, the term "colony" is defined as a population of dozens to typically several tens of thousand honeybees that cooperate in nest building, food collection, and brood rearing. A colony normally has a single queen, the remainder of the bees being either "workers" (females) or "drones" (males). The social structure of the colony is maintained by the queen and workers and depends on an effective system of communication. Division of labor within the worker caste primarily depends on the age of the bee but varies with the needs of the colony. Reproduction and colony strength depend on the queen, the quantity of food stores, and the size of the worker force. Honeybees can also be subdivided into the categories of "hive bees", usually for the first part of a workers lifetime, during which the "hive bee" performs tasks within the hive, and "forager bee", during the latter part of the bee's lifetime, during which the "forager" locates and collects pollen and nectar from outside the hive, and brings the nectar or pollen into the hive for consumption and storage.

As used herein, the term "susceptibility" is defined as the ability of a bee or bee colony to become infested or infected by and/or support proliferation of a pathogen, including, but not limited to, degree of infection, severity of symptoms, infectivity to other individuals (contagion), and the like. Susceptibility can be assessed, for example, by monitoring infectivity, presence of symptoms, such as, but not limited to, hunger, vitality, flight range, etc, presence of pathogenic organisms, mortality or time course of a disease in an individual bee or bee population following a challenge with the pathogen.

As used herein, the terms "bee disease" or "bee colony disease" are defined as undesirable changes in the behavior, physiology, morphology, reproductive fitness, economic value, viability, honey production, pollination capability, resistance to infection and/or infestation of a bee, a population of bees and/or a bee colony, directly or indirectly resulting from contact with a parasite or a parasite-infected bee or other organism.

As used herein, the term "downregulating expression" is defined as causing, directly or indirectly, reduction in the transcription of a desired gene, reduction in the amount, stability or translatability of transcription products (e.g. RNA) of said gene, reduction in translation of the polypeptide(s) encoded by the desired gene and/or reduction in the amount, stability, or alteration of biochemical function of the polypeptides encoded by the desired gene, so as to reduce the amount or function of the gene products. Downregulating expression of a gene RNA can be monitored, for example, by direct detection of gene transcripts (for example, by PCR), by detection of polypeptide(s) encoded by the gene or bee RNA (for example, by Western blot or immunoprecipitation), by detection of biological activity of polypeptides encode by the gene (for example, catalytic activity, ligand binding, and the like), or by monitoring changes in a cell or organism resulting from reduction in expression of a desired gene or RNA.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

The term "operably linked", as used in reference to a regulatory sequence and a structural nucleotide sequence, means that the regulatory sequence causes regulated expression of the linked structural nucleotide sequence. "Regulatory sequences" or "control elements" refer to nucleotide sequences located upstream, within, or downstream of a structural nucleotide sequence, and which influence the timing and level or amount of transcription, RNA processing or stability, or translation of the associated structural nucleotide sequence. Regulatory sequences may include promoters, translation leader sequences, introns, enhancers, stem-loop structures, repressor binding sequences, termination sequences, pausing sequences, polyadenylation recognition sequences, and the like.

As used herein, the term "RNA silencing agent" refers to an RNA which is capable of inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference commonly refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse eukaryotic species, including plants and animals. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

The term "siRNA" refers to small inhibitory RNA duplexes (generally between 18-30 basepairs, between 19 and 25 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop.

The terms "subject," "individual," and the like are used interchangeably herein, and refer to any animal, or cells thereof whether in vitro or in situ, amenable to the methods described herein. In certain non-limiting embodiments, subject or individual is a bee.

"Sample" or "biological sample" as used herein means a biological material isolated from a subject. The biological sample may comprise cellular and/or non-cellular material obtained from the subject. One example of a biological sample is a tissue sample.

According to one embodiment of the present disclosure, the nucleic acid in the expression cassette is capable of causing cleavage and/or degradation of a target polynucleotide sequence. As used herein, the phrases "target" or "target polynucleotide sequence" refer to any sequence present in a target cell (e.g., viral or microbial pathogen), whether naturally occurring sequence or a heterologous sequence present due to an intracellular or extracellular pathogenic infection or a disease, which polynucleotide sequence has a function that is desired to be reduced or inhibited. The target sequence may be a coding sequence, that is, it is translated to express a protein or a functional fragment thereof. Alternatively, the target sequence may be non-coding, but may have a regulatory function, or it may be without any known function.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The term "gene" is intended to include any target sequence intended to be "silenced", whether or not transcribed and/or translated, including regulatory sequences, such as promoters, enhancers and other non-coding sequences.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

In one embodiment, the present invention relates to a method for the production of an encoded molecule in an arthropod in vivo, comprising administering a genetically engineered bacterium to the arthropod, wherein the genetically engineered bacterium comprises a nucleic acid for expression of the gene encoded molecule. Therefore, in various embodiments the invention relates to nucleic acid molecules for expression of an encoded molecule, engineered bacteria comprising the nucleic acid molecules, arthropods comprising the engineered bacteria, and methods of use of the nucleic acid molecules and engineered bacteria to treat or prevent a disease or disorder of the arthropod. In one embodiment, the invention provides compositions and methods of using engineered bacteria to deliver nucleic acid molecules to insects for therapeutic purposes. In one embodiment, the invention provides compositions and methods of using engineered bacteria to deliver nucleic acid molecules to insects for purposes of modulating at least one of the level or activity of a gene, the level or activity of a protein or a behavior of the insect. Exemplary behaviors that can be modified according to the invention include, but are not limited to, foraging behavior and aggression. In one embodiment, the invention provides compositions and methods of using engineered bacteria to deliver nucleic acid molecules to insects for purposes of killing or otherwise impairing the insect. In one embodiment, the invention provides compositions and methods of using engineered bacteria to deliver nucleic acid molecules to insects to harm or to kill a pathogen or parasite of the insect through expression of a nucleic acid molecule that is harmful for the pathogen or parasite of the insect.

In some embodiments, the invention relates to methods of use of the engineered bacteria to treat or prevent a disease or disorder of a bee or colony of bees. In one embodiment, the disease or disorder is associated with a bee or bee colony parasite or pathogen.

Compositions

In one embodiment, the invention provides nucleic acid molecules for expression of a heterologous protein or polypeptide. In certain aspects, the heterologous polypeptide is a polypeptide that improves the health of a host insect. In one embodiment, the heterologous polypeptide is a pesticide-degrading polypeptide or a cytochrome.

In one embodiment, the invention provides nucleic acid molecules for expression of a modulator of a gene or protein of interest. Consequently, in the context of the present invention, the term "nucleic acid molecule" refers to a DNA or RNA molecule. DNA is understood as double-stranded deoxyribonucleic acid molecules. These may be linear or circular. Exemplary RNA molecules that can be encoded by the nucleic acid molecules of the invention, include, but are not limited to RNAi, dsRNA, siRNA, shRNA, miRNA and short guide RNA (sgRNA). In one embodiment, the encoded RNA molecule functions as an inhibitor of a target RNA. In one embodiment, the target RNA is an RNA of a pathogen or other organism that may harm the host insect. In one embodiment, the target RNA is an RNA of the host insect.

In specific aspects, the modulator is an inhibitory nucleic acid. In particular aspects, the inhibitory nucleic acid comprises an antisense DNA. In some aspects, the inhibitory nucleic acid is a dsRNA, siRNA, shRNA, sgRNA, or miRNA. The nucleic acid may be at least 15 base pairs in length, such as 19 to 25 base pairs in length. In other aspects, the nucleic acid is longer in length, such as at least 30 base pairs.

An RNAi construct is understood as a double-stranded RNA that works in accordance with the principle of an interfering RNA. It is known in the state of the art how RNAi constructs have to be designed that degrade target RNA (Voorhoeve et al. (2003). "Knockdown stands up". Trends Biotechnol. 21 (1): 2-4; Henschel A, Buchholz F, Habermann B (2004). "DEQOR: a web-based tool for the design and quality control of siRNAs". Nucleic Acids Res 32 (Web Sever issue): Wl 13-20). In this context, it relates to genes that encode for double-stranded RNA. In particular, the RNAi construct may encode for a dsRNA (double-stranded RNA) against an organism that harms the insect. In certain cases, the inhibitory nucleic acid can be targeted to an insect gene, such a bee gene. For example, insect genes can be targeted to improve the health or alter the development of a host insect. For example, vitellogenin can be targeted to alter foraging behavior, and thus modulate pollinator effectiveness.

The nucleic acid may be (i) plasmid DNA, (ii) linear DNA, (iii) circular DNA, (iv) single stranded DNA, (v) RNA, (vi) non natural DNA like molecules or (vii) a hybrid formed out of any of these molecules. These molecules are known in the art (see Sambrook and Russel, 2001). In one embodiment, the nucleic acid molecule is a broad-host-range vector. In one embodiment, the nucleic acid molecule is integrated into the bacterial genomic DNA.

Broad Host Vector

In one embodiment, at least one nucleic acid molecule to be expressed is cloned into a broad-host-range vector backbone. Therefore, in one embodiment, the invention provides broad host vectors for use in the generation of genetically modified bacteria for expression of a gene product. The broad host vectors of the invention may comprise at least one of: a broad-host-range promoter, an antibiotic resistance cassette, an oriT sequence for delivery into recipient cells via conjugation, a ribosome binding site, an origin of replication, a bacterial terminator, at least one nucleic acid sequence for expression, and a sequence that encodes for a detectable marker.

Promoters are operably linked with those encoding sequences of which they initiate transcription. The encoding sequences may encode for RNA constructs, peptides or proteins. Exemplary promoters are promoters that are active in a broad range of cells including, but not limited to, CMV promoter, TK promoter, PA1, PA2, and PA3 from bacteriophage T7, cp12b, cp18, cp32, cp6, and cp25 promoters, and SV40. In one embodiment, the promoter is inducible. An exemplary inducible promoter includes a modified CP25 promoter with lacO sites (cp25 (lacO); SEQ ID NO:12).

Generally, a promoter of the invention is understood to enable the transcription of DNA sequences in genetically engineered bacteria. The particular promoter sequence will depend on the bacteria in which the gene product is to be expressed. In this context, a number of DNAs or vectors could be cloned that present a combination of different promoters having the gene sequence encoding for the desired gene product or a reporter such as GFP.

In exemplary embodiments, the broad host range vector comprises the RSF 1010 origin of replication and further comprises at least one heterologous nucleic acid sequence under the control of one or more (e.g., 2 or 3) broad host range promoters, such as PA1, PA2, PA3, cp12b, cp18, cp32, cp6, cp25 and cp25 (lacO). In one embodiment, the nucleic acid molecule of the invention comprises paired, convergent transcriptional promoters on a broad range vector. Exemplary pairs of transcriptional promoters that can be included on a nucleic acid molecule (e.g., for the generation of dsRNA molecules) include, but are not limited to at least two of PA1, PA2, PA3, cp12b, cp18, cp32, cp6, cp25 and cp25 (lacO). Exemplary, paired convergent transcriptional promoters include, but are not limited to, paired convergent cp25 promoters, paired convergent cp6 promoters, paired convergent cp18 promoters and paired convergent cp25 (lacO) promoters.

In one embodiment, the origin of replication is selected based on the bacterial species to be engineered to express the broad range vector. Origins of replication that can be included in the broad-range-vector of the invention include, but are not limited to, the RSF1010 plasmid origin of replication, the pBBR1 plasmid origin of replication, the RK2 plasmid origin of replication, the RP4 plasmid origin of replication and the pAMβ1 plasmid origin of replication.

Furthermore, the nucleic acid molecules of the invention may also comprise enhancers. Enhancers may enhance the transcription initiation of a promoter, while they are not directly attached to the sequence of the promoter or the encoding sequence. Enhancers may be located far away or even on another DNA. Preferably, they are located on the same DNA as the promoter and the encoding sequence.

Toolkit for Modular Assembly of Broad-Host-Range Plasmids

In one embodiment, the invention provides one or more plasmids comprising genetic parts for the modular construction of vectors of the invention. In one embodiment, one or more plasmids comprises at least one of a broad-host-range promoter, an antibiotic resistance cassette, an oriT sequence for delivery into recipient cells via conjugation, a ribosome binding site, an origin of replication, a bacterial terminator, at least one nucleic acid sequence for expression, and a sequence that encodes for a detectable marker.

In one embodiment, the toolkit comprises a plasmid containing a promoter sequence for use in generating a vector of the invention. In one embodiment, the plasmid further comprises a ribosome binding site (RBS). Promoter sequences that may be included in a toolkit plasmid of the invention include, but are not limited to, SEQ ID NO:12, SEQ ID NO:37, SEQ ID NO:38, SEQ ID NO:39, SEQ ID NO:40, SEQ ID NO: 41, SEQ ID NO:42; SEQ ID NO:43, SEQ ID NO:44, and SEQ ID NO:45. Exemplary plasmids comprising a promoter sequence for use in generating a vector of the invention include, but are not limited to, SEQ ID NO:51, SEQ ID NO:52, SEQ ID NO:53, SEQ ID NO:54, SEQ ID NO:55, SEQ ID NO:56, SEQ ID NO:57, SEQ ID NO:58 and SEQ ID NO:59.

In one embodiment, the toolkit comprises a plasmid containing a reverse promoter sequence for use in generating a vector of the invention. In one embodiment, the plasmid further comprises a ribosome binding site (RBS). An exemplary reverse promoter sequence that may be included in a toolkit plasmid of the invention is set forth in SEQ ID NO:46. An exemplary plasmid comprising a reverse promoter sequence for use in generating a vector of the invention is SEQ ID NO:60.

In one embodiment, the toolkit comprises a plasmid containing a coding sequence for use in generating a vector of the invention. Coding sequences that may be included in a toolkit plasmid of the invention include, but are not limited to, a coding sequence encoding a sgRNA, dsRNA, siRNA, shRNA, miRNA, protein, or peptide. In one embodiment, the coding sequence encodes dCas9. An exemplary dCas9 coding sequence that may be included in a toolkit plasmid of the invention is set forth in SEQ ID NO:47. An exemplary plasmid comprising a coding sequence encoding dCas9 for use in generating a vector of the invention is SEQ ID NO:65. Exemplary plasmids comprising coding sequences for T7 RNA Polymerase, LacI repressor, GFP optim-1, Nanoluc, E2-Crimson and Kanamycin Resistance are provided as SEQ ID NO:61, SEQ ID NO:62, SEQ ID NO:63, SEQ ID NO:64, SEQ ID NO:67 and SEQ ID NO:68 respectively.

In one embodiment, the toolkit comprises a plasmid containing a terminator sequence for use in generating a vector of the invention. Terminator sequences that may be included in a toolkit plasmid of the invention include, but are not limited to, rpoC, BBa_B0015 and T7 terminators. Exemplary terminator coding sequences that may be included in a toolkit plasmid of the invention are set forth in SEQ ID NO:48, SEQ ID NO:49 and SEQ ID NO:50. Exemplary plasmids comprising a terminator sequence for use in generating a vector of the invention include, but are not limited to, SEQ ID NO:69, SEQ ID NO:70 and SEQ ID NO:71.

In one embodiment, the toolkit comprises a plasmid containing a repressor sequence for use in generating a vector of the invention. An exemplary plasmid comprising a repressor sequence for use in generating a vector of the invention is SEQ ID NO:66.

In one embodiment, the toolkit comprises a plasmid containing an origin of replication sequence for use in generating a vector of the invention. Origin of replication sequences that may be included in a toolkit plasmid of the invention include, but are not limited to, RSF1010 and R6k. Exemplary plasmids comprising an origin of replication sequence for use in generating a vector of the invention include, but are not limited to, SEQ ID NO:401, SEQ ID NO:402, SEQ ID NO:403 and SEQ ID NO:11.

Inducible System

In one embodiment, the invention provides an inducible system for inducible expression of a gene product in bacteria. In one embodiment, the inducible system of the invention comprises lacI driven by the CP25 promoter, and a cp25 (lacO) promoter (SEQ ID NO:12) operably linked to a nucleic acid sequence to be expressed. In one embodiment, the inducible system comprises lacI driven by the CP25 promoter, T7 RNAP under control of the inducible lac promoter, and a T7 promoter with lacO sites operably linked to a nucleic acid sequence to be expressed. In one embodiment, the inducible system is on a single plasmid or vector. Alternatively, the inducible plasmid system may be on two or more plasmids or vectors.

Vectors for Integration into the Bacterial Genome

In one embodiment, the vector of the invention is capable of integrating into the genome of a target bacterial species. In one embodiment, the vector may comprise homology arms flanking at least one of a broad-host-range promoter, an antibiotic resistance cassette, a ribosome binding site, a bacterial terminator, a nucleic acid sequence for expression, and a sequence that encodes for a detectable marker. In one embodiment, a homology arm comprises at least 100 bp, at least 200 bp, at least 300 bp, at least 400 bp, at least 500 bp, at least 600 bp, at least 700 bp, at least 800 bp, at least 900 bp, at least 1000 bp, at least 1100 bp, at least 1200 bp, at least 1300 bp, at least 1400 bp, or at least 1500 bp having at least 90%, at least 91%, at least 92%, at least 93%, at least 94%, at least 95%, at least 96%, at least 97%, at least 98%, at least 99% or 100% sequence identity to a target genomic DNA sequence. Alternatively the vector that is capable of integrating into the genome of a target bacterial species may be integrated using any method that is known in the art, including, but not limited to, lambda/red recombination, and may therefore comprises one or more elements allowing for the integration of the vector or selection or counter selection of bacteria comprising the integrated vector.

In one embodiment, the vector for integration comprises an origin of replication of a suicide plasmid that prevents plasmid replication in the target bacterial species. An exemplary suicide plasmid origin that can be used on a vector for integration includes, but is not limited to, the R6K plasmid origin of replication.

Nucleic Acid Sequences for Expression

In one embodiment, the broad-host-range vector of the invention comprises at least one nucleic acid sequence to be expressed. In one embodiment, the nucleic acid sequence expresses a RNA, protein or peptide. In one embodiment the nucleic acid sequence encodes a therapeutic molecule. For example, in various embodiments, the nucleic acid sequence encodes a pesticide degrading polypeptide or a cytochrome, or encodes an enzyme in a biosynthetic pathway producing neuro-active molecules that affect behaviors such as those determining aggression or pollinator effectiveness.

In one embodiment, the nucleic acid sequence to be expressed is a modulator of (e.g., an inhibitor or activator) of a target gene or gene product. In various embodiments, the present invention includes compositions for modulating the level or activity of a target gene or gene product in a subject, a cell, a tissue, or an organ in need thereof. In various embodiments, the compositions of the invention modulate the amount or activity of a target polypeptide, the amount or activity of a target protein, the amount or activity of a target mRNA. In one embodiment, the compositions of the invention modulate the amount or activity of a target polypeptide, the amount or activity of a target protein, the amount or activity of a target mRNA in an insect. In one embodiment, the compositions of the invention modulate the amount or activity of a target polypeptide, the amount or activity of a target protein, the amount or activity of a target mRNA in a pathogen, or parasite of an insect.

Activators

In one embodiment, the nucleic acid molecules and engineered bacteria of the invention can be used to activate or increase the levels of expression or activity of a target gene or protein in a subject. Therefore, in one embodiment, the invention relates to nucleic acid molecules encoding, a protein, a recombinant polypeptide, an active polypeptide fragment, or combinations thereof, which function to increase, or activate, the expression or activity of a target gene or protein. It will be understood by one skilled in the art, based upon the disclosure provided herein, that an increase in the level of a target gene or protein encompasses the increase in gene expression, including transcription, translation, or both. The skilled artisan will also appreciate, once armed with the teachings of the present invention, that an increase in the level of a protein includes an increase in protein activity (e.g., enzymatic activity, receptor binding activity, etc.). Thus, increasing the level or activity of a target gene or protein includes, but is not limited to, increasing the amount of polypeptide, increasing transcription, translation, or both, of a nucleic acid encoding a target polypeptide; and it also includes increasing any activity of a target polypeptide as well.

Examples of host proteins for which it would be beneficial to have increased expression using the methods of the invention include, but are not limited to, immune system proteins (e.g., Dorsal, argonaut (ago2), relish, and proteins in the toll and imd pathways) conferring greater disease resistance or enzymes in pathways producing neuro-active molecules that affect behaviors such as those determining aggression or pollinator effectiveness.

Inhibitors

In various embodiments, the modulator of the invention comprises an inhibitor of a target gene or protein. In one embodiment, the inhibitor of the invention decreases the amount of polypeptide, the amount of mRNA, the amount of activity, or a combination thereof, of the target gene or protein. Exemplary target genes that can be inhibited according to the methods of the invention include, but are not limited to, TOM70, TIM22, TOM40, Imp2, mitochondrial Hsp70, ATM1-ABC transporter proteins, Frataxin, Ferredoxin, ERV1, ferredoxin, NADPH oxido-reductase [FNR], pyruvate dehydrogenase α subunit, pyruvate dehydrogenase β subunit, mitochondrial glycerol-3-phosphate dehydrogenase (mtG3PDH), manganese-containing superoxide dismutase (MnSOD), DNAJ (Hsp70 interacting), Iron Sulfur cluster ISU1, Cystein desulfurase Nsf1, NAR1, RLI1, ATPase subunit A, RNA polymerase I, RNA polymerase III, Inhibitor of apoptosis (IAP), and FAS apoptotic.

It will be understood by one skilled in the art, based upon the disclosure provided herein, that a decrease in the level of a target gene or protein encompasses the decrease in the expression, including transcription, translation, or both. The skilled artisan will also appreciate, once armed with the teachings of the present invention, that a decrease in the level of a target protein includes a decrease in the activity of the target protein. Thus, decrease in the level or activity of a target protein includes, but is not limited to, decreasing the amount of polypeptide, and decreasing transcription, translation, or both, of a nucleic acid encoding a target protein; and it also includes decreasing any activity of the target protein as well.

In one embodiment, the invention provides a generic concept for inhibiting an essential gene of a virus or parasite of a bee. In one embodiment, the inhibitor is selected from the group consisting of a small interfering RNA (siRNA), a microRNA, an antisense nucleic acid, and a ribozyme.

One skilled in the art will appreciate, based on the disclosure provided herein, that one way to decrease the mRNA and/or protein levels of a target protein in a cell is by reducing or inhibiting expression of the nucleic acid encoding the target protein. Thus, the protein level can be decreased using a molecule or compound that inhibits or reduces gene expression such as, for example, dsRNA, siRNA, an antisense molecule or a ribozyme. However, the invention should not be limited to these examples.

In one embodiment, siRNA is used to decrease the level of a target gene or protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19): 306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, Pa. (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing protein levels using RNAi technology.

In other related aspects, the invention includes a nucleic acid encoding an inhibitor, wherein an inhibitor such as a dsRNA, siRNA or antisense molecule, inhibits a target gene, operably linked to a nucleic acid comprising a promoter/regulatory sequence such that the nucleic acid is preferably capable of directing expression of the dsRNA, siRNA or antisense molecule encoded by the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York) and as described elsewhere herein.

In another aspect, the invention includes a vector comprising an siRNA or antisense polynucleotide. The dsRNA, siRNA or antisense polynucleotide can be cloned into a number of types of vectors as described elsewhere herein. For expression of the dsRNA, siRNA or antisense polynucleotide, at least one module in each promoter functions to position the start site for RNA synthesis.

In order to assess the expression of the dsRNA, siRNA or antisense polynucleotide, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

In one embodiment of the invention, an antisense nucleic acid sequence which is expressed by a plasmid vector is used to inhibit a target gene or protein. The antisense expressing vector is used to transfect a bacterial cell to generate a genetically engineered bacteria of the invention.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Compositions and methods for the synthesis and expression of antisense nucleic acids are as described elsewhere herein.

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Modified Cas9 System

In one embodiment, the invention provides a modified CRISPR system for expression of a sgRNA in bacteria, wherein one or more components of the CRISPR system is encoded on a broad-host-range vector of the invention. In one embodiment, the CRISPR system of the invention comprises an endonuclease enzyme (e.g., Cas9) which binds to a target nucleic acid sequence via a sgRNA, to modulate the target sequence. In one embodiment, the CRISPR system of the invention can be used to modulate a target sequence in an insect. In one embodiment, the CRISPR system of the invention can be used to modulate a target sequence in a parasite or pathogen of an insect.

In some embodiments, the Cas9 enzyme comprises catalytically dead Cas9 (dCas9) or a homolog, an ortholog or mimic thereof. Orthologs of Cas9 may be from a genus which includes but is not limited to *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma* and *Campylobacter*. Catalytically dead Cas9 mimics include, but are not limited to, proteins or peptides which are capable of interaction with an sgRNA to target the CRISPR fusion construct to a site of interest. Catalytically dead or inactive Cas9, and homologs, orthologs or mimics thereof are referred to herein collectively as "dCas9."

In one embodiment, dCas9 lacks cleavage or nickase activity. In one embodiment dCas9, or an ortholog thereof, has a diminished nuclease activity of at least 60%, 70%, 80%, 90%, 91%, 92%, 93%, 94%, 95%, 96, 97%, 98%, 99% or 100% as compared with a wild-type Cas9 enzyme or ortholog. In one embodiment, the CRISPR fusion constructs comprising dCas9 serve as DNA-binding proteins with very little or no catalytic activity. In one embodiment, a dCas9 comprises one or more mutations in its catalytic domain which disrupt or inactivate the nuclease activity of the Cas9 enzyme.

Guide RNAs

The present system may be used with any short guide RNA (sgRNA.) In embodiments of the invention the terms guide sequence and guide RNA are used interchangeably. In general, a guide sequence is any polynucleotide sequence having sufficient complementarity with a target polynucleotide sequence to hybridize with the target sequence and direct sequence-specific binding of a CRISPR complex to the target sequence, in some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustaiW, Clustal X, BLAT, Novoalign, ELAND (Illumina, San Diego, Calif.), SOAP, and Maq. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In some embodiments, the guide sequence is 10-30 nucleotides long. The ability of a guide sequence to direct sequence-specific binding of a CRISPR complex to a target sequence may be assessed by any suitable assay. For example, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence may be selected to target any target sequence. In one embodiment, the sgRNAs for use in the system of the invention hybridize to a target sequence in an insect administered the genetically engineered bacteria. In one embodiment, the sgRNAs for use in the system of the invention hybridize to a target sequence in a pathogen or a pest of an insect administered the genetically engineered bacteria.

Constructs Encoding Multiple Gene Products

In one embodiment, the compositions of the invention encode at least 1, at least 2, at least 3, at least 4, at least 5 or more than 5 gene products. In one embodiments, multiple gene products may be encoded on a single nucleic acid molecule. In an alternative embodiment, multiple gene products may be encoded on multiple nucleic acid molecules, for example, at least 1, at least 2, at least 3, at least 4, at least 5 or more than 5 gene products may be encoded on at least 1, at least 2, at least 3, at least 4, at least 5 or more than 5 nucleic acid molecules. In one embodiment, a single bacterial cell comprises multiple nucleic acid molecules encoding multiple gene products of the invention.

In one embodiment, the compositions of the invention comprise multiple genetically modified bacteria or populations thereof wherein each genetically modified bacteria or populations comprises at least one nucleic acid molecule encoding at least one inhibitor of the invention. Therefore, in various embodiments, the invention provides a composition comprising at least 1, at least 2, at least 3, at least 4, at least 5 or more than 5 genetically modified bacteria or populations comprising nucleic acid molecules encoding for at least 1, at least 2, at least 3, at least 4, at least 5 or more than 5 gene products of the invention. In one embodiment, multiple genetically modified bacterial populations are of the same bacterial species. In one embodiment, multiple genetically modified bacterial populations are of different bacterial species.

In one embodiment, multiple nucleic acid molecules encode multiple gene products of the same target gene or protein. In an alternative embodiment, multiple nucleic acid molecules encode gene products of the multiple target genes or proteins. Multiple target genes or proteins may be multiple targets in a single pathogen or parasite, or multiple targets in multiple pathogens or parasite. Therefore, in one embodiment, the invention provides a composition comprising multiple genetically encoded bacteria comprising multiple nucleic acid constructs for inhibiting at least 1, at least 2, at least 3, at least 4, at least 5 or more than 5 target genes or proteins. In one embodiment, the invention provides a composition comprising multiple genetically encoded bacteria comprising multiple nucleic acid constructs for inhibiting or modulating at least 1, at least 2, at least 3, at least 4, at least 5 or more than 5 target pathogens or parasites.

Genetically Modified Bacteria

In one embodiment, the invention provides genetically modified bacteria comprising a nucleic acid molecule for expression of a heterologous nucleic acid sequence. In one embodiment the present disclosure provides microbial compositions comprising one or more bacteria genetically engineered to express a heterologous nucleic acid. In one embodiment, the one or more bacteria are native to the microbiome of an arthropod. In one embodiment, the one or more bacteria are native to the microbiome of a bee. In some aspects, the one or more bacteria are *Snodgrassella alvi, Bartonella apis, Gilliamella apicola, Serratia marcescens* or *Parasaccharibacter apium*. In one embodiment, the one or more bacteria are bacterial species that can live in bee hive materials. In one embodiment, *Parasaccharibacter apium* or *Lactobacillus* sp. In some aspects, the composition comprises 2, 3, 4, or 5 genetically engineered bacterial species.

In one embodiment, one or more nucleic acid molecule for expression of a heterologous nucleic acid sequence is contained in the bacterial cell. In one embodiment, one or more nucleic acid molecule for expression of a heterologous nucleic acid sequence is integrated into the genome of said one or more bacteria. In certain aspects, the one or more bacteria express at least two heterologous nucleic acids.

Host Organisms

The methods of the present invention can be applied to all arthropods. The compositions and methods of the invention can be used for all purposes where the production of a gene encoded molecule in an arthropod is suitable and/or desirable. This includes the use of the method of the invention to generate a host arthropod, where at least one genetically modified bacteria for production of a gene encoded molecule has been administered to the host arthropod.

In one embodiment of the present invention, the arthropod may be, but is not limited, to an insect, an arachnid, a crustacean and a myriapodum. In one embodiment, the arthropod is an insect. Insects that can serve as hosts according to the methods of the invention include, but are not limited to, a holometabolic insect, a hemimetabolic insect, and an insect from the order Hymenoptera, Coleoptera or Orthoptera. Exemplary insects include, but are not limited to, a honey bee (*Apis mellifera*) and a small hive beetle (*Aethina tumida*). In another embodiment of the present invention, the arthropod is an arachnid, for example, a mite.

In some embodiments, the insect is a bee. As used herein, the term "bee" refers to both an adult bee and pupal cells thereof. According to one embodiment, the bee is in a hive. An adult bee is defined as any of several winged, hairy-bodied, usually stinging insects of the superfamily Apoidea in the order Hymenoptera, including both solitary and social species and characterized by sucking and chewing mouthparts for gathering nectar and pollen. Exemplary bee species include, but are not limited to, *Apis, Bombus, Trigona, Osmia* and the like. In one embodiment, bees include, but are not limited to bumblebees (*Bombus terrestris*), honeybees (*Apis mellifera*) (including foragers and hive bees) and *Apis* cerana.

According to one embodiment, the bee is part of a colony. The term "colony" refers to a population of bees comprising dozens to typically several tens of thousand bees that cooperate in nest building, food collection, and brood rearing. A colony normally has a single queen, the remainder of the bees being either "workers" (females) or "drones" (males). The social structure of the colony is maintained by the queen and workers and depends on an effective system of communication. Division of labor within the worker caste primarily depends on the age of the bee but varies with the needs of the colony. Reproduction and colony strength depend on the queen, the quantity of food stores, and the size of the worker force. Honeybees can also be subdivided into the categories of "hive bees", usually for the first part of a workers lifetime, during which the "hive bee" performs tasks within the hive, and "forager bee", during the latter part of the bee's lifetime, during which the "forager" locates and collects pollen and nectar from outside the hive, and brings the nectar or pollen into the hive for consumption and storage.

Formulations

In some embodiments, the composition is a bee-ingestible composition. In certain aspects, the bacteria are present as a live suspension or a lyophilized powder. The composition may be in solid form or liquid form, such as a sucrose solution or a corn syrup solution. In some aspects, the composition comprises protein and/or pollen. In additional aspects, the composition further comprises a carbohydrate or sugar supplement or other additive or excipient as described elsewhere herein.

Methods

The present invention also relates to the use of a genetically engineered bacteria comprising a nucleic acid encoding a molecule for use in a method for protecting an arthropod against pest influences, parasites or ectoparasites or for use in a method for treating an arthropod disease in an arthropod, wherein the genetically engineered bacteria is fed to the arthropod or is administered orally. All embodiments described above with respect to the method of the invention also apply to said use of the invention.

In one embodiment, there is provided a method for producing a genetically engineered bacterial species according to the composition of the embodiments (e.g., engineered bacteria) comprising transfecting said bacterial species with an expression cassette comprising at least one heterologous nucleic acid.

In one embodiment, there is provided a method for downregulating expression of a target gene product in an insect pathogen or parasite comprising administering an effective amount of one or more genetically engineered bacteria to a host insect, wherein said bacteria express an inhibitor of the target gene product. In some aspects, the target gene product is a pathogen or parasite-specific gene product, such as a virus- or mite-specific gene product. Parasites and pathogens that can be targeted using the methods of the invention include, but are not limited to, Acute Bee Paralysis Virus (ABPV), Kashmir Bee Virus (KBV), Israeli Acute Paralysis Virus (IAPV), *Nosema ceranae*, deformed wing virus, or *Varroa destructor* mite and other parasites or pathogens which infect insects.

In one embodiment, there is provided a method for downregulating expression of a target gene product in a target insect. In one embodiment, the method comprises administering an effective amount of one or more genetically engineered bacteria to a food source of a target insect, wherein said bacteria express a dsRNA complementary to a gene product of the target insect. In one embodiment, the target insect is a pest insect. In one embodiment, the target insect is a Small Hive Beetle, and a food source of the target insect is a bee hive.

In some aspects, the one or more genetically engineered bacteria are comprised in a composition of the embodiments described herein. In particular aspects, the one or more genetically engineered bacteria are selected from the group consisting of *Snodgrassella alvi, Bartonella apis, Gilliamella apicola, Serratia marcescens, Parasaccharibacter apium*, and *Lactobacillus* sp.

In one embodiment, there is provided a method for expression of a heterologous nucleic acid sequence in an arthropod. In one embodiment, the method comprises administering to the arthropod a composition comprising one or more genetically modified bacteria, wherein the one or more genetically modified bacteria comprise a vector for expression of a heterologous nucleic acid sequence. In one embodiment, one or more bacteria is native to the host arthropod microbiome and as such is able to persist in the gut of the arthropod for at least one day, at least two days, at least three days, at least 4 days, at least 5 days, at least 6 days, at least 7 days, at least 8 days, at least 9 days, at least 10 days, at least 11 days, at least 12 days, at least 13 days, at least 14 days, at least 15 days, or for more than 15 days. In one embodiment, the one or more bacteria persists in the gut of the arthropod for the duration of the arthropod's lifespan.

In a further embodiment, there is provided a method for reducing the susceptibility of a bee to a disease or disorder associated with a pathogen or parasite. In one embodiment, the disease or disorder is Colony Collapse Disorder (CCD). Therefore, in one embodiment, the invention provides a method of treating or preventing CCD comprising administering an effective amount of one or more genetically engineered bacteria to a bee, or bee hive component, wherein said bacteria express a dsRNA complementary to a pathogen or parasite-specific gene product.

In another embodiment, there is provided method for reducing the susceptibility of a bee to an infection comprising feeding the bee an effective amount of one or more genetically engineered bacteria to said bee, wherein said bacteria express a dsRNA complementary to a pathogen or parasite-specific gene product.

In some aspects of the above embodiments, the pathogen or parasite is Acute Bee Paralysis Virus (ABPV), Kashmir Bee Virus (KBV), Israeli Acute Paralysis Virus (IAPV), *Nosema ceranae*, deformed wing virus, *Varroa destructor* mite, or Small Hive Beetle. In certain aspects, the *Nosema ceranae* is *N. cerana* or *N. apis*. In specific aspects, the pathogen or parasite-specific gene product is an mRNA encoding a *Nosema* mitosomal protein. In some aspects, the *Nosema* mitosomal protein is selected from the group consisting of TOM70, TIM22, TOM40, Imp2, mitochondrial Hsp70, ATM1-ABC transporter proteins, Frataxin, Ferredoxin, ERV1, ferredoxin, NADPH oxido-reductase [FNR], pyruvate dehydrogenase $\alpha$ subunit, pyruvate dehydrogenase $\beta$ subunit, mitochondrial glycerol-3-phosphate dehydrogenase (mtG3PDH), manganese-containing superoxide dismutase (MnSOD), DNAJ (Hsp70 interacting), Iron Sulfur cluster ISU1, Cystein desulfurase Nsf1, NAR1 and RLI1. In other aspects, the parasite-specific gene product is ATPase subunit A, RNA polymerase I, RNA polymerase III, Inhibitor of apoptosis (IAP), or FAS apoptotic. In certain aspects, the bacteria express at least two non-contiguous dsRNAs targeting a gene product of at least one of Acute Bee Paralysis Virus (ABPV), Kashmir Bee Virus (KBV), Israeli Acute Paralysis Virus (IAPV), *Nosema ceranae*, deformed wing virus, *Varroa destructor* mite, and/or Small Hive Beetle. In certain aspects, the bacteria express at least two non-contiguous dsRNAs targeting a gene product of at least two of Acute Bee Paralysis Virus (ABPV), Kashmir Bee Virus (KBV), Israeli Acute Paralysis Virus (IAPV), *Nosema ceranae*, deformed wing virus, *Varroa destructor* mite, and/or Small Hive Beetle.

In one embodiment, the agents of the present invention are used to prevent the *Varroa destructor* mite from living as a parasite on the bee, or larvae thereof. In one embodiment, the agents of the present invention are used to prevent the Small Hive Beetle from living as a parasite on the bee colony. Therefore, in one embodiment, the agents of the present invention are capable of down-regulating expression of a gene product of a *Varroa destructor* mite or Small Hive Beetle.

In one embodiment, the agents of the present invention are used to prevent a viral infection of the bee, or larvae thereof. Therefore, in one embodiment, the agents of the present invention are capable of down-regulating expression of a gene product of a viral gene.

As used herein, the phrase "gene product" refers to an RNA molecule or a protein. According to one embodiment, the targeted gene product is one which is essential for parasite viability, parasite reproduction, viral replication or viral pathogenicity. Down-regulation of such a gene product would typically result in killing of a parasite, extermination of the parasite population or reduced viral pathogenicity.

It will be appreciated that whilst the agents of the present invention are capable of downregulating expression of a gene product of a parasite or pathogen, it is preferable that they downregulate to a lesser extent expression of the gene product in other animals, such as the bee. Accordingly, the agents of the present invention must be able to distinguish between the target gene and the bee gene, down-regulating the former to a greater extent than the latter. According to another embodiment the agents of the present invention do not down-regulate the bee gene whatsoever. This may be effected by targeting a gene that is present or expressed in the target pathogen or parasite and not in the bee. Alternatively, the agents of the present invention may be targeted to parasite-specific sequences of a gene that is expressed both in the target parasite and in the bee.

According to one embodiment the agents of the present invention target segments of genes that are at least 100 bases long and do not carry any sequence longer than 19 bases that is entirely homologous to any bee-genome sequence or human-genome sequence.

Downregulating expression of a gene product can be monitored, for example, by direct detection of gene transcripts (for example, by PCR), by detection of polypeptide(s) encoded by the gene or bee pathogen RNA (for example, by Western blot or immunoprecipitation), by detection of biological activity of polypeptides encode by the gene (for example, catalytic activity, ligand binding, and the like), or by monitoring changes in the parasite or pathogen (for example, reduced proliferation, reduced virulence, reduced motility etc) and by testing bee infectivity/pathogenicity.

Downregulation of a target gene product can be effected on the genomic and/or the transcript level using a variety of agents which interfere with transcription and/or translation (e.g., RNA silencing agents, Ribozyme, DNAzyme and antisense).

According to one embodiment, the agent which downregulates expression of a target gene product is a polynucleotide agent, such as an RNA silencing agent. According to this embodiment, the polynucleotide agent is greater than 15 base pairs in length.

As used herein, the phrase "RNA silencing" refers to a group of regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene or bee pathogen RNA sequence. RNA silencing has been observed in many types of organisms, including plants, animals, and fungi.

In one embodiment of the present disclosure, synthesis of RNA silencing agents suitable for use with the present invention can be effected as follows. First, the pathogen polypeptide mRNA or other target sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (see Ambion® technical library 91/912 at the Ambion® website).

Second, potential target sites are compared to an appropriate genomic database (e.g., human, mouse, rat, insect, etc.) using any sequence alignment software, such as the BLAST software available from the NCBI server of the NIH. Putative target sites which exhibit significant homology to other coding sequences are filtered out. For example, host (e.g. bee) target sites can be filtered out in this manner.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene or sequence for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to host gene sequences, or non-relevant pathogen target sequences.

It will be appreciated that the dsRNA sequences target RNA transcripts complementary to DNA sequences of the targeted gene which are expressed in the parasite (transcribed into RNA), and that the actual complementation taking place in the RNAi pathways occurs following reduction of the dsRNA to smaller fragments by the RNAi enzymes.

It will be appreciated that since *Varroa* mites use their mouths to puncture the bee exoskeleton and feed on the bee's hemolymph, the present invention contemplates delivering the polynucleotide agents of the present invention to the bees via the genetically engineered bacteria, whereby they become presented in the bee's hemolymph thereby becoming available to the mite. Thus, according to another embodiment, the nucleic acid agents are delivered indirectly to the mites (e.g. via the bee). In this embodiment, the promoter of the nucleic acid construct is typically operational in bee gut bacterial cells.

In one embodiment said nucleic acid encodes an siRNA or an antisense RNA. In this case, the siRNA or antisense RNA molecule is produced in the arthropod by feeding the arthropod with the genetically engineered bacteria. In this context, the nucleic acid is preferably a vector encoding the siRNA and further containing promoter sequences enabling the production of the siRNA.

In one embodiment, of the present invention, the genetically engineered bacteria is fed to the arthropod. In principle, every feed can be used that is accepted by the arthropod to be fed. This includes any kind material that is consumed orally by the arthropods, independent on whether it is natural feed, agricultural feed or laboratory feed and independent on whether it is consumed naturally or is administered by means of technical devices or is taken up casually. In one embodiment, the feed that is used to induce the production of the gene encoded molecules in the arthropods is either a liquid feed comprising the genetically engineered bacteria, a dry feed mixed with a solution comprising the genetically engineered bacteria or a dry feed comprising the genetically engineered bacteria in any of these formulations.

As detailed herein, bee feeding is common practice amongst bee-keepers, for providing both nutritional and other, for example, supplemental needs. Bees typically feed on honey and pollen, but have been known to ingest non-natural feeds as well. Bees can be fed various foodstuffs including, but not limited to Wheast (a dairy yeast grown on cottage cheese), soybean flour, yeast (e.g. brewer's yeast, torula yeast) and yeast products products-fed singly or in combination and soybean flour fed as a dry mix or moist cake inside the hive or as a dry mix in open feeders outside the hive. Also useful is sugar, or a sugar syrup. The addition of 10 to 12 percent pollen to a supplement fed to bees improves palatability. The addition of 25 to 30 percent pollen improves the quality and quantity of essential nutrients that are required by bees for vital activity.

Cane or beet sugar, isomerized corn syrup, and type-50 sugar syrup are satisfactory substitutes for honey in the natural diet of honey bees. The last two can be supplied only as a liquid to bees.

Liquid feed can be supplied to bees inside the hive by, for example, any of the following methods: friction-top pail, combs within the brood chamber, division board feeder, boardman feeder, etc. Dry sugar may be fed by placing a pound or two on the inverted inner cover. A supply of water must be available to bees at all times. In one embodiment, pan or trays in which floating supports-such as wood chips, cork, or plastic sponge—are present are envisaged. Detailed descriptions of supplemental feeds for bees can be found in, for example, USDA publication by Standifer, et al 1977, entitled "Supplemental Feeding of Honey Bee Colonies" (USDA, Agriculture Information Bulletin No. 413).

All the bees in a hive are potentially susceptible to the pathogenic diseases detailed herein. Thus, according to some embodiments, the bees can be honeybees, forager bees, hive bees and the like.

Also provided is a method for reducing the susceptibility of a bee to a disease caused by pathogens, the method effected by feeding the bee on an effective amount of a nucleic acid or nucleic acid construct comprising a nucleic acid agent downregulating expression of a polypeptide of the bee pathogen and/or causing cleavage and/or degradation of a bee pathogen RNA. Methods for reducing the susceptibility of a bee colony or bee-hive to bee pathogens by feeding oligonucleotides and/or polynucleotides are envisaged. Thus, in some embodiments, the present invention can be used to benefit any numbers of bees, from a few in the hive, to the entire bee population within a hive and its surrounding area. It will be appreciated, that in addition to feeding of oligonucleotides and/or polynucleotides for reduction of the bee pathogen infection and infestation, enforcement of proper sanitation (for example, refraining from reuse of infested hives) can augment the effectiveness of treatment and prevention of infections.

Kits

The invention also includes a kit comprising a composition of the invention, for example, a kit comprising one or more plasmid comprising a genetic part for the modular construction of a vector for use in generating a genetically modified bacterium of the invention or a genetically modified bacterium comprising a nucleic acid molecule for expression of a heterologous gene product. In one embodiment, the kit may also comprise instructional material which describes, for instance, methods of generation of a vector of the invention, methods of generating a genetically engineered bacterium of the invention, or methods of administering a genetically engineered bacterium of the invention to a target arthropod.

I. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Microbiome Engineering in Honey Bee Gut

Several bacterial species including *Snodgrassella alvi, Bartonella apis, Gilliamella apicola*, and *Parasaccharibacter apium* from the bee gut were engineered to express heterologous genes. A broad host range plasmid pMMB67EH was used to express the heterologous gene. It was then confirmed that these modified bacteria can reestablish and be maintained in bees.

A variety of broad host range promoters were tested for their ability to express GFP in vitro in the various bacterial species. The promoters that were tested included PA1, PA2, PA3, and cp25 (FIG. 1). For *S. alvi*, all of the promoters tested resulted in similar expression of GFP. PA2, PA3, and cp25 resulted in higher GFP expression as compared to PA1 in *G. apicola*. Finally, PA1 was observed to have the highest expression of GFP in *B. apis*.

Figures 2A, 2B, 2C:
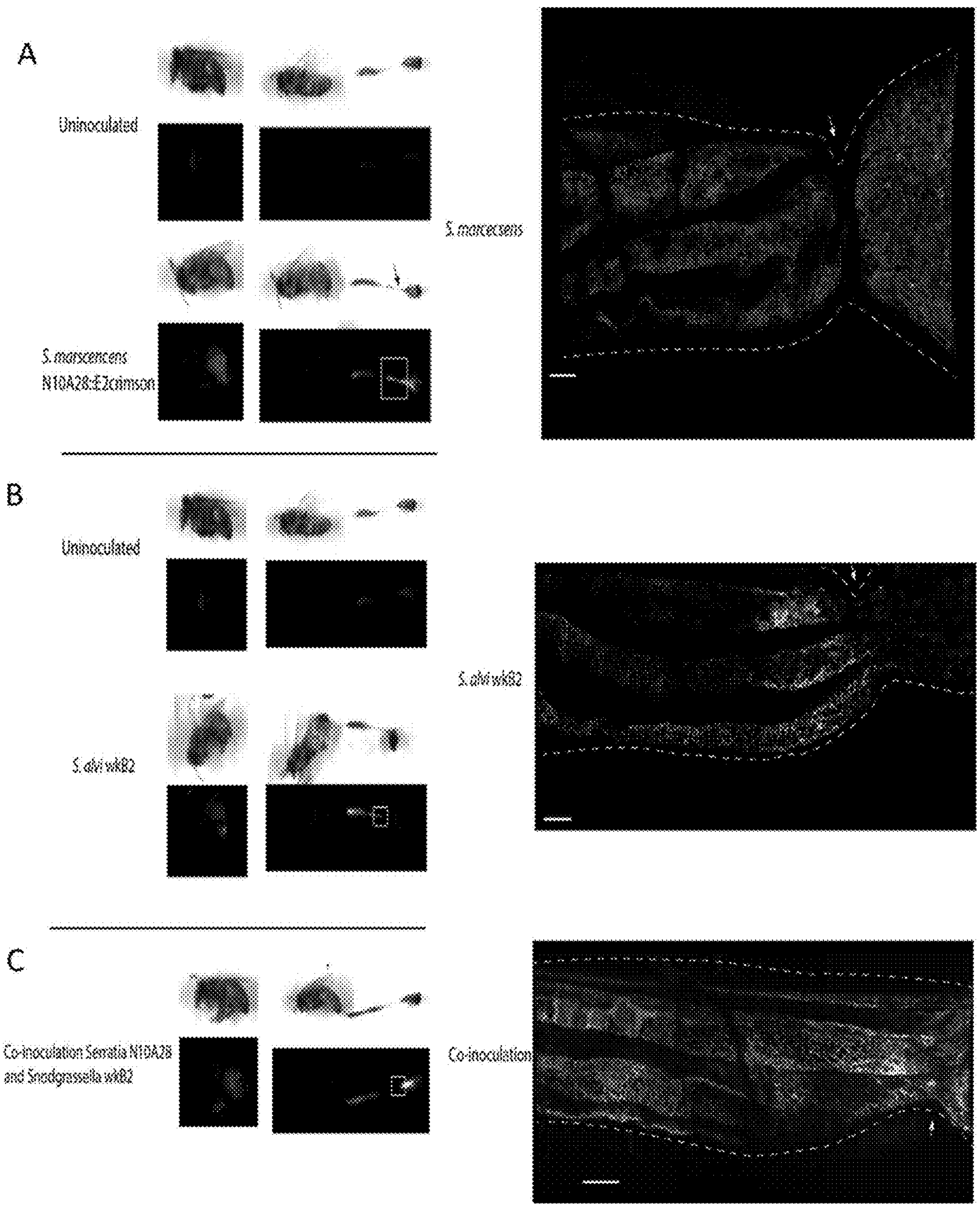
FIGS. 2A-2C: Fluorescent imaging of engineered bee gut bacteria colonizing the bee gut microbiome.

To determine if the modified bacteria could continue to function in the bee gut, the engineered strains *Snodgrassella alvi* and *Serratia marcescens* producing fluorescent proteins were inoculated into germ-free bees and the guts were fluorescently imaged 5 days later (FIG. 2). The control uninoculated bees showed no fluorescent signal. On the other hand, bees inoculated with either the *S. marcecsens* or *S. alvi* had expression of the fluorescent proteins. In addition, co-inoculation with both fluorescent strains resulted in expression of both fluorescent proteins.

Figure 3:
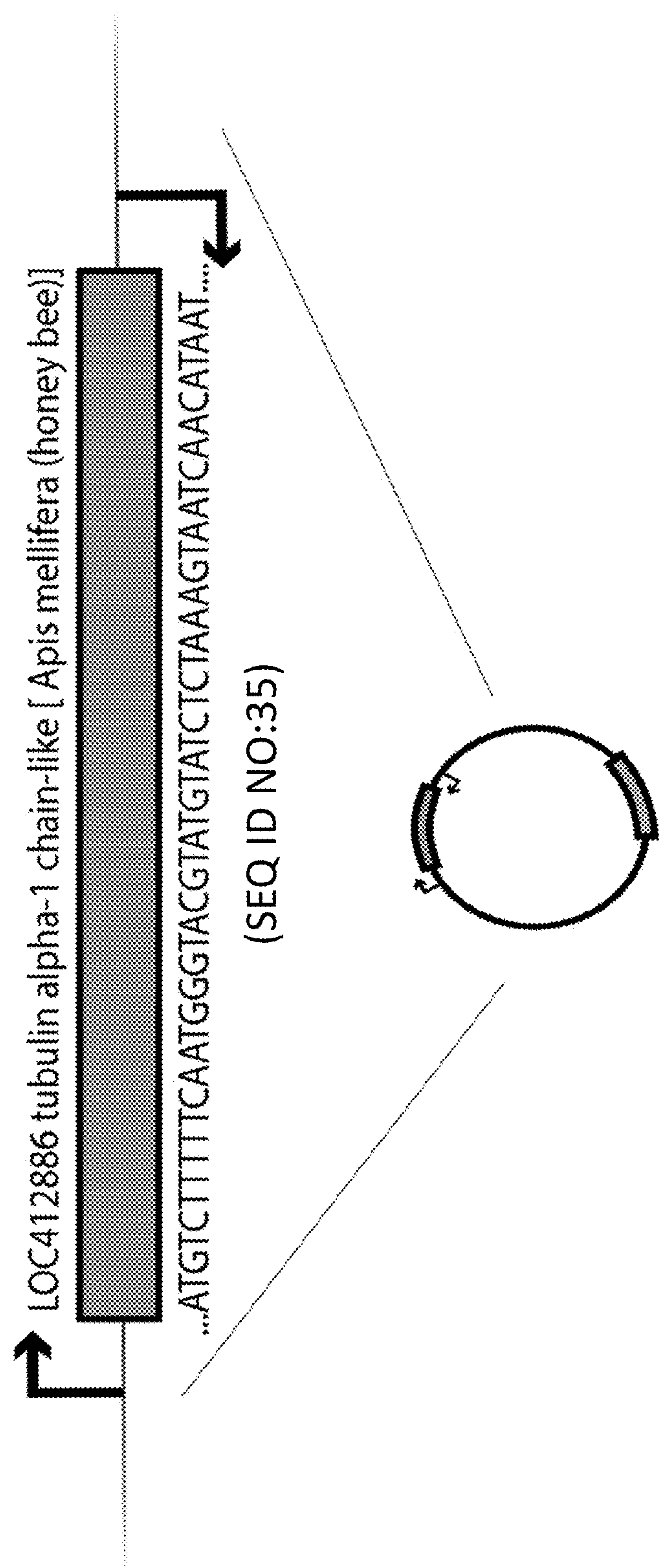
FIG. 3: Schematic of dsRNA-expressing broad-host-range construct.
Figure 4:
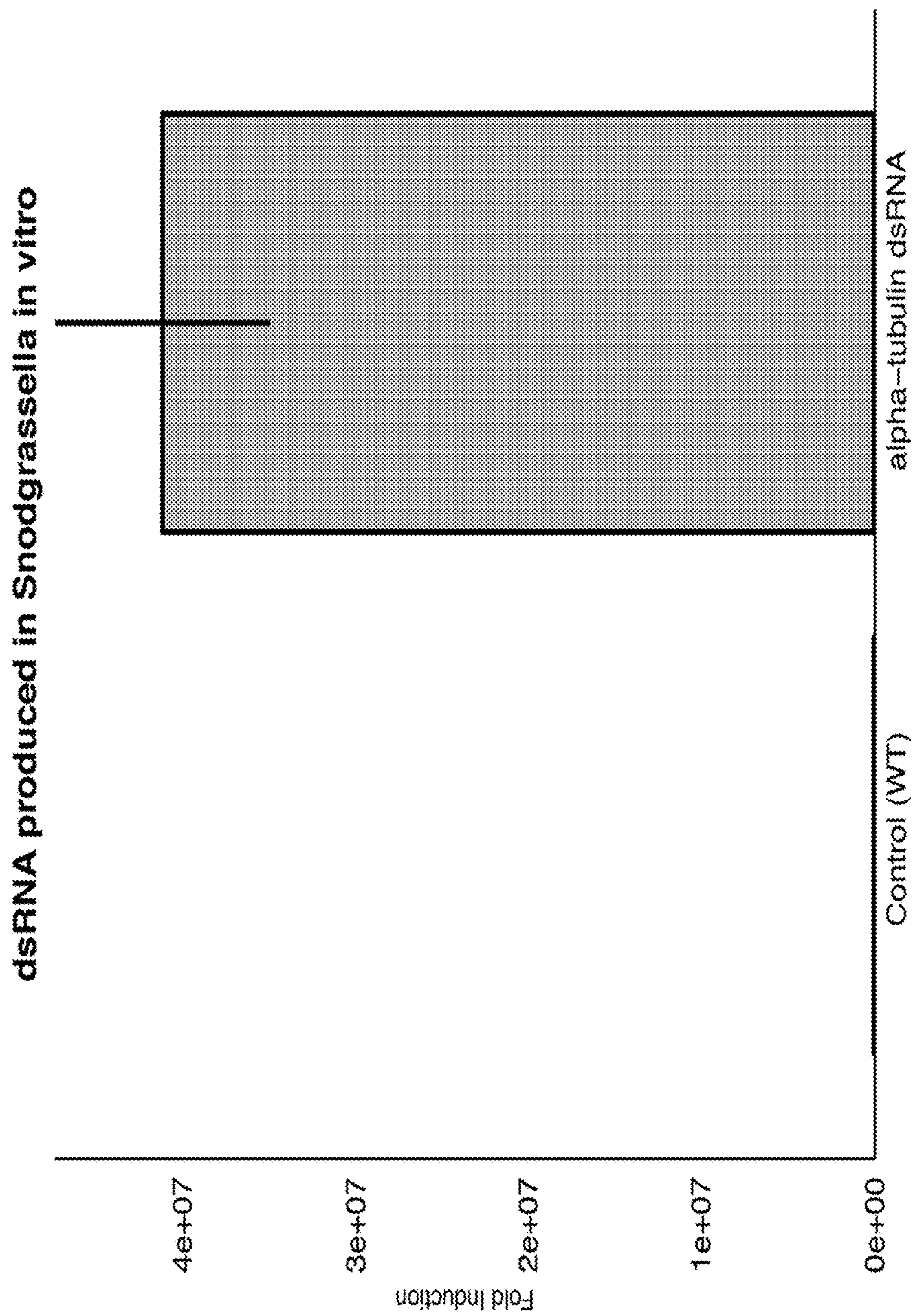
FIG. 4: In vitro production of dsRNA by engineered *S. alvi.*

In order to test the ability of the engineered bacterial species to produce dsRNA in honey bees, the broad host range backbone plasmid and the knowledge of promoter strength in bee gut species were used to produce a dsRNA-producing construct (FIG. 3). The construct has flanking broad range promoters driving RNA transcription of the tubulin alpha-1 chain-like gene (*Apis mellifera* (honey bee)). The *Snodgrassella alvi* wkB2 strain was used to produce dsRNA using the construct and was then grown in cultures in vitro for 48 hours. RNA was extracted, transcribed to cDNA, and qPCR was performed, normalizing to bacterial 16S copies (FIG. 4). The bacteria was found to produce dsRNA in vitro for alpha tubulin.

Figure 5:
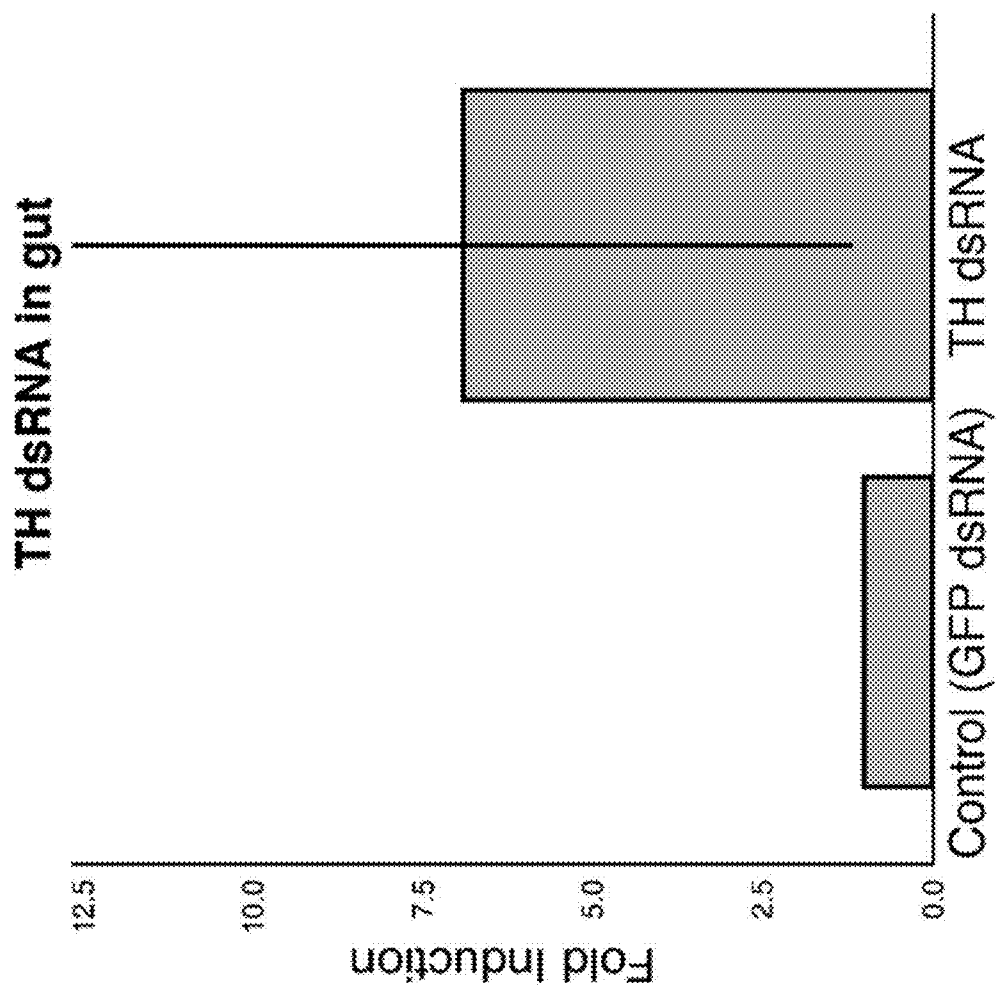
FIG. 5: In vivo production of dsRNA in the bee gut.

Next, it was determined whether the bacteria would produce dsRNA in vivo in bees. Bees were inoculated with *S. alvi* expressing Tyrosine Hydroxylase (TH) dsRNA or a GFP dsRNA control. After 6 days, guts were homogenized and RNA was extracted. Quantitative RT-PCR was used to assess the relative amount of TH RNA present in the gut compared to an actin control (FIG. 5).

Example 2—Induction of RNAi in Honey Bees

The broad-host-range backbone was used to build two dsRNA-producing constructs to test in vivo. In one construct, a dsRNA cassette targeting alpha-tubulin, an essential bee gene, was used. Downregulation of this essential gene by induction of an RNAi response should result in increased mortality. Newly emerged workers were colonized with *S.*

Figure 6:
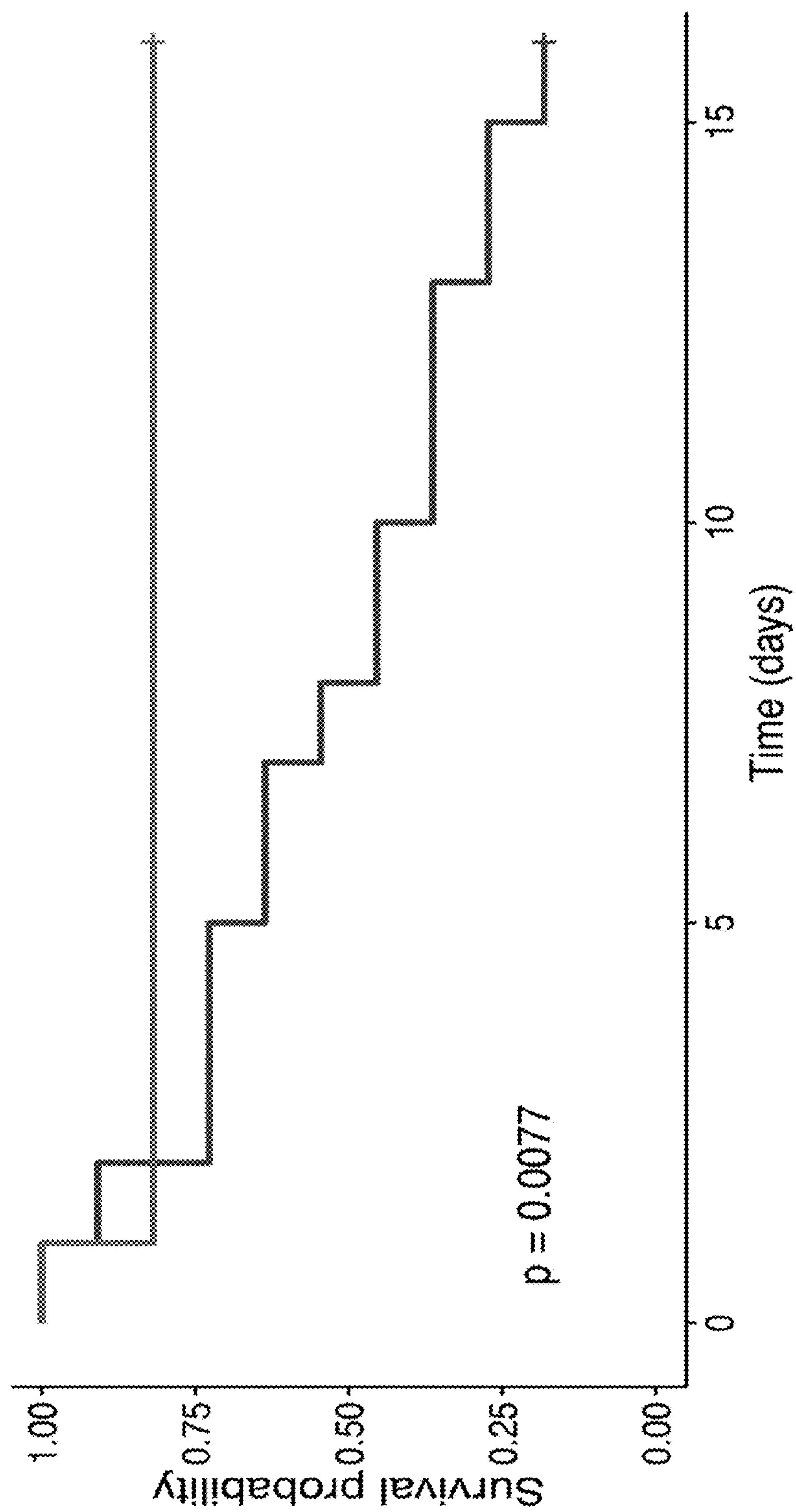
FIG. 6: dsRNA against essential honey bee gene alpha-tubulin increases mortality.

*alvi* wkB2 containing dsRNA constructs targeting alpha-tubulin or GFP-control. Survival was monitored daily (FIG. 6). The bees with dsRNA constructs targeting alpha tubulin were observed to have increased mortality. Thus, the microbe-produced dsRNA can induces RNAi in vivo in honey bees.

Figure 7:
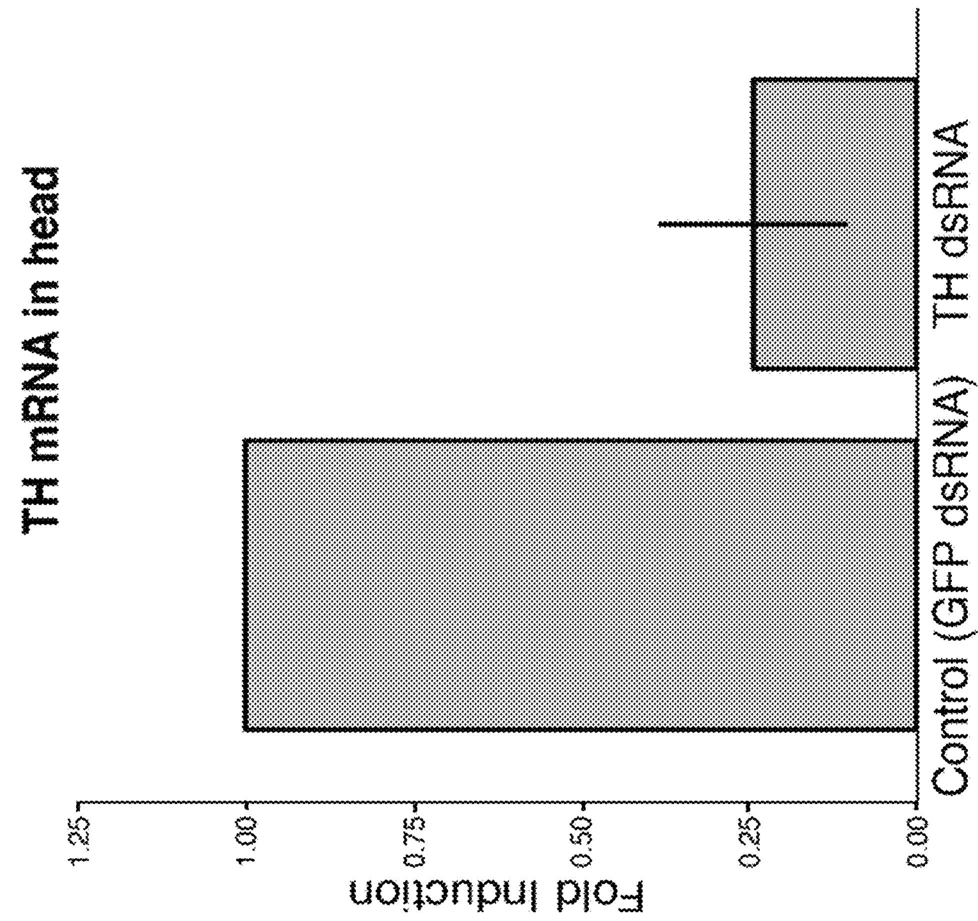
FIG. 7: Quantification of tyrosine hydrolase mRNA in the head of bees.

The second construct that was tested had dsRNA targeting of tyrosine hydroxylase (TH). Bees were inoculated with bacteria containing the construct targeting TH and the ability to induce a systemic RNAi response and down regulated gene transcription in other both sites was determined. FIG. 7 shows that the dsRNA construct was able to induce RNAi and downregulated expression of TH in the bee head. Therefore, the present methods can be used to engineer bacteria which are introduced to bees and induce expression of a gene or induce RNAi against a target gene. This method may be broadly useful for downregulating honey bee genes for research as well as industrial uses to improve bee health and lower the impact of bee pathogens.

Example 3—Materials and Methods

Figure 8A:
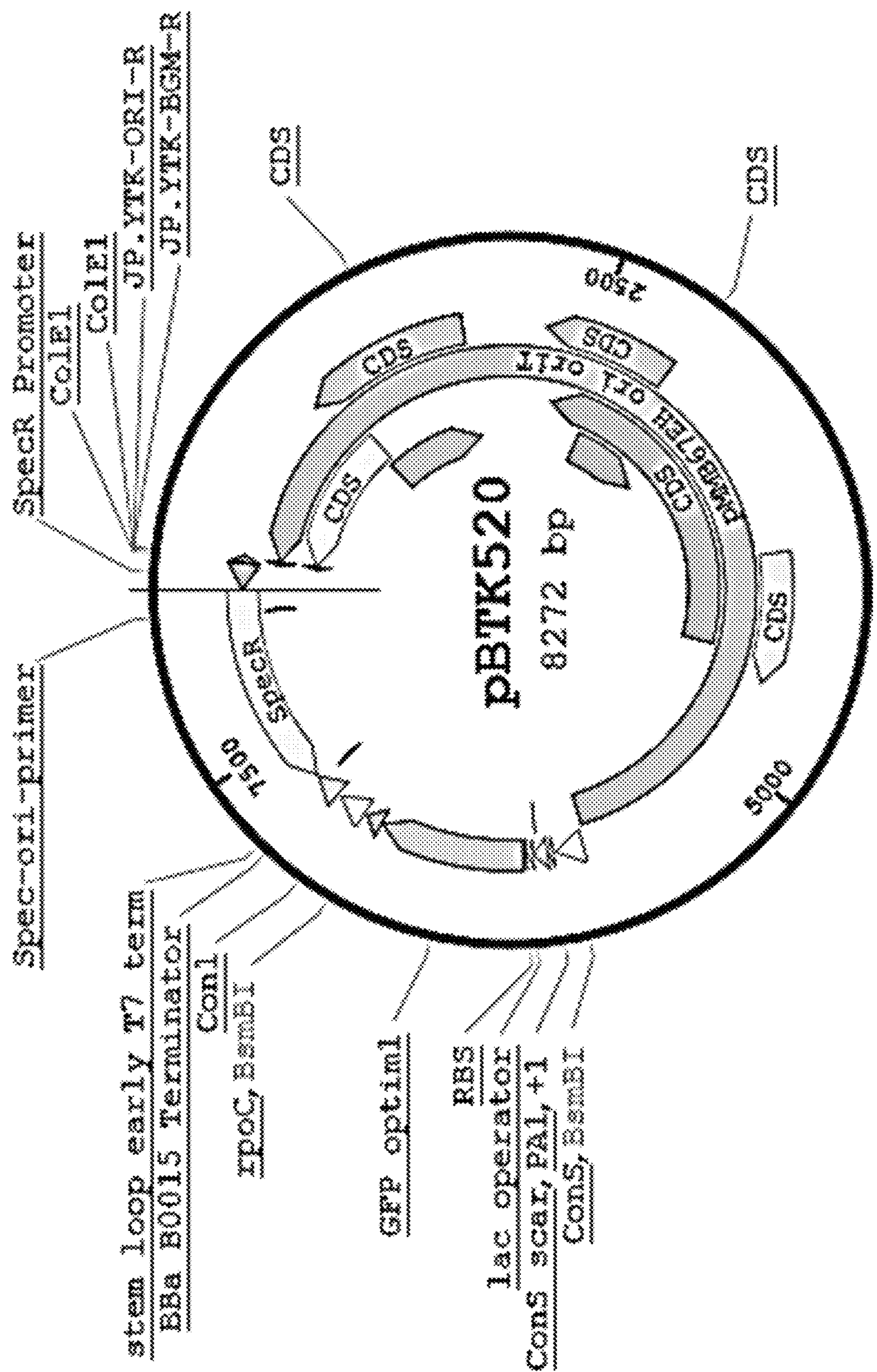
FIGS. 8A-8E: Schematics depicting various plasmids including pBTK520, pBTK570, pBTK562, pBTK561, and pBTK590.
Figure 8B:
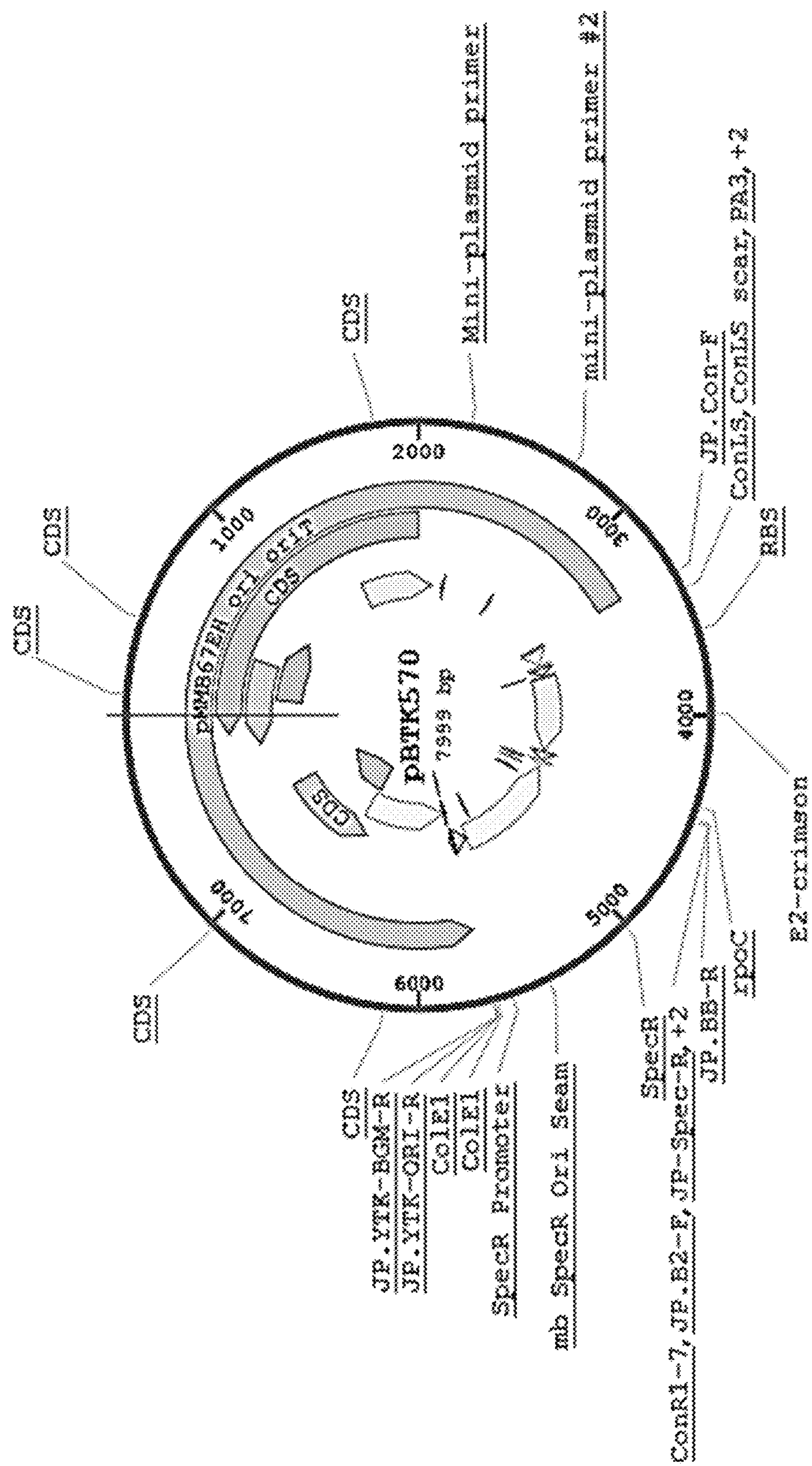
Figure 8C:
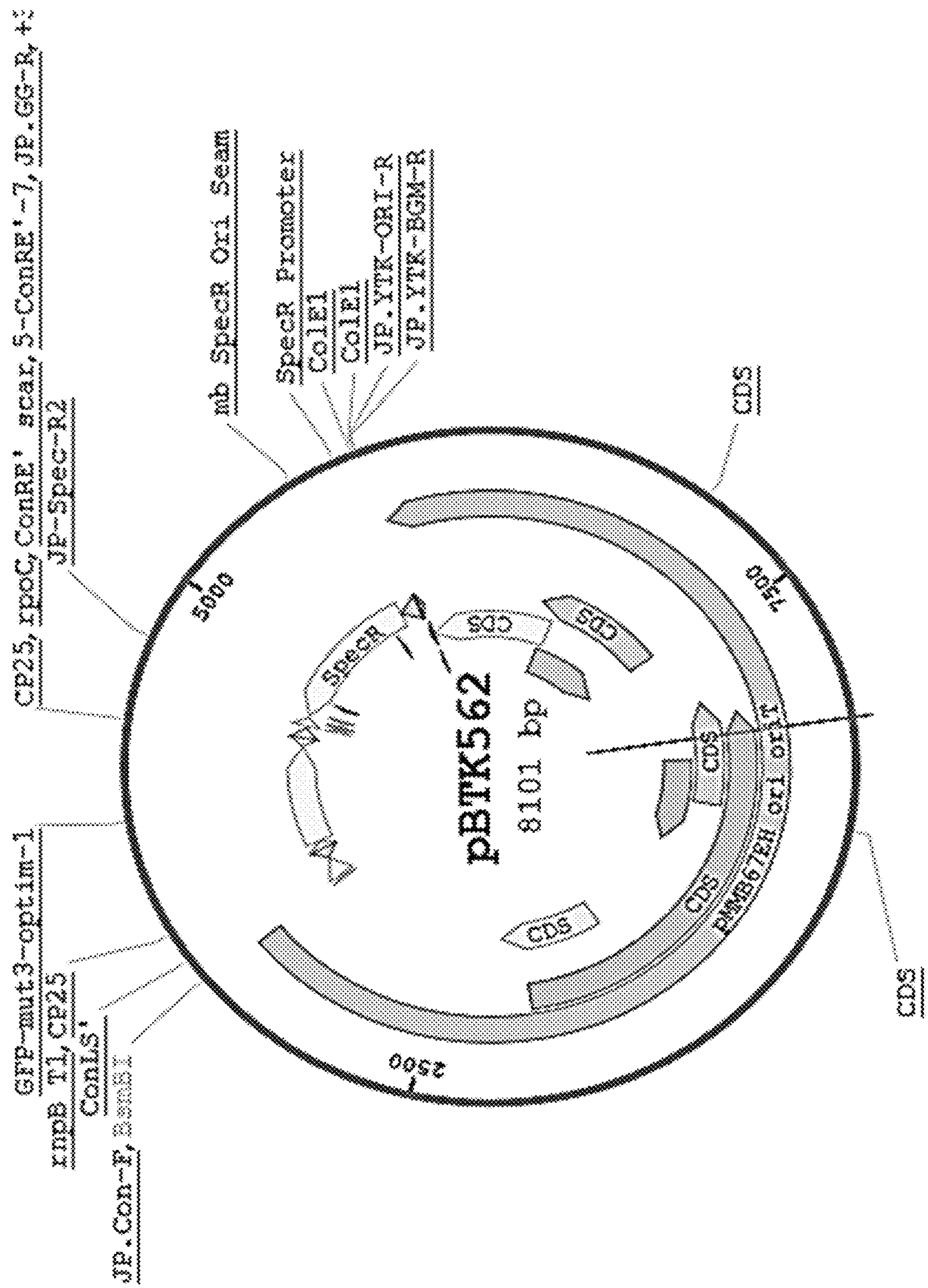
Figure 8D:
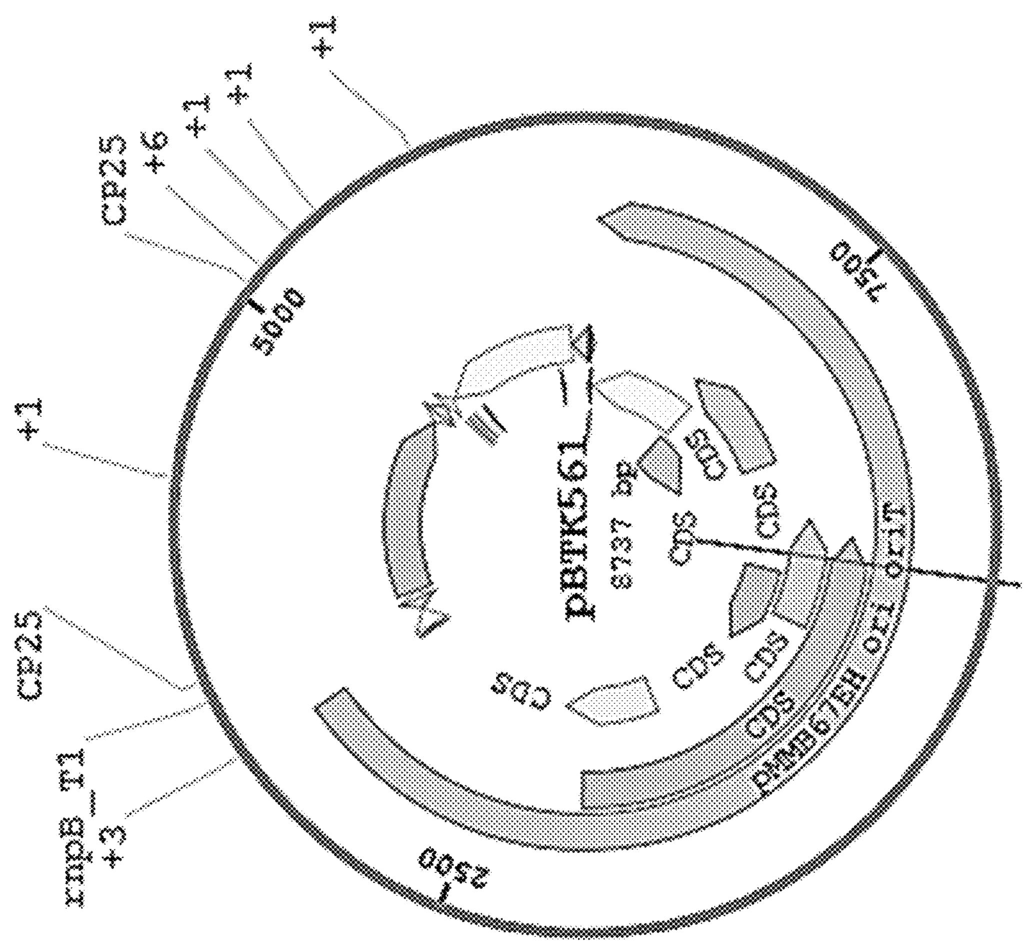
Figure 8E:
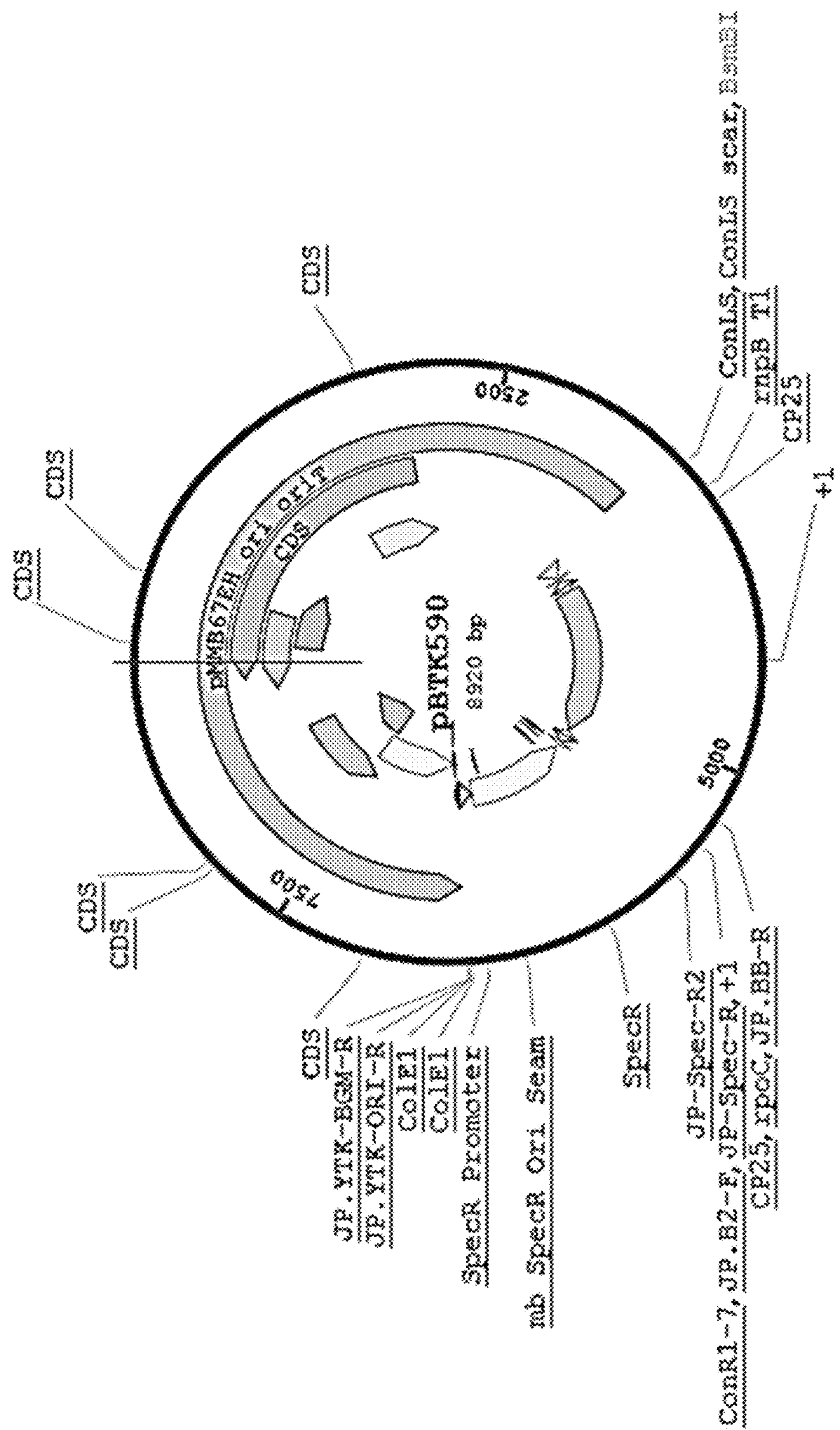

The plasmids used for the above experiments were all derived from the rsf1010 origin from the pMMB67EH broad host range *E. coli* plasmid. The pBTK520 plasmid was used to express GFP fluorescent protein and had spectinomycin resistance (FIG. 8A). The pBTK570 (FIG. 8B) plasmid expressing E2-Crimson fluorescent protein was used to validate gene expression in vivo. The pBTK562 plasmid (FIG. 8C) expressing dsRNA against GFP was used as control in dsRNA experiments. The pBTK561 plasmid (FIG. 8D) expressing dsRNA against bee alpha tubulin was used to show in vivo killing of bees and expression of dsRNA in vitro. Finally, the pBTK590 plasmid (FIG. 8E) expressing dsRNA against Tyrosine Hydroxlyase was used to confirm gene knock down in the head in vivo.

Example 4—Genetic Engineering of Bee Gut Microbiome Bacteria with a Toolkit for Modular Assembly of Broad-Host-Range Plasmids A preliminary screen with a variety of broad-host-range plasmids was performed with different replication origins (RP4, pBBR1, RSF1010) and antibiotic resistance markers (kanamycin, ampicillin, chloramphenicol, spectinomycin) for their ability to be transferred by conjugation and stably maintained in two bacterial species, *S. alvi* and *G. apicola*, which are both abundant in the honey bee gut (FIG. 16). Plasmid pMMB67EH, a synthetic plasmid containing an RSF1010 origin (Furste J P, et al., 1986, Gene, 48:119-131), was the most versatile: it replicated in both species. Plasmids containing an RSF1010 origin are known to be extremely broad-hostrange (BHR) because they encode multiple ORFs that make them less dependent on the presence of specific proteins in a host cell for replication (Jain A. et al., 2013, FEMS Microbiol Lett., 348:87-96; Meyer R. et al., 2009, Plasmid, 62:57-70). Additionally, they contain a promiscuous origin of transfer (oriT) that enables one-way transfer of the plasmid to a recipient cell from a donor cell encoding a conjugation apparatus in trans on the chromosome, such as *E. coli* MFDpir (Ferrieres L. et al., 2010, J Bacteriol., 192:6418-6427).

Figures 9A, 9B, 9C:
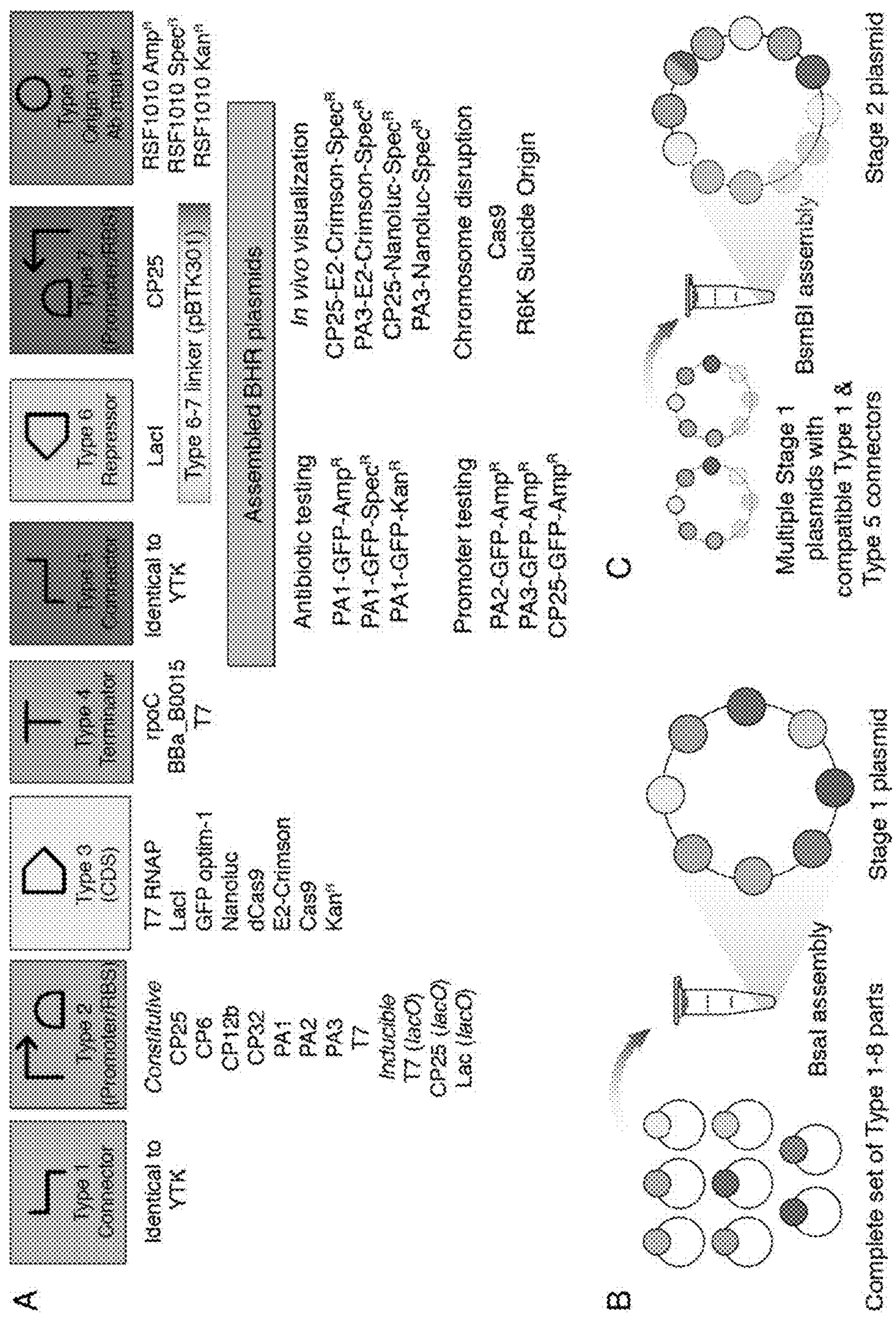
FIGS. 9A-9C: Depicts design of the bee microbiome toolkit (BTK) and schematic assembly.

Because of these characteristics of pMMB67EH, it was decided to create a toolkit of genetic parts for hierarchical and combinatorial assembly into its RSF1010-derived backbone for testing in additional species (FIG. 9A). These BTK parts are compatible with the Golden Gate cloning scheme used by the Yeast Toolkit (YTK) (Lee M E, 2015, ACS Synth Biol., 4:975-986), and connector parts from the YTK are required for BTK assembly. BTK parts are classified into eight types defined by the specific flanking overhangs generated by type IIS restriction enzyme cleavage. Entry vectors containing any complete set of parts labeled 1-8 can be combined via one BsaI Golden Gate assembly reaction into a complete plasmid (FIG. 9B). This assembly creates a Stage 1 plasmid comprising parts 2-4 flanked by assembly connector parts 1 and 5 with vector backbone components in parts 6-8. Transcriptional units from multiple Stage 1 plasmids that have matching sets of connector parts can be further composed into one vector by Stage 2 assembly using BsmBI (FIG. 9C).

To create BTK vector backbone parts, the high-copy number bacterial ColE1 origin of YTK part 8 plasmids ($Amp^R$, $Kan^R$, $Spec^R$) was replaced with the RSF1010 origin from pMMB67EH. These backbones retain the oriT for delivery into recipient cells via conjugation, which is useful for genetically modifying bacterial species and strains lacking established chemical or electrical transformation techniques. In the original YTK, Type 6 and 7 parts encode a yeast marker and a yeast origin, respectively. Type 6 part overhangs was repurposed for flanking a DNA sequence encoding an optional additional CDS (such as a repressor) in the reverse orientation relative to the Type 2 part CDS, and Type 7 part overhangs for incorporating an optional reverse promoter for driving expression of the part 6 CDS. A combined Type 6-7 linker (pBTK301) can be used in lieu of these parts to create constructs lacking this extra reverse gene. These vectors were used to construct a variety of plasmids containing a single fluorescent protein driven by a broad-host-range promoter. To build more complex assemblies, such as those with T7 RNA polymerase driving inducible expression of GFP, multiple vectors from BsaI Stage 1 assembly in a Stage 2 BsmBI assembly were combined. Notable components of the BTK that expand on the set of genetic parts available in the YTK for compatible assembly include: 3 BHR plasmids with different antibiotic resistance cassettes and oriT as Type 8 origin parts for Stage 1 assembly; 2 BHR plasmids ready for Stage 2 assembly ($Spec^R$, $Kan^R$); 11 bacterial promoter/RBS combinations as Type 2 parts; 6 new CDSs including E2-Crimson (Strack R L et al., 2009, Biochemistry, 48:8279-8281) and Nanoluc (Hall M P et al., 2012, ACS Chem Biol., 7:1848-1857) for in vivo visualization as Type 3 parts; 3 bacterial terminators as Type 4 parts; 1 transcriptional repressor (LacI) as a Type 6 part; 2 R6K-origin plasmid backbones to assemble suicide plasmids for gene disruption or chromosomal modification and pre-assembled plasmids with BHR promoters for immediate testing in new bacterial strains.

In summary, BTK, the first Golden Gate toolkit designed specifically for the combinatorial assembly of broad-host-range plasmids was built, with the aim of expanding synthetic biology into diverse bacteria native to non-laboratory environments. In this study, BTK was applied to modify bacteria found in the honey bee gut microbiome. These species are typical of many other bacteria in natural microbial communities of interest: they have only been cultured recently, are phylogenetically diverse, and have few or no established genetic tools. Fundamental BTK components needed for genetic modification was validated, including antibiotic selection markers, conjugation procedures, and promoters to express proteins under constitutive or inducible control. BGM strains engineered with the BTK colonize the guts of newly emerged bees, and fluorescent in vivo imaging revealed a characteristic spatial distribution of each species in the gut.

The species engineered are within the Proteobacteria, a diverse Gram-negative phylum that is a common component of animal- and plant-associated communities. Although it has not yet being tested more broadly, BTK components should also be useful for genetically modifying other bacteria native to other natural communities. The core of the BTK is the RSF1010 plasmid origin, which is known to replicate in diverse bacterial lineages including *Cyanobacteria, Agrobacterium*, and others (Jain A et el., 2013, FEMS Microbiol Lett., 348:87-96; Meyer R et al., 2009, Plasmid, 62:57-71; Taton A et al., 2014, Nucleic Acids Res., 42:gku673-e136; Clewell D B et al., 1974, J Bacteriol., 117:283-289). The BTK also includes promoters that have previously been shown to function in both Gram-negative and Gram-positive bacteria (Jensen P R et al., 1998, Appl Environ Microbiol., 64:82-87). The E2-Crimson reporter gene fluoresces at far-red excitation wavelengths, which is ideal for in vivo imaging of bacteria through tissue in host-associated systems (Strack R L et al., 2009, Biochemistry, 48:8279-8281). While broadhost-range plasmids have already been extensively used to study newly isolated bacteria in the past (Clewell D B et al., 1974, J Bacteriol., 117:283-289), the combinatorial nature of this new toolkit makes it possible to test multiple antibiotic resistance markers and promoters, which are more difficult to replace in plasmids that rely on classical cloning approaches.

Standard part definitions enable researchers to customize a toolkit by adding new capabilities for their own applications, as it was done with re-using parts from the yeast toolkit (YTK) (Lee M E et al., 2015, ACS Synth Biol., 4:975-986). Separating antibiotic resistance cassettes and replication origins into different subparts and adding to the library of choices available for each function allows more combinations of antibiotics and origins to be tested when first working with a new species. Gram-positive origins, such as pAMβ1 (Clewell D B et al., 1974, J Bacteriol., 117:283-289), would be especially useful for the manipulation of other common host-associated phyla such as Firmicutes and Actinobacteria (Robinson C J et al., 2010, Microbiol Mol Biol Rev., 74:453-476). Further validation of some BTK parts, such as the dCas9 and Cas9 systems, is needed to conclude that they will function reliably across diverse species. Other established broad-host-range tools—such as Tn7-transposon integration (Choi K H et al., 2005, Nat Meth., 2:443-448), Group II intron-based gene disruption (Enyeart P J et al., 2013, Mol Syst Biol., 9:685-685), and emerging CRISPR methods for targeted mutagenesis (Banno S et al., 2018, Nat Microbiol., 339:819)—could also be incorporated into the BTK-compatible Golden Gate framework in the future.

Application of the BTK to engineering bee gut bacteria enables new approaches to microbiome research in these insect species that are important pollinators and model systems for studying social behavior and learning. For example, gene disruption combined with fluorescent visualization of bacterial cells in living bees can be used to improve understanding of the molecular basis of host-microbe and microbe-microbe interactions and their relevance to host health. The BTK can also be used to implement and test biotechnological approaches for mitigating threats to bee health. For example, it could be used to engineer commensal gut bacteria to degrade pesticides or suppress pathogen populations (i.e., paratransgenesis) (Rangberg A et al., 2012, Integr Comp Biol., 52:89-99). These efforts could one day profoundly affect the health of the bee colonies that sustain modern agriculture.

The materials and methods employed in these experiments are now described.

Bacterial Culture

A complete list of bacterial strains used in this work and their sources is available as FIG. 17. Unless otherwise specified, bacterial strains *S. alvi* wkB2, *G. apicola* wkB7, *Parasaccharibacter apium* wkB6, *B. apis* PEB0150, *G. apicola* PEB0183, *B. apis* PEB0149, and *S. alvi* PEB0171, *S. marcescens* N10A28 were grown on Columbia agar supplemented with 5% sterile sheep's blood (B-COL) and incubated at 35° C. in a 5% CO2 atmosphere as static cultures. *E. coli* were cultured at 37° C. with orbital shaking at 225 rpm over a 1-inch diameter. *E. coli* MFDpir was grown in LB supplemented with 0.3 mM diaminopimelic acid (DAP). *E. coli* EC100D and *E. coli* DH5α were grown in LB.

For antibiotic selection, the following concentrations were used: ampicillin (100 μg/mL *E. coli,* 30 μg/mL *S. alvi,* 30 μg/mL *G. apicola,* 30 μg/mL *B. apis,* 300 μg/mL *S. marcescens*), kanamycin (50 μg/mL *E. coli,* 20 μg/mL *S. alvi,* 20 μg/mL *G. apicola,* 20 μg/mL *B. apis*), spectinomycin (60 μg/mL *E. coli,* 30 μg/mL for *S. alvi,* 30 μg/mL *G. apicola,* 30 μg/mL *B. apis,* 30 μg/mL *P. apium,* 180 μg/mL *S. marcescens*).

Bioparenal Conjugation

MFDpir with mobilizable plasmid ("donor strain") was grown overnight, shaking in LB with appropriate selective antibiotics and DAP (0.3 mM) supplementation. Recipient strains (wkB2, wkB7, PEB0150, PEB0183, PEB0171, N10A28, wkB6, wkB12, Snod 2-15, Pens 2-2-5) were grown overnight on solid media. Recipient and donor strains were washed in 1 mL PBS, spun down (1006×g for 5 minutes), and resuspended with 1 mL of PBS. These two suspensions were mixed in a 9:1 OD ratio of recipient:donor and spotted (without filter) onto a B-COL plate supplemented with 0.3 mM DAP. Conjugations proceeded overnight (~12-14 hours) and were scraped from the plate into PBS the next morning. Conjugation mixtures were again gently spun down (1006×g) and washed twice in PBS to remove residual DAP. Approximately 100 μL of this mixture (and 1:10, 1:100 dilutions) was plated onto selective antibiotic plates and incubated 2-3 days to obtain transconjugant colonies. Transconjugants were passaged again on selective media and confirmed by PCR amplification of a plasmid sequence and visible fluorescence, when appropriate. For the initial broad-host-range plasmid screen, transconjugants were further verified by plasmid reisolation and electroporation into *E. coli* DH5α cells. To determine conjugation efficiency, mating mixtures were serially diluted and plated on selective and non-selective plates. Conjugation frequency was calculated as the number of fluorescent transconjugant CFUs on selective plates per total CFUs on non-selective plates.

BTK Construction

Construction of the BTK backbone was carried out with Gibson assembly (Gibson D G et al., 2009, Nat Meth., 6:343-345) following established protocols. New part plasmids were constructed using a previously published BsmBI assembly protocol for the yeast toolkit (YTK) (LEE M E et al., 2015, ACS Synth Biol., 4:975-986) with inserts synthesized as doublestranded DNA gBlocks (IDT). New parts were cloned into the pYTK001 entry vector. The BTK kit uses the entry vector plasmid, connector parts (Type 1 and Type 5), and part sequence overhangs of the YTK. In contrast to the YTK, Type 3 parts of the BTK include a stop codon, as the Type 4 terminators do not include a stop codon. A list of BTK plasmids is available in FIG. 18.

Measuring BGM GFP In Vitro

To measure fluorescence, 50 μL of ~0.2 OD bacterial cultures were pooled on B-COL agar plates and incubated for 48 hours. Cells were scraped into PBS and then loaded into wells of a 96 well plate to measure fluorescent excitation using a Tecan Spark 10M multimode microplate reader at excitation/emission wavelengths of 485/535. Fluorescent readings were corrected with blank values, and then normalized by OD. Gain was set manually and consistent throughout experiments.

Flow Cytometry Analysis of GFP Expression

As with plate reader measurements, 50 μL of ~0.2 OD bacterial culture was pulled onto BCOL agar plates and incubated for 48 hours. Bacteria were scraped into PBS, washed, and then gently spun down (1006×g for 5 minutes). Cells were resuspended vigorously to disrupt any biofilm, and then diluted to ~0.1 OD in HPLC-grade water. Cells were counterstained with SYTO 17 red nucleic acid stain (Thermo-Fisher), and then ran samples on a BD LSR-Fortessa SORP Flow Cytometer. Data were acquired with FACSDiva v6.1.3, and then analyzed with FlowJo v10.4.2. All samples were run under identical conditions. GFP-A voltage was consistent throughout experiments. Nonfluorescent controls were used to determine forward-scatter, side-scatter, and APC-A (counterstain) gates that were then set individually for each species.

Tn7-Transposition in *B. apis*

For the chromosomal insertion of gfp into *B. apis*, a tri-parental mating was performed with *B. apis, E. coli* MFDpir with pTNS2, and *E. coli* MFDpir with pTN7-PA1-gfp-kan in an 8:1:1 ratio. Conjugation proceeded for 12 hours, and transformed *B. apis* was selected with kanamycin as in biparental conjugation.

Broad-host-range dCas9 plasmids are created by BsmBI assembly of 3 parts plasmids containing: (1) the sgRNA transcriptional unit (pBTK615), (2) the dCas9 transcriptional unit (pBTK614), and (3) the broad-host-range backbone with ConLE and ConRE connector sequences (pBTK527a). To repress gfp expression in *B. apis*, the gfp nontemplate strand was targeted by using the N20 sequence: 5'-CGTCTAATTCCACGAGGATT (SEQ ID NO:7). The sgRNA plasmid can be retargeted using MEGAWHOP cloning (Miyazaki K et al., 2011, Meth Enz., 498:399-406). Briefly, in MEGAWHOP cloning a double-stranded PCR product containing the sequence change to be introduced, but otherwise identical to a portion of the plasmid, is used as a "megaprimer" to re-amplify the whole plasmid in a second PCR reaction. Because the sgRNA targeting sequence is short, it is possible to include a new target sequence flanked by 20 bp of homology to the plasmid on either side in one of the primers used in the initial PCR reaction to generate the megaprimer. The fully assembled CRISPRi plasmid (pBTK618) was conjugated into *B. apis* with chromosomally integrated PA1-gfp, and GFP fluorescence was measured as above.

Chromosomal Disruption Using Cas9 and Homologous Recombination

Plasmid pBTK601 contains Cas9 driven by the kanamycin resistance gene promoter on the broad-host-range backbone. This plasmid was conjugated into *S. alvi* wkB2, *G. apicola* wkB7, and *B. apis* PEB0150 and maintained with spectinomycin. The CP25-driven sgRNA is on plasmid pBTK615 and can be retargeted using MEGAWHOP cloning (Miyazaki K et al., 2011, Meth Enz., 498:399-406). A full description of homology donor plasmid assembly is available in FIG. 23. Briefly, a genomic homology segment upstream of the gene of interest to disrupt or replace is amplified with Type 2 part overhangs, and a downstream genomic homology segment is amplified as a Type 4 part. Upstream homology, antibiotic resistance cassette (Type 3), and downstream homology are combined in a single BsaI reaction with ConLE and ConRE to form a Stage 1 assembly of the replacement cassette. The final BsmBI assembly includes: (1) the sgRNA plasmid, (2) the replacement cassette plasmid, and (3) pBTK599 (R6K suicide plasmid backbone). This final assembly must be transformed into $pir^+$ strains, such as EC100D or MFDpir.

Efficiency of Chromosomal Disruption with and without Cas9

Recipient BGM strains (wkB2, wkB2::pBTK601, wkB7, wkB7::pBTK601, PEB0150, PEB0150::pBTK601) were grown on B-COL plates for 48 hours prior to conjugation. Donor *E. coli* strains were grown in liquid culture overnight prior to conjugation. Donor and recipients were washed in PBS and mixed in a 1:9 ratio (by OD), and 100 μL was plated on B-COL+0.3 mM DAP media for overnight conjugation. After 14 hours, the entire conjugation mixtures were scraped into PBS and washed twice to remove residual DAP, and dilutions were plated on selective agar plates (B-COL+Kanamycin 20 μg/mL) and nonselective agar plates (B-COL). Efficiency of gene disruption was calculated as (# of transconjugant cells)/(# of total cells). To identify single-crossover and double-crossover mutants, a series of PCR reactions were conducted as described in FIG. 23. Briefly, transconjugants were screened for the appropriate upstream and downstream junctions with colony PCR. Potential double-crossover mutants were then further screened for the size of the disrupted region, and loss of the suicide plasmid backbone.

Laboratory Care of Honey Bees

Microbiota-free bees were obtained and raised using methods described previously (Kwong W K et al., 2014, Proc Natl Acad Sci USA., 111:11509-11514). Briefly, pupae were pulled under sterile conditions from brood combs obtained from outdoor hives. These pupae emerged in a sterile incubator (becoming newly emerged adult workers) and were then sorted into individual cup cages for further development in the laboratory. Prior to inoculation, newly emerged workers were allowed to feed on sterile irradiated pollen (Betterbee) and 50% sucrose solution ad libitum. For any individual experiment, all pupae were obtained from the same hive. When raised in this manner, *Apis mellifera* workers remain uncolonized by core BGM bacteria species and show very low levels of environmental bacteria in their guts (Powell J E et al., 2014, Appl Environ Microbiol., 80:7378-7387). It is critical to pull the pupae from frames at an early stage, before the mouthparts have hardened, as later pupal stages will begin to ingest hive material and may be colonized.

Mono- and Co-Innoculation of Engineered BGM into Honey Bees

After obtaining newly emerged workers, bees were chilled at 4° C. for 30 minutes and then coated in sugar syrup containing resuspended bacterial inoculum, transferred to cup cages, and allowed to groom each other. The inoculum generally contained 200 μL of OD ~0.1 bacterial suspension combined with 800 μL of 1:1 sucrose:water solution. Approximately 30 μL of this solution per bee was used for inoculations (corresponding to $10^4$ bacteria per bee to ensure robust inoculation). Plate counts of the inoculum were used to confirm concentrations.

In Vivo Imaging of Bacterial Burden Using E2-Crimson

To visualize in vivo expression of E2-Crimson in living bees, a Syngene G:Box Chemi XX6 gel doc system was used. Bees were chilled on ice for 30 min to minimize movement, then imaged using manufacturers recommended instructions for far-red fluorescent probe visualization: "Red LED" light source and "Filter 705M" emission filter. All bees were imaged under identical conditions: 5 minutes exposure time for whole bee and 30 seconds for bees with dissected guts. Images were saved as TIFF files for further analysis in FIJI (Schindelin J et al., 2012, Nat Meth., 9:676-682). In FIJI, fluorescence intensity was mapped to the "mplmagma" scale. A representative bee for each condition is shown. No further image manipulation was performed. Different scales are used for comparing fluorescent *S. marcescens* and fluorescent BGM species due to the increased fluorescent protein production and titer of *S. marcescens*.

Confocal Fluorescence Microscopy

Fluorescent images were obtained at the UT ICMB Microscopy core on a Zeiss 710 Laser Scanning Confocal microscope. Bees were chilled and then dissected to expose rectum, ileum, and midgut. Without puncturing the gut, the entire gut compartment was transferred to an Ibidi p-Dish 35 mm (CAT #81156) and then placed on the microscope. Images were taken with a 20× objective and tiled using Zeiss software. Z-stack 2-channel fluorescent images were taken and combined using Imaris software. Intensity on individual channels was false colored to correspond to species-specific coloring. Display intensity of individual channels was scaled linearly to aid in visualization of different species, but no further transformations or background reduction was used.

qPCR to Assess Colonization of StaA Mutant

Absolute quantification of 16S rRNA gene copies specific to *S. alvi* was performed as described previously (Powell J E et al., 2016, Proc Natl Acad Sci USA., 113:13887-13892). Cohorts of newly emerged bees were hand-fed with equal amounts (~$10^4$ CFU/bee) of either wild-type *S. alvi* or the staA mutant. Control bees were maintained identically but remained uninoculated. After five days, five bees from each group were dissected and DNA was isolated from individual bee guts using the cetyltrimethylammonium bromide (CTAB) extraction method outlined previously (Powell J E et al., 2014, Apl Environ Microbiol., 80:7378-7387). After extraction, *S. alvi*-specific primers were used for quantitative PCR and absolute quantification based on 10-fold dilution of the target sequence in a pGEM-T plasmid vector. Reactions were run in triplicate.

Quantification and Statistical Analysis

All data processing and statistical analyses were done in R. Kruskal-Wallis rank sum tests were used to assess significance in the dCas9 gene repression experiment and the Cas9-assisted genome modification experiments.

The results of the experiments are now described.

BTK Plasmids Function in Diverse Bacterial Species Found in the Bee Gut

Figures 10A, 10B, 10C:
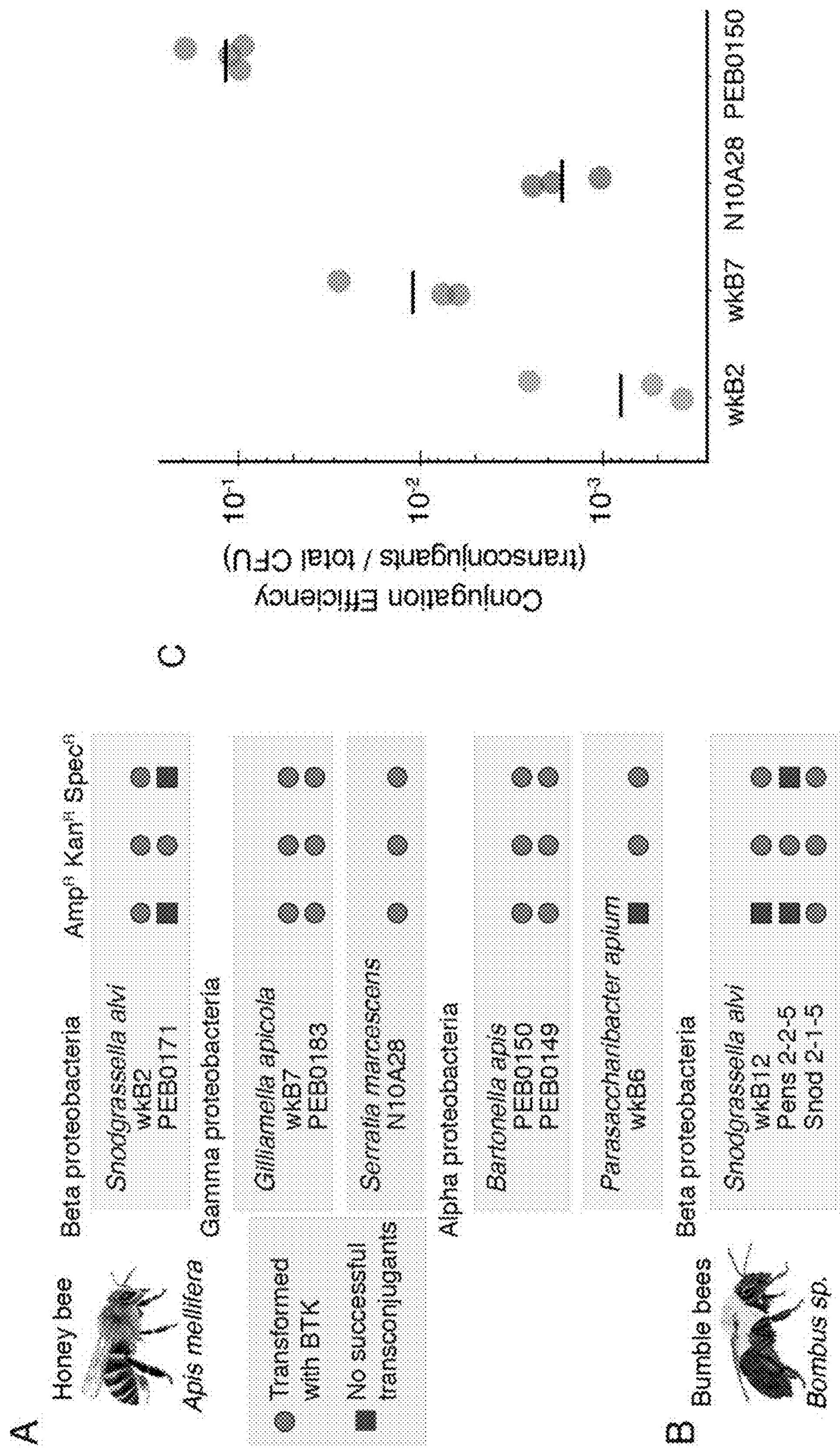
FIGS. 10A-10B: Depicts the bee microbiome toolkit (BTK) functions in diverse bee-associated bacteria.
FIG. 10C depicts conjugation frequency in four bee gut-associated strains. Black bars are the geometric mean and each point is an independent conjugation. Conjugation in *B. apis* is the most efficient, with conjugation efficiency approximately 10%.

It was sought to explore the host range of the RSF1010 origin used as a basis for the BTK in the context of a larger set of bee-associated bacterial strains. Simultaneously, it was needed to identify antibiotic resistance genes able to function in each bacterial strain. To do so, three BTK plasmids were constructed, each with a different antibiotic resistance marker and encoding GFP driven by the PA1 promoter: pBTK501 ($Amp^R$), pBTK519 ($Kan^R$), pBTK520 ($Spec^R$). Biparental matings were performed between *E. coli* MFDpir donors containing each plasmid and bee gut-associated strains (see Methods). Stable transconjugants were obtained for all of the Gram-negative strains tested with at least one of these three plasmids, as verified by further passaging on antibiotic-containing media, PCR amplification of plasmid sequences, and GFP expression (FIG. 10A). Successfully transformed bacterial species include Alpha-, Beta-, and Gammaproteobacteria and strains isolated from different bee species (*A. mellifera, Bombus terrestris, Bombus impatiens*, and *Bombus pensylvanicus*). Several of the bacterial species (*S. alvi, G. apicola, B. apis*, and *Parasaccharibacter apium*) are phylogenetically distant from any established model organisms and have no previously reported genetic tools. Transfer of the BTK plasmids was efficient, with >$10^{-3}$ transconjugants per CFU for four diverse bacterial species (FIG. 10B).

Identifying Functional Promoters in BGM Species

While some sequence features of transcriptional promoters are conserved across bacterial species, there is no guarantee that promoters designed to function in model organisms will function effectively in new bacterial isolates from a natural community of interest (Whitaker W R et al., 2017, Cell, 169:538-538). The BTK includes BHR promoters and RBS combinations as Type 2 parts that can be used to build plasmids to identify functional sequences for driving protein expression in new bacterial hosts. The function of the BHR promoters PA1 (pBTK501), PA2 (pBTK509), PA3 (pBTK510), and CP25 (pBTK503) were compared in *S. alvi* wkB2, *G. apicola* wkB7, *B. apis* PEB0150, and *S. marcescens* N10A28, all isolated from honey bee gut communities. Promoters PA1, PA2, PA3 are strong early promoters from bacteriophage T7 (Siebenlist U, 1979, Nucleic Acids Res., 6:1895-1907). The synthetic CP25 promoter was originally designed to function in *Lactococcus* strains (Jensen P R et al., 1998, Appl Environ Microbiol., 64:82-87), and the BTK includes other promoters from this series.

Figure 20:
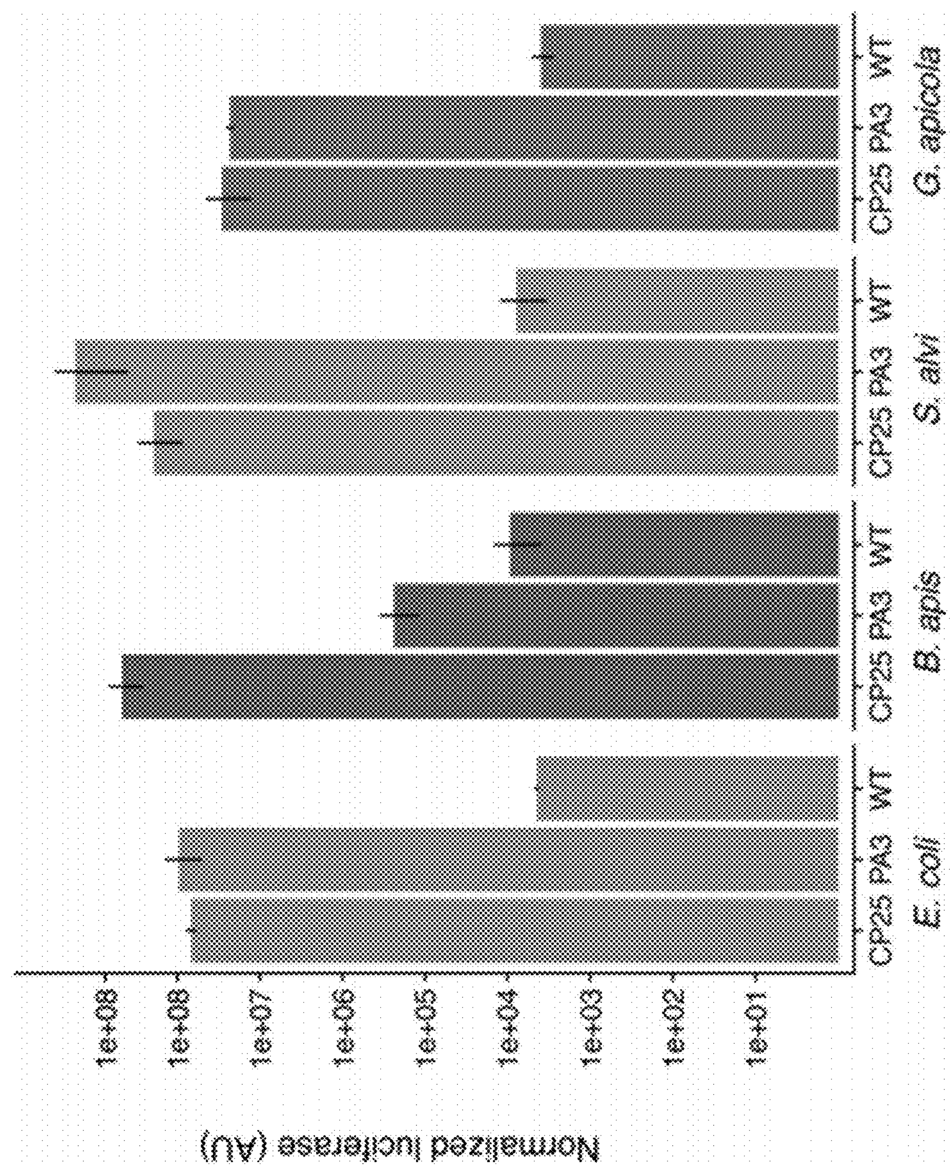
FIG. 20 depicts expression of nanoluc in BGM strains. Bee gut microbiota strains were conjugated with pBTK563 (CP25-Nanoluc) or pBTK564 (PA3-Nanoluc) and luciferase activity measured per manufacturer's instructions. Luciferase is plotted on a log10 scale. Bars are the mean from three biological replicates and error bars are standard deviation.
Figure 21:
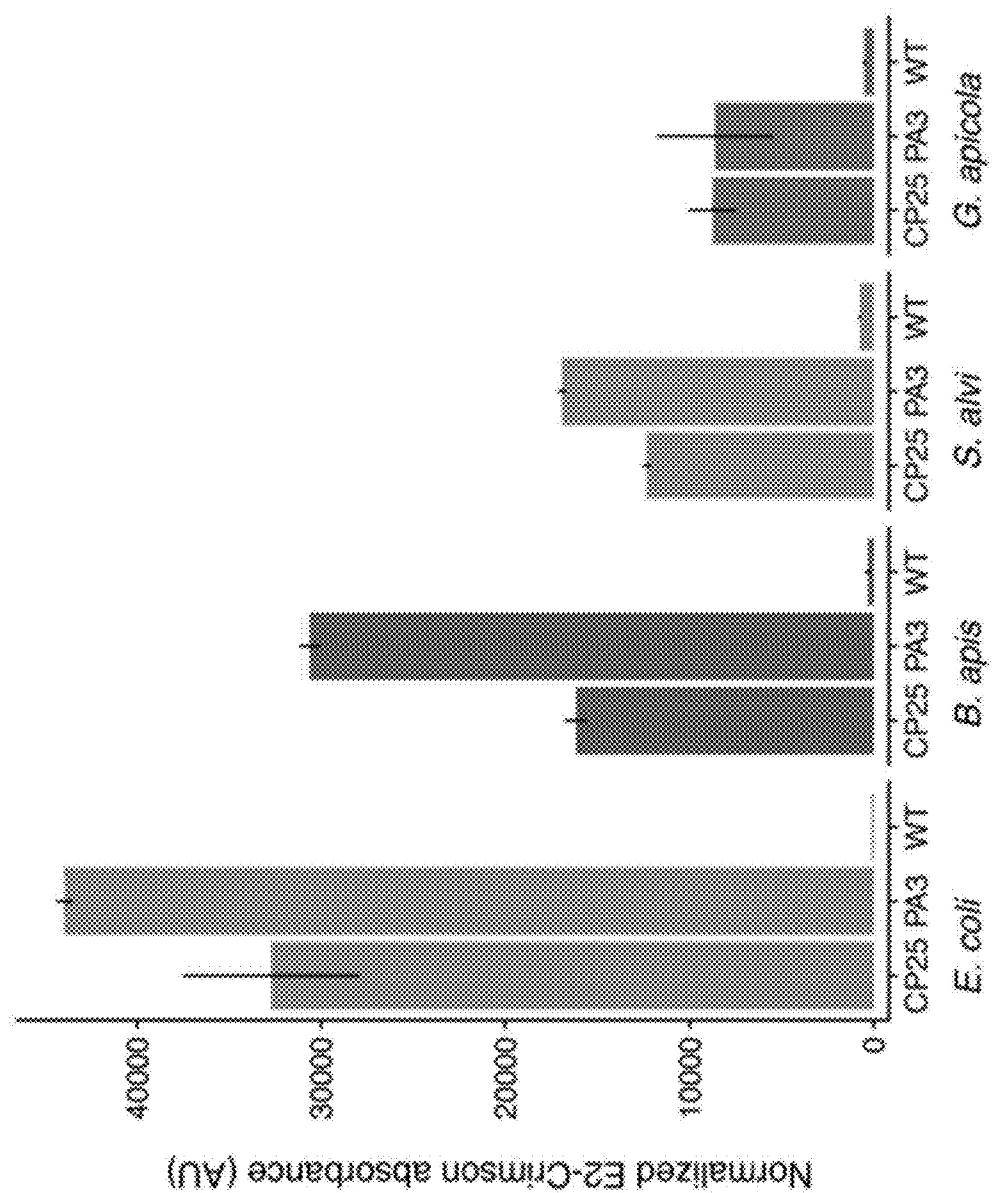
FIG. 21 depicts expression of E2-Crimson in BGM strains. Bee gut microbiota strains with pBTK569 (CP25-E2-Crimson) or pBTK570 (PA3-E2-Crimson) were measured for expression of E2-Crimson. Bars are the mean from three biological replicates and error bars are standard deviation. E2-Crimson fluorescence expression was measured as GFP, except using excitation/emission wavelengths of 611/646 nm.
Figure 22:
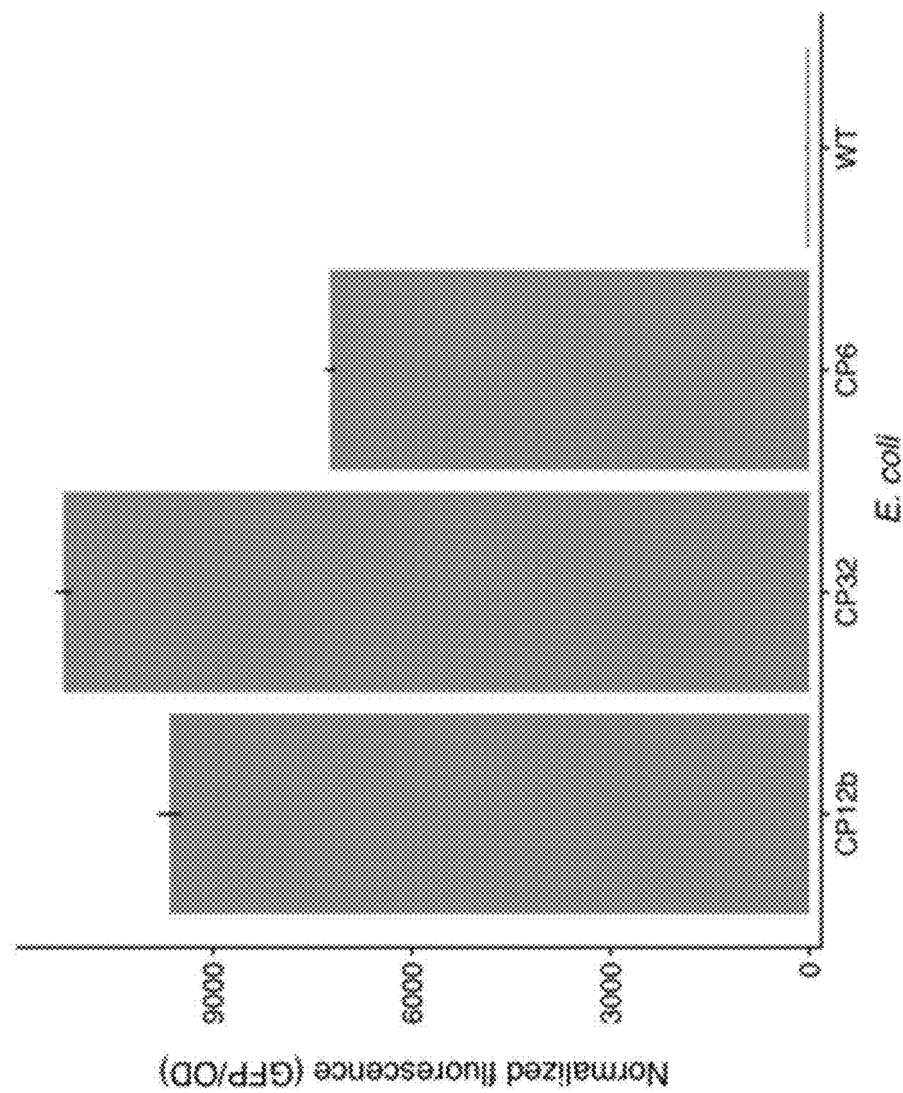
FIG. 22 depicts validation of additional BTK promoters in *E. coli*. Promoter parts CP12b, CP32, and CP6 were used to build GFP expression plasmids (pBTK619, pBTK620, pBTK621) and tested in *E. coli* MFDpir. Bars are the mean from three biological replicates and error bars are standard deviation.

Using flow cytometry, fluorescent protein expression from these promoters (FIG. 10A) was characterized. These promoters display significant variability in activity across strains when they are all tested with the same RBS. As expected, the promoter-RBS pairs function most strongly in *S. marcescens*, which is most closely related to *E. coli*. In the other BGM strains, expression was weaker, but there was a signal above background for most promoters that were tested with this RBS. Fluorescence is generally lower in *S. alvi, G. apicola*, and *B. apis* than it is in *E. coli*. In *E. coli* the distributions of fluorescent per cell for the PA2, PA3, and CP25 promoters are noticeably bimodal. This may be an intrinsic property of the promoter or due to the accumulation of "broken" plasmids with mutations that inactivate burdensome GFP expression (Sleight S C et al., 2010, J Biol Eng., 4:12). In BGM strains, with the exception of CP25 in *G. apicola*, these distributions are unimodal, indicating consistent fluorescent expression across single cells. PA3 expression was strong in *S. alvi*, and this observation was used to design a constitutive E2-Crimson-expressing plasmid (pBTK570) to test expression in vivo, as described in later sections. Validation of additional parts (E2-Crimson, Nanoluc, and other CP-series promoters) is available in FIG. 20, FIG. 21, FIG. 22.

Inducible Gene Expression in BGM Species

Induction systems are required for the temporal control of gene expression, and are useful for testing the functional roles of microbes in gut environments (Lim B et al., 2017, Cell, 169:547-558). Two lacI induction systems were tested: one simple system composed of a modified CP25 promoter with lacO sites and a more complex system that uses T7 RNA polymerase (T7 RNAP). IPTG-induction of these systems was tested in *E. coli* MFDpir, *S. alvi* wkB2, *G.*

Figures 11A, 11B, 11C:
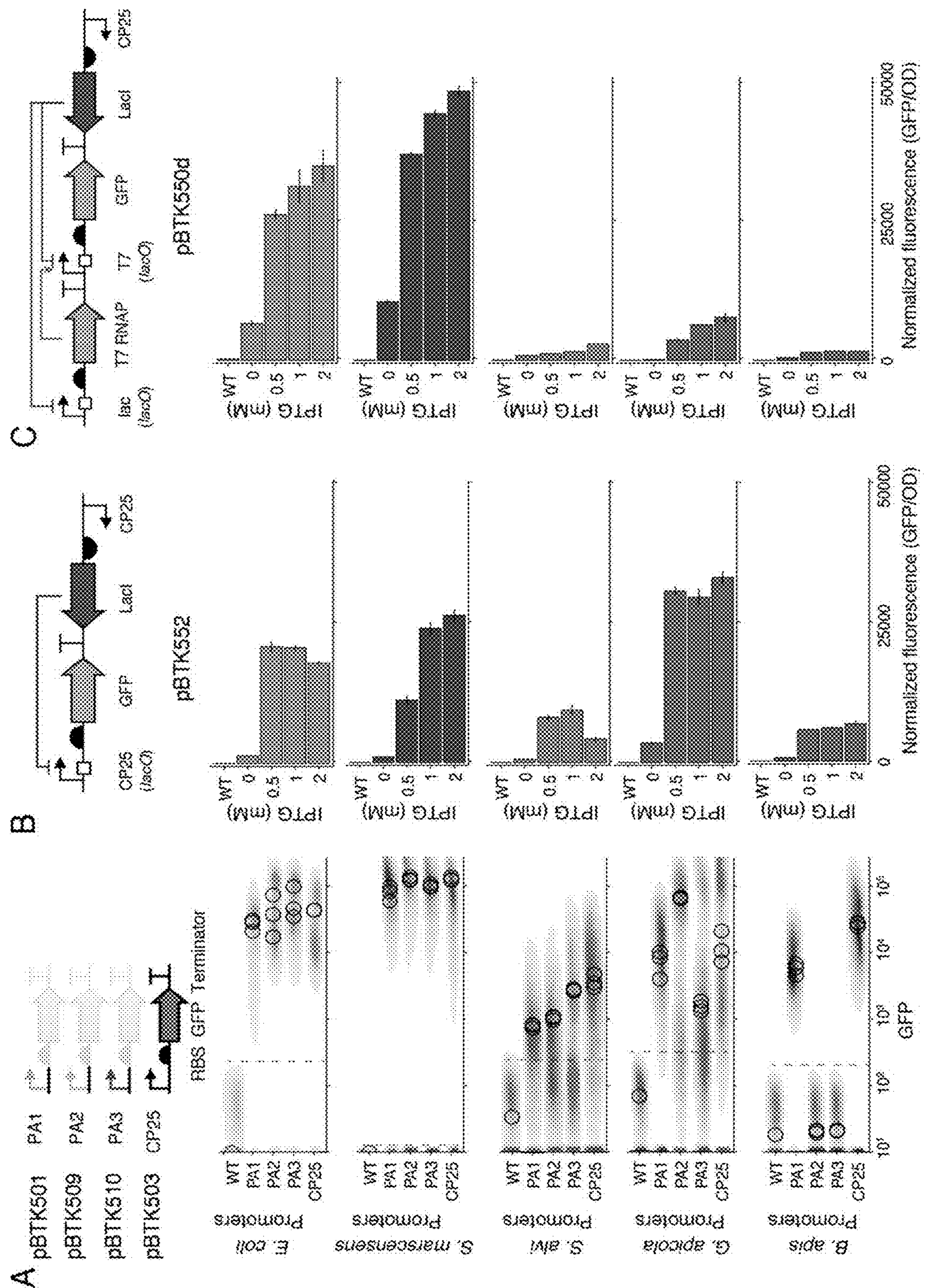
FIGS. 11A-11C: Depicts constitutive and inducible control of in vitro gene expression in bee gut bacteria.

*apicola* wkB7, *B. apis* PEB0150, and *S. marcescens* N10A28. The simple system (pBTK552) showed robust induction of GFP in all strains tested (FIG. 11B). Interestingly, *G. apicola* GFP expression with this system surpassed that of *E. coli* and *S. marcescens.*

For the T7 RNAP system, two transcriptional unit plasmids (pBTK549d, pBTK541) were built, one bearing lacI driven by the CP25 promoter and T7 RNAP under control of the inducible lac promoter and the other with GFP expressed from a T7 promoter with lacO sites, and combined them into a composite plasmid (pBTK550d). (FIG. 11C). Expression was strong in *S. marcescens* N10A28 and *E. coli* MFDpir, with maximal GFP expression after induction surpassing the simpler system in which lacI directly regulates GFP expression. However, in *G. apicola* wkB7, *S. alvi* wkB2, and *B. apis* PEB0150, a weaker induction of GFP was seen compared to the simpler system. The cause of this weak expression is unknown. It may be due to poor transcription from the lac promoter driving T7 RNAP or to an intrinsic incompatibility between T7 RNAP and the intracellular environment in the BGM species tested. In all strains, the inducible T7 RNAP construct showed appreciable background expression when not induced.

CRISPRi Repression of Chromosomal Gene Expression in *Bartonella apis*

Figure 12A:
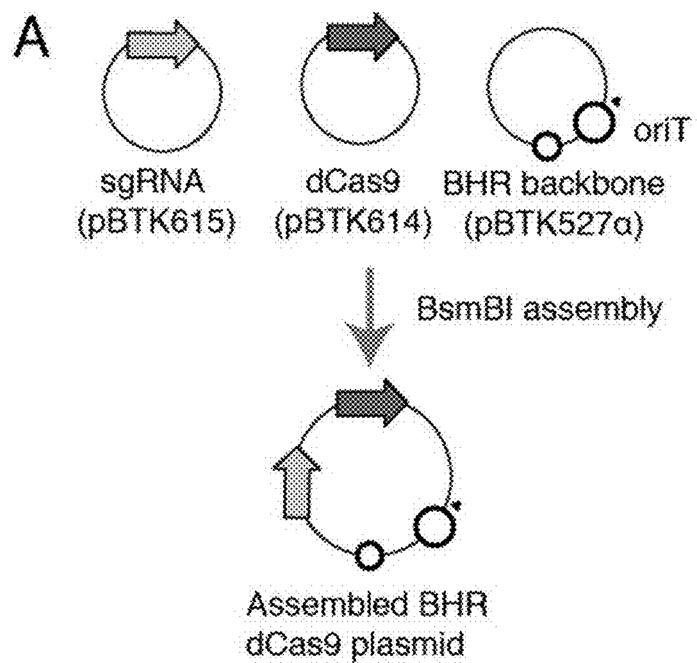
FIGS. 12A-12B: Depicts dCas9 gene silencing in *Bartonella apis*.
Figure 12B:
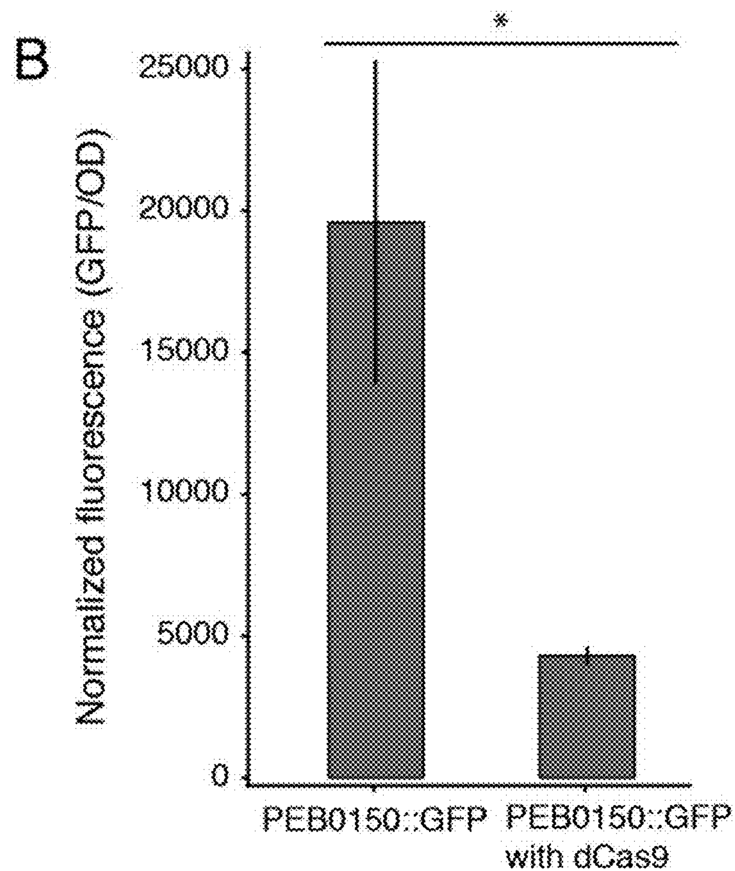

BTK was used to suppress gene activity in a BGM bacterium. Catalytic mutants of Cas9 (dCas9) have been used to reduce transcription of target genes, an approach termed CRISPR interference (CRISPRi), in diverse mammalian and bacterial systems (Barrangou R et al., 2017, Nat Microbiol., 2:1-9). To expand this approach to new non-model bacterial species, a modified dCas9 system was established in which targeting is achieved by a BTK part encoding a small guide RNA (sgRNA) (FIG. 12A) (Bikard D et al., 2013, Nucleic Acids Res., 41:7429-7437). To test the system, the sgRNA was targeted to a PA1-driven GFP gene in *B. apis* PEB0150, which was inserted into the chromosome using Tn7-based integration (Choi K H et al., 2005, Nat Meth., 2:443-448). GFP expression was significantly reduced in the presence of a sgRNA targeted to the GFP sequence (FIG. 12B). Coupled with the induction system, this ability to repress a target gene enables functional studies of essential genes that cannot be disrupted entirely.

Cas9-Assisted Gene Disruption in the BGM

Figures 13A, 13B, 13C, 13D, 13E:
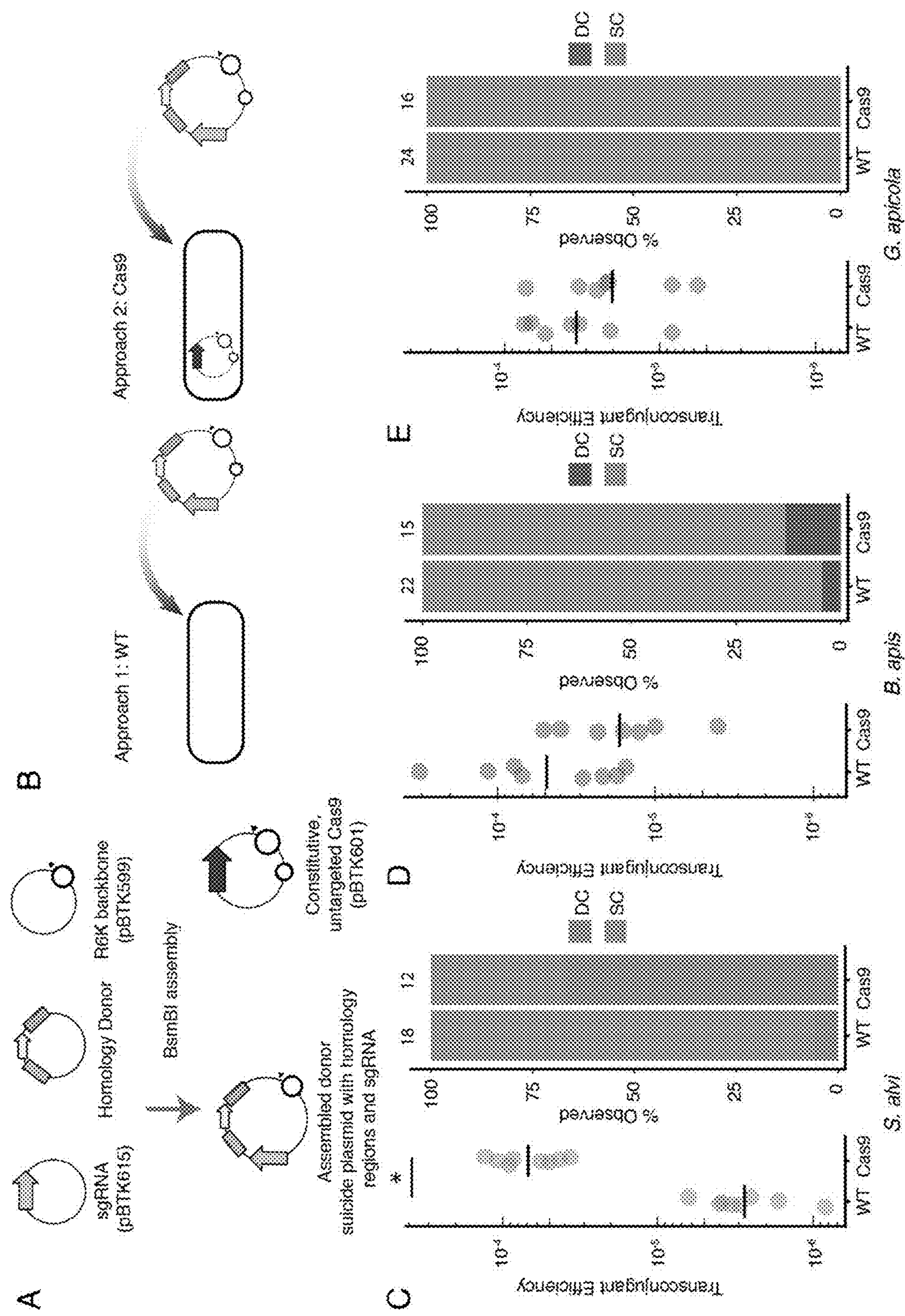
FIGS. 13A-13E: Depicts Cas9 assisted gene disruption in species from the bee gut microbiota.
Figures 23A, 23B, 23C:
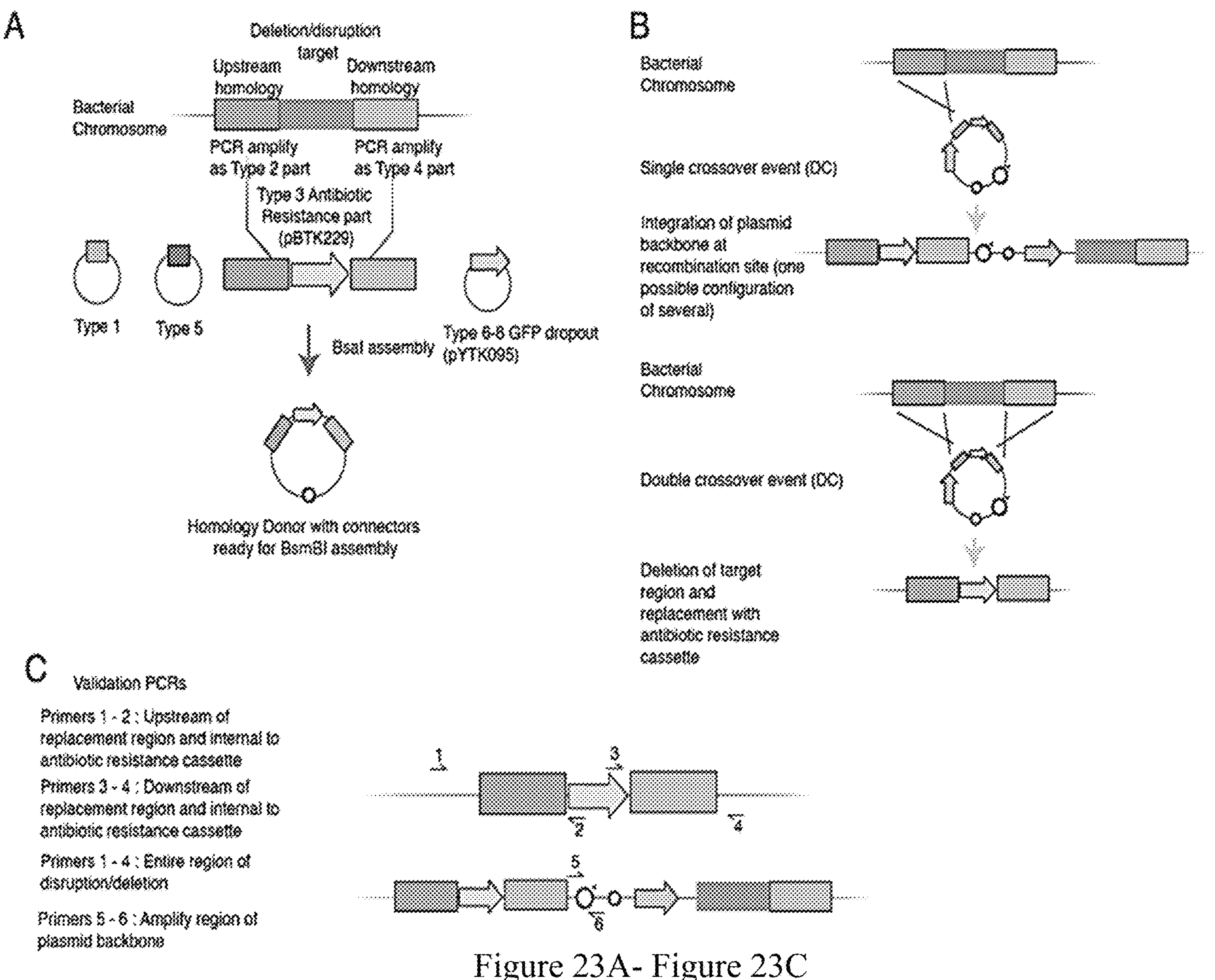
FIGS. 23A-23C: Depicts construction of replacement cassette plasmids.

Gene disruption is an important tool for establishing gene function and for studying interactions between genes. After identifying functional antibiotic cassettes in the earlier plasmid-replication screen, it was attempted to use homologous recombination to disrupt chromosomal genes in the BGM strains. To improve the efficacy of targeted gene disruption, a two-step approach was implemented based on using Cas9 cleavage for chromosomal modifications (Barrangou R et al., 2017, Nat Microbiol., 2:1-9) (see Methods). In step one, Cas9 is introduced into a cell on the BTK backbone (pBTK601) without any targeting sgRNA. In step two, a second round of conjugation is used to deliver a suicide plasmid with the replacement cassette (~1000 bp homology flanking a functional antibiotic resistance gene) and the sgRNA targeting the desired chromosomal location. The suicide plasmid is made with Golden Gate assembly using repurposed Type 2-4 overhangs and an R6K origin of replication (FIG. 13A, FIG. 13B). The sgRNA can be retargeted using MEGAWHOP cloning (Miyazaki K, 2011, Meth Enz., 498:399-406) (see Methods). A detailed description of suicide plasmid assembly and validation of mutants is shown in FIG. 23. It was expected that Cas9 cleavage might facilitate recombination into the chromosome and that it would also select against single-crossover integrations, in which the suicide plasmid backbone is incorporated into the chromosome, because they preserve the cleavage site, whereas double-crossover integrations result in replacement of the targeted gene sequence with just the antibiotic resistance cassette and delete the cleavage site.

Figure 24A:
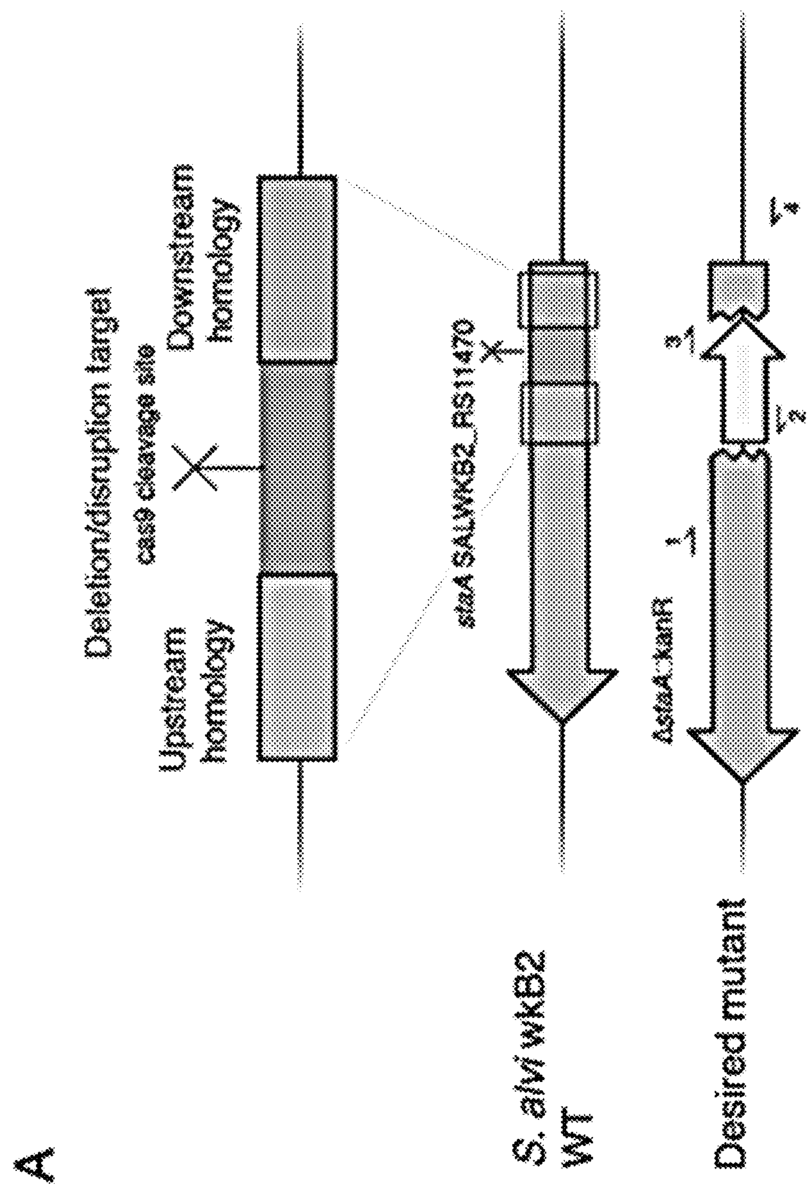
FIGS. 24A-24E: Depicts schematic and validation of staA disruption in *S. alvi*.
Figures 24B, 24C, 24D, 24E:
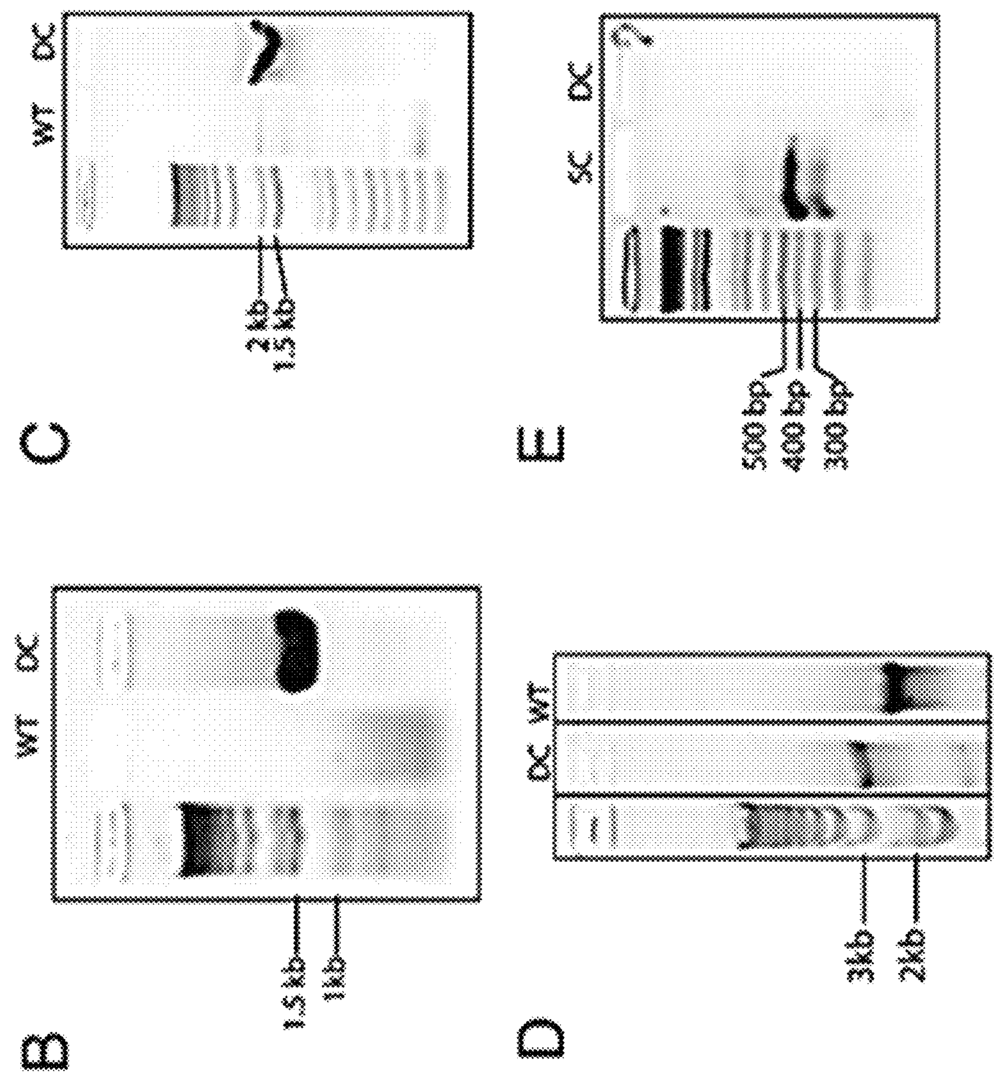
Figure 25A:
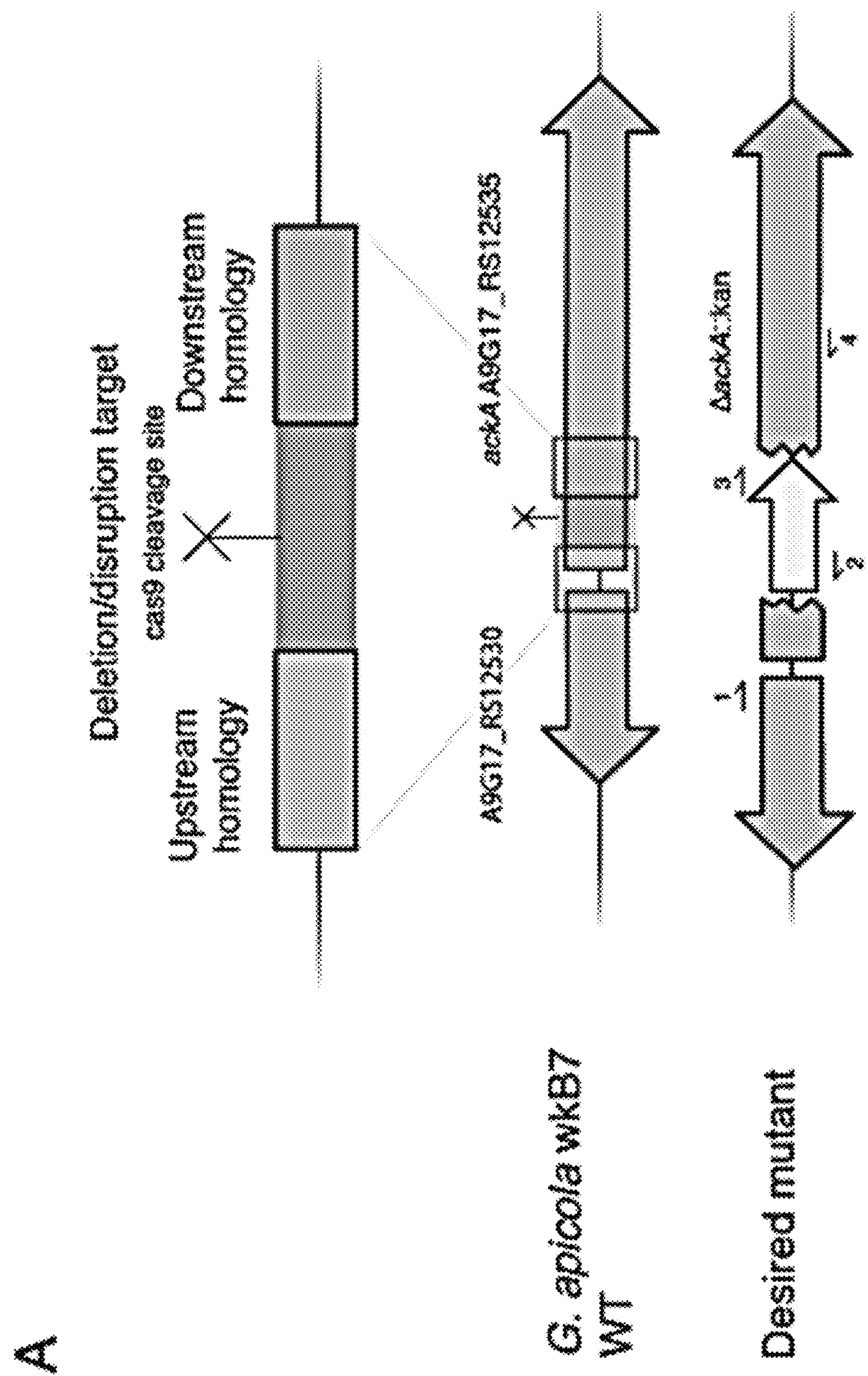
FIGS. 25A-25C: Depicts schematic and validation of ackA disruption in *G. apicola*.
Figures 25B, 25C:
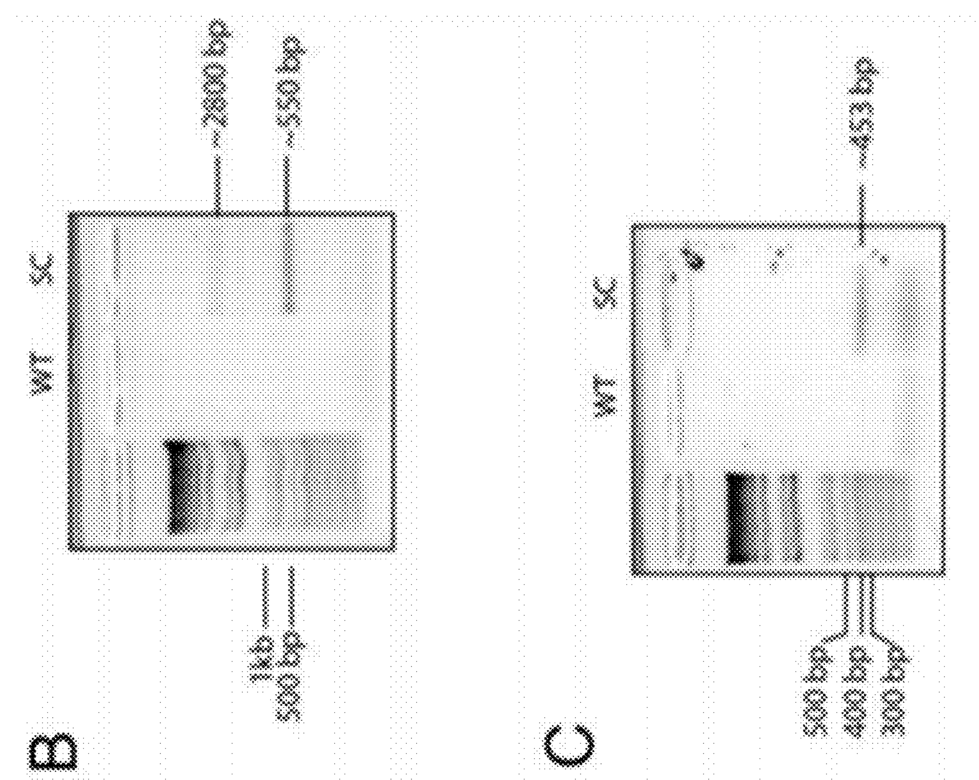
Figure 26A:
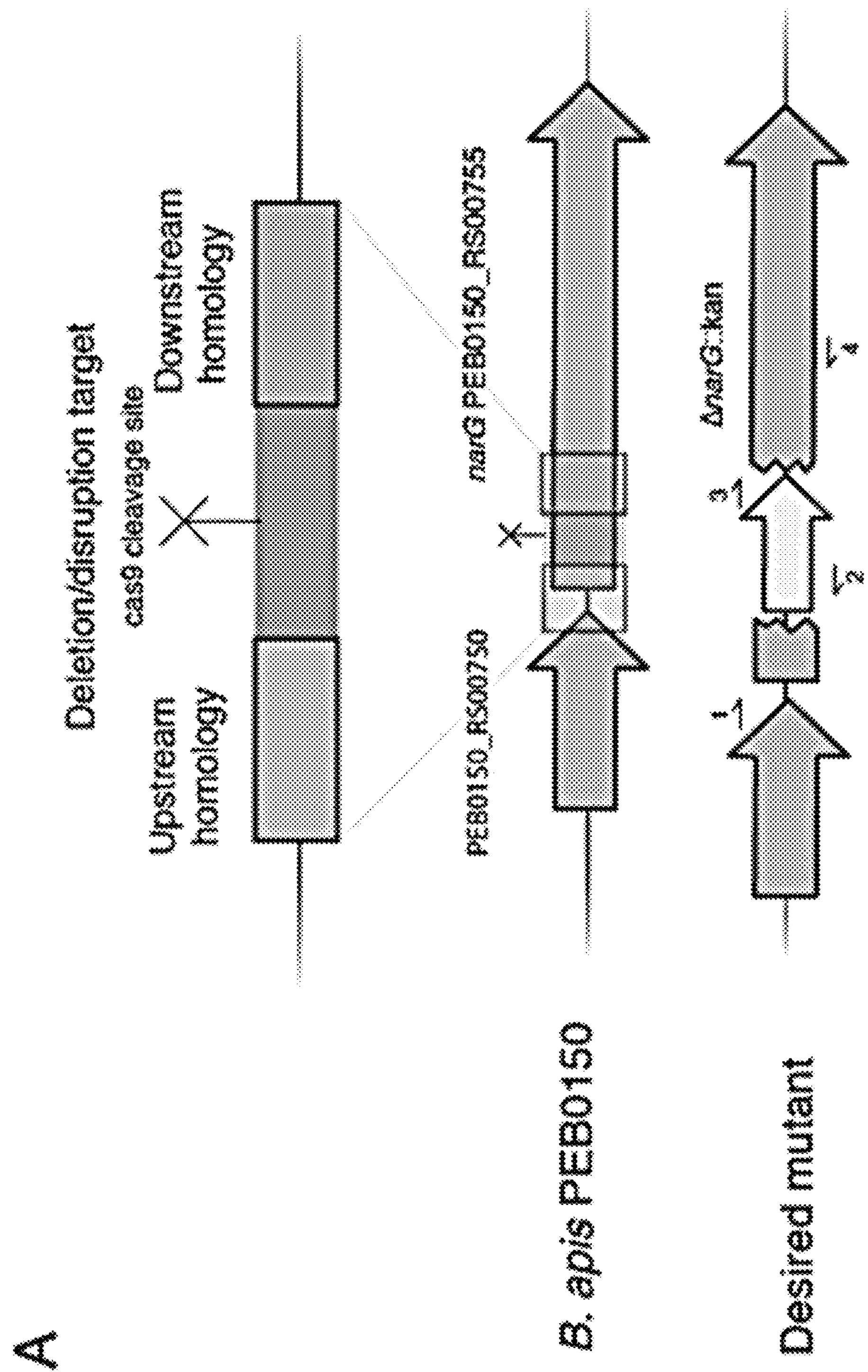
FIGS. 26A-26E: Depicts schematic and validation of narG disruption in *B. apis*.
Figures 26B, 26C, 26D, 26E:
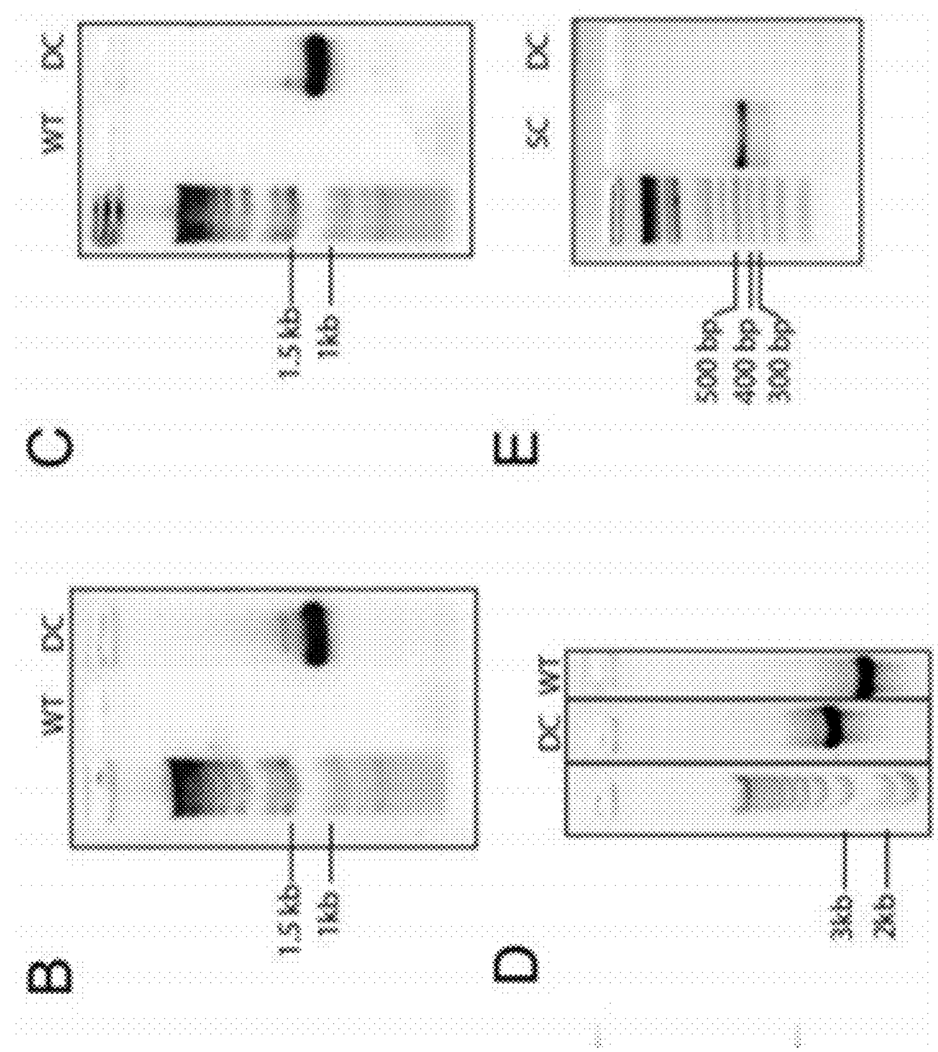

To test the utility of this scheme, it was attempted to generate gene disruptions in three BGM species. In *S. alvi* wkB2 staA (SALWKB2_RS11470) was targeted, an adhesion gene previously implicated in a genome-wide screen as important for gut colonization (FIG. 24) (Powell J E et al., 2016, Proc Natl Acad Sci USA, 113:13887-13892). In *G. apicola* wkB7 acetate kinase ackA was targeted (A9G17_RS12535) (FIG. 25), and in *B. apis* PEB0150 nitrate reductase narG (PEB0150_RS00755) was targeted (FIG. 26). Homology regions were designed to be internal to each coding sequence, so that even single-crossover events would disrupt gene function. For *S. alvi* wkB2, the multistep system showed higher efficiency compared to basic homologous recombination not using Cas9. In the presence of Cas9, wkB2 mutants were obtained more frequently and were more often double-crossover mutants (FIG. 13D). In contrast, *B. apis* PEB0150 showed relatively high gene disruption efficiency even in the absence of Cas9, and the Cas9 system had little effect on improving the number of double-crossover mutants (FIG. 13C). In *G. apicola* wkB7 the Cas9 was also not helpful, and no double-crossover mutants were obtained (FIG. 13E). The *G. apicola* wkB7 mutants isolated showed irregular PCR amplification at the expected junctions (FIG. 25), indicating that it could not effectively disrupt ackA, perhaps because it is an essential gene in this species. These experiments validated this general approach to gene disruption in multiple BGM species.

Engineered Strains Colonize Bees and can be Directly Visualized in the Ileum

Figures 14A, 14B, 14C, 14D, 14E:
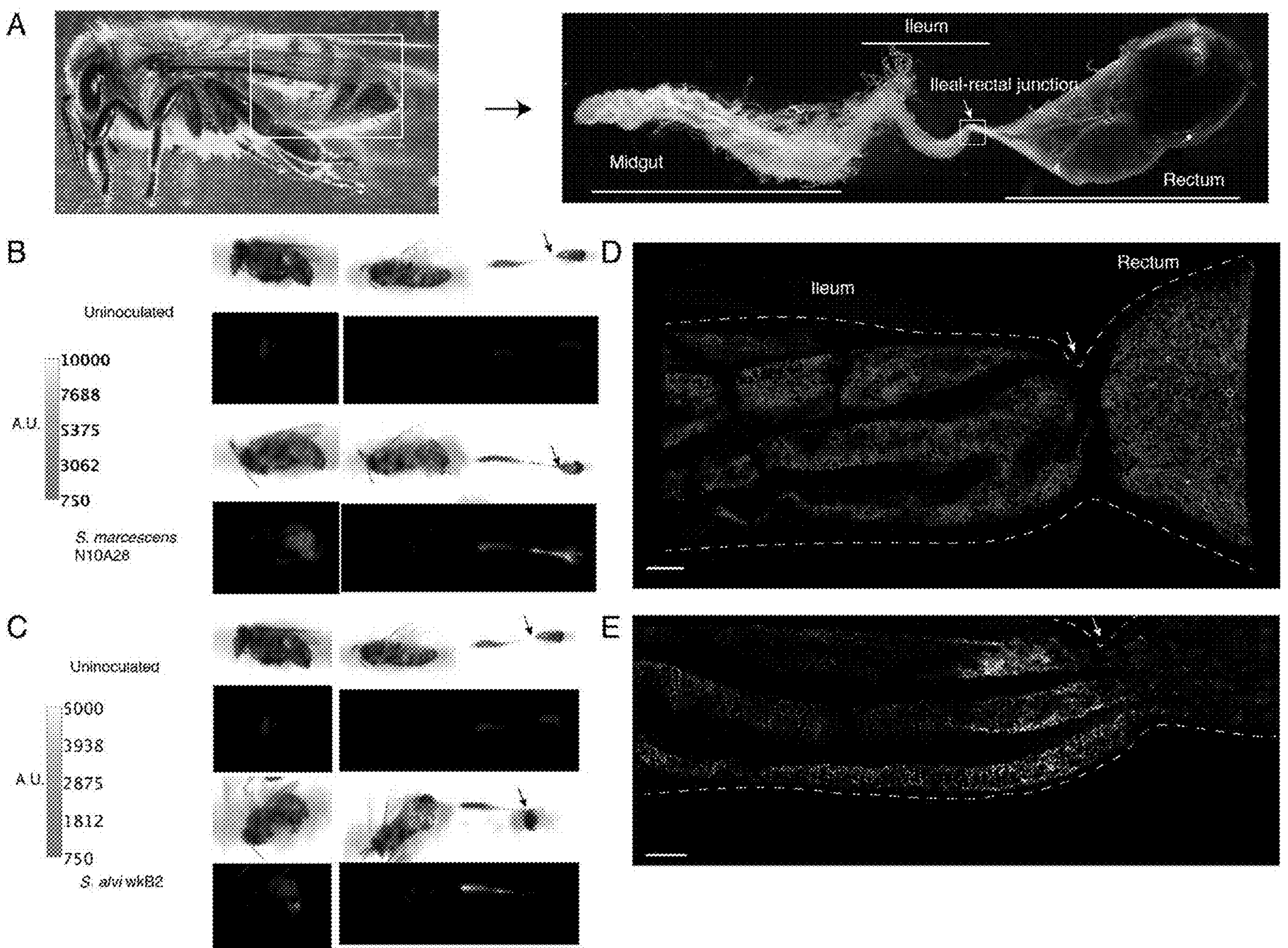
FIGS. 14A-14E: Depicts visualization of engineered bacteria in the honey bee gut.
Figures 15A, 15B, 15C, 15D:
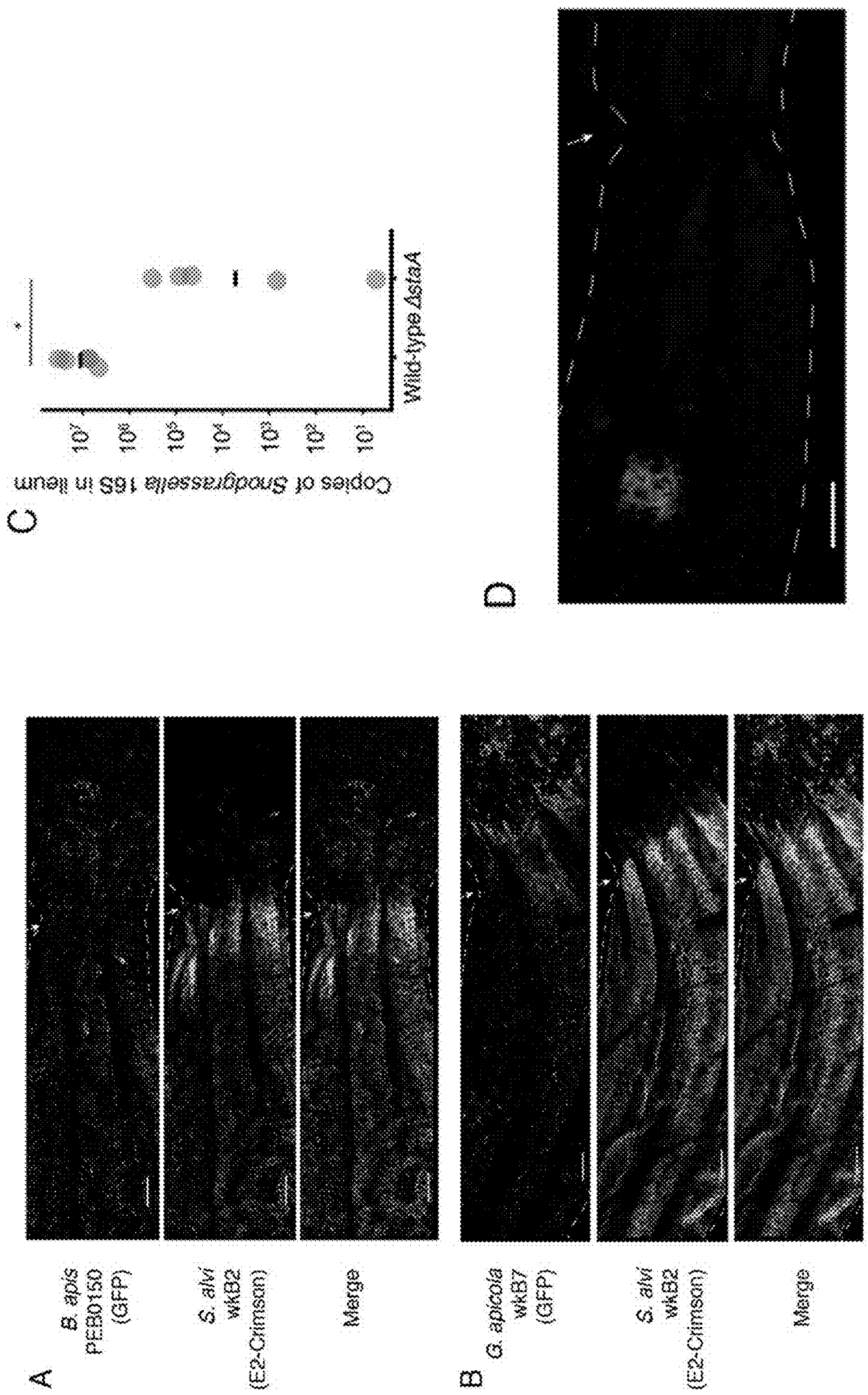
FIGS. 15A-15D: Depicts visible co-inoculation of the bee gut with species from the bee gut microbiota and the role of staA in colonization.

Next the ability of engineered BGM strains to colonize newly emerged worker bees removed from the hive before they acquire a normal microbiota was tested. Previously, *S. alvi* and *G. apicola* have been visualized in bees using fluorescent in situ hybridization (Martinson V G et al., 2012, Apl Environ Microbiol., 78:2830-2840). However, this technique can only be used at one time point because it requires sacrificing the bee. In contrast, fluorescent reporter strains can be used to non-destructively estimate bacterial abundance and observe how bacterial community structure changes over time in live bees. Previous studies have examined how *S. alvi* colonizes the honey bee gut (Kwong W K et al., 2014, Proc Narl Acad Sci USA., 111:11509-11514; Engel P et al., 2013, J of Api Res., 52:1-24), but colonization by *G. apicola, B. apis*, and *S. marcescens* has not been investigated (Raymann K et al., 2017, PLoS Biol., 15:e2001861; Burritt N L et al., 2016, PLoS One., 11:e0167752). Newly emerged workers with ~$10^4$ CFU per bee of either *S. marcescens* N10A28 or *S. alvi* wkB2 was inoculated, each carrying a constitutively expressed E2-Crimson fluorescent protein (pBTK570). After 5 days, bees from each group were dissected and their guts were examined (FIG. 14). Fluorescent bacteria were successfully imaged directly in guts without preparation or fixation, preserving natural community structure. *S. marcescens* N10A28 shows robust colonization in all gut compartments, while other species show spatially restricted colonization. As previously reported, *S. alvi* wkB2 robustly colonizes the ileum, with little colonization in the midgut and rectum. Additionally, co-inoculations with *S. alvi* wkB2 and either *B. apis* PEB0150 or *G. apicola* wkB7 engineered were performed to express GFP (pBTK520). The guts of colonized bees were again dissected and fluorescently imaged in vivo co-colonization of these defined communities (FIG. 15A, FIG. 15B). While both *B. apis* and *G. apicola* are found in the ileum colocated with *S. alvi*, they also colonize the rectum, in contrast to *S. alvi*.

*Snodgrassella* StaA Contributes to Gut Colonization In Vivo

Finally, it was sought to validate the usefulness of the BTK for disrupting specific genes in BGM species in order to investigate their function. StaA belongs to a family of YadA-like adhesion proteins important for colonization and pathogenicity in multiple host-associated species (Linke D et al., 2006, Trends Microbiol., 14:264-270). These trimeric autotransporter proteins localize to the bacterial membrane and form "lollipop" structures that allow bacteria to adhere to epithelial cells (Ribet D et al., 2015, Microbes Infect, 17:173-183; Tahir El Y et al., 2001, Int J Med Microbiol., 291:209-218). Orthologs of these genes are found in multiple *S. alvi* genomes, including those from honey bee- and bumble bee-associated strains (Kwong W K et a., 2014, Proc Natl Acad Sci USA., 111:11509-11514). In the previous works screening a transposon mutant library identified staA (SALWKB2_RS11470) as necessary for the fitness of *S. alvi* during gut colonization (Powell J E et al., 2016, Proc Natl Acad Sci USA., 113:13887-13892). However, it was not able to isolate a mutant from the library with a transposon disrupting staA, and thus it could not fully characterize and validate the role of this gene. Using the BTK, a ΔstaA mutant was generated in *S. alvi* wkB2 (as described above). The ΔstaA mutant and a wild-type control was labeled with a BTK plasmid expressing E2-Crimson (pBTK570) to assess the effects of disrupting this gene in the context of the bee gut. The wkB2 ΔstaA mutant shows reduced colonization efficacy compared to a wild-type control, as measured by qPCR of *S. alvi* 16S rRNA gene copies (FIG. 15C). The colonization pattern of this mutant in terms of its localization within the gut (FIG. 15D) is distinct from that of wild-type *S. alvi* (FIG. 14E). After 6 days, the mutant does not form the contiguous, robust colonization of the ileum wall seen for the wild type strain. Instead, colonization is apparently restricted to small patches, while the majority of the ileum remains uncolonized.

Example 5: Engineering Bee Guts with Symbiont-Produced dsRNA

These experiments provide data to demonstrate the use of engineered gut bacteria (*Snodgrassella alvi*) to manipulate bee gene expression, behavior, and immune response.

Engineered Symbionts Reduce Viral Replication in Bees.

Emerged bees were engineered with gut bacteria harboring one of six plasmids: (1) "NR"—this is an empty plasmid control, expressing no double-stranded RNA; (2) "dsGFP"—this is a dsRNA control, expressing GFP dsRNA; (3) "DWV T1"—dsRNA with DWV target 1, (4) "DWV T2"—dsRNA with DWV target 2; (5) "DWV T3"—dsRNA with DWV target 3, (6) "DWV T5"—dsRNA with DWV target 5.

After 5 days, bees from each condition were hand fed 5.7e6 viral particles of DWV.

Figure 27:
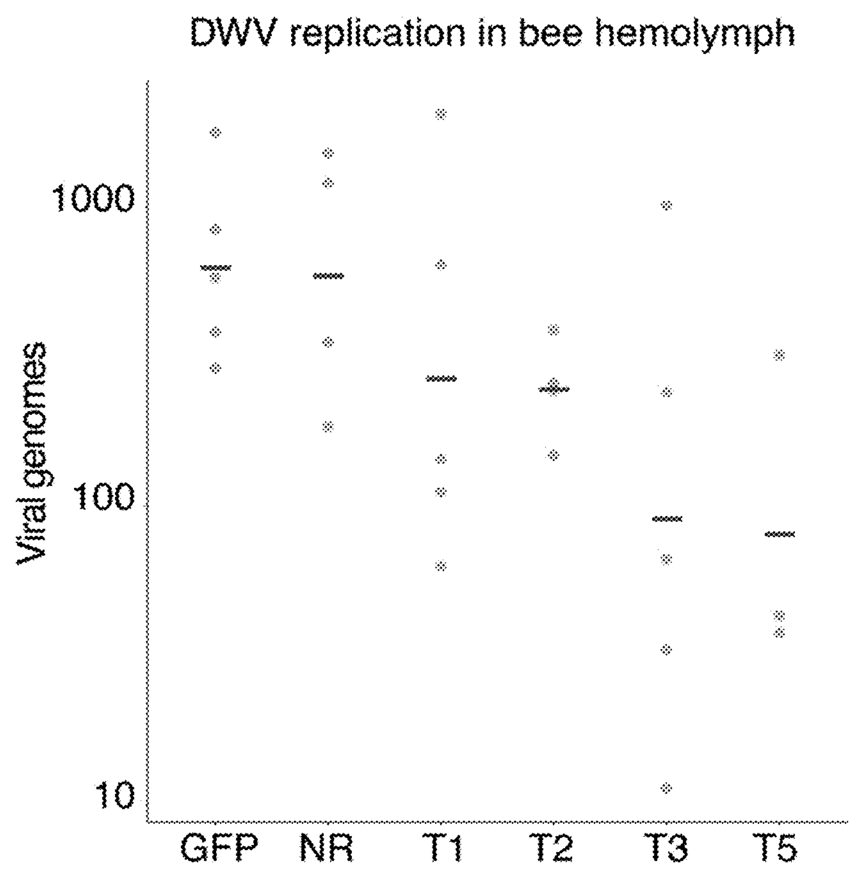
FIG. 27: Depicts exemplary experimental results of DWV replication in bee hemolymph.

After 48 hours, the fat bodies and hemolymph of the bees was dissected, and RNA was isolated from this tissue. cDNA was generated and then absolute qPCR quantification was performed to determine viral genomes (FIG. 27).

Engineered Symbionts Reduce Expression of Target Genes Across Body Tissues.

Emerged bees were engineered with gut bacteria harboring one of three plasmids: (1) "NR"—an empty plasmid control, expressing no double-stranded RNA; (2) "dsGFP"—a dsRNA control, expressing GFP dsRNA; (3) "dsTH"—dsRNA targeting Tyrosine Hydroxylase (TH).

Figure 28:
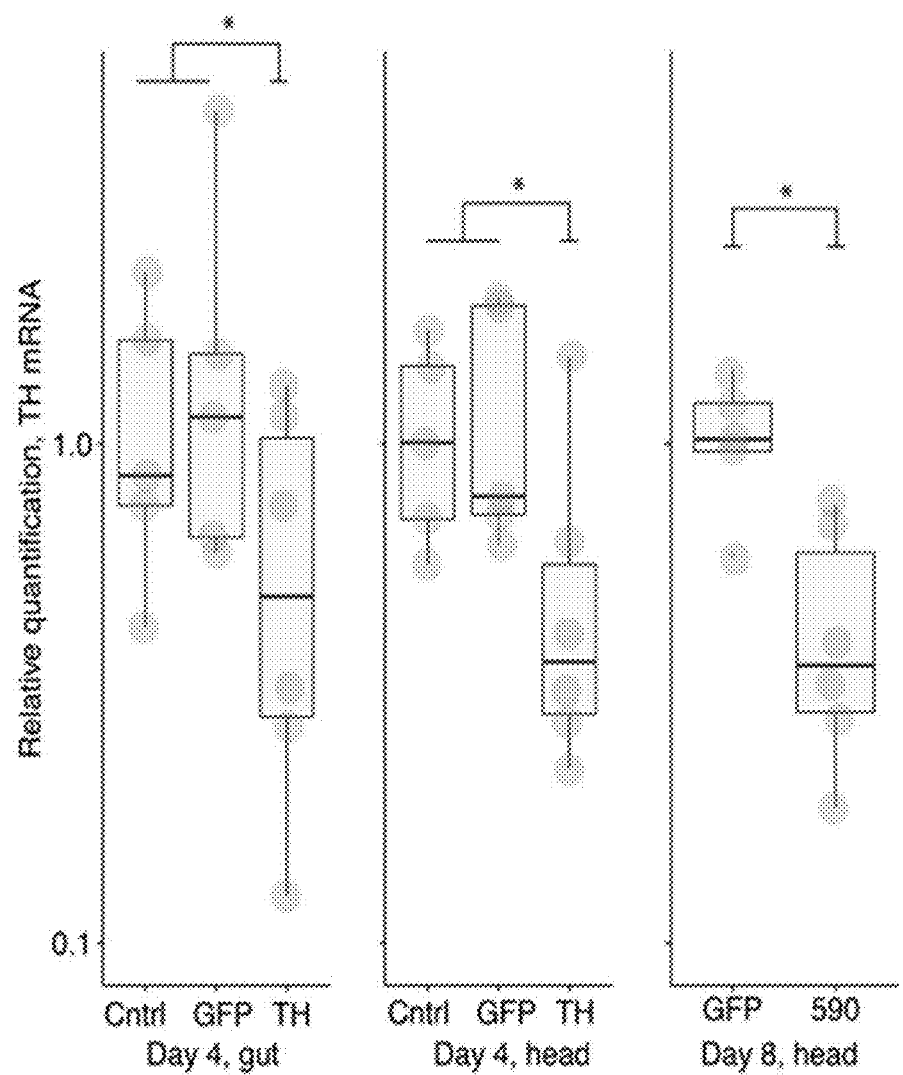
FIG. 28: Depicts exemplary experimental results demonstrating the relative quantification of TH mRNA.

At two time points, Day 4 and Day 8, RNA was isolated from the gut and head, cDNA was generated, and relative quantitation was performed to determine expression (FIG. 28).

Engineered Gut Bacteria Alter Host Behavior.

Behavioral assays were performed on emerged bees engineered with gut bacteria harboring one of three plasmids: (1) "NR"—an empty plasmid control, expressing no double-stranded RNA; (2) "dsGFP"—a dsRNA control, expressing GFP dsRNA; (3) "dsTH"—dsRNA targeting Tyrosine Hydroxylase (TH).

Figure 29:
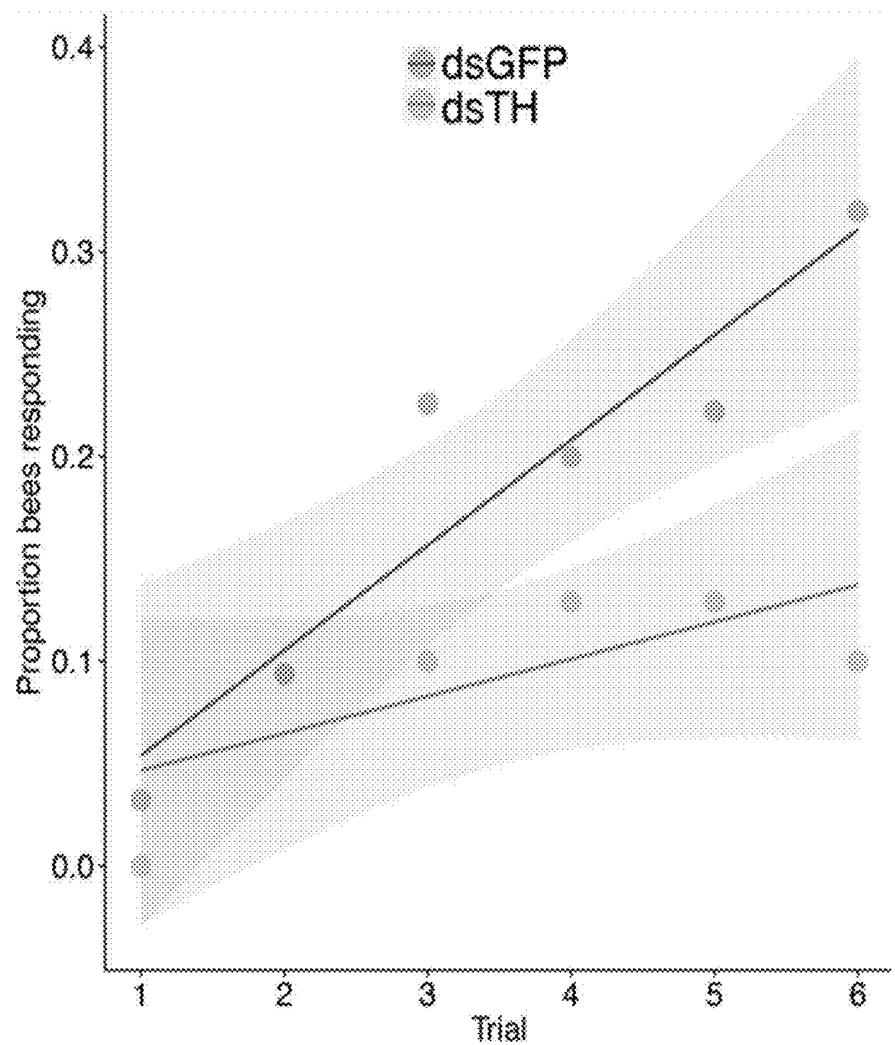
FIG. 29: Depicts exemplary experimental results demonstrating the proportion of bees responding to dsTH or dsGFP.

This behavioral assay measured aversive learning, the ability of bees to learn to associate a scent with a shock. Bees colonized with bacteria expressing dsTH learned significantly more slowly than bees colonized with control bacteria (dsGFP) (FIG. 29).

Suppression of *Varroa* with Engineered Gut Bacteria.

*Varroa* mites are the major bee pest, and suppressing them is a promising application of dsRNA technology. Emerged bees are engineered with gut bacteria expressing at least one dsRNA with sequence specific to essential *Varroa* genes. Targets are present individually or as a composite of multiple targeting sequences. This dsRNA moves into the bee hemolymph and when *Varroa* mites feed, they will induce a lethal self-targeting RNAi response. This is different from the previous described RNAi work because the RNAi response is in the *Varroa* mite, not the bee.

Experimental Design: Colonize bees with gut bacteria expressing *Varroa* targeting constructs (dsVarroa), capture live *Varroa* mites from hives, expose defined number of *Varroa* mites to bees, and measure mortality of *Varroa* mites fed on dsVarroa bees. Compare to control NR and dsGFP colonized bees.

Suppression of *Nosema* with Engineered Gut Bacteria.

*Nosema* is another pathogen of bees. Suppression of *Nosema* in bees is approached in two ways: (1) use symbiont-mediated RNAi to alter and strengthen the bee immune response, and (2) trigger lethal RNAi in *Nosema*.

Experimental Design: Colonize bees with gut bacteria expression lethal *Nosema* RNAi or immune-strengthening RNAi, expose bees to a defined number of *Nosema* spores, after 48-72 hours, count the number of *Nosema* spores. Compare to control bees with no RNAi or control dsGFP RNAi.

Suppression of Small Hive Beetle with Engineered Gut Bacteria.

The small hive beetle is another major pest in beekeeping. Unlike DWV, *Varroa*, and *Nosema*, however, it does not attack bees directly, but instead it feeds on hive components. Therefore, to target this insect with bacterially induced RNAi, the approach is different. For this a different bacterial species that can live in hive materials, such as *Parasaccharibacter apium* or *Lactobacillus* sp. is used. These bacteria are transformed to produce dsRNA identical to an essential hive beetle gene. When these bacteria are consumed by the hive beetle, they would kill the beetles or impair their reproduction.

Example 6: Persistence of Engineered Bacteria in Host

Two separate cohorts of bees were obtained from different hives and allowed to emerge in lab. Within 24 hours after emergence, bees were inoculated with ~1e04 CFU of *S. alvi* wkB2 engineered to constitutively express GFP (plasmid pBTK520) and separated into individual cups with 5-10 bees. Bees were fed sucrose solution supplemented with 60 ug/mL spectinomycin. Every five days, five to eight bees from each cohort were dissected and their entire gut contents plated on selective media with spectinomycin to estimate the CFU of engineered *S. alvi* remaining in their gut.

Figure 30:
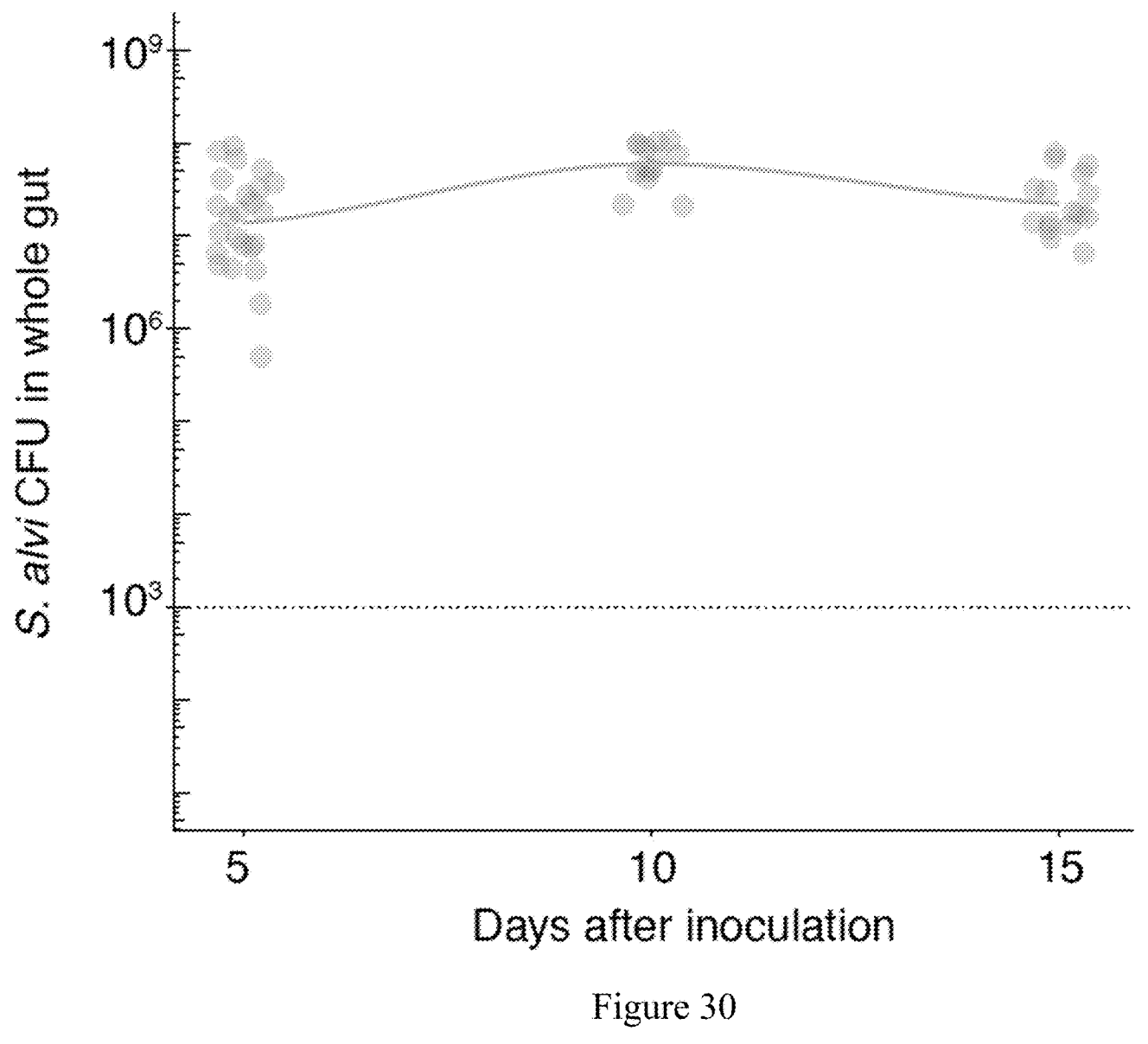

Across all three time points, no significant difference existed between time points or hives in this experiment. Over 99% of colonies were fluorescent in each sample, indicating the genetic device remained functional (FIG. 30). This shows that engineered *S. alvi* wkB2 persistently colonizes and functions in the bee gut despite different bee genetic backgrounds. Bees were fed spectinomycin to maintain the plasmid, but other strategies could be used to ensure maintenance and function of the device in engineered strains (ie, chromosomal incorporation).

Engineered *S. alvi* persists and functions over the measured lifetime of the bee in laboratory environments. Without being bound by theory, it is expected that the engineered gut bacteria would persist over the lifetime in bees in their natural environment, as well.

Example 7: Sequences

| SEQ ID NO | Description |
| --- | --- |
| SEQ ID NO: 1 | pMMB67EH |
| SEQ ID NO: 2 | pBTK520 |
| SEQ ID NO: 3 | pBTK570 |
| SEQ ID NO: 4 | pBTK562 |
| SEQ ID NO: 5 | pBTK561 |
| SEQ ID NO: 6 | pBTK590 |
| SEQ ID NO: 8 | pBTK401 |
| SEQ ID NO: 9 | pBTK402 |
| SEQ ID NO: 10 | pBTK403 |
| SEQ ID NO: 11 | pBTK599 |
| SEQ ID NO: 12 | CP25 (lacO) promoter |
| SEQ ID NO: 36 | pBTK001 |
| SEQ ID NO: 37 | T7 promoter + RBS |
| SEQ ID NO: 38 | Lac lacO inducible promoter + RBS |
| SEQ ID NO: 39 | CP25 pomoter + RBS |
| SEQ ID NO: 40 | CP6 promoter + RBS |
| SEQ ID NO: 41 | CP12b promoter + RBS |
| SEQ ID NO: 42 | CP32 promoter + RBS |
| SEQ ID NO: 43 | PA1 promoter + RBS |
| SEQ ID NO: 44 | PA2 promoter + RBS |
| SEQ ID NO: 45 | PA3 promoter + RBS |
| SEQ ID NO: 46 | CP25 + RBS reverse |
| SEQ ID NO: 47 | dCas9 |
| SEQ ID NO: 48 | rpoC terminator |
| SEQ ID NO: 49 | Bba_B0015 terminator |
| SEQ ID NO: 50 | T7 terminator |
| SEQ ID NO: 51 | pBTK102 |
| SEQ ID NO: 52 | pBTK103 |
| SEQ ID NO: 53 | pBTK107 |

-continued

| SEQ ID NO | Description |
| --- | --- |
| SEQ ID NO: 54 | pBTK110 |
| SEQ ID NO: 55 | pBTK112 |
| SEQ ID NO: 56 | pBTK113 |
| SEQ ID NO: 57 | pBTK119 |
| SEQ ID NO: 58 | pBTK120 |
| SEQ ID NO: 59 | pBTK121 |
| SEQ ID NO: 60 | pBTK138 |
| SEQ ID NO: 61 | pBTK200 |
| SEQ ID NO: 62 | pBTK203 |
| SEQ ID NO: 63 | pBTK205 |
| SEQ ID NO: 64 | pBTK206 |
| SEQ ID NO: 65 | pBTK209 |
| SEQ ID NO: 66 | pBTK211 |
| SEQ ID NO: 67 | pBTK224 |
| SEQ ID NO: 68 | pBTK229 |
| SEQ ID NO: 69 | pBTK300 |
| SEQ ID NO: 70 | pBTK301 |
| SEQ ID NO: 71 | pBTK305 |
| SEQ ID NO: 72 | pBTK527 |
| SEQ ID NO: 73 | pBTK57alpha |
| SEQ ID NO: 74 | pBTK599s |
| SEQ ID NO: 75 | pBTK501 |
| SEQ ID NO: 76 | pBTK503 |
| SEQ ID NO: 77 | pBTK509 |
| SEQ ID NO: 78 | pBTK510 |
| SEQ ID NO: 79 | pBTK519 |
| SEQ ID NO: 80 | pBTK520 |
| SEQ ID NO: 81 | pBTK549 |
| SEQ ID NO: 82 | pBTK541 |
| SEQ ID NO: 83 | pBTK550d |
| SEQ ID NO: 84 | pBTK552 |
| SEQ ID NO: 85 | pBTK563 |
| SEQ ID NO: 86 | pBTK564 |
| SEQ ID NO: 87 | pBTK569 |
| SEQ ID NO: 88 | pBTK570 |
| SEQ ID NO: 89 | pBTK601 |
| SEQ ID NO: 90 | pBTK614 |
| SEQ ID NO: 91 | pBTK615 |
| SEQ ID NO: 92 | pBTK619 |
| SEQ ID NO: 93 | pBTK620 |
| SEQ ID NO: 94 | pBTK621 |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A bee-ingestible microbial composition comprising one or more bacteria genetically engineered to express at least one heterologous nucleic acid, wherein the heterologous nucleic acid is heterologous to a host bee, and further wherein the one or more bacteria are selected from the group consisting of *Snodgrassella alvi, Bartonella apis, Gilliamella apicola*, and *Parasaccharibacter apium*.

2. The composition of claim 1, wherein the host bee is selected from the group consisting of a honey bee and a bumble bee.

3. The composition of claim 1, wherein the composition comprises 2, 3, 4, or 5 bacterial species selected from the group consisting of *Snodgrassella alvi, Bartonella apis, Gilliamella apicola, Serratia marcescens*, and *Parasaccharibacter apium.*

4. The composition of claim 1, wherein the one or more bacteria express at least two heterologous nucleic acids.

5. The composition of claim 1, wherein the heterologous nucleic acid encodes a polypeptide.

6. The composition of claim 5, wherein the heterologous nucleic acid encodes a pesticide degrading polypeptide or a cytochrome.

7. The composition of claim 1, wherein the heterologous nucleic acid is an inhibitory nucleic acid.

8. The composition of claim 7, wherein the inhibitory nucleic acid is selected from the group consisting of an antisense DNA, dsRNA, siRNA, shRNA, sgRNA and a miRNA.

9. The composition of claim 1, wherein the composition comprises a broad host range plasmid that either comprises or can express the at least one heterologous nucleic acid.

10. The composition of claim 9, wherein the broad host range plasmid comprises at least one regulatory sequence selected from the group consisting of an RSF 1010 origin of replication, a PA1 promoter sequence, a PA2 promoter sequence, a PA3 promoter sequence, a cp25 promoter sequence, and a detectable marker.

11. The composition of claim 1, wherein the composition comprises at least one selected from the group consisting of:

a) a live suspension comprising the bacteria,
b) a lyophilized powder comprising the bacteria,
c) a solid comprising the bacteria,
d) a liquid comprising the bacteria,
e) protein,
f) pollen,
g) a sucrose solution comprising the bacteria, and
h) a corn syrup solution comprising the bacteria.

12. The composition of claim 11, further comprising a carbohydrate or sugar supplement.

13. A bee comprising the composition of claim 1.

14. The bee of claim 13, wherein the bee is a honey bee.

* * * * *

SEQUENCE LISTING

<160> NUMBER OF SEQ ID NOS: 94

<210> SEQ ID NO 1
<211> LENGTH: 8828
<212> TYPE: DNA
<213> ORGANISM: Artificial Sequence
<220> FEATURE:
<223> OTHER INFORMATION: Chemically Synthesized,

<400> SEQUENCE: 1

-continued

```
agcttggctg ttttggcgga tgagagaaga ttttcagcct gatacagatt aaatcagaac     60
gcagaagcgg tctgataaaa cagaatttgc ctggcggcag tagcgcggtg gtcccacctg    120
accccatgcc gaactcagaa gtgaaacgcc gtagcgccga tggtagtgtg gggtctcccc    180
atgcgagagt agggaactgc caggcatcaa ataaaacgaa aggctcagtc gaaagactgg    240
gcctttcgtt ttatctgttg tttgtcggtg aacgctctcc tgagtaggac aaatccgccg    300
ggagcggatt tgaacgttgc gaagcaacgg cccggagggt ggcgggcagg acgcccgcca    360
taaactgcca ggcatcaaat taagcagaag gccatcctga cggatggcct ttttgcgttt    420
ctacaaactc ttttgtttat ttttctaaat acattcaaat atgtatccgc tcatgagaca    480
ataaccctga taaatgcttc aataatattg aaaaaggaag agtatgagta ttcaacattt    540
ccgtgtcgcc cttattccct tttttgcggc attttgcctt cctgtttttg ctcacccaga    600
aacgctggtg aaagtaaaag atgctgaaga tcagttgggt gcacgagtgg gttacatcga    660
actggatctc aacagcggta agatccttga gagttttcgc cccgaagaac gttttccaat    720
gatgagcact tttaaagttc tgctatgtgg cgcggtatta tcccgtgttg acgccgggca    780
agagcaactc ggtcgccgca tacactattc tcagaatgac ttggttgagt actcaccagt    840
cacagaaaag catcttacgg atggcatgac agtaagagaa ttatgcagtg ctgccataac    900
catgagtgat aacactgcgg ccaacttact tctgacaacg atcggaggac cgaaggagct    960
aaccgctttt ttgcacaaca tgggggatca tgtaactcgc cttgatcgtt gggaaccgga   1020
gctgaatgaa gccataccaa acgacgagcg tgacaccacg atgcctgtag caatggcaac   1080
aacgttgcgc aaactattaa ctggcgaact acttactcta gcttcccggc aacaattaat   1140
agactggatg gaggcggata aagttgcagg accacttctg cgctcggccc ttccggctgg   1200
ctggtttatt gctgataaat ctggagccgg tgagcgtggg tctcgcggta tcattgcagc   1260
actggggcca gatggtaagc cctcccgtat cgtagttatc tacacgacgg ggagtcaggc   1320
aactatggat gaacgaaata gacagatcgc tgagataggt gcctcactga ttaagcattg   1380
gtaactgtca gaccaagttt actcatatat actttagatt gatttctgaa agcgaccagg   1440
tgctcggcgt ggcaagactc gcagcgaacc cgtagaaagc catgctccag ccgcccgcat   1500
tggagaaatt cttcaaattc ccgttgcaca tagcccggca attcctttcc ctgctctgcc   1560
ataagcgcag cgaatgccgg gtaatactcg tcaacgatct gatagagaag ggtttgctcg   1620
ggtcggtggc tctggtaacg accagtatcc cgatcccggc tggccgtcct ggccgccaca   1680
tgaggcatgt tccgcgtcct tgcaatactg tgtttacata cagtctatcg cttagcggaa   1740
agttctttta ccctcagccg aaatgcctgc cgttgctaga cattgccagc cagtgcccgt   1800
cactcccgta ctaactgtca cgaacccctg caataactgt cacgcccccc tgcaataact   1860
gtcacgaacc cctgcaataa ctgtcacgcc cccaaacctg caaacccagc aggggcgggg   1920
gctggcgggg tgttggaaaa atccatccat gattatctaa gaataatcca ctaggcgcgg   1980
ttatcagcgc ccttgtgggg cgctgctgcc cttgcccaat atgcccggcc agaggccgga   2040
tagctggtct attcgctgcg ctaggctaca caccgcccca ccgctgcgcg gcagggggaa   2100
aggcgggcaa agcccgctaa accccacacc aaaccccgca gaaatacgct ggagcgcttt   2160
tagccgcttt agcggccttt ccccctaccc gaagggtggg ggcgcgtgtg cagccccgca   2220
gggcctgtct cggtcgatca ttcagcccgg ctcatccttc tggcgtggcg gcagaccgaa   2280
caaggcgcgg tcgtggtcgc gttcaaggta cgcatccatt gccgccatga gccgatcctc   2340
```

```
cggccactcg ctgctgttca ccttggccaa aatcatggcc cccaccagca ccttgcgcct   2400

tgtttcgttc ttgcgctctt gctgctgttc ccttgcccgc tcccgctgaa tttcggcatt   2460

gattcgcgct cgttgttctt cgagcttggc cagccgatcc gccgccttgt tgctcccctt   2520

aaccatcttg acaccccatt gttaatgtgc tgtctcgtag gctatcatgg aggcacagcg   2580

gcggcaatcc cgaccctact ttgtagggga gggcgcactt accggtttct cttcgagaaa   2640

ctggcctaac ggccaccctt cgggcggtgc gctctccgag ggccattgca tggagccgaa   2700

aagcaaaagc aacagcgagg cagcatggcg atttatcacc ttacggcgaa aaccggcagc   2760

aggtcgggcg gccaatcggc cagggccaag gccgactaca tccagcgcga aggcaagtat   2820

gcccgcgaca tggatgaagt cttgcacgcc gaatccgggc acatgccgga gttcgtcgag   2880

cggcccgccg actactggga tgctgccgac ctgtatgaac gcgccaatgg gcggctgttc   2940

aaggaggtcg aatttgccct gccggtcgag ctgaccctcg accagcagaa ggcgctggcg   3000

tccgagttcg cccagcacct gaccggtgcc gagcgcctgc cgtatacgct ggccatccat   3060

gccggtggcg gcgagaaccc gcactgccac ctgatgatct ccgagcggat caatgacggc   3120

atcgagcggc ccgccgctca gtggttcaag cggtacaacg gcaagacccc ggagaagggc   3180

ggggcacaga agaccgaagc gctcaagccc aaggcatggc ttgagcagac ccgcgaggca   3240

tgggccgacc atgccaaccg ggcattagag cgggctggcc acgacgcccg cattgaccac   3300

agaacacttg aggcgcaggg catcgagcgc ctgcccggtg ttcacctggg gccgaacgtg   3360

gtggagatgg aaggccgggg catccgcacc gaccgggcag acgtggccct gaacatcgac   3420

accgccaacg cccagatcat cgacttacag gaataccggg aggcaataga ccatgaacgc   3480

aatcgacaga gtgaagaaat ccagaggcat caacgagtta gcggagcaga tcgaaccgct   3540

ggcccagagc atggcgacac tggccgacga agcccggcag gtcatgagcc agaccaagca   3600

ggccagcgag gcgcaggcgg cggagtggct gaaagcccag cgccagacag ggcggcatg    3660

ggtggagctg gccaaagagt tgcgggaggt agccgccgag gtgagcagcg ccgcgcagag   3720

cgcccggagc gcgtcgcggg ggtggcactg gaagctatgg ctaaccgtga tgctggcttc   3780

catgatgcct acggtggtgc tgctgatcgc atcgttgctc ttgctcgacc tgacgccact   3840

gacaaccgag gacggctcga tctggctgcg cttggtggcc cgatgaagaa cgacaggact   3900

ttgcaggcca taggccgaca gctcaaggcc atgggctgtg agcgcttcga tatcggcgtc   3960

agggacgcac ccaccggcca gatgatgaac cgggaatggt cagccgccga agtgctccag   4020

aacacgccat ggctcaagcg gatgaatgcc cagggcaatg acgtgtatat caggcccgcc   4080

gagcaggagc ggcatggtct ggtgctggtg gacgacctca gcgagtttga cctggatgac   4140

atgaaagccg agggccggga gcctgccctg gtagtggaaa ccagcccgaa gaactatcag   4200

gcatgggtca aggtggccga cgccgcaggc ggtgaacttc gggggcagat tgcccggacg   4260

ctggccagcg agtacgacgc cgacccggcc agcgccgaca gccgccacta tggccgcttg   4320

gcgggcttca ccaaccgcaa ggacaagcac accacccgcg ccggttatca gccgtgggtg   4380

ctgctgcgtg aatccaaggg caagaccgcc accgctggcc cggcgctggt gcagcaggct   4440

ggccagcaga tcgagcaggc ccagcggcag caggagaagg cccgcaggct ggccagcctc   4500

gaactgcccg agcggcagct tagccgccac cggcgcacgg cgctggacga gtaccgcagc   4560

gagatggccg ggctggtcaa gcgcttcggt catgacctca gcaagtgcga ctttatcgcc   4620

gcgcagaagc tggccagccg gggccgcagt gccgaggaaa tcggcaaggc catggccgag   4680

gccagcccag cgctggcaga gcgcaagccc ggccacgaag cggattacat cgagcgcacc   4740
```

```
gtcagcaagg tcatgggtct gcccagcgtc cagcttgcgc gggccgagct ggcacgggca   4800
ccggcacccc gccagcgagg catggacagg ggcgggccag atttcagcat gtagtgcttg   4860
cgttggtact cacgcctgtt atactatgag tactcacgca cagaaggggg ttttatggaa   4920
tacgaaaaaa gcgcttcagg gtcggtctac ctgatcaaaa gtgacaaggg ctattggttg   4980
cccggtggct ttggttatac gtcaaacaag gccgaggctg gccgcttttc agtcgctgat   5040
atggccagcc ttaaccttga cggctgcacc ttgtccttgt tccgcgaaga caagcctttc   5100
ggccccggca agtttctcgg tgactgatat gaaagaccaa aaggacaagc agaccggcga   5160
cctgctggcc agccctgacg ctgtacgcca agcgcgatat gccgagcgca tgaaggccaa   5220
agggatgcgt cagcgcaagt tctggctgac cgacgacgaa tacgaggcgc tgcgcgagtg   5280
cctggaagaa ctcagagcgg cgcagggcgg gggtagtgac ccgccagcg cctaaccacc   5340
aactgcctgc aaaggaggca atcaatggct acccataagc ctatcaatat tctggaggcg   5400
ttcgcagcag cgccgccacc gctggactac gttttgccca acatggtggc cggtacggtc   5460
ggggcgctgg tgtcgcccgg tggtgccggt aaatccatgc tggccctgca actggccgca   5520
cagattgcag gcgggccgga tctgctggag gtgggcgaac tgcccaccgg cccggtgatc   5580
tacctgcccg ccgaagaccc gcccaccgcc attcatcacc gcctgcacgc ccttggggcg   5640
cacctcagcg ccgaggaacg gcaagccgtg gctgacggcc tgctgatcca gccgctgatc   5700
ggcagcctgc ccaacatcat ggccccggag tggttcgacg gcctcaagcg cgccgccgag   5760
ggccgccgcc tgatggtgct ggacacgctg cgccggttcc acatcgagga agaaaacgcc   5820
agcggcccca tggcccaggt catcggtcgc atggaggcca tcgccgccga taccgggtgc   5880
tctatcgtgt tcctgcacca tgccagcaag ggcgcggcca tgatgggcgc aggcgaccag   5940
cagcaggcca gccggggcag ctcggtactg gtcgataaca tccgctggca gtcctacctg   6000
tcgagcatga ccagcgccga ggccgaggaa tggggtgtgg acgacgacca gcgccggttc   6060
ttcgtccgct tcggtgtgag caaggccaac tatggcgcac cgttcgctga tcggtggttc   6120
aggcggcatg acggcggggt gctcaagccc gccgtgctgg agaggcagcg caagagcaag   6180
ggggtgcccc gtggtgaagc ctaagaacaa gcacagcctc agccacgtcc ggcacgaccc   6240
ggcgcactgt ctggcccccg gcctgttccg tgccctcaag cggggcgagc gcaagcgcag   6300
caagctggac gtgacgtatg actacggcga cggcaagcgg atcgagttca gcggcccgga   6360
gccgctgggc gctgatgatc tgcgcatcct gcaagggctg gtggccatgg ctgggcctaa   6420
tggcctagtg cttggcccgg aacccaagac cgaaggcgga cggcagctcc ggctgttcct   6480
ggaacccaag tgggaggccg tcaccgctga atgccatgtg gtcaaaggta gctatcgggc   6540
gctggcaaag gaaatcgggg cagaggtcga tagtggtggg gcgctcaagc acatacagga   6600
ctgcatcgag cgcctttgga aggtatccat catcgcccag aatggccgca agcggcaggg   6660
gtttcggctg ctgtcggagt acgccagcga cgaggcggac gggcgcctgt acgtggccct   6720
gaaccccttg atcgcgcagg ccgtcatggg tggcggccag catgtgcgca tcagcatgga   6780
cgaggtgcgg gcgctggaca gcgaaaccgc ccgcctgctg caccagcggc tgtgtggctg   6840
gatcgacccc ggcaaaaccg gcaaggcttc catagatacc ttgtgcggct atgtctggcc   6900
gtcagaggcc agtggttcga ccatgcgcaa gcgccgcaag cgggtgcgcg aggcgttgcc   6960
ggagctggtc gcgctgggct ggacggtaac cgagttcgcg gcgggcaagt acgacatcac   7020
ccggcccaag gcggcaggct gaccccccc actctattgt aaacaagaca tttttatctt   7080
```

```
ttatattcaa tggcttattt tcctgctaat tggtaatacc atgaaaaata ccatgctcag   7140

aaaaggctta acaatatttt gaaaaattgc ctactgagcg ctgccgcaca gctccatagg   7200

ccgctttcct ggctttgctt ccagatgtat gctcttctgc tcccgaacgc cagcaagacg   7260

tagcccagcg cgtcggccag cttgcaattc gcgctaactt acattaattg cgttgcgctc   7320

actgcccgct ttccagtcgg gaaacctgtc gtgccagctg cattaatgaa tcggccaacg   7380

cgcggggaga ggcggtttgc gtattgggcg ccagggtggt ttttcttttc accagtgaga   7440

cgggcaacag ctgattgccc ttcaccgcct ggccctgaga gagttgcagc aagcggtcca   7500

cgtggtttgc cccagcaggc gaaaatcctg tttgatggtg gttaacggcg ggatataaca   7560

tgagctgtct tcggtatcgt cgtatcccac taccgagata tccgcaccaa cgcgcagccc   7620

ggactcggta atggcgcgca ttgcgcccag cgccatctga tcgttggcaa ccagcatcgc   7680

agtgggaacg atgccctcat tcagcatttg catggtttgt tgaaaaccgg acatggcact   7740

ccagtcgcct tcccgttccg ctatcggctg aatttgattg cgagtgagat atttatgcca   7800

gccagccaga cgcagacgcg ccgagacaga acttaatggg cccgctaaca gcgcgatttg   7860

ctggtgaccc aatgcgacca gatgctccac gcccagtcgc gtaccgtctt catgggagaa   7920

aataatactg ttgatgggtg tctggtcaga gacatcaaga aataacgccg gaacattagt   7980

gcaggcagct tccacagcaa tggcatcctg gtcatccagc ggatagttaa tgatcagccc   8040

actgacgcgt tgcgcgagaa gattgtgcac cgccgcttta caggcttcga cgccgcttcg   8100

ttctaccatc gacaccacca cgctggcacc cagttgatcg gcgcgagatt taatcgccgc   8160

gacaatttgc gacggcgcgt gcagggccag actggaggtg gcaacgccaa tcagcaacga   8220

ctgtttgccc gccagttgtt gtgccacgcg gttgggaatg taattcagct ccgccatcgc   8280

cgcttccact ttttcccgcg ttttcgcaga aacgtggctg gcctggttca ccacgcggga   8340

aacggtctga taagagacac cggcatactc tgcgacatcg tataacgtta ctggtttcac   8400

attcaccacc ctgaattgac tctcttccgg gcgctatcat gccataccgc gaaaggtttt   8460

gcaccattcg atggtgtcaa cgtaaatgcc gcttcgcctt cgcgcgcgaa ttgcaagctg   8520

atccgggctt atcgactgca cggtgcacca atgcttctgg cgtcaggcag ccatcggaag   8580

ctgtggtatg gctgtgcagg tcgtaaatca ctgcataatt cgtgtcgctc aaggcgcact   8640

cccgttctgg ataatgtttt ttgcgccgac atcataacgg ttctggcaaa tattctgaaa   8700

tgagctgttg acaattaatc atcggctcgt ataatgtgtg gaattgtgag cggataacaa   8760

tttcacacag gaaacagaat tcgagctcgg tacccgggga tcctctagag tcgacctgca   8820

ggcatgca                                                            8828
```

<210> SEQ ID NO 2
<211> LENGTH: 8272
<212> TYPE: DNA
<213> ORGANISM: Artificial Sequence
<220> FEATURE:
<223> OTHER INFORMATION: Chemically Synthesized,

<400> SEQUENCE: 2

```
acgctacttg cattacagct tacgaaccga acaggcttat gtccactggg ttcgtgcctt     60

catccgtttc cacggtgtgc gtcacccggc aaccttgggt agcagcgaag tcgaggcatt    120

tctgtcctgg ctggtcatga ccaaaatccc ttaacgtgag tcagcctgcc gccttgggcc    180

gggtgatgtc gtacttgccc gccgcgaact cggttaccgt ccagcccagc gcgaccagct    240

ccggcaacgc ctcgcgcacc cgcttgcggc gcttgcgcat ggtcgaacca ctggcctctg    300
```

```
acggccagac atagccgcac aaggtatcta tggaagcctt gccggttttg ccggggtcga    360
tccagccaca cagccgctgg tgcagcaggc gggcggtttc gctgtccagc gcccgcacct    420
cgtccatgct gatgcgcaca tgctggccgc cacccatgac ggcctgcgcg atcaaggggt    480
tcagggccac gtacaggcgc ccgtccgcct cgtcgctggc gtactccgac agcagccgaa    540
acccctgccg cttgcggcca ttctgggcga tgatggatac cttccaaagg cgctcgatgc    600
agtcctgtat gtgcttgagc gccccaccac tatcgacctc tgccccgatt tcctttgcca    660
gcgcccgata gctacctttg accacatggc attcagcggt gacggcctcc cacttgggtt    720
ccaggaacag ccggagctgc cgtccgcctt cggtcttggg ttccgggcca agcactaggc    780
cattaggccc agccatggcc accagccctt gcaggatgcg cagatcatca gcgcccagcg    840
gctccgggcc gctgaactcg atccgcttgc cgtcgccgta gtcatacgtc acgtccagct    900
tgctgcgctt gcgctcgccc cgcttgaggg cacggaacag gccgggggcc agacagtgcg    960
ccgggtcgtg ccggacgtgg ctgaggctgt gcttgttctt aggcttcacc acggggcacc   1020
cccttgctct tgcgctgcct ctccagcacg gcgggcttga gcaccccgcc gtcatgccgc   1080
ctgaaccacc gatcagcgaa cggtgcgcca tagttggcct tgctcacacc gaagcggacg   1140
aagaaccggc gctggtcgtc gtccacaccc cattcctcgg cctcggcgct ggtcatgctc   1200
gacaggtagg actgccagcg gatgttatcg accagtaccg agctgccccg gctggcctgc   1260
tgctggtcgc ctgcgcccat catggccgcg cccttgctgg catggtgcag gaacacgata   1320
gagcacccgg tatcggcggc gatggcctcc atgcgaccga tgacctgggc catggggccg   1380
ctggcgtttt cttcctcgat gtggaaccgg cgcagcgtgt ccagcaccat caggcggcgg   1440
ccctcggcgg cgcgcttgag gccgtcgaac cactccgggg ccatgatgtt gggcaggctg   1500
ccgatcagcg gctggatcag caggccgtca gccacggctt gccgttcctc ggcgctgagg   1560
tgcgccccaa gggcgtgcag gcggtgatga atggcggtgg gcgggtcttc ggcgggcagg   1620
tagatcaccg ggccggtggg cagttcgccc acctccagca gatccggccc gcctgcaatc   1680
tgtgcggcca gttgcagggc cagcatggat ttaccggcac caccgggcga caccagcgcc   1740
ccgaccgtac cggccaccat gttgggcaaa acgtagtcca gcggtggcgg cgctgctgcg   1800
aacgcctcca gaatattgat aggcttatgg gtagccattg attgcctcct ttgcaggcag   1860
ttggtggtta ggcgctggcg gggtcactac ccccgccctg cgccgctctg agttcttcca   1920
ggcactcgcg cagcgcctcg tattcgtcgt cggtcagcca gaacttgcgc tgacgcatcc   1980
ctttggcctt catgcgctcg gcatatcgcg cttggcgtac agcgtcaggg ctggccagca   2040
ggtcgccggt ctgcttgtcc ttttggtctt tcatatcagt caccgagaaa cttgccgggg   2100
ccgaaaggct tgtcttcgcg gaacaaggac aaggtgcagc cgtcaaggtt aaggctggcc   2160
atatcagcga ctgaaaagcg gccagcctcg gccttgtttg acgtataacc aaagccaccg   2220
ggcaaccaat agcccttgtc acttttgatc aggtagaccg accctgaagc gcttttttcg   2280
tattccataa aaccccccttc tgtgcgtgag tactcatagt ataacaggcg tgagtaccaa   2340
cgcaagcact acatgctgaa atctggcccg cccctgtcca tgcctcgctg gcggggtgcc   2400
ggtgcccgtg ccagctcggc ccgcgcaagc tggacgctgg gcagacccat gaccttgctg   2460
acggtgcgct cgatgtaatc cgcttcgtgg ccgggcttgc gctctgccag cgctgggctg   2520
gcctcggcca tggccttgcc gatttcctcg gcactgcggc cccggctggc cagcttctgc   2580
gcggcgataa agtcgcactt gctgaggtca tgaccgaagc gcttgaccag cccggccatc   2640
```

-continued

```
tcgctgcggt actcgtccag cgccgtgcgc cggtggcggc taagctgccg ctcgggcagt   2700
tcgaggctgg ccagcctgcg ggccttctcc tgctgccgct gggcctgctc gatctgctgg   2760
ccagcctgct gcaccagcgc cgggccagcg gtggcggtct tgcccttgga ttcacgcagc   2820
agcacccacg gctgataacc ggcgcgggtg gtgtgcttgt ccttgcggtt ggtgaagccc   2880
gccaagcggc catagtggcg gctgtcggcg ctggccgggt cggcgtcgta ctcgctggcc   2940
agcgtccggg caatctgccc ccgaagttca ccgcctgcgg cgtcggccac cttgacccat   3000
gcctgatagt tcttcgggct ggtttccact accagggcag gctcccggcc ctcggctttc   3060
atgtcatcca ggtcaaactc gctgaggtcg tccaccagca ccagaccatg ccgctcctgc   3120
tcggcgggcc tgatatacac gtcattgccc tgggcattca tccgcttgag ccatggcgtg   3180
ttctggagca cttcggcggc tgaccattcc cggttcatca tctggccggt gggtgcgtcc   3240
ctgacgccga tatcgaagcg ctcacagccc atggccttga gctgtcggcc tatggcctgc   3300
aaagtcctgt cgttcttcat cgggccacca agcgcagcca gatcgagccg tcctcggttg   3360
tcagtggcgt caggtcgagc aagagcaacg atgcgatcag cagcaccacc gtaggcatca   3420
tggaagccag catcacggtt agccatagct tccagtgcca cccccgcgac gcgctccggg   3480
cgctctgcgc ggcgctgctc acctcggcgg ctacctcccg caactctttg gccagctcca   3540
cccatgccgc ccctgtctgg cgctgggctt tcagccactc cgccgcctgc gcctcgctgg   3600
cctgcttggt ctggctcatg acctgccggg cttcgtcggc cagtgtcgcc atgctctggg   3660
ccagcggttc gatctgctcc gctaactcgt tgatgcctct ggatttcttc actctgtcga   3720
ttgcgttcat ggtctattgc ctcccggtat tcctgtaagt cgatgatctg ggcgttggcg   3780
gtgtcgatgt tcagggccac gtctgcccgg tcggtgcgga tgccccggcc ttccatctcc   3840
accacgttcg gccccaggtg aacaccgggc aggcgctcga tgccctgcgc ctcaagtgtt   3900
ctgtggtcaa tgcgggcgtc gtggccagcc cgctctaatg cccggttggc atggtcggcc   3960
catgcctcgc gggtctgctc aagccatgcc ttgggcttga gcgcttcggt cttctgtgcc   4020
ccgcccttct ccggggtctt gccgttgtac cgcttgaacc actgagcggc gggccgctcg   4080
atgccgtcat tgatccgctc ggagatcatc aggtggcagt gcgggttctc gccgccaccg   4140
gcatggatgg ccagcgtata cggcaggcgc tcggcaccgg tcaggtgctg ggcgaactcg   4200
gacgccagcg ccttctgctg gtcgagggtc agctcgaccg gcagggcaaa ttcgacctcc   4260
ttgaacagcc gcccattggc gcgttcatac aggtcggcag catcccagta gtcggcgggc   4320
cgctcgacga actccggcat gtgcccggat tcggcgtgca agacttcatc catgtcgcgg   4380
gcatacttgc cttcgcgctg gatgtagtcg gccttggccc tggccgattg gccgcccgac   4440
ctgctgccgg ttttcgccgt aaggtgataa atcgccatgc tgcctcgctg ttgcttttgc   4500
ttttcggctc catgcaatgg ccctcggaga gcgcaccgcc cgaagggtgg ccgttaggcc   4560
agtttctcga agagaaaccg gtaagtgcgc cctcccctac aaagtagggt cgggattgcc   4620
gccgctgtgc ctccatgata gcctacgaga cagcacatta acaatggggt gtcaagatgg   4680
ttaaggggag caacaaggcg gcggatcggc tggccaagct cgaagaacaa cgagcgcgaa   4740
tcaatgccga aattcagcgg gagcgggcaa gggaacagca gcaagagcgc aagaacgaaa   4800
caaggcgcaa ggtgctggtg gggcccatga ttttggccaa ggtgaacagc agcgagtggc   4860
cggaggatcg gctcatggcg gcaatggatg cgtaccttga acgcgaccac gaccgcgcct   4920
tgttcggtct gccgccacgc cagaaggatg agccgggctg aatgatcgac cgagacaggc   4980
cctgcggggc tgcacacgcg cccccaccct tcgggtaggg ggaaaggccg ctaaagcggc   5040
```

-continued

```
taaaagcgct ccagcgtatt tctgcggggt ttggtgtggg gtttagcggg ctttgcccgc   5100
ctttcccccct gccgcgcagc ggtggggcgg tgtgtagcct agcgcagcga atagaccagc   5160
tatccggcct ctggccgggc atattgggca agggcagcag cgccccacaa gggcgctgat   5220
aaccgcgcct agtggattat tcttagataa tcatggatgg atttttccaa caccccgcca   5280
gcccccgccc ctgctgggtt tgcaggtttg ggggcgtgac agttattgca ggggttcgtg   5340
acagttattg caggggggcg tgacagttat tgcaggggtt cgtgacagtt agtacgggag   5400
tgacgggcac tggctggcaa tgtctagcaa cggcaggcat ttcggctgag ggtaaaagaa   5460
ctttccgcta agcgatagac tgtatgtaaa cacagtattg caaggacgcg gaacatgcct   5520
catgtggcgg ccaggacggc cagccgggat cgggatactg gtcgttacca gagccaccga   5580
cccgagcaaa cccttctcta tcagatcgtt gacgagtatt acccggcatt cgctgcgctt   5640
atggcagagc agggaaagga attgccgggc tatgtgcaac gggaatttga agaatttctc   5700
caatgcgggc ggctggagca tggctttcta cgggttcgct gcgagtcttg ccacgccgag   5760
cacctggtcg ctttcagaaa tcaatctaaa gtatatatga gtaaacttgg tctgacaggc   5820
ccctgaattc gcatctagat ggtagagcca caaacagccg gtacaagcaa cgatctccag   5880
gaccatctga atcatgcgcg gatgacacga actcacgacg gcgatcacag acattaaccc   5940
acagtacaga cactgcgaca acgtggcaat tcgtcgcaat accgtctcac tgaactggcc   6000
gataattgca gacgaacgtt atcaaaaaga gtattgactt aaagtctaac ctataggata   6060
cttacagcca tcgagaggga cacggcgagg aattgtgagc ggataacaat tccatacaga   6120
aacagaggag atattacata tgagtaaagg agaagagctt ttcacaggag ttgtcccaat   6180
cctcgtggaa ttagacggtg atgttaatgg gcacaagttc tctgtcagtg gagagggtga   6240
aggcgacgca acatatggca agctgaccct taaatttatt tgcaccacgg gtaaactacc   6300
tgttccatgg ccaacactgg tcactacgtt cgggtatggg gttcagtgct ttgcgcgcta   6360
cccagatcac atgaaacagc acgacttttt caagagtgca atgcccgaag gctatgtaca   6420
ggagagaacc atctttttta aggatgacgg caactataag acacgcgccg aagtgaagtt   6480
cgagggtgat acccttgtta atagaatcga gttaaagggt attgacttta aggaagatgg   6540
aaatatttta ggccacaaac tggaatataa ctataactcc cataatgtgt acattatggc   6600
cgacaagcaa aagaacggta tcaaggttaa cttcaagatc agacacaaca ttgaggatgg   6660
aagcgttcaa ctagccgacc attaccaaca aaacacccca attggcgatg ggcctgtgct   6720
gttaccagac aaccattacc tgtccactca atctgccctt tcgaaagatc ccaacgaaaa   6780
gcgcgaccac atggtccttc ttgagtttgt cacggctgct gggattacac acggcatgga   6840
tgaactatac aaataaatcc gtaatcgtta atccgcaaat aacgtaaaaa cccgcttcgg   6900
cgggtttttt tatgggggga gtttagggaa agagcatttg tcagctgcca atgagacgac   6960
ggggtcatca cggctcatca tgcgccaaac aaatgtgtgc aatacacgct cggatgactg   7020
catgatgacc gcactgactg ggacagcag atccacctaa gcctgtgaga gaagcagaca   7080
cccgacagat caaggcagtt aactagtgca ctgcagtaca ccaggcatca aataaaacga   7140
aaggctcagt cgaaagactg ggcctttcgt tttatctgtt gtttgtcggt gaacgctctc   7200
tactagagtc acactggctc accttcgggt gggcctttct gcgtttatac cgagcggccg   7260
cttatttgcc gactaccttg gtgatctcgc ctttcacgta gtggacaaat tcttccaact   7320
gatctgcgcg cgaggccaag cgatcttctt cttgtccaag ataagcctgt ctagcttcaa   7380
```

```
gtatgacggg ctgatactgg gccggcaggc gctccattgc ccagtcggca gcgacatcct   7440

tcggcgcgat tttgccggtt actgcgctgt accaaatgcg ggacaacgta agcactacat   7500

ttcgctcatc gccagcccag tcgggcggcg agttccatag cgttaaggtt tcatttagcg   7560

cctcaaatag atcctgttca ggaaccggat caaagagttc ctccgccgct ggacctacca   7620

aggcaacgct atgttctctt gcttttgtca gcaagatagc cagatcaatg tcgatcgtgg   7680

ctggctcgaa gatacccgca agaatgtcat tgcgctgcca ttctccaaat tgcagttcgc   7740

gcttagctgg ataacgccac ggaatgatgt cgtcgtgcac aacaatggtg acttctacag   7800

cgcggagaat ctcgctctct ccaggggaag ccgaagtttc caaaaggtcg ttgatcaaag   7860

ctcgccgcgt tgtttcatca agccttacgg tcaccgtaac cagcaaatca atatcactgt   7920

gtggcttcag gccgccatcc actgcggagc cgtacaaatg tacggccagc aacgtcggtt   7980

cgagatggcg ctcgatgacg ccaactacct ctgatagttg agtcgatact tcggcgatca   8040

ccgcttccct cataatgttt aactttgttt tagggcgact gccctgctgc gtaacatcgt   8100

tgctgctcca taacatcaaa catcgaccca cggcgtaacg cgcttgctgc ttggatgccc   8160

gaggcataga ctgtacccca aaaaaacagt cataacaagc catgaaaacc gccactgcgc   8220

cgttaccacc gctgcgttcg gtcaaggttc tggaccagtt gcgtgagcgc at           8272
```

<210> SEQ ID NO 3
<211> LENGTH: 7999
<212> TYPE: DNA
<213> ORGANISM: Artificial Sequence
<220> FEATURE:
<223> OTHER INFORMATION: Chemically Synthesized,

<400> SEQUENCE: 3

```
tccgcttcgt ggccgggctt gcgctctgcc agcgctgggc tggcctcggc catggccttg     60

ccgatttcct cggcactgcg gccccggctg gccagcttct gcgcggcgat aaagtcgcac    120

ttgctgaggt catgaccgaa gcgcttgacc agcccggcca tctcgctgcg gtactcgtcc    180

agcgccgtgc gccggtggcg gctaagctgc cgctcgggca gttcgaggct ggccagcctg    240

cgggccttct cctgctgccg ctgggcctgc tcgatctgct ggccagcctg ctgcaccagc    300

gccgggccag cggtggcggt cttgcccttg gattcacgca gcagcaccca cggctgataa    360

ccggcgcggg tggtgtgctt gtccttgcgg ttggtgaagc ccgccaagcg gccatagtgg    420

cggctgtcgg cgctggccgg gtcggcgtcg tactcgctgg ccagcgtccg ggcaatctgc    480

ccccgaagtt caccgcctgc ggcgtcggcc accttgaccc atgcctgata gttcttcggg    540

ctggtttcca ctaccagggc aggctcccgg ccctcggctt tcatgtcatc caggtcaaac    600

tcgctgaggt cgtccaccag caccagacca tgccgctcct gctcggcggg cctgatatac    660

acgtcattgc cctgggcatt catccgcttg agccatggcg tgttctggag cacttcggcg    720

gctgaccatt cccggttcat catctggccg gtgggtgcgt ccctgacgcc gatatcgaag    780

cgctcacagc ccatggcctt gagctgtcgg cctatggcct gcaaagtcct gtcgttcttc    840

atcgggccac caagcgcagc cagatcgagc cgtcctcggt tgtcagtggc gtcaggtcga    900

gcaagagcaa cgatgcgatc agcagcacca ccgtaggcat catggaagcc agcatcacgg    960

ttagccatag cttccagtgc caccccccgcg acgcgctccg ggcgctctgc gcggcgctgc   1020

tcacctcggc ggctacctcc cgcaactctt tggccagctc cacccatgcc gcccctgtct   1080

ggcgctgggc tttcagccac tccgccgcct gcgcctcgct ggcctgcttg gtctggctca   1140

tgacctgccg ggcttcgtcg gccagtgtcg ccatgctctg ggccagcggt tcgatctgct   1200
```

```
ccgctaactc gttgatgcct ctggatttct tcactctgtc gattgcgttc atggtctatt   1260
gcctcccggt attcctgtaa gtcgatgatc tgggcgttgg cggtgtcgat gttcagggcc   1320
acgtctgccc ggtcggtgcg gatgccccgg ccttccatct ccaccacgtt cggccccagg   1380
tgaacaccgg gcaggcgctc gatgccctgc gcctcaagtg ttctgtggtc aatgcgggcg   1440
tcgtggccag cccgctctaa tgcccggttg gcatggtcgg cccatgcctc gcgggtctgc   1500
tcaagccatg ccttgggctt gagcgcttcg gtcttctgtg ccccgccctt ctccggggtc   1560
ttgccgttgt accgcttgaa ccactgagcg gcgggccgct cgatgccgtc attgatccgc   1620
tcggagatca tcaggtggca gtgcgggttc tcgccgccac cggcatggat ggccagcgta   1680
tacggcaggc gctcggcacc ggtcaggtgc tgggcgaact cggacgccag cgccttctgc   1740
tggtcgaggg tcagctcgac cggcagggca aattcgacct ccttgaacag ccgcccattg   1800
gcgcgttcat acaggtcggc agcatcccag tagtcggcgg gccgctcgac gaactccggc   1860
atgtgcccgg attcggcgtg caagacttca tccatgtcgc gggcatactt gccttcgcgc   1920
tggatgtagt cggccttggc cctggccgat tggccgcccg acctgctgcc ggttttcgcc   1980
gtaaggtgat aaatcgccat gctgcctcgc tgttgctttt gcttttcggc tccatgcaat   2040
ggccctcgga gagcgcaccg cccgaagggt ggccgttagg ccagtttctc gaagagaaac   2100
cggtaagtgc gccctcccct acaaagtagg gtcgggattg ccgccgctgt gcctccatga   2160
tagcctacga gacagcacat taacaatggg gtgtcaagat ggttaagggg agcaacaagg   2220
cggcggatcg gctggccaag ctcgaagaac aacgagcgcg aatcaatgcc gaaattcagc   2280
gggagcgggc aagggaacag cagcaagagc gcaagaacga aacaaggcgc aaggtgctgg   2340
tgggggccat gattttggcc aaggtgaaca gcagcgagtg gccggaggat cggctcatgg   2400
cggcaatgga tgcgtacctt gaacgcgacc acgaccgcgc cttgttcggt ctgccgccac   2460
gccagaagga tgagccgggc tgaatgatcg accgagacag gccctgcggg gctgcacacg   2520
cgcccccacc cttcgggtag gggaaaggc cgctaaagcg gctaaaagcg ctccagcgta   2580
tttctgcggg gtttggtgtg gggtttagcg ggctttgccc gcctttcccc ctgccgcgca   2640
gcggtggggc ggtgtgtagc ctagcgcagc gaatagacca gctatccggc ctctggccgg   2700
gcatattggg caagggcagc agcgccccac aagggcgctg ataaccgcgc ctagtggatt   2760
attcttagat aatcatggat ggatttttcc aacaccccgc cagcccccgc ccctgctggg   2820
tttgcaggtt tgggggcgtg acagttattg caggggttcg tgacagttat tgcagggggg   2880
cgtgacagtt attgcagggg ttcgtgacag ttagtacggg agtgacgggc actggctggc   2940
aatgtctagc aacggcaggc atttcggctg agggtaaaag aactttccgc taagcgatag   3000
actgtatgta aacacagtat tgcaaggacg cggaacatgc ctcatgtggc ggccaggacg   3060
gccagccggg atcgggatac tggtcgttac cagagccacc gacccgagca aacccttctc   3120
tatcagatcg ttgacgagta ttacccggca ttcgctgcgc ttatggcaga gcagggaaag   3180
gaattgccgg gctatgtgca acgggaattt gaagaatttc tccaatgcgg gcggctggag   3240
catggctttc tacgggttcg ctgcgagtct tgccacgccg agcacctggt cgctttcaga   3300
aatcaatcta aagtatatat gagtaaactt ggtctgacag gcccctgaat tcgcatctag   3360
atggtagagc cacaaacagc cggtacaagc aacgatctcc aggaccatct gaatcatgcg   3420
cggatgacac gaactcacga cggcgatcac agacattaac ccacagtaca gacactgcga   3480
caacgtggca attcgtcgca ataccgtctc actgaactgg ccgataattg cagacgaacg   3540
```

```
ggtgaaacaa aacggttgac aacatgaagt aaacacggta cgatgtacca catgaaacga   3600
cagtgagtca atacagaaac agaggagata ttacatatgg atagcactga gaacgtcatc   3660
aagcccttca tgcgcttcaa ggtgcacatg gagggctccg tgaacggcca cgagttcgag   3720
atcgagggcg tgggcgaggg caagccctac gagggcaccc agaccgccaa gctgcaagtg   3780
accaagggcg gcccctgcc  cttcgcctgg gacatcctgt ccccccagtt cttctacggc   3840
tccaaggcgt acatcaagca ccccgccgac atccccgact acctcaagca gtccttcccc   3900
gagggcttca agtgggagcg cgtgatgaac ttcgaggacg gcggcgtggt gaccgtgacc   3960
caggactcct ccctgcagga cggcaccctc atctaccacg tgaagttcat cggcgtgaac   4020
ttcccctccg acggccccgt aatgcagaag aagactctgg gctgggagcc ctccactgag   4080
cgcaactacc cccgcgacgg cgtgctgaag ggcgagaacc acatggcgct gaagctgaag   4140
ggcggcggcc actacctgtg tgagttcaag tccatctaca tggccaagaa gcccgtgaag   4200
ctgcccggct accactacgt ggactacaag ctcgacatca cctcccacaa cgaggactac   4260
accgtggtgg agcagtacga gcgcgccgag gcccgccacc acctgttcca gactcacggt   4320
atggacgaat tgtacaagca cgacgaattg taaatccgta atcgttaatc cgcaaataac   4380
gtaaaaaccc gcttcggcgg gtttttttat ggggggagtt tagggaaaga gcatttgtca   4440
gctggatcag cagatgggaa ccggatactc ctcagcctcc agagtagcca atgagacgcc   4500
gagcggccgc ttatttgccg actaccttgg tgatctcgcc tttcacgtag tggacaaatt   4560
cttccaactg atctgcgcgc gaggccaagc gatcttcttc ttgtccaaga taagcctgtc   4620
tagcttcaag tatgacgggc tgatactggg ccggcaggcg ctccattgcc cagtcggcag   4680
cgacatcctt cggcgcgatt ttgccggtta ctgcgctgta ccaaatgcgg gacaacgtaa   4740
gcactacatt tcgctcatcg ccagcccagt cgggcggcga gttccatagc gttaaggttt   4800
catttagcgc ctcaaataga tcctgttcag gaaccggatc aaagagttcc tccgccgctg   4860
gacctaccaa ggcaacgcta tgttctcttg cttttgtcag caagatagcc agatcaatgt   4920
cgatcgtggc tggctcgaag atacccgcaa gaatgtcatt gcgctgccat tctccaaatt   4980
gcagttcgcg cttagctgga taacgccacg gaatgatgtc gtcgtgcaca acaatggtga   5040
cttctacagc gcggagaatc tcgctctctc caggggaagc cgaagtttcc aaaaggtcgt   5100
tgatcaaagc tcgccgcgtt gtttcatcaa gccttacggt caccgtaacc agcaaatcaa   5160
tatcactgtg tggcttcagg ccgccatcca ctgcggagcc gtacaaatgt acggccagca   5220
acgtcggttc gagatggcgc tcgatgacgc caactacctc tgatagttga gtcgatactt   5280
cggcgatcac cgcttccctc ataatgttta actttgtttt agggcgactg ccctgctgcg   5340
taacatcgtt gctgctccat aacatcaaac atcgacccac ggcgtaacgc gcttgctgct   5400
tggatgcccg aggcatagac tgtaccccaa aaaaacagtc ataacaagcc atgaaaaccg   5460
ccactgcgcc gttaccaccg ctgcgttcgg tcaaggttct ggaccagttg cgtgagcgca   5520
tacgctactt gcattacagc ttacgaaccg aacaggctta tgtccactgg gttcgtgcct   5580
tcatccgttt ccacggtgtg cgtcacccgg caaccttggg tagcagcgaa gtcgaggcat   5640
ttctgtcctg gctggtcatg accaaaatcc cttaacgtga gtcagcctgc cgccttgggc   5700
cgggtgatgt cgtacttgcc cgccgcgaac tcggttaccg tccagcccag cgcgaccagc   5760
tccggcaacg cctcgcgcac ccgcttgcgg cgcttgcgca tggtcgaacc actggcctct   5820
gacggccaga catagccgca caaggtatct atggaagcct tgccggtttt gccggggtcg   5880
atccagccac acagccgctg gtgcagcagg cgggcggttt cgctgtccag cgcccgcacc   5940
```

```
tcgtccatgc tgatgcgcac atgctggccg ccacccatga cggcctgcgc gatcaagggg   6000
ttcagggcca cgtacaggcg cccgtccgcc tcgtcgctgg cgtactccga cagcagccga   6060
aaccccctgcc gcttgcggcc attctgggcg atgatggata ccttccaaag gcgctcgatg   6120
cagtcctgta tgtgcttgag cgccccacca ctatcgacct ctgccccgat ttcctttgcc   6180
agcgcccgat agctaccttt gaccacatgg cattcagcgg tgacggcctc ccacttgggt   6240
tccaggaaca gccggagctg ccgtccgcct tcggtcttgg gttccgggcc aagcactagg   6300
ccattaggcc cagccatggc caccagccct tgcaggatgc gcagatcatc agcgcccagc   6360
ggctccgggc cgctgaactc gatccgcttg ccgtcgccgt agtcatacgt cacgtccagc   6420
ttgctgcgct tgcgctcgcc ccgcttgagg gcacggaaca ggccgggggc cagacagtgc   6480
gccgggtcgt gccggacgtg gctgaggctg tgcttgttct taggcttcac cacggggcac   6540
cccccttgctc ttgcgctgcc tctccagcac ggcgggcttg agcaccccgc cgtcatgccg   6600
cctgaaccac cgatcagcga acggtgcgcc atagttggcc ttgctcacac cgaagcggac   6660
gaagaaccgg cgctggtcgt cgtccacacc ccattcctcg gcctcggcgc tggtcatgct   6720
cgacaggtag gactgccagc ggatgttatc gaccagtacc gagctgcccc ggctggcctg   6780
ctgctggtcg cctgcgccca tcatggccgc gcccttgctg gcatggtgca ggaacacgat   6840
agagcacccg gtatcggcgg cgatggcctc catgcgaccg atgacctggg ccatggggcc   6900
gctggcgttt tcttcctcga tgtggaaccg gcgcagcgtg tccagcacca tcaggcggcg   6960
gccctcggcg gcgcgcttga ggccgtcgaa ccactccggg gccatgatgt tgggcaggct   7020
gccgatcagc ggctggatca gcaggccgtc agccacggct tgccgttcct cggcgctgag   7080
gtgcgcccca agggcgtgca ggcggtgatg aatggcggtg ggcgggtctt cggcgggcag   7140
gtagatcacc gggccggtgg gcagttcgcc cacctccagc agatccggcc cgcctgcaat   7200
ctgtgcggcc agttgcaggg ccagcatgga tttaccggca ccaccgggcg acaccagcgc   7260
cccgaccgta ccggccacca tgttgggcaa aacgtagtcc agcggtggcg gcgctgctgc   7320
gaacgcctcc agaatattga taggcttatg ggtagccatt gattgcctcc tttgcaggca   7380
gttggtggtt aggcgctggc ggggtcacta cccccgccct gcgccgctct gagttcttcc   7440
aggcactcgc gcagcgcctc gtattcgtcg tcggtcagcc agaacttgcg ctgacgcatc   7500
cctttggcct tcatgcgctc ggcatatcgc gcttggcgta cagcgtcagg gctggccagc   7560
aggtcgccgg tctgcttgtc cttttggtct ttcatatcag tcaccgagaa acttgccggg   7620
gccgaaaggc ttgtcttcgc ggaacaagga caaggtgcag ccgtcaaggt taaggctggc   7680
catatcagcg actgaaaagc ggccagcctc ggccttgttt gacgtataac caaagccacc   7740
gggcaaccaa tagcccttgt cacttttgat caggtagacc gaccctgaag cgcttttttc   7800
gtattccata aaaccccctt ctgtgcgtga gtactcatag tataacaggc gtgagtacca   7860
acgcaagcac tacatgctga aatctggccc gcccctgtcc atgcctcgct ggcggggtgc   7920
cggtgcccgt gccagctcgg cccgcgcaag ctggacgctg ggcagaccca tgaccttgct   7980
gacggtgcgc tcgatgtaa                                                 7999
```

<210> SEQ ID NO 4
<211> LENGTH: 8101
<212> TYPE: DNA
<213> ORGANISM: Artificial Sequence
<220> FEATURE:
<223> OTHER INFORMATION: Chemically Synthesized,

<400> SEQUENCE: 4

```
ctcgatgtaa tccgcttcgt ggccgggctt gcgctctgcc agcgctgggc tggcctcggc      60
catggccttg ccgatttcct cggcactgcg gccccggctg gccagcttct gcgcggcgat     120
aaagtcgcac ttgctgaggt catgaccgaa gcgcttgacc agcccggcca tctcgctgcg     180
gtactcgtcc agcgccgtgc gccggtggcg gctaagctgc cgctcgggca gttcgaggct     240
ggccagcctg cgggccttct cctgctgccg ctgggcctgc tcgatctgct ggccagcctg     300
ctgcaccagc gccgggccag cggtggcggt cttgcccttg gattcacgca gcagcaccca     360
cggctgataa ccggcgcggg tggtgtgctt gtccttgcgg ttggtgaagc ccgccaagcg     420
gccatagtgg cggctgtcgg cgctggccgg gtcggcgtcg tactcgctgg ccagcgtccg     480
ggcaatctgc ccccgaagtt caccgcctgc ggcgtcggcc accttgaccc atgcctgata     540
gttcttcggg ctggtttcca ctaccagggc aggctcccgg ccctcggctt tcatgtcatc     600
caggtcaaac tcgctgaggt cgtccaccag caccagacca tgccgctcct gctcggcggg     660
cctgatatac acgtcattgc cctgggcatt catccgcttg agccatggcg tgttctggag     720
cacttcggcg gctgaccatt cccggttcat catctggccg gtgggtgcgt ccctgacgcc     780
gatatcgaag cgctcacagc ccatggcctt gagctgtcgg cctatggcct gcaaagtcct     840
gtcgttcttc atcgggccac caagcgcagc cagatcgagc cgtcctcggt tgtcagtggc     900
gtcaggtcga gcaagagcaa cgatgcgatc agcagcacca ccgtaggcat catggaagcc     960
agcatcacgg ttagccatag cttccagtgc cacccccgcg acgcgctccg ggcgctctgc    1020
gcggcgctgc tcacctcggc ggctacctcc cgcaactctt tggccagctc cacccatgcc    1080
gcccctgtct ggcgctgggc tttcagccac tccgccgcct gcgcctcgct ggcctgcttg    1140
gtctggctca tgacctgccg ggcttcgtcg gccagtgtcg ccatgctctg ggccagcggt    1200
tcgatctgct ccgctaactc gttgatgcct ctggatttct tcactctgtc gattgcgttc    1260
atggtctatt gcctcccggt attcctgtaa gtcgatgatc tgggcgttgg cggtgtcgat    1320
gttcagggcc acgtctgccc ggtcggtgcg gatgccccgg ccttccatct ccaccacgtt    1380
cggccccagg tgaacaccgg gcaggcgctc gatgccctgc gcctcaagtg ttctgtggtc    1440
aatgcgggcg tcgtggccag cccgctctaa tgcccggttg gcatggtcgg cccatgcctc    1500
gcgggtctgc tcaagccatg ccttgggctt gagcgcttcg gtcttctgtg ccccgccctt    1560
ctccggggtc ttgccgttgt accgcttgaa ccactgagcg gcgggccgct cgatgccgtc    1620
attgatccgc tcggagatca tcaggtggca gtgcgggttc tcgccgccac cggcatggat    1680
ggccagcgta tacggcaggc gctcggcacc ggtcaggtgc tgggcgaact cggacgccag    1740
cgccttctgc tggtcgaggg tcagctcgac cggcagggca aattcgacct ccttgaacag    1800
ccgcccattg gcgcgttcat acaggtcggc agcatcccag tagtcggcgg gccgctcgac    1860
gaactccggc atgtgcccgg attcggcgtg caagacttca tccatgtcgc gggcatactt    1920
gccttcgcgc tggatgtagt cggccttggc cctggccgat tggccgcccg acctgctgcc    1980
ggttttcgcc gtaaggtgat aaatcgccat gctgcctcgc tgttgctttt gcttttcggc    2040
tccatgcaat ggccctcgga gagcgcaccg cccgaagggt ggccgttagg ccagtttctc    2100
gaagagaaac cggtaagtgc gccctcccct acaaagtagg gtcgggattg ccgccgctgt    2160
gcctccatga tagcctacga gacagcacat taacaatggg gtgtcaagat ggttaagggg    2220
agcaacaagg cggcggatcg gctggccaag ctcgaagaac aacgagcgcg aatcaatgcc    2280
gaaattcagc gggagcgggc aagggaacag cagcaagagc gcaagaacga aacaaggcgc    2340
```

```
aaggtgctgg tgggggccat gattttggcc aaggtgaaca gcagcgagtg gccggaggat   2400
cggctcatgg cggcaatgga tgcgtacctt gaacgcgacc acgaccgcgc cttgttcggt   2460
ctgccgccac gccagaagga tgagccgggc tgaatgatcg accgagacag gccctgcggg   2520
gctgcacacg cgcccccacc cttcgggtag gggaaaggc cgctaaagcg gctaaaagcg   2580
ctccagcgta tttctgcggg gtttggtgtg gggtttagcg ggctttgccc gcctttcccc   2640
ctgccgcgca gcggtggggc ggtgtgtagc ctagcgcagc gaatagacca gctatccggc   2700
ctctggccgg gcatattggg caagggcagc agcgccccac aagggcgctg ataaccgcgc   2760
ctagtggatt attcttagat aatcatggat ggatttttcc aacaccccgc cagcccccgc   2820
ccctgctggg tttgcaggtt tgggggcgtg acagttattg caggggttcg tgacagttat   2880
tgcagggggg cgtgacagtt attgcagggg ttcgtgacag ttagtacggg agtgacgggc   2940
actggctggc aatgtctagc aacggcaggc atttcggctg agggtaaaag aactttccgc   3000
taagcgatag actgtatgta aacacagtat tgcaaggacg cggaacatgc ctcatgtggc   3060
ggccaggacg gccagccggg atcgggatac tggtcgttac cagagccacc gacccgagca   3120
aacccttctc tatcagatcg ttgacgagta ttacccggca ttcgctgcgc ttatggcaga   3180
gcagggaaag gaattgccgg gctatgtgca acgggaattt gaagaatttc tccaatgcgg   3240
gcggctggag catggctttc tacgggttcg ctgcgagtct tgccacgccg agcacctggt   3300
cgctttcaga aatcaatcta aagtatatat gagtaaactt ggtctgacag gcccctgaat   3360
tcgcatctag actgatgaga cgtggtagag ccacaaacag ccggtacaag caacgatctc   3420
caggaccatc tgaatcatgc gcggatgaca cgaactcacg acggcgatca cagacattaa   3480
cccacagtac agacactgcg acaacgtggc aattcgtcgc aatacaacgg acagtcattc   3540
atctttctgc cctccaaaa gcaaaaaccc gccgaagcgg gtttttacgt aaatcaggtg   3600
aaactgaccg actttggcag tttattcttg acatgtagtg agggggctgg tataatcaca   3660
tagtactgtt tatgagtaaa ggagaagagc ttttcacagg agttgtccca atcctcgtgg   3720
aattagacgg tgatgttaat gggcacaagt tctctgtcag tggagagggt gaaggcgacg   3780
caacatatgg caagctgacc cttaaattta tttgcaccac gggtaaacta cctgttccat   3840
ggccaacact ggtcactacg ttcgggtatg gggttcagtg ctttgcgcgc tacccagatc   3900
acatgaaaca gcacgacttt ttcaagagtg caatgcccga aggctatgta caggagagaa   3960
ccatcttttt taaggatgac ggcaactata agacacgcgc cgaagtgaag ttcgagggtg   4020
ataccttgt taatagaatc gagttaaagg gtattgactt taaggaagat ggaaatattt   4080
taggccacaa actggaatat aactataact cccataatgt gtacattatg gccgacaagc   4140
aaaagaacgg tatcaaggtt aacttcaaga tcagacacaa cattgaggat ggaagcgttc   4200
aactagccga ccattaccaa caaaacaccc caattggcga tgggcctgtg ctgttaccag   4260
acaaccatta cctgtccact caatctgccc tttcgaaaga tcccaacgaa aagcgcgacc   4320
acatggtcct tcttgagttt gtcacggctg ctgggattac acacggcatg gatgaactat   4380
acaaataaat ccaacagtac tatgtgatta taccagcccc ctcactacat gtcaagaata   4440
aactgccaaa ggtaatcgtt aatccgcaaa taacgtaaaa acccgcttcg gcgggttttt   4500
ttatgggggg agtttaggga aagagcattt gtcagctgcg tctcaagcag ttacagagat   4560
gttacgaacc cccaggacat ccgagaatgc gaggcgatgg agggtacaac ccgagcggcc   4620
gcttatttgc cgactacctt ggtgatctcg cctttcacgt agtggacaaa ttcttccaac   4680
```

```
tgatctgcgc gcgaggccaa gcgatcttct tcttgtccaa gataagcctg tctagcttca   4740
agtatgacgg gctgatactg ggccggcagg cgctccattg cccagtcggc agcgacatcc   4800
ttcggcgcga ttttgccggt tactgcgctg taccaaatgc gggacaacgt aagcactaca   4860
tttcgctcat cgccagccca gtcgggcggc gagttccata gcgttaaggt ttcatttagc   4920
gcctcaaata gatcctgttc aggaaccgga tcaaagagtt cctccgccgc tggacctacc   4980
aaggcaacgc tatgttctct tgcttttgtc agcaagatag ccagatcaat gtcgatcgtg   5040
gctggctcga agatacccgc aagaatgtca ttgcgctgcc attctccaaa ttgcagttcg   5100
cgcttagctg gataacgcca cggaatgatg tcgtcgtgca caacaatggt gacttctaca   5160
gcgcggagaa tctcgctctc tccaggggaa gccgaagttt ccaaaaggtc gttgatcaaa   5220
gctcgccgcg ttgtttcatc aagccttacg gtcaccgtaa ccagcaaatc aatatcactg   5280
tgtggcttca ggccgccatc cactgcggag ccgtacaaat gtacggccag caacgtcggt   5340
tcgagatggc gctcgatgac gccaactacc tctgatagtt gagtcgatac ttcggcgatc   5400
accgcttccc tcataatgtt taactttgtt ttagggcgac tgccctgctg cgtaacatcg   5460
ttgctgctcc ataacatcaa acatcgaccc acggcgtaac gcgcttgctg cttggatgcc   5520
cgaggcatag actgtacccc aaaaaaacag tcataacaag ccatgaaaac cgccactgcg   5580
ccgttaccac cgctgcgttc ggtcaaggtt ctggaccagt tgcgtgagcg catacgctac   5640
ttgcattaca gcttacgaac cgaacaggct tatgtccact gggttcgtgc cttcatccgt   5700
ttccacggtg tgcgtcaccc ggcaaccttg ggtagcagcg aagtcgaggc atttctgtcc   5760
tggctggtca tgaccaaaat cccttaacgt gagtcagcct gccgccttgg gccgggtgat   5820
gtcgtacttg cccgccgcga actcggttac cgtccagccc agcgcgacca gctccggcaa   5880
cgcctcgcgc acccgcttgc ggcgcttgcg catggtcgaa ccactggcct ctgacggcca   5940
gacatagccg cacaaggtat ctatggaagc cttgccggtt ttgccggggt cgatccagcc   6000
acacagccgc tggtgcagca ggcgggcggt ttcgctgtcc agcgcccgca cctcgtccat   6060
gctgatgcgc acatgctggc cgccacccat gacggcctgc gcgatcaagg ggttcagggc   6120
cacgtacagg cgcccgtccg cctcgtcgct ggcgtactcc gacagcagcc gaaacccctg   6180
ccgcttgcgg ccattctggg cgatgatgga taccttccaa aggcgctcga tgcagtcctg   6240
tatgtgcttg agcgccccac cactatcgac ctctgccccg atttcctttg ccagcgcccg   6300
atagctacct ttgaccacat ggcattcagc ggtgacggcc tcccacttgg gttccaggaa   6360
cagccggagc tgccgtccgc cttcggtctt gggttccggg ccaagcacta ggccattagg   6420
cccagccatg gccaccagcc cttgcaggat gcgcagatca tcagcgccca gcggctccgg   6480
gccgctgaac tcgatccgct tgccgtcgcc gtagtcatac gtcacgtcca gcttgctgcg   6540
cttgcgctcg ccccgcttga gggcacggaa caggccgggg gccagacagt gcgccgggtc   6600
gtgccggacg tggctgaggc tgtgcttgtt cttaggcttc accacggggc acccccttgc   6660
tcttgcgctg cctctccagc acggcgggct tgagcacccc gccgtcatgc cgcctgaacc   6720
accgatcagc gaacggtgcg ccatagttgg ccttgctcac accgaagcgg acgaagaacc   6780
ggcgctggtc gtcgtccaca ccccattcct cggcctcggc gctggtcatg ctcgacaggt   6840
aggactgcca gcggatgtta tcgaccagta ccgagctgcc ccggctggcc tgctgctggt   6900
cgcctgcgcc catcatggcc gcgcccttgc tggcatggtg caggaacacg atagagcacc   6960
cggtatcggc ggcgatggcc tccatgcgac cgatgacctg ggccatgggg ccgctggcgt   7020
tttcttcctc gatgtggaac cggcgcagcg tgtccagcac catcaggcgg cggccctcgg   7080
```

```
cggcgcgctt gaggccgtcg aaccactccg gggccatgat gttgggcagg ctgccgatca   7140

gcggctggat cagcaggccg tcagccacgg cttgccgttc ctcggcgctg aggtgcgccc   7200

caagggcgtg caggcggtga tgaatggcgg tgggcgggtc ttcggcgggc aggtagatca   7260

ccgggccggt gggcagttcg cccacctcca gcagatccgg cccgcctgca atctgtgcgg   7320

ccagttgcag ggccagcatg gatttaccgg caccaccggg cgacaccagc gccccgaccg   7380

taccggccac catgttgggc aaaacgtagt ccagcggtgg cggcgctgct gcgaacgcct   7440

ccagaatatt gataggctta tgggtagcca ttgattgcct cctttgcagg cagttggtgg   7500

ttaggcgctg gcggggtcac tacccccgcc ctgcgccgct ctgagttctt ccaggcactc   7560

gcgcagcgcc tcgtattcgt cgtcggtcag ccagaacttg cgctgacgca tccctttggc   7620

cttcatgcgc tcggcatatc gcgcttggcg tacagcgtca gggctggcca gcaggtcgcc   7680

ggtctgcttg tccttttggt ctttcatatc agtcaccgag aaacttgccg gggccgaaag   7740

gcttgtcttc gcggaacaag gacaaggtgc agccgtcaag gttaaggctg gccatatcag   7800

cgactgaaaa gcggccagcc tcggccttgt ttgacgtata accaaagcca ccgggcaacc   7860

aatagccctt gtcacttttg atcaggtaga ccgaccctga agcgcttttt tcgtattcca   7920

taaaaccccc ttctgtgcgt gagtactcat agtataacag gcgtgagtac caacgcaagc   7980

actacatgct gaaatctggc ccgcccctgt ccatgcctcg ctggcggggt gccggtgccc   8040

gtgccagctc ggcccgcgca agctggacgc tgggcagacc catgaccttg ctgacggtgc   8100

g                                                                   8101
```

<210> SEQ ID NO 5
<211> LENGTH: 8737
<212> TYPE: DNA
<213> ORGANISM: Artificial Sequence
<220> FEATURE:
<223> OTHER INFORMATION: Chemically Synthesized,

<400> SEQUENCE: 5

```
taatccgctt cgtggccggg cttgcgctct gccagcgctg ggctggcctc ggccatggcc     60

ttgccgattt cctcggcact gcggccccgg ctggccagct tctgcgcggc gataaagtcg    120

cacttgctga ggtcatgacc gaagcgcttg accagcccgg ccatctcgct gcggtactcg    180

tccagcgccg tgcgccggtg gcggctaagc tgccgctcgg gcagttcgag gctggccagc    240

ctgcgggcct tctcctgctg ccgctgggcc tgctcgatct gctggccagc ctgctgcacc    300

agcgccgggc cagcggtggc ggtcttgccc ttggattcac gcagcagcac ccacggctga    360

taaccggcgc gggtggtgtg cttgtccttg cggttggtga agcccgccaa gcggccatag    420

tggcggctgt cggcgctggc cgggtcggcg tcgtactcgc tggccagcgt ccgggcaatc    480

tgcccccgaa gttcaccgcc tgcggcgtcg gccaccttga cccatgcctg atagttcttc    540

gggctggttt ccactaccag ggcaggctcc cggccctcgg ctttcatgtc atccaggtca    600

aactcgctga ggtcgtccac cagcaccaga ccatgccgct cctgctcggc gggcctgata    660

tacacgtcat tgccctgggc attcatccgc ttgagccatg gcgtgttctg gagcacttcg    720

gcggctgacc attcccggtt catcatctgg ccggtgggtg cgtccctgac gccgatatcg    780

aagcgctcac agcccatggc cttgagctgt cggcctatgg cctgcaaagt cctgtcgttc    840

ttcatcgggc caccaagcgc agccagatcg agccgtcctc ggttgtcagt ggcgtcaggt    900

cgagcaagag caacgatgcg atcagcagca ccaccgtagg catcatggaa gccagcatca    960
```

-continued

```
cggttagcca tagcttccag tgccaccccc gcgacgcgct ccgggcgctc tgcgcggcgc   1020
tgctcacctc ggcggctacc tcccgcaact ctttggccag ctccacccat gccgcccctg   1080
tctggcgctg ggctttcagc cactccgccg cctgcgcctc gctggcctgc ttggtctggc   1140
tcatgacctg ccgggcttcg tcggccagtg tcgccatgct ctgggccagc ggttcgatct   1200
gctccgctaa ctcgttgatg cctctggatt tcttcactct gtcgattgcg ttcatggtct   1260
attgcctccc ggtattcctg taagtcgatg atctgggcgt tggcggtgtc gatgttcagg   1320
gccacgtctg cccggtcggt gcggatgccc cggccttcca tctccaccac gttcggcccc   1380
aggtgaacac cgggcaggcg ctcgatgccc tgcgcctcaa gtgttctgtg gtcaatgcgg   1440
gcgtcgtggc cagcccgctc taatgcccgg ttggcatggt cggcccatgc ctcgcgggtc   1500
tgctcaagcc atgccttggg cttgagcgct tcggtcttct gtgccccgcc cttctccggg   1560
gtcttgccgt tgtaccgctt gaaccactga gcggcgggcc gctcgatgcc gtcattgatc   1620
cgctcggaga tcatcaggtg gcagtgcggg ttctcgccgc caccggcatg gatggccagc   1680
gtatacggca ggcgctcggc accggtcagg tgctgggcga actcggacgc cagcgccttc   1740
tgctggtcga gggtcagctc gaccggcagg gcaaattcga cctccttgaa cagccgccca   1800
ttggcgcgtt catacaggtc ggcagcatcc cagtagtcgg cgggccgctc gacgaactcc   1860
ggcatgtgcc cggattcggc gtgcaagact tcatccatgt cgcgggcata cttgccttcg   1920
cgctggatgt agtcggcctt ggccctggcc gattggccgc ccgacctgct gccggttttc   1980
gccgtaaggt gataaatcgc catgctgcct cgctgttgct tttgcttttc ggctccatgc   2040
aatggccctc ggagagcgca ccgcccgaag ggtggccgtt aggccagttt ctcgaagaga   2100
aaccggtaag tgcgccctcc cctacaaagt agggtcggga ttgccgccgc tgtgcctcca   2160
tgatagccta cgagacagca cattaacaat ggggtgtcaa gatggttaag ggagcaaca    2220
aggcggcgga tcggctggcc aagctcgaag aacaacgagc gcgaatcaat gccgaaattc   2280
agcgggagcg ggcaagggaa cagcagcaag agcgcaagaa cgaaacaagg cgcaaggtgc   2340
tggtgggggc catgattttg gccaaggtga acagcagcga gtggccggag gatcggctca   2400
tggcggcaat ggatgcgtac cttgaacgcg accacgaccg cgccttgttc ggtctgccgc   2460
cacgccagaa ggatgagccg ggctgaatga tcgaccgaga caggccctgc ggggctgcac   2520
acgcgccccc acccttcggg tagggggaaa ggccgctaaa gcggctaaaa gcgctccagc   2580
gtatttctgc ggggtttggt gtggggttta gcgggctttg cccgcctttc cccctgccgc   2640
gcagcggtgg ggcggtgtgt agcctagcgc agcgaataga ccagctatcc ggcctctggc   2700
cgggcatatt gggcaagggc agcagcgccc cacaagggcg ctgataaccg cgcctagtgg   2760
attattctta gataatcatg gatggatttt tccaacaccc cgccagcccc cgcccctgct   2820
gggtttgcag gtttgggggc gtgacagtta ttgcaggggt tcgtgacagt tattgcaggg   2880
gggcgtgaca gttattgcag gggttcgtga cagttagtac gggagtgacg ggcactggct   2940
ggcaatgtct agcaacggca ggcatttcgg ctgagggtaa aagaactttc cgctaagcga   3000
tagactgtat gtaaacacag tattgcaagg acgcggaaca tgcctcatgt ggcggccagg   3060
acggccagcc gggatcggga tactggtcgt taccagagcc accgacccga gcaaaccctt   3120
ctctatcaga tcgttgacga gtattacccg gcattcgctg cgcttatggc agagcaggga   3180
aaggaattgc cgggctatgt gcaacgggaa tttgaagaat ttctccaatg cgggcggctg   3240
gagcatggct ttctacgggt tcgctgcgag tcttgccacg ccgagcacct ggtcgctttc   3300
agaaatcaat ctaaagtata tatgagtaaa cttggtctga caggcccctg aattcgcatc   3360
```

```
tagactgatg agacgtggta gagccacaaa cagccggtac aagcaacgat ctccaggacc   3420
atctgaatca tgcgcggatg acacgaactc acgacggcga tcacagacat taacccacag   3480
tacagacact gcgacaacgt ggcaattcgt cgcaatacaa cggacagtca ttcatctttc   3540
tgcccctcca aaagcaaaaa cccgccgaag cgggttttta cgtaaatcag gtgaaactga   3600
ccgactttgg cagtttattc ttgacatgta gtgagggggc tggtataatc acatagtact   3660
gtttatgcgt gaatgtatct caatccacgt tggccaggct ggagtccaaa ttggtaatgc   3720
ctgttgggaa ttatattgtc tggaacatgg catccaacct gatggtcaga tgccatcaga   3780
caaaaccatt ggaggaggag atgatagttt caatactttc ttcagtgaaa caggtgccgg   3840
aaaacacgtt cccagagcgg ttttcatcga cttagagcct acagtagtcg acgaggttcg   3900
cacaggcact tatcgtcaac tcttccatcc agaacaactg atcacgggca aagaggatgc   3960
agcaaacaat tatgcccgtg gtcattacac aattggcaag gaaattgttg accttgtctt   4020
ggatcgtatt cgtaaacttg cagatcaatg tactggactc caaggtttcc tcatcttcca   4080
ttcctttgga ggtggcactg gctctggttt cacatctctg ttgatggaac gtctgtctgt   4140
ggattatgga aagaagtcaa aattggaatt cgcaatttat ccagcaccac aagtttccac   4200
tgctgtggtc gaaccttata attcaattct caccacccat actactttag aacattccga   4260
ttgtgcattt atggtcgaca atgaggctat ttatgatatc tgtcgccgta acttggacat   4320
cgaaagaccg acgtatacaa acttgaaccg actgattggt caaatcgttt cttctatcac   4380
tgcctcactt cgtttcgatg gcgcccttaa tgttgatctg acggaattcc aaactaattt   4440
agtaccctat ccaagaattc atttcccatt ggttacctat gcgccagtca tttccgctga   4500
aaaagcgtat cacgaacaac tttctgtagc ggaaatcacg aatgcttgct tcgaaccggc   4560
taatcagatg gtaaaatgcg atcctcgtca tggaaaatat atggcgtgtt gtatgctgta   4620
cagaggagat gttgtaccta aggatgttaa tgcagccatt gcaactatca agactaagcg   4680
caccattcaa tttgtcgatt ggtgcccaac tggattcaaa gttggcatta attatcaacc   4740
acctactgtt gtaccaggtg gtgatcttgc taaagtacaa cgagctgttt gcatgttatc   4800
caatactact gctatcgcag aagcttgggc cagacttgac cataaatttg atttaatgta   4860
cgctaagaga gcatttgtac actggtacgt cggtgagggt atggaggaag gtgagttctc   4920
cgaagcacgt gaagatcttg ctgctttgga gaaggattat gaagaggttg gtatggattc   4980
cgcagaaggt gagggagagg gagctgaaga atactaaatc caacagtact atgtgattat   5040
accagccccc tcactacatg tcaagaataa actgccaaag gtaatcgtta atccgcaaat   5100
aacgtaaaaa cccgcttcgg cgggtttttt tatgggggga gtttagggaa agagcatttg   5160
tcagctgcgt ctcaagcagt tacagagatg ttacgaaccc ccaggacatc cgagaatgcg   5220
aggcgatgga gggtacaacc cgagcggccg cttatttgcc gactaccttg gtgatctcgc   5280
ctttcacgta gtggacaaat tcttccaact gatctgcgcg cgaggccaag cgatcttctt   5340
cttgtccaag ataagcctgt ctagcttcaa gtatgacggg ctgatactgg gccggcaggc   5400
gctccattgc ccagtcggca gcgacatcct tcggcgcgat tttgccggtt actgcgctgt   5460
accaaatgcg ggacaacgta agcactacat ttcgctcatc gccagcccag tcgggcggcg   5520
agttccatag cgttaaggtt tcatttagcg cctcaaatag atcctgttca ggaaccggat   5580
caaagagttc ctccgccgct ggacctacca aggcaacgct atgttctctt gcttttgtca   5640
gcaagatagc cagatcaatg tcgatcgtgg ctggctcgaa gatacccgca agaatgtcat   5700
```

```
tgcgctgcca ttctccaaat tgcagttcgc gcttagctgg ataacgccac ggaatgatgt   5760
cgtcgtgcac aacaatggtg acttctacag cgcggagaat ctcgctctct ccaggggaag   5820
ccgaagtttc caaaaggtcg ttgatcaaag ctcgccgcgt tgtttcatca agccttacgg   5880
tcaccgtaac cagcaaatca atatcactgt gtggcttcag gccgccatcc actgcggagc   5940
cgtacaaatg tacggccagc aacgtcggtt cgagatggcg ctcgatgacg ccaactacct   6000
ctgatagttg agtcgatact tcggcgatca ccgcttccct cataatgttt aactttgttt   6060
tagggcgact gccctgctgc gtaacatcgt tgctgctcca taacatcaaa catcgaccca   6120
cggcgtaacg cgcttgctgc ttggatgccc gaggcataga ctgtacccca aaaaaacagt   6180
cataacaagc catgaaaacc gccactgcgc cgttaccacc gctgcgttcg gtcaaggttc   6240
tggaccagtt gcgtgagcgc atacgctact tgcattacag cttacgaacc gaacaggctt   6300
atgtccactg ggttcgtgcc ttcatccgtt tccacggtgt gcgtcacccg gcaaccttgg   6360
gtagcagcga agtcgaggca tttctgtcct ggctggtcat gaccaaaatc ccttaacgtg   6420
agtcagcctg ccgccttggg ccgggtgatg tcgtacttgc ccgccgcgaa ctcggttacc   6480
gtccagccca gcgcgaccag ctccggcaac gcctcgcgca cccgcttgcg gcgcttgcgc   6540
atggtcgaac cactggcctc tgacggccag acatagccgc acaaggtatc tatggaagcc   6600
ttgccggttt tgccggggtc gatccagcca cacagccgct ggtgcagcag gcgggcggtt   6660
tcgctgtcca gcgcccgcac ctcgtccatg ctgatgcgca catgctggcc gccacccatg   6720
acggcctgcg cgatcaaggg gttcagggcc acgtacaggc gcccgtccgc ctcgtcgctg   6780
gcgtactccg acagcagccg aaacccctgc cgcttgcggc cattctgggc gatgatggat   6840
accttccaaa ggcgctcgat gcagtcctgt atgtgcttga gcgccccacc actatcgacc   6900
tctgccccga tttcctttgc cagcgcccga tagctacctt tgaccacatg gcattcagcg   6960
gtgacggcct cccacttggg ttccaggaac agccggagct gccgtccgcc ttcggtcttg   7020
ggttccgggc caagcactag gccattaggc ccagccatgg ccaccagccc ttgcaggatg   7080
cgcagatcat cagcgcccag cggctccggg ccgctgaact cgatccgctt gccgtcgccg   7140
tagtcatacg tcacgtccag cttgctgcgc ttgcgctcgc cccgcttgag ggcacggaac   7200
aggccggggg ccagacagtg cgccgggtcg tgccggacgt ggctgaggct gtgcttgttc   7260
ttaggcttca ccacggggca cccccttgct cttgcgctgc ctctccagca cggcgggctt   7320
gagcaccccg ccgtcatgcc gcctgaacca ccgatcagcg aacggtgcgc catagttggc   7380
cttgctcaca ccgaagcgga cgaagaaccg gcgctggtcg tcgtccacac cccattcctc   7440
ggcctcggcg ctggtcatgc tcgacaggta ggactgccag cggatgttat cgaccagtac   7500
cgagctgccc cggctggcct gctgctggtc gcctgcgccc atcatggccg cgcccttgct   7560
ggcatggtgc aggaacacga tagagcaccc ggtatcggcg gcgatggcct ccatgcgacc   7620
gatgacctgg gccatggggc cgctggcgtt ttcttcctcg atgtggaacc ggcgcagcgt   7680
gtccagcacc atcaggcggc ggccctcggc ggcgcgcttg aggccgtcga accactccgg   7740
ggccatgatg ttgggcaggc tgccgatcag cggctggatc agcaggccgt cagccacggc   7800
ttgccgttcc tcggcgctga ggtgcgcccc aagggcgtgc aggcggtgat gaatggcggt   7860
gggcgggtct tcggcgggca ggtagatcac cgggccggtg ggcagttcgc ccacctccag   7920
cagatccggc ccgcctgcaa tctgtgcggc cagttgcagg gccagcatgg atttaccggc   7980
accaccgggc gacaccagcg ccccgaccgt accggccacc atgttgggca aaacgtagtc   8040
cagcggtggc ggcgctgctg cgaacgcctc cagaatattg ataggcttat gggtagccat   8100
```

```
tgattgcctc ctttgcaggc agttggtggt taggcgctgg cggggtcact acccccgccc   8160

tgcgccgctc tgagttcttc caggcactcg cgcagcgcct cgtattcgtc gtcggtcagc   8220

cagaacttgc gctgacgcat ccctttggcc ttcatgcgct cggcatatcg cgcttggcgt   8280

acagcgtcag ggctggccag caggtcgccg gtctgcttgt ccttttggtc tttcatatca   8340

gtcaccgaga aacttgccgg ggccgaaagg cttgtcttcg cggaacaagg acaaggtgca   8400

gccgtcaagg ttaaggctgg ccatatcagc gactgaaaag cggccagcct cggccttgtt   8460

tgacgtataa ccaaagccac cgggcaacca atagcccttg tcacttttga tcaggtagac   8520

cgaccctgaa gcgctttttt cgtattccat aaaacccccct tctgtgcgtg agtactcata   8580

gtataacagg cgtgagtacc aacgcaagca ctacatgctg aaatctggcc cgcccctgtc   8640

catgcctcgc tggcggggtg ccggtgcccg tgccagctcg gcccgcgcaa gctggacgct   8700

gggcagaccc atgaccttgc tgacggtgcg ctcgatg                            8737
```

```
<210> SEQ ID NO 6
<211> LENGTH: 8920
<212> TYPE: DNA
<213> ORGANISM: Artificial Sequence
<220> FEATURE:
<223> OTHER INFORMATION: Chemically Synthesized,

<400> SEQUENCE: 6

taatccgctt cgtggccggg cttgcgctct gccagcgctg ggctggcctc ggccatggcc     60

ttgccgattt cctcggcact gcggccccgg ctggccagct tctgcgcggc gataaagtcg    120

cacttgctga ggtcatgacc gaagcgcttg accagcccgg ccatctcgct gcggtactcg    180

tccagcgccg tgcgccggtg gcggctaagc tgccgctcgg gcagttcgag gctggccagc    240

ctgcgggcct tctcctgctg ccgctgggcc tgctcgatct gctggccagc ctgctgcacc    300

agcgccgggc cagcggtggc ggtcttgccc ttggattcac gcagcagcac ccacggctga    360

taaccggcgc gggtggtgtg cttgtccttg cggttggtga agcccgccaa gcggccatag    420

tggcggctgt cggcgctggc cgggtcggcg tcgtactcgc tggccagcgt ccgggcaatc    480

tgcccccgaa gttcaccgcc tgcggcgtcg gccaccttga cccatgcctg atagttcttc    540

gggctggttt ccactaccag ggcaggctcc cggccctcgg ctttcatgtc atccaggtca    600

aactcgctga ggtcgtccac cagcaccaga ccatgccgct cctgctcggc gggcctgata    660

tacacgtcat tgccctgggc attcatccgc ttgagccatg gcgtgttctg gagcacttcg    720

gcggctgacc attcccggtt catcatctgg ccggtgggtg cgtccctgac gccgatatcg    780

aagcgctcac agcccatggc cttgagctgt cggcctatgg cctgcaaagt cctgtcgttc    840

ttcatcgggc caccaagcgc agccagatcg agccgtcctc ggttgtcagt ggcgtcaggt    900

cgagcaagag caacgatgcg atcagcagca ccaccgtagg catcatggaa gccagcatca    960

cggttagcca tagcttccag tgccaccccc gcgacgcgct ccgggcgctc tgcgcggcgc   1020

tgctcacctc ggcggctacc tcccgcaact ctttggccag ctccacccat gccgcccctg   1080

tctggcgctg ggctttcagc cactccgccg cctgcgcctc gctggcctgc ttggtctggc   1140

tcatgacctg ccgggcttcg tcggccagtg tcgccatgct ctgggccagc ggttcgatct   1200

gctccgctaa ctcgttgatg cctctggatt tcttcactct gtcgattgcg ttcatggtct   1260

attgcctccc ggtattcctg taagtcgatg atctgggcgt tggcggtgtc gatgttcagg   1320

gccacgtctg cccggtcggt gcggatgccc cggccttcca tctccaccac gttcggcccc   1380
```

```
aggtgaacac cgggcaggcg ctcgatgccc tgcgcctcaa gtgttctgtg gtcaatgcgg   1440
gcgtcgtggc cagcccgctc taatgcccgg ttggcatggt cggcccatgc ctcgcgggtc   1500
tgctcaagcc atgccttggg cttgagcgct tcggtcttct gtgccccgcc cttctccggg   1560
gtcttgccgt tgtaccgctt gaaccactga gcggcgggcc gctcgatgcc gtcattgatc   1620
cgctcggaga tcatcaggtg gcagtgcggg ttctcgccgc caccggcatg gatggccagc   1680
gtatacggca ggcgctcggc accggtcagg tgctgggcga actcggacgc cagcgccttc   1740
tgctggtcga gggtcagctc gaccggcagg gcaaattcga cctccttgaa cagccgccca   1800
ttggcgcgtt catacaggtc ggcagcatcc cagtagtcgg cgggccgctc gacgaactcc   1860
ggcatgtgcc cggattcggc gtgcaagact tcatccatgt cgcgggcata cttgccttcg   1920
cgctggatgt agtcggcctt ggccctggcc gattggccgc ccgacctgct gccggttttc   1980
gccgtaaggt gataaatcgc catgctgcct cgctgttgct tttgcttttc ggctccatgc   2040
aatggccctc ggagagcgca ccgcccgaag ggtggccgtt aggccagttt ctcgaagaga   2100
aaccggtaag tgcgccctcc cctacaaagt agggtcggga ttgccgccgc tgtgcctcca   2160
tgatagccta cgagacagca cattaacaat ggggtgtcaa gatggttaag gggagcaaca   2220
aggcggcgga tcggctggcc aagctcgaag aacaacgagc gcgaatcaat gccgaaattc   2280
agcgggagcg ggcaagggaa cagcagcaag agcgcaagaa cgaaacaagg cgcaaggtgc   2340
tggtgggggc catgatttg gccaaggtga acagcagcga gtggccggag gatcggctca   2400
tggcggcaat ggatgcgtac cttgaacgcg accacgaccg cgccttgttc ggtctgccgc   2460
cacgccagaa ggatgagccg ggctgaatga tcgaccgaga caggccctgc ggggctgcac   2520
acgcgccccc acccttcggg tagggggaaa ggccgctaaa gcggctaaaa gcgctccagc   2580
gtatttctgc ggggtttggt gtggggttta gcgggctttg cccgcctttc cccctgccgc   2640
gcagcggtgg ggcggtgtgt agcctagcgc agcgaataga ccagctatcc ggcctctggc   2700
cgggcatatt gggcaagggc agcagcgccc cacaagggcg ctgataaccg cgcctagtgg   2760
attattctta gataatcatg gatggatttt tccaacaccc cgccagcccc cgcccctgct   2820
gggtttgcag gtttgggggc gtgacagtta ttgcaggggt tcgtgacagt tattgcaggg   2880
gggcgtgaca gttattgcag gggttcgtga cagttagtac gggagtgacg ggcactggct   2940
ggcaatgtct agcaacggca ggcatttcgg ctgagggtaa aagaactttc cgctaagcga   3000
tagactgtat gtaaacacag tattgcaagg acgcggaaca tgcctcatgt ggcggccagg   3060
acggccagcc gggatcggga tactggtcgt taccagagcc accgacccga gcaaaccctt   3120
ctctatcaga tcgttgacga gtattacccg gcattcgctg cgcttatggc agagcaggga   3180
aaggaattgc cgggctatgt gcaacgggaa tttgaagaat ttctccaatg cgggcggctg   3240
gagcatggct ttctacgggt tcgctgcgag tcttgccacg ccgagcacct ggtcgctttc   3300
agaaatcaat ctaaagtata tatgagtaaa cttggtctga caggcccctg aattcgcatc   3360
tagatggtag agccacaaac agccggtaca agcaacgatc tccaggacca tctgaatcat   3420
gcgcggatga cacgaactca cgacggcgat cacagacatt aacccacagt acagacactg   3480
cgacaacgtg gcaattcgtc gcaataccgt ctcactgaac tggccgataa ttgcagacga   3540
acggacagtc attcatcttt ctgcccctcc aaaagcaaaa acccgccgaa gcgggttttt   3600
acgtaaatca ggtgaaactg accgactttg gcagtttatt cttgacatgt agtgaggggg   3660
ctggtataat cacatagtac tgtttatgat ggctgtagca gcggcgcaga agaaccgcga   3720
gatgttcgct atcaagaaat cttacagcat cgagaatgga tatccggcga ggcgacgatc   3780
```

```
tctcgtggac gatgctcggt ttgaaacttt ggtcgtcaag caaacgaagc agagcgtttt   3840
ggaagaagca cgtcaacggg cgaatgacgc tggactgacc gaggaggaag tggtgctggc   3900
caagacgata gcggaatgcc cggagagcga gaacacggtg caaaaagctg cgcttgtgct   3960
gcgcctgaga gaggggatcg gttcactcgc gaggatcctg aagacgatcg agaacttcaa   4020
ggggacggtg acccacgtgg agtcccggcc gtccaagaag gagggcctcc agttcgacgt   4080
gctcgtcaag gtcgacatga cgaggcaata cttgctccaa ctgatcagga atctccgcca   4140
gagctcagcc ctggacggcg tcaccctgct cgcggacaac tcggtcagca tcaaggatcc   4200
atggttcccg aggcacgcgt ccgacctcga caattgcaac cacctgatga ccaaattcga   4260
gcctgaccta gacatgaatc atcctggatt cgcggacaag gagtaccgcg cccgtagaaa   4320
gttcatcgct gaaattgcat tcgcgtacag gtacggtgac gcgataccca ccgtcccgta   4380
cacggaaacg gaaaccgaga cttggacccg ggtgttcaac accctcgtcg atctggtgcc   4440
gaaacacgct tgcgcggaat atagaagaaa ttttaagaag atgcaggagg agaagatatt   4500
cgagcctcac cgtatacctc agctgcagga ggtgagcgag ttcttgaaga agaacacagg   4560
gttcacgttg aggccagcgg ccggactgct cacgtccagg gacttcttgt cgagtttggc   4620
gttcagagtg ttccagagca ctcagtacat tcgtcacatc aagagcccgt atcataccc   4680
ggaaccagat tgcatccacg agctgttggg acacatgccg ttgttggccg atccaagctt   4740
cgcccaattc tcccaggaaa tcggcctcgc ctcgctcggt gcctccgacg aggaaatcga   4800
gaaattgtcc acgatttact ggttcaccgt cgaattcggc ctctgcaagg aggggccgga   4860
tgtgaaagcc tacggtgccg gcctttttgtc cgcctacggg gagcttcttc acgcgcttac   4920
gagcggcaaa tgcgagcatc gacctttcga gccgaaatcc accgccgttc aaaagtacca   4980
ggatcaagat taccaaccga tctacttcgt cgcggatagc ttcgaggatg ccaaagagaa   5040
attccgccgt tgggtgtcca ccatgagccg acctttttgag gttaggtacg atccgtacac   5100
gcagcgggtt gagatactgg acagcgtgga caggttggac aatctgatgg ctcaagtgaa   5160
cacggaaatg acgcatctca cgaacgctgt caacaagctg aagacatcgt tcgcgtaaat   5220
ccaacagtac tatgtgatta taccagcccc ctcactacat gtcaagaata aactgccaaa   5280
ggtaatcgtt aatccgcaaa taacgtaaaa acccgcttcg gcgggttttt ttatgggggg   5340
agtttaggga aagagcattt gtcagctgga tcagcagatg ggaaccggat actcctcagc   5400
ctccagagta gccaatgaga cgccgagcgg ccgcttattt gccgactacc ttggtgatct   5460
cgcctttcac gtagtggaca aattcttcca actgatctgc gcgcgaggcc aagcgatctt   5520
cttcttgtcc aagataagcc tgtctagctt caagtatgac gggctgatac tgggccggca   5580
ggcgctccat tgcccagtcg gcagcgacat ccttcggcgc gattttgccg gttactgcgc   5640
tgtaccaaat gcgggacaac gtaagcacta catttcgctc atcgccagcc cagtcgggcg   5700
gcgagttcca tagcgttaag gtttcattta gcgcctcaaa tagatcctgt tcaggaaccg   5760
gatcaaagag ttcctccgcc gctggaccta ccaaggcaac gctatgttct cttgcttttg   5820
tcagcaagat agccagatca atgtcgatcg tggctggctc gaagataccc gcaagaatgt   5880
cattgcgctg ccattctcca aattgcagtt cgcgcttagc tggataacgc cacggaatga   5940
tgtcgtcgtg cacaacaatg gtgacttcta cagcgcggag aatctcgctc tctccagggg   6000
aagccgaagt ttccaaaagg tcgttgatca aagctcgccg cgttgtttca tcaagcctta   6060
cggtcaccgt aaccagcaaa tcaatatcac tgtgtggctt caggccgcca tccactgcgg   6120
```

```
agccgtacaa atgtacggcc agcaacgtcg gttcgagatg gcgctcgatg acgccaacta   6180

cctctgatag ttgagtcgat acttcggcga tcaccgcttc cctcataatg tttaactttg   6240

ttttagggcg actgccctgc tgcgtaacat cgttgctgct ccataacatc aaacatcgac   6300

ccacggcgta acgcgcttgc tgcttggatg cccgaggcat agactgtacc ccaaaaaaac   6360

agtcataaca agccatgaaa accgccactg cgccgttacc accgctgcgt tcggtcaagg   6420

ttctggacca gttgcgtgag cgcatacgct acttgcatta cagcttacga accgaacagg   6480

cttatgtcca ctgggttcgt gccttcatcc gtttccacgg tgtgcgtcac ccggcaacct   6540

tgggtagcag cgaagtcgag gcatttctgt cctggctggt catgaccaaa atcccttaac   6600

gtgagtcagc ctgccgcctt gggccgggtg atgtcgtact tgcccgccgc gaactcggtt   6660

accgtccagc ccagcgcgac cagctccggc aacgcctcgc gcacccgctt gcggcgcttg   6720

cgcatggtcg aaccactggc ctctgacggc cagacatagc cgcacaaggt atctatggaa   6780

gccttgccgg ttttgccggg gtcgatccag ccacacagcc gctggtgcag caggcgggcg   6840

gtttcgctgt ccagcgcccg cacctcgtcc atgctgatgc gcacatgctg gccgccaccc   6900

atgacggcct gcgcgatcaa ggggttcagg gccacgtaca ggcgcccgtc cgcctcgtcg   6960

ctggcgtact ccgacagcag ccgaaacccc tgccgcttgc ggccattctg ggcgatgatg   7020

gataccttcc aaaggcgctc gatgcagtcc tgtatgtgct tgagcgcccc accactatcg   7080

acctctgccc cgatttcctt tgccagcgcc cgatagctac ctttgaccac atggcattca   7140

gcggtgacgg cctcccactt gggttccagg aacagccgga gctgccgtcc gccttcggtc   7200

ttgggttccg ggccaagcac taggccatta ggcccagcca tggccaccag cccttgcagg   7260

atgcgcagat catcagcgcc cagcggctcc gggccgctga actcgatccg cttgccgtcg   7320

ccgtagtcat acgtcacgtc cagcttgctg cgcttgcgct cgccccgctt gagggcacgg   7380

aacaggccgg gggccagaca gtgcgccggg tcgtgccgga cgtggctgag gctgtgcttg   7440

ttcttaggct tcaccacggg gcaccccctt gctcttgcgc tgcctctcca gcacggcggg   7500

cttgagcacc ccgccgtcat gccgcctgaa ccaccgatca gcgaacggtg cgccatagtt   7560

ggccttgctc acaccgaagc ggacgaagaa ccggcgctgg tcgtcgtcca caccccattc   7620

ctcggcctcg gcgctggtca tgctcgacag gtaggactgc cagcggatgt tatcgaccag   7680

taccgagctg ccccggctgg cctgctgctg gtcgcctgcg cccatcatgg ccgcgccctt   7740

gctggcatgg tgcaggaaca cgatagagca cccggtatcg gcggcgatgg cctccatgcg   7800

accgatgacc tgggccatgg ggccgctggc gttttcttcc tcgatgtgga accggcgcag   7860

cgtgtccagc accatcaggc ggcggccctc ggcggcgcgc ttgaggccgt cgaaccactc   7920

cggggccatg atgttgggca ggctgccgat cagcggctgg atcagcaggc cgtcagccac   7980

ggcttgccgt tcctcggcgc tgaggtgcgc cccaagggcg tgcaggcggt gatgaatggc   8040

ggtgggcggg tcttcggcgg gcaggtagat caccgggccg gtgggcagtt cgcccacctc   8100

cagcagatcc ggcccgcctg caatctgtgc ggccagttgc agggccagca tggatttacc   8160

ggcaccaccg ggcgacacca gcgccccgac cgtaccggcc accatgttgg gcaaaacgta   8220

gtccagcggt ggcggcgctg ctgcgaacgc ctccagaata ttgataggct tatgggtagc   8280

cattgattgc ctcctttgca ggcagttggt ggttaggcgc tggcggggtc actacccccg   8340

ccctgcgccg ctctgagttc ttccaggcac tcgcgcagcg cctcgtattc gtcgtcggtc   8400

agccagaact tgcgctgacg catccctttg gccttcatgc gctcggcata tcgcgcttgg   8460

cgtacagcgt cagggctggc cagcaggtcg ccggtctgct tgtccttttg gtctttcata   8520
```

tcagtcaccg agaaacttgc cggggccgaa aggcttgtct tcgcggaaca aggacaaggt 8580
gcagccgtca aggttaaggc tggccatatc agcgactgaa aagcggccag cctcggcctt 8640
gtttgacgta taaccaaagc caccgggcaa ccaatagccc ttgtcacttt tgatcaggta 8700
gaccgaccct gaagcgcttt tttcgtattc cataaaaccc ccttctgtgc gtgagtactc 8760
atagtataac aggcgtgagt accaacgcaa gcactacatg ctgaaatctg gcccgcccct 8820
gtccatgcct cgctggcggg gtgccggtgc ccgtgccagc tcggcccgcg caagctggac 8880
gctgggcaga cccatgacct tgctgacggt gcgctcgatg 8920

<210> SEQ ID NO 7
<211> LENGTH: 20
<212> TYPE: DNA
<213> ORGANISM: Artificial Sequence
<220> FEATURE:
<223> OTHER INFORMATION: Chemically Synthesized,

<400> SEQUENCE: 7
cgtctaattc cacgaggatt 20

<210> SEQ ID NO 8
<211> LENGTH: 7703
<212> TYPE: DNA
<213> ORGANISM: Artificial Sequence
<220> FEATURE:
<223> OTHER INFORMATION: Chemically Synthesized, pBTK401 plasmid backbone sequence, circular

<400> SEQUENCE: 8
ccaatgctta atcagtgagg cacctatctc agcgatctgt ctatttcgtt catccatagt 60
tgcctgactc cccgtcgtgt agataactac gatacgggag ggcttaccat ctggccccag 120
tgctgcaatg ataccgcggg acccacgctc accggctcca gatttatcag caataaacca 180
gccagccgga agggccgagc gcagaagtgg tcctgcaact ttatccgcct ccatccagtc 240
tattaattgt tgccgggaag ctagagtaag tagttcgcca gttaatagtt tgcgcaacgt 300
tgttgccatt gctacaggca tcgtggtgtc acgctcgtcg tttggtatgg cttcattcag 360
ctccggttcc caacgatcaa ggcgagttac atgatccccc atgttgtgca aaaaagcggt 420
tagctccttc ggtcctccga tcgttgtcag aagtaagttg gccgcagtgt tatcactcat 480
ggttatggca gcactgcata attctcttac tgtcatgcca tccgtaagat gcttttctgt 540
gactggtgag tactcaacca agtcattctg agaatagtgt atgcggcgac cgagttgctc 600
ttgcccggcg tcaatacggg ataataccgc gccacatagc agaactttaa aagtgctcat 660
cattggaaaa cgttcttcgg ggcgaaaact ctcaaggatc ttaccgctgt tgagatccag 720
ttcgatgtaa cccactcgtg cacccaactg atcttcagca tcttttactt tcaccagcgt 780
ttctgggtga gcaaaaacag gaaggcaaaa tgccgcaaaa aagggaataa gggcgacacg 840
gaaatgttga atactcatac tcttcctttt tcaatattat tgaagcattt atcagggtta 900
ttgtctcatg agcggataca tatttgaatg tatttagaaa aataaacaaa taggggttcc 960
gcgcacattt ccccgaaaag tgccacctgt catgaccaaa atcccttaac gtgagtcagc 1020
ctgccgcctt gggccgggtg atgtcgtact tgcccgccgc gaactcggtt accgtccagc 1080
ccagcgcgac cagctccggc aacgcctcgc gcacccgctt gcggcgcttg cgcatggtcg 1140
aaccactggc ctctgacggc cagacatagc cgcacaaggt atctatggaa gccttgccgg 1200
ttttgccggg gtcgatccag ccacacagcc gctggtgcag caggcgggcg gtttcgctgt 1260

```
ccagcgcccg cacctcgtcc atgctgatgc gcacatgctg gccgccaccc atgacggcct   1320

gcgcgatcaa ggggttcagg gccacgtaca ggcgcccgtc cgcctcgtcg ctggcgtact   1380

ccgacagcag ccgaaacccc tgccgcttgc ggccattctg ggcgatgatg gataccttcc   1440

aaaggcgctc gatgcagtcc tgtatgtgct tgagcgcccc accactatcg acctctgccc   1500

cgatttcctt tgccagcgcc cgatagctac ctttgaccac atggcattca gcggtgacgg   1560

cctcccactt gggttccagg aacagccgga gctgccgtcc gccttcggtc ttgggttccg   1620

ggccaagcac taggccatta ggcccagcca tggccaccag cccttgcagg atgcgcagat   1680

catcagcgcc cagcggctcc gggccgctga actcgatccg cttgccgtcg ccgtagtcat   1740

acgtcacgtc cagcttgctg cgcttgcgct cgccccgctt gagggcacgg aacaggccgg   1800

gggccagaca gtgcgccggg tcgtgccgga cgtggctgag gctgtgcttg ttcttaggct   1860

tcaccacggg gcaccccctt gctcttgcgc tgcctctcca gcacggcggg cttgagcacc   1920

ccgccgtcat gccgcctgaa ccaccgatca gcgaacggtg cgccatagtt ggccttgctc   1980

acaccgaagc ggacgaagaa ccggcgctgg tcgtcgtcca caccccattc ctcggcctcg   2040

gcgctggtca tgctcgacag gtaggactgc cagcggatgt tatcgaccag taccgagctg   2100

ccccggctgg cctgctgctg gtcgcctgcg cccatcatgg ccgcgccctt gctggcatgg   2160

tgcaggaaca cgatagagca cccggtatcg gcggcgatgg cctccatgcg accgatgacc   2220

tgggccatgg ggccgctggc gtttttcttcc tcgatgtgga accggcgcag cgtgtccagc   2280

accatcaggc ggcggccctc ggcggcgcgc ttgaggccgt cgaaccactc cggggccatg   2340

atgttgggca ggctgccgat cagcggctgg atcagcaggc cgtcagccac ggcttgccgt   2400

tcctcggcgc tgaggtgcgc cccaagggcg tgcaggcggt gatgaatggc ggtgggcggg   2460

tcttcggcgg gcaggtagat caccgggccg gtgggcagtt cgcccacctc cagcagatcc   2520

ggcccgcctg caatctgtgc ggccagttgc agggccagca tggatttacc ggcaccaccg   2580

ggcgacacca gcgccccgac cgtaccggcc accatgttgg gcaaaacgta gtccagcggt   2640

ggcggcgctg ctgcgaacgc ctccagaata ttgataggct tatgggtagc cattgattgc   2700

ctcctttgca ggcagttggt ggttaggcgc tggcggggtc actacccccg ccctgcgccg   2760

ctctgagttc ttccaggcac tcgcgcagcg cctcgtattc gtcgtcggtc agccagaact   2820

tgcgctgacg catccctttg gccttcatgc gctcggcata tcgcgcttgg cgtacagcgt   2880

cagggctggc cagcaggtcg ccggtctgct tgtccttttg gtctttcata tcagtcaccg   2940

agaaacttgc cggggccgaa aggcttgtct tcgcggaaca aggacaaggt gcagccgtca   3000

aggttaaggc tggccatatc agcgactgaa aagcggccag cctcggcctt gtttgacgta   3060

taaccaaagc caccgggcaa ccaatagccc ttgtcacttt tgatcaggta gaccgaccct   3120

gaagcgcttt tttcgtattc cataaaaccc ccttctgtgc gtgagtactc atagtataac   3180

aggcgtgagt accaacgcaa gcactacatg ctgaaatctg gcccgcccct gtccatgcct   3240

cgctggcggg gtgccggtgc ccgtgccagc tcggcccgcg caagctggac gctgggcaga   3300

cccatgacct tgctgacggt gcgctcgatg taatccgctt cgtggccggg cttgcgctct   3360

gccagcgctg ggctggcctc ggccatggcc ttgccgattt cctcggcact gcggccccgg   3420

ctggccagct tctgcgcggc gataaagtcg cacttgctga ggtcatgacc gaagcgcttg   3480

accagcccgg ccatctcgct gcggtactcg tccagcgccg tgcgccggtg gcggctaagc   3540

tgccgctcgg gcagttcgag gctggccagc ctgcgggcct tctcctgctg ccgctgggcc   3600
```

```
tgctcgatct gctggccagc ctgctgcacc agcgccgggc cagcggtggc ggtcttgccc   3660
ttggattcac gcagcagcac ccacggctga taaccggcgc gggtggtgtg cttgtccttg   3720
cggttggtga agcccgccaa gcggccatag tggcggctgt cggcgctggc cgggtcggcg   3780
tcgtactcgc tggccagcgt ccgggcaatc tgcccccgaa gttcaccgcc tgcggcgtcg   3840
gccaccttga cccatgcctg atagttcttc gggctggttt ccactaccag ggcaggctcc   3900
cggccctcgg ctttcatgtc atccaggtca aactcgctga ggtcgtccac cagcaccaga   3960
ccatgccgct cctgctcggc gggcctgata tacacgtcat tgccctgggc attcatccgc   4020
ttgagccatg gcgtgttctg gagcacttcg gcggctgacc attcccggtt catcatctgg   4080
ccggtgggtg cgtccctgac gccgatatcg aagcgctcac agcccatggc cttgagctgt   4140
cggcctatgg cctgcaaagt cctgtcgttc ttcatcgggc caccaagcgc agccagatcg   4200
agccgtcctc ggttgtcagt ggcgtcaggt cgagcaagag caacgatgcg atcagcagca   4260
ccaccgtagg catcatggaa gccagcatca cggttagcca tagcttccag tgccaccccc   4320
gcgacgcgct ccgggcgctc tgcgcggcgc tgctcacctc ggcggctacc tcccgcaact   4380
ctttggccag ctccacccat gccgcccctg tctggcgctg ggctttcagc cactccgccg   4440
cctgcgcctc gctggcctgc ttggtctggc tcatgacctg ccgggcttcg tcggccagtg   4500
tcgccatgct ctgggccagc ggttcgatct gctccgctaa ctcgttgatg cctctggatt   4560
tcttcactct gtcgattgcg ttcatggtct attgcctccc ggtattcctg taagtcgatg   4620
atctgggcgt tggcggtgtc gatgttcagg gccacgtctg cccggtcggt gcggatgccc   4680
cggccttcca tctccaccac gttcggcccc aggtgaacac cgggcaggcg ctcgatgccc   4740
tgcgcctcaa gtgttctgtg gtcaatgcgg gcgtcgtggc cagcccgctc taatgcccgg   4800
ttggcatggt cggcccatgc ctcgcgggtc tgctcaagcc atgccttggg cttgagcgct   4860
tcggtcttct gtgccccgcc cttctccggg gtcttgccgt tgtaccgctt gaaccactga   4920
gcggcgggcc gctcgatgcc gtcattgatc cgctcggaga tcatcaggtg gcagtgcggg   4980
ttctcgccgc caccggcatg gatggccagc gtatacggca ggcgctcggc accggtcagg   5040
tgctgggcga actcggacgc cagcgccttc tgctggtcga gggtcagctc gaccggcagg   5100
gcaaattcga cctccttgaa cagccgccca ttggcgcgtt catacaggtc ggcagcatcc   5160
cagtagtcgg cgggccgctc gacgaactcc ggcatgtgcc cggattcggc gtgcaagact   5220
tcatccatgt cgcgggcata cttgccttcg cgctggatgt agtcggcctt ggccctggcc   5280
gattggccgc ccgacctgct gccggttttc gccgtaaggt gataaatcgc catgctgcct   5340
cgctgttgct tttgcttttc ggctccatgc aatggccctc ggagagcgca ccgcccgaag   5400
ggtggccgtt aggccagttt ctcgaagaga aaccggtaag tgcgccctcc cctacaaagt   5460
agggtcggga ttgccgccgc tgtgcctcca tgatagccta cgagacagca cattaacaat   5520
ggggtgtcaa gatggttaag gggagcaaca aggcggcgga tcggctggcc aagctcgaag   5580
aacaacgagc gcgaatcaat gccgaaattc agcgggagcg ggcaagggaa cagcagcaag   5640
agcgcaagaa cgaaacaagg cgcaaggtgc tggtgggggc catgattttg gccaaggtga   5700
acagcagcga gtggccggag gatcggctca tggcggcaat ggatgcgtac cttgaacgcg   5760
accacgaccg cgccttgttc ggtctgccgc cacgccagaa ggatgagccg ggctgaatga   5820
tcgaccgaga caggccctgc ggggctgcac acgcgccccc acccttcggg taggggggaa   5880
ggccgctaaa gcggctaaaa gcgctccagc gtatttctgc ggggtttggt gtggggttta   5940
gcgggctttg cccgcctttc cccctgccgc gcagcggtgg ggcggtgtgt agcctagcgc   6000
```

```
agcgaatagc ccagctatcc ggcctctggc cgggcatatt gggcaagggc agcagcgccc   6060

cacaagggcg ctgataaccg cgcctagtgg attattctta gataatcatg gatggatttt   6120

tccaacaccc cgccagcccc cgcccctgct gggtttgcag gtttgggggc gtgacagtta   6180

ttgcaggggt tcgtgacagt tattgcaggg gggcgtgaca gttattgcag gggttcgtga   6240

cagttagtac gggagtgacg ggcactggct ggcaatgtct agcaacggca ggcatttcgg   6300

ctgagggtaa aagaactttc cgctaagcga tagactgtat gtaaacacag tattgcaagg   6360

acgcggaaca tgcctcatgt ggcggccagg acggccagcc gggatcggga tactggtcgt   6420

taccagagcc accgacccga gcaaaccctt ctctatcaga tcgttgacga gtattacccg   6480

gcattcgctg cgcttatggc agagcaggga aaggaattgc cgggctatgt gcaacgggaa   6540

tttgaagaat ttctccaatg cgggcggctg gagcatggct ttctacgggt tcgctgcgag   6600

tcttgccacg ccgagcacct ggtcgctttc agaaatcaat ctaaagtata tatgagtaaa   6660

cttggtctga caggcccctt gagaccagtc cctatcagtg atagagattg acatccctat   6720

cagtgataga gatactgagc acggatctga aagaggagaa aggatctatg gcgagtagcg   6780

aagacgttat caaagagttc atgcgtttca aagttcgtat ggaaggttcc gttaacggtc   6840

acgagttcga aatcgaaggt gaaggtgaag gtcgtccgta cgaaggtact cagaccgcta   6900

aactgaaagt taccaaaggt ggtccgctgc cgttcgcttg ggacatcctg tccccgcagt   6960

tccagtacgg ttccaaagct tacgttaaac acccggctga catcccggac tacctgaaac   7020

tgtccttccc ggaaggtttc aaatgggaac gtgttatgaa cttcgaagac ggtggtgttg   7080

ttaccgttac ccaggactcc tccctgcaag acggtgagtt catctacaaa gttaaactgc   7140

gtggtactaa cttcccgtcc gacggtccgg ttatgcagaa aaaaaccatg ggttgggaag   7200

cttccaccga acgtatgtac ccggaagacg gtgctctgaa aggtgaaatc aaaatgcgtc   7260

tgaaactgaa agacggtggt cactacgacg ctgaagttaa aaccacctac atggctaaaa   7320

aaccggttca gctgccgggt gcttacaaaa ccgacatcaa actggacatc acctcccaca   7380

acgaagacta caccatcgtt gaacagtacg aacgtgctga aggtcgtcac tccaccggtg   7440

cttaataagg atctccaggc atcaaataaa acgaaaggct cagtcgaaag actgggcctt   7500

tcgttttatc tgttgtttgt cggtgaacgc tctctactag agtcacactg gctcaccttc   7560

gggtgggcct ttctgcgttt ataagtcggt ctcaccgagc ggccgcgatt atcaaaaagg   7620

atcttcacct agatcctttt aaattaaaaa tgaagtttta aatcaatcta aagtatatat   7680

gagtaaactt ggtctgacag tta                                           7703
```

<210> SEQ ID NO 9
<211> LENGTH: 7608
<212> TYPE: DNA
<213> ORGANISM: Artificial Sequence
<220> FEATURE:
<223> OTHER INFORMATION: Chemically Synthesized, pBTK402 plasmid backbone sequence, circular

<400> SEQUENCE: 9

```
ttagaaaaac tcatcgagca tcaaatgaaa ctgcaattta ttcatatcag gattatcaat     60

accatatttt tgaaaaagcc gtttctgtaa tgaaggagaa aactcaccga ggcagttcca    120

taggatggca agatcctggt atcggtctgc gattccgact cgtccaacat caatacaacc    180

tattaatttc ccctcgtcaa aaataaggtt atcaagtgag aaatcaccat gagtgacgac    240

tgaatccggt gagaatggca aaagcttatg catttctttc cagacttgtt caacaggcca    300
```

```
gccattacgc tcgtcatcaa aatcactcgc atcaaccaaa ccgttattca ttcgtgattg    360
cgcctgagcg aggcgaaata cgcgatcgct gttaaaagga caattacaaa caggaatcga    420
atgcaaccgg cgcaggaaca ctgccagcgc atcaacaata ttttcacctg aatcaggata    480
ttcttctaat acctggaatg ctgttttccc ggggatcgca gtggtgagta accatgcatc    540
atcaggagta cggataaaat gcttgatggt cggaagaggc ataaattccg tcagccagtt    600
tagtctgacc atctcatctg taacatcatt ggcaacgcta cctttgccat gtttcagaaa    660
caactctggc gcatcgggct tcccatacaa tcgatagatt gtcgcacctg attgcccgac    720
attatcgcga gcccatttat acccatataa atcagcatcc atgttggaat ttaatcgcgg    780
cctggagcaa gacgtttccc gttgaatatg gctcataaca ccccttgtat tactgtttat    840
gtaagcagac agttttattg ttcatgatga tatattttta tcttgtgcaa tgtaacatca    900
gagattttga gacacaacgt ggctttgttg aataaatcga acttttgctg agttgaagga    960
tcagtcatga ccaaaatccc ttaacgtgag tcagcctgcc gccttgggcc gggtgatgtc   1020
gtacttgccc gccgcgaact cggttaccgt ccagcccagc gcgaccagct ccggcaacgc   1080
ctcgcgcacc cgcttgcggc gcttgcgcat ggtcgaacca ctggcctctg acggccagac   1140
atagccgcac aaggtatcta tggaagcctt gccggttttg ccggggtcga tccagccaca   1200
cagccgctgg tgcagcaggc gggcggtttc gctgtccagc gcccgcacct cgtccatgct   1260
gatgcgcaca tgctggccgc cacccatgac ggcctgcgcg atcaaggggt tcagggccac   1320
gtacaggcgc ccgtccgcct cgtcgctggc gtactccgac agcagccgaa acccctgccg   1380
cttgcggcca ttctgggcga tgatggatac cttccaaagg cgctcgatgc agtcctgtat   1440
gtgcttgagc gccccaccac tatcgacctc tgccccgatt tcctttgcca gcgcccgata   1500
gctacctttg accacatggc attcagcggt gacggcctcc cacttgggtt ccaggaacag   1560
ccggagctgc cgtccgcctt cggtcttggg ttccgggcca agcactaggc cattaggccc   1620
agccatggcc accagccctt gcaggatgcg cagatcatca gcgcccagcg gctccgggcc   1680
gctgaactcg atccgcttgc cgtcgccgta gtcatacgtc acgtccagct tgctgcgctt   1740
gcgctcgccc cgcttgaggg cacggaacag gccgggggcc agacagtgcg ccgggtcgtg   1800
ccggacgtgg ctgaggctgt gcttgttctt aggcttcacc acggggcacc cccttgctct   1860
tgcgctgcct ctccagcacg gcgggcttga gcaccccgcc gtcatgccgc ctgaaccacc   1920
gatcagcgaa cggtgcgcca tagttggcct tgctcacacc gaagcggacg aagaaccggc   1980
gctggtcgtc gtccacaccc cattcctcgg cctcggcgct ggtcatgctc gacaggtagg   2040
actgccagcg gatgttatcg accagtaccg agctgccccg gctggcctgc tgctggtcgc   2100
ctgcgcccat catggccgcg cccttgctgg catggtgcag gaacacgata gagcacccgg   2160
tatcggcggc gatggcctcc atgcgaccga tgacctgggc catggggccg ctggcgtttt   2220
cttcctcgat gtggaaccgg cgcagcgtgt ccagcaccat caggcggcgg ccctcggcgg   2280
cgcgcttgag gccgtcgaac cactccgggg ccatgatgtt gggcaggctg ccgatcagcg   2340
gctggatcag caggccgtca gccacggctt gccgttcctc ggcgctgagg tgcgccccaa   2400
gggcgtgcag gcggtgatga atggcggtgg gcgggtcttc ggcgggcagg tagatcaccg   2460
ggccggtggg cagttcgccc acctccagca gatccggccc gcctgcaatc tgtgcggcca   2520
gttgcagggc cagcatggat ttaccggcac caccgggcga caccagcgcc ccgaccgtac   2580
cggccaccat gttgggcaaa acgtagtcca gcggtggcgg cgctgctgcg aacgcctcca   2640
```

```
gaatattgat aggcttatgg gtagccattg attgcctcct ttgcaggcag ttggtggtta   2700

ggcgctggcg gggtcactac cccgccctg cgccgctctg agttcttcca ggcactcgcg   2760

cagcgcctcg tattcgtcgt cggtcagcca gaacttgcgc tgacgcatcc ctttggcctt   2820

catgcgctcg gcatatcgcg cttggcgtac agcgtcaggg ctggccagca ggtcgccggt   2880

ctgcttgtcc ttttggtctt tcatatcagt caccgagaaa cttgccgggg ccgaaaggct   2940

tgtcttcgcg gaacaaggac aaggtgcagc cgtcaaggtt aaggctggcc atatcagcga   3000

ctgaaaagcg gccagcctcg gccttgtttg acgtataacc aaagccaccg ggcaaccaat   3060

agcccttgtc acttttgatc aggtagaccg accctgaagc gctttttttcg tattccataa   3120

aacccccttc tgtgcgtgag tactcatagt ataacaggcg tgagtaccaa cgcaagcact   3180

acatgctgaa atctggcccg cccctgtcca tgcctcgctg gcggggtgcc ggtgcccgtg   3240

ccagctcggc ccgcgcaagc tggacgctgg gcagacccat gaccttgctg acggtgcgct   3300

cgatgtaatc cgcttcgtgg ccgggcttgc gctctgccag cgctgggctg gcctcggcca   3360

tggccttgcc gatttcctcg gcactgcggc cccggctggc cagcttctgc gcggcgataa   3420

agtcgcactt gctgaggtca tgaccgaagc gcttgaccag cccggccatc tcgctgcggt   3480

actcgtccag cgccgtgcgc cggtggcggc taagctgccg ctcgggcagt tcgaggctgg   3540

ccagcctgcg ggccttctcc tgctgccgct gggcctgctc gatctgctgg ccagcctgct   3600

gcaccagcgc cgggccagcg gtggcggtct tgcccttgga ttcacgcagc agcacccacg   3660

gctgataacc ggcgcgggtg gtgtgcttgt ccttgcggtt ggtgaagccc gccaagcggc   3720

catagtggcg gctgtcggcg ctggccgggt cggcgtcgta ctcgctggcc agcgtccggg   3780

caatctgccc ccgaagttca ccgcctgcgg cgtcggccac cttgacccat gcctgatagt   3840

tcttcgggct ggtttccact accagggcag gctcccggcc ctcggctttc atgtcatcca   3900

ggtcaaactc gctgaggtcg tccaccagca ccagaccatg ccgctcctgc tcggcgggcc   3960

tgatatacac gtcattgccc tgggcattca tccgcttgag ccatggcgtg ttctggagca   4020

cttcggcggc tgaccattcc cggttcatca tctggccggt gggtgcgtcc ctgacgccga   4080

tatcgaagcg ctcacagccc atggccttga gctgtcggcc tatggcctgc aaagtcctgt   4140

cgttcttcat cgggccacca agcgcagcca gatcgagccg tcctcggttg tcagtggcgt   4200

caggtcgagc aagagcaacg atgcgatcag cagcaccacc gtaggcatca tggaagccag   4260

catcacggtt agccatagct tccagtgcca cccccgcgac gcgctccggg cgctctgcgc   4320

ggcgctgctc acctcggcgg ctacctcccg caactctttg gccagctcca cccatgccgc   4380

ccctgtctgg cgctgggctt tcagccactc cgccgcctgc gcctcgctgg cctgcttggt   4440

ctggctcatg acctgccggg cttcgtcggc cagtgtcgcc atgctctggg ccagcggttc   4500

gatctgctcc gctaactcgt tgatgcctct ggatttcttc actctgtcga ttgcgttcat   4560

ggtctattgc ctcccggtat tcctgtaagt cgatgatctg ggcgttggcg gtgtcgatgt   4620

tcagggccac gtctgcccgg tcggtgcgga tgccccggcc ttccatctcc accacgttcg   4680

gccccaggtg aacaccgggc aggcgctcga tgccctgcgc ctcaagtgtt ctgtggtcaa   4740

tgcgggcgtc gtggccagcc cgctctaatg cccggttggc atggtcggcc catgcctcgc   4800

gggtctgctc aagccatgcc ttgggcttga gcgcttcggt cttctgtgcc ccgcccttct   4860

ccggggtctt gccgttgtac cgcttgaacc actgagcggc gggccgctcg atgccgtcat   4920

tgatccgctc ggagatcatc aggtggcagt gcgggttctc gccgccaccg gcatggatgg   4980

ccagcgtata cggcaggcgc tcggcaccgg tcaggtgctg ggcgaactcg gacgccagcg   5040
```

```
ccttctgctg gtcgagggtc agctcgaccg gcagggcaaa ttcgacctcc ttgaacagcc   5100

gcccattggc gcgttcatac aggtcggcag catcccagta gtcggcgggc cgctcgacga   5160

actccggcat gtgcccggat tcggcgtgca agacttcatc catgtcgcgg gcatacttgc   5220

cttcgcgctg gatgtagtcg gccttggccc tggccgattg gccgcccgac ctgctgccgg   5280

ttttcgccgt aaggtgataa atcgccatgc tgcctcgctg ttgcttttgc ttttcggctc   5340

catgcaatgg ccctcggaga gcgcaccgcc cgaagggtgg ccgttaggcc agtttctcga   5400

agagaaaccg gtaagtgcgc cctcccctac aaagtagggt cgggattgcc gccgctgtgc   5460

ctccatgata gcctacgaga cagcacatta acaatggggt gtcaagatgg ttaaggggag   5520

caacaaggcg gcggatcggc tggccaagct cgaagaacaa cgagcgcgaa tcaatgccga   5580

aattcagcgg gagcgggcaa gggaacagca gcaagagcgc aagaacgaaa caaggcgcaa   5640

ggtgctggtg gggccatga ttttggccaa ggtgaacagc agcgagtggc cggaggatcg   5700

gctcatggcg gcaatggatg cgtaccttga acgcgaccac gaccgcgcct tgttcggtct   5760

gccgccacgc cagaaggatg agccgggctg aatgatcgac cgagacaggc cctgcggggc   5820

tgcacacgcg cccccaccct tcgggtaggg ggaaaggccg ctaaagcggc taaaagcgct   5880

ccagcgtatt tctgcggggt ttggtgtggg gtttagcggg ctttgcccgc ctttcccccct   5940

gccgcgcagc ggtggggcgg tgtgtagcct agcgcagcga atagaccagc tatccggcct   6000

ctggccgggc atattgggca agggcagcag cgccccacaa gggcgctgat aaccgcgcct   6060

agtggattat tcttagataa tcatggatgg atttttccaa caccccgcca gcccccgccc   6120

ctgctgggtt tgcaggtttg gggcgtgac agttattgca ggggttcgtg acagttattg   6180

cagggggcg tgacagttat tgcaggggtt cgtgacagtt agtacgggag tgacgggcac   6240

tggctggcaa tgtctagcaa cggcaggcat ttcggctgag ggtaaaagaa ctttccgcta   6300

agcgatagac tgtatgtaaa cacagtattg caaggacgcg gaacatgcct catgtggcgg   6360

ccaggacggc cagccgggat cgggatactg gtcgttacca gagccaccga cccgagcaaa   6420

cccttctcta tcagatcgtt gacgagtatt acccggcatt cgctgcgctt atggcagagc   6480

agggaaagga attgccgggc tatgtgcaac gggaatttga agaatttctc caatgcgggc   6540

ggctggagca tggctttcta cgggttcgct gcgagtcttg ccacgccgag cacctggtcg   6600

ctttcagaaa tcaatctaaa gtatatatga gtaaacttgg tctgacaggc cccttgagac   6660

cagtccctat cagtgataga gattgacatc cctatcagtg atagagatac tgagcacgga   6720

tctgaaagag gagaaaggat ctatggcgag tagcgaagac gttatcaaag agttcatgcg   6780

tttcaaagtt cgtatggaag gttccgttaa cggtcacgag ttcgaaatcg aaggtgaagg   6840

tgaaggtcgt ccgtacgaag gtactcagac cgctaaactg aaagttacca aaggtggtcc   6900

gctgccgttc gcttgggaca tcctgtcccc gcagttccag tacggttcca aagcttacgt   6960

taaacacccg gctgacatcc cggactacct gaaactgtcc ttcccggaag gtttcaaatg   7020

ggaacgtgtt atgaacttcg aagacggtgg tgttgttacc gttacccagg actcctccct   7080

gcaagacggt gagttcatct acaaagttaa actgcgtggt actaacttcc cgtccgacgg   7140

tccggttatg cagaaaaaaa ccatgggttg ggaagcttcc accgaacgta tgtacccgga   7200

agacggtgct ctgaaaggtg aaatcaaaat gcgtctgaaa ctgaaagacg gtggtcacta   7260

cgacgctgaa gttaaaacca cctacatggc taaaaaaccg gttcagctgc cgggtgctta   7320

caaaaccgac atcaaactgg acatcacctc ccacaacgaa gactacacca tcgttgaaca   7380
```

```
gtacgaacgt gctgaaggtc gtcactccac cggtgcttaa taaggatctc caggcatcaa   7440

ataaaacgaa aggctcagtc gaaagactgg gcctttcgtt ttatctgttg tttgtcggtg   7500

aacgctctct actagagtca cactggctca ccttcgggtg ggcctttctg cgtttataag   7560

tcggtctcac cgagcggccg cgtgttacaa ccaattaacc aattctga                7608
```

<210> SEQ ID NO 10
<211> LENGTH: 7762
<212> TYPE: DNA
<213> ORGANISM: Artificial Sequence
<220> FEATURE:
<223> OTHER INFORMATION: Chemically Synthesized, pBTK403 plasmid backbone sequence, circular

<400> SEQUENCE: 10

```
ttatttgccg actaccttgg tgatctcgcc tttcacgtag tggacaaatt cttccaactg     60

atctgcgcgc gaggccaagc gatcttcttc ttgtccaaga taagcctgtc tagcttcaag    120

tatgacgggc tgatactggg ccggcaggcg ctccattgcc cagtcggcag cgacatcctt    180

cggcgcgatt ttgccggtta ctgcgctgta ccaaatgcgg gacaacgtaa gcactacatt    240

tcgctcatcg ccagcccagt cgggcggcga gttccatagc gttaaggttt catttagcgc    300

ctcaaataga tcctgttcag gaaccggatc aaagagttcc tccgccgctg gacctaccaa    360

ggcaacgcta tgttctcttg cttttgtcag caagatagcc agatcaatgt cgatcgtggc    420

tggctcgaag atacccgcaa gaatgtcatt gcgctgccat tctccaaatt gcagttcgcg    480

cttagctgga taacgccacg gaatgatgtc gtcgtgcaca acaatggtga cttctacagc    540

gcggagaatc tcgctctctc caggggaagc cgaagtttcc aaaaggtcgt tgatcaaagc    600

tcgccgcgtt gtttcatcaa gccttacggt caccgtaacc agcaaatcaa tatcactgtg    660

tggcttcagg ccgccatcca ctgcggagcc gtacaaatgt acggccagca acgtcggttc    720

gagatggcgc tcgatgacgc caactacctc tgatagttga gtcgatactt cggcgatcac    780

cgcttccctc ataatgttta actttgtttt agggcgactg ccctgctgcg taacatcgtt    840

gctgctccat aacatcaaac atcgacccac ggcgtaacgc gcttgctgct tggatgcccg    900

aggcatagac tgtaccccaa aaaaacagtc ataacaagcc atgaaaaccg ccactgcgcc    960

gttaccaccg ctgcgttcgg tcaaggttct ggaccagttg cgtgagcgca tacgctactt   1020

gcattacagc ttacgaaccg aacaggctta tgtccactgg gttcgtgcct tcatccgttt   1080

ccacggtgtg cgtcacccgg caaccttggg tagcagcgaa gtcgaggcat ttctgtcctg   1140

gctggtcatg accaaaatcc cttaacgtga gtcagcctgc cgccttgggc cgggtgatgt   1200

cgtacttgcc cgccgcgaac tcggttaccg tccagcccag cgcgaccagc tccggcaacg   1260

cctcgcgcac ccgcttgcgg cgcttgcgca tggtcgaacc actggcctct gacggccaga   1320

catagccgca caaggtatct atggaagcct tgccggtttt gccggggtcg atccagccac   1380

acagccgctg gtgcagcagg cgggcggttt cgctgtccag cgcccgcacc tcgtccatgc   1440

tgatgcgcac atgctggccg ccacccatga cggcctgcgc gatcaagggg ttcagggcca   1500

cgtacaggcg cccgtccgcc tcgtcgctgg cgtactccga cagcagccga aacccctgcc   1560

gcttgcggcc attctgggcg atgatggata ccttccaaag gcgctcgatg cagtcctgta   1620

tgtgcttgag cgccccacca ctatcgacct ctgccccgat ttcctttgcc agcgcccgat   1680

agctaccttt gaccacatgg cattcagcgg tgacggcctc ccacttgggt tccaggaaca   1740

gccggagctg ccgtccgcct tcggtcttgg gttccgggcc aagcactagg ccattaggcc   1800
```

```
cagccatggc caccagccct tgcaggatgc gcagatcatc agcgcccagc ggctccgggc   1860
cgctgaactc gatccgcttg ccgtcgccgt agtcatacgt cacgtccagc ttgctgcgct   1920
tgcgctcgcc ccgcttgagg gcacggaaca ggccgggggc cagacagtgc gccgggtcgt   1980
gccggacgtg gctgaggctg tgcttgttct taggcttcac cacggggcac cccettgctc   2040
ttgcgctgcc tctccagcac ggcgggcttg agcaccccgc cgtcatgccg cctgaaccac   2100
cgatcagcga acggtgcgcc atagttggcc ttgctcacac cgaagcggac gaagaaccgg   2160
cgctggtcgt cgtccacacc ccattcctcg gcctcggcgc tggtcatgct cgacaggtag   2220
gactgccagc ggatgttatc gaccagtacc gagctgcccc ggctggcctg ctgctggtcg   2280
cctgcgccca tcatggccgc gcccttgctg gcatggtgca ggaacacgat agagcacccg   2340
gtatcggcgg cgatggcctc catgcgaccg atgacctggg ccatggggcc gctggcgttt   2400
tcttcctcga tgtggaaccg gcgcagcgtg tccagcacca tcaggcggcg gccctcggcg   2460
gcgcgcttga ggccgtcgaa ccactccggg gccatgatgt tgggcaggct gccgatcagc   2520
ggctggatca gcaggccgtc agccacggct tgccgttcct cggcgctgag gtgcgcccca   2580
agggcgtgca ggcggtgatg aatggcggtg ggcgggtctt cggcgggcag gtagatcacc   2640
gggccggtgg gcagttcgcc cacctccagc agatccggcc cgcctgcaat ctgtgcggcc   2700
agttgcaggg ccagcatgga tttaccggca ccaccgggcg acaccagcgc cccgaccgta   2760
ccggccacca tgttgggcaa aacgtagtcc agcggtggcg gcgctgctgc gaacgcctcc   2820
agaatattga taggcttatg ggtagccatt gattgcctcc tttgcaggca gttggtggtt   2880
aggcgctggc ggggtcacta cccccgccct gcgccgctct gagttcttcc aggcactcgc   2940
gcagcgcctc gtattcgtcg tcggtcagcc agaacttgcg ctgacgcatc cctttggcct   3000
tcatgcgctc ggcatatcgc gcttggcgta cagcgtcagg gctggccagc aggtcgccgg   3060
tctgcttgtc cttttggtct ttcatatcag tcaccgagaa acttgccggg gccgaaaggc   3120
ttgtcttcgc ggaacaagga caaggtgcag ccgtcaaggt taaggctggc catatcagcg   3180
actgaaaagc ggccagcctc ggccttgttt gacgtataac caaagccacc gggcaaccaa   3240
tagcccttgt cacttttgat caggtagacc gaccctgaag cgcttttttc gtattccata   3300
aaaccccctt ctgtgcgtga gtactcatag tataacaggc gtgagtacca acgcaagcac   3360
tacatgctga aatctggccc gcccctgtcc atgcctcgct ggcggggtgc cggtgcccgt   3420
gccagctcgg cccgcgcaag ctggacgctg ggcagaccca tgaccttgct gacggtgcgc   3480
tcgatgtaat ccgcttcgtg gccgggcttg cgctctgcca gcgctgggct ggcctcggcc   3540
atggccttgc cgatttcctc ggcactgcgg ccccggctgg ccagcttctg cgcggcgata   3600
aagtcgcact tgctgaggtc atgaccgaag cgcttgacca gcccggccat ctcgctgcgg   3660
tactcgtcca gcgccgtgcg ccggtggcgg ctaagctgcc gctcgggcag ttcgaggctg   3720
gccagcctgc gggccttctc ctgctgccgc tgggcctgct cgatctgctg gccagcctgc   3780
tgcaccagcg ccgggccagc ggtggcggtc ttgcccttgg attcacgcag cagcacccac   3840
ggctgataac cggcgcgggt ggtgtgcttg tccttgcggt tggtgaagcc cgccaagcgg   3900
ccatagtggc ggctgtcggc gctggccggg tcggcgtcgt actcgctggc cagcgtccgg   3960
gcaatctgcc cccgaagttc accgcctgcg gcgtcggcca ccttgaccca tgcctgatag   4020
ttcttcgggc tggtttccac taccagggca ggctcccggc cctcggcttt catgtcatcc   4080
aggtcaaact cgctgaggtc gtccaccagc accagaccat gccgctcctg ctcggcgggc   4140
ctgatataca cgtcattgcc ctgggcattc atccgcttga gccatggcgt gttctggagc   4200
```

```
acttcggcgg ctgaccattc ccggttcatc atctggccgg tgggtgcgtc cctgacgccg   4260
atatcgaagc gctcacagcc catggccttg agctgtcggc ctatggcctg caaagtcctg   4320
tcgttcttca tcgggccacc aagcgcagcc agatcgagcc gtcctcggtt gtcagtggcg   4380
tcaggtcgag caagagcaac gatgcgatca gcagcaccac cgtaggcatc atggaagcca   4440
gcatcacggt tagccatagc ttccagtgcc acccccgcga cgcgctccgg gcgctctgcg   4500
cggcgctgct cacctcggcg gctacctccc gcaactcttt ggccagctcc acccatgccg   4560
cccctgtctg gcgctgggct ttcagccact ccgccgcctg cgcctcgctg gcctgcttgg   4620
tctggctcat gacctgccgg gcttcgtcgg ccagtgtcgc catgctctgg gccagcggtt   4680
cgatctgctc cgctaactcg ttgatgcctc tggatttctt cactctgtcg attgcgttca   4740
tggtctattg cctcccggta ttcctgtaag tcgatgatct gggcgttggc ggtgtcgatg   4800
ttcagggcca cgtctgcccg gtcggtgcgg atgccccggc cttccatctc caccacgttc   4860
ggccccaggt gaacaccggg caggcgctcg atgccctgcg cctcaagtgt tctgtggtca   4920
atgcgggcgt cgtggccagc ccgctctaat gcccggttgg catggtcggc ccatgcctcg   4980
cgggtctgct caagccatgc cttgggcttg agcgcttcgg tcttctgtgc cccgcccttc   5040
tccggggtct tgccgttgta ccgcttgaac cactgagcgg cgggccgctc gatgccgtca   5100
ttgatccgct cggagatcat caggtggcag tgcgggttct cgccgccacc ggcatggatg   5160
gccagcgtat acggcaggcg ctcggcaccg gtcaggtgct gggcgaactc ggacgccagc   5220
gccttctgct ggtcgagggt cagctcgacc ggcagggcaa attcgacctc cttgaacagc   5280
cgcccattgg cgcgttcata caggtcggca gcatcccagt agtcggcggg ccgctcgacg   5340
aactccggca tgtgcccgga ttcggcgtgc aagacttcat ccatgtcgcg ggcatacttg   5400
ccttcgcgct ggatgtagtc ggccttggcc ctggccgatt ggccgcccga cctgctgccg   5460
gttttcgccg taaggtgata aatcgccatg ctgcctcgct gttgcttttg cttttcggct   5520
ccatgcaatg gccctcggag agcgcaccgc ccgaagggtg gccgttaggc cagtttctcg   5580
aagagaaacc ggtaagtgcg ccctccccta caaagtaggg tcgggattgc cgccgctgtg   5640
cctccatgat agcctacgag acagcacatt aacaatgggg tgtcaagatg gttaagggga   5700
gcaacaaggc ggcggatcgg ctggccaagc tcgaagaaca acgagcgcga atcaatgccg   5760
aaattcagcg ggagcgggca agggaacagc agcaagagcg caagaacgaa acaaggcgca   5820
aggtgctggt gggggccatg attttggcca aggtgaacag cagcgagtgg ccggaggatc   5880
ggctcatggc ggcaatggat gcgtaccttg aacgcgacca cgaccgcgcc ttgttcggtc   5940
tgccgccacg ccagaaggat gagccgggct gaatgatcga ccgagacagg ccctgcgggg   6000
ctgcacacgc gcccccaccc ttcgggtagg gggaaaggcc gctaaagcgg ctaaaagcgc   6060
tccagcgtat ttctgcgggg tttggtgtgg ggtttagcgg gctttgcccg cctttccccc   6120
tgccgcgcag cggtggggcg gtgtgtagcc tagcgcagcg aatagaccag ctatccggcc   6180
tctggccggg catattgggc aagggcagca gcgccccaca agggcgctga taaccgcgcc   6240
tagtggatta ttcttagata atcatggatg gatttttcca acaccccgcc agcccccgcc   6300
cctgctgggt ttgcaggttt gggggcgtga cagttattgc aggggttcgt gacagttatt   6360
gcaggggggc gtgacagtta ttgcaggggt tcgtgacagt tagtacggga gtgacgggca   6420
ctggctggca atgtctagca acggcaggca tttcggctga gggtaaaaga actttccgct   6480
aagcgataga ctgtatgtaa acacagtatt gcaaggacgc ggaacatgcc tcatgtggcg   6540
```

```
gccaggacgg ccagccggga tcgggatact ggtcgttacc agagccaccg acccgagcaa   6600

acccttctct atcagatcgt tgacgagtat tacccggcat tcgctgcgct tatggcagag   6660

cagggaaagg aattgccggg ctatgtgcaa cgggaatttg aagaatttct ccaatgcggg   6720

cggctggagc atggctttct acgggttcgc tgcgagtctt gccacgccga gcacctggtc   6780

gctttcagaa atcaatctaa agtatatatg agtaaacttg gtctgacagg ccccttgaga   6840

ccagtcccta tcagtgatag agattgacat ccctatcagt gatagagata ctgagcacgg   6900

atctgaaaga ggagaaagga tctatggcga gtagcgaaga cgttatcaaa gagttcatgc   6960

gtttcaaagt tcgtatggaa ggttccgtta acggtcacga gttcgaaatc gaaggtgaag   7020

gtgaaggtcg tccgtacgaa ggtactcaga ccgctaaact gaaagttacc aaaggtggtc   7080

cgctgccgtt cgcttgggac atcctgtccc cgcagttcca gtacggttcc aaagcttacg   7140

ttaaacaccc ggctgacatc ccggactacc tgaaactgtc cttcccggaa ggtttcaaat   7200

gggaacgtgt tatgaacttc gaagacggtg gtgttgttac cgttacccag gactcctccc   7260

tgcaagacgg tgagttcatc tacaaagtta aactgcgtgg tactaacttc ccgtccgacg   7320

gtccggttat gcagaaaaaa accatgggtt gggaagcttc caccgaacgt atgtacccgg   7380

aagacggtgc tctgaaaggt gaaatcaaaa tgcgtctgaa actgaaagac ggtggtcact   7440

acgacgctga agttaaaacc acctacatgg ctaaaaaacc ggttcagctg ccgggtgctt   7500

acaaaaccga catcaaactg gacatcacct cccacaacga agactacacc atcgttgaac   7560

agtacgaacg tgctgaaggt cgtcactcca ccggtgctta ataaggatct ccaggcatca   7620

aataaaacga aaggctcagt cgaaagactg ggcctttcgt tttatctgtt gtttgtcggt   7680

gaacgctctc tactagagtc acactggctc accttcgggt gggcctttct gcgtttataa   7740

gtcggtctca ccgagcggcc gc                                             7762
```

<210> SEQ ID NO 11
<211> LENGTH: 3199
<212> TYPE: DNA
<213> ORGANISM: Artificial Sequence
<220> FEATURE:
<223> OTHER INFORMATION: Chemically Synthesized, pBTK599 backbone sequence, circular

<400> SEQUENCE: 11

```
aggggggatca attccgtgat aggtgggctg ccccttcctgg ttggcttggt ttcatcagcc     60

atccgcttgc cctcatctgt tacgccggcg gtagccggcc agcctcgcag agcaggattc    120

ccgttgagca ccgccaggtg cgaataaggg acagtgaaga aggaacaccc gctcgcgggt    180

gggcctactt cacctatcct gcccggctga cgccgttgga tacaccaagg aaagtctaca    240

cgaacccttt ggcaaaatcc tgtatatcgt gcgaaaaagg atggatatac cgaaaaaatc    300

gctataatga ccccgaagca gggttatgca gcggaaaacg gaattgatcc ggccacgatg    360

cgtccggcgt agaggatctg aagatcagca gttcaacctg ttgatagtac gtactaagct    420

ctcatgtttc acgtactaag ctctcatgtt taacgtacta agctctcatg tttaacgaac    480

taaaccctca tggctaacgt actaagctct catggctaac gtactaagct ctcatgtttc    540

acgtactaag ctctcatgtt tgaacaataa aattaatata aatcagcaac ttaaatagcc    600

tctaaggttt taagttttat aagaaaaaaa agaatatata aggcttttaa agcttttaag    660

gtttaacggt tgtggacaac aagccaggga tgtaacgcac tgagaagccc ttagagcctc    720

tcaaagcaat tttgagtgac acaggaacac ttaacggctg acatgggaat tcccctccac    780
```

-continued

```
cgcggtggcg gccgctctag aactagtgga tcccccgggc tgcaggaatt cgatatcaag    840
cttatcgata ccgtcgacct cgaggggggg cccggtaccg aggacgcgtc gaattaattc    900
cgctagcttc acgctgccgc aagcactcag ggcgcaaggg ctgctaaagg aagcggaaca    960
cgtagaaagc cagtccgcag aaacggtgct gaccccggat gaatgtcagc tactgggcta   1020
tctggacaag ggaaaacgca agcgcaaaga gaaagcaggt agcttgcagt gggattatca   1080
aaaaggatct tcacctagat ccttttaaat taaaaatgaa gttttaaatc aatctaaagt   1140
atatatgagt aaacttggtc tgacagttac caatgcttaa tcagtgaggc acctatctca   1200
gcgatctgtc tatttcgttc atccatagtt gcctgactcc ccgtcgtgta gataactacg   1260
atacgggagg gcttaccatc tggccccagt gctgcaatga taccgcggga cccacgctca   1320
ccggctccag atttatcagc aataaaccag ccagccggaa gggccgagcg cagaagtggt   1380
cctgcaactt tatccgcctc catccagtct attaattgtt gccgggaagc tagagtaagt   1440
agttcgccag ttaatagttt gcgcaacgtt gttgccattg ctacaggcat cgtggtgtca   1500
cgctcgtcgt ttggtatggc ttcattcagc tccggttccc aacgatcaag gcgagttaca   1560
tgatccccca tgttgtgcaa aaaagcggtt agctccttcg gtcctccgat cgttgtcaga   1620
agtaagttgg ccgcagtgtt atcactcatg gttatggcag cactgcataa ttctcttact   1680
gtcatgccat ccgtaagatg cttttctgtg actggtgagt actcaaccaa gtcattctga   1740
gaatagtgta tgcggcgacc gagttgctct tgcccggcgt caatacggga taataccgcg   1800
ccacatagca gaactttaaa agtgctcatc attggaaaac gttcttcggg gcgaaaactc   1860
tcaaggatct taccgctgtt gagatccagt tcgatgtaac ccactcgtgc acccaactga   1920
tcttcagcat cttttacttt caccagcgtt tctgggtgag caaaaacagg aaggcaaaat   1980
gccgcaaaaa agggaataag ggcgacacgg aaatgttgaa tactcatact cttccttttt   2040
caatattatt gaagcattta tcagggttat tgtctcatga gcggatacat atttgaatgt   2100
atttagaaaa ataaacaaat aggggttccg cgcacatttc cccgaaaagt gccacctgcc   2160
tgatgagacg atgaaagtga aacgtgattt catgcgtcat tttgaacatt ttgtaaatct   2220
tatttaataa tgtgtgcggc aattcacatt taatttatga atgttttctt aacatcgcgg   2280
caactcaaga aacggcaggt tcggatctta gctactagag aaagaggaga aatactagat   2340
gcgtaaaggc gaagagctgt tcactggtgt cgtccctatt ctggtggaac tggatggtga   2400
tgtcaacggt cataagtttt ccgtgcgtgg cgagggtgaa ggtgacgcaa ctaatggtaa   2460
actgacgctg aagttcatct gtactactgg taaactgccg gttccttggc cgactctggt   2520
aacgacgctg acttatggtg ttcagtgctt tgctcgttat ccggaccata tgaagcagca   2580
tgacttcttc aagtccgcca tgccggaagg ctatgtgcag gaacgcacga tttcctttaa   2640
ggatgacggc acgtacaaaa cgcgtgcgga agtgaaattt gaaggcgata ccctggtaaa   2700
ccgcattgag ctgaaaggca ttgactttaa agaggacggc aatatcctgg gccataagct   2760
ggaatacaat tttaacagcc acaatgttta catcaccgcc gataaacaaa aaaatggcat   2820
taaagcgaat tttaaaattc gccacaacgt ggaggatggc agcgtgcagc tggctgatca   2880
ctaccagcaa aacactccaa tcggtgatgg tcctgttctg ctgccagaca atcactatct   2940
gagcacgcaa agcgttctgt ctaaagatcc gaacgagaaa cgcgatcata tggttctgct   3000
ggagttcgta accgcagcgg gcatcacgca tggtatggat gaactgtaca aatgaccagg   3060
catcaaataa aacgaaaggc tcagtcgaaa gactgggcct ttcgttttat ctgttgtttg   3120
tcggtgaacg ctctctacta gagtcacact ggctcacctt cgggtgggcc tttctgcgtt   3180
```

```
tataagtccg tctcaagca                                                 3199


<210> SEQ ID NO 12
<211> LENGTH: 109
<212> TYPE: DNA
<213> ORGANISM: Artificial Sequence
<220> FEATURE:
<223> OTHER INFORMATION: Chemically Synthesized, CP25_lacO sequence

<400> SEQUENCE: 12

ctttggcagt ttattcttga catgtagtga gggggctggt ataatcacat agtactgttg     60

gaattgtgag cggataacaa ttccatacag aaacagagga gatattaca               109


<210> SEQ ID NO 13
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 13

taccaacagc gacagaaccc                                                 20


<210> SEQ ID NO 14
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 14

ctcaggcgca atcacgaatg                                                 20


<210> SEQ ID NO 15
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 15

aatgctgttt tcccggggat                                                 20


<210> SEQ ID NO 16
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 16

ctggaaattg ctgctgccag                                                 20


<210> SEQ ID NO 17
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 17

tcgcttgttc acagcgatag a                                               21


<210> SEQ ID NO 18
```

<211> LENGTH: 20
<212> TYPE: DNA
<213> ORGANISM: Artificial Sequence
<220> FEATURE:
<223> OTHER INFORMATION: Chemically Synthesized

<400> SEQUENCE: 18
gcttttgcca ttctcaccgg 20

<210> SEQ ID NO 19
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 19
attggcaacg ctacctttgc 20

<210> SEQ ID NO 20
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 20
gtcgtggtat tgtcaggagc a 21

<210> SEQ ID NO 21
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 21
tgttcaggac gtcaatacac cttat 25

<210> SEQ ID NO 22
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 22
aaattgcagt ttcatttgat gctcg 25

<210> SEQ ID NO 23
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 23
gcgagcccat ttatacccat ataaa 25

<210> SEQ ID NO 24
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 24
ttcaaggttc catttgcctt tttca 25

<210> SEQ ID NO 25
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 25
acctgttgat agtacgtact aagctc 26

<210> SEQ ID NO 26
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 26
tcaaaattgc tttgagaggc tctaag 26

<210> SEQ ID NO 27
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 27
tcatgtcatc caggtcaaac tc 22

<210> SEQ ID NO 28
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 28
tgaagaaatc cagaggcatc aa 22

<210> SEQ ID NO 29
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 29
cttagagata ggagagtg 18

<210> SEQ ID NO 30
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 30
taatgatggc aactaatgac aa 22

<210> SEQ ID NO 31
<211> LENGTH: 23
<212> TYPE: DNA

<213> ORGANISM: Artificial Sequence
<220> FEATURE:
<223> OTHER INFORMATION: Chemically Synthesized

<400> SEQUENCE: 31
cccaatcctc gtggaattag acg 23

<210> SEQ ID NO 32
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 32
gaattcgaag cataagaatt 20

<210> SEQ ID NO 33
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 33
ttccacttaa tacgtgcatc 20

<210> SEQ ID NO 34
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 34
acaccatgtc catgcgaaaa 20

<210> SEQ ID NO 35
<211> LENGTH: 49
<212> TYPE: DNA
<213> ORGANISM: Artificial Sequence
<220> FEATURE:
<223> OTHER INFORMATION: Chemically Sythesized

<400> SEQUENCE: 35
atgtcttttt caatgggtac gtatgtatct ctaaagtaat caacataat 49

<210> SEQ ID NO 36
<211> LENGTH: 2481
<212> TYPE: DNA
<213> ORGANISM: Artificial Sequence
<220> FEATURE:
<223> OTHER INFORMATION: chemically synthesized, pBTK001

<400> SEQUENCE: 36
agcgagctcg atatcaaatt acgccccgcc ctgccactca tcgcagtact gttgtaattc 60
attaagcatt ctgccgacat ggaagccatc acaaacggca tgatgaacct gaatcgccag 120
cggcatcagc accttgtcgc cttgcgtata atatttgccc atggtgaaaa cgggggcgaa 180
gaagttgtcc atattggcca cgtttaaatc aaaactggtg aaactcaccc agggattggc 240
tgaaacgaaa aacatattct caataaaccc tttagggaaa taggccaggt tttcaccgta 300
acacgccaca tcttgcgaat atatgtgtag aaactgccgg aaatcgtcgt ggtattcact 360
ccagagcgat gaaaacgttt cagtttgctc atggaaaacg gtgtaacaag ggtgaacact 420

```
atcccatatc accagctcac cgtctttcat tgccatacga aattccggat gagcattcat    480

caggcgggca agaatgtgaa taaaggccgg ataaaacttg tgcttatttt tctttacggt    540

ctttaaaaag gccgtaatat ccagctgaac ggtctggtta taggtacatt gagcaactga    600

ctgaaatgcc tcaaaatgtt ctttacgatg ccattgggat atatcaacgg tggtatatcc    660

agtgattttt ttctccattt tagcttcctt agctcctgaa aatctcgata actcaaaaaa    720

tacgcccggt agtgatctta tttcattatg gtgaaagttg gaacctctta cgtgcccgat    780

caatttccat aggctccgcc cccctgacaa gcatcacgaa atctgacgct caaatcagtg    840

gtggcgaaac ccgacaggac tataaagata ccaggcgttt ccccctggcg gctccctcgt    900

gcgctctcct gttcctgcct ttcggtttac cggtgtcatt ccgctgttat ggccgcgttt    960

gtctcattcc acgcctgaca ctcagttccg ggtaggcagt tcgctccaag ctggactgta   1020

tgcacgaacc ccccgttcag tccgaccgct gcgccttatc cggtaactat cgtcttgagt   1080

ccaacccgga aagacatgca aaagcaccac tggcagcagc cactggtaat tgatttagag   1140

gagttagtct tgaagtcatg cgccggttaa ggctaaactg aaaggacaag ttttggtgac   1200

tgcgctcctc caagccagtt acctcggttc aaagagttgg tagctcagag aaccttcgaa   1260

aaaccgccct gcaaggcggt tttttcgttt tcagagcaag agattacgcg cagaccaaaa   1320

cgatctcaac ccctgattct gtggataacc gtagtcggcg agacggaaag tgaaacgtga   1380

tttcatgcgt cattttgaac attttgtaaa tcttatttaa taatgtgtgc ggcaattcac   1440

atttaattta tgaatgtttt cttaacatcg cggcaactca agaaacggca ggttcggatc   1500

ttagctacta gagaaagagg agaaatacta gatgcgtaaa ggcgaagagc tgttcactgg   1560

tgtcgtccct attctggtgg aactggatgg tgatgtcaac ggtcataagt tttccgtgcg   1620

tggcgagggt gaaggtgacg caactaatgg taaactgacg ctgaagttca tctgtactac   1680

tggtaaactg ccggttcctt ggccgactct ggtaacgacg ctgacttatg gtgttcagtg   1740

ctttgctcgt tatccggacc atatgaagca gcatgacttc ttcaagtccg ccatgccgga   1800

aggctatgtg caggaacgca cgatttcctt taaggatgac ggcacgtaca aaacgcgtgc   1860

ggaagtgaaa tttgaaggcg ataccctggt aaaccgcatt gagctgaaag gcattgactt   1920

taaagaggac ggcaatatcc tgggccataa gctggaatac aattttaaca gccacaatgt   1980

ttacatcacc gccgataaac aaaaaaatgg cattaaagcg aattttaaaa ttcgccacaa   2040

cgtggaggat ggcagcgtgc agctggctga tcactaccag caaaacactc caatcggtga   2100

tggtcctgtt ctgctgccag acaatcacta tctgagcacg caaagcgttc tgtctaaaga   2160

tccgaacgag aaacgcgatc atatggttct gctggagttc gtaaccgcag cgggcatcac   2220

gcatggtatg gatgaactgt acaaatgacc aggcatcaaa taaaacgaaa ggctcagtcg   2280

aaagactggg cctttcgttt tatctgttgt ttgtcggtga acgctctcta ctagagtcac   2340

actggctcac cttcgggtgg gcctttctgc gtttatacgt ctctgaccag accaataaaa   2400

aacgcccggc ggcaaccgag cgttctgaac aaatccagat ggagttctga ggtcattact   2460

ggatctatca acaggagtcc a                                             2481
```

<210> SEQ ID NO 37
<211> LENGTH: 52
<212> TYPE: DNA
<213> ORGANISM: Artificial Sequence
<220> FEATURE:
<223> OTHER INFORMATION: Chemically synthesized, T7 + RBS promoter from pBTK102

<400> SEQUENCE: 37
aacgtaatac gactcactat aggatacaga aacagaggag atattacata tg 52

<210> SEQ ID NO 38
<211> LENGTH: 84
<212> TYPE: DNA
<213> ORGANISM: Artificial Sequence
<220> FEATURE:
<223> OTHER INFORMATION: Chemically Synthesized, Lac LacO + RBS from pBTK103

<400> SEQUENCE: 38
aacgtttaca ctttatgctt ccggctcgta tgttgtgtgg aattgtgagc ggataacaat 60
tttaaagagg agaaattaac tatg 84

<210> SEQ ID NO 39
<211> LENGTH: 92
<212> TYPE: DNA
<213> ORGANISM: Artificial Sequence
<220> FEATURE:
<223> OTHER INFORMATION: Chemically Synthesized, cp25 + RBS from pBTK107

<400> SEQUENCE: 39
aacgctttgg cagtttattc ttgacatgta gtgagggggc tggtataatc acatagtact 60
gttatacaga aacagaggag atattacata tg 92

<210> SEQ ID NO 40
<211> LENGTH: 93
<212> TYPE: DNA
<213> ORGANISM: Artificial Sequence
<220> FEATURE:
<223> OTHER INFORMATION: Chemically synthesized, CP6 + RBS from pBTK110

<400> SEQUENCE: 40
aacgcatgtg ggagtttatt cttgacacag atatttccgg atgatataat aactgagtac 60
tgttatacag aaacagagga gatattacat atg 93

<210> SEQ ID NO 41
<211> LENGTH: 93
<212> TYPE: DNA
<213> ORGANISM: Artificial Sequence
<220> FEATURE:
<223> OTHER INFORMATION: Chemically Synthesized, cp12b + RBS from pBTK112

<400> SEQUENCE: 41
aacgcatata caagtttatt cttgacacta gtcggccaaa atgatataat acctgagtac 60
tgttatacag aaacagagga gatattacat atg 93

<210> SEQ ID NO 42
<211> LENGTH: 93
<212> TYPE: DNA
<213> ORGANISM: Artificial Sequence
<220> FEATURE:
<223> OTHER INFORMATION: Chemically Syntesized, cp32 + RBS from pBTK113

<400> SEQUENCE: 42
aacgcatacg ggagtttatt cttgacatat tgccggtgtg ttggtataat aacttagtac 60
tgttatacag aaacagagga gatattacat atg 93

<210> SEQ ID NO 43

<211> LENGTH: 103
<212> TYPE: DNA
<213> ORGANISM: Artificial Sequence
<220> FEATURE:
<223> OTHER INFORMATION: Chemically Synthesized, PA1 + RBS from pBTK119

<400> SEQUENCE: 43
aacgttatca aaaagagtat tgacttaaag tctaacctat aggatactta cagccatcga 60
gagggacacg gcgaatacag aaacagagga gatattacat atg 103

<210> SEQ ID NO 44
<211> LENGTH: 104
<212> TYPE: DNA
<213> ORGANISM: Artificial Sequence
<220> FEATURE:
<223> OTHER INFORMATION: Chemically Synthesized, PA2 + RBS from pBTK120

<400> SEQUENCE: 44
aacgcacgaa aaacaggtat tgacaacatg aagtaacatg cagtaagata caaatcgcta 60
ggtaacacta gcagcataca gaaacagagg agatattaca tatg 104

<210> SEQ ID NO 45
<211> LENGTH: 103
<212> TYPE: DNA
<213> ORGANISM: Artificial Sequence
<220> FEATURE:
<223> OTHER INFORMATION: Chemically Synthesized, PA3 + RBS from pBTK121

<400> SEQUENCE: 45
aacgggtgaa acaaaacggt tgacaacatg aagtaaacac ggtacgatgt accacatgaa 60
acgacagtga gtcaatacag aaacagagga gatattacat atg 103

<210> SEQ ID NO 46
<211> LENGTH: 122
<212> TYPE: DNA
<213> ORGANISM: Artificial Sequence
<220> FEATURE:
<223> OTHER INFORMATION: Chemically Synthesized, CP25 + RBS reverse promoter from pBTK138

<400> SEQUENCE: 46
gagtacctct cctgtatctt gtgtacttgc gtaccgtaat atctcctctg tttctgtata 60
acagtactat gtgattatac cagccccctc actacatgtc aagaataaac tgccaaagcc 120
ga 122

<210> SEQ ID NO 47
<211> LENGTH: 4115
<212> TYPE: DNA
<213> ORGANISM: Artificial Sequence
<220> FEATURE:
<223> OTHER INFORMATION: Chemically Synthesized, dCas9 from pBTK209

<400> SEQUENCE: 47
tatgatggat aagaaatact caataggctt agctatcggc acaaatagcg tcggatgggc 60
ggtgatcact gatgaatata aggttccgtc taaaaagttc aaggttctgg gaaatacaga 120
ccgccacagt atcaaaaaaa atcttatagg ggctctttta tttgacagtg gagagacagc 180
ggaagcgact cgtcgtaaac ggacagctcg tagaaggtat acacgtcgga agaatcgtat 240
ttgttatcta caggagattt tttcaaatga gatggcgaaa gtagatgata gtttctttca 300
tcgacttgaa gagtcttttt tggtggaaga agacaagaag catgaacgtc atcctatttt 360

```
tggaaatata gtagatgaag ttgcttatca tgagaaatat ccaactatct atcatctgcg    420
aaaaaaattg gtagattcta ctgataaagc ggatttgcgc ttaatctatt tggccttagc    480
gcatatgatt aagtttcgtg gtcatttttt gattgaggga gatttaaatc ctgataatag    540
tgatgtggac aaactattta tccagttggt acaaacctac aatcaattat ttgaagaaaa    600
ccctattaac gcaagtggag tagatgctaa agcgattctt tctgcacgat tgagtaaatc    660
aagacgatta gaaaatctca ttgctcagct ccccggtgag aagaaaaatg gcttatttgg    720
gaatctcatt gctttgtcat tgggtttgac ccctaatttt aaatcaaatt ttgatttggc    780
agaagatgct aaattacagc tttcaaaaga tacttacgat gatgatttag ataatttatt    840
ggcgcaaatt ggagatcaat atgctgattt gtttttggca gctaagaatt tatcagatgc    900
tattttactt tcagatatcc taagagtaaa tactgaaata actaaggctc ccctatcagc    960
ttcaatgatt aaacgctacg atgaacatca tcaagacttg actcttttaa aagctttagt   1020
tcgacaacaa cttccagaaa agtataaaga aatctttttt gatcaatcaa aaaacggata   1080
tgcaggttat attgatgggg gagctagcca agaagaattt tataaattta tcaaaccaat   1140
tttagaaaaa atggatggta ctgaggaatt attggtgaaa ctaaatcgtg aagatttgct   1200
gcgcaagcaa cggacctttg acaacggctc tattccccat caaattcact tgggtgagct   1260
gcatgctatt ttgagaagac aagaagactt ttatccattt ttaaaagaca atcgtgagaa   1320
gattgaaaaa atcttgactt ttcgaattcc ttattatgtt ggtccattgg cgcgtggcaa   1380
tagtcgtttt gcatggatga ctcggaagtc tgaagaaaca attacccccat ggaattttga   1440
agaagttgtc gataaaggtg cttcagctca atcatttatt gaacgcatga caaactttga   1500
taaaaatctt ccaaatgaaa aagtactacc aaaacatagt ttgctttatg agtattttac   1560
ggtttataac gaattgacaa aggtcaaata tgttactgaa ggaatgcgaa aaccagcatt   1620
tctttcaggt gaacagaaga aagccattgt tgatttactc ttcaaaacaa atcgaaaagt   1680
aaccgttaag caattaaaag aagattattt caaaaaaata gaatgttttg atagtgttga   1740
aatttcagga gttgaagata gatttaatgc ttcattaggt acctaccatg atttgctaaa   1800
aattattaaa gataaagatt ttttggataa tgaagaaaat gaagatatct tagaggatat   1860
tgttttaaca ttgaccttat ttgaagatag ggagatgatt gaggaaagac ttaaaacata   1920
tgctcacctc tttgatgata aggtgatgaa acagcttaaa cgtcgccgtt atactggttg   1980
ggacgtttg tctcgaaaat tgattaatgg tattagggat aagcaatctg gcaaaacaat    2040
attagatttt ttgaaatcag atggttttgc caatcgcaat tttatgcagc tgatccatga   2100
tgatagtttg acatttaaag aagacattca aaaagcacaa gtgtctggac aaggcgatag   2160
tttacatgaa catattgcaa atttagctgg tagccctgct attaaaaaag gtattttaca   2220
gactgtaaaa gttgttgatg aattggtcaa agtaatgggg cggcataagc cagaaaatat   2280
cgttattgaa atggcacgtg aaaatcagac aactcaaaag ggccagaaaa attcgcgaga   2340
gcgtatgaaa cgaatcgaag aaggtatcaa agaattagga agtcagattc ttaaagagca   2400
tcctgttgaa aatactcaat tgcaaaatga aaagctctat ctctattatc tccaaaatgg   2460
aagagacatg tatgtggacc aagaattaga tattaatcgt ttaagtgatt atgatgtcga   2520
tgccattgtt ccacaaagtt tccttaaaga cgattcaata gacaataagg tcttaacgcg   2580
ttctgataaa aatcgtggta aatcggataa cgttccaagt gaagaagtag tcaaaaagat   2640
gaaaaactat tggagacaac ttctaaacgc caagttaatc actcaacgta agtttgataa   2700
tttaacgaaa gctgaacgtg gaggtttgag tgaacttgat aaagctggtt ttatcaaacg   2760
```

```
ccaattggtt gaaactcgcc aaatcactaa gcatgtggca caaattttgg atagtcgcat   2820

gaatactaaa tacgatgaaa atgataaact tattcgagag gttaaagtga ttaccttaaa   2880

atctaaatta gtttctgact tccgaaaaga tttccaattc tataaagtac gtgagattaa   2940

caattaccat catgcccatg atgcgtatct aaatgccgtc gttggaactg ctttgattaa   3000

gaaatatcca aaacttgaat cggagtttgt ctatggtgat tataaagttt atgatgttcg   3060

taaaatgatt gctaagtctg agcaagaaat aggcaaagca accgcaaaat atttctttta   3120

ctctaatatc atgaacttct tcaaaacaga aattacactt gcaaatggag agattcgcaa   3180

acgccctcta atcgaaacta atggggaaac tggagaaatt gtctgggata aagggcgaga   3240

ttttgccaca gtgcgcaaag tattgtccat gccccaagtc aatattgtca agaaaacaga   3300

agtacagaca ggcggattct ccaaggagtc aattttacca aaaagaaatt cggacaagct   3360

tattgctcgt aaaaaagact gggatccaaa aaaatatggt ggttttgata gtccaacggt   3420

agcttattca gtcctagtgg ttgctaaggt ggaaaaaggg aaatcgaaga agttaaaatc   3480

cgttaaagag ttactaggga tcacaattat ggaaagaagt tcctttgaaa aaaatccgat   3540

tgacttttta gaagctaaag gatataagga agttaaaaaa gacttaatca ttaaactacc   3600

taaatatagt ctttttgagt tagaaaacgg tcgtaaacgg atgctggcta gtgccggaga   3660

attacaaaaa ggaaatgagc tggctctgcc aagcaaatat gtgaattttt tatatttagc   3720

tagtcattat gaaaagttga agggtagtcc agaagataac gaacaaaaac aattgtttgt   3780

ggagcagcat aagcattatt tagatgagat tattgagcaa atcagtgaat tttctaagcg   3840

tgttatttta gcagatgcca atttagataa agttcttagt gcatataaca aacatagaga   3900

caaaccaata cgtgaacaag cagaaaatat tattcattta tttacgttga cgaatcttgg   3960

agctcccgct gcttttaaat attttgatac aacaattgat cgtaaacgat atacgtctac   4020

aaaagaagtt ttagatgcca ctcttatcca tcaatccatc actggtcttt atgaaacacg   4080

cattgatttg agtcagctag gaggtgactg aatcc                              4115
```

<210> SEQ ID NO 48
<211> LENGTH: 91
<212> TYPE: DNA
<213> ORGANISM: Artificial Sequence
<220> FEATURE:
<223> OTHER INFORMATION: Chemically Synthesized, rpoC terminator from pBTK300

<400> SEQUENCE: 48

```
atccgtaatc gttaatccgc aaataacgta aaaacccgct tcggcgggtt tttttatggg     60

gggagtttag ggaaagagca tttgtcagct g                                    91
```

<210> SEQ ID NO 49
<211> LENGTH: 137
<212> TYPE: DNA
<213> ORGANISM: Artificial Sequence
<220> FEATURE:
<223> OTHER INFORMATION: Chemically Synthesized, BBa_B0015 terminator from pBTK301

<400> SEQUENCE: 49

```
tacaccaggc atcaaataaa acgaaaggct cagtcgaaag actgggcctt tcgttttatc     60

tgttgtttgt cggtgaacgc tctctactag agtcacactg gctcaccttc gggtgggcct    120

ttctgcgttt ataccga                                                   137
```

<210> SEQ ID NO 50
<211> LENGTH: 62
<212> TYPE: DNA
<213> ORGANISM: Artificial Sequence
<220> FEATURE:
<223> OTHER INFORMATION: Chemically Synthesized, T7 terminator from pBTK305

<400> SEQUENCE: 50
atcctaacta gcataacccc ttggggcctc taaacgggtc ttgaggggtt ttttgctggc 60
tg 62

<210> SEQ ID NO 51
<211> LENGTH: 1710
<212> TYPE: DNA
<213> ORGANISM: Artificial Sequence
<220> FEATURE:
<223> OTHER INFORMATION: Chemically Synthesized, pBTK102

<400> SEQUENCE: 51
tcaccgtctt tcattgccat acgaaattcc ggatgagcat tcatcaggcg ggcaagaatg 60
tgaataaagg ccggataaaa cttgtgctta tttttcttta cggtctttaa aaaggccgta 120
atatccagct gaacggtctg gttataggta cattgagcaa ctgactgaaa tgcctcaaaa 180
tgttctttac gatgccattg ggatatatca acggtggtat atccagtgat ttttttctcc 240
attttagctt ccttagctcc tgaaaatctc gataactcaa aaaatacgcc cggtagtgat 300
cttatttcat tatggtgaaa gttggaacct cttacgtgcc cgatcaatca tgaccaaaat 360
cccttaacgt gagttttcgt tccactgagc gtcagacccc gtagaaaaga tcaaaggatc 420
ttcttgagat cctttttttc tgcgcgtaat ctgctgcttg caaacaaaaa aaccaccgct 480
accagcggtg gtttgtttgc cggatcaaga gctaccaact ctttttccga aggtaactgg 540
cttcagcaga gcgcagatac caaatactgt tcttctagtg tagccgtagt taggccacca 600
cttcaagaac tctgtagcac cgcctacata cctcgctctg ctaatcctgt taccagtggc 660
tgctgccagt ggcgataagt cgtgtcttac cgggttggac tcaagacgat agttaccgga 720
taaggcgcag cggtcgggct gaacgggggg ttcgtgcaca cagcccagct tggagcgaac 780
gacctacacc gaactgagat acctacagcg tgagctatga gaaagcgcca cgcttcccga 840
agggagaaag gcggacaggt atccggtaag cggcagggtc ggaacaggag agcgcacgag 900
ggagcttcca gggggaaacg cctggtatct ttatagtcct gtcgggtttc gccacctctg 960
acttgagcgt cgatttttgt gatgctcgtc aggggggcgg agcctatgga aaaacgccag 1020
caacgcggcc tttttacggt tcctggcctt ttgctggcct tttgctcaca tgttctttcc 1080
tgcgttatcc cctgattctg tggataaccg tagtcggtct caaacgtaat acgactcact 1140
ataggataca gaaacagagg agatattaca tatgtgagac cagaccaata aaaaacgccc 1200
ggcggcaacc gagcgttctg aacaaatcca gatggagttc tgaggtcatt actggatcta 1260
tcaacaggag tccaagcgag ctcgatatca aattacgccc cgccctgcca ctcatcgcag 1320
tactgttgta attcattaag cattctgccg acatggaagc catcacaaac ggcatgatga 1380
acctgaatcg ccagcggcat cagcaccttg tcgccttgcg tataatattt gcccatggtg 1440
aaaacggggg cgaagaagtt gtccatattg gccacgttta aatcaaaact ggtgaaactc 1500
acccagggat tggctgaaac gaaaaacata ttctcaataa accctttagg gaaataggcc 1560
aggttttcac cgtaacacgc cacatcttgc gaatatatgt gtagaaactg ccggaaatcg 1620

```
tcgtggtatt cactccagag cgatgaaaac gtttcagttt gctcatggaa aacggtgtaa   1680

caagggtgaa cactatccca tatcaccagc                                    1710
```

<210> SEQ ID NO 52
<211> LENGTH: 1742
<212> TYPE: DNA
<213> ORGANISM: Artificial Sequence
<220> FEATURE:
<223> OTHER INFORMATION: Chemically Synthesized, pBTK103

<400> SEQUENCE: 52

```
tttagcttcc ttagctcctg aaaatctcga taactcaaaa aatacgcccg gtagtgatct     60

tatttcatta tggtgaaagt tggaacctct tacgtgcccg atcaatcatg accaaaatcc    120

cttaacgtga gttttcgttc cactgagcgt cagaccccgt agaaaagatc aaaggatctt    180

cttgagatcc tttttttctg cgcgtaatct gctgcttgca aacaaaaaaa ccaccgctac    240

cagcggtggt ttgtttgccg gatcaagagc taccaactct ttttccgaag gtaactggct    300

tcagcagagc gcagatacca aatactgttc ttctagtgta gccgtagtta ggccaccact    360

tcaagaactc tgtagcaccg cctacatacc tcgctctgct aatcctgtta ccagtggctg    420

ctgccagtgg cgataagtcg tgtcttaccg ggttggactc aagacgatag ttaccggata    480

aggcgcagcg gtcgggctga acggggggtt cgtgcacaca gcccagcttg gagcgaacga    540

cctacaccga actgagatac ctacagcgtg agctatgaga aagcgccacg cttcccgaag    600

ggagaaaggc ggacaggtat ccggtaagcg gcagggtcgg aacaggagag cgcacgaggg    660

agcttccagg gggaaacgcc tggtatcttt atagtcctgt cgggtttcgc cacctctgac    720

ttgagcgtcg atttttgtga tgctcgtcag gggggcggag cctatggaaa aacgccagca    780

acgcggcctt tttacggttc ctggcctttt gctggccttt tgctcacatg ttctttcctg    840

cgttatcccc tgattctgtg gataaccgta gtcggtctca aacgtttaca ctttatgctt    900

ccggctcgta tgttgtgtgg aattgtgagc ggataacaat tttaaagagg agaaattaac    960

tatgtgagac cagaccaata aaaaacgccc ggcggcaacc gagcgttctg aacaaatcca   1020

gatggagttc tgaggtcatt actggatcta tcaacaggag tccaagcgag ctcgatatca   1080

aattacgccc cgccctgcca ctcatcgcag tactgttgta attcattaag cattctgccg   1140

acatggaagc catcacaaac ggcatgatga acctgaatcg ccagcggcat cagcaccttg   1200

tcgccttgcg tataatattt gcccatggtg aaaacggggg cgaagaagtt gtccatattg   1260

gccacgttta aatcaaaact ggtgaaactc acccagggat tggctgaaac gaaaaacata   1320

ttctcaataa accctttagg gaaataggcc aggttttcac cgtaacacgc cacatcttgc   1380

gaatatatgt gtagaaactg ccggaaatcg tcgtggtatt cactccagag cgatgaaaac   1440

gtttcagttt gctcatggaa aacggtgtaa caagggtgaa cactatccca tatcaccagc   1500

tcaccgtctt tcattgccat acgaaattcc ggatgagcat tcatcaggcg ggcaagaatg   1560

tgaataaagg ccggataaaa cttgtgctta tttttcttta cggtctttaa aaaggccgta   1620

atatccagct gaacggtctg gttataggta cattgagcaa ctgactgaaa tgcctcaaaa   1680

tgttctttac gatgccattg ggatatatca acggtggtat atccagtgat ttttttctcc   1740

at                                                                  1742
```

<210> SEQ ID NO 53
<211> LENGTH: 1750
<212> TYPE: DNA
<213> ORGANISM: Artificial Sequence
<220> FEATURE:
<223> OTHER INFORMATION: Chemically Synthesized, pBTK107

<400> SEQUENCE: 53

```
tcatgaccaa aatcccttaa cgtgagtttt cgttccactg agcgtcagac cccgtagaaa     60

agatcaaagg atcttcttga gatccttttt ttctgcgcgt aatctgctgc ttgcaaacaa    120

aaaaaccacc gctaccagcg gtggtttgtt tgccggatca agagctacca actctttttc    180

cgaaggtaac tggcttcagc agagcgcaga taccaaatac tgttcttcta gtgtagccgt    240

agttaggcca ccacttcaag aactctgtag caccgcctac atacctcgct ctgctaatcc    300

tgttaccagt ggctgctgcc agtggcgata agtcgtgtct taccgggttg gactcaagac    360

gatagttacc ggataaggcg cagcggtcgg gctgaacggg gggttcgtgc acacagccca    420

gcttggagcg aacgacctac accgaactga gatacctaca gcgtgagcta tgagaaagcg    480

ccacgcttcc cgaagggaga aaggcggaca ggtatccggt aagcggcagg gtcggaacag    540

gagagcgcac gagggagctt ccagggggaa acgcctggta tctttatagt cctgtcgggt    600

ttcgccacct ctgacttgag cgtcgatttt tgtgatgctc gtcagggggg cggagcctat    660

ggaaaaacgc cagcaacgcg gcctttttac ggttcctggc cttttgctgg ccttttgctc    720

acatgttctt tcctgcgtta tcccctgatt ctgtggataa ccgtagtcgg tctcaaacgc    780

tttggcagtt tattcttgac atgtagtgag gggctggta taatcacata gtactgttat    840

acagaaacag aggagatatt acatatgtga gaccagacca ataaaaaacg cccggcggca    900

accgagcgtt ctgaacaaat ccagatggag ttctgaggtc attactggat ctatcaacag    960

gagtccaagc gagctcgata tcaaattacg ccccgccctg ccactcatcg cagtactgtt   1020

gtaattcatt aagcattctg ccgacatgga agccatcaca aacggcatga tgaacctgaa   1080

tcgccagcgg catcagcacc ttgtcgcctt gcgtataata tttgcccatg gtgaaaacgg   1140

gggcgaagaa gttgtccata ttggccacgt ttaaatcaaa actggtgaaa ctcacccagg   1200

gattggctga aacgaaaaac atattctcaa taaacccttt agggaaatag gccaggtttt   1260

caccgtaaca cgccacatct tgcgaatata tgtgtagaaa ctgccggaaa tcgtcgtggt   1320

attcactcca gagcgatgaa aacgtttcag tttgctcatg gaaaacggtg taacaagggt   1380

gaacactatc ccatatcacc agctcaccgt ctttcattgc catacgaaat tccggatgag   1440

cattcatcag gcgggcaaga atgtgaataa aggccggata aaacttgtgc ttatttttct   1500

ttacggtctt taaaaaggcc gtaatatcca gctgaacggt ctggttatag gtacattgag   1560

caactgactg aaatgcctca aaatgttctt tacgatgcca ttgggatata tcaacggtgg   1620

tatatccagt gatttttttc tccattttag cttccttagc tcctgaaaat ctcgataact   1680

caaaaaatac gcccggtagt gatcttattt cattatggtg aaagttggaa cctcttacgt   1740

gcccgatcaa                                                         1750
```

<210> SEQ ID NO 54
<211> LENGTH: 1751
<212> TYPE: DNA
<213> ORGANISM: Artificial Sequence
<220> FEATURE:
<223> OTHER INFORMATION: Chemically Synthesized, pBTK110

<400> SEQUENCE: 54

```
ggataaggcg cagcggtcgg gctgaacggg gggttcgtgc acacagccca gcttggagcg     60

aacgacctac accgaactga gatacctaca gcgtgagcta tgagaaagcg ccacgcttcc    120
```

```
cgaagggaga aaggcggaca ggtatccggt aagcggcagg gtcggaacag gagagcgcac    180

gagggagctt ccagggggaa acgcctggta tctttatagt cctgtcgggt ttcgccacct    240

ctgacttgag cgtcgatttt tgtgatgctc gtcagggggg cggagcctat ggaaaaacgc    300

cagcaacgcg gcctttttac ggttcctggc cttttgctgg ccttttgctc acatgttctt    360

tcctgcgtta tcccctgatt ctgtggataa ccgtagtcgg tctcaaacgc atgtgggagt    420

ttattcttga cacagatatt tccggatgat ataataactg agtactgtta tacagaaaca    480

gaggagatat tacatatgtg agaccagacc aataaaaaac gcccggcggc aaccgagcgt    540

tctgaacaaa tccagatgga gttctgaggt cattactgga tctatcaaca ggagtccaag    600

cgagctcgat atcaaattac gccccgccct gccactcatc gcagtactgt tgtaattcat    660

taagcattct gccgacatgg aagccatcac aaacggcatg atgaacctga atcgccagcg    720

gcatcagcac cttgtcgcct tgcgtataat atttgcccat ggtgaaaacg ggggcgaaga    780

agttgtccat attggccacg tttaaatcaa aactggtgaa actcacccag ggattggctg    840

aaacgaaaaa catattctca ataaaccctt tagggaaata ggccaggttt tcaccgtaac    900

acgccacatc ttgcgaatat atgtgtagaa actgccggaa atcgtcgtgg tattcactcc    960

agagcgatga aaacgtttca gtttgctcat ggaaaacggt gtaacaaggg tgaacactat   1020

cccatatcac cagctcaccg tctttcattg ccatacgaaa ttccggatga gcattcatca   1080

ggcgggcaag aatgtgaata aaggccggat aaaacttgtg cttatttttc tttacggtct   1140

ttaaaaaggc cgtaatatcc agctgaacgg tctggttata ggtacattga gcaactgact   1200

gaaatgcctc aaaatgttct ttacgatgcc attgggatat atcaacggtg gtatatccag   1260

tgattttttt ctccatttta gcttccttag ctcctgaaaa tctcgataac tcaaaaaata   1320

cgcccggtag tgatcttatt tcattatggt gaaagttgga acctcttacg tgcccgatca   1380

atcatgacca aaatccctta acgtgagttt tcgttccact gagcgtcaga ccccgtagaa   1440

aagatcaaag gatcttcttg agatcctttt tttctgcgcg taatctgctg cttgcaaaca   1500

aaaaaaccac cgctaccagc ggtggtttgt ttgccggatc aagagctacc aactcttttt   1560

ccgaaggtaa ctggcttcag cagagcgcag ataccaaata ctgttcttct agtgtagccg   1620

tagttaggcc accacttcaa gaactctgta gcaccgccta catacctcgc tctgctaatc   1680

ctgttaccag tggctgctgc cagtggcgat aagtcgtgtc ttaccgggtt ggactcaaga   1740

cgatagttac c                                                        1751
```

<210> SEQ ID NO 55
<211> LENGTH: 1751
<212> TYPE: DNA
<213> ORGANISM: Artificial Sequence
<220> FEATURE:
<223> OTHER INFORMATION: Chemically Synthesized, pBTK112

<400> SEQUENCE: 55

```
tcatgaccaa aatcccttaa cgtgagtttt cgttccactg agcgtcagac cccgtagaaa     60

agatcaaagg atcttcttga gatccttttt ttctgcgcgt aatctgctgc ttgcaaacaa    120

aaaaaccacc gctaccagcg gtggtttgtt tgccggatca agagctacca actctttttc    180

cgaaggtaac tggcttcagc agagcgcaga taccaaatac tgttcttcta gtgtagccgt    240

agttaggcca ccacttcaag aactctgtag caccgcctac atacctcgct ctgctaatcc    300

tgttaccagt ggctgctgcc agtggcgata agtcgtgtct taccgggttg gactcaagac    360

gatagttacc ggataaggcg cagcggtcgg gctgaacggg gggttcgtgc acacagccca    420
```

```
gcttggagcg aacgacctac accgaactga gatacctaca gcgtgagcta tgagaaagcg    480

ccacgcttcc cgaagggaga aaggcggaca ggtatccggt aagcggcagg gtcggaacag    540

gagagcgcac gagggagctt ccagggggaa acgcctggta tctttatagt cctgtcgggt    600

ttcgccacct ctgacttgag cgtcgatttt tgtgatgctc gtcagggggg cggagcctat    660

ggaaaaacgc cagcaacgcg gcctttttac ggttcctggc cttttgctgg ccttttgctc    720

acatgttctt tcctgcgtta tcccctgatt ctgtggataa ccgtagtcgg tctcaaacgc    780

atatacaagt ttattcttga cactagtcgg ccaaaatgat ataatacctg agtactgtta    840

tacagaaaca gaggagatat tacatatgtg agaccagacc aataaaaaac gcccggcggc    900

aaccgagcgt tctgaacaaa tccagatgga gttctgaggt cattactgga tctatcaaca    960

ggagtccaag cgagctcgat atcaaattac gccccgccct gccactcatc gcagtactgt   1020

tgtaattcat taagcattct gccgacatgg aagccatcac aaacggcatg atgaacctga   1080

atcgccagcg gcatcagcac cttgtcgcct tgcgtataat atttgcccat ggtgaaaacg   1140

ggggcgaaga agttgtccat attggccacg tttaaatcaa aactggtgaa actcacccag   1200

ggattggctg aaacgaaaaa catattctca ataaaccctt tagggaaata ggccaggttt   1260

tcaccgtaac acgccacatc ttgcgaatat atgtgtagaa actgccggaa atcgtcgtgg   1320

tattcactcc agagcgatga aaacgtttca gtttgctcat ggaaaacggt gtaacaaggg   1380

tgaacactat cccatatcac cagctcaccg tctttcattg ccatacgaaa ttccggatga   1440

gcattcatca ggcgggcaag aatgtgaata aaggccggat aaaacttgtg cttatttttc   1500

tttacggtct ttaaaaaggc cgtaatatcc agctgaacgg tctggttata ggtacattga   1560

gcaactgact gaaatgcctc aaaatgttct ttacgatgcc attgggatat atcaacggtg   1620

gtatatccag tgattttttt ctccatttta gcttccttag ctcctgaaaa tctcgataac   1680

tcaaaaaata cgcccggtag tgatcttatt tcattatggt gaaagttgga acctcttacg   1740

tgcccgatca a                                                        1751
```

<210> SEQ ID NO 56
<211> LENGTH: 1751
<212> TYPE: DNA
<213> ORGANISM: Artificial Sequence
<220> FEATURE:
<223> OTHER INFORMATION: Chemically Synthesized, pBTK113

<400> SEQUENCE: 56

```
tcatgaccaa aatcccttaa cgtgagtttt cgttccactg agcgtcagac cccgtagaaa     60

agatcaaagg atcttcttga gatccttttt ttctgcgcgt aatctgctgc ttgcaaacaa    120

aaaaaccacc gctaccagcg gtggtttgtt tgccggatca agagctacca actctttttc    180

cgaaggtaac tggcttcagc agagcgcaga taccaaatac tgttcttcta gtgtagccgt    240

agttaggcca ccacttcaag aactctgtag caccgcctac atacctcgct ctgctaatcc    300

tgttaccagt ggctgctgcc agtggcgata agtcgtgtct taccgggttg gactcaagac    360

gatagttacc ggataaggcg cagcggtcgg gctgaacggg gggttcgtgc acacagccca    420

gcttggagcg aacgacctac accgaactga gatacctaca gcgtgagcta tgagaaagcg    480

ccacgcttcc cgaagggaga aaggcggaca ggtatccggt aagcggcagg gtcggaacag    540

gagagcgcac gagggagctt ccagggggaa acgcctggta tctttatagt cctgtcgggt    600

ttcgccacct ctgacttgag cgtcgatttt tgtgatgctc gtcagggggg cggagcctat    660
```

```
ggaaaaacgc cagcaacgcg gcctttttac ggttcctggc cttttgctgg ccttttgctc    720
acatgttctt tcctgcgtta tcccctgatt ctgtggataa ccgtagtcgg tctcaaacgc    780
atacgggagt ttattcttga catattgccg gtgtgttggt ataataactt agtactgtta    840
tacagaaaca gaggagatat tacatatgtg agaccagacc aataaaaaac gcccggcggc    900
aaccgagcgt tctgaacaaa tccagatgga gttctgaggt cattactgga tctatcaaca    960
ggagtccaag cgagctcgat atcaaattac gccccgccct gccactcatc gcagtactgt   1020
tgtaattcat taagcattct gccgacatgg aagccatcac aaacggcatg atgaacctga   1080
atcgccagcg gcatcagcac cttgtcgcct tgcgtataat atttgcccat ggtgaaaacg   1140
ggggcgaaga agttgtccat attggccacg tttaaatcaa aactggtgaa actcacccag   1200
ggattggctg aaacgaaaaa catattctca ataaaccctt tagggaaata ggccaggttt   1260
tcaccgtaac acgccacatc ttgcgaatat atgtgtagaa actgccggaa atcgtcgtgg   1320
tattcactcc agagcgatga aaacgtttca gtttgctcat ggaaaacggt gtaacaaggg   1380
tgaacactat cccatatcac cagctcaccg tctttcattg ccatacgaaa ttccggatga   1440
gcattcatca ggcgggcaag aatgtgaata aaggccggat aaaacttgtg cttatttttc   1500
tttacggtct ttaaaaaggc cgtaatatcc agctgaacgg tctggttata ggtacattga   1560
gcaactgact gaaatgcctc aaaatgttct ttacgatgcc attgggatat atcaacggtg   1620
gtatatccag tgattttttt ctccatttta gcttccttag ctcctgaaaa tctcgataac   1680
tcaaaaaata cgcccggtag tgatcttatt tcattatggt gaaagttgga acctcttacg   1740
tgcccgatca a                                                        1751
```

<210> SEQ ID NO 57
<211> LENGTH: 1761
<212> TYPE: DNA
<213> ORGANISM: Artificial Sequence
<220> FEATURE:
<223> OTHER INFORMATION: Chemically Synthesized, pBTK119

<400> SEQUENCE: 57

```
acctacaccg aactgagata cctacagcgt gagctatgag aaagcgccac gcttcccgaa     60
gggagaaagg cggacaggta tccggtaagc ggcagggtcg gaacaggaga gcgcacgagg    120
gagcttccag ggggaaacgc ctggtatctt tatagtcctg tcgggtttcg ccacctctga    180
cttgagcgtc gatttttgtg atgctcgtca ggggggcgga gcctatggaa aaacgccagc    240
aacgcggcct ttttacggtt cctggccttt tgctggcctt ttgctcacat gttctttcct    300
gcgttatccc ctgattctgt ggataaccgt agtcggtctc aaacgttatc aaaaagagta    360
ttgacttaaa gtctaaccta taggatactt acagccatcg agagggacac ggcgaataca    420
gaaacagagg agatattaca tatgtgagac cagaccaata aaaaacgccc ggcggcaacc    480
gagcgttctg aacaaatcca gatggagttc tgaggtcatt actggatcta tcaacaggag    540
tccaagcgag ctcgatatca aattacgccc cgccctgcca ctcatcgcag tactgttgta    600
attcattaag cattctgccg acatggaagc catcacaaac ggcatgatga acctgaatcg    660
ccagcggcat cagcaccttg tcgccttgcg tataatattt gcccatggtg aaaacggggg    720
cgaagaagtt gtccatattg gccacgttta aatcaaaact ggtgaaactc acccagggat    780
tggctgaaac gaaaaacata ttctcaataa accctttagg gaaataggcc aggttttcac    840
cgtaacacgc cacatcttgc gaatatatgt gtagaaactg ccggaaatcg tcgtggtatt    900
cactccagag cgatgaaaac gtttcagttt gctcatggaa aacggtgtaa caagggtgaa    960
```

```
cactatccca tatcaccagc tcaccgtctt tcattgccat acgaaattcc ggatgagcat   1020

tcatcaggcg ggcaagaatg tgaataaagg ccggataaaa cttgtgctta tttttcttta   1080

cggtctttaa aaaggccgta atatccagct gaacggtctg gttataggta cattgagcaa   1140

ctgactgaaa tgcctcaaaa tgttctttac gatgccattg ggatatatca acggtggtat   1200

atccagtgat ttttttctcc attttagctt ccttagctcc tgaaaatctc gataactcaa   1260

aaaatacgcc cggtagtgat cttatttcat tatggtgaaa gttggaacct cttacgtgcc   1320

cgatcaatca tgaccaaaat cccttaacgt gagttttcgt tccactgagc gtcagacccc   1380

gtagaaaaga tcaaaggatc ttcttgagat cctttttttc tgcgcgtaat ctgctgcttg   1440

caaacaaaaa aaccaccgct accagcggtg gtttgtttgc cggatcaaga gctaccaact   1500

ctttttccga aggtaactgg cttcagcaga gcgcagatac caaatactgt tcttctagtg   1560

tagccgtagt taggccacca cttcaagaac tctgtagcac cgcctacata cctcgctctg   1620

ctaatcctgt taccagtggc tgctgccagt ggcgataagt cgtgtcttac cgggttggac   1680

tcaagacgat agttaccgga taaggcgcag cggtcgggct gaacgggggg ttcgtgcaca   1740

cagcccagct tggagcgaac g                                              1761
```

```
<210> SEQ ID NO 58
<211> LENGTH: 1762
<212> TYPE: DNA
<213> ORGANISM: Artificial Sequence
<220> FEATURE:
<223> OTHER INFORMATION: Chemically Synthesized, pBTK120

<400> SEQUENCE: 58

cagcccagct tggagcgaac gacctacacc gaactgagat acctacagcg tgagctatga     60

gaaagcgcca cgcttcccga agggagaaag gcggacaggt atccggtaag cggcagggtc    120

ggaacaggag agcgcacgag ggagcttcca gggggaaacg cctggtatct ttatagtcct    180

gtcgggtttc gccacctctg acttgagcgt cgatttttgt gatgctcgtc aggggggcgg    240

agcctatgga aaaacgccag caacgcggcc tttttacggt tcctggcctt ttgctggcct    300

tttgctcaca tgttctttcc tgcgttatcc cctgattctg tggataaccg tagtcggtct    360

caaacgcacg aaaaacaggt attgacaaca tgaagtaaca tgcagtaaga tacaaatcgc    420

taggtaacac tagcagcata cagaaacaga ggagatatta catatgtgag accagaccaa    480

taaaaaacgc ccggcggcaa ccgagcgttc tgaacaaatc cagatggagt tctgaggtca    540

ttactggatc tatcaacagg agtccaagcg agctcgatat caaattacgc cccgccctgc    600

cactcatcgc agtactgttg taattcatta agcattctgc cgacatggaa gccatcacaa    660

acggcatgat gaacctgaat cgccagcggc atcagcacct tgtcgccttg cgtataatat    720

ttgcccatgg tgaaaacggg ggcgaagaag ttgtccatat tggccacgtt taaatcaaaa    780

ctggtgaaac tcacccaggg attggctgaa acgaaaaaca tattctcaat aaacccttta    840

gggaaatagg ccaggttttc accgtaacac gccacatctt gcgaatatat gtgtagaaac    900

tgccggaaat cgtcgtggta ttcactccag agcgatgaaa acgtttcagt ttgctcatgg    960

aaaacggtgt aacaagggtg aacactatcc catatcacca gctcaccgtc tttcattgcc   1020

atacgaaatt ccggatgagc attcatcagg cgggcaagaa tgtgaataaa ggccggataa   1080

aacttgtgct tatttttctt tacggtcttt aaaaaggccg taatatccag ctgaacggtc   1140

tggttatagg tacattgagc aactgactga aatgcctcaa aatgttcttt acgatgccat   1200
```

```
tgggatatat caacggtggt atatccagtg atttttttct ccattttagc ttccttagct   1260

cctgaaaatc tcgataactc aaaaaatacg cccggtagtg atcttatttc attatggtga   1320

aagttggaac ctcttacgtg cccgatcaat catgaccaaa atcccttaac gtgagttttc   1380

gttccactga gcgtcagacc ccgtagaaaa gatcaaagga tcttcttgag atcctttttt   1440

tctgcgcgta atctgctgct tgcaaacaaa aaaaccaccg ctaccagcgg tggtttgttt   1500

gccggatcaa gagctaccaa ctctttttcc gaaggtaact ggcttcagca gagcgcagat   1560

accaaatact gttcttctag tgtagccgta gttaggccac cacttcaaga actctgtagc   1620

accgcctaca tacctcgctc tgctaatcct gttaccagtg gctgctgcca gtggcgataa   1680

gtcgtgtctt accgggttgg actcaagacg atagttaccg gataaggcgc agcggtcggg   1740

ctgaacgggg ggttcgtgca ca                                             1762
```

<210> SEQ ID NO 59
<211> LENGTH: 1761
<212> TYPE: DNA
<213> ORGANISM: Artificial Sequence
<220> FEATURE:
<223> OTHER INFORMATION: Chemically Synthesized, pBTK121

<400> SEQUENCE: 59

```
ctgagatacc tacagcgtga gctatgagaa agcgccacgc ttcccgaagg gagaaaggcg     60

gacaggtatc cggtaagcgg cagggtcgga acaggagagc gcacgaggga gcttccaggg    120

ggaaacgcct ggtatcttta tagtcctgtc gggtttcgcc acctctgact tgagcgtcga    180

tttttgtgat gctcgtcagg ggggcggagc ctatggaaaa acgccagcaa cgcggccttt    240

ttacggttcc tggccttttg ctggcctttt gctcacatgt tctttcctgc gttatcccct    300

gattctgtgg ataaccgtag tcggtctcaa acgggtgaaa caaaacggtt gacaacatga    360

agtaaacacg gtacgatgta ccacatgaaa cgacagtgag tcaatacaga aacagaggag    420

atattacata tgtgagacca gaccaataaa aaacgcccgg cggcaaccga gcgttctgaa    480

caaatccaga tggagttctg aggtcattac tggatctatc aacaggagtc caagcgagct    540

cgatatcaaa ttacgccccg ccctgccact catcgcagta ctgttgtaat tcattaagca    600

ttctgccgac atggaagcca tcacaaacgg catgatgaac ctgaatcgcc agcggcatca    660

gcaccttgtc gccttgcgta taatatttgc ccatggtgaa aacgggggcg aagaagttgt    720

ccatattggc cacgtttaaa tcaaaactgg tgaaactcac ccagggattg gctgaaacga    780

aaaacatatt ctcaataaac cctttaggga aataggccag gttttcaccg taacacgcca    840

catcttgcga atatatgtgt agaaactgcc ggaaatcgtc gtggtattca ctccagagcg    900

atgaaaacgt ttcagtttgc tcatggaaaa cggtgtaaca agggtgaaca ctatcccata    960

tcaccagctc accgtctttc attgccatac gaaattccgg atgagcattc atcaggcggg   1020

caagaatgtg aataaaggcc ggataaaact tgtgcttatt tttctttacg gtctttaaaa   1080

aggccgtaat atccagctga acggtctggt tataggtaca ttgagcaact gactgaaatg   1140

cctcaaaatg ttctttacga tgccattggg atatatcaac ggtggtatat ccagtgattt   1200

ttttctccat tttagcttcc ttagctcctg aaaatctcga taactcaaaa aatacgcccg   1260

gtagtgatct tatttcatta tggtgaaagt tggaacctct tacgtgcccg atcaatcatg   1320

accaaaatcc cttaacgtga gttttcgttc cactgagcgt cagaccccgt agaaaagatc   1380

aaaggatctt cttgagatcc tttttttctg cgcgtaatct gctgcttgca aacaaaaaaa   1440

ccaccgctac cagcggtggt ttgtttgccg gatcaagagc taccaactct ttttccgaag   1500
```

```
gtaactggct tcagcagagc gcagatacca aatactgttc ttctagtgta gccgtagtta   1560

ggccaccact tcaagaactc tgtagcaccg cctacatacc tcgctctgct aatcctgtta   1620

ccagtggctg ctgccagtgg cgataagtcg tgtcttaccg ggttggactc aagacgatag   1680

ttaccggata aggcgcagcg gtcgggctga acggggggtt cgtgcacaca gcccagcttg   1740

gagcgaacga cctacaccga a                                             1761
```

<210> SEQ ID NO 60
<211> LENGTH: 1780
<212> TYPE: DNA
<213> ORGANISM: Artificial Sequence
<220> FEATURE:
<223> OTHER INFORMATION: Chemically Synthesized, pBTK138

<400> SEQUENCE: 60

```
tcatgaccaa aatcccttaa cgtgagtttt cgttccactg agcgtcagac cccgtagaaa     60

agatcaaagg atcttcttga gatccttttt ttctgcgcgt aatctgctgc ttgcaaacaa    120

aaaaaccacc gctaccagcg gtggtttgtt tgccggatca agagctacca actctttttc    180

cgaaggtaac tggcttcagc agagcgcaga taccaaatac tgttcttcta gtgtagccgt    240

agttaggcca ccacttcaag aactctgtag caccgcctac atacctcgct ctgctaatcc    300

tgttaccagt ggctgctgcc agtggcgata agtcgtgtct taccgggttg gactcaagac    360

gatagttacc ggataaggcg cagcggtcgg gctgaacggg gggttcgtgc acacagccca    420

gcttggagcg aacgacctac accgaactga gatacctaca gcgtgagcta tgagaaagcg    480

ccacgcttcc cgaagggaga aaggcggaca ggtatccggt aagcggcagg gtcggaacag    540

gagagcgcac gagggagctt ccagggggaa acgcctggta tctttatagt cctgtcgggt    600

ttcgccacct ctgacttgag cgtcgatttt tgtgatgctc gtcagggggg cggagcctat    660

ggaaaaacgc cagcaacgcg gcctttttac ggttcctggc cttttgctgg ccttttgctc    720

acatgttctt tcctgcgtta tcccctgatt ctgtggataa ccgtagtcgg tctcagagta    780

cctctcctgt atcttgtgta cttgcgtacc gtaatatctc ctctgtttct gtataacagt    840

actatgtgat tataccagcc ccctcactac atgtcaagaa taaactgcca aagccgatga    900

gaccagacca ataaaaaacg cccggcggca accgagcgtt ctgaacaaat ccagatggag    960

ttctgaggtc attactggat ctatcaacag gagtccaagc gagctcgata tcaaattacg   1020

ccccgccctg ccactcatcg cagtactgtt gtaattcatt aagcattctg ccgacatgga   1080

agccatcaca aacggcatga tgaacctgaa tcgccagcgg catcagcacc ttgtcgcctt   1140

gcgtataata tttgcccatg gtgaaaacgg gggcgaagaa gttgtccata ttggccacgt   1200

ttaaatcaaa actggtgaaa ctcacccagg gattggctga aacgaaaaac atattctcaa   1260

taaacccttt agggaaatag gccaggtttt caccgtaaca cgccacatct tgcgaatata   1320

tgtgtagaaa ctgccggaaa tcgtcgtggt attcactcca gagcgatgaa aacgtttcag   1380

tttgctcatg gaaaacggtg taacaagggt gaacactatc ccatatcacc agctcaccgt   1440

ctttcattgc catacgaaat tccggatgag cattcatcag gcgggcaaga atgtgaataa   1500

aggccggata aaacttgtgc ttatttttct ttacggtctt taaaaaggcc gtaatatcca   1560

gctgaacggt ctggttatag gtacattgag caactgactg aaatgcctca aaatgttctt   1620

tacgatgcca ttgggatata tcaacggtgg tatatccagt gatttttttc tccattttag   1680

cttccttagc tcctgaaaat ctcgataact caaaaaatac gcccggtagt gatcttattt   1740
```

cattatggtg aaagttggaa cctcttacgt gcccgatcaa 1780

<210> SEQ ID NO 61
<211> LENGTH: 4315
<212> TYPE: DNA
<213> ORGANISM: Artificial Sequence
<220> FEATURE:
<223> OTHER INFORMATION: Chemically Synthesized, pBTK200

<400> SEQUENCE: 61
tcatgaccaa aatcccttaa cgtgagtttt cgttccactg agcgtcagac cccgtagaaa 60
agatcaaagg atcttcttga gatccttttt ttctgcgcgt aatctgctgc ttgcaaacaa 120
aaaaaccacc gctaccagcg gtggtttgtt tgccggatca agagctacca actctttttc 180
cgaaggtaac tggcttcagc agagcgcaga taccaaatac tgttcttcta gtgtagccgt 240
agttaggcca ccacttcaag aactctgtag caccgcctac atacctcgct ctgctaatcc 300
tgttaccagt ggctgctgcc agtggcgata agtcgtgtct taccgggttg gactcaagac 360
gatagttacc ggataaggcg cagcggtcgg gctgaacggg gggttcgtgc acacagccca 420
gcttggagcg aacgacctac accgaactga gatacctaca gcgtgagcta tgagaaagcg 480
ccacgcttcc cgaagggaga aaggcggaca ggtatccggt aagcggcagg gtcggaacag 540
gagagcgcac gagggagctt ccagggggaa acgcctggta tctttatagt cctgtcgggt 600
ttcgccacct ctgacttgag cgtcgatttt tgtgatgctc gtcagggggg cggagcctat 660
ggaaaaacgc cagcaacgcg gcctttttac ggttcctggc cttttgctgg ccttttgctc 720
acatgttctt tcctgcgtta tcccctgatt ctgtggataa ccgtagtcgg tctcatatga 780
acacgattaa catcgctaag aacgacttct ctgacatcga actggctgct atcccgttca 840
acactctggc tgaccattac ggtgagcgtt tagctcgcga acagttggcc cttgagcatg 900
agtcttacga gatgggtgaa gcacgcttcc gcaagatgtt tgagcgtcaa cttaaagctg 960
gtgaggttgc ggataacgct gccgccaagc ctctcatcac taccctactc cctaagatga 1020
ttgcacgcat caacgactgg tttgaggaag tgaaagctaa gcgcggcaag cgcccgacag 1080
ccttccagtt cctgcaagaa atcaagccgg aagccgtagc gtacatcacc attaagacca 1140
ctctggcttg cctaaccagt gctgacaata caaccgttca ggctgtagca agcgcaatcg 1200
gtcgggccat tgaggacgag gctcgcttcg gtcgtatccg tgaccttgaa gctaagcact 1260
tcaagaaaaa cgttgaggaa caactcaaca agcgcgtagg gcacgtctac aagaaagcat 1320
ttatgcaagt tgtcgaggct gacatgctct ctaagggtct actcggtggc gaggcgtggt 1380
cttcgtggca taaggaagac tctattcatg taggagtacg ctgcatcgag atgctcattg 1440
agtcaaccgg aatggttagc ttacaccgcc aaaatgctgg cgtagtaggt caagactctg 1500
agactatcga actcgcacct gaatacgctg aggctatcgc aacccgtgca ggtgcgctgg 1560
ctggcatctc tccgatgttc caaccttgcg tagttcctcc taagccgtgg actggcatta 1620
ctggtggtgg ctattgggct aacggtcgtc gtcctctggc gctggtgcgt actcacagta 1680
agaaagcact gatgcgctac gaagacgttt acatgcctga ggtgtacaaa gcgattaaca 1740
ttgcgcaaaa caccgcatgg aaaatcaaca agaaagtcct agcggtcgcc aacgtaatca 1800
ccaagtggaa gcattgtccg gtcgaggaca tccctgcgat tgagcgtgaa gaactcccga 1860
tgaaaccgga agacatcgac atgaatcctg aggctctcac cgcgtggaaa cgtgctgccg 1920
ctgctgtgta ccgcaaggac aaggctcgca agtctcgccg tatcagcctt gagttcatgc 1980
ttgagcaagc caataagttt gctaaccata aggccatctg gttcccttac aacatggact 2040

```
ggcgcggtcg tgtttacgct gtgtcaatgt tcaacccgca aggtaacgat atgaccaaag   2100
gactgcttac gctggcgaaa ggtaaaccaa tcggtaagga aggttactac tggctgaaaa   2160
tccacggtgc aaactgtgcg ggtgtcgata aggttccgtt ccctgagcgc atcaagttca   2220
ttgaggaaaa ccacgagaac atcatggctt gcgctaagtc tccactggag aacacttggt   2280
gggctgagca agattctccg ttctgcttcc ttgcgttctg ctttgagtac gctggggtac   2340
agcaccacgg cctgagctat aactgctccc ttccgctggc gtttgacggg tcttgctctg   2400
gcatccagca cttctccgcg atgctccgag atgaggtagg tggtcgcgcg gttaacttgc   2460
ttcctagtga aaccgttcag gacatctacg ggattgttgc taagaaagtc aacgagattc   2520
tacaagcaga cgcaatcaat gggaccgata acgaagtagt taccgtgacc gatgagaaca   2580
ctggtgaaat ctctgagaaa gtcaagctgg gcactaaggc actggctggt caatggctgg   2640
cttacggtgt tactcgcagt gtgactaagc gttcagtcat gacgctggct tacgggtcca   2700
aagagttcgg cttccgtcaa caagtgctgg aagataccat tcagccagct attgattccg   2760
gcaagggtct gatgttcact cagccgaatc aggctgctgg atacatggct aagctgattt   2820
gggaatctgt gagcgtgacg gtggtagctg cggttgaagc aatgaactgg cttaagtctg   2880
ctgctaagct gctggctgct gaggtcaaag ataagaagac tggagagatt cttcgcaagc   2940
gttgcgctgt gcattgggta actcctgatg gtttccctgt gtggcaggaa tacaagaagc   3000
ctattcagac gcgcttgaac ctgatgttcc tcggtcagtt ccgcttacag cctaccatta   3060
acaccaacaa agatagcgag attgatgcac acaaacagga gtctggtatc gctcctaact   3120
ttgtacacag ccaagacggt agccaccttc gtaagactgt agtgtgggca cacgagaagt   3180
acggaatcga atcttttgca ctgattcacg actccttcgg taccattccg gctgacgctg   3240
cgaacctgtt caaagcagtg cgcgaaacta tggttgacac atatgagtct tgtgatgtac   3300
tggctgattt ctacgaccag ttcgctgacc agttgcacga gtctcaattg gacaaaatgc   3360
cagcacttcc ggctaaaggt aacttgaacc tccgtgacat cttagagtcg gacttcgcgt   3420
tcgcgtaaat cctgagacca gaccaataaa aaacgcccgg cggcaaccga gcgttctgaa   3480
caaatccaga tggagttctg aggtcattac tggatctatc aacaggagtc caagcgagct   3540
cgatatcaaa ttacgccccg ccctgccact catcgcagta ctgttgtaat tcattaagca   3600
ttctgccgac atggaagcca tcacaaacgg catgatgaac ctgaatcgcc agcggcatca   3660
gcaccttgtc gccttgcgta taatatttgc ccatggtgaa aacgggggcg aagaagttgt   3720
ccatattggc cacgtttaaa tcaaaactgg tgaaactcac ccagggattg gctgaaacga   3780
aaaacatatt ctcaataaac cctttaggga aataggccag gttttcaccg taacacgcca   3840
catcttgcga atatatgtgt agaaactgcc ggaaatcgtc gtggtattca ctccagagcg   3900
atgaaaacgt ttcagtttgc tcatggaaaa cggtgtaaca agggtgaaca ctatcccata   3960
tcaccagctc accgtctttc attgccatac gaaattccgg atgagcattc atcaggcggg   4020
caagaatgtg aataaaggcc ggataaaact tgtgcttatt tttctttacg gtctttaaaa   4080
aggccgtaat atccagctga acggtctggt tataggtaca ttgagcaact gactgaaatg   4140
cctcaaaatg ttctttacga tgccattggg atatatcaac ggtggtatat ccagtgattt   4200
ttttctccat tttagcttcc ttagctcctg aaaatctcga taactcaaaa aatacgcccg   4260
gtagtgatct tatttcatta tggtgaaagt tggaacctct tacgtgcccg atcaa        4315
```

<210> SEQ ID NO 62

<211> LENGTH: 2746
<212> TYPE: DNA
<213> ORGANISM: Artificial Sequence
<220> FEATURE:
<223> OTHER INFORMATION: Chemically Synthesized, pBTK203

<400> SEQUENCE: 62

```
tcatgaccaa aatcccttaa cgtgagtttt cgttccactg agcgtcagac cccgtagaaa     60
agatcaaagg atcttcttga gatccttttt ttctgcgcgt aatctgctgc ttgcaaacaa    120
aaaaaccacc gctaccagcg gtggtttgtt tgccggatca agagctacca actctttttc    180
cgaaggtaac tggcttcagc agagcgcaga taccaaatac tgttcttcta gtgtagccgt    240
agttaggcca ccacttcaag aactctgtag caccgcctac atacctcgct ctgctaatcc    300
tgttaccagt ggctgctgcc agtggcgata agtcgtgtct taccgggttg gactcaagac    360
gatagttacc ggataaggcg cagcggtcgg gctgaacggg gggttcgtgc acacagccca    420
gcttggagcg aacgacctac accgaactga gatacctaca gcgtgagcta tgagaaagcg    480
ccacgcttcc cgaagggaga aaggcggaca ggtatccggt aagcggcagg gtcggaacag    540
gagagcgcac gagggagctt ccagggggaa acgcctggta tctttatagt cctgtcgggt    600
ttcgccacct ctgacttgag cgtcgatttt tgtgatgctc gtcagggggg cggagcctat    660
ggaaaaacgc cagcaacgcg gcctttttac ggttcctggc cttttgctgg ccttttgctc    720
acatgttctt tcctgcgtta tcccctgatt ctgtggataa ccgtagtcgg tctcatatga    780
aaccagtaac gttatacgat gtcgcagagt atgccggtgt ctcttatcag accgtttccc    840
gcgtggtgaa ccaggccagc cacgtttctg cgaaaacgcg ggaaaaagtg gaagcggcga    900
tggcggagct gaattacatt cccaaccgcg tggcacaaca actggcgggc aaacagtcgt    960
tgctgattgg cgttgccacc tccagtctgg ccctgcacgc gccgtcgcaa attgtcgcgg   1020
cgattaaatc tcgcgccgat caactgggtg ccagcgtggt ggtgtcgatg gtagaacgaa   1080
gcggcgtcga agcctgtaaa gcggcggtgc acaatcttct cgcgcaacgc gtcagtgggc   1140
tgatcattaa ctatccgctg gatgaccagg atgccattgc tgtggaagct gcctgcacta   1200
atgttccggc gttatttctt gatgtctctg accagacacc catcaacagt attattttct   1260
cccatgaaga cggtacgcga ctgggcgtgg agcatctggt cgcattgggt caccagcaaa   1320
tcgcgctgtt agcgggccca ttaagttctg tctcggcgcg tctgcgtctg gctggctggc   1380
ataaatatct cactcgcaat caaattcagc cgatagcgga acgggaaggc gactggagtg   1440
ccatgtccgg ttttcaacaa accatgcaaa tgctgaatga gggcatcgtt cccactgcga   1500
tgctggttgc caacgatcag atggcgctgg gcgcaatgcg cgccattacc gagtccgggc   1560
tgcgcgttgg tgcggatatc tcggtagtgg gatacgacga taccgaagac agctcatgtt   1620
atatcccgcc gttaaccacc atcaaacagg attttcgcct gctggggcaa accagcgtgg   1680
accgcttgct gcaactctct cagggccagg cggtgaaggg caatcagctg ttgccggtgt   1740
cactggtgaa aagaaaaacc accctggcgc ccaatacgca aaccgcctct ccccgcgcgt   1800
tggccgattc attaatgcag ctggcacgac aggtttcccg actggaaagc gggcagtgaa   1860
tcctgagacc agaccaataa aaaacgcccg gcggcaaccg agcgttctga acaaatccag   1920
atggagttct gaggtcatta ctggatctat caacaggagt ccaagcgagc tcgatatcaa   1980
attacgcccc gccctgccac tcatcgcagt actgttgtaa ttcattaagc attctgccga   2040
catggaagcc atcacaaacg gcatgatgaa cctgaatcgc cagcggcatc agcaccttgt   2100
cgccttgcgt ataatatttg cccatggtga aaacgggggc gaagaagttg tccatattgg   2160
```

```
ccacgtttaa atcaaaactg gtgaaactca cccagggatt ggctgaaacg aaaaacatat   2220

tctcaataaa ccctttaggg aaataggcca ggttttcacc gtaacacgcc acatcttgcg   2280

aatatatgtg tagaaactgc cggaaatcgt cgtggtattc actccagagc gatgaaaacg   2340

tttcagtttg ctcatggaaa acggtgtaac aagggtgaac actatcccat atcaccagct   2400

caccgtcttt cattgccata cgaaattccg gatgagcatt catcaggcgg gcaagaatgt   2460

gaataaaggc cggataaaac ttgtgcttat ttttctttac ggtctttaaa aaggccgtaa   2520

tatccagctg aacggtctgg ttataggtac attgagcaac tgactgaaat gcctcaaaat   2580

gttctttacg atgccattgg gatatatcaa cggtggtata tccagtgatt tttttctcca   2640

ttttagcttc cttagctcct gaaaatctcg ataactcaaa aaatacgccc ggtagtgatc   2700

ttatttcatt atggtgaaag ttggaacctc ttacgtgccc gatcaa                  2746
```

<210> SEQ ID NO 63
<211> LENGTH: 2380
<212> TYPE: DNA
<213> ORGANISM: Artificial Sequence
<220> FEATURE:
<223> OTHER INFORMATION: Chemically Synthesized, pBTK205

<400> SEQUENCE: 63

```
tcatgaccaa aatcccttaa cgtgagtttt cgttccactg agcgtcagac cccgtagaaa     60

agatcaaagg atcttcttga gatccttttt ttctgcgcgt aatctgctgc ttgcaaacaa    120

aaaaaccacc gctaccagcg gtggtttgtt tgccggatca agagctacca actctttttc    180

cgaaggtaac tggcttcagc agagcgcaga taccaaatac tgttcttcta gtgtagccgt    240

agttaggcca ccacttcaag aactctgtag caccgcctac atacctcgct ctgctaatcc    300

tgttaccagt ggctgctgcc agtggcgata agtcgtgtct taccgggttg gactcaagac    360

gatagttacc ggataaggcg cagcggtcgg gctgaacggg gggttcgtgc acacagccca    420

gcttggagcg aacgacctac accgaactga gatacctaca gcgtgagcta tgagaaagcg    480

ccacgcttcc cgaagggaga aaggcggaca ggtatccggt aagcggcagg gtcggaacag    540

gagagcgcac gagggagctt ccagggggaa acgcctggta tctttatagt cctgtcgggt    600

ttcgccacct ctgacttgag cgtcgatttt tgtgatgctc gtcagggggg cggagcctat    660

ggaaaaacgc cagcaacgcg gcctttttac ggttcctggc cttttgctgg ccttttgctc    720

acatgttctt tcctgcgtta tcccctgatt ctgtggataa ccgtagtcgg tctcatatga    780

gtaaaggaga agagcttttc acaggagttg tcccaatcct cgtggaatta gacggtgatg    840

ttaatgggca caagttctct gtcagtggag agggtgaagg cgacgcaaca tatggcaagc    900

tgacccttaa atttatttgc accacgggta aactacctgt tccatggcca acactggtca    960

ctacgttcgg gtatggggtt cagtgctttg cgcgctaccc agatcacatg aaacagcacg   1020

actttttcaa gagtgcaatg cccgaaggct atgtacagga gagaaccatc tttttaagg    1080

atgacggcaa ctataagaca cgcgccgaag tgaagttcga gggtgatacc cttgttaata   1140

gaatcgagtt aaagggtatt gactttaagg aagatggaaa tattttaggc cacaaactgg   1200

aatataacta taactcccat aatgtgtaca ttatggccga caagcaaaag aacggtatca   1260

aggttaactt caagatcaga cacaacattg aggatggaag cgttcaacta gccgaccatt   1320

accaacaaaa caccccaatt ggcgatgggc ctgtgctgtt accagacaac cattacctgt   1380

ccactcaatc tgccctttcg aaagatccca acgaaaagcg cgaccacatg gtccttcttg   1440
```

-continued

```
agtttgtcac ggctgctggg attacacacg gcatggatga actatacaaa taaatcctga   1500
gaccagacca ataaaaaacg cccggcggca accgagcgtt ctgaacaaat ccagatggag   1560
ttctgaggtc attactggat ctatcaacag gagtccaagc gagctcgata tcaaattacg   1620
ccccgccctg ccactcatcg cagtactgtt gtaattcatt aagcattctg ccgacatgga   1680
agccatcaca aacggcatga tgaacctgaa tcgccagcgg catcagcacc ttgtcgcctt   1740
gcgtataata tttgcccatg gtgaaaacgg gggcgaagaa gttgtccata ttggccacgt   1800
ttaaatcaaa actggtgaaa ctcacccagg gattggctga aacgaaaaac atattctcaa   1860
taaacccttt agggaaatag gccaggtttt caccgtaaca cgccacatct tgcgaatata   1920
tgtgtagaaa ctgccggaaa tcgtcgtggt attcactcca gagcgatgaa aacgtttcag   1980
tttgctcatg gaaaacggtg taacaagggt gaacactatc ccatatcacc agctcaccgt   2040
ctttcattgc catacgaaat tccggatgag cattcatcag gcgggcaaga atgtgaataa   2100
aggccggata aaacttgtgc ttatttttct ttacggtctt taaaaaggcc gtaatatcca   2160
gctgaacggt ctggttatag gtacattgag caactgactg aaatgcctca aaatgttctt   2220
tacgatgcca ttgggatata tcaacggtgg tatatccagt gatttttttc tccattttag   2280
cttccttagc tcctgaaaat ctcgataact caaaaaatac gcccggtagt gatcttattt   2340
cattatggtg aaagttggaa cctcttacgt gcccgatcaa                         2380
```

<210> SEQ ID NO 64
<211> LENGTH: 2179
<212> TYPE: DNA
<213> ORGANISM: Artificial Sequence
<220> FEATURE:
<223> OTHER INFORMATION: Chemically Synthesized, pBTK206

<400> SEQUENCE: 64

```
tcatgaccaa aatcccttaa cgtgagtttt cgttccactg agcgtcagac cccgtagaaa     60
agatcaaagg atcttcttga gatccttttt ttctgcgcgt aatctgctgc ttgcaaacaa    120
aaaaaccacc gctaccagcg gtggtttgtt tgccggatca agagctacca actctttttc    180
cgaaggtaac tggcttcagc agagcgcaga taccaaatac tgttcttcta gtgtagccgt    240
agttaggcca ccacttcaag aactctgtag caccgcctac atacctcgct ctgctaatcc    300
tgttaccagt ggctgctgcc agtggcgata agtcgtgtct taccgggttg gactcaagac    360
gatagttacc ggataaggcg cagcggtcgg gctgaacggg gggttcgtgc acacagccca    420
gcttggagcg aacgacctac accgaactga gatacctaca gcgtgagcta tgagaaagcg    480
ccacgcttcc cgaagggaga aaggcggaca ggtatccggt aagcggcagg gtcggaacag    540
gagagcgcac gagggagctt ccagggggaa acgcctggta tctttatagt cctgtcgggt    600
ttcgccacct ctgacttgag cgtcgatttt tgtgatgctc gtcagggggg cggagcctat    660
ggaaaaacgc cagcaacgcg gcctttttac ggttcctggc cttttgctgg ccttttgctc    720
acatgttctt tcctgcgtta tcccctgatt ctgtggataa ccgtagtcgg tctcatatgg    780
tcttcacact cgaagatttc gttggggact ggcgacagac agccggctac aacctggacc    840
aagtccttga acagggaggt gtgtccagtt tgtttcagaa tctcggggtg tccgtaactc    900
cgatccaaag gattgtcctg agcggtgaaa atgggctgaa gatcgacatc catgtcatca    960
tcccgtatga aggtctgagc ggcgaccaaa tgggccagat cgaaaaaatt tttaaggtgg   1020
tgtaccctgt ggatgatcat cactttaagg tgatcctgca ctatggcaca ctggtaatcg   1080
acggggttac gccgaacatg atcgactatt tcggacggcc gtatgaaggc atcgccgtgt   1140
```

```
tcgacggcaa aaagatcact gtaacaggga ccctgtggaa cggcaacaaa attatcgacg   1200

agcgcctgat caaccccgac ggctccctgc tgttccgagt aaccatcaac ggagtgaccg   1260

gctggcggct gtgcgaacgc attctggcgt aaatcctgag accagaccaa taaaaaacgc   1320

ccggcggcaa ccgagcgttc tgaacaaatc cagatggagt tctgaggtca ttactggatc   1380

tatcaacagg agtccaagcg agctcgatat caaattacgc cccgccctgc cactcatcgc   1440

agtactgttg taattcatta agcattctgc cgacatggaa gccatcacaa acggcatgat   1500

gaacctgaat cgccagcggc atcagcacct tgtcgccttg cgtataatat ttgcccatgg   1560

tgaaaacggg ggcgaagaag ttgtccatat tggccacgtt taaatcaaaa ctggtgaaac   1620

tcacccaggg attggctgaa acgaaaaaca tattctcaat aaacccttta gggaaatagg   1680

ccaggttttc accgtaacac gccacatctt gcgaatatat gtgtagaaac tgccggaaat   1740

cgtcgtggta ttcactccag agcgatgaaa acgtttcagt ttgctcatgg aaaacggtgt   1800

aacaagggtg aacactatcc catatcacca gctcaccgtc tttcattgcc atacgaaatt   1860

ccggatgagc attcatcagg cgggcaagaa tgtgaataaa ggccggataa aacttgtgct   1920

tatttttctt tacggtcttt aaaaaggccg taatatccag ctgaacggtc tggttatagg   1980

tacattgagc aactgactga aatgcctcaa aatgttcttt acgatgccat tgggatatat   2040

caacggtggt atatccagtg atttttttct ccattttagc ttccttagct cctgaaaatc   2100

tcgataactc aaaaaatacg cccggtagtg atcttatttc attatggtga aagttggaac   2160

ctcttacgtg cccgatcaa                                                2179
```

<210> SEQ ID NO 65
<211> LENGTH: 5773
<212> TYPE: DNA
<213> ORGANISM: Artificial Sequence
<220> FEATURE:
<223> OTHER INFORMATION: Chemically Synthesized, pBTK209

<400> SEQUENCE: 65

```
tcatgaccaa aatcccttaa cgtgagtttt cgttccactg agcgtcagac cccgtagaaa     60

agatcaaagg atcttcttga gatccttttt ttctgcgcgt aatctgctgc ttgcaaacaa    120

aaaaaccacc gctaccagcg gtggtttgtt tgccggatca agagctacca actctttttc    180

cgaaggtaac tggcttcagc agagcgcaga taccaaatac tgttcttcta gtgtagccgt    240

agttaggcca ccacttcaag aactctgtag caccgcctac atacctcgct ctgctaatcc    300

tgttaccagt ggctgctgcc agtggcgata agtcgtgtct taccgggttg gactcaagac    360

gatagttacc ggataaggcg cagcggtcgg gctgaacggg gggttcgtgc acacagccca    420

gcttggagcg aacgacctac accgaactga gatacctaca gcgtgagcta tgagaaagcg    480

ccacgcttcc cgaagggaga aaggcggaca ggtatccggt aagcggcagg gtcggaacag    540

gagagcgcac gagggagctt ccagggggaa acgcctggta tctttatagt cctgtcgggt    600

ttcgccacct ctgacttgag cgtcgatttt tgtgatgctc gtcagggggg cggagcctat    660

ggaaaaacgc cagcaacgcg gcctttttac ggttcctggc cttttgctgg ccttttgctc    720

acatgttctt tcctgcgtta tcccctgatt ctgtggataa ccgtagtcgg tctcatatga    780

tggataagaa atactcaata ggcttagcta tcggcacaaa tagcgtcgga tgggcggtga    840

tcactgatga atataaggtt ccgtctaaaa agttcaaggt tctgggaaat acagaccgcc    900

acagtatcaa aaaaaatctt ataggggctc ttttatttga cagtggagag acagcggaag    960
```

```
cgactcgtcg taaacggaca gctcgtagaa ggtatacacg tcggaagaat cgtatttgtt   1020
atctacagga gatttttca aatgagatgg cgaaagtaga tgatagtttc tttcatcgac   1080
ttgaagagtc ttttttggtg gaagaagaca agaagcatga acgtcatcct atttttggaa   1140
atatagtaga tgaagttgct tatcatgaga aatatccaac tatctatcat ctgcgaaaaa   1200
aattggtaga ttctactgat aaagcggatt tgcgcttaat ctatttggcc ttagcgcata   1260
tgattaagtt tcgtggtcat tttttgattg agggagattt aaatcctgat aatagtgatg   1320
tggacaaact atttatccag ttggtacaaa cctacaatca attatttgaa gaaaacccta   1380
ttaacgcaag tggagtagat gctaaagcga ttctttctgc acgattgagt aaatcaagac   1440
gattagaaaa tctcattgct cagctccccg gtgagaagaa aaatggctta tttgggaatc   1500
tcattgcttt gtcattgggt ttgaccccta attttaaatc aaattttgat ttggcagaag   1560
atgctaaatt acagctttca aaagatactt acgatgatga tttagataat ttattggcgc   1620
aaattggaga tcaatatgct gatttgtttt tggcagctaa gaatttatca gatgctattt   1680
tactttcaga tatcctaaga gtaaatactg aaataactaa ggctcccccta tcagcttcaa   1740
tgattaaacg ctacgatgaa catcatcaag acttgactct tttaaaagct ttagttcgac   1800
aacaacttcc agaaaagtat aaagaaatct tttttgatca atcaaaaaac ggatatgcag   1860
gttatattga tgggggagct agccaagaag aattttataa atttatcaaa ccaattttag   1920
aaaaaatgga tggtactgag gaattattgg tgaaactaaa tcgtgaagat ttgctgcgca   1980
agcaacggac ctttgacaac ggctctattc cccatcaaat tcacttgggt gagctgcatg   2040
ctattttgag aagacaagaa gacttttatc catttttaaa agacaatcgt gagaagattg   2100
aaaaaatctt gacttttcga attccttatt atgttggtcc attggcgcgt ggcaatagtc   2160
gttttgcatg gatgactcgg aagtctgaag aaacaattac cccatggaat tttgaagaag   2220
ttgtcgataa aggtgcttca gctcaatcat ttattgaacg catgacaaac tttgataaaa   2280
atcttccaaa tgaaaaagta ctaccaaaac atagtttgct ttatgagtat tttacggttt   2340
ataacgaatt gacaaaggtc aaatatgtta ctgaaggaat gcgaaaacca gcatttcttt   2400
caggtgaaca gaagaaagcc attgttgatt tactcttcaa aacaaatcga aaagtaaccg   2460
ttaagcaatt aaaagaagat tatttcaaaa aaatagaatg ttttgatagt gttgaaattt   2520
caggagttga agatagattt aatgcttcat taggtaccta ccatgatttg ctaaaaatta   2580
ttaaagataa agattttttg gataatgaag aaaatgaaga tatcttagag gatattgttt   2640
taacattgac cttatttgaa gatagggaga tgattgagga aagacttaaa acatatgctc   2700
acctctttga tgataaggtg atgaaacagc ttaaacgtcg ccgttatact ggttggggac   2760
gtttgtctcg aaaattgatt aatggtatta gggataagca atctggcaaa acaatattag   2820
attttttgaa atcagatggt tttgccaatc gcaattttat gcagctgatc catgatgata   2880
gtttgacatt taaagaagac attcaaaaag cacaagtgtc tggacaaggc gatagtttac   2940
atgaacatat tgcaaattta gctggtagcc ctgctattaa aaaaggtatt ttacagactg   3000
taaaagttgt tgatgaattg gtcaaagtaa tggggcggca taagccagaa aatatcgtta   3060
ttgaaatggc acgtgaaaat cagacaactc aaaagggcca gaaaaattcg cgagagcgta   3120
tgaaacgaat cgaagaaggt atcaaagaat taggaagtca gattcttaaa gagcatcctg   3180
ttgaaaatac tcaattgcaa aatgaaaagc tctatctcta ttatctccaa aatggaagag   3240
acatgtatgt ggaccaagaa ttagatatta atcgtttaag tgattatgat gtcgatgcca   3300
ttgttccaca aagtttcctt aaagacgatt caatagacaa taaggtctta acgcgttctg   3360
```

```
ataaaaatcg tggtaaatcg gataacgttc caagtgaaga agtagtcaaa aagatgaaaa   3420
actattggag acaacttcta aacgccaagt taatcactca acgtaagttt gataatttaa   3480
cgaaagctga acgtggaggt ttgagtgaac ttgataaagc tggttttatc aaacgccaat   3540
tggttgaaac tcgccaaatc actaagcatg tggcacaaat tttggatagt cgcatgaata   3600
ctaaatacga tgaaaatgat aaacttattc gagaggttaa agtgattacc ttaaaatcta   3660
aattagtttc tgacttccga aaagatttcc aattctataa agtacgtgag attaacaatt   3720
accatcatgc ccatgatgcg tatctaaatg ccgtcgttgg aactgctttg attaagaaat   3780
atccaaaact tgaatcggag tttgtctatg gtgattataa agtttatgat gttcgtaaaa   3840
tgattgctaa gtctgagcaa gaaataggca aagcaaccgc aaaatatttc ttttactcta   3900
atatcatgaa cttcttcaaa acagaaatta cacttgcaaa tggagagatt cgcaaacgcc   3960
ctctaatcga aactaatggg gaaactggag aaattgtctg ggataaaggg cgagattttg   4020
ccacagtgcg caaagtattg tccatgcccc aagtcaatat tgtcaagaaa acagaagtac   4080
agacaggcgg attctccaag gagtcaattt taccaaaaag aaattcggac aagcttattg   4140
ctcgtaaaaa agactgggat ccaaaaaaat atggtggttt tgatagtcca acggtagctt   4200
attcagtcct agtggttgct aaggtggaaa aagggaaatc gaagaagtta aaatccgtta   4260
aagagttact agggatcaca attatggaaa gaagttcctt tgaaaaaaat ccgattgact   4320
ttttagaagc taaaggatat aaggaagtta aaaaagactt aatcattaaa ctacctaaat   4380
atagtctttt tgagttagaa aacggtcgta aacggatgct ggctagtgcc ggagaattac   4440
aaaaaggaaa tgagctggct ctgccaagca aatatgtgaa tttttttatat ttagctagtc   4500
attatgaaaa gttgaagggt agtccagaag ataacgaaca aaaacaattg tttgtggagc   4560
agcataagca ttatttagat gagattattg agcaaatcag tgaattttct aagcgtgtta   4620
ttttagcaga tgccaattta gataaagttc ttagtgcata taacaaacat agagacaaac   4680
caatacgtga acaagcagaa aatattattc atttatttac gttgacgaat cttggagctc   4740
ccgctgcttt taaatatttt gatacaacaa ttgatcgtaa acgatatacg tctacaaaag   4800
aagttttaga tgccactctt atccatcaat ccatcactgg tctttatgaa acacgcattg   4860
atttgagtca gctaggaggt gactgaatcc tgagaccaga ccaataaaaa acgcccggcg   4920
gcaaccgagc gttctgaaca aatccagatg gagttctgag gtcattactg gatctatcaa   4980
caggagtcca agcgagctcg atatcaaatt acgccccgcc ctgccactca tcgcagtact   5040
gttgtaattc attaagcatt ctgccgacat ggaagccatc acaaacggca tgatgaacct   5100
gaatcgccag cggcatcagc accttgtcgc cttgcgtata atatttgccc atggtgaaaa   5160
cgggggcgaa gaagttgtcc atattggcca cgtttaaatc aaaactggtg aaactcaccc   5220
agggattggc tgaaacgaaa aacatattct caataaaccc tttagggaaa taggccaggt   5280
tttcaccgta acacgccaca tcttgcgaat atatgtgtag aaactgccgg aaatcgtcgt   5340
ggtattcact ccagagcgat gaaaacgttt cagtttgctc atggaaaacg gtgtaacaag   5400
ggtgaacact atcccatatc accagctcac cgtctttcat tgccatacga aattccggat   5460
gagcattcat caggcgggca agaatgtgaa taaaggccgg ataaaacttg tgcttatttt   5520
tctttacggt ctttaaaaag gccgtaatat ccagctgaac ggtctggtta taggtacatt   5580
gagcaactga ctgaaatgcc tcaaaatgtt ctttacgatg ccattgggat atatcaacgg   5640
tggtatatcc agtgattttt ttctccattt tagcttcctt agctcctgaa aatctcgata   5700
```

```
actcaaaaaa tacgcccggt agtgatctta tttcattatg gtgaaagttg gaacctctta   5760

cgtgcccgat caa                                                      5773
```

<210> SEQ ID NO 66
<211> LENGTH: 2749
<212> TYPE: DNA
<213> ORGANISM: Artificial Sequence
<220> FEATURE:
<223> OTHER INFORMATION: Chemically Synthesized, pBTK211

<400> SEQUENCE: 66

```
tttagcttcc ttagctcctg aaaatctcga taactcaaaa aatacgcccg gtagtgatct     60
tatttcatta tggtgaaagt tggaacctct tacgtgcccg atcaatcatg accaaaatcc    120
cttaacgtga gttttcgttc cactgagcgt cagaccccgt agaaaagatc aaaggatctt    180
cttgagatcc tttttttctg cgcgtaatct gctgcttgca aacaaaaaaa ccaccgctac    240
cagcggtggt ttgtttgccg gatcaagagc taccaactct ttttccgaag gtaactggct    300
tcagcagagc gcagatacca aatactgttc ttctagtgta gccgtagtta ggccaccact    360
tcaagaactc tgtagcaccg cctacatacc tcgctctgct aatcctgtta ccagtggctg    420
ctgccagtgg cgataagtcg tgtcttaccg ggttggactc aagacgatag ttaccggata    480
aggcgcagcg gtcgggctga acggggggtt cgtgcacaca gcccagcttg gagcgaacga    540
cctacaccga actgagatac ctacagcgtg agctatgaga aagcgccacg cttcccgaag    600
ggagaaaggc ggacaggtat ccggtaagcg gcagggtcgg aacaggagag cgcacgaggg    660
agcttccagg gggaaacgcc tggtatcttt atagtcctgt cgggtttcgc cacctctgac    720
ttgagcgtcg atttttgtga tgctcgtcag gggggcggag cctatggaaa aacgccagca    780
acgcggcctt tttacggttc ctggcctttt gctggccttt tgctcacatg ttctttcctg    840
cgttatcccc tgattctgtg gataaccgta gtcggtctca tacatcactg cccgctttcc    900
agtcgggaaa cctgtcgtgc cagctgcatt aatgaatcgg ccaacgcgcg gggagaggcg    960
gtttgcgtat tgggcgccag ggtggttttt cttttcacca gtgacaccgg caacagctga   1020
ttgcccttca ccgcctggcc ctgagagagt tgcagcaagc ggtccacgct ggtttgcccc   1080
agcaggcgaa aatcctgttt gatggtggtt aacggcggga tataacatga gctgtcttcg   1140
gtatcgtcgt atcccactac cgagatatcc gcaccaacgc gcagcccgga ctcggtaatg   1200
gcgcgcattg cgcccagcgc catctgatcg ttggcaacca gcatcgcagt gggaacgatg   1260
ccctcattca gcatttgcat ggtttgttga aaaccggaca tggcactcca gtcgccttcc   1320
cgttccgcta tcggctgaat ttgattgcga gtgagatatt tatgccagcc agccagacgc   1380
agacgcgccg agacagaact taatgggccc gctaacagcg cgatttgctg gtgacccaat   1440
gcgaccagat gctccacgcc cagtcgcgta ccgtcttcat gggagaaaat aatactgttg   1500
atgggtgtct ggtcagagac atcaagaaat aacgccggaa cattagtgca ggcagcttcc   1560
acagcaatgg catcctggtc atccagcgga tagttaatga tcagcccact gacgcgttgc   1620
gcgagaagat tgtgcaccgc cgctttacag gcttcgacgc cgcttcgttc taccatcgac   1680
accaccacgc tggcacccag ttgatcggcg cgagatttaa tcgccgcgac aatttgcgac   1740
ggcgcgtgca gggccagact ggaggtggca acgccaatca gcaacgactg tttgcccgcc   1800
agttgttgtg ccacgcggtt gggaatgtaa ttcagctccg ccatcgccgc ttccactttt   1860
tcccgcgttt tcgcagaaac gtggctggcc tggttcacca cgcgggaaac ggtctgataa   1920
gagacaccgg catactctgc gacatcgtat aacgttactg gtttcatgag ttgagaccag   1980
```

accaataaaa aacgcccggc ggcaaccgag cgttctgaac aaatccagat ggagttctga 2040
ggtcattact ggatctatca acaggagtcc aagcgagctc gatatcaaat tacgccccgc 2100
cctgccactc atcgcagtac tgttgtaatt cattaagcat tctgccgaca tggaagccat 2160
cacaaacggc atgatgaacc tgaatcgcca gcggcatcag caccttgtcg ccttgcgtat 2220
aatatttgcc catggtgaaa acgggggcga agaagttgtc catattggcc acgtttaaat 2280
caaaactggt gaaactcacc cagggattgg ctgaaacgaa aaacatattc tcaataaacc 2340
ctttagggaa ataggccagg ttttcaccgt aacacgccac atcttgcgaa tatatgtgta 2400
gaaactgccg gaaatcgtcg tggtattcac tccagagcga tgaaaacgtt tcagtttgct 2460
catggaaaac ggtgtaacaa gggtgaacac tatcccatat caccagctca ccgtctttca 2520
ttgccatacg aaattccgga tgagcattca tcaggcgggc aagaatgtga ataaaggccg 2580
gataaaactt gtgcttattt ttctttacgg tctttaaaaa ggccgtaata tccagctgaa 2640
cggtctggtt ataggtacat tgagcaactg actgaaatgc ctcaaaatgt tctttacgat 2700
gccattggga tatatcaacg gtggtatatc cagtgatttt tttctccat 2749

<210> SEQ ID NO 67
<211> LENGTH: 2380
<212> TYPE: DNA
<213> ORGANISM: Artificial Sequence
<220> FEATURE:
<223> OTHER INFORMATION: Chemically Synthesized, pBTK224

<400> SEQUENCE: 67
tcatgaccaa aatcccttaa cgtgagtttt cgttccactg agcgtcagac cccgtagaaa 60
agatcaaagg atcttcttga gatccttttt ttctgcgcgt aatctgctgc ttgcaaacaa 120
aaaaaccacc gctaccagcg gtggtttgtt tgccggatca agagctacca actctttttc 180
cgaaggtaac tggcttcagc agagcgcaga taccaaatac tgttcttcta gtgtagccgt 240
agttaggcca ccacttcaag aactctgtag caccgcctac atacctcgct ctgctaatcc 300
tgttaccagt ggctgctgcc agtggcgata agtcgtgtct taccgggttg gactcaagac 360
gatagttacc ggataaggcg cagcggtcgg gctgaacggg gggttcgtgc acacagccca 420
gcttggagcg aacgacctac accgaactga gatacctaca gcgtgagcta tgagaaagcg 480
ccacgcttcc cgaagggaga aaggcggaca ggtatccggt aagcggcagg gtcggaacag 540
gagagcgcac gagggagctt ccagggggaa acgcctggta tctttatagt cctgtcgggt 600
ttcgccacct ctgacttgag cgtcgatttt tgtgatgctc gtcagggggg cggagcctat 660
ggaaaaacgc cagcaacgcg gcctttttac ggttcctggc cttttgctgg ccttttgctc 720
acatgttctt tcctgcgtta tcccctgatt ctgtggataa ccgtagtcgg tctcatatgg 780
atagcactga gaacgtcatc aagcccttca tgcgcttcaa ggtgcacatg gagggctccg 840
tgaacggcca cgagttcgag atcgagggcg tgggcgaggg caagccctac gagggcaccc 900
agaccgccaa gctgcaagtg accaagggcg gccccctgcc cttcgcctgg gacatcctgt 960
ccccccagtt cttctacggc tccaaggcgt acatcaagca ccccgccgac atccccgact 1020
acctcaagca gtccttcccc gagggcttca agtgggagcg cgtgatgaac ttcgaggacg 1080
gcggcgtggt gaccgtgacc caggactcct ccctgcagga cggcaccctc atctaccacg 1140
tgaagttcat cggcgtgaac ttcccctccg acggccccgt aatgcagaag aagactctgg 1200
gctgggagcc ctccactgag cgcaactacc cccgcgacgg cgtgctgaag ggcgagaacc 1260

```
acatggcgct gaagctgaag ggcggcggcc actacctgtg tgagttcaag tccatctaca   1320

tggccaagaa gcccgtgaag ctgcccggct accactacgt ggactacaag ctcgacatca   1380

cctcccacaa cgaggactac accgtggtgg agcagtacga gcgcgccgag gcccgccacc   1440

acctgttcca gactcacggt atggacgaat tgtacaagca cgacgaattg taaatcctga   1500

gaccagacca ataaaaaacg cccggcggca accgagcgtt ctgaacaaat ccagatggag   1560

ttctgaggtc attactggat ctatcaacag gagtccaagc gagctcgata tcaaattacg   1620

ccccgccctg ccactcatcg cagtactgtt gtaattcatt aagcattctg ccgacatgga   1680

agccatcaca aacggcatga tgaacctgaa tcgccagcgg catcagcacc ttgtcgcctt   1740

gcgtataata tttgcccatg gtgaaaacgg gggcgaagaa gttgtccata ttggccacgt   1800

ttaaatcaaa actggtgaaa ctcacccagg gattggctga aacgaaaaac atattctcaa   1860

taaacccttt agggaaatag gccaggtttt caccgtaaca cgccacatct tgcgaatata   1920

tgtgtagaaa ctgccggaaa tcgtcgtggt attcactcca gagcgatgaa aacgtttcag   1980

tttgctcatg gaaaacggtg taacaagggt gaacactatc ccatatcacc agctcaccgt   2040

ctttcattgc catacgaaat tccggatgag cattcatcag gcgggcaaga atgtgaataa   2100

aggccggata aaacttgtgc ttatttttct ttacggtctt taaaaaggcc gtaatatcca   2160

gctgaacggt ctggttatag gtacattgag caactgactg aaatgcctca aaatgttctt   2220

tacgatgcca ttgggatata tcaacggtgg tatatccagt gatttttttc tccattttag   2280

cttccttagc tcctgaaaat ctcgataact caaaaaatac gcccggtagt gatcttattt   2340

cattatggtg aaagttggaa cctcttacgt gcccgatcaa                         2380
```

<210> SEQ ID NO 68
<211> LENGTH: 2673
<212> TYPE: DNA
<213> ORGANISM: Artificial Sequence
<220> FEATURE:
<223> OTHER INFORMATION: Chemically Synthesized, pBTK229

<400> SEQUENCE: 68

```
atagttaccg gataaggcgc agcggtcggg ctgaacgggg ggttcgtgca cacagcccag     60

cttggagcga acgacctaca ccgaactgag atacctacag cgtgagctat gagaaagcgc    120

cacgcttccc gaagggagaa aggcggacag gtatccggta agcggcaggg tcggaacagg    180

agagcgcacg agggagcttc caggggggaaa cgcctggtat ctttatagtc ctgtcgggtt    240

tcgccacctc tgacttgagc gtcgattttt gtgatgctcg tcaggggggc ggagcctatg    300

gaaaaacgcc agcaacgcgg cctttttacg gttcctggcc ttttgctggc cttttgctca    360

catgttcttt cctgcgttat cccctgattc tgtggataac cgtagtcggt ctcatatgta    420

taccgagcgg ccgcgtgtta caaccaatta accaattctg attagaaaaa ctcatcgagc    480

atcaaatgaa actgcaattt attcatatca ggattatcaa taccatattt ttgaaaaagc    540

cgtttctgta atgaaggaga aaactcaccg aggcagttcc ataggatggc aagatcctgg    600

tatcggtctg cgattccgac tcgtccaaca tcaatacaac ctattaattt cccctcgtca    660

aaaataaggt tatcaagtga gaaatcacca tgagtgacga ctgaatccgg tgagaatggc    720

aaaagcttat gcatttcttt ccagacttgt tcaacaggcc agccattacg ctcgtcatca    780

aaatcactcg catcaaccaa accgttattc attcgtgatt gcgcctgagc gaggcgaaat    840

acgcgatcgc tgttaaaagg acaattacaa acaggaatcg aatgcaaccg gcgcaggaac    900

actgccagcg catcaacaat attttcacct gaatcaggat attcttctaa tacctggaat    960
```

```
gctgttttcc cggggatcgc agtggtgagt aaccatgcat catcaggagt acggataaaa   1020

tgcttgatgg tcggaagagg cataaattcc gtcagccagt ttagtctgac catctcatct   1080

gtaacatcat tggcaacgct acctttgcca tgtttcagaa acaactctgg cgcatcgggc   1140

ttcccataca atcgatagat tgtcgcacct gattgcccga cattatcgcg agcccattta   1200

tacccatata aatcagcatc catgttggaa tttaatcgcg gcctggagca agacgtttcc   1260

cgttgaatat ggctcataac accccttgta ttactgttta tgtaagcaga cagttttatt   1320

gttcatgatg atatattttt atcttgtgca atgtaacatc agagattttg agacacaacg   1380

tggctttgtt gaataaatcg aacttttgct gagttgaagg atcagatcct gagaccagac   1440

caataaaaaa cgcccggcgg caaccgagcg ttctgaacaa atccagatgg agttctgagg   1500

tcattactgg atctatcaac aggagtccaa gcgagctcga tatcaaatta cgccccgccc   1560

tgccactcat cgcagtactg ttgtaattca ttaagcattc tgccgacatg gaagccatca   1620

caaacggcat gatgaacctg aatcgccagc ggcatcagca ccttgtcgcc ttgcgtataa   1680

tatttgccca tggtgaaaac gggggcgaag aagttgtcca tattggccac gtttaaatca   1740

aaactggtga aactcaccca gggattggct gaaacgaaaa acatattctc aataaaccct   1800

ttagggaaat aggccaggtt ttcaccgtaa cacgccacat cttgcgaata tatgtgtaga   1860

aactgccgga aatcgtcgtg gtattcactc cagagcgatg aaaacgtttc agtttgctca   1920

tggaaaacgg tgtaacaagg gtgaacacta tcccatatca ccagctcacc gtctttcatt   1980

gccatacgaa attccggatg agcattcatc aggcgggcaa gaatgtgaat aaaggccgga   2040

taaaacttgt gcttattttt ctttacggtc tttaaaaagg ccgtaatatc cagctgaacg   2100

gtctggttat aggtacattg agcaactgac tgaaatgcct caaaatgttc tttacgatgc   2160

cattgggata tatcaacggt ggtatatcca gtgatttttt tctccatttt agcttcctta   2220

gctcctgaaa atctcgataa ctcaaaaaat acgcccggta gtgatcttat ttcattatgg   2280

tgaaagttgg aacctcttac gtgcccgatc aatcatgacc aaaatccctt aacgtgagtt   2340

ttcgttccac tgagcgtcag accccgtaga aaagatcaaa ggatcttctt gagatccttt   2400

ttttctgcgc gtaatctgct gcttgcaaac aaaaaaacca ccgctaccag cggtggtttg   2460

tttgccggat caagagctac caactctttt tccgaaggta actggcttca gcagagcgca   2520

gataccaaat actgttcttc tagtgtagcc gtagttaggc caccacttca agaactctgt   2580

agcaccgcct acatacctcg ctctgctaat cctgttacca gtggctgctg ccagtggcga   2640

taagtcgtgt cttaccgggt tggactcaag acg                                2673
```

<210> SEQ ID NO 69
<211> LENGTH: 1749
<212> TYPE: DNA
<213> ORGANISM: Artificial Sequence
<220> FEATURE:
<223> OTHER INFORMATION: Chemically Synthesized, pBTK300

<400> SEQUENCE: 69

```
tcatgaccaa aatcccttaa cgtgagtttt cgttccactg agcgtcagac cccgtagaaa     60

agatcaaagg atcttcttga gatccttttt ttctgcgcgt aatctgctgc ttgcaaacaa    120

aaaaaccacc gctaccagcg gtggtttgtt tgccggatca agagctacca actctttttc    180

cgaaggtaac tggcttcagc agagcgcaga taccaaatac tgttcttcta gtgtagccgt    240

agttaggcca ccacttcaag aactctgtag caccgcctac atacctcgct ctgctaatcc    300
```

```
tgttaccagt ggctgctgcc agtggcgata agtcgtgtct taccgggttg gactcaagac    360

gatagttacc ggataaggcg cagcggtcgg gctgaacggg gggttcgtgc acacagccca    420

gcttggagcg aacgacctac accgaactga gatacctaca gcgtgagcta tgagaaagcg    480

ccacgcttcc cgaagggaga aaggcggaca ggtatccggt aagcggcagg gtcggaacag    540

gagagcgcac gagggagctt ccagggggaa acgcctggta tctttatagt cctgtcgggt    600

ttcgccacct ctgacttgag cgtcgatttt tgtgatgctc gtcagggggg cggagcctat    660

ggaaaaacgc cagcaacgcg gcctttttac ggttcctggc cttttgctgg ccttttgctc    720

acatgttctt tcctgcgtta tcccctgatt ctgtggataa ccgtagtcgg tctcaatccg    780

taatcgttaa tccgcaaata acgtaaaaac ccgcttcggc gggttttttt atgggggag    840

tttagggaaa gagcatttgt cagctgtgag accagaccaa taaaaaacgc ccggcggcaa    900

ccgagcgttc tgaacaaatc cagatggagt tctgaggtca ttactggatc tatcaacagg    960

agtccaagcg agctcgatat caaattacgc cccgccctgc cactcatcgc agtactgttg   1020

taattcatta agcattctgc cgacatggaa gccatcacaa acggcatgat gaacctgaat   1080

cgccagcggc atcagcacct tgtcgccttg cgtataatat ttgcccatgg tgaaaacggg   1140

ggcgaagaag ttgtccatat tggccacgtt taaatcaaaa ctggtgaaac tcacccaggg   1200

attggctgaa acgaaaaaca tattctcaat aaacccttta gggaaatagg ccaggttttc   1260

accgtaacac gccacatctt gcgaatatat gtgtagaaac tgccggaaat cgtcgtggta   1320

ttcactccag agcgatgaaa acgtttcagt ttgctcatgg aaaacggtgt aacaagggtg   1380

aacactatcc catatcacca gctcaccgtc tttcattgcc atacgaaatt ccggatgagc   1440

attcatcagg cgggcaagaa tgtgaataaa ggccggataa aacttgtgct tatttttctt   1500

tacggtcttt aaaaaggccg taatatccag ctgaacggtc tggttatagg tacattgagc   1560

aactgactga aatgcctcaa aatgttcttt acgatgccat tgggatatat caacggtggt   1620

atatccagtg atttttttct ccattttagc ttccttagct cctgaaaatc tcgataactc   1680

aaaaaatacg cccggtagtg atcttatttc attatggtga aagttggaac ctcttacgtg   1740

cccgatcaa                                                           1749
```

```
<210> SEQ ID NO 70
<211> LENGTH: 1795
<212> TYPE: DNA
<213> ORGANISM: Artificial Sequence
<220> FEATURE:
<223> OTHER INFORMATION: Chemically Synthesized, pBTK301

<400> SEQUENCE: 70

tcatgaccaa aatcccttaa cgtgagtttt cgttccactg agcgtcagac cccgtagaaa     60

agatcaaagg atcttcttga gatccttttt ttctgcgcgt aatctgctgc ttgcaaacaa    120

aaaaaccacc gctaccagcg gtggtttgtt tgccggatca agagctacca actctttttc    180

cgaaggtaac tggcttcagc agagcgcaga taccaaatac tgttcttcta gtgtagccgt    240

agttaggcca ccacttcaag aactctgtag caccgcctac atacctcgct ctgctaatcc    300

tgttaccagt ggctgctgcc agtggcgata agtcgtgtct taccgggttg gactcaagac    360

gatagttacc ggataaggcg cagcggtcgg gctgaacggg gggttcgtgc acacagccca    420

gcttggagcg aacgacctac accgaactga gatacctaca gcgtgagcta tgagaaagcg    480

ccacgcttcc cgaagggaga aaggcggaca ggtatccggt aagcggcagg gtcggaacag    540

gagagcgcac gagggagctt ccagggggaa acgcctggta tctttatagt cctgtcgggt    600
```

```
ttcgccacct ctgacttgag cgtcgatttt tgtgatgctc gtcagggggg cggagcctat    660
ggaaaaacgc cagcaacgcg gcctttttac ggttcctggc cttttgctgg ccttttgctc    720
acatgttctt tcctgcgtta tcccctgatt ctgtggataa ccgtagtcgg tctcatacac    780
caggcatcaa ataaaacgaa aggctcagtc gaaagactgg gcctttcgtt ttatctgttg    840
tttgtcggtg aacgctctct actagagtca cactggctca ccttcgggtg ggcctttctg    900
cgtttatacc gatgagacca gaccaataaa aaacgcccgg cggcaaccga gcgttctgaa    960
caaatccaga tggagttctg aggtcattac tggatctatc aacaggagtc caagcgagct   1020
cgatatcaaa ttacgccccg ccctgccact catcgcagta ctgttgtaat tcattaagca   1080
ttctgccgac atggaagcca tcacaaacgg catgatgaac ctgaatcgcc agcggcatca   1140
gcaccttgtc gccttgcgta taatatttgc ccatggtgaa aacgggggcg aagaagttgt   1200
ccatattggc cacgtttaaa tcaaaactgg tgaaactcac ccagggattg gctgaaacga   1260
aaaacatatt ctcaataaac cctttaggga aataggccag gttttcaccg taacacgcca   1320
catcttgcga atatatgtgt agaaactgcc ggaaatcgtc gtggtattca ctccagagcg   1380
atgaaaacgt ttcagtttgc tcatggaaaa cggtgtaaca agggtgaaca ctatcccata   1440
tcaccagctc accgtctttc attgccatac gaaattccgg atgagcattc atcaggcggg   1500
caagaatgtg aataaaggcc ggataaaact tgtgcttatt tttctttacg gtctttaaaa   1560
aggccgtaat atccagctga acggtctggt tataggtaca ttgagcaact gactgaaatg   1620
cctcaaaatg ttctttacga tgccattggg atatatcaac ggtggtatat ccagtgattt   1680
ttttctccat tttagcttcc ttagctcctg aaaatctcga taactcaaaa aatacgcccg   1740
gtagtgatct tatttcatta tggtgaaagt tggaacctct tacgtgcccg atcaa        1795
```

```
<210> SEQ ID NO 71
<211> LENGTH: 1720
<212> TYPE: DNA
<213> ORGANISM: Artificial Sequence
<220> FEATURE:
<223> OTHER INFORMATION: Chemically Synthesized, pBTK305

<400> SEQUENCE: 71
```

```
ggtcgggctg aacggggggt tcgtgcacac agcccagctt ggagcgaacg acctacaccg     60
aactgagata cctacagcgt gagctatgag aaagcgccac gcttcccgaa gggagaaagg    120
cggacaggta tccggtaagc ggcagggtcg gaacaggaga gcgcacgagg gagcttccag    180
ggggaaacgc ctggtatctt tatagtcctg tcgggtttcg ccacctctga cttgagcgtc    240
gatttttgtg atgctcgtca ggggggcgga gcctatggaa aaacgccagc aacgcggcct    300
ttttacggtt cctggccttt tgctggcctt ttgctcacat gttctttcct gcgttatccc    360
ctgattctgt ggataaccgt agtcggtctc aatcctaact agcataaccc cttggggcct    420
ctaaacgggt cttgaggggt tttttgctgg ctgtgagacc agaccaataa aaaacgcccg    480
gcggcaaccg agcgttctga acaaatccag atggagttct gaggtcatta ctggatctat    540
caacaggagt ccaagcgagc tcgatatcaa attacgcccc gccctgccac tcatcgcagt    600
actgttgtaa ttcattaagc attctgccga catggaagcc atcacaaacg gcatgatgaa    660
cctgaatcgc cagcggcatc agcaccttgt cgccttgcgt ataatatttg cccatggtga    720
aaacgggggc gaagaagttg tccatattgg ccacgtttaa atcaaaactg gtgaaactca    780
cccagggatt ggctgaaacg aaaaacatat tctcaataaa ccctttaggg aaataggcca    840
```

ggttttcacc gtaacacgcc acatcttgcg aatatatgtg tagaaactgc cggaaatcgt 900
cgtggtattc actccagagc gatgaaaacg tttcagtttg ctcatggaaa acggtgtaac 960
aagggtgaac actatcccat atcaccagct caccgtcttt cattgccata cgaaattccg 1020
gatgagcatt catcaggcgg gcaagaatgt gaataaaggc cggataaaac ttgtgcttat 1080
ttttctttac ggtctttaaa aaggccgtaa tatccagctg aacggtctgg ttataggtac 1140
attgagcaac tgactgaaat gcctcaaaat gttctttacg atgccattgg gatatatcaa 1200
cggtggtata tccagtgatt tttttctcca ttttagcttc cttagctcct gaaaatctcg 1260
ataactcaaa aaatacgccc ggtagtgatc ttatttcatt atggtgaaag ttggaacctc 1320
ttacgtgccc gatcaatcat gaccaaaatc ccttaacgtg agttttcgtt ccactgagcg 1380
tcagaccccg tagaaaagat caaaggatct tcttgagatc ctttttttct gcgcgtaatc 1440
tgctgcttgc aaacaaaaaa accaccgcta ccagcggtgg tttgtttgcc ggatcaagag 1500
ctaccaactc tttttccgaa ggtaactggc ttcagcagag cgcagatacc aaatactgtt 1560
cttctagtgt agccgtagtt aggccaccac ttcaagaact ctgtagcacc gcctacatac 1620
ctcgctctgc taatcctgtt accagtggct gctgccagtg gcgataagtc gtgtcttacc 1680
gggttggact caagacgata gttaccggat aaggcgcagc 1720

<210> SEQ ID NO 72
<211> LENGTH: 7536
<212> TYPE: DNA
<213> ORGANISM: Artificial Sequence
<220> FEATURE:
<223> OTHER INFORMATION: Chemically Synthesized, pBTK527

<400> SEQUENCE: 72
ggctggccag cctgcgggcc ttctcctgct gccgctgggc ctgctcgatc tgctggccag 60
cctgctgcac cagcgccggg ccagcggtgg cggtcttgcc cttggattca cgcagcagca 120
cccacggctg ataaccggcg cgggtggtgt gcttgtcctt gcggttggtg aagcccgcca 180
agcggccata gtggcggctg tcggcgctgg ccgggtcggc gtcgtactcg ctggccagcg 240
tccgggcaat ctgcccccga agttcaccgc ctgcggcgtc ggccaccttg acccatgcct 300
gatagttctt cgggctggtt tccactacca gggcaggctc ccggccctcg gctttcatgt 360
catccaggtc aaactcgctg aggtcgtcca ccagcaccag accatgccgc tcctgctcgg 420
cgggcctgat atacacgtca ttgccctggg cattcatccg cttgagccat ggcgtgttct 480
ggagcacttc ggcggctgac cattcccggt tcatcatctg gccggtgggt gcgtccctga 540
cgccgatatc gaagcgctca cagcccatgg ccttgagctg tcggcctatg gcctgcaaag 600
tcctgtcgtt cttcatcggg ccaccaagcg cagccagatc gagccgtcct cggttgtcag 660
tggcgtcagg tcgagcaaga gcaacgatgc gatcagcagc accaccgtag gcatcatgga 720
agccagcatc acggttagcc atagcttcca gtgccacccc cgcgacgcgc tccgggcgct 780
ctgcgcggcg ctgctcacct cggcggctac ctcccgcaac tctttggcca gctccaccca 840
tgccgcccct gtctggcgct gggctttcag ccactccgcc gcctgcgcct cgctggcctg 900
cttggtctgg ctcatgacct gccgggcttc gtcggccagt gtcgccatgc tctgggccag 960
cggttcgatc tgctccgcta actcgttgat gcctctggat ttcttcactc tgtcgattgc 1020
gttcatggtc tattgcctcc cggtattcct gtaagtcgat gatctgggcg ttggcggtgt 1080
cgatgttcag ggccacgtct gcccggtcgg tgcggatgcc ccggccttcc atctccacca 1140
cgttcggccc caggtgaaca ccgggcaggc gctcgatgcc ctgcgcctca agtgttctgt 1200

```
ggtcaatgcg ggcgtcgtgg ccagcccgct ctaatgcccg gttggcatgg tcggcccatg   1260
cctcgcgggt ctgctcaagc catgccttgg gcttgagcgc ttcggtcttc tgtgccccgc   1320
ccttctccgg ggtcttgccg ttgtaccgct tgaaccactg agcggcgggc cgctcgatgc   1380
cgtcattgat ccgctcggag atcatcaggt ggcagtgcgg gttctcgccg ccaccggcat   1440
ggatggccag cgtatacggc aggcgctcgg caccggtcag gtgctgggcg aactcggacg   1500
ccagcgcctt ctgctggtcg agggtcagct cgaccggcag ggcaaattcg acctccttga   1560
acagccgccc attggcgcgt tcatacaggt cggcagcatc ccagtagtcg gcgggccgct   1620
cgacgaactc cggcatgtgc ccggattcgg cgtgcaagac ttcatccatg tcgcgggcat   1680
acttgccttc gcgctggatg tagtcggcct tggccctggc cgattggccg cccgacctgc   1740
tgccggtttt cgccgtaagg tgataaatcg ccatgctgcc tcgctgttgc ttttgctttt   1800
cggctccatg caatggccct cggagagcgc accgcccgaa gggtggccgt taggccagtt   1860
tctcgaagag aaaccggtaa gtgcgccctc ccctacaaag tagggtcggg attgccgccg   1920
ctgtgcctcc atgatagcct acgagacagc acattaacaa tggggtgtca agatggttaa   1980
ggggagcaac aaggcggcgg atcggctggc caagctcgaa gaacaacgag cgcgaatcaa   2040
tgccgaaatt cagcgggagc gggcaaggga acagcagcaa gagcgcaaga acgaaacaag   2100
gcgcaaggtg ctggtggggg ccatgatttt ggccaaggtg aacagcagcg agtggccgga   2160
ggatcggctc atggcggcaa tggatgcgta ccttgaacgc gaccacgacc gcgccttgtt   2220
cggtctgccg ccacgccaga aggatgagcc gggctgaatg atcgaccgag acaggccctg   2280
cggggctgca cacgcgcccc caccccttcgg gtagggggaa aggccgctaa agcggctaaa   2340
agcgctccag cgtatttctg cggggtttgg tgtggggttt agcgggcttt gcccgccttt   2400
ccccctgccg cgcagcggtg ggcggtgtg tagcctagcg cagcgaatag accagctatc   2460
cggcctctgg ccgggcatat tgggcaaggg cagcagcgcc ccacaagggc gctgataacc   2520
gcgcctagtg gattattctt agataatcat ggatggattt ttccaacacc ccgccagccc   2580
ccgcccctgc tgggtttgca ggtttggggg cgtgacagtt attgcagggg ttcgtgacag   2640
ttattgcagg ggggcgtgac agttattgca ggggttcgtg acagttagta cgggagtgac   2700
gggcactggc tggcaatgtc tagcaacggc aggcatttcg gctgagggta aaagaacttt   2760
ccgctaagcg atagactgta tgtaaacaca gtattgcaag gacgcggaac atgcctcatg   2820
tggcggccag gacggccagc cgggatcggg atactggtcg ttaccagagc caccgacccg   2880
agcaaaccct tctctatcag atcgttgacg agtattaccc ggcattcgct gcgcttatgg   2940
cagagcaggg aaaggaattg ccgggctatg tgcaacggga atttgaagaa tttctccaat   3000
gcgggcggct ggagcatggc tttctacggg ttcgctgcga gtcttgccac gccgagcacc   3060
tggtcgcttt cagaaatcaa tctaaagtat atatgagtaa acttggtctg acaggcccct   3120
gaattcgcat ctagactgat gagacgtggt agagccacaa acagccggta caagcaacga   3180
tctccaggac catctgaatc atgcgcggat gacacgaact cacgacggcg atcacagaca   3240
ttaacccaca gtacagacac tgcgacaacg tggcaattcg tcgcaataca acgtaacggg   3300
cttcccatac aatcgattag agattgtcat cgcacctgat tgcccgacat tatcgcgagt   3360
tataacccat ttatacccat ataaatcagc atccatgttg gaatttaatc gcgtgagcct   3420
atgtaacggg cttcccatac aatcgattag agattgtcat cgcacctgat tgcccgacat   3480
tatcgcgagt tataacccat ttatacccat ataaatcagc atccatgttg gaatttaatc   3540
```

-continued

```
gcgtgagcca tccgtaatcg ttaatccgca aataacgtaa aaacccgctt cggcgggttt   3600
ttttatgggg ggagtttagg gaaagagcat ttgtcagctg gaaatctgct cgtcagtggt   3660
gctcacactg acgaatcatg tacagatcat accgatgact gcctggcgac tcacaactaa   3720
gcaagacagc cggaaccagc gccggcgaac accactgcat atatggcata tcacaacagt   3780
ccacgtctca agcagttaca gagatgttac gaaccactag tgcactgcag tacaccaggc   3840
atcaaataaa acgaaaggct cagtcgaaag actgggcctt tcgttttatc tgttgtttgt   3900
cggtgaacgc tctctactag agtcacactg gctcaccttc gggtgggcct ttctgcgttt   3960
ataccgagcg gccgcgtgtt acaaccaatt aaccaattct gattagaaaa actcatcgag   4020
catcaaatga aactgcaatt tattcatatc aggattatca ataccatatt tttgaaaaag   4080
ccgtttctgt aatgaaggag aaaactcacc gaggcagttc cataggatgg caagatcctg   4140
gtatcggtct gcgattccga ctcgtccaac atcaatacaa cctattaatt tcccctcgtc   4200
aaaaataagg ttatcaagtg agaaatcacc atgagtgacg actgaatccg gtgagaatgg   4260
caaaagctta tgcatttctt tccagacttg ttcaacaggc cagccattac gctcgtcatc   4320
aaaatcactc gcatcaacca aaccgttatt cattcgtgat tgcgcctgag cgaggcgaaa   4380
tacgcgatcg ctgttaaaag gacaattaca aacaggaatc gaatgcaacc ggcgcaggaa   4440
cactgccagc gcatcaacaa tattttcacc tgaatcagga tattcttcta atacctggaa   4500
tgctgttttc ccggggatcg cagtggtgag taaccatgca tcatcaggag tacggataaa   4560
atgcttgatg gtcggaagag gcataaattc cgtcagccag tttagtctga ccatctcatc   4620
tgtaacatca ttggcaacgc tacctttgcc atgtttcaga aacaactctg gcgcatcggg   4680
cttcccatac aatcgataga ttgtcgcacc tgattgcccg acattatcgc gagcccattt   4740
atacccatat aaatcagcat ccatgttgga atttaatcgc ggcctggagc aagacgtttc   4800
ccgttgaata tggctcataa caccccttgt attactgttt atgtaagcag acagttttat   4860
tgttcatgat gatatatttt tatcttgtgc aatgtaacat cagagatttt gagacacaac   4920
gtggctttgt tgaataaatc gaacttttgc tgagttgaag gatcagtcat gaccaaaatc   4980
ccttaacgtg agtcagcctg ccgccttggg ccgggtgatg tcgtacttgc ccgccgcgaa   5040
ctcggttacc gtccagccca gcgcgaccag ctccggcaac gcctcgcgca cccgcttgcg   5100
gcgcttgcgc atggtcgaac cactggcctc tgacggccag acatagccgc acaaggtatc   5160
tatggaagcc ttgccggttt tgccggggtc gatccagcca cacagccgct ggtgcagcag   5220
gcgggcggtt tcgctgtcca gcgcccgcac ctcgtccatg ctgatgcgca catgctggcc   5280
gccacccatg acggcctgcg cgatcaaggg gttcagggcc acgtacaggc gcccgtccgc   5340
ctcgtcgctg gcgtactccg acagcagccg aaacccctgc cgcttgcggc cattctgggc   5400
gatgatggat accttccaaa ggcgctcgat gcagtcctgt atgtgcttga gcgccccacc   5460
actatcgacc tctgccccga tttcctttgc cagcgcccga tagctacctt tgaccacatg   5520
gcattcagcg gtgacggcct cccacttggg ttccaggaac agccggagct gccgtccgcc   5580
ttcggtcttg ggttccgggc caagcactag gccattaggc ccagccatgg ccaccagccc   5640
ttgcaggatg cgcagatcat cagcgcccag cggctccggg ccgctgaact cgatccgctt   5700
gccgtcgccg tagtcatacg tcacgtccag cttgctgcgc ttgcgctcgc cccgcttgag   5760
ggcacggaac aggccggggg ccagacagtg cgccgggtcg tgccggacgt ggctgaggct   5820
gtgcttgttc ttaggcttca ccacggggca ccccccttgct cttgcgctgc ctctccagca   5880
cggcgggctt gagcaccccg ccgtcatgcc gcctgaacca ccgatcagcg aacggtgcgc   5940
```

```
catagttggc cttgctcaca ccgaagcgga cgaagaaccg gcgctggtcg tcgtccacac   6000

cccattcctc ggcctcggcg ctggtcatgc tcgacaggta ggactgccag cggatgttat   6060

cgaccagtac cgagctgccc cggctggcct gctgctggtc gcctgcgccc atcatggccg   6120

cgccccttgct ggcatggtgc aggaacacga tagagcaccc ggtatcggcg gcgatggcct   6180

ccatgcgacc gatgacctgg gccatggggc cgctggcgtt ttcttcctcg atgtggaacc   6240

ggcgcagcgt gtccagcacc atcaggcggc ggccctcggc ggcgcgcttg aggccgtcga   6300

accactccgg ggccatgatg ttgggcaggc tgccgatcag cggctggatc agcaggccgt   6360

cagccacggc ttgccgttcc tcggcgctga ggtgcgcccc aagggcgtgc aggcggtgat   6420

gaatggcggt gggcgggtct tcggcgggca ggtagatcac cgggccggtg ggcagttcgc   6480

ccacctccag cagatccggc ccgcctgcaa tctgtgcggc cagttgcagg gccagcatgg   6540

atttaccggc accaccgggc gacaccagcg ccccgaccgt accggccacc atgttgggca   6600

aaacgtagtc cagcggtggc ggcgctgctg cgaacgcctc cagaatattg ataggcttat   6660

gggtagccat tgattgcctc ctttgcaggc agttggtggt taggcgctgg cggggtcact   6720

acccccgccc tgcgccgctc tgagttcttc caggcactcg cgcagcgcct cgtattcgtc   6780

gtcggtcagc cagaacttgc gctgacgcat ccctttggcc ttcatgcgct cggcatatcg   6840

cgcttggcgt acagcgtcag ggctggccag caggtcgccg gtctgcttgt ccttttggtc   6900

tttcatatca gtcaccgaga aacttgccgg ggccgaaagg cttgtcttcg cggaacaagg   6960

acaaggtgca gccgtcaagg ttaaggctgg ccatatcagc gactgaaaag cggccagcct   7020

cggccttgtt tgacgtataa ccaaagccac cgggcaacca atagcccttg tcacttttga   7080

tcaggtagac cgaccctgaa gcgctttttt cgtattccat aaaacccccct tctgtgcgtg   7140

agtactcata gtataacagg cgtgagtacc aacgcaagca ctacatgctg aaatctggcc   7200

cgcccctgtc catgcctcgc tggcggggtg ccggtgcccg tgccagctcg gcccgcgcaa   7260

gctggacgct gggcagaccc atgaccttgc tgacggtgcg ctcgatgtaa tccgcttcgt   7320

ggccgggctt gcgctctgcc agcgctgggc tggcctcggc catggccttg ccgatttcct   7380

cggcactgcg gccccggctg gccagcttct gcgcggcgat aaagtcgcac ttgctgaggt   7440

catgaccgaa gcgcttgacc agcccggcca tctcgctgcg gtactcgtcc agcgccgtgc   7500

gccggtggcg gctaagctgc cgctcgggca gttcga                             7536
```

<210> SEQ ID NO 73
<211> LENGTH: 7439
<212> TYPE: DNA
<213> ORGANISM: Artificial Sequence
<220> FEATURE:
<223> OTHER INFORMATION: Chemically Synthesized, pBTK527alpha

<400> SEQUENCE: 73

```
ggggccgaaa ggcttgtctt cgcggaacaa ggacaaggtg cagccgtcaa ggttaaggct     60

ggccatatca gcgactgaaa agcggccagc ctcggccttg tttgacgtat aaccaaagcc    120

accgggcaac caatagccct tgtcactttt gatcaggtag accgaccctg aagcgctttt    180

ttcgtattcc ataaaacccc cttctgtgcg tgagtactca tagtataaca ggcgtgagta    240

ccaacgcaag cactacatgc tgaaatctgg cccgcccctg tccatgcctc gctggcgggg    300

tgccggtgcc cgtgccagct cggcccgcgc aagctggacg ctgggcagac ccatgacctt    360

gctgacggtg cgctcgatgt aatccgcttc gtggccgggc ttgcgctctg ccagcgctgg    420
```

-continued

```
gctggcctcg gccatggcct tgccgatttc ctcggcactg cggccccggc tggccagctt    480
ctgcgcggcg ataaagtcgc acttgctgag gtcatgaccg aagcgcttga ccagcccggc    540
catctcgctg cggtactcgt ccagcgccgt gcgccggtgg cggctaagct gccgctcggg    600
cagttcgagg ctggccagcc tgcgggcctt ctcctgctgc cgctgggcct gctcgatctg    660
ctggccagcc tgctgcacca gcgccgggcc agcggtggcg gtcttgccct tggattcacg    720
cagcagcacc cacggctgat aaccggcgcg ggtggtgtgc ttgtccttgc ggttggtgaa    780
gcccgccaag cggccatagt ggcggctgtc ggcgctggcc gggtcggcgt cgtactcgct    840
ggccagcgtc cgggcaatct gcccccgaag ttcaccgcct gcggcgtcgg ccaccttgac    900
ccatgcctga tagttcttcg ggctggtttc cactaccagg gcaggctccc ggccctcggc    960
tttcatgtca tccaggtcaa actcgctgag gtcgtccacc agcaccagac catgccgctc   1020
ctgctcggcg ggcctgatat acacgtcatt gccctgggca ttcatccgct tgagccatgg   1080
cgtgttctgg agcacttcgg cggctgacca ttcccggttc atcatctggc cggtgggtgc   1140
gtccctgacg ccgatatcga agcgctcaca gcccatggcc ttgagctgtc ggcctatggc   1200
ctgcaaagtc ctgtcgttct tcatcgggcc accaagcgca gccagatcga gccgtcctcg   1260
gttgtcagtg gcgtcaggtc gagcaagagc aacgatgcga tcagcagcac caccgtaggc   1320
atcatggaag ccagcatcac ggttagccat agcttccagt gccacccccg cgacgcgctc   1380
cgggcgctct gcgcggcgct gctcacctcg gcggctacct cccgcaactc tttggccagc   1440
tccacccatg ccgcccctgt ctggcgctgg gctttcagcc actccgccgc ctgcgcctcg   1500
ctggcctgct tggtctggct catgacctgc cgggcttcgt cggccagtgt cgccatgctc   1560
tgggccagcg gttcgatctg ctccgctaac tcgttgatgc ctctggattt cttcactctg   1620
tcgattgcgt tcatggtcta ttgcctcccg gtattcctgt aagtcgatga tctgggcgtt   1680
ggcggtgtcg atgttcaggg ccacgtctgc ccggtcggtg cggatgcccc ggccttccat   1740
ctccaccacg ttcggcccca ggtgaacacc gggcaggcgc tcgatgccct gcgcctcaag   1800
tgttctgtgg tcaatgcggg cgtcgtggcc agcccgctct aatgcccggt tggcatggtc   1860
ggcccatgcc tcgcgggtct gctcaagcca tgccttgggc ttgagcgctt cggtcttctg   1920
tgccccgccc ttctccgggg tcttgccgtt gtaccgcttg aaccactgag cggcgggccg   1980
ctcgatgccg tcattgatcc gctcggagat catcaggtgg cagtgcgggt tctcgccgcc   2040
accggcatgg atggccagcg tatacggcag gcgctcggca ccggtcaggt gctgggcgaa   2100
ctcggacgcc agcgccttct gctggtcgag ggtcagctcg accggcaggg caaattcgac   2160
ctccttgaac agccgcccat tggcgcgttc atacaggtcg gcagcatccc agtagtcggc   2220
gggccgctcg acgaactccg gcatgtgccc ggattcggcg tgcaagactt catccatgtc   2280
gcgggcatac ttgccttcgc gctggatgta gtcggccttg gccctggccg attggccgcc   2340
cgacctgctg ccggttttcg ccgtaaggtg ataaatcgcc atgctgcctc gctgttgctt   2400
ttgcttttcg gctccatgca atggccctcg gagagcgcac cgcccgaagg gtggccgtta   2460
ggccagtttc tcgaagagaa accggtaagt gcgccctccc ctacaaagta gggtcgggat   2520
tgccgccgct gtgcctccat gatagcctac gagacagcac attaacaatg gggtgtcaag   2580
atggttaagg ggagcaacaa ggcggcggat cggctggcca agctcgaaga acaacgagcg   2640
cgaatcaatg ccgaaattca gcgggagcgg gcaagggaac agcagcaaga gcgcaagaac   2700
gaaacaaggc gcaaggtgct ggtgggggcc atgattttgg ccaaggtgaa cagcagcgag   2760
tggccggagg atcggctcat ggcggcaatg gatgcgtacc ttgaacgcga ccacgaccgc   2820
```

```
gccttgttcg gtctgccgcc acgccagaag gatgagccgg gctgaatgat cgaccgagac   2880
aggccctgcg gggctgcaca cgcgccccca cccttcgggt agggggaaag gccgctaaag   2940
cggctaaaag cgctccagcg tatttctgcg ggtttggtg tggggtttag cgggctttgc   3000
ccgcctttcc ccctgccgcg cagcggtggg gcggtgtgta gcctagcgca gcgaatagac   3060
cagctatccg gcctctggcc gggcatattg ggcaagggca gcagcgcccc acaagggcgc   3120
tgataaccgc gcctagtgga ttattcttag ataatcatgg atggattttt ccaacacccc   3180
gccagccccc gcccctgctg ggtttgcagg tttgggggcg tgacagttat tgcaggggtt   3240
cgtgacagtt attgcagggg ggcgtgacag ttattgcagg ggttcgtgac agttagtacg   3300
ggagtgacgg gcactggctg gcaatgtcta gcaacggcag gcatttcggc tgagggtaaa   3360
agaactttcc gctaagcgat agactgtatg taaacacagt attgcaagga cgcggaacat   3420
gcctcatgtg gcggccagga cggccagccg ggatcgggat actggtcgtt accagagcca   3480
ccgacccgag caaacccttc tctatcagat cgttgacgag tattacccgg cattcgctgc   3540
gcttatggca gagcagggaa aggaattgcc gggctatgtg caacgggaat ttgaagaatt   3600
tctccaatgc gggcggctgg agcatggctt tctacgggtt cgctgcgagt cttgccacgc   3660
cgagcacctg gtcgctttca gaaatcaatc taaagtatat atgagtaaac ttggtctgac   3720
aggcccctga attcgcatct agactgatga gacgtggtag agccacaaac agccggtaca   3780
agcaacgatc tccaggacca tctgaatcat gcgcggatga cacgaactca cgacggcgat   3840
cacagacatt aacccacagt acagacactg cgacaacgtg gcaattcgtc gcaatacaac   3900
gtaacgggct tcccatacaa tcgattagag attgtcatcg cacctgattg cccgacatta   3960
tcgcgagtta taacccattt atacccatat aaatcagcat ccatgttgga atttaatcgc   4020
gtgagcctat gtaacgggct tcccatacaa tcgattagag attgtcatcg cacctgattg   4080
cccgacatta tcgcgagtta taacccattt atacccatat aaatcagcat ccatgttgga   4140
atttaatcgc gtgagccatc cgtaatcgtt aatccgcaaa taacgtaaaa acccgcttcg   4200
gcgggttttt ttatgggggg agtttaggga aagagcattt gtcagctgcg tctcaagcag   4260
ttacagagat gttacgaacc cccaggacat ccgagaatgc gaggcgatgg agggtacaac   4320
ccgagcggcc gcttatttgc cgactacctt ggtgatctcg cctttcacgt agtggacaaa   4380
ttcttccaac tgatctgcgc gcgaggccaa gcgatcttct tcttgtccaa gataagcctg   4440
tctagcttca agtatgacgg gctgatactg ggccggcagg cgctccattg cccagtcggc   4500
agcgacatcc ttcggcgcga ttttgccggt tactgcgctg taccaaatgc gggacaacgt   4560
aagcactaca tttcgctcat cgccagccca gtcgggcggc gagttccata gcgttaaggt   4620
ttcatttagc gcctcaaata gatcctgttc aggaaccgga tcaaagagtt cctccgccgc   4680
tggacctacc aaggcaacgc tatgttctct tgcttttgtc agcaagatag ccagatcaat   4740
gtcgatcgtg gctggctcga agatacccgc aagaatgtca ttgcgctgcc attctccaaa   4800
ttgcagttcg cgcttagctg gataacgcca cggaatgatg tcgtcgtgca caacaatggt   4860
gacttctaca gcgcggagaa tctcgctctc tccaggggaa gccgaagttt ccaaaaggtc   4920
gttgatcaaa gctcgccgcg ttgtttcatc aagccttacg gtcaccgtaa ccagcaaatc   4980
aatatcactg tgtggcttca ggccgccatc cactgcggag ccgtacaaat gtacggccag   5040
caacgtcggt tcgagatggc gctcgatgac gccaactacc tctgatagtt gagtcgatac   5100
ttcggcgatc accgcttccc tcataatgtt taactttgtt ttagggcgac tgccctgctg   5160
```

```
cgtaacatcg ttgctgctcc ataacatcaa acatcgaccc acggcgtaac gcgcttgctg   5220
cttggatgcc cgaggcatag actgtacccc aaaaaaacag tcataacaag ccatgaaaac   5280
cgccactgcg ccgttaccac cgctgcgttc ggtcaaggtt ctggaccagt tgcgtgagcg   5340
catacgctac ttgcattaca gcttacgaac cgaacaggct tatgtccact gggttcgtgc   5400
cttcatccgt ttccacggtg tgcgtcaccc ggcaaccttg ggtagcagcg aagtcgaggc   5460
atttctgtcc tggctggtca tgaccaaaat cccttaacgt gagtcagcct gccgccttgg   5520
gccgggtgat gtcgtacttg cccgccgcga actcggttac cgtccagccc agcgcgacca   5580
gctccggcaa cgcctcgcgc acccgcttgc ggcgcttgcg catggtcgaa ccactggcct   5640
ctgacggcca gacatagccg cacaaggtat ctatggaagc cttgccggtt ttgccggggt   5700
cgatccagcc acacagccgc tggtgcagca ggcgggcggt ttcgctgtcc agcgcccgca   5760
cctcgtccat gctgatgcgc acatgctggc cgccacccat gacggcctgc gcgatcaagg   5820
ggttcagggc cacgtacagg cgcccgtccg cctcgtcgct ggcgtactcc gacagcagcc   5880
gaaacccctg ccgcttgcgg ccattctggg cgatgatgga taccttccaa aggcgctcga   5940
tgcagtcctg tatgtgcttg agcgccccac cactatcgac ctctgccccg atttcctttg   6000
ccagcgcccg atagctacct ttgaccacat ggcattcagc ggtgacggcc tcccacttgg   6060
gttccaggaa cagccggagc tgccgtccgc cttcggtctt gggttccggg ccaagcacta   6120
ggccattagg cccagccatg gccaccagcc cttgcaggat gcgcagatca tcagcgccca   6180
gcggctccgg gccgctgaac tcgatccgct tgccgtcgcc gtagtcatac gtcacgtcca   6240
gcttgctgcg cttgcgctcg ccccgcttga gggcacggaa caggccgggg gccagacagt   6300
gcgccgggtc gtgccggacg tggctgaggc tgtgcttgtt cttaggcttc accacggggc   6360
accccccttgc tcttgcgctg cctctccagc acggcgggct tgagcacccc gccgtcatgc   6420
cgcctgaacc accgatcagc gaacggtgcg ccatagttgg ccttgctcac accgaagcgg   6480
acgaagaacc ggcgctggtc gtcgtccaca ccccattcct cggcctcggc gctggtcatg   6540
ctcgacaggt aggactgcca gcggatgtta tcgaccagta ccgagctgcc ccggctggcc   6600
tgctgctggt cgcctgcgcc catcatggcc gcgcccttgc tggcatggtg caggaacacg   6660
atagagcacc cggtatcggc ggcgatggcc tccatgcgac cgatgacctg ggccatgggg   6720
ccgctggcgt ttcttcctcc gatgtggaac cggcgcagcg tgtccagcac catcaggcgg   6780
cggccctcgg cggcgcgctt gaggccgtcg aaccactccg gggccatgat gttgggcagg   6840
ctgccgatca gcggctggat cagcaggccg tcagccacgg cttgccgttc ctcggcgctg   6900
aggtgcgccc caagggcgtg caggcggtga tgaatggcgg tgggcgggtc ttcggcgggc   6960
aggtagatca ccgggccggt gggcagttcg cccacctcca gcagatccgg cccgcctgca   7020
atctgtgcgg ccagttgcag ggccagcatg gatttaccgg caccaccggg cgacaccagc   7080
gccccgaccg taccggccac catgttgggc aaaacgtagt ccagcggtgg cggcgctgct   7140
gcgaacgcct ccagaatatt gataggctta tgggtagcca ttgattgcct cctttgcagg   7200
cagttggtgg ttaggcgctg gcggggtcac taccccccgcc ctgcgccgct ctgagttctt   7260
ccaggcactc gcgcagcgcc tcgtattcgt cgtcggtcag ccagaacttg cgctgacgca   7320
tccctttggc cttcatgcgc tcggcatatc gcgcttggcg tacagcgtca gggctggcca   7380
gcaggtcgcc ggtctgcttg tccttttggt ctttcatatc agtcaccgag aaacttgcc    7439
```

<210> SEQ ID NO 74
<211> LENGTH: 3384

<212> TYPE: DNA
<213> ORGANISM: Artificial Sequence
<220> FEATURE:
<223> OTHER INFORMATION: Chemically Synthesized, pBTK599s

<400> SEQUENCE: 74

```
ccgaaaagtg ccacctgcct gatgagacga tgaaagtgaa acgtgatttc atgcgtcatt     60
ttgaacattt tgtaaatctt atttaataat gtgtgcggca attcacattt aatttatgaa    120
tgttttctta acatcgcggc aactcaagaa acggcaggtt cggatcttag ctactagaga    180
aagaggagaa atactagatg cgtaaaggcg aagagctgtt cactggtgtc gtccctattc    240
tggtggaact ggatggtgat gtcaacggtc ataagttttc cgtgcgtggc gagggtgaag    300
gtgacgcaac taatggtaaa ctgacgctga agttcatctg tactactggt aaactgccgg    360
ttccttggcc gactctggta acgacgctga cttatggtgt tcagtgcttt gctcgttatc    420
cggaccatat gaagcagcat gacttcttca agtccgccat gccggaaggc tatgtgcagg    480
aacgcacgat ttcctttaag gatgacggca cgtacaaaac gcgtgcggaa gtgaaatttg    540
aaggcgatac cctggtaaac cgcattgagc tgaaaggcat tgactttaaa gaggacggca    600
atatcctggg ccataagctg gaatacaatt ttaacagcca caatgtttac atcaccgccg    660
ataaacaaaa aaatggcatt aaagcgaatt ttaaaattcg ccacaacgtg gaggatggca    720
gcgtgcagct ggctgatcac taccagcaaa acactccaat cggtgatggt cctgttctgc    780
tgccagacaa tcactatctg agcacgcaaa gcgttctgtc taaagatccg aacgagaaac    840
gcgatcatat ggttctgctg gagttcgtaa ccgcagcggg catcacgcat ggtatggatg    900
aactgtacaa atgaccaggc atcaaataaa acgaaaggct cagtcgaaag actgggcctt    960
tcgttttatc tgttgtttgt cggtgaacgc tctctactag agtcacactg gctcaccttc   1020
gggtgggcct ttctgcgttt ataagtccgt ctcaagcaag gggatcaat  tccgtgatag   1080
gtgggctgcc cttcctggtt ggcttggttt catcagccat ccgcttgccc tcatctgtta   1140
cgccggcggt agccggccag cctcgcagag caggattccc gttgagcacc gccaggtgcg   1200
aataagggac agtgaagaag gaacacccgc tcgcgggtgg gcctacttca cctatcctgc   1260
ccggctgacg ccgttggata caccaaggaa agtctacacg aaccctttgg caaaatcctg   1320
tatatcgtgc gaaaaaggat ggatataccg aaaaaatcgc tataatgacc ccgaagcagg   1380
gttatgcagc ggaaaacgga attgatccgg ccacgatgcg tccggcgtag aggatctgaa   1440
gatcagcagt tcaacctgtt gatagtacgt actaagctct catgtttcac gtactaagct   1500
ctcatgttta acgtactaag ctctcatgtt taacgaacta aaccctcatg gctaacgtac   1560
taagctctca tggctaacgt actaagctct catgtttcac gtactaagct ctcatgtttg   1620
aacaataaaa ttaatataaa tcagcaactt aaatagcctc taaggtttta agttttataa   1680
gaaaaaaaag aatatataag gcttttaaag cttttaaggt ttaacggttg tggacaacaa   1740
gccagggatg taacgcactg agaagccctt agagcctctc aaagcaattt tgagtgacac   1800
aggaacactt aacggctgac atgggaattc ccctccaccg cggtggcggc cgctctagaa   1860
ctagtggatc ccccgggctg caggaattcg atatcaagct tatcgatacc gtcgacctcg   1920
aggggggggcc cggtaccgag gacgcgtcga attaattccg ctagcttcac gctgccgcaa   1980
gcactcaggg cgcaagggct gctaaaggaa gcggaacacg tagaaagcca gtccgcagaa   2040
acggtgctga ccccggatga atgtcagcta ctgggctatc tggacaaggg aaaacgcaag   2100
cgcaaagaga aagcaggtag cttgcagtgg gattatcaaa aaggatcttc acctagatcc   2160
```

```
ttttaaatta aaaatgaagt tttaaatcaa tctaaagtat atatgagtaa acttggtctg   2220

acagttaccg agcggccgct tatttgccga ctaccttggt gatctcgcct ttcacgtagt   2280

ggacaaattc ttccaactga tctgcgcgcg aggccaagcg atcttcttct tgtccaagat   2340

aagcctgtct agcttcaagt atgacgggct gatactgggc cggcaggcgc tccattgccc   2400

agtcggcagc gacatccttc ggcgcgattt tgccggttac tgcgctgtac caaatgcggg   2460

acaacgtaag cactacattt cgctcatcgc cagcccagtc gggcggcgag ttccatagcg   2520

ttaaggtttc atttagcgcc tcaaatagat cctgttcagg aaccggatca aagagttcct   2580

ccgccgctgg acctaccaag gcaacgctat gttctcttgc ttttgtcagc aagatagcca   2640

gatcaatgtc gatcgtggct ggctcgaaga tacccgcaag aatgtcattg cgctgccatt   2700

ctccaaattg cagttcgcgc ttagctggat aacgccacgg aatgatgtcg tcgtgcacaa   2760

caatggtgac ttctacagcg cggagaatct cgctctctcc aggggaagcc gaagtttcca   2820

aaaggtcgtt gatcaaagct cgccgcgttg tttcatcaag ccttacggtc accgtaacca   2880

gcaaatcaat atcactgtgt ggcttcaggc cgccatccac tgcggagccg tacaaatgta   2940

cggccagcaa cgtcggttcg agatggcgct cgatgacgcc aactacctct gatagttgag   3000

tcgatacttc ggcgatcacc gcttccctca taatgtttaa ctttgtttta gggcgactgc   3060

cctgctgcgt aacatcgttg ctgctccata acatcaaaca tcgacccacg gcgtaacgcg   3120

cttgctgctt ggatgcccga ggcatagact gtaccccaaa aaaacagtca taacaagcca   3180

tgaaaaccgc cactgcgccg ttaccaccgc tgcgttcggt caaggttctg gaccagttgc   3240

gtgagcgcat acgctacttg cattacagct tacgaaccga acaggcttat gtccactggg   3300

ttcgtgcctt catccgtttc cacggtgtgc gtcacccggc aaccttgggt agcagcgaag   3360

tcgaggcatt tctgtcctgg ctgg                                          3384
```

<210> SEQ ID NO 75
<211> LENGTH: 8801
<212> TYPE: DNA
<213> ORGANISM: Artificial Sequence
<220> FEATURE:
<223> OTHER INFORMATION: Chemically Synthesized, pBTK501

<400> SEQUENCE: 75

```
actcttcctt tttcaatatt attgaagcat ttatcagggt tattgtctca tgagcggata     60

catatttgaa tgtatttaga aaaataaaca aataggggtt ccgcgcacat ttccccgaaa    120

agtgccacct gtcatgacca aaatccctta acgtgagtca gcctgccgcc ttgggccggg    180

tgatgtcgta cttgcccgcc gcgaactcgg ttaccgtcca gcccagcgcg accagctccg    240

gcaacgcctc gcgcacccgc ttgcggcgct tgcgcatggt cgaaccactg gcctctgacg    300

gccagacata gccgcacaag gtatctatgg aagccttgcc ggttttgccg gggtcgatcc    360

agccacacag ccgctggtgc agcaggcggg cggtttcgct gtccagcgcc cgcacctcgt    420

ccatgctgat gcgcacatgc tggccgccac ccatgacggc ctgcgcgatc aaggggttca    480

gggccacgta caggcgcccg tccgcctcgt cgctggcgta ctccgacagc agccgaaacc    540

cctgccgctt gcggccattc tgggcgatga tggatacctt ccaaaggcgc tcgatgcagt    600

cctgtatgtg cttgagcgcc ccaccactat cgacctctgc ccgatttcc tttgccagcg     660

cccgatagct acctttgacc acatggcatt cagcggtgac ggcctcccac ttgggttcca    720

ggaacagccg gagctgccgt ccgccttcgg tcttgggttc cgggccaagc actaggccat    780

taggcccagc catggccacc agcccttgca ggatgcgcag atcatcagcg cccagcggct    840
```

```
ccgggccgct gaactcgatc cgcttgccgt cgccgtagtc atacgtcacg tccagcttgc    900
tgcgcttgcg ctcgccccgc ttgagggcac ggaacaggcc gggggccaga cagtgcgccg    960
ggtcgtgccg gacgtggctg aggctgtgct tgttcttagg cttcaccacg gggcaccccc   1020
ttgctcttgc gctgcctctc cagcacggcg ggcttgagca ccccgccgtc atgccgcctg   1080
aaccaccgat cagcgaacgg tgcgccatag ttggccttgc tcacaccgaa gcggacgaag   1140
aaccggcgct ggtcgtcgtc cacaccccat tcctcggcct cggcgctggt catgctcgac   1200
aggtaggact gccagcggat gttatcgacc agtaccgagc tgccccggct ggcctgctgc   1260
tggtcgcctg cgcccatcat ggccgcgccc ttgctggcat ggtgcaggaa cacgatagag   1320
cacccggtat cggcggcgat ggcctccatg cgaccgatga cctgggccat ggggccgctg   1380
gcgttttctt cctcgatgtg gaaccggcgc agcgtgtcca gcaccatcag gcggcggccc   1440
tcggcggcgc gcttgaggcc gtcgaaccac tccggggcca tgatgttggg caggctgccg   1500
atcagcggct ggatcagcag gccgtcagcc acggcttgcc gttcctcggc gctgaggtgc   1560
gccccaaggg cgtgcaggcg gtgatgaatg gcggtgggcg ggtcttcggc gggcaggtag   1620
atcaccgggc cggtgggcag ttcgcccacc tccagcagat ccggcccgcc tgcaatctgt   1680
gcggccagtt gcagggccag catggattta ccggcaccac cgggcgacac cagcgccccg   1740
accgtaccgg ccaccatgtt gggcaaaacg tagtccagcg gtggcggcgc tgctgcgaac   1800
gcctccagaa tattgatagg cttatgggta gccattgatt gcctcctttg caggcagttg   1860
gtggttaggc gctggcgggg tcactacccc cgccctgcgc cgctctgagt tcttccaggc   1920
actcgcgcag cgcctcgtat tcgtcgtcgg tcagccagaa cttgcgctga cgcatccctt   1980
tggccttcat gcgctcggca tatcgcgctt ggcgtacagc gtcagggctg gccagcaggt   2040
cgccggtctg cttgtccttt tggtctttca tatcagtcac cgagaaactt gccggggccg   2100
aaaggcttgt cttcgcggaa caaggacaag gtgcagccgt caaggttaag gctggccata   2160
tcagcgactg aaaagcggcc agcctcggcc ttgtttgacg tataaccaaa gccaccgggc   2220
aaccaatagc ccttgtcact tttgatcagg tagaccgacc ctgaagcgct tttttcgtat   2280
tccataaaac cccctttctgt gcgtgagtac tcatagtata acaggcgtga gtaccaacgc   2340
aagcactaca tgctgaaatc tggcccgccc ctgtccatgc ctcgctggcg gggtgccggt   2400
gcccgtgcca gctcggcccg cgcaagctgg acgctgggca gacccatgac cttgctgacg   2460
gtgcgctcga tgtaatccgc ttcgtggccg ggcttgcgct ctgccagcgc tgggctggcc   2520
tcggccatgg ccttgccgat ttcctcggca ctgcggcccc ggctggccag cttctgcgcg   2580
gcgataaagt cgcacttgct gaggtcatga ccgaagcgct tgaccagccc ggccatctcg   2640
ctgcggtact cgtccagcgc cgtgcgccgg tggcggctaa gctgccgctc gggcagttcg   2700
aggctggcca gcctgcgggc cttctcctgc tgccgctggg cctgctcgat ctgctggcca   2760
gcctgctgca ccagcgccgg gccagcggtg gcggtcttgc ccttggattc acgcagcagc   2820
acccacggct gataaccggc gcgggtggtg tgcttgtcct tgcggttggt gaagcccgcc   2880
aagcggccat agtggcggct gtcggcgctg gccgggtcgg cgtcgtactc gctggccagc   2940
gtccgggcaa tctgccccccg aagttcaccg cctgcggcgt cggccacctt gacccatgcc   3000
tgatagttct tcgggctggt ttccactacc agggcaggct cccggccctc ggctttcatg   3060
tcatccaggt caaactcgct gaggtcgtcc accagcacca gaccatgccg ctcctgctcg   3120
gcgggcctga tatacacgtc attgccctgg gcattcatcc gcttgagcca tggcgtgttc   3180
```

-continued

```
tggagcactt cggcggctga ccattcccgg ttcatcatct ggccggtggg tgcgtccctg   3240
acgccgatat cgaagcgctc acagcccatg gccttgagct gtcggcctat ggcctgcaaa   3300
gtcctgtcgt tcttcatcgg gccaccaagc gcagccagat cgagccgtcc tcggttgtca   3360
gtggcgtcag gtcgagcaag agcaacgatg cgatcagcag caccaccgta ggcatcatgg   3420
aagccagcat cacggttagc catagcttcc agtgccaccc ccgcgacgcg ctccgggcgc   3480
tctgcgcggc gctgctcacc tcggcggcta cctcccgcaa ctctttggcc agctccaccc   3540
atgccgcccc tgtctggcgc tgggctttca gccactccgc cgcctgcgcc tcgctggcct   3600
gcttggtctg gctcatgacc tgccgggctt cgtcggccag tgtcgccatg ctctgggcca   3660
gcggttcgat ctgctccgct aactcgttga tgcctctgga tttcttcact ctgtcgattg   3720
cgttcatggt ctattgcctc ccggtattcc tgtaagtcga tgatctgggc gttggcggtg   3780
tcgatgttca gggccacgtc tgcccggtcg gtgcggatgc cccggccttc catctccacc   3840
acgttcggcc ccaggtgaac accgggcagg cgctcgatgc cctgcgcctc aagtgttctg   3900
tggtcaatgc gggcgtcgtg gccagcccgc tctaatgccc ggttggcatg gtcggcccat   3960
gcctcgcggg tctgctcaag ccatgccttg ggcttgagcg cttcggtctt ctgtgccccg   4020
cccttctccg ggtcttgccg gttgtaccgc ttgaaccact gagcggcggg ccgctcgatg   4080
ccgtcattga tccgctcgga gatcatcagg tggcagtgcg ggttctcgcc gccaccggca   4140
tggatggcca gcgtatacgg caggcgctcg gcaccggtca ggtgctgggc gaactcggac   4200
gccagcgcct tctgctggtc gagggtcagc tcgaccggca gggcaaattc gacctccttg   4260
aacagccgcc cattggcgcg ttcatacagg tcggcagcat cccagtagtc ggcgggccgc   4320
tcgacgaact ccggcatgtg cccggattcg gcgtgcaaga cttcatccat gtcgcgggca   4380
tacttgcctt cgcgctggat gtagtcggcc ttggccctgg ccgattggcc gcccgacctg   4440
ctgccggttt tcgccgtaag gtgataaatc gccatgctgc ctcgctgttg cttttgcttt   4500
tcggctccat gcaatggccc tcggagagcg caccgcccga agggtggccg ttaggccagt   4560
ttctcgaaga gaaaccggta agtgcgccct cccctacaaa gtagggtcgg gattgccgcc   4620
gctgtgcctc catgatagcc tacgagacag cacattaaca atggggtgtc aagatggtta   4680
aggggagcaa caaggcggcg gatcggctgg ccaagctcga agaacaacga gcgcgaatca   4740
atgccgaaat tcagcgggag cgggcaaggg aacagcagca agagcgcaag aacgaaacaa   4800
ggcgcaaggt gctggtgggg gccatgattt tggccaaggt gaacagcagc gagtggccgg   4860
aggatcggct catggcggca atggatgcgt accttgaacg cgaccacgac cgcgccttgt   4920
tcggtctgcc gccacgccag aaggatgagc cgggctgaat gatcgaccga gacaggccct   4980
gcggggctgc acacgcgccc ccacccttcg ggtaggggga aaggccgcta aagcggctaa   5040
aagcgctcca gcgtatttct gcggggtttg gtgtggggtt tagcgggctt tgcccgcctt   5100
tccccctgcc gcgcagcggt ggggcggtgt gtagcctagc gcagcgaata gaccagctat   5160
ccggcctctg gccgggcata ttgggcaagg gcagcagcgc cccacaaggg cgctgataac   5220
cgcgcctagt ggattattct tagataatca tggatggatt tttccaacac cccgccagcc   5280
cccgcccctg ctgggtttgc aggtttgggg gcgtgacagt tattgcaggg gttcgtgaca   5340
gttattgcag gggggcgtga cagttattgc aggggttcgt gacagttagt acgggagtga   5400
cgggcactgg ctggcaatgt ctagcaacgg caggcatttc ggctgagggt aaaagaactt   5460
tccgctaagc gatagactgt atgtaaacac agtattgcaa ggacgcggaa catgcctcat   5520
gtggcggcca ggacggccag ccgggatcgg gatactggtc gttaccagag ccaccgaccc   5580
```

```
gagcaaaccc ttctctatca gatcgttgac gagtattacc cggcattcgc tgcgcttatg   5640
gcagagcagg gaaaggaatt gccgggctat gtgcaacggg aatttgaaga atttctccaa   5700
tgcgggcggc tggagcatgg ctttctacgg gttcgctgcg agtcttgcca cgccgagcac   5760
ctggtcgctt tcagaaatca atctaaagta tatatgagta aacttggtct gacaggcccc   5820
tgaattcgca tctagactga tgagacgtgg tagagccaca aacagccggt acaagcaacg   5880
atctccagga ccatctgaat catgcgcgga tgacacgaac tcacgacggc gatcacagac   5940
attaacccac agtacagaca ctgcgacaac gtggcaattc gtcgcaatac aacgttatca   6000
aaaagagtat tgacttaaag tctaacctat aggatactta cagccatcga gagggacacg   6060
gcgaatacag aaacagagga gatattacat atgagtaaag gagaagagct tttcacagga   6120
gttgtcccaa tcctcgtgga attagacggt gatgttaatg ggcacaagtt ctctgtcagt   6180
ggagagggtg aaggcgacgc aacatatggc aagctgaccc ttaaatttat ttgcaccacg   6240
ggtaaactac ctgttccatg gccaacactg gtcactacgt tcgggtatgg ggttcagtgc   6300
tttgcgcgct acccagatca catgaaacag cacgactttt tcaagagtgc aatgcccgaa   6360
ggctatgtac aggagagaac catctttttt aaggatgacg gcaactataa gacacgcgcc   6420
gaagtgaagt tcgagggtga tacccttgtt aatagaatcg agttaaaggg tattgacttt   6480
aaggaagatg gaaatatttt aggccacaaa ctggaatata actataactc ccataatgtg   6540
tacattatgg ccgacaagca aaagaacggt atcaaggtta acttcaagat cagacacaac   6600
attgaggatg gaagcgttca actagccgac cattaccaac aaaacacccc aattggcgat   6660
gggcctgtgc tgttaccaga caaccattac ctgtccactc aatctgccct ttcgaaagat   6720
cccaacgaaa agcgcgacca catggtcctt cttgagtttg tcacggctgc tgggattaca   6780
cacggcatgg atgaactata caaataaatc cgtaatcgtt aatccgcaaa taacgtaaaa   6840
acccgcttcg gcgggttttt ttatgggggg agtttaggga aagagcattt gtcagctgga   6900
aatctgctcg tcagtggtgc tcacactgac gaatcatgta cagatcatac cgatgactgc   6960
ctggcgactc acaactaagc aagacagccg gaaccagcgc cggcgaacac cactgcatat   7020
atggcatatc acaacagtcc acgtctcaag cagttacaga gatgttacga accactagtg   7080
cactgcagta cacaaaaaac ccctcaagac ccgtttagag gccccaaggg gttatgctaa   7140
tgctgcttta agacccactt tcacatttaa gttgtttttc taatccgcat atgatcaatt   7200
caaggccgaa taagaaggct ggctctgcac cttggtgatc aaataattcg atagcttgtc   7260
gtaataatgg cggcatacta tcagtagtag gtgtttccct ttcttcttta gcgacttgat   7320
gctcttgatc ttccaatacg caacctaaag taaaatgccc cactgcgctg agtgcatata   7380
atgcattctc tagtgaaaaa ccttgttggc ataaaaaggc taattgattt tcgagagttt   7440
catactgttt ttctgtaggc cgtgtaccta aatgtacttt tgctccatcg cgatgactta   7500
gtaaagcaca tctaaaactt ttagcgttat tacgtaaaaa atcttgccag ctttcccctt   7560
ctaaagggca aaagtgagta tggtgcctat ctaacatctc aatggctaag gcgtcgagca   7620
aagcccgctt atttttttaca tgccaataca atgtaggctg ctctacacct agcttctggg   7680
cgagtttacg ggttgttaaa ccttcgattc cgacctcatt aagcagctct aatgcgctgt   7740
taatcacttt acttttatct aaacgagaca tgagtatatc tccttctaca aaattatttc   7800
tagatctctc ccctatagtg agtcgtatta atttccgagc ggccgcgatt atcaaaaagg   7860
atcttcacct agatcctttt aaattaaaaa tgaagtttta aatcaatcta aagtatatat   7920
```

gagtaaactt ggtctgacag ttaccaatgc ttaatcagtg aggcacctat ctcagcgatc 7980
tgtctatttc gttcatccat agttgcctga ctccccgtcg tgtagataac tacgatacgg 8040
gagggcttac catctggccc cagtgctgca atgataccgc gggacccacg ctcaccggct 8100
ccagatttat cagcaataaa ccagccagcc ggaagggccg agcgcagaag tggtcctgca 8160
actttatccg cctccatcca gtctattaat tgttgccggg aagctagagt aagtagttcg 8220
ccagttaata gtttgcgcaa cgttgttgcc attgctacag gcatcgtggt gtcacgctcg 8280
tcgtttggta tggcttcatt cagctccggt tcccaacgat caaggcgagt tacatgatcc 8340
cccatgttgt gcaaaaaagc ggttagctcc ttcggtcctc cgatcgttgt cagaagtaag 8400
ttggccgcag tgttatcact catggttatg gcagcactgc ataattctct tactgtcatg 8460
ccatccgtaa gatgcttttc tgtgactggt gagtactcaa ccaagtcatt ctgagaatag 8520
tgtatgcggc gaccgagttg ctcttgcccg gcgtcaatac gggataatac cgcgccacat 8580
agcagaactt taaaagtgct catcattgga aaacgttctt cggggcgaaa actctcaagg 8640
atcttaccgc tgttgagatc cagttcgatg taacccactc gtgcacccaa ctgatcttca 8700
gcatctttta ctttcaccag cgtttctggg tgagcaaaaa caggaaggca aaatgccgca 8760
aaaaagggaa taagggcgac acggaaatgt tgaatactca t 8801

<210> SEQ ID NO 76
<211> LENGTH: 8790
<212> TYPE: DNA
<213> ORGANISM: Artificial Sequence
<220> FEATURE:
<223> OTHER INFORMATION: Chemically Synthesized, pBTK503

<400> SEQUENCE: 76
actcttcctt tttcaatatt attgaagcat ttatcagggt tattgtctca tgagcggata 60
catatttgaa tgtatttaga aaaataaaca aataggggtt ccgcgcacat ttccccgaaa 120
agtgccacct gtcatgacca aaatccctta acgtgagtca gcctgccgcc ttgggccggg 180
tgatgtcgta cttgcccgcc gcgaactcgg ttaccgtcca gcccagcgcg accagctccg 240
gcaacgcctc gcgcacccgc ttgcggcgct tgcgcatggt cgaaccactg gcctctgacg 300
gccagacata gccgcacaag gtatctatgg aagccttgcc ggttttgccg gggtcgatcc 360
agccacacag ccgctggtgc agcaggcggg cggtttcgct gtccagcgcc cgcacctcgt 420
ccatgctgat gcgcacatgc tggccgccac ccatgacggc ctgcgcgatc aaggggttca 480
gggccacgta caggcgcccg tccgcctcgt cgctggcgta ctccgacagc agccgaaacc 540
cctgccgctt gcggccattc tgggcgatga tggatacctt ccaaaggcgc tcgatgcagt 600
cctgtatgtg cttgagcgcc ccaccactat cgacctctgc ccgatttcc tttgccagcg 660 cccgatagct acctttgacc acatggcatt cagcggtgac ggcctcccac ttgggttcca 720
ggaacagccg gagctgccgt ccgccttcgg tcttgggttc cgggccaagc actaggccat 780
taggcccagc catggccacc agcccttgca ggatgcgcag atcatcagcg cccagcggct 840
ccgggccgct gaactcgatc cgcttgccgt cgccgtagtc atacgtcacg tccagcttgc 900
tgcgcttgcg ctcgccccgc ttgagggcac ggaacaggcc gggggccaga cagtgcgccg 960
ggtcgtgccg gacgtggctg aggctgtgct tgttcttagg cttcaccacg gggcaccccc 1020
ttgctcttgc gctgcctctc cagcacggcg ggcttgagca ccccgccgtc atgccgcctg 1080
aaccaccgat cagcgaacgg tgcgccatag ttggccttgc tcacaccgaa gcggacgaag 1140
aaccggcgct ggtcgtcgtc cacaccccat tcctcggcct cggcgctggt catgctcgac 1200

```
aggtaggact gccagcggat gttatcgacc agtaccgagc tgccccggct ggcctgctgc   1260
tggtcgcctg cgcccatcat ggccgcgccc ttgctggcat ggtgcaggaa cacgatagag   1320
cacccggtat cggcggcgat ggcctccatg cgaccgatga cctgggccat ggggccgctg   1380
gcgttttctt cctcgatgtg gaaccggcgc agcgtgtcca gcaccatcag gcggcggccc   1440
tcggcggcgc gcttgaggcc gtcgaaccac tccggggcca tgatgttggg caggctgccg   1500
atcagcggct ggatcagcag gccgtcagcc acggcttgcc gttcctcggc gctgaggtgc   1560
gccccaaggg cgtgcaggcg gtgatgaatg gcggtgggcg ggtcttcggc gggcaggtag   1620
atcaccgggc cggtgggcag ttcgcccacc tccagcagat ccggcccgcc tgcaatctgt   1680
gcggccagtt gcagggccag catggattta ccggcaccac cgggcgacac cagcgccccg   1740
accgtaccgg ccaccatgtt gggcaaaacg tagtccagcg gtggcggcgc tgctgcgaac   1800
gcctccagaa tattgatagg cttatgggta gccattgatt gcctcctttg caggcagttg   1860
gtggttaggc gctggcgggg tcactacccc cgccctgcgc cgctctgagt tcttccaggc   1920
actcgcgcag cgcctcgtat tcgtcgtcgg tcagccagaa cttgcgctga cgcatccctt   1980
tggccttcat gcgctcggca tatcgcgctt ggcgtacagc gtcagggctg gccagcaggt   2040
cgccggtctg cttgtccttt tggtctttca tatcagtcac cgagaaactt gccggggccg   2100
aaaggcttgt cttcgcggaa caaggacaag gtgcagccgt caaggttaag gctggccata   2160
tcagcgactg aaaagcggcc agcctcggcc ttgtttgacg tataaccaaa gccaccgggc   2220
aaccaatagc ccttgtcact tttgatcagg tagaccgacc ctgaagcgct tttttcgtat   2280
tccataaaac cccctctgt gcgtgagtac tcatagtata acaggcgtga gtaccaacgc   2340
aagcactaca tgctgaaatc tggcccgccc ctgtccatgc ctcgctggcg gggtgccggt   2400
gcccgtgcca gctcggcccg cgcaagctgg acgctgggca gacccatgac cttgctgacg   2460
gtgcgctcga tgtaatccgc ttcgtggccg ggcttgcgct ctgccagcgc tgggctggcc   2520
tcggccatgg ccttgccgat ttcctcggca ctgcggcccc ggctggccag cttctgcgcg   2580
gcgataaagt cgcacttgct gaggtcatga ccgaagcgct tgaccagccc ggccatctcg   2640
ctgcggtact cgtccagcgc cgtgcgccgg tggcggctaa gctgccgctc gggcagttcg   2700
aggctggcca gcctgcgggc cttctcctgc tgccgctggg cctgctcgat ctgctggcca   2760
gcctgctgca ccagcgccgg gccagcggtg gcggtcttgc ccttggattc acgcagcagc   2820
acccacggct gataaccggc gcgggtggtg tgcttgtcct tgcggttggt gaagcccgcc   2880
aagcggccat agtggcggct gtcggcgctg gccgggtcgg cgtcgtactc gctggccagc   2940
gtccgggcaa tctgcccccg aagttcaccg cctgcggcgt cggccacctt gacccatgcc   3000
tgatagttct tcgggctggt ttccactacc agggcaggct cccggccctc ggctttcatg   3060
tcatccaggt caaactcgct gaggtcgtcc accagcacca gaccatgccg ctcctgctcg   3120
gcgggcctga tatacacgtc attgccctgg gcattcatcc gcttgagcca tggcgtgttc   3180
tggagcactt cggcggctga ccattcccgg ttcatcatct ggccggtggg tgcgtccctg   3240
acgccgatat cgaagcgctc acagcccatg gccttgagct gtcggcctat ggcctgcaaa   3300
gtcctgtcgt tcttcatcgg gccaccaagc gcagccagat cgagccgtcc tcggttgtca   3360
gtggcgtcag gtcgagcaag agcaacgatg cgatcagcag caccaccgta ggcatcatgg   3420
aagccagcat cacggttagc catagcttcc agtgccaccc ccgcgacgcg ctccgggcgc   3480
tctgcgcggc gctgctcacc tcggcggcta cctcccgcaa ctctttggcc agctccaccc   3540
```

-continued

```
atgccgcccc tgtctggcgc tgggctttca gccactccgc cgcctgcgcc tcgctggcct   3600
gcttggtctg gctcatgacc tgccgggctt cgtcggccag tgtcgccatg ctctgggcca   3660
gcggttcgat ctgctccgct aactcgttga tgcctctgga tttcttcact ctgtcgattg   3720
cgttcatggt ctattgcctc ccggtattcc tgtaagtcga tgatctgggc gttggcggtg   3780
tcgatgttca gggccacgtc tgcccggtcg gtgcggatgc cccggccttc catctccacc   3840
acgttcggcc ccaggtgaac accgggcagg cgctcgatgc cctgcgcctc aagtgttctg   3900
tggtcaatgc gggcgtcgtg gccagcccgc tctaatgccc ggttggcatg gtcggcccat   3960
gcctcgcggg tctgctcaag ccatgccttg ggcttgagcg cttcggtctt ctgtgccccg   4020
cccttctccg ggtcttgccg gttgtaccgc ttgaaccact gagcggcggg ccgctcgatg   4080
ccgtcattga tccgctcgga gatcatcagg tggcagtgcg ggttctcgcc gccaccggca   4140
tggatggcca gcgtatacgg caggcgctcg gcaccggtca ggtgctgggc gaactcggac   4200
gccagcgcct tctgctggtc gagggtcagc tcgaccggca gggcaaattc gacctccttg   4260
aacagccgcc cattggcgcg ttcatacagg tcggcagcat cccagtagtc ggcgggccgc   4320
tcgacgaact ccggcatgtg cccggattcg gcgtgcaaga cttcatccat gtcgcgggca   4380
tacttgcctt cgcgctggat gtagtcggcc ttggccctgg ccgattggcc gcccgacctg   4440
ctgccggttt tcgccgtaag gtgataaatc gccatgctgc ctcgctgttg cttttgcttt   4500
tcggctccat gcaatggccc tcggagagcg caccgcccga agggtggccg ttaggccagt   4560
ttctcgaaga gaaaccggta agtgcgccct cccctacaaa gtagggtcgg gattgccgcc   4620
gctgtgcctc catgatagcc tacgagacag cacattaaca atggggtgtc aagatggtta   4680
aggggagcaa caaggcggcg gatcggctgg ccaagctcga agaacaacga gcgcgaatca   4740
atgccgaaat tcagcgggag cgggcaaggg aacagcagca agagcgcaag aacgaaacaa   4800
ggcgcaaggt gctggtgggg gccatgattt tggccaaggt gaacagcagc gagtggccgg   4860
aggatcggct catggcggca atggatgcgt accttgaacg cgaccacgac cgcgccttgt   4920
tcggtctgcc gccacgccag aaggatgagc cgggctgaat gatcgaccga gacaggccct   4980
gcggggctgc acacgcgccc ccacccttcg ggtaggggga aaggccgcta aagcggctaa   5040
aagcgctcca gcgtatttct gcggggtttg gtgtggggtt tagcgggctt tgcccgcctt   5100
tccccctgcc gcgcagcggt ggggcggtgt gtagcctagc gcagcgaata gaccagctat   5160
ccggcctctg gccgggcata ttgggcaagg gcagcagcgc cccacaaggg cgctgataac   5220
cgcgcctagt ggattattct tagataatca tggatggatt tttccaacac cccgccagcc   5280
cccgcccctg ctgggtttgc aggtttgggg gcgtgacagt tattgcaggg gttcgtgaca   5340
gttattgcag gggggcgtga cagttattgc aggggttcgt gacagttagt acgggagtga   5400
cgggcactgg ctggcaatgt ctagcaacgg caggcatttc ggctgagggt aaaagaactt   5460
tccgctaagc gatagactgt atgtaaacac agtattgcaa ggacgcggaa catgcctcat   5520
gtggcggcca ggacggccag ccgggatcgg gatactggtc gttaccagag ccaccgaccc   5580
gagcaaaccc ttctctatca gatcgttgac gagtattacc cggcattcgc tgcgcttatg   5640
gcagagcagg gaaaggaatt gccgggctat gtgcaacggg aatttgaaga atttctccaa   5700
tgcgggcggc tggagcatgg ctttctacgg gttcgctgcg agtcttgcca cgccgagcac   5760
ctggtcgctt tcagaaatca atctaaagta tatatgagta aacttggtct gacaggcccc   5820
tgaattcgca tctagactga tgagacgtgg tagagccaca aacagccggt acaagcaacg   5880
atctccagga ccatctgaat catgcgcgga tgacacgaac tcacgacggc gatcacagac   5940
```

```
attaacccac agtacagaca ctgcgacaac gtggcaattc gtcgcaatac aacgctttgg   6000
cagtttattc ttgacatgta gtgagggggc tggtataatc acatagtact gttatacaga   6060
aacagaggag atattacata tgagtaaagg agaagagctt ttcacaggag ttgtcccaat   6120
cctcgtggaa ttagacggtg atgttaatgg gcacaagttc tctgtcagtg gagagggtga   6180
aggcgacgca acatatggca agctgaccct taaatttatt tgcaccacgg gtaaactacc   6240
tgttccatgg ccaacactgg tcactacgtt cgggtatggg gttcagtgct ttgcgcgcta   6300
cccagatcac atgaaacagc acgacttttt caagagtgca atgcccgaag gctatgtaca   6360
ggagagaacc atctttttta aggatgacgg caactataag acacgcgccg aagtgaagtt   6420
cgagggtgat acccttgtta atagaatcga gttaaagggt attgacttta aggaagatgg   6480
aaatatttta ggccacaaac tggaatataa ctataactcc cataatgtgt acattatggc   6540
cgacaagcaa aagaacggta tcaaggttaa cttcaagatc agacacaaca ttgaggatgg   6600
aagcgttcaa ctagccgacc attaccaaca aaacacccca attggcgatg gccctgtgct   6660
gttaccagac aaccattacc tgtccactca atctgccctt tcgaaagatc ccaacgaaaa   6720
gcgcgaccac atggtccttc ttgagtttgt cacggctgct gggattacac acggcatgga   6780
tgaactatac aaataaatcc gtaatcgtta atccgcaaat aacgtaaaaa cccgcttcgg   6840
cgggtttttt tatgggggga gtttagggaa agagcatttg tcagctggaa atctgctcgt   6900
cagtggtgct cacactgacg aatcatgtac agatcatacc gatgactgcc tggcgactca   6960
caactaagca agacagccgg aaccagcgcc ggcgaacacc actgcatata tggcatatca   7020
caacagtcca cgtctcaagc agttacagag atgttacgaa ccactagtgc actgcagtac   7080
acaaaaaacc cctcaagacc cgtttagagg ccccaagggg ttatgctaat gctgctttaa   7140
gacccacttt cacatttaag ttgtttttct aatccgcata tgatcaattc aaggccgaat   7200
aagaaggctg gctctgcacc ttggtgatca aataattcga tagcttgtcg taataatggc   7260
ggcatactat cagtagtagg tgtttccctt tcttctttag cgacttgatg ctcttgatct   7320
tccaatacgc aacctaaagt aaaatgcccc actgcgctga gtgcatataa tgcattctct   7380
agtgaaaaac cttgttggca taaaaaggct aattgatttt cgagagtttc atactgtttt   7440
tctgtaggcc gtgtacctaa atgtactttt gctccatcgc gatgacttag taaagcacat   7500
ctaaaacttt tagcgttatt acgtaaaaaa tcttgccagc tttccccttc taaagggcaa   7560
aagtgagtat ggtgcctatc taacatctca atggctaagg cgtcgagcaa agcccgctta   7620
ttttttacat gccaatacaa tgtaggctgc tctacaccta gcttctgggc gagtttacgg   7680
gttgttaaac cttcgattcc gacctcatta agcagctcta atgcgctgtt aatcacttta   7740
cttttatcta aacgagacat gagtatatct ccttctacaa aattatttct agatctctcc   7800
cctatagtga gtcgtattaa tttccgagcg gccgcgatta tcaaaaagga tcttcaccta   7860
gatcctttta aattaaaaat gaagttttaa atcaatctaa agtatatatg agtaaacttg   7920
gtctgacagt taccaatgct taatcagtga ggcacctatc tcagcgatct gtctatttcg   7980
ttcatccata gttgcctgac tccccgtcgt gtagataact acgatacggg agggcttacc   8040
atctggcccc agtgctgcaa tgataccgcg ggacccacgc tcaccggctc cagatttatc   8100
agcaataaac cagccagccg gaagggccga gcgcagaagt ggtcctgcaa ctttatccgc   8160
ctccatccag tctattaatt gttgccggga agctagagta agtagttcgc cagttaatag   8220
tttgcgcaac gttgttgcca ttgctacagg catcgtggtg tcacgctcgt cgtttggtat   8280
```

```
ggcttcattc agctccggtt cccaacgatc aaggcgagtt acatgatccc ccatgttgtg   8340

caaaaaagcg gttagctcct tcggtcctcc gatcgttgtc agaagtaagt tggccgcagt   8400

gttatcactc atggttatgg cagcactgca taattctctt actgtcatgc catccgtaag   8460

atgcttttct gtgactggtg agtactcaac caagtcattc tgagaatagt gtatgcggcg   8520

accgagttgc tcttgcccgg cgtcaatacg ggataatacc gcgccacata gcagaacttt   8580

aaaagtgctc atcattggaa aacgttcttc ggggcgaaaa ctctcaagga tcttaccgct   8640

gttgagatcc agttcgatgt aacccactcg tgcacccaac tgatcttcag catcttttac   8700

tttcaccagc gtttctgggt gagcaaaaac aggaaggcaa aatgccgcaa aaaagggaat   8760

aagggcgaca cggaaatgtt gaatactcat                                    8790
```

<210> SEQ ID NO 77
<211> LENGTH: 8802
<212> TYPE: DNA
<213> ORGANISM: Artificial Sequence
<220> FEATURE:
<223> OTHER INFORMATION: Chemically Synthesized, pBTK509

<400> SEQUENCE: 77

```
actcttcctt tttcaatatt attgaagcat ttatcagggt tattgtctca tgagcggata     60

catatttgaa tgtatttaga aaaataaaca aataggggtt ccgcgcacat ttccccgaaa    120

agtgccacct gtcatgacca aaatccctta acgtgagtca gcctgccgcc ttgggccggg    180

tgatgtcgta cttgcccgcc gcgaactcgg ttaccgtcca gcccagcgcg accagctccg    240

gcaacgcctc gcgcacccgc ttgcggcgct tgcgcatggt cgaaccactg gcctctgacg    300

gccagacata gccgcacaag gtatctatgg aagccttgcc ggttttgccg gggtcgatcc    360

agccacacag ccgctggtgc agcaggcggg cggtttcgct gtccagcgcc cgcacctcgt    420

ccatgctgat gcgcacatgc tggccgccac ccatgacggc ctgcgcgatc aaggggttca    480

gggccacgta caggcgcccg tccgcctcgt cgctggcgta ctccgacagc agccgaaacc    540

cctgccgctt gcggccattc tgggcgatga tggatacctt ccaaaggcgc tcgatgcagt    600

cctgtatgtg cttgagcgcc ccaccactat cgacctctgc cccgatttcc tttgccagcg    660

cccgatagct acctttgacc acatggcatt cagcggtgac ggcctcccac ttgggttcca    720

ggaacagccg gagctgccgt ccgccttcgg tcttgggttc cgggccaagc actaggccat    780

taggcccagc catggccacc agcccttgca ggatgcgcag atcatcagcg cccagcggct    840

ccgggccgct gaactcgatc cgcttgccgt cgccgtagtc atacgtcacg tccagcttgc    900

tgcgcttgcg ctcgccccgc ttgagggcac ggaacaggcc gggggccaga cagtgcgccg    960

ggtcgtgccg gacgtggctg aggctgtgct tgttcttagg cttcaccacg gggcaccccc   1020

ttgctcttgc gctgcctctc cagcacggcg ggcttgagca ccccgccgtc atgccgcctg   1080

aaccaccgat cagcgaacgg tgcgccatag ttggccttgc tcacaccgaa gcggacgaag   1140

aaccggcgct ggtcgtcgtc cacaccccat tcctcggcct cggcgctggt catgctcgac   1200

aggtaggact gccagcggat gttatcgacc agtaccgagc tgccccggct ggcctgctgc   1260

tggtcgcctg cgcccatcat ggccgcgccc ttgctggcat ggtgcaggaa cacgatagag   1320

cacccggtat cggcggcgat ggcctccatg cgaccgatga cctgggccat ggggccgctg   1380

gcgttttctt cctcgatgtg gaaccggcgc agcgtgtcca gcaccatcag gcggcggccc   1440

tcggcggcgc gcttgaggcc gtcgaaccac tccggggcca tgatgttggg caggctgccg   1500

atcagcggct ggatcagcag gccgtcagcc acggcttgcc gttcctcggc gctgaggtgc   1560
```

```
gccccaaggg cgtgcaggcg gtgatgaatg gcggtgggcg ggtcttcggc gggcaggtag   1620

atcaccgggc cggtgggcag ttcgcccacc tccagcagat ccggcccgcc tgcaatctgt   1680

gcggccagtt gcagggccag catggattta ccggcaccac cgggcgacac cagcgccccg   1740

accgtaccgg ccaccatgtt gggcaaaacg tagtccagcg gtggcggcgc tgctgcgaac   1800

gcctccagaa tattgatagg cttatgggta gccattgatt gcctcctttg caggcagttg   1860

gtggttaggc gctggcgggg tcactacccc cgccctgcgc cgctctgagt tcttccaggc   1920

actcgcgcag cgcctcgtat tcgtcgtcgg tcagccagaa cttgcgctga cgcatccctt   1980

tggccttcat gcgctcggca tatcgcgctt ggcgtacagc gtcagggctg gccagcaggt   2040

cgccggtctg cttgtccttt tggtctttca tatcagtcac cgagaaactt gccggggccg   2100

aaaggcttgt cttcgcggaa caaggacaag gtgcagccgt caaggttaag gctggccata   2160

tcagcgactg aaaagcggcc agcctcggcc ttgtttgacg tataaccaaa gccaccgggc   2220

aaccaatagc ccttgtcact tttgatcagg tagaccgacc ctgaagcgct tttttcgtat   2280

tccataaaac cccctctgt gcgtgagtac tcatagtata acaggcgtga gtaccaacgc   2340

aagcactaca tgctgaaatc tggcccgccc ctgtccatgc ctcgctggcg gggtgccggt   2400

gcccgtgcca gctcggcccg cgcaagctgg acgctgggca gacccatgac cttgctgacg   2460

gtgcgctcga tgtaatccgc ttcgtggccg ggcttgcgct ctgccagcgc tgggctggcc   2520

tcggccatgg ccttgccgat ttcctcggca ctgcggcccc ggctggccag cttctgcgcg   2580

gcgataaagt cgcacttgct gaggtcatga ccgaagcgct tgaccagccc ggccatctcg   2640

ctgcggtact cgtccagcgc cgtgcgccgg tggcggctaa gctgccgctc gggcagttcg   2700

aggctggcca gcctgcgggc cttctcctgc tgccgctggg cctgctcgat ctgctggcca   2760

gcctgctgca ccagcgccgg gccagcggtg gcggtcttgc ccttggattc acgcagcagc   2820

acccacggct gataaccggc gcgggtggtg tgcttgtcct tgcggttggt gaagcccgcc   2880

aagcggccat agtggcggct gtcggcgctg gccgggtcgg cgtcgtactc gctggccagc   2940

gtccgggcaa tctgcccccg aagttcaccg cctgcggcgt cggccacctt gacccatgcc   3000

tgatagttct tcgggctggt ttccactacc agggcaggct cccggccctc ggctttcatg   3060

tcatccaggt caaactcgct gaggtcgtcc accagcacca gaccatgccg ctcctgctcg   3120

gcgggcctga tatacacgtc attgccctgg gcattcatcc gcttgagcca tggcgtgttc   3180

tggagcactt cggcggctga ccattcccgg ttcatcatct ggccggtggg tgcgtccctg   3240

acgccgatat cgaagcgctc acagcccatg gccttgagct gtcggcctat ggcctgcaaa   3300

gtcctgtcgt tcttcatcgg gccaccaagc gcagccagat cgagccgtcc tcggttgtca   3360

gtggcgtcag gtcgagcaag agcaacgatg cgatcagcag caccaccgta ggcatcatgg   3420

aagccagcat cacggttagc catagcttcc agtgccaccc ccgcgacgcg ctccgggcgc   3480

tctgcgcggc gctgctcacc tcggcggcta cctcccgcaa ctctttggcc agctccaccc   3540

atgccgcccc tgtctggcgc tgggctttca gccactccgc cgcctgcgcc tcgctggcct   3600

gcttggtctg gctcatgacc tgccgggctt cgtcggccag tgtcgccatg ctctgggcca   3660

gcggttcgat ctgctccgct aactcgttga tgcctctgga tttcttcact ctgtcgattg   3720

cgttcatggt ctattgcctc ccggtattcc tgtaagtcga tgatctgggc gttggcggtg   3780

tcgatgttca gggccacgtc tgcccggtcg gtgcggatgc ccggccttc catctccacc   3840

acgttcggcc ccaggtgaac accgggcagg cgctcgatgc cctgcgcctc aagtgttctg   3900
```

```
tggtcaatgc gggcgtcgtg gccagcccgc tctaatgccc ggttggcatg gtcggcccat   3960
gcctcgcggg tctgctcaag ccatgccttg ggcttgagcg cttcggtctt ctgtgccccg   4020
cccttctccg ggtcttgcc gttgtaccgc ttgaaccact gagcggcggg ccgctcgatg    4080
ccgtcattga tccgctcgga gatcatcagg tggcagtgcg ggttctcgcc gccaccggca   4140
tggatggcca gcgtatacgg caggcgctcg gcaccggtca ggtgctgggc gaactcggac   4200
gccagcgcct tctgctggtc gagggtcagc tcgaccggca gggcaaattc gacctccttg   4260
aacagccgcc cattggcgcg ttcatacagg tcggcagcat cccagtagtc ggcgggccgc   4320
tcgacgaact ccggcatgtg cccggattcg gcgtgcaaga cttcatccat gtcgcgggca   4380
tacttgcctt cgcgctggat gtagtcggcc ttggccctgg ccgattggcc gcccgacctg   4440
ctgccggttt tcgccgtaag gtgataaatc gccatgctgc ctcgctgttg cttttgcttt   4500
tcggctccat gcaatggccc tcggagagcg caccgcccga agggtggccg ttaggccagt   4560
ttctcgaaga gaaaccggta agtgcgccct cccctacaaa gtagggtcgg gattgccgcc   4620
gctgtgcctc catgatagcc tacgagacag cacattaaca atggggtgtc aagatggtta   4680
aggggagcaa caaggcggcg gatcggctgg ccaagctcga agaacaacga gcgcgaatca   4740
atgccgaaat tcagcgggag cgggcaaggg aacagcagca agagcgcaag aacgaaacaa   4800
ggcgcaaggt gctggtgggg gccatgattt tggccaaggt gaacagcagc gagtggccgg   4860
aggatcggct catggcggca atggatgcgt accttgaacg cgaccacgac cgcgccttgt   4920
tcggtctgcc gccacgccag aaggatgagc cgggctgaat gatcgaccga gacaggccct   4980
gcggggctgc acacgcgccc ccacccttcg ggtaggggga aaggccgcta aagcggctaa   5040
aagcgctcca gcgtatttct gcggggtttg gtgtggggtt tagcgggctt tgcccgcctt   5100
tccccctgcc gcgcagcggt ggggcggtgt gtagcctagc gcagcgaata gaccagctat   5160
ccggcctctg gccgggcata ttgggcaagg gcagcagcgc cccacaaggg cgctgataac   5220
cgcgcctagt ggattattct tagataatca tggatggatt tttccaacac cccgccagcc   5280
cccgcccctg ctgggtttgc aggtttgggg gcgtgacagt tattgcaggg gttcgtgaca   5340
gttattgcag gggggcgtga cagttattgc aggggttcgt gacagttagt acgggagtga   5400
cgggcactgg ctggcaatgt ctagcaacgg caggcatttc ggctgagggt aaaagaactt   5460
tccgctaagc gatagactgt atgtaaacac agtattgcaa ggacgcggaa catgcctcat   5520
gtggcggcca ggacggccag ccgggatcgg gatactggtc gttaccagag ccaccgaccc   5580
gagcaaaccc ttctctatca gatcgttgac gagtattacc cggcattcgc tgcgcttatg   5640
gcagagcagg gaaaggaatt gccgggctat gtgcaacggg aatttgaaga atttctccaa   5700
tgcgggcggc tggagcatgg ctttctacgg gttcgctgcg agtcttgcca cgccgagcac   5760
ctggtcgctt tcagaaatca atctaaagta tatatgagta aacttggtct gacaggcccc   5820
tgaattcgca tctagactga tgagacgtgg tagagccaca aacagccggt acaagcaacg   5880
atctccagga ccatctgaat catgcgcgga tgacacgaac tcacgacggc gatcacagac   5940
attaacccac agtacagaca ctgcgacaac gtggcaattc gtcgcaatac aacgcacgaa   6000
aaacaggtat tgacaacatg aagtaacatg cagtaagata caaatcgcta ggtaacacta   6060
gcagcataca gaaacagagg agatattaca tatgagtaaa ggagaagagc ttttcacagg   6120
agttgtccca atcctcgtgg aattagacgg tgatgttaat gggcacaagt tctctgtcag   6180
tggagagggt gaaggcgacg caacatatgg caagctgacc cttaaattta tttgcaccac   6240
gggtaaacta cctgttccat ggccaacact ggtcactacg ttcgggtatg ggttcagtg    6300
```

```
ctttgcgcgc tacccagatc acatgaaaca gcacgacttt ttcaagagtg caatgcccga   6360
aggctatgta caggagagaa ccatcttttt taaggatgac ggcaactata agacacgcgc   6420
cgaagtgaag ttcgagggtg atacccttgt taatagaatc gagttaaagg gtattgactt   6480
taaggaagat ggaaatattt taggccacaa actggaatat aactataact cccataatgt   6540
gtacattatg gccgacaagc aaaagaacgg tatcaaggtt aacttcaaga tcagacacaa   6600
cattgaggat ggaagcgttc aactagccga ccattaccaa caaaacaccc caattggcga   6660
tgggcctgtg ctgttaccag acaaccatta cctgtccact caatctgccc tttcgaaaga   6720
tcccaacgaa aagcgcgacc acatggtcct tcttgagttt gtcacggctg ctgggattac   6780
acacggcatg gatgaactat acaaataaat ccgtaatcgt taatccgcaa ataacgtaaa   6840
aacccgcttc ggcgggtttt tttatggggg gagtttaggg aaagagcatt tgtcagctgg   6900
aaatctgctc gtcagtggtg ctcacactga cgaatcatgt acagatcata ccgatgactg   6960
cctggcgact cacaactaag caagacagcc ggaaccagcg ccggcgaaca ccactgcata   7020
tatggcatat cacaacagtc cacgtctcaa gcagttacag agatgttacg aaccactagt   7080
gcactgcagt acacaaaaaa cccctcaaga cccgtttaga ggccccaagg ggttatgcta   7140
atgctgcttt aagacccact ttcacattta agttgttttt ctaatccgca tatgatcaat   7200
tcaaggccga ataagaaggc tggctctgca ccttggtgat caaataattc gatagcttgt   7260
cgtaataatg gcggcatact atcagtagta ggtgtttccc tttcttcttt agcgacttga   7320
tgctcttgat cttccaatac gcaacctaaa gtaaaatgcc ccactgcgct gagtgcatat   7380
aatgcattct ctagtgaaaa accttgttgg cataaaaagg ctaattgatt ttcgagagtt   7440
tcatactgtt tttctgtagg ccgtgtacct aaatgtactt ttgctccatc gcgatgactt   7500
agtaaagcac atctaaaact tttagcgtta ttacgtaaaa aatcttgcca gctttcccct   7560
tctaaagggc aaaagtgagt atggtgccta tctaacatct caatggctaa ggcgtcgagc   7620
aaagcccgct tatttttac atgccaatac aatgtaggct gctctacacc tagcttctgg   7680
gcgagtttac gggttgttaa accttcgatt ccgacctcat taagcagctc taatgcgctg   7740
ttaatcactt tacttttatc taaacgagac atgagtatat ctccttctac aaaattattt   7800
ctagatctct cccctatagt gagtcgtatt aatttccgag cggccgcgat tatcaaaaag   7860
gatcttcacc tagatccttt taaattaaaa atgaagtttt aaatcaatct aaagtatata   7920
tgagtaaact tggtctgaca gttaccaatg cttaatcagt gaggcaccta tctcagcgat   7980
ctgtctattt cgttcatcca tagttgcctg actccccgtc gtgtagataa ctacgatacg   8040
ggagggctta ccatctggcc ccagtgctgc aatgataccg cgggacccac gctcaccggc   8100
tccagattta tcagcaataa accagccagc cggaagggcc gagcgcagaa gtggtcctgc   8160
aactttatcc gcctccatcc agtctattaa ttgttgccgg gaagctagag taagtagttc   8220
gccagttaat agtttgcgca acgttgttgc cattgctaca ggcatcgtgg tgtcacgctc   8280
gtcgtttggt atggcttcat tcagctccgg ttcccaacga tcaaggcgag ttacatgatc   8340
ccccatgttg tgcaaaaaag cggttagctc cttcggtcct ccgatcgttg tcagaagtaa   8400
gttggccgca gtgttatcac tcatggttat ggcagcactg cataattctc ttactgtcat   8460
gccatccgta agatgctttt ctgtgactgg tgagtactca accaagtcat tctgagaata   8520
gtgtatgcgg cgaccgagtt gctcttgccc ggcgtcaata cgggataata ccgcgccaca   8580
tagcagaact ttaaaagtgc tcatcattgg aaaacgttct tcggggcgaa aactctcaag   8640
```

gatcttaccg ctgttgagat ccagttcgat gtaacccact cgtgcaccca actgatcttc 8700
agcatctttt actttcacca gcgtttctgg gtgagcaaaa acaggaaggc aaaatgccgc 8760
aaaaaaggga ataagggcga cacggaaatg ttgaatactc at 8802

<210> SEQ ID NO 78
<211> LENGTH: 8801
<212> TYPE: DNA
<213> ORGANISM: Artificial Sequence
<220> FEATURE:
<223> OTHER INFORMATION: Chemically Synthesized, pBTK510

<400> SEQUENCE: 78
actcttcctt tttcaatatt attgaagcat ttatcagggt tattgtctca tgagcggata 60
catatttgaa tgtatttaga aaaataaaca aataggggtt ccgcgcacat ttccccgaaa 120
agtgccacct gtcatgacca aaatccctta acgtgagtca gcctgccgcc ttgggccggg 180
tgatgtcgta cttgcccgcc gcgaactcgg ttaccgtcca gcccagcgcg accagctccg 240
gcaacgcctc gcgcacccgc ttgcggcgct tgcgcatggt cgaaccactg gcctctgacg 300
gccagacata gccgcacaag gtatctatgg aagccttgcc ggttttgccg gggtcgatcc 360
agccacacag ccgctggtgc agcaggcggg cggtttcgct gtccagcgcc cgcacctcgt 420
ccatgctgat gcgcacatgc tggccgccac ccatgacggc ctgcgcgatc aaggggttca 480
gggccacgta caggcgcccg tccgcctcgt cgctggcgta ctccgacagc agccgaaacc 540
cctgccgctt gcggccattc tgggcgatga tggatacctt ccaaaggcgc tcgatgcagt 600
cctgtatgtg cttgagcgcc ccaccactat cgacctctgc cccgatttcc tttgccagcg 660
cccgatagct acctttgacc acatggcatt cagcggtgac ggcctcccac ttgggttcca 720
ggaacagccg gagctgccgt ccgccttcgg tcttgggttc cgggccaagc actaggccat 780
taggcccagc catggccacc agcccttgca ggatgcgcag atcatcagcg cccagcggct 840
ccgggccgct gaactcgatc cgcttgccgt cgccgtagtc atacgtcacg tccagcttgc 900
tgcgcttgcg ctcgccccgc ttgagggcac ggaacaggcc gggggccaga cagtgcgccg 960
ggtcgtgccg gacgtggctg aggctgtgct tgttcttagg cttcaccacg gggcaccccc 1020
ttgctcttgc gctgcctctc cagcacggcg ggcttgagca ccccgccgtc atgccgcctg 1080
aaccaccgat cagcgaacgg tgcgccatag ttggccttgc tcacaccgaa gcggacgaag 1140
aaccggcgct ggtcgtcgtc cacaccccat tcctcggcct cggcgctggt catgctcgac 1200
aggtaggact gccagcggat gttatcgacc agtaccgagc tgccccggct ggcctgctgc 1260
tggtcgcctg cgcccatcat ggccgcgccc ttgctggcat ggtgcaggaa cacgatagag 1320
cacccggtat cggcggcgat ggcctccatg cgaccgatga cctgggccat ggggccgctg 1380
gcgttttctt cctcgatgtg gaaccggcgc agcgtgtcca gcaccatcag gcggcggccc 1440
tcggcggcgc gcttgaggcc gtcgaaccac tccggggcca tgatgttggg caggctgccg 1500
atcagcggct ggatcagcag gccgtcagcc acggcttgcc gttcctcggc gctgaggtgc 1560
gccccaaggg cgtgcaggcg gtgatgaatg gcggtgggcg ggtcttcggc gggcaggtag 1620
atcaccgggc cggtgggcag ttcgcccacc tccagcagat ccggcccgcc tgcaatctgt 1680
gcggccagtt gcagggccag catggattta ccggcaccac cgggcgacac cagcgccccg 1740
accgtaccgg ccaccatgtt gggcaaaacg tagtccagcg gtggcggcgc tgctgcgaac 1800
gcctccagaa tattgatagg cttatgggta gccattgatt gcctcctttg caggcagttg 1860
gtggttaggc gctggcgggg tcactacccc cgccctgcgc cgctctgagt tcttccaggc 1920

```
actcgcgcag cgcctcgtat tcgtcgtcgg tcagccagaa cttgcgctga cgcatccctt   1980
tggccttcat gcgctcggca tatcgcgctt ggcgtacagc gtcagggctg gccagcaggt   2040
cgccggtctg cttgtccttt tggtctttca tatcagtcac cgagaaactt gccggggccg   2100
aaaggcttgt cttcgcggaa caaggacaag gtgcagccgt caaggttaag gctggccata   2160
tcagcgactg aaaagcggcc agcctcggcc ttgtttgacg tataaccaaa gccaccgggc   2220
aaccaatagc ccttgtcact tttgatcagg tagaccgacc ctgaagcgct tttttcgtat   2280
tccataaaac ccccttctgt gcgtgagtac tcatagtata acaggcgtga gtaccaacgc   2340
aagcactaca tgctgaaatc tggcccgccc ctgtccatgc ctcgctggcg gggtgccggt   2400
gcccgtgcca gctcggcccg cgcaagctgg acgctgggca gacccatgac cttgctgacg   2460
gtgcgctcga tgtaatccgc ttcgtggccg ggcttgcgct ctgccagcgc tgggctggcc   2520
tcggccatgg ccttgccgat ttcctcggca ctgcggcccc ggctggccag cttctgcgcg   2580
gcgataaagt cgcacttgct gaggtcatga ccgaagcgct tgaccagccc ggccatctcg   2640
ctgcggtact cgtccagcgc cgtgcgccgg tggcggctaa gctgccgctc gggcagttcg   2700
aggctggcca gcctgcgggc cttctcctgc tgccgctggg cctgctcgat ctgctggcca   2760
gcctgctgca ccagcgccgg gccagcggtg gcggtcttgc ccttggattc acgcagcagc   2820
acccacggct gataaccggc gcgggtggtg tgcttgtcct tgcggttggt gaagcccgcc   2880
aagcggccat agtggcggct gtcggcgctg gccgggtcgg cgtcgtactc gctggccagc   2940
gtccgggcaa tctgccccg  aagttcaccg cctgcggcgt cggccacctt gacccatgcc   3000
tgatagttct tcgggctggt ttccactacc agggcaggct cccggccctc ggctttcatg   3060
tcatccaggt caaactcgct gaggtcgtcc accagcacca gaccatgccg ctcctgctcg   3120
gcgggcctga tatacacgtc attgccctgg gcattcatcc gcttgagcca tggcgtgttc   3180
tggagcactt cggcggctga ccattcccgg ttcatcatct ggccggtggg tgcgtccctg   3240
acgccgatat cgaagcgctc acagcccatg gccttgagct gtcggcctat ggcctgcaaa   3300
gtcctgtcgt tcttcatcgg gccaccaagc gcagccagat cgagccgtcc tcggttgtca   3360
gtggcgtcag gtcgagcaag agcaacgatg cgatcagcag caccaccgta ggcatcatgg   3420
aagccagcat cacggttagc catagcttcc agtgccaccc ccgcgacgcg ctccgggcgc   3480
tctgcgcggc gctgctcacc tcggcggcta cctcccgcaa ctctttggcc agctccaccc   3540
atgccgcccc tgtctggcgc tgggctttca gccactccgc cgcctgcgcc tcgctggcct   3600
gcttggtctg gctcatgacc tgccgggctt cgtcggccag tgtcgccatg ctctgggcca   3660
gcggttcgat ctgctccgct aactcgttga tgcctctgga tttcttcact ctgtcgattg   3720
cgttcatggt ctattgcctc ccggtattcc tgtaagtcga tgatctgggc gttggcggtg   3780
tcgatgttca gggccacgtc tgcccggtcg gtgcggatgc cccggccttc catctccacc   3840
acgttcggcc ccaggtgaac accgggcagg cgctcgatgc cctgcgcctc aagtgttctg   3900
tggtcaatgc gggcgtcgtg gccagcccgc tctaatgccc ggttggcatg gtcggcccat   3960
gcctcgcggg tctgctcaag ccatgccttg ggcttgagcg cttcggtctt ctgtgccccg   4020
cccttctccg ggtcttgccg gttgtaccgc ttgaaccact gagcggcggg ccgctcgatg   4080
ccgtcattga tccgctcgga gatcatcagg tggcagtgcg ggttctcgcc gccaccggca   4140
tggatggcca gcgtatacgg caggcgctcg gcaccggtca ggtgctgggc gaactcggac   4200
gccagcgcct tctgctggtc gagggtcagc tcgaccggca gggcaaattc gacctccttg   4260
```

-continued

```
aacagccgcc cattggcgcg ttcatacagg tcggcagcat cccagtagtc ggcgggccgc   4320
tcgacgaact ccggcatgtg cccggattcg gcgtgcaaga cttcatccat gtcgcgggca   4380
tacttgcctt cgcgctggat gtagtcggcc ttggccctgg ccgattggcc gcccgacctg   4440
ctgccggttt tcgccgtaag gtgataaatc gccatgctgc ctcgctgttg cttttgcttt   4500
tcggctccat gcaatggccc tcggagagcg caccgcccga agggtggccg ttaggccagt   4560
ttctcgaaga gaaaccggta agtgcgccct cccctacaaa gtagggtcgg gattgccgcc   4620
gctgtgcctc catgatagcc tacgagacag cacattaaca atggggtgtc aagatggtta   4680
aggggagcaa caaggcggcg gatcggctgg ccaagctcga agaacaacga gcgcgaatca   4740
atgccgaaat tcagcgggag cgggcaaggg aacagcagca agagcgcaag aacgaaacaa   4800
ggcgcaaggt gctggtgggg gccatgattt tggccaaggt gaacagcagc gagtggccgg   4860
aggatcggct catggcggca atggatgcgt accttgaacg cgaccacgac cgcgccttgt   4920
tcggtctgcc gccacgccag aaggatgagc cgggctgaat gatcgaccga gacaggccct   4980
gcggggctgc acacgcgccc ccacccttcg ggtaggggga aaggccgcta aagcggctaa   5040
aagcgctcca gcgtatttct gcggggtttg gtgtggggtt tagcgggctt tgcccgcctt   5100
tcccctgcc gcgcagcggt ggggcggtgt gtagcctagc gcagcgaata gaccagctat   5160
ccggcctctg gccgggcata ttgggcaagg gcagcagcgc cccacaaggg cgctgataac   5220
cgcgcctagt ggattattct tagataatca tggatggatt tttccaacac cccgccagcc   5280
cccgcccctg ctgggtttgc aggtttgggg gcgtgacagt tattgcaggg gttcgtgaca   5340
gttattgcag gggggcgtga cagttattgc aggggttcgt gacagttagt acgggagtga   5400
cgggcactgg ctggcaatgt ctagcaacgg caggcatttc ggctgagggt aaaagaactt   5460
tccgctaagc gatagactgt atgtaaacac agtattgcaa ggacgcggaa catgcctcat   5520
gtggcggcca ggacggccag ccgggatcgg gatactggtc gttaccagag ccaccgaccc   5580
gagcaaaccc ttctctatca gatcgttgac gagtattacc cggcattcgc tgcgcttatg   5640
gcagagcagg gaaaggaatt gccgggctat gtgcaacggg aatttgaaga atttctccaa   5700
tgcgggcggc tggagcatgg ctttctacgg gttcgctgcg agtcttgcca cgccgagcac   5760
ctggtcgctt tcagaaatca atctaaagta tatatgagta aacttggtct gacaggcccc   5820
tgaattcgca tctagactga tgagacgtgg tagagccaca aacagccggt acaagcaacg   5880
atctccagga ccatctgaat catgcgcgga tgacacgaac tcacgacggc gatcacagac   5940
attaacccac agtacagaca ctgcgacaac gtggcaattc gtcgcaatac aacgggtgaa   6000
acaaaacggt tgacaacatg aagtaaacac ggtacgatgt accacatgaa acgacagtga   6060
gtcaatacag aaacagagga gatattacat atgagtaaag gagaagagct tttcacagga   6120
gttgtcccaa tcctcgtgga attagacggt gatgttaatg ggcacaagtt ctctgtcagt   6180
ggagagggtg aaggcgacgc aacatatggc aagctgaccc ttaaatttat ttgcaccacg   6240
ggtaaactac ctgttccatg gccaacactg gtcactacgt tcgggtatgg ggttcagtgc   6300
tttgcgcgct acccagatca catgaaacag cacgactttt tcaagagtgc aatgcccgaa   6360
ggctatgtac aggagagaac catctttttt aaggatgacg gcaactataa gacacgcgcc   6420
gaagtgaagt tcgagggtga tacccttgtt aatagaatcg agttaaaggg tattgacttt   6480
aaggaagatg gaaatatttt aggccacaaa ctggaatata actataactc ccataatgtg   6540
tacattatgg ccgacaagca aaagaacggt atcaaggtta acttcaagat cagacacaac   6600
attgaggatg gaagcgttca actagccgac cattaccaac aaaacacccc aattggcgat   6660
```

```
gggcctgtgc tgttaccaga caaccattac ctgtccactc aatctgccct ttcgaaagat   6720
cccaacgaaa agcgcgacca catggtcctt cttgagtttg tcacggctgc tgggattaca   6780
cacggcatgg atgaactata caaataaatc cgtaatcgtt aatccgcaaa taacgtaaaa   6840
acccgcttcg gcgggttttt ttatgggggg agtttaggga aagagcattt gtcagctgga   6900
aatctgctcg tcagtggtgc tcacactgac gaatcatgta cagatcatac cgatgactgc   6960
ctggcgactc acaactaagc aagacagccg gaaccagcgc cggcgaacac cactgcatat   7020
atggcatatc acaacagtcc acgtctcaag cagttacaga gatgttacga accactagtg   7080
cactgcagta cacaaaaaac cctcaagac ccgtttagag gccccaaggg gttatgctaa   7140
tgctgcttta agacccactt tcacatttaa gttgtttttc taatccgcat atgatcaatt   7200
caaggccgaa taagaaggct ggctctgcac cttggtgatc aaataattcg atagcttgtc   7260
gtaataatgg cggcatacta tcagtagtag gtgtttccct ttcttcttta gcgacttgat   7320
gctcttgatc ttccaatacg caacctaaag taaaatgccc cactgcgctg agtgcatata   7380
atgcattctc tagtgaaaaa ccttgttggc ataaaaaggc taattgattt tcgagagttt   7440
catactgttt ttctgtaggc cgtgtaccta aatgtacttt tgctccatcg cgatgactta   7500
gtaaagcaca tctaaaactt ttagcgttat tacgtaaaaa atcttgccag ctttcccctt   7560
ctaaagggca aaagtgagta tggtgcctat ctaacatctc aatggctaag gcgtcgagca   7620
aagcccgctt atttttaca tgccaataca atgtaggctg ctctacacct agcttctggg   7680
cgagtttacg ggttgttaaa ccttcgattc cgacctcatt aagcagctct aatgcgctgt   7740
taatcacttt actttatct aaacgagaca tgagtatatc tccttctaca aaattatttc   7800
tagatctctc ccctatagtg agtcgtatta atttccgagc ggccgcgatt atcaaaaagg   7860
atcttcacct agatcctttt aaattaaaaa tgaagtttta aatcaatcta aagtatatat   7920
gagtaaactt ggtctgacag ttaccaatgc ttaatcagtg aggcacctat ctcagcgatc   7980
tgtctatttc gttcatccat agttgcctga ctccccgtcg tgtagataac tacgatacgg   8040
gagggcttac catctggccc cagtgctgca atgataccgc gggacccacg ctcaccggct   8100
ccagatttat cagcaataaa ccagccagcc ggaagggccg agcgcagaag tggtcctgca   8160
actttatccg cctccatcca gtctattaat tgttgccggg aagctagagt aagtagttcg   8220
ccagttaata gtttgcgcaa cgttgttgcc attgctacag gcatcgtggt gtcacgctcg   8280
tcgtttggta tggcttcatt cagctccggt tcccaacgat caaggcgagt tacatgatcc   8340
cccatgttgt gcaaaaaagc ggttagctcc ttcggtcctc cgatcgttgt cagaagtaag   8400
ttggccgcag tgttatcact catggttatg gcagcactgc ataattctct tactgtcatg   8460
ccatccgtaa gatgcttttc tgtgactggt gagtactcaa ccaagtcatt ctgagaatag   8520
tgtatgcggc gaccgagttg ctcttgcccg gcgtcaatac gggataatac cgcgccacat   8580
agcagaactt taaaagtgct catcattgga aaacgttctt cggggcgaaa actctcaagg   8640
atcttaccgc tgttgagatc cagttcgatg taacccactc gtgcacccaa ctgatcttca   8700
gcatctttta ctttcaccag cgtttctggg tgagcaaaaa caggaaggca aaatgccgca   8760
aaaaagggaa taagggcgac acggaaatgt tgaatactca t                       8801
```

<210> SEQ ID NO 79
<211> LENGTH: 8118
<212> TYPE: DNA
<213> ORGANISM: Artificial Sequence
<220> FEATURE:

<223> OTHER INFORMATION: Chemically Synthesized, pBTK519

<400> SEQUENCE: 79

```
aacacccctt gtattactgt ttatgtaagc agacagtttt attgttcatg atgatatatt     60
tttatcttgt gcaatgtaac atcagagatt ttgagacaca acgtggcttt gttgaataaa    120
tcgaactttt gctgagttga aggatcagtc atgaccaaaa tcccttaacg tgagtcagcc    180
tgccgccttg ggccgggtga tgtcgtactt gcccgccgcg aactcggtta ccgtccagcc    240
cagcgcgacc agctccggca acgcctcgcg cacccgcttg cggcgcttgc gcatggtcga    300
accactggcc tctgacggcc agacatagcc gcacaaggta tctatggaag ccttgccggt    360
tttgccgggg tcgatccagc cacacagccg ctggtgcagc aggcgggcgg tttcgctgtc    420
cagcgcccgc acctcgtcca tgctgatgcg cacatgctgg ccgccaccca tgacggcctg    480
cgcgatcaag ggggttcaggg ccacgtacag gcgcccgtcc gcctcgtcgc tggcgtactc    540
cgacagcagc cgaaacccct gccgcttgcg gccattctgg gcgatgatgg ataccttcca    600
aaggcgctcg atgcagtcct gtatgtgctt gagcgcccca ccactatcga cctctgcccc    660
gatttccttt gccagcgccc gatagctacc tttgaccaca tggcattcag cggtgacggc    720
ctcccacttg ggttccagga acagccggag ctgccgtccg ccttcggtct tgggttccgg    780
gccaagcact aggccattag gcccagccat ggccaccagc ccttgcagga tgcgcagatc    840
atcagcgccc agcggctccg ggccgctgaa ctcgatccgc ttgccgtcgc cgtagtcata    900
cgtcacgtcc agcttgctgc gcttgcgctc gccccgcttg agggcacgga acaggccggg    960
ggccagacag tgcgccgggt cgtgccggac gtggctgagg ctgtgcttgt tcttaggctt   1020
caccacgggg cacccccttg ctcttgcgct gcctctccag cacggcgggc ttgagcaccc   1080
cgccgtcatg ccgcctgaac caccgatcag cgaacggtgc gccatagttg gccttgctca   1140
caccgaagcg gacgaagaac cggcgctggt cgtcgtccac accccattcc tcggcctcgg   1200
cgctggtcat gctcgacagg taggactgcc agcggatgtt atcgaccagt accgagctgc   1260
cccggctggc ctgctgctgg tcgcctgcgc ccatcatggc cgcgcccttg ctggcatggt   1320
gcaggaacac gatagagcac ccggtatcgg cggcgatggc ctccatgcga ccgatgacct   1380
gggccatggg gccgctggcg ttttcttcct cgatgtggaa ccggcgcagc gtgtccagca   1440
ccatcaggcg gcggccctcg gcggcgcgct tgaggccgtc gaaccactcc ggggccatga   1500
tgttgggcag gctgccgatc agcggctgga tcagcaggcc gtcagccacg gcttgccgtt   1560
cctcggcgct gaggtgcgcc ccaagggcgt gcaggcggtg atgaatggcg gtgggcgggt   1620
cttcggcggg caggtagatc accgggccgg tgggcagttc gcccacctcc agcagatccg   1680
gcccgcctgc aatctgtgcg gccagttgca gggccagcat ggatttaccg gcaccaccgg   1740
gcgacaccag cgccccgacc gtaccggcca ccatgttggg caaaacgtag tccagcggtg   1800
gcggcgctgc tgcgaacgcc tccagaatat tgataggctt atgggtagcc attgattgcc   1860
tcctttgcag gcagttggtg gttaggcgct ggcggggtca ctaccccgc cctgcgccgc   1920
tctgagttct tccaggcact cgcgcagcgc ctcgtattcg tcgtcggtca gccagaactt   1980
gcgctgacgc atccctttgg ccttcatgcg ctcggcatat cgcgcttggc gtacagcgtc   2040
agggctggcc agcaggtcgc cggtctgctt gtccttttgg tctttcatat cagtcaccga   2100
gaaacttgcc ggggccgaaa ggcttgtctt cgcggaacaa ggacaaggtg cagccgtcaa   2160
ggttaaggct ggccatatca gcgactgaaa agcggccagc ctcggccttg tttgacgtat   2220
aaccaaagcc accgggcaac caatagccct tgtcactttt gatcaggtag accgaccctg   2280
```

```
aagcgctttt ttcgtattcc ataaaacccc cttctgtgcg tgagtactca tagtataaca   2340
ggcgtgagta ccaacgcaag cactacatgc tgaaatctgg cccgcccctg tccatgcctc   2400
gctggcgggg tgccggtgcc cgtgccagct cggcccgcgc aagctggacg ctgggcagac   2460
ccatgacctt gctgacggtg cgctcgatgt aatccgcttc gtggccgggc ttgcgctctg   2520
ccagcgctgg gctggcctcg gccatggcct tgccgatttc ctcggcactg cggccccggc   2580
tggccagctt ctgcgcggcg ataaagtcgc acttgctgag gtcatgaccg aagcgcttga   2640
ccagcccggc catctcgctg cggtactcgt ccagcgccgt gcgccggtgg cggctaagct   2700
gccgctcggg cagttcgagg ctggccagcc tgcgggcctt ctcctgctgc cgctgggcct   2760
gctcgatctg ctggccagcc tgctgcacca gcgccgggcc agcggtggcg gtcttgccct   2820
tggattcacg cagcagcacc cacggctgat aaccggcgcg ggtggtgtgc ttgtccttgc   2880
ggttggtgaa gcccgccaag cggccatagt ggcggctgtc ggcgctggcc gggtcggcgt   2940
cgtactcgct ggccagcgtc cgggcaatct gcccccgaag ttcaccgcct gcggcgtcgg   3000
ccaccttgac ccatgcctga tagttcttcg ggctggtttc cactaccagg gcaggctccc   3060
ggccctcggc tttcatgtca tccaggtcaa actcgctgag gtcgtccacc agcaccagac   3120
catgccgctc ctgctcggcg ggcctgatat acacgtcatt gccctgggca ttcatccgct   3180
tgagccatgg cgtgttctgg agcacttcgg cggctgacca ttcccggttc atcatctggc   3240
cggtgggtgc gtccctgacg ccgatatcga agcgctcaca gcccatggcc ttgagctgtc   3300
ggcctatggc ctgcaaagtc ctgtcgttct tcatcgggcc accaagcgca gccagatcga   3360
gccgtcctcg gttgtcagtg gcgtcaggtc gagcaagagc aacgatgcga tcagcagcac   3420
caccgtaggc atcatggaag ccagcatcac ggttagccat agcttccagt gccacccccg   3480
cgacgcgctc cgggcgctct gcgcggcgct gctcacctcg gcggctacct cccgcaactc   3540
tttggccagc tccacccatg ccgcccctgt ctggcgctgg gctttcagcc actccgccgc   3600
ctgcgcctcg ctggcctgct tggtctggct catgacctgc cgggcttcgt cggccagtgt   3660
cgccatgctc tgggccagcg gttcgatctg ctccgctaac tcgttgatgc ctctggattt   3720
cttcactctg tcgattgcgt tcatggtcta ttgcctcccg gtattcctgt aagtcgatga   3780
tctgggcgtt ggcggtgtcg atgttcaggg ccacgtctgc ccggtcggtg cggatgcccc   3840
ggccttccat ctccaccacg ttcggcccca ggtgaacacc gggcaggcgc tcgatgccct   3900
gcgcctcaag tgttctgtgg tcaatgcggg cgtcgtggcc agcccgctct aatgcccggt   3960
tggcatggtc ggcccatgcc tcgcgggtct gctcaagcca tgccttgggc ttgagcgctt   4020
cggtcttctg tgccccgccc ttctccgggg tcttgccgtt gtaccgcttg aaccactgag   4080
cggcgggccg ctcgatgccg tcattgatcc gctcggagat catcaggtgg cagtgcgggt   4140
tctcgccgcc accggcatgg atggccagcg tatacggcag gcgctcggca ccggtcaggt   4200
gctgggcgaa ctcggacgcc agcgccttct gctggtcgag ggtcagctcg accggcaggg   4260
caaattcgac ctccttgaac agccgcccat tggcgcgttc atacaggtcg gcagcatccc   4320
agtagtcggc gggccgctcg acgaactccg gcatgtgccc ggattcggcg tgcaagactt   4380
catccatgtc gcgggcatac ttgccttcgc gctggatgta gtcggccttg gccctggccg   4440
attggccgcc cgacctgctg ccggttttcg ccgtaaggtg ataaatcgcc atgctgcctc   4500
gctgttgctt ttgcttttcg gctccatgca atggccctcg gagagcgcac cgcccgaagg   4560
gtggccgtta ggccagtttc tcgaagagaa accggtaagt gcgccctccc ctacaaagta   4620
```

```
gggtcgggat tgccgccgct gtgcctccat gatagcctac gagacagcac attaacaatg   4680
gggtgtcaag atggttaagg ggagcaacaa ggcggcggat cggctggcca agctcgaaga   4740
acaacgagcg cgaatcaatg ccgaaattca gcgggagcgg gcaagggaac agcagcaaga   4800
gcgcaagaac gaaacaaggc gcaaggtgct ggtgggggcc atgattttgg ccaaggtgaa   4860
cagcagcgag tggccggagg atcggctcat ggcggcaatg gatgcgtacc ttgaacgcga   4920
ccacgaccgc gccttgttcg gtctgccgcc acgccagaag gatgagccgg gctgaatgat   4980
cgaccgagac aggccctgcg gggctgcaca cgcgcccccca cccttcgggt agggggaaag   5040
gccgctaaag cggctaaaag cgctccagcg tatttctgcg ggtttggtg tggggtttag   5100
cgggctttgc ccgcctttcc ccctgccgcg cagcggtggg gcggtgtgta gcctagcgca   5160
gcgaatagac cagctatccg gcctctggcc gggcatattg ggcaagggca gcagcgcccc   5220
acaagggcgc tgataaccgc gcctagtgga ttattcttag ataatcatgg atggattttt   5280
ccaacacccc gccagccccc gcccctgctg ggtttgcagg tttgggggcg tgacagttat   5340
tgcaggggtt cgtgacagtt attgcagggg ggcgtgacag ttattgcagg ggttcgtgac   5400
agttagtacg ggagtgacgg gcactggctg gcaatgtcta gcaacggcag gcatttcggc   5460
tgagggtaaa agaactttcc gctaagcgat agactgtatg taaacacagt attgcaagga   5520
cgcggaacat gcctcatgtg gcggccagga cggccagccg ggatcgggat actggtcgtt   5580
accagagcca ccgacccgag caaacccttc tctatcagat cgttgacgag tattacccgg   5640
cattcgctgc gcttatggca gagcagggaa aggaattgcc gggctatgtg caacgggaat   5700
ttgaagaatt tctccaatgc gggcggctgg agcatggctt tctacgggtt cgctgcgagt   5760
cttgccacgc cgagcacctg gtcgctttca gaaatcaatc taaagtatat atgagtaaac   5820
ttggtctgac aggcccctga attcgcatct agatggtaga gccacaaaca gccggtacaa   5880
gcaacgatct ccaggaccat ctgaatcatg cgcggatgac acgaactcac gacggcgatc   5940
acagacatta acccacagta cagacactgc gacaacgtgg caattcgtcg caataccgtc   6000
tcactgaact ggccgataat tgcagacgaa cgttatcaaa aagagtattg acttaaagtc   6060
taacctatag gatacttaca gccatcgaga gggacacggc gaggaattgt gagcggataa   6120
caattccata cagaaacaga ggagatatta catatgagta aaggagaaga gcttttcaca   6180
ggagttgtcc caatcctcgt ggaattagac ggtgatgtta atgggcacaa gttctctgtc   6240
agtggagagg gtgaaggcga cgcaacatat ggcaagctga cccttaaatt tatttgcacc   6300
acgggtaaac tacctgttcc atggccaaca ctggtcacta cgttcgggta tggggttcag   6360
tgctttgcgc gctacccaga tcacatgaaa cagcacgact ttttcaagag tgcaatgccc   6420
gaaggctatg tacaggagag aaccatcttt tttaaggatg acggcaacta taagacacgc   6480
gccgaagtga agttcgaggg tgataccctt gttaatagaa tcgagttaaa gggtattgac   6540
tttaaggaag atggaaatat tttaggccac aaactggaat ataactataa ctcccataat   6600
gtgtacatta tggccgacaa gcaaaagaac ggtatcaagg ttaacttcaa gatcagacac   6660
aacattgagg atggaagcgt tcaactagcc gaccattacc aacaaaacac cccaattggc   6720
gatgggcctg tgctgttacc agacaaccat tacctgtcca ctcaatctgc cctttcgaaa   6780
gatcccaacg aaaagcgcga ccacatggtc cttcttgagt ttgtcacggc tgctgggatt   6840
acacacggca tggatgaact atacaaataa atccgtaatc gttaatccgc aaataacgta   6900
aaaacccgct tcggcgggtt tttttatggg gggagtttag ggaaagagca tttgtcagct   6960
gccaatgaga cgacggggtc atcacggctc atcatgcgcc aaacaaatgt gtgcaataca   7020
```

cgctcggatg actgcatgat gaccgcactg actggggaca gcagatccac ctaagcctgt 7080
gagagaagca gacacccgac agatcaaggc agttaactag tgcactgcag tacaccaggc 7140
atcaaataaa acgaaaggct cagtcgaaag actgggcctt tcgttttatc tgttgtttgt 7200
cggtgaacgc tctctactag agtcacactg gctcaccttc gggtgggcct ttctgcgttt 7260
ataccgagcg gccgcgtgtt acaaccaatt aaccaattct gattagaaaa actcatcgag 7320
catcaaatga aactgcaatt tattcatatc aggattatca ataccatatt tttgaaaaag 7380
ccgtttctgt aatgaaggag aaaactcacc gaggcagttc cataggatgg caagatcctg 7440
gtatcggtct gcgattccga ctcgtccaac atcaatacaa cctattaatt tcccctcgtc 7500
aaaaataagg ttatcaagtg agaaatcacc atgagtgacg actgaatccg gtgagaatgg 7560
caaaagctta tgcatttctt tccagacttg ttcaacaggc cagccattac gctcgtcatc 7620
aaaatcactc gcatcaacca aaccgttatt cattcgtgat tgcgcctgag cgaggcgaaa 7680
tacgcgatcg ctgttaaaag gacaattaca aacaggaatc gaatgcaacc ggcgcaggaa 7740
cactgccagc gcatcaacaa tattttcacc tgaatcagga tattcttcta atacctggaa 7800
tgctgttttc ccggggatcg cagtggtgag taaccatgca tcatcaggag tacggataaa 7860
atgcttgatg gtcggaagag gcataaattc cgtcagccag tttagtctga ccatctcatc 7920
tgtaacatca ttggcaacgc tacctttgcc atgtttcaga aacaactctg gcgcatcggg 7980
cttcccatac aatcgataga ttgtcgcacc tgattgcccg acattatcgc gagcccattt 8040
atacccatat aaatcagcat ccatgttgga atttaatcgc ggcctggagc aagacgtttc 8100
ccgttgaata tggctcat 8118

<210> SEQ ID NO 80
<211> LENGTH: 8272
<212> TYPE: DNA
<213> ORGANISM: Artificial Sequence
<220> FEATURE:
<223> OTHER INFORMATION: Chemically Synthesized, pBTK520

<400> SEQUENCE: 80
acgctacttg cattacagct tacgaaccga acaggcttat gtccactggg ttcgtgcctt 60
catccgtttc cacggtgtgc gtcacccggc aaccttgggt agcagcgaag tcgaggcatt 120
tctgtcctgg ctggtcatga ccaaaatccc ttaacgtgag tcagcctgcc gccttgggcc 180
gggtgatgtc gtacttgccc gccgcgaact cggttaccgt ccagcccagc gcgaccagct 240
ccggcaacgc ctcgcgcacc cgcttgcggc gcttgcgcat ggtcgaacca ctggcctctg 300
acggccagac atagccgcac aaggtatcta tggaagcctt gccggttttg ccggggtcga 360
tccagccaca cagccgctgg tgcagcaggc gggcggtttc gctgtccagc gcccgcacct 420
cgtccatgct gatgcgcaca tgctggccgc cacccatgac ggcctgcgcg atcaaggggt 480
tcagggccac gtacaggcgc ccgtccgcct cgtcgctggc gtactccgac agcagccgaa 540
acccctgccg cttgcggcca ttctgggcga tgatggatac cttccaaagg cgctcgatgc 600
agtcctgtat gtgcttgagc gccccaccac tatcgacctc tgccccgatt tcctttgcca 660
gcgcccgata gctacctttg accacatggc attcagcggt gacggcctcc cacttgggtt 720
ccaggaacag ccggagctgc cgtccgcctt cggtcttggg ttccgggcca agcactaggc 780
cattaggccc agccatggcc accagccctt gcaggatgcg cagatcatca gcgcccagcg 840
gctccgggcc gctgaactcg atccgcttgc cgtcgccgta gtcatacgtc acgtccagct 900

```
tgctgcgctt gcgctcgccc cgcttgaggg cacggaacag gccgggggcc agacagtgcg    960
ccgggtcgtg ccggacgtgg ctgaggctgt gcttgttctt aggcttcacc acggggcacc   1020
cccttgctct tgcgctgcct ctccagcacg gcgggcttga gcaccccgcc gtcatgccgc   1080
ctgaaccacc gatcagcgaa cggtgcgcca tagttggcct tgctcacacc gaagcggacg   1140
aagaaccggc gctggtcgtc gtccacaccc cattcctcgg cctcggcgct ggtcatgctc   1200
gacaggtagg actgccagcg gatgttatcg accagtaccg agctgccccg gctggcctgc   1260
tgctggtcgc ctgcgcccat catggccgcg ccccttgctgg catggtgcag gaacacgata   1320
gagcacccgg tatcggcggc gatggcctcc atgcgaccga tgacctgggc catggggccg   1380
ctggcgtttt cttcctcgat gtggaaccgg cgcagcgtgt ccagcaccat caggcggcgg   1440
ccctcggcgg cgcgcttgag gccgtcgaac cactccgggg ccatgatgtt gggcaggctg   1500
ccgatcagcg gctggatcag caggccgtca gccacggctt gccgttcctc ggcgctgagg   1560
tgcgccccaa gggcgtgcag gcggtgatga atggcggtgg gcgggtcttc ggcgggcagg   1620
tagatcaccg ggccggtggg cagttcgccc acctccagca gatccggccc gcctgcaatc   1680
tgtgcggcca gttgcagggc cagcatggat ttaccggcac caccgggcga caccagcgcc   1740
ccgaccgtac cggccaccat gttgggcaaa acgtagtcca gcggtggcgg cgctgctgcg   1800
aacgcctcca gaatattgat aggcttatgg gtagccattg attgcctcct ttgcaggcag   1860
ttggtggtta ggcgctggcg gggtcactac ccccgccctg cgccgctctg agttcttcca   1920
ggcactcgcg cagcgcctcg tattcgtcgt cggtcagcca gaacttgcgc tgacgcatcc   1980
ctttggcctt catgcgctcg gcatatcgcg cttggcgtac agcgtcaggg ctggccagca   2040
ggtcgccggt ctgcttgtcc ttttggtctt tcatatcagt caccgagaaa cttgccgggg   2100
ccgaaaggct tgtcttcgcg gaacaaggac aaggtgcagc cgtcaaggtt aaggctggcc   2160
atatcagcga ctgaaaagcg gccagcctcg gccttgtttg acgtataacc aaagccaccg   2220
ggcaaccaat agcccttgtc acttttgatc aggtagaccg accctgaagc gcttttttcg   2280
tattccataa aaccccccttc tgtgcgtgag tactcatagt ataacaggcg tgagtaccaa   2340
cgcaagcact acatgctgaa atctggcccg cccctgtcca tgcctcgctg gcggggtgcc   2400
ggtgcccgtg ccagctcggc ccgcgcaagc tggacgctgg gcagacccat gaccttgctg   2460
acggtgcgct cgatgtaatc cgcttcgtgg ccgggcttgc gctctgccag cgctgggctg   2520
gcctcggcca tggccttgcc gatttcctcg gcactgcggc cccggctggc cagcttctgc   2580
gcggcgataa agtcgcactt gctgaggtca tgaccgaagc gcttgaccag cccggccatc   2640
tcgctgcggt actcgtccag cgccgtgcgc cggtggcggc taagctgccg ctcgggcagt   2700
tcgaggctgg ccagcctgcg ggccttctcc tgctgccgct gggcctgctc gatctgctgg   2760
ccagcctgct gcaccagcgc cgggccagcg gtggcggtct tgcccttgga ttcacgcagc   2820
agcacccacg gctgataacc ggcgcgggtg gtgtgcttgt ccttgcggtt ggtgaagccc   2880
gccaagcggc catagtggcg gctgtcggcg ctggccgggt cggcgtcgta ctcgctggcc   2940
agcgtccggg caatctgccc ccgaagttca ccgcctgcgg cgtcggccac cttgacccat   3000
gcctgatagt tcttcgggct ggtttccact accagggcag gctcccggcc ctcggctttc   3060
atgtcatcca ggtcaaactc gctgaggtcg tccaccagca ccagaccatg ccgctcctgc   3120
tcggcgggcc tgatatacac gtcattgccc tgggcattca tccgcttgag ccatggcgtg   3180
ttctggagca cttcggcggc tgaccattcc cggttcatca tctggccggt gggtgcgtcc   3240
ctgacgccga tatcgaagcg ctcacagccc atggccttga gctgtcggcc tatggcctgc   3300
```

```
aaagtcctgt cgttcttcat cgggccacca agcgcagcca gatcgagccg tcctcggttg   3360
tcagtggcgt caggtcgagc aagagcaacg atgcgatcag cagcaccacc gtaggcatca   3420
tggaagccag catcacggtt agccatagct tccagtgcca cccccgcgac gcgctccggg   3480
cgctctgcgc ggcgctgctc acctcggcgg ctacctcccg caactctttg gccagctcca   3540
cccatgccgc ccctgtctgg cgctgggctt tcagccactc cgccgcctgc gcctcgctgg   3600
cctgcttggt ctggctcatg acctgccggg cttcgtcggc cagtgtcgcc atgctctggg   3660
ccagcggttc gatctgctcc gctaactcgt tgatgcctct ggatttcttc actctgtcga   3720
ttgcgttcat ggtctattgc ctcccggtat tcctgtaagt cgatgatctg ggcgttggcg   3780
gtgtcgatgt tcagggccac gtctgcccgg tcggtgcgga tgccccggcc ttccatctcc   3840
accacgttcg gccccaggtg aacaccgggc aggcgctcga tgccctgcgc ctcaagtgtt   3900
ctgtggtcaa tgcgggcgtc gtggccagcc cgctctaatg cccggttggc atggtcggcc   3960
catgcctcgc gggtctgctc aagccatgcc ttgggcttga gcgcttcggt cttctgtgcc   4020
ccgcccttct ccggggtctt gccgttgtac cgcttgaacc actgagcggc gggccgctcg   4080
atgccgtcat tgatccgctc ggagatcatc aggtggcagt gcgggttctc gccgccaccg   4140
gcatggatgg ccagcgtata cggcaggcgc tcggcaccgg tcaggtgctg ggcgaactcg   4200
gacgccagcg ccttctgctg gtcgagggtc agctcgaccg gcagggcaaa ttcgacctcc   4260
ttgaacagcc gcccattggc gcgttcatac aggtcggcag catcccagta gtcggcgggc   4320
cgctcgacga actccggcat gtgcccggat tcggcgtgca agacttcatc catgtcgcgg   4380
gcatacttgc cttcgcgctg gatgtagtcg gccttggccc tggccgattg gccgcccgac   4440
ctgctgccgg ttttcgccgt aaggtgataa atcgccatgc tgcctcgctg ttgcttttgc   4500
ttttcggctc catgcaatgg ccctcggaga gcgcaccgcc cgaagggtgg ccgttaggcc   4560
agtttctcga agagaaaccg gtaagtgcgc cctcccctac aaagtagggt cgggattgcc   4620
gccgctgtgc ctccatgata gcctacgaga cagcacatta acaatggggt gtcaagatgg   4680
ttaaggggag caacaaggcg gcggatcggc tggccaagct cgaagaacaa cgagcgcgaa   4740
tcaatgccga aattcagcgg gagcgggcaa gggaacagca gcaagagcgc aagaacgaaa   4800
caaggcgcaa ggtgctggtg gggggccatga ttttggccaa ggtgaacagc agcgagtggc   4860
cggaggatcg gctcatggcg gcaatggatg cgtaccttga acgcgaccac gaccgcgcct   4920
tgttcggtct gccgccacgc cagaaggatg agccgggctg aatgatcgac cgagacaggc   4980
cctgcggggc tgcacacgcg cccccaccct tcgggtaggg ggaaaggccg ctaaagcggc   5040
taaaagcgct ccagcgtatt tctgcggggt ttggtgtggg gtttagcggg ctttgcccgc   5100
ctttccccct gccgcgcagc ggtggggcgg tgtgtagcct agcgcagcga atagaccagc   5160
tatccggcct ctggccgggc atattgggca agggcagcag cgccccacaa gggcgctgat   5220
aaccgcgcct agtggattat tcttagataa tcatggatgg atttttccaa caccccgcca   5280
gcccccgccc ctgctgggtt tgcaggtttg ggggcgtgac agttattgca ggggttcgtg   5340
acagttattg caggggggcg tgacagttat tgcaggggtt cgtgacagtt agtacgggag   5400
tgacgggcac tggctggcaa tgtctagcaa cggcaggcat ttcggctgag ggtaaaagaa   5460
ctttccgcta agcgatagac tgtatgtaaa cacagtattg caaggacgcg gaacatgcct   5520
catgtggcgg ccaggacggc cagccgggat cgggatactg gtcgttacca gagccaccga   5580
cccgagcaaa cccttctcta tcagatcgtt gacgagtatt acccggcatt cgctgcgctt   5640
```

```
atggcagagc agggaaagga attgccgggc tatgtgcaac gggaatttga agaatttctc   5700
caatgcgggc ggctggagca tggctttcta cgggttcgct gcgagtcttg ccacgccgag   5760
cacctggtcg ctttcagaaa tcaatctaaa gtatatatga gtaaacttgg tctgacaggc   5820
ccctgaattc gcatctagat ggtagagcca caaacagccg gtacaagcaa cgatctccag   5880
gaccatctga atcatgcgcg gatgacacga actcacgacg gcgatcacag acattaaccc   5940
acagtacaga cactgcgaca acgtggcaat tcgtcgcaat accgtctcac tgaactggcc   6000
gataattgca gacgaacgtt atcaaaaaga gtattgactt aaagtctaac ctataggata   6060
cttacagcca tcgagaggga cacggcgagg aattgtgagc ggataacaat tccatacaga   6120
aacagaggag atattacata tgagtaaagg agaagagctt ttcacaggag ttgtcccaat   6180
cctcgtggaa ttagacggtg atgttaatgg gcacaagttc tctgtcagtg gagagggtga   6240
aggcgacgca acatatggca agctgaccct taaatttatt tgcaccacgg gtaaactacc   6300
tgttccatgg ccaacactgg tcactacgtt cgggtatggg gttcagtgct ttgcgcgcta   6360
cccagatcac atgaaacagc acgacttttt caagagtgca atgcccgaag gctatgtaca   6420
ggagagaacc atctttttta aggatgacgg caactataag acacgcgccg aagtgaagtt   6480
cgagggtgat acccttgtta atagaatcga gttaaagggt attgacttta aggaagatgg   6540
aaatatttta ggccacaaac tggaatataa ctataactcc cataatgtgt acattatggc   6600
cgacaagcaa aagaacggta tcaaggttaa cttcaagatc agacacaaca ttgaggatgg   6660
aagcgttcaa ctagccgacc attaccaaca aaacacccca attggcgatg ggcctgtgct   6720
gttaccagac aaccattacc tgtccactca atctgccctt tcgaaagatc ccaacgaaaa   6780
gcgcgaccac atggtccttc ttgagtttgt cacggctgct gggattacac acggcatgga   6840
tgaactatac aaataaatcc gtaatcgtta atccgcaaat aacgtaaaaa cccgcttcgg   6900
cgggtttttt tatgggggga gtttagggaa agagcatttg tcagctgcca atgagacgac   6960
ggggtcatca cggctcatca tgcgccaaac aaatgtgtgc aatacacgct cggatgactg   7020
catgatgacc gcactgactg gggacagcag atccacctaa gcctgtgaga gaagcagaca   7080
cccgacagat caaggcagtt aactagtgca ctgcagtaca ccaggcatca aataaaacga   7140
aaggctcagt cgaaagactg ggcctttcgt tttatctgtt gtttgtcggt gaacgctctc   7200
tactagagtc acactggctc accttcgggt gggcctttct gcgtttatac cgagcggccg   7260
cttatttgcc gactaccttg gtgatctcgc ctttcacgta gtggacaaat tcttccaact   7320
gatctgcgcg cgaggccaag cgatcttctt cttgtccaag ataagcctgt ctagcttcaa   7380
gtatgacggg ctgatactgg gccggcaggc gctccattgc ccagtcggca gcgacatcct   7440
tcggcgcgat tttgccggtt actgcgctgt accaaatgcg ggacaacgta agcactacat   7500
ttcgctcatc gccagcccag tcgggcggcg agttccatag cgttaaggtt tcatttagcg   7560
cctcaaatag atcctgttca ggaaccggat caaagagttc ctccgccgct ggacctacca   7620
aggcaacgct atgttctctt gcttttgtca gcaagatagc cagatcaatg tcgatcgtgg   7680
ctggctcgaa gatacccgca agaatgtcat tgcgctgcca ttctccaaat tgcagttcgc   7740
gcttagctgg ataacgccac ggaatgatgt cgtcgtgcac aacaatggtg acttctacag   7800
cgcggagaat ctcgctctct ccaggggaag ccgaagtttc caaaaggtcg ttgatcaaag   7860
ctcgccgcgt tgtttcatca agccttacgg tcaccgtaac cagcaaatca atatcactgt   7920
gtggcttcag gccgccatcc actgcggagc cgtacaaatg tacggccagc aacgtcggtt   7980
cgagatggcg ctcgatgacg ccaactacct ctgatagttg agtcgatact tcggcgatca   8040
```

ccgcttccct cataatgttt aactttgttt tagggcgact gccctgctgc gtaacatcgt 8100
tgctgctcca taacatcaaa catcgaccca cggcgtaacg cgcttgctgc ttggatgccc 8160
gaggcataga ctgtacccca aaaaaacagt cataacaagc catgaaaacc gccactgcgc 8220
cgttaccacc gctgcgttcg gtcaaggttc tggaccagtt gcgtgagcgc at 8272

<210> SEQ ID NO 81
<211> LENGTH: 11299
<212> TYPE: DNA
<213> ORGANISM: Artificial Sequence
<220> FEATURE:
<223> OTHER INFORMATION: Chemically Synthesized, pBTK549

<400> SEQUENCE: 81
gcccgcgcaa gctggacgct gggcagaccc atgaccttgc tgacggtgcg ctcgatgtaa 60
tccgcttcgt ggccgggctt gcgctctgcc agcgctgggc tggcctcggc catggccttg 120
ccgatttcct cggcactgcg gccccggctg gccagcttct gcgcggcgat aaagtcgcac 180
ttgctgaggt catgaccgaa gcgcttgacc agcccggcca tctcgctgcg gtactcgtcc 240
agcgccgtgc gccggtggcg gctaagctgc cgctcgggca gttcgaggct ggccagcctg 300
cgggccttct cctgctgccg ctgggcctgc tcgatctgct ggccagcctg ctgcaccagc 360
gccgggccag cggtggcggt cttgcccttg gattcacgca gcagcaccca cggctgataa 420
ccggcgcggg tggtgtgctt gtccttgcgg ttggtgaagc ccgccaagcg gccatagtgg 480
cggctgtcgg cgctggccgg gtcggcgtcg tactcgctgg ccagcgtccg ggcaatctgc 540
ccccgaagtt caccgcctgc ggcgtcggcc accttgaccc atgcctgata gttcttcggg 600
ctggtttcca ctaccagggc aggctcccgg ccctcggctt tcatgtcatc caggtcaaac 660
tcgctgaggt cgtccaccag caccagacca tgccgctcct gctcggcggg cctgatatac 720
acgtcattgc cctgggcatt catccgcttg agccatggcg tgttctggag cacttcggcg 780
gctgaccatt cccggttcat catctggccg gtgggtgcgt ccctgacgcc gatatcgaag 840
cgctcacagc ccatggcctt gagctgtcgg cctatggcct gcaaagtcct gtcgttcttc 900
atcgggccac caagcgcagc cagatcgagc cgtcctcggt tgtcagtggc gtcaggtcga 960
gcaagagcaa cgatgcgatc agcagcacca ccgtaggcat catggaagcc agcatcacgg 1020
ttagccatag cttccagtgc cacccccgcg acgcgctccg ggcgctctgc gcggcgctgc 1080
tcacctcggc ggctacctcc cgcaactctt tggccagctc cacccatgcc gcccctgtct 1140
ggcgctgggc tttcagccac tccgccgcct gcgcctcgct ggcctgcttg gtctggctca 1200
tgacctgccg ggcttcgtcg gccagtgtcg ccatgctctg ggccagcggt tcgatctgct 1260
ccgctaactc gttgatgcct ctggatttct tcactctgtc gattgcgttc atggtctatt 1320
gcctcccggt attcctgtaa gtcgatgatc tgggcgttgg cggtgtcgat gttcagggcc 1380
acgtctgccc ggtcggtgcg gatgccccgg ccttccatct ccaccacgtt cggccccagg 1440
tgaacaccgg gcaggcgctc gatgccctgc gcctcaagtg ttctgtggtc aatgcgggcg 1500
tcgtggccag cccgctctaa tgcccggttg gcatggtcgg cccatgcctc gcgggtctgc 1560
tcaagccatg ccttgggctt gagcgcttcg gtcttctgtg ccccgccctt ctccggggtc 1620
ttgccgttgt accgcttgaa ccactgagcg gcgggccgct cgatgccgtc attgatccgc 1680
tcggagatca tcaggtggca gtgcgggttc tcgccgccac cggcatggat ggccagcgta 1740
tacggcaggc gctcggcacc ggtcaggtgc tgggcgaact cggacgccag cgccttctgc 1800

```
tggtcgaggg tcagctcgac cggcagggca aattcgacct ccttgaacag ccgcccattg   1860
gcgcgttcat acaggtcggc agcatcccag tagtcggcgg gccgctcgac gaactccggc   1920
atgtgcccgg attcggcgtg caagacttca tccatgtcgc gggcatactt gccttcgcgc   1980
tggatgtagt cggccttggc cctggccgat tggccgcccg acctgctgcc ggttttcgcc   2040
gtaaggtgat aaatcgccat gctgcctcgc tgttgctttt gcttttcggc tccatgcaat   2100
ggccctcgga gagcgcaccg cccgaagggt ggccgttagg ccagtttctc gaagagaaac   2160
cggtaagtgc gccctcccct acaaagtagg gtcgggattg ccgccgctgt gcctccatga   2220
tagcctacga gacagcacat taacaatggg gtgtcaagat ggttaagggg agcaacaagg   2280
cggcggatcg gctggccaag ctcgaagaac aacgagcgcg aatcaatgcc gaaattcagc   2340
gggagcgggc aagggaacag cagcaagagc gcaagaacga aacaaggcgc aaggtgctgg   2400
tgggggccat gattttggcc aaggtgaaca gcagcgagtg gccggaggat cggctcatgg   2460
cggcaatgga tgcgtacctt gaacgcgacc acgaccgcgc cttgttcggt ctgccgccac   2520
gccagaagga tgagccgggc tgaatgatcg accgagacag gccctgcggg gctgcacacg   2580
cgcccccacc cttcgggtag ggggaaaggc cgctaaagcg gctaaaagcg ctccagcgta   2640
tttctgcggg gtttggtgtg ggtttagcg ggctttgccc gcctttcccc ctgccgcgca   2700
gcggtggggc ggtgtgtagc ctagcgcagc gaatagacca gctatccggc ctctggccgg   2760
gcatattggg caagggcagc agcgccccac aagggcgctg ataaccgcgc ctagtggatt   2820
attcttagat aatcatggat ggatttttcc aacaccccgc cagcccccgc ccctgctggg   2880
tttgcaggtt tgggggcgtg acagttattg caggggttcg tgacagttat tgcagggggg   2940
cgtgacagtt attgcagggg ttcgtgacag ttagtacggg agtgacgggc actggctggc   3000
aatgtctagc aacggcaggc atttcggctg agggtaaaag aactttccgc taagcgatag   3060
actgtatgta aacacagtat tgcaaggacg cggaacatgc ctcatgtggc ggccaggacg   3120
gccagccggg atcgggatac tggtcgttac cagagccacc gacccgagca aacccttctc   3180
tatcagatcg ttgacgagta ttacccggca ttcgctgcgc ttatggcaga gcagggaaag   3240
gaattgccgg gctatgtgca acgggaattt gaagaatttc tccaatgcgg gcggctggag   3300
catggctttc tacgggttcg ctgcgagtct tgccacgccg agcacctggt cgctttcaga   3360
aatcaatcta aagtatatat gagtaaactt ggtctgacag gcccctgaat tcgcatctag   3420
acagggtctt gctctgtcac cctcaagaca acctgcccct caacgtaacg ggcttcccat   3480
acaatcgatt agagattgtc atcgcacctg attgcccgac attatcgcga gttataaccc   3540
atttataccc atataaatca gcatccatgt tggaatttaa tcgcgtgagc ctatgaacac   3600
gattaacatc gctaagaacg acttctctga catcgaactg gctgctatcc cgttcaacac   3660
tctggctgac cattacggtg agcgtttagc tcgcgaacag ttggcccttg agcatgagtc   3720
ttacgagatg ggtgaagcac gcttccgcaa gatgtttgag cgtcaactta aagctggtga   3780
ggttgcggat aacgctgccg ccaagcctct catcactacc ctactcccta agatgattgc   3840
acgcatcaac gactggtttg aggaagtgaa agctaagcgc ggcaagcgcc cgacagcctt   3900
ccagttcctg caagaaatca agccggaagc cgtagcgtac atcaccatta agaccactct   3960
ggcttgccta accagtgctg acaatacaac cgttcaggct gtagcaagcg caatcggtcg   4020
ggccattgag gacgaggctc gcttcggtcg tatccgtgac cttgaagcta agcacttcaa   4080
gaaaaacgtt gaggaacaac tcaacaagcg cgtagggcac gtctacaaga aagcatttat   4140
gcaagttgtc gaggctgaca tgctctctaa gggtctactc ggtggcgagg cgtggtcttc   4200
```

```
gtggcataag gaagactcta ttcatgtagg agtacgctgc atcgagatgc tcattgagtc   4260
aaccggaatg gttagcttac accgccaaaa tgctggcgta gtaggtcaag actctgagac   4320
tatcgaactc gcacctgaat acgctgaggc tatcgcaacc cgtgcaggtg cgctggctgg   4380
catctctccg atgttccaac cttgcgtagt tcctcctaag ccgtggactg gcattactgg   4440
tggtggctat tgggctaacg gtcgtcgtcc tctggcgctg gtgcgtactc acagtaagaa   4500
agcactgatg cgctacgaag acgtttacat gcctgaggtg tacaaagcga ttaacattgc   4560
gcaaaacacc gcatggaaaa tcaacaagaa agtcctagcg gtcgccaacg taatcaccaa   4620
gtggaagcat tgtccggtcg aggacatccc tgcgattgag cgtgaagaac tcccgatgaa   4680
accggaagac atcgacatga atcctgaggc tctcaccgcg tggaaacgtg ctgccgctgc   4740
tgtgtaccgc aaggacaagg ctcgcaagtc tcgccgtatc agccttgagt tcatgcttga   4800
gcaagccaat aagtttgcta accataaggc catctggttc ccttacaaca tggactggcg   4860
cggtcgtgtt tacgctgtgt caatgttcaa cccgcaaggt aacgatatga ccaaaggact   4920
gcttacgctg gcgaaaggta aaccaatcgg taaggaaggt tactactggc tgaaaatcca   4980
cggtgcaaac tgtgcgggtg tcgataaggt tccgttccct gagcgcatca agttcattga   5040
ggaaaaccac gagaacatca tggcttgcgc taagtctcca ctggagaaca cttggtgggc   5100
tgagcaagat tctccgttct gcttccttgc gttctgcttt gagtacgctg gggtacagca   5160
ccacggcctg agctataact gctcccttcc gctggcgttt gacgggtctt gctctggcat   5220
ccagcacttc tccgcgatgc tccgagatga ggtaggtggt cgcgcggtta acttgcttcc   5280
tagtgaaacc gttcaggaca tctacgggat tgttgctaag aaagtcaacg agattctaca   5340
agcagacgca atcaatggga ccgataacga agtagttacc gtgaccgatg agaacactgg   5400
tgaaatctct gagaaagtca agctgggcac taaggcactg gctggtcaat ggctggctta   5460
cggtgttact cgcagtgtga ctaagcgttc agtcatgacg ctggcttacg ggtccaaaga   5520
gttcggcttc cgtcaacaag tgctggaaga taccattcag ccagctattg attccggcaa   5580
gggtctgatg ttcactcagc cgaatcaggc tgctggatac atggctaagc tgatttggga   5640
atctgtgagc gtgacggtgg tagctgcggt tgaagcaatg aactggctta agtctgctgc   5700
taagctgctg gctgctgagg tcaaagataa gaagactgga gagattcttc gcaagcgttg   5760
cgctgtgcat tgggtaactc ctgatggttt ccctgtgtgg caggaataca agaagcctat   5820
tcagacgcgc ttgaacctga tgttcctcgg tcagttccgc ttacagccta ccattaacac   5880
caacaaagat agcgagattg atgcacacaa acaggagtct ggtatcgctc ctaactttgt   5940
acacagccaa gacggtagcc accttcgtaa gactgtagtg tgggcacacg agaagtacgg   6000
aatcgaatct tttgcactga ttcacgactc cttcggtacc attccggctg acgctgcgaa   6060
cctgttcaaa gcagtgcgcg aaactatggt tgacacatat gagtcttgtg atgtactggc   6120
tgatttctac gaccagttcg ctgaccagtt gcacgagtct caattggaca aaatgccagc   6180
acttccggct aaaggtaact tgaacctccg tgacatctta gagtcggact tcgcgttcgc   6240
gtaaatccgt aatcgttaat ccgcaaataa cgtaaaaacc cgcttcggcg ggttttttta   6300
tgggggggagt ttagggaaag agcatttgtc agctgctgat gagacggatc agcagatggg   6360
aaccggctcc tcagcctcca gagtagcgtc tcaagcagtt acagagatgt tacgaacccc   6420
caggacatcc gagaatgcga ggcgatggag ggtacaaccg ggagagtgtt caccgacaaa   6480
caacagataa aacaaaaggc ccagtcttcc gactgagcct tttgttttat ttgatgtctg   6540
```

```
gcagttcccc gccgctatct gatcatcaaa taataatttc ttcatgttga aaatctccaa   6600
aaaaaaaggc tccaaaagga gcctttaatt gtatcggttt atcagcttgc ttttacatca   6660
ctgcccgctt tccagtcggg aaacctgtcg tgccagctgc attaatgaat cggccaacgc   6720
gcggggagag gcggtttgcg tattgggcgc cagggtggtt tttcttttca ccagtgacac   6780
cggcaacagc tgattgccct tcaccgcctg gccctgagag agttgcagca agcggtccac   6840
gctggtttgc cccagcaggc gaaaatcctg tttgatggtg gttaacggcg ggatataaca   6900
tgagctgtct tcggtatcgt cgtatcccac taccgagata tccgcaccaa cgcgcagccc   6960
ggactcggta atggcgcgca ttgcgcccag cgccatctga tcgttggcaa ccagcatcgc   7020
agtgggaacg atgccctcat tcagcatttg catggtttgt tgaaaaccgg acatggcact   7080
ccagtcgcct tcccgttccg ctatcggctg aatttgattg cgagtgagat atttatgcca   7140
gccagccaga cgcagacgcg ccgagacaga acttaatggg cccgctaaca gcgcgatttg   7200
ctggtgaccc aatgcgacca gatgctccac gcccagtcgc gtaccgtctt catgggagaa   7260
aataatactg ttgatgggtg tctggtcaga gacatcaaga aataacgccg gaacattagt   7320
gcaggcagct tccacagcaa tggcatcctg gtcatccagc ggatagttaa tgatcagccc   7380
actgacgcgt tgcgcgagaa gattgtgcac cgccgcttta caggcttcga cgccgcttcg   7440
ttctaccatc gacaccacca cgctggcacc cagttgatcg gcgcgagatt taatcgccgc   7500
gacaatttgc gacggcgcgt gcagggccag actggaggtg gcaacgccaa tcagcaacga   7560
ctgtttgccc gccagttgtt gtgccacgcg gttgggaatg taattcagct ccgccatcgc   7620
cgcttccact ttttcccgcg ttttcgcaga aacgtggctg gcctggttca ccacgcggga   7680
aacggtctga taagagacac cggcatactc tgcgacatcg tataacgtta ctggtttcat   7740
gagtacctct cctgtatctt gtgtacttgc gtaccgtaat atctcctctg tttctgtata   7800
acagtactat gtgattatac cagccccctc actacatgtc aagaataaac tgccaaagcc   7860
gagcggccgc ttatttgccg actaccttgg tgatctcgcc tttcacgtag tggacaaatt   7920
cttccaactg atctgcgcgc gaggccaagc gatcttcttc ttgtccaaga taagcctgtc   7980
tagcttcaag tatgacgggc tgatactggg ccggcaggcg ctccattgcc cagtcggcag   8040
cgacatcctt cggcgcgatt ttgccggtta ctgcgctgta ccaaatgcgg gacaacgtaa   8100
gcactacatt tcgctcatcg ccagcccagt cgggcggcga gttccatagc gttaaggttt   8160
catttagcgc ctcaaataga tcctgttcag gaaccggatc aaagagttcc tccgccgctg   8220
gacctaccaa ggcaacgcta tgttctcttg cttttgtcag caagatagcc agatcaatgt   8280
cgatcgtggc tggctcgaag atacccgcaa gaatgtcatt gcgctgccat tctccaaatt   8340
gcagttcgcg cttagctgga taacgccacg gaatgatgtc gtcgtgcaca acaatggtga   8400
cttctacagc gcggagaatc tcgctctctc caggggaagc cgaagtttcc aaaaggtcgt   8460
tgatcaaagc tcgccgcgtt gtttcatcaa gccttacggt caccgtaacc agcaaatcaa   8520
tatcactgtg tggcttcagg ccgccatcca ctgcggagcc gtacaaatgt acggccagca   8580
acgtcggttc gagatggcgc tcgatgacgc caactacctc tgatagttga gtcgatactt   8640
cggcgatcac cgcttccctc ataatgttta actttgtttt agggcgactg ccctgctgcg   8700
taacatcgtt gctgctccat aacatcaaac atcgacccac ggcgtaacgc gcttgctgct   8760
tggatgcccg aggcatagac tgtaccccaa aaaaacagtc ataacaagcc atgaaaaccg   8820
ccactgcgcc gttaccaccg ctgcgttcgg tcaaggttct ggaccagttg cgtgagcgca   8880
tacgctactt gcattacagc ttacgaaccg aacaggctta tgtccactgg gttcgtgcct   8940
```

```
tcatccgttt ccacggtgtg cgtcacccgg caaccttggg tagcagcgaa gtcgaggcat   9000
ttctgtcctg gctggtcatg accaaaatcc cttaacgtga gtcagcctgc cgccttgggc   9060
cgggtgatgt cgtacttgcc cgccgcgaac tcggttaccg tccagcccag cgcgaccagc   9120
tccggcaacg cctcgcgcac ccgcttgcgg cgcttgcgca tggtcgaacc actggcctct   9180
gacggccaga catagccgca caaggtatct atggaagcct tgccggtttt gccggggtcg   9240
atccagccac acagccgctg gtgcagcagg cgggcggttt cgctgtccag cgcccgcacc   9300
tcgtccatgc tgatgcgcac atgctggccg ccacccatga cggcctgcgc gatcaagggg   9360
ttcagggcca cgtacaggcg cccgtccgcc tcgtcgctgg cgtactccga cagcagccga   9420
aacccctgcc gcttgcggcc attctgggcg atgatggata ccttccaaag gcgctcgatg   9480
cagtcctgta tgtgcttgag cgccccacca ctatcgacct ctgccccgat ttcctttgcc   9540
agcgcccgat agctaccttt gaccacatgg cattcagcgg tgacggcctc ccacttgggt   9600
tccaggaaca gccggagctg ccgtccgcct tcggtcttgg gttccgggcc aagcactagg   9660
ccattaggcc cagccatggc caccagccct tgcaggatgc gcagatcatc agcgcccagc   9720
ggctccgggc cgctgaactc gatccgcttg ccgtcgccgt agtcatacgt cacgtccagc   9780
ttgctgcgct tgcgctcgcc ccgcttgagg gcacggaaca ggccgggggc cagacagtgc   9840
gccgggtcgt gccggacgtg gctgaggctg tgcttgttct taggcttcac cacggggcac   9900
ccccttgctc ttgcgctgcc tctccagcac ggcgggcttg agcaccccgc cgtcatgccg   9960
cctgaaccac cgatcagcga acggtgcgcc atagttggcc ttgctcacac cgaagcggac  10020
gaagaaccgg cgctggtcgt cgtccacacc ccattcctcg gcctcggcgc tggtcatgct  10080
cgacaggtag gactgccagc ggatgttatc gaccagtacc gagctgcccc ggctggcctg  10140
ctgctggtcg cctgcgccca tcatggccgc gcccttgctg gcatggtgca ggaacacgat  10200
agagcacccg gtatcggcgg cgatggcctc catgcgaccg atgacctggg ccatggggcc  10260
gctggcgttt tcttcctcga tgtggaaccg gcgcagcgtg tccagcacca tcaggcggcg  10320
gccctcggcg gcgcgcttga ggccgtcgaa ccactccggg gccatgatgt tgggcaggct  10380
gccgatcagc ggctggatca gcaggccgtc agccacggct tgccgttcct cggcgctgag  10440
gtgcgcccca agggcgtgca ggcggtgatg aatggcggtg ggcgggtctt cggcgggcag  10500
gtagatcacc gggccggtgg gcagttcgcc cacctccagc agatccggcc cgcctgcaat  10560
ctgtgcggcc agttgcaggg ccagcatgga tttaccggca ccaccgggcg acaccagcgc  10620
cccgaccgta ccggccacca tgttgggcaa aacgtagtcc agcggtggcg gcgctgctgc  10680
gaacgcctcc agaatattga taggcttatg ggtagccatt gattgcctcc tttgcaggca  10740
gttggtggtt aggcgctggc ggggtcacta cccccgccct gcgccgctct gagttcttcc  10800
aggcactcgc gcagcgcctc gtattcgtcg tcggtcagcc agaacttgcg ctgacgcatc  10860
cctttggcct tcatgcgctc ggcatatcgc gcttggcgta cagcgtcagg gctggccagc  10920
aggtcgccgg tctgcttgtc cttttggtct ttcatatcag tcaccgagaa acttgccggg  10980
gccgaaaggc ttgtcttcgc ggaacaagga caaggtgcag ccgtcaaggt taaggctggc  11040
catatcagcg actgaaaagc ggccagcctc ggccttgttt gacgtataac caaagccacc  11100
gggcaaccaa tagcccttgt cacttttgat caggtagacc gaccctgaag cgcttttttc  11160
gtattccata aaacccccct ctgtgcgtga gtactcatag tataacaggc gtgagtacca  11220
acgcaagcac tacatgctga aatctggccc gcccctgtcc atgcctcgct ggcggggtgc  11280
```

cggtgcccgt gccagctcg 11299

<210> SEQ ID NO 82
<211> LENGTH: 8039
<212> TYPE: DNA
<213> ORGANISM: Artificial Sequence
<220> FEATURE:
<223> OTHER INFORMATION: Chemically Synthesized, pBTK541

<400> SEQUENCE: 82
gcactgcggc cccggctggc cagcttctgc gcggcgataa agtcgcactt gctgaggtca 60
tgaccgaagc gcttgaccag cccggccatc tcgctgcggt actcgtccag cgccgtgcgc 120
cggtggcggc taagctgccg ctcgggcagt tcgaggctgg ccagcctgcg ggccttctcc 180
tgctgccgct gggcctgctc gatctgctgg ccagcctgct gcaccagcgc cgggccagcg 240
gtggcggtct tgcccttgga ttcacgcagc agcacccacg gctgataacc ggcgcgggtg 300
gtgtgcttgt ccttgcggtt ggtgaagccc gccaagcggc catagtggcg gctgtcggcg 360
ctggccgggt cggcgtcgta ctcgctggcc agcgtccggg caatctgccc ccgaagttca 420
ccgcctgcgg cgtcggccac cttgacccat gcctgatagt tcttcgggct ggtttccact 480
accagggcag gctcccggcc ctcggctttc atgtcatcca ggtcaaactc gctgaggtcg 540
tccaccagca ccagaccatg ccgctcctgc tcggcgggcc tgatatacac gtcattgccc 600
tgggcattca tccgcttgag ccatggcgtg ttctggagca cttcggcggc tgaccattcc 660
cggttcatca tctggccggt gggtgcgtcc ctgacgccga tatcgaagcg ctcacagccc 720
atggccttga gctgtcggcc tatggcctgc aaagtcctgt cgttcttcat cgggccacca 780
agcgcagcca gatcgagccg tcctcggttg tcagtggcgt caggtcgagc aagagcaacg 840
atgcgatcag cagcaccacc gtaggcatca tggaagccag catcacggtt agccatagct 900
tccagtgcca cccccgcgac gcgctccggg cgctctgcgc ggcgctgctc acctcggcgg 960
ctacctcccg caactctttg gccagctcca cccatgccgc ccctgtctgg cgctgggctt 1020
tcagccactc cgccgcctgc gcctcgctgg cctgcttggt ctggctcatg acctgccggg 1080
cttcgtcggc cagtgtcgcc atgctctggg ccagcggttc gatctgctcc gctaactcgt 1140
tgatgcctct ggatttcttc actctgtcga ttgcgttcat ggtctattgc ctcccggtat 1200
tcctgtaagt cgatgatctg ggcgttggcg gtgtcgatgt tcagggccac gtctgcccgg 1260
tcggtgcgga tgccccggcc ttccatctcc accacgttcg gccccaggtg aacaccgggc 1320
aggcgctcga tgccctgcgc ctcaagtgtt ctgtggtcaa tgcgggcgtc gtggccagcc 1380
cgctctaatg cccggttggc atggtcggcc catgcctcgc gggtctgctc aagccatgcc 1440
ttgggcttga gcgcttcggt cttctgtgcc ccgcccttct ccggggtctt gccgttgtac 1500
cgcttgaacc actgagcggc gggccgctcg atgccgtcat tgatccgctc ggagatcatc 1560
aggtggcagt gcgggttctc gccgccaccg gcatggatgg ccagcgtata cggcaggcgc 1620
tcggcaccgg tcaggtgctg ggcgaactcg gacgccagcg ccttctgctg gtcgagggtc 1680
agctcgaccg gcagggcaaa ttcgacctcc ttgaacagcc gcccattggc gcgttcatac 1740
aggtcggcag catcccagta gtcggcgggc cgctcgacga actccggcat gtgcccggat 1800
tcggcgtgca agacttcatc catgtcgcgg gcatacttgc cttcgcgctg gatgtagtcg 1860
gccttggccc tggccgattg gccgcccgac ctgctgccgg ttttcgccgt aaggtgataa 1920
atcgccatgc tgcctcgctg ttgcttttgc ttttcggctc catgcaatgg ccctcggaga 1980
gcgcaccgcc cgaagggtgg ccgttaggcc agtttctcga agagaaaccg gtaagtgcgc 2040

```
cctcccctac aaagtagggt cgggattgcc gccgctgtgc ctccatgata gcctacgaga   2100
cagcacatta acaatggggt gtcaagatgg ttaaggggag caacaaggcg gcggatcggc   2160
tggccaagct cgaagaacaa cgagcgcgaa tcaatgccga aattcagcgg gagcgggcaa   2220
gggaacagca gcaagagcgc aagaacgaaa caaggcgcaa ggtgctggtg ggggccatga   2280
ttttggccaa ggtgaacagc agcgagtggc cggaggatcg gctcatggcg gcaatggatg   2340
cgtaccttga acgcgaccac gaccgcgcct tgttcggtct gccgccacgc cagaaggatg   2400
agccgggctg aatgatcgac cgagacaggc cctgcggggc tgcacacgcg cccccaccct   2460
tcgggtaggg ggaaaggccg ctaaagcggc taaaagcgct ccagcgtatt tctgcggggt   2520
ttggtgtggg gtttagcggg ctttgcccgc ctttcccct gccgcgcagc ggtggggcgg   2580
tgtgtagcct agcgcagcga atagaccagc tatccggcct ctggccgggc atattgggca   2640
agggcagcag cgccccacaa gggcgctgat aaccgcgcct agtggattat tcttagataa   2700
tcatggatgg atttttccaa caccccgcca gcccccgccc ctgctgggtt tgcaggtttg   2760
ggggcgtgac agttattgca ggggttcgtg acagttattg caggggggcg tgacagttat   2820
tgcaggggtt cgtgacagtt agtacgggag tgacgggcac tggctggcaa tgtctagcaa   2880
cggcaggcat ttcggctgag ggtaaaagaa ctttccgcta agcgatagac tgtatgtaaa   2940
cacagtattg caaggacgcg gaacatgcct catgtggcgg ccaggacggc cagccgggat   3000
cgggatactg gtcgttacca gagccaccga cccgagcaaa cccttctcta tcagatcgtt   3060
gacgagtatt acccggcatt cgctgcgctt atggcagagc agggaaagga attgccgggc   3120
tatgtgcaac gggaatttga agaatttctc caatgcgggc ggctggagca tggctttcta   3180
cgggttcgct gcgagtcttg ccacgccgag cacctggtcg ctttcagaaa tcaatctaaa   3240
gtatatatga gtaaacttgg tctgacaggc ccctgaattc gcatctagat ggtagagcca   3300
caaacagccg gtacaagcaa cgatctccag gaccatctga atcatgcgcg gatgacacga   3360
actcacgacg gcgatcacag acattaaccc acagtacaga cactgcgaca acgtggcaat   3420
tcgtcgcaat accgtctcac tgaactggcc gataattgca gacgaacgtc ggtcagtttc   3480
acctgattta cgtaaaaacc cgcttcggcg ggtttttgct tttggagggg cagaaagatg   3540
aatgactgtc aaattaatac gactcactat agggagagga attgtgagcg gataacaatt   3600
ccatacagaa acagaggaga tatatgagta aaggagaaga gcttttcaca ggagttgtcc   3660
caatcctcgt ggaattagac ggtgatgtta atgggcacaa gttctctgtc agtggagagg   3720
gtgaaggcga cgcaacatat ggcaagctga cccttaaatt tatttgcacc acgggtaaac   3780
tacctgttcc atggccaaca ctggtcacta cgttcgggta tggggttcag tgctttgcgc   3840
gctacccaga tcacatgaaa cagcacgact tttcaagag tgcaatgccc gaaggctatg   3900
tacaggagag aaccatcttt tttaaggatg acggcaacta taagacacgc gccgaagtga   3960
agttcgaggg tgataccctt gttaatagaa tcgagttaaa gggtattgac tttaaggaag   4020
atggaaatat tttaggccac aaactggaat ataactataa ctcccataat gtgtacatta   4080
tggccgacaa gcaaaagaac ggtatcaagg ttaacttcaa gatcagacac aacattgagg   4140
atggaagcgt tcaactagcc gaccattacc aacaaaacac cccaattggc gatgggcctg   4200
tgctgttacc agacaaccat tacctgtcca ctcaatctgc cctttcgaaa gatcccaacg   4260
aaaagcgcga ccacatggtc cttcttgagt ttgtcacggc tgctgggatt acacacggca   4320
tggatgaact atacaaataa atccctgcta acaaagcccg aaaggaagct gagttggctg   4380
```

-continued

```
ctgccaccgc tgagcaataa ctagcataac cccttggggc ctctaaacgg gtcttgaggg   4440
gtttttgct gaaaggagga actatatgct gccatccctg aaaaccaccc catagtcagg   4500
atcacaagga ccccagcatg agacgccgag cggccgcgat tatcaaaaag gatcttcacc   4560
tagatccttt taaattaaaa atgaagtttt aaatcaatct aaagtatata tgagtaaact   4620
tggtctgaca gttaccaatg cttaatcagt gaggcaccta tctcagcgat ctgtctattt   4680
cgttcatcca tagttgcctg actccccgtc gtgtagataa ctacgatacg ggagggctta   4740
ccatctggcc ccagtgctgc aatgataccg cgggacccac gctcaccggc tccagattta   4800
tcagcaataa accagccagc cggaagggcc gagcgcagaa gtggtcctgc aactttatcc   4860
gcctccatcc agtctattaa ttgttgccgg gaagctagag taagtagttc gccagttaat   4920
agtttgcgca acgttgttgc cattgctaca ggcatcgtgg tgtcacgctc gtcgtttggt   4980
atggcttcat tcagctccgg ttcccaacga tcaaggcgag ttacatgatc ccccatgttg   5040
tgcaaaaaag cggttagctc cttcggtcct ccgatcgttg tcagaagtaa gttggccgca   5100
gtgttatcac tcatggttat ggcagcactg cataattctc ttactgtcat gccatccgta   5160
agatgctttt ctgtgactgg tgagtactca accaagtcat tctgagaata gtgtatgcgg   5220
cgaccgagtt gctcttgccc ggcgtcaata cgggataata ccgcgccaca tagcagaact   5280
ttaaaagtgc tcatcattgg aaaacgttct tcggggcgaa aactctcaag gatcttaccg   5340
ctgttgagat ccagttcgat gtaacccact cgtgcaccca actgatcttc agcatctttt   5400
actttcacca gcgtttctgg gtgagcaaaa acaggaaggc aaaatgccgc aaaaaaggga   5460
ataagggcga cacggaaatg ttgaatactc atactcttcc tttttcaata ttattgaagc   5520
atttatcagg gttattgtct catgagcgga tacatatttg aatgtattta gaaaaataaa   5580
caaatagggg ttccgcgcac atttccccga aaagtgccac ctgtcatgac caaaatccct   5640
taacgtgagt cagcctgccg ccttgggccg ggtgatgtcg tacttgcccg ccgcgaactc   5700
ggttaccgtc cagcccagcg cgaccagctc cggcaacgcc tcgcgcaccc gcttgcggcg   5760
cttgcgcatg gtcgaaccac tggcctctga cggccagaca tagccgcaca aggtatctat   5820
ggaagccttg ccggttttgc cggggtcgat ccagccacac agccgctggt gcagcaggcg   5880
ggcggtttcg ctgtccagcg cccgcacctc gtccatgctg atgcgcacat gctggccgcc   5940
acccatgacg gcctgcgcga tcaaggggtt cagggccacg tacaggcgcc cgtccgcctc   6000
gtcgctggcg tactccgaca gcagccgaaa cccctgccgc ttgcggccat tctgggcgat   6060
gatggatacc ttccaaaggc gctcgatgca gtcctgtatg tgcttgagcg ccccaccact   6120
atcgacctct gccccgattt cctttgccag cgcccgatag ctacctttga ccacatggca   6180
ttcagcggtg acggcctccc acttgggttc caggaacagc cggagctgcc gtccgccttc   6240
ggtcttgggt tccgggccaa gcactaggcc attaggccca gccatggcca ccagcccttg   6300
caggatgcgc agatcatcag cgcccagcgg ctccgggccg ctgaactcga tccgcttgcc   6360
gtcgccgtag tcatacgtca cgtccagctt gctgcgcttg cgctcgcccc gcttgagggc   6420
acggaacagg ccgggggcca gacagtgcgc cgggtcgtgc cggacgtggc tgaggctgtg   6480
cttgttctta ggcttcacca cggggcaccc ccttgctctt gcgctgcctc tccagcacgg   6540
cgggcttgag caccccgccg tcatgccgcc tgaaccaccg atcagcgaac ggtgcgccat   6600
agttggcctt gctcacaccg aagcggacga agaaccggcg ctggtcgtcg tccacacccc   6660
attcctcggc ctcggcgctg gtcatgctcg acaggtagga ctgccagcgg atgttatcga   6720
ccagtaccga gctgccccgg ctggcctgct gctggtcgcc tgcgcccatc atggccgcgc   6780
```

```
ccttgctggc atggtgcagg aacacgatag agcacccggt atcggcggcg atggcctcca   6840
tgcgaccgat gacctgggcc atggggccgc tggcgttttc ttcctcgatg tggaaccggc   6900
gcagcgtgtc cagcaccatc aggcggcggc cctcggcggc gcgcttgagg ccgtcgaacc   6960
actccggggc catgatgttg ggcaggctgc cgatcagcgg ctggatcagc aggccgtcag   7020
ccacggcttg ccgttcctcg gcgctgaggt gcgccccaag ggcgtgcagg cggtgatgaa   7080
tggcggtggg cgggtcttcg gcgggcaggt agatcaccgg gccggtgggc agttcgccca   7140
cctccagcag atccggcccg cctgcaatct gtgcggccag ttgcagggcc agcatggatt   7200
taccggcacc accgggcgac accagcgccc cgaccgtacc ggccaccatg ttgggcaaaa   7260
cgtagtccag cggtggcggc gctgctgcga acgcctccag aatattgata ggcttatggg   7320
tagccattga ttgcctcctt tgcaggcagt tggtggttag gcgctggcgg ggtcactacc   7380
cccgccctgc gccgctctga gttcttccag gcactcgcgc agcgcctcgt attcgtcgtc   7440
ggtcagccag aacttgcgct gacgcatccc tttggccttc atgcgctcgg catatcgcgc   7500
ttggcgtaca gcgtcagggc tggccagcag gtcgccggtc tgcttgtcct tttggtcttt   7560
catatcagtc accgagaaac ttgccggggc cgaaaggctt gtcttcgcgg aacaaggaca   7620
aggtgcagcc gtcaaggtta aggctggcca tatcagcgac tgaaaagcgg ccagcctcgg   7680
ccttgtttga cgtataacca aagccaccgg gcaaccaata gcccttgtca cttttgatca   7740
ggtagaccga ccctgaagcg cttttttcgt attccataaa acccccttct gtgcgtgagt   7800
actcatagta taacaggcgt gagtaccaac gcaagcacta catgctgaaa tctggcccgc   7860
ccctgtccat gcctcgctgg cggggtgccg gtgcccgtgc cagctcggcc cgcgcaagct   7920
ggacgctggg cagacccatg accttgctga cggtgcgctc gatgtaatcc gcttcgtggc   7980
cgggcttgcg ctctgccagc gctgggctgg cctcggccat ggccttgccg atttcctcg    8039
```

<210> SEQ ID NO 83
<211> LENGTH: 12266
<212> TYPE: DNA
<213> ORGANISM: Artificial Sequence
<220> FEATURE:
<223> OTHER INFORMATION: Chemically Synthesized, pBTK550d

<400> SEQUENCE: 83

```
ctcggcactg cggccccggc tggccagctt ctgcgcggcg ataaagtcgc acttgctgag     60
gtcatgaccg aagcgcttga ccagcccggc catctcgctg cggtactcgt ccagcgccgt    120
gcgccggtgg cggctaagct gccgctcggg cagttcgagg ctggccagcc tgcgggcctt    180
ctcctgctgc cgctgggcct gctcgatctg ctggccagcc tgctgcacca gcgccgggcc    240
agcggtggcg gtcttgccct tggattcacg cagcagcacc cacggctgat aaccggcgcg    300
ggtggtgtgc ttgtccttgc ggttggtgaa gcccgccaag cggccatagt ggcggctgtc    360
ggcgctggcc gggtcggcgt cgtactcgct ggccagcgtc cgggcaatct gcccccgaag    420
ttcaccgcct gcggcgtcgg ccaccttgac ccatgcctga tagttcttcg ggctggtttc    480
cactaccagg gcaggctccc ggccctcggc tttcatgtca tccaggtcaa actcgctgag    540
gtcgtccacc agcaccagac catgccgctc ctgctcggcg ggcctgatat acacgtcatt    600
gccctgggca ttcatccgct tgagccatgg cgtgttctgg agcacttcgg cggctgacca    660
ttcccggttc atcatctggc cggtgggtgc gtccctgacg ccgatatcga agcgctcaca    720
gcccatggcc ttgagctgtc ggcctatggc ctgcaaagtc ctgtcgttct tcatcgggcc    780
```

-continued

```
accaagcgca gccagatcga gccgtcctcg gttgtcagtg gcgtcaggtc gagcaagagc    840
aacgatgcga tcagcagcac caccgtaggc atcatggaag ccagcatcac ggttagccat    900
agcttccagt gccacccccg cgacgcgctc cgggcgctct gcgcggcgct gctcacctcg    960
gcggctacct cccgcaactc tttggccagc tccacccatg ccgcccctgt ctggcgctgg   1020
gctttcagcc actccgccgc ctgcgcctcg ctggcctgct tggtctggct catgacctgc   1080
cgggcttcgt cggccagtgt cgccatgctc tgggccagcg gttcgatctg ctccgctaac   1140
tcgttgatgc ctctggattt cttcactctg tcgattgcgt tcatggtcta ttgcctcccg   1200
gtattcctgt aagtcgatga tctgggcgtt ggcggtgtcg atgttcaggg ccacgtctgc   1260
ccggtcggtg cggatgcccc ggccttccat ctccaccacg ttcggcccca ggtgaacacc   1320
gggcaggcgc tcgatgccct gcgcctcaag tgttctgtgg tcaatgcggg cgtcgtggcc   1380
agcccgctct aatgcccggt tggcatggtc ggcccatgcc tcgcgggtct gctcaagcca   1440
tgccttgggc ttgagcgctt cggtcttctg tgccccgccc ttctccgggg tcttgccgtt   1500
gtaccgcttg aaccactgag cggcgggccg ctcgatgccg tcattgatcc gctcggagat   1560
catcaggtgg cagtgcgggt tctcgccgcc accggcatgg atggccagcg tatacggcag   1620
gcgctcggca ccggtcaggt gctgggcgaa ctcggacgcc agcgccttct gctggtcgag   1680
ggtcagctcg accggcaggg caaattcgac ctccttgaac agccgcccat tggcgcgttc   1740
atacaggtcg gcagcatccc agtagtcggc gggccgctcg acgaactccg gcatgtgccc   1800
ggattcggcg tgcaagactt catccatgtc gcgggcatac ttgccttcgc gctggatgta   1860
gtcggccttg gccctggccg attggccgcc cgacctgctg ccggttttcg ccgtaaggtg   1920
ataaatcgcc atgctgcctc gctgttgctt ttgcttttcg gctccatgca atggccctcg   1980
gagagcgcac cgcccgaagg gtggccgtta ggccagtttc tcgaagagaa accggtaagt   2040
gcgccctccc ctacaaagta gggtcgggat tgccgccgct gtgcctccat gatagcctac   2100
gagacagcac attaacaatg gggtgtcaag atggttaagg ggagcaacaa ggcggcggat   2160
cggctggcca agctcgaaga acaacgagcg cgaatcaatg ccgaaattca gcgggagcgg   2220
gcaagggaac agcagcaaga gcgcaagaac gaaacaaggc gcaaggtgct ggtgggggcc   2280
atgattttgg ccaaggtgaa cagcagcgag tggccggagg atcggctcat ggcggcaatg   2340
gatgcgtacc ttgaacgcga ccacgaccgc gccttgttcg gtctgccgcc acgccagaag   2400
gatgagccgg gctgaatgat cgaccgagac aggccctgcg gggctgcaca cgcgcccccca   2460
cccttcgggt agggggaaag gccgctaaag cggctaaaag cgctccagcg tatttctgcg   2520
gggtttggtg tggggtttag cgggctttgc ccgcctttcc ccctgccgcg cagcggtggg   2580
gcggtgtgta gcctagcgca gcgaatagac cagctatccg gcctctggcc gggcatattg   2640
ggcaagggca gcagcgcccc acaagggcgc tgataaccgc gcctagtgga ttattcttag   2700
ataatcatgg atggattttt ccaacacccc gccagccccc gcccctgctg ggtttgcagg   2760
tttgggggcg tgacagttat tgcaggggtt cgtgacagtt attgcagggg ggcgtgacag   2820
ttattgcagg ggttcgtgac agttagtacg ggagtgacgg gcactggctg gcaatgtcta   2880
gcaacggcag gcatttcggc tgagggtaaa agaactttcc gctaagcgat agactgtatg   2940
taaacacagt attgcaagga cgcggaacat gcctcatgtg gcggccagga cggccagccg   3000
ggatcgggat actggtcgtt accagagcca ccgacccgag caaacccttc tctatcagat   3060
cgttgacgag tattacccgg cattcgctgc gcttatggca gagcagggaa aggaattgcc   3120
gggctatgtg caacgggaat ttgaagaatt tctccaatgc gggcggctgg agcatggctt   3180
```

```
tctacgggtt cgctgcgagt cttgccacgc cgagcacctg gtcgctttca gaaatcaatc   3240
taaagtatat atgagtaaac ttggtctgac aggcccctga attcgcatct agacagggtc   3300
ttgctctgtc accctcaaga caacctgccc ctcaacgttt acactttatg cttccggctc   3360
gtatgttgtg tggaattgtg agcggataac aattttaaag aggagaaatt aactatgaac   3420
acgattaaca tcgctaagaa cgacttctct gacatcgaac tggctgctat cccgttcaac   3480
actctggctg accattacgg tgagcgttta gctcgcgaac agttggccct tgagcatgag   3540
tcttacgaga tgggtgaagc acgcttccgc aagatgtttg agcgtcaact taaagctggt   3600
gaggttgcgg ataacgctgc cgccaagcct ctcatcacta ccctactccc taagatgatt   3660
gcacgcatca acgactggtt tgaggaagtg aaagctaagc gcggcaagcg cccgacagcc   3720
ttccagttcc tgcaagaaat caagccggaa gccgtagcgt acatcaccat taagaccact   3780
ctggcttgcc taaccagtgc tgacaataca accgttcagg ctgtagcaag cgcaatcggt   3840
cgggccattg aggacgaggc tcgcttcggt cgtatccgtg accttgaagc taagcacttc   3900
aagaaaaacg ttgaggaaca actcaacaag cgcgtagggc acgtctacaa gaaagcattt   3960
atgcaagttg tcgaggctga catgctctct aagggtctac tcggtggcga ggcgtggtct   4020
tcgtggcata aggaagactc tattcatgta ggagtacgct gcatcgagat gctcattgag   4080
tcaaccggaa tggttagctt acaccgccaa aatgctggcg tagtaggtca agactctgag   4140
actatcgaac tcgcacctga atacgctgag gctatcgcaa cccgtgcagg tgcgctggct   4200
ggcatctctc cgatgttcca accttgcgta gttcctccta agccgtggac tggcattact   4260
ggtggtggct attgggctaa cggtcgtcgt cctctggcgc tggtgcgtac tcacagtaag   4320
aaagcactga tgcgctacga agacgtttac atgcctgagg tgtacaaagc gattaacatt   4380
gcgcaaaaca ccgcatggaa aatcaacaag aaagtcctag cggtcgccaa cgtaatcacc   4440
aagtggaagc attgtccggt cgaggacatc cctgcgattg agcgtgaaga actcccgatg   4500
aaaccggaag acatcgacat gaatcctgag gctctcaccg cgtggaaacg tgctgccgct   4560
gctgtgtacc gcaaggacaa ggctcgcaag tctcgccgta tcagccttga gttcatgctt   4620
gagcaagcca ataagtttgc taaccataag gccatctggt tcccttacaa catggactgg   4680
cgcggtcgtg tttacgctgt gtcaatgttc aacccgcaag gtaacgatat gaccaaagga   4740
ctgcttacgc tggcgaaagg taaaccaatc ggtaaggaag gttactactg gctgaaaatc   4800
cacggtgcaa actgtgcggg tgtcgataag gttccgttcc ctgagcgcat caagttcatt   4860
gaggaaaacc acgagaacat catggcttgc gctaagtctc cactggagaa cacttggtgg   4920
gctgagcaag attctccgtt ctgcttcctt gcgttctgct ttgagtacgc tggggtacag   4980
caccacggcc tgagctataa ctgctccctt ccgctggcgt ttgacgggtc ttgctctggc   5040
atccagcact tctccgcgat gctccgagat gaggtaggtg gtcgcgcggt taacttgctt   5100
cctagtgaaa ccgttcagga catctacggg attgttgcta agaaagtcaa cgagattcta   5160
caagcagacg caatcaatgg gaccgataac gaagtagtta ccgtgaccga tgagaacact   5220
ggtgaaatct ctgagaaagt caagctgggc actaaggcac tggctggtca atggctggct   5280
tacggtgtta ctcgcagtgt gactaagcgt tcagtcatga cgctggctta cgggtccaaa   5340
gagttcggct tccgtcaaca agtgctggaa gataccattc agccagctat tgattccggc   5400
aagggtctga tgttcactca gccgaatcag gctgctggat acatggctaa gctgatttgg   5460
gaatctgtga gcgtgacggt ggtagctgcg gttgaagcaa tgaactggct taagtctgct   5520
```

```
gctaagctgc tggctgctga ggtcaaagat aagaagactg gagagattct tcgcaagcgt   5580
tgcgctgtgc attgggtaac tcctgatggt ttccctgtgt ggcaggaata caagaagcct   5640
attcagacgc gcttgaacct gatgttcctc ggtcagttcc gcttacagcc taccattaac   5700
accaacaaag atagcgagat tgatgcacac aaacaggagt ctggtatcgc tcctaacttt   5760
gtacacagcc aagacggtag ccaccttcgt aagactgtag tgtgggcaca cgagaagtac   5820
ggaatcgaat cttttgcact gattcacgac tccttcggta ccattccggc tgacgctgcg   5880
aacctgttca aagcagtgcg cgaaactatg gttgacacat atgagtcttg tgatgtactg   5940
gctgatttct acgaccagtt cgctgaccag ttgcacgagt ctcaattgga caaaatgcca   6000
gcacttccgg ctaaaggtaa cttgaacctc cgtgacatct tagagtcgga cttcgcgttc   6060
gcgtaaatcc gtaatcgtta atccgcaaat aacgtaaaaa cccgcttcgg cgggtttttt   6120
tatgggggga gtttagggaa agagcatttg tcagctgctg aactggccga taattgcaga   6180
cgaacgtcgg tcagtttcac ctgatttacg taaaaacccg cttcggcggg tttttgcttt   6240
tggaggggca gaaagatgaa tgactgtcaa attaatacga ctcactatag ggagaggaat   6300
tgtgagcgga taacaattcc atacagaaac agaggagata tatgagtaaa ggagaagagc   6360
ttttcacagg agttgtccca atcctcgtgg aattagacgg tgatgttaat gggcacaagt   6420
tctctgtcag tggagagggt gaaggcgacg caacatatgg caagctgacc cttaaattta   6480
tttgcaccac gggtaaacta cctgttccat ggccaacact ggtcactacg ttcgggtatg   6540
gggttcagtg ctttgcgcgc tacccagatc acatgaaaca gcacgacttt ttcaagagtg   6600
caatgcccga aggctatgta caggagagaa ccatcttttt taaggatgac ggcaactata   6660
agacacgcgc cgaagtgaag ttcgagggtg ataccctttgt taatagaatc gagttaaagg   6720
gtattgactt taaggaagat ggaaatattt taggccacaa actggaatat aactataact   6780
cccataatgt gtacattatg gccgacaagc aaaagaacgg tatcaaggtt aacttcaaga   6840
tcagacacaa cattgaggat ggaagcgttc aactagccga ccattaccaa caaaacaccc   6900
caattggcga tgggcctgtg ctgttaccag acaaccatta cctgtccact caatctgccc   6960
tttcgaaaga tcccaacgaa aagcgcgacc acatggtcct tcttgagttt gtcacggctg   7020
ctgggattac acacggcatg gatgaactat acaaataaat ccctgctaac aaagcccgaa   7080
aggaagctga gttggctgct gccaccgctg agcaataact agcataaccc cttggggcct   7140
ctaaacgggt cttgaggggt tttttgctga aaggaggaac tatatgctgc catccctgaa   7200
aaccacccca tagtcaggat cacaaggacc ccagcagtta cagagatgtt acgaaccccc   7260
aggacatccg agaatgcgag gcgatggagg gtacaaccgg gagagtgttc accgacaaac   7320
aacagataaa acaaaaggcc cagtcttccg actgagcctt ttgttttatt tgatgtctgg   7380
cagttccccg ccgctatctg atcatcaaat aataatttct tcatgttgaa aatctccaaa   7440
aaaaaaggct ccaaaaggag cctttaattg tatcggttta tcagcttgct tttacatcac   7500
tgcccgcttt ccagtcggga aacctgtcgt gccagctgca ttaatgaatc ggccaacgcg   7560
cggggagagg cggtttgcgt attgggcgcc agggtggttt ttcttttcac cagtgacacc   7620
ggcaacagct gattgccctt caccgcctgg ccctgagaga gttgcagcaa gcggtccacg   7680
ctggtttgcc ccagcaggcg aaaatcctgt ttgatggtgg ttaacggcgg gatataacat   7740
gagctgtctt cggtatcgtc gtatcccact accgagatat ccgcaccaac gcgcagcccg   7800
gactcggtaa tggcgcgcat tgcgcccagc gccatctgat cgttggcaac cagcatcgca   7860
gtgggaacga tgccctcatt cagcatttgc atggtttgtt gaaaaccgga catggcactc   7920
```

```
cagtcgcctt cccgttccgc tatcggctga atttgattgc gagtgagata tttatgccag   7980
ccagccagac gcagacgcgc cgagacagaa cttaatgggc ccgctaacag cgcgatttgc   8040
tggtgaccca atgcgaccag atgctccacg cccagtcgcg taccgtcttc atgggagaaa   8100
ataatactgt tgatgggtgt ctggtcagag acatcaagaa ataacgccgg aacattagtg   8160
caggcagctt ccacagcaat ggcatcctgg tcatccagcg gatagttaat gatcagccca   8220
ctgacgcgtt gcgcgagaag attgtgcacc gccgctttac aggcttcgac gccgcttcgt   8280
tctaccatcg acaccaccac gctggcaccc agttgatcgg cgcgagattt aatcgccgcg   8340
acaatttgcg acggcgcgtg cagggccaga ctggaggtgg caacgccaat cagcaacgac   8400
tgtttgcccg ccagttgttg tgccacgcgg ttgggaatgt aattcagctc cgccatcgcc   8460
gcttccactt tttcccgcgt tttcgcagaa acgtggctgg cctggttcac cacgcgggaa   8520
acggtctgat aagagacacc ggcatactct gcgacatcgt ataacgttac tggtttcatg   8580
agtacctctc ctgtatcttg tgtacttgcg taccgtaata tctcctctgt ttctgtataa   8640
cagtactatg tgattatacc agccccctca ctacatgtca agaataaact gccaaagccg   8700
agcggccgct tatttgccga ctaccttggt gatctcgcct ttcacgtagt ggacaaattc   8760
ttccaactga tctgcgcgcg aggccaagcg atcttcttct tgtccaagat aagcctgtct   8820
agcttcaagt atgacgggct gatactgggc cggcaggcgc tccattgccc agtcggcagc   8880
gacatccttc ggcgcgattt tgccggttac tgcgctgtac caaatgcggg acaacgtaag   8940
cactacattt cgctcatcgc cagcccagtc gggcggcgag ttccatagcg ttaaggtttc   9000
atttagcgcc tcaaatagat cctgttcagg aaccggatca aagagttcct ccgccgctgg   9060
acctaccaag gcaacgctat gttctcttgc ttttgtcagc aagatagcca gatcaatgtc   9120
gatcgtggct ggctcgaaga tacccgcaag aatgtcattg cgctgccatt ctccaaattg   9180
cagttcgcgc ttagctggat aacgccacgg aatgatgtcg tcgtgcacaa caatggtgac   9240
ttctacagcg cggagaatct cgctctctcc aggggaagcc gaagtttcca aaaggtcgtt   9300
gatcaaagct cgccgcgttg tttcatcaag ccttacggtc accgtaacca gcaaatcaat   9360
atcactgtgt ggcttcaggc cgccatccac tgcggagccg tacaaatgta cggccagcaa   9420
cgtcggttcg agatggcgct cgatgacgcc aactacctct gatagttgag tcgatacttc   9480
ggcgatcacc gcttccctca taatgtttaa ctttgtttta gggcgactgc cctgctgcgt   9540
aacatcgttg ctgctccata acatcaaaca tcgacccacg gcgtaacgcg cttgctgctt   9600
ggatgcccga ggcatagact gtaccccaaa aaaacagtca taacaagcca tgaaaaccgc   9660
cactgcgccg ttaccaccgc tgcgttcggt caaggttctg gaccagttgc gtgagcgcat   9720
acgctacttg cattacagct tacgaaccga acaggcttat gtccactggg ttcgtgcctt   9780
catccgtttc cacggtgtgc gtcacccggc aaccttgggt agcagcgaag tcgaggcatt   9840
tctgtcctgg ctggtcatga ccaaaatccc ttaacgtgag tcagcctgcc gccttgggcc   9900
gggtgatgtc gtacttgccc gccgcgaact cggttaccgt ccagcccagc gcgaccagct   9960
ccggcaacgc ctcgcgcacc cgcttgcggc gcttgcgcat ggtcgaacca ctggcctctg  10020
acggccagac atagccgcac aaggtatcta tggaagcctt gccggttttg ccggggtcga  10080
tccagccaca cagccgctgg tgcagcaggc gggcggtttc gctgtccagc gcccgcacct  10140
cgtccatgct gatgcgcaca tgctggccgc cacccatgac ggcctgcgcg atcaaggggt  10200
tcagggccac gtacaggcgc ccgtccgcct cgtcgctggc gtactccgac agcagccgaa  10260
```

acccctgccg cttgcggcca ttctgggcga tgatggatac cttccaaagg cgctcgatgc 10320
agtcctgtat gtgcttgagc gccccaccac tatcgacctc tgccccgatt tcctttgcca 10380
gcgcccgata gctacctttg accacatggc attcagcggt gacggcctcc cacttgggtt 10440
ccaggaacag ccggagctgc cgtccgcctt cggtcttggg ttccgggcca agcactaggc 10500
cattaggccc agccatggcc accagccctt gcaggatgcg cagatcatca gcgcccagcg 10560
gctccgggcc gctgaactcg atccgcttgc cgtcgccgta gtcatacgtc acgtccagct 10620
tgctgcgctt gcgctcgccc cgcttgaggg cacggaacag gccgggggcc agacagtgcg 10680
ccgggtcgtg ccggacgtgg ctgaggctgt gcttgttctt aggcttcacc acggggcacc 10740
cccttgctct tgcgctgcct ctccagcacg gcgggcttga gcaccccgcc gtcatgccgc 10800
ctgaaccacc gatcagcgaa cggtgcgcca tagttggcct tgctcacacc gaagcggacg 10860
aagaaccggc gctggtcgtc gtccacaccc cattcctcgg cctcggcgct ggtcatgctc 10920
gacaggtagg actgccagcg gatgttatcg accagtaccg agctgccccg gctggcctgc 10980
tgctggtcgc ctgcgcccat catggccgcg cccttgctgg catggtgcag gaacacgata 11040
gagcacccgg tatcggcggc gatggcctcc atgcgaccga tgacctgggc catggggccg 11100
ctggcgtttt cttcctcgat gtggaaccgg cgcagcgtgt ccagcaccat caggcggcgg 11160
ccctcggcgg cgcgcttgag gccgtcgaac cactccgggg ccatgatgtt gggcaggctg 11220
ccgatcagcg gctggatcag caggccgtca gccacggctt gccgttcctc ggcgctgagg 11280
tgcgccccaa gggcgtgcag gcggtgatga atggcggtgg gcgggtcttc ggcgggcagg 11340
tagatcaccg ggccggtggg cagttcgccc acctccagca gatccggccc gcctgcaatc 11400
tgtgcggcca gttgcagggc cagcatggat ttaccggcac caccgggcga caccagcgcc 11460
ccgaccgtac cggccaccat gttgggcaaa acgtagtcca gcggtggcgg cgctgctgcg 11520
aacgcctcca gaatattgat aggcttatgg gtagccattg attgcctcct ttgcaggcag 11580
ttggtggtta ggcgctggcg ggtcactac ccccgccctg cgccgctctg agttcttcca 11640
ggcactcgcg cagcgcctcg tattcgtcgt cggtcagcca gaacttgcgc tgacgcatcc 11700
ctttggcctt catgcgctcg gcatatcgcg cttggcgtac agcgtcaggg ctggccagca 11760
ggtcgccggt ctgcttgtcc ttttggtctt tcatatcagt caccgagaaa cttgccgggg 11820
ccgaaaggct tgtcttcgcg gaacaaggac aaggtgcagc cgtcaaggtt aaggctggcc 11880
atatcagcga ctgaaaagcg gccagcctcg gccttgtttg acgtataacc aaagccaccg 11940
ggcaaccaat agcccttgtc acttttgatc aggtagaccg accctgaagc gctttttcg 12000 tattccataa aacccccttc tgtgcgtgag tactcatagt ataacaggcg tgagtaccaa 12060
cgcaagcact acatgctgaa atctggcccg cccctgtcca tgcctcgctg gcggggtgcc 12120
ggtgcccgtg ccagctcggc ccgcgcaagc tggacgctgg gcagacccat gaccttgctg 12180
acggtgcgct cgatgtaatc cgcttcgtgg ccgggcttgc gctctgccag cgctgggctg 12240
gcctcggcca tggccttgcc gatttc 12266

<210> SEQ ID NO 84
<211> LENGTH: 9492
<212> TYPE: DNA
<213> ORGANISM: Artificial Sequence
<220> FEATURE:
<223> OTHER INFORMATION: Chemically Synthesized, pBTK552

<400> SEQUENCE: 84
ctgaaatctg gcccgcccct gtccatgcct cgctggcggg gtgccggtgc ccgtgccagc 60

```
tcggcccgcg caagctggac gctgggcaga cccatgacct tgctgacggt gcgctcgatg    120
taatccgctt cgtggccggg cttgcgctct gccagcgctg ggctggcctc ggccatggcc    180
ttgccgattt cctcggcact gcggccccgg ctggccagct tctgcgcggc gataaagtcg    240
cacttgctga ggtcatgacc gaagcgcttg accagcccgg ccatctcgct gcggtactcg    300
tccagcgccg tgcgccggtg gcggctaagc tgccgctcgg gcagttcgag gctggccagc    360
ctgcgggcct tctcctgctg ccgctgggcc tgctcgatct gctggccagc ctgctgcacc    420
agcgccgggc cagcggtggc ggtcttgccc ttggattcac gcagcagcac ccacggctga    480
taaccggcgc gggtggtgtg cttgtccttg cggttggtga agcccgccaa gcggccatag    540
tggcggctgt cggcgctggc cgggtcggcg tcgtactcgc tggccagcgt ccgggcaatc    600
tgcccccgaa gttcaccgcc tgcggcgtcg gccaccttga cccatgcctg atagttcttc    660
gggctggttt ccactaccag ggcaggctcc cggccctcgg ctttcatgtc atccaggtca    720
aactcgctga ggtcgtccac cagcaccaga ccatgccgct cctgctcggc gggcctgata    780
tacacgtcat tgccctgggc attcatccgc ttgagccatg gcgtgttctg gagcacttcg    840
gcggctgacc attcccggtt catcatctgg ccggtgggtg cgtccctgac gccgatatcg    900
aagcgctcac agcccatggc cttgagctgt cggcctatgg cctgcaaagt cctgtcgttc    960
ttcatcgggc caccaagcgc agccagatcg agccgtcctc ggttgtcagt ggcgtcaggt   1020
cgagcaagag caacgatgcg atcagcagca ccaccgtagg catcatggaa gccagcatca   1080
cggttagcca tagcttccag tgccaccccc gcgacgcgct ccgggcgctc tgcgcggcgc   1140
tgctcacctc ggcggctacc tcccgcaact ctttggccag ctccacccat gccgcccctg   1200
tctggcgctg ggctttcagc cactccgccg cctgcgcctc gctggcctgc ttggtctggc   1260
tcatgacctg ccgggcttcg tcggccagtg tcgccatgct ctgggccagc ggttcgatct   1320
gctccgctaa ctcgttgatg cctctggatt tcttcactct gtcgattgcg ttcatggtct   1380
attgcctccc ggtattcctg taagtcgatg atctgggcgt tggcggtgtc gatgttcagg   1440
gccacgtctg cccggtcggt gcggatgccc cggccttcca tctccaccac gttcggcccc   1500
aggtgaacac cgggcaggcg ctcgatgccc tgcgcctcaa gtgttctgtg gtcaatgcgg   1560
gcgtcgtggc cagcccgctc taatgcccgg ttggcatggt cggcccatgc ctcgcgggtc   1620
tgctcaagcc atgccttggg cttgagcgct tcggtcttct gtgccccgcc cttctccggg   1680
gtcttgccgt tgtaccgctt gaaccactga gcggcgggcc gctcgatgcc gtcattgatc   1740
cgctcggaga tcatcaggtg gcagtgcggg ttctcgccgc caccggcatg gatggccagc   1800
gtatacggca ggcgctcggc accggtcagg tgctgggcga actcggacgc cagcgccttc   1860
tgctggtcga gggtcagctc gaccggcagg gcaaattcga cctccttgaa cagccgccca   1920
ttggcgcgtt catacaggtc ggcagcatcc cagtagtcgg cgggccgctc gacgaactcc   1980
ggcatgtgcc cggattcggc gtgcaagact tcatccatgt cgcgggcata cttgccttcg   2040
cgctggatgt agtcggcctt ggccctggcc gattggccgc ccgacctgct gccggttttc   2100
gccgtaaggt gataaatcgc catgctgcct cgctgttgct tttgcttttc ggctccatgc   2160
aatggccctc ggagagcgca ccgcccgaag ggtggccgtt aggccagttt ctcgaagaga   2220
aaccggtaag tgcgccctcc cctacaaagt agggtcggga ttgccgccgc tgtgcctcca   2280
tgatagccta cgagacagca cattaacaat ggggtgtcaa gatggttaag gggagcaaca   2340
aggcggcgga tcggctggcc aagctcgaag aacaacgagc gcgaatcaat gccgaaattc   2400
```

```
agcgggagcg ggcaagggaa cagcagcaag agcgcaagaa cgaaacaagg cgcaaggtgc   2460
tggtgggggc catgattttg gccaaggtga acagcagcga gtggccggag gatcggctca   2520
tggcggcaat ggatgcgtac cttgaacgcg accacgaccg cgccttgttc ggtctgccgc   2580
cacgccagaa ggatgagccg ggctgaatga tcgaccgaga caggccctgc ggggctgcac   2640
acgcgccccc acccttcggg tagggggaaa ggccgctaaa gcggctaaaa gcgctccagc   2700
gtatttctgc ggggtttggt gtggggttta gcgggctttg cccgcctttc cccctgccgc   2760
gcagcggtgg ggcggtgtgt agcctagcgc agcgaataga ccagctatcc ggcctctggc   2820
cgggcatatt gggcaagggc agcagcgccc cacaagggcg ctgataaccg cgcctagtgg   2880
attattctta gataatcatg gatggatttt tccaacaccc cgccagcccc cgcccctgct   2940
gggtttgcag gtttgggggc gtgacagtta ttgcaggggt tcgtgacagt tattgcaggg   3000
gggcgtgaca gttattgcag gggttcgtga cagttagtac gggagtgacg ggcactggct   3060
ggcaatgtct agcaacggca ggcatttcgg ctgagggtaa aagaactttc cgctaagcga   3120
tagactgtat gtaaacacag tattgcaagg acgcggaaca tgcctcatgt ggcggccagg   3180
acggccagcc gggatcggga tactggtcgt taccagagcc accgacccga gcaaacccct   3240
ctctatcaga tcgttgacga gtattacccg gcattcgctg cgcttatggc agagcaggga   3300
aaggaattgc cgggctatgt gcaacgggaa tttgaagaat ttctccaatg cgggcggctg   3360
gagcatggct ttctacgggt tcgctgcgag tcttgccacg ccgagcacct ggtcgctttc   3420
agaaatcaat ctaaagtata tatgagtaaa cttggtctga caggcccctg aattcgcatc   3480
tagactgatg agacgtggta gagccacaaa cagccggtac aagcaacgat ctccaggacc   3540
atctgaatca tgcgcggatg acacgaactc acgacggcga tcacagacat taacccacag   3600
tacagacact gcgacaacgt ggcaattcgt cgcaatacaa cgtcggtcag tttcacctga   3660
tttacgtaaa aacccgcttc ggcgggtttt tgcttttgga ggggcagaaa gatgaatgac   3720
tgtcctttgg cagtttattc ttgacatgta gtgagggggc tggtataatc acatagtact   3780
gttggaattg tgagcggata acaattccat acagaaacag aggagatatt acatatgagt   3840
aaaggagaag agcttttcac aggagttgtc ccaatcctcg tggaattaga cggtgatgtt   3900
aatgggcaca agttctctgt cagtggagag ggtgaaggcg acgcaacata tggcaagctg   3960
acccttaaat ttatttgcac cacgggtaaa ctacctgttc catggccaac actggtcact   4020
acgttcgggt atggggttca gtgctttgcg cgctacccag atcacatgaa acagcacgac   4080
tttttcaaga gtgcaatgcc cgaaggctat gtacaggaga gaaccatctt ttttaaggat   4140
gacggcaact ataagacacg cgccgaagtg aagttcgagg gtgataccct tgttaataga   4200
atcgagttaa agggtattga ctttaaggaa gatggaaata ttttaggcca caaactggaa   4260
tataactata actcccataa tgtgtacatt atggccgaca agcaaaagaa cggtatcaag   4320
gttaacttca agatcagaca caacattgag gatggaagcg ttcaactagc cgaccattac   4380
caacaaaaca ccccaattgg cgatgggcct gtgctgttac cagacaacca ttacctgtcc   4440
actcaatctg ccctttcgaa agatcccaac gaaaagcgcg accacatggt ccttcttgag   4500
tttgtcacgg ctgctgggat tacacacggc atggatgaac tatacaaata aatccgtaat   4560
cgttaatccg caaataacgt aaaaacccgc ttcggcgggt ttttttatgg ggggagttta   4620
gggaaagagc atttgtcagc tgcgtctcaa gcagttacag agatgttacg aacccccagg   4680
acatccgaga atgcgaggcg atggagggta caaccgggag agtgttcacc gacaaacaac   4740
agataaaaca aaaggcccag tcttccgact gagccttttg ttttatttga tgtctggcag   4800
```

```
ttccccgccg ctatctgatc atcaaataat aatttcttca tgttgaaaat ctccaaaaaa   4860

aaaggctcca aaaggagcct ttaattgtat cggtttatca gcttgctttt acatcactgc   4920

ccgctttcca gtcgggaaac ctgtcgtgcc agctgcatta atgaatcggc caacgcgcgg   4980

ggagaggcgg tttgcgtatt gggcgccagg gtggtttttc ttttcaccag tgacaccggc   5040

aacagctgat tgcccttcac cgcctggccc tgagagagtt gcagcaagcg gtccacgctg   5100

gtttgcccca gcaggcgaaa atcctgtttg atggtggtta acggcgggat ataacatgag   5160

ctgtcttcgg tatcgtcgta tcccactacc gagatatccg caccaacgcg cagcccggac   5220

tcggtaatgg cgcgcattgc gcccagcgcc atctgatcgt tggcaaccag catcgcagtg   5280

ggaacgatgc cctcattcag catttgcatg gtttgttgaa aaccggacat ggcactccag   5340

tcgccttccc gttccgctat cggctgaatt tgattgcgag tgagatattt atgccagcca   5400

gccagacgca gacgcgccga gacagaactt aatgggcccg ctaacagcgc gatttgctgg   5460

tgacccaatg cgaccagatg ctccacgccc agtcgcgtac cgtcttcatg ggagaaaata   5520

atactgttga tgggtgtctg gtcagagaca tcaagaaata acgccggaac attagtgcag   5580

gcagcttcca cagcaatggc atcctggtca tccagcggat agttaatgat cagcccactg   5640

acgcgttgcg cgagaagatt gtgcaccgcc gctttacagg cttcgacgcc gcttcgttct   5700

accatcgaca ccaccacgct ggcacccagt tgatcggcgc gagatttaat cgccgcgaca   5760

atttgcgacg gcgcgtgcag ggccagactg gaggtggcaa cgccaatcag caacgactgt   5820

ttgcccgcca gttgttgtgc cacgcggttg ggaatgtaat tcagctccgc catcgccgct   5880

tccacttttt cccgcgtttt cgcagaaacg tggctggcct ggttcaccac gcgggaaacg   5940

gtctgataag agacaccggc atactctgcg acatcgtata acgttactgg tttcatgagt   6000

acctctcctg tatcttgtgt acttgcgtac cgtaatatct cctctgtttc tgtataacag   6060

tactatgtga ttataccagc cccctcacta catgtcaaga ataaactgcc aaagccgagc   6120

ggccgcttat ttgccgacta ccttggtgat ctcgcctttc acgtagtgga caaattcttc   6180

caactgatct gcgcgcgagg ccaagcgatc ttcttcttgt ccaagataag cctgtctagc   6240

ttcaagtatg acgggctgat actgggccgg caggcgctcc attgcccagt cggcagcgac   6300

atccttcggc gcgattttgc cggttactgc gctgtaccaa atgcgggaca acgtaagcac   6360

tacatttcgc tcatcgccag cccagtcggg cggcgagttc catagcgtta aggtttcatt   6420

tagcgcctca aatagatcct gttcaggaac cggatcaaag agttcctccg ccgctggacc   6480

taccaaggca acgctatgtt ctcttgcttt tgtcagcaag atagccagat caatgtcgat   6540

cgtggctggc tcgaagatac ccgcaagaat gtcattgcgc tgccattctc caaattgcag   6600

ttcgcgctta gctggataac gccacggaat gatgtcgtcg tgcacaacaa tggtgacttc   6660

tacagcgcgg agaatctcgc tctctccagg ggaagccgaa gtttccaaaa ggtcgttgat   6720

caaagctcgc cgcgttgttt catcaagcct tacggtcacc gtaaccagca aatcaatatc   6780

actgtgtggc ttcaggccgc catccactgc ggagccgtac aaatgtacgg ccagcaacgt   6840

cggttcgaga tggcgctcga tgacgccaac tacctctgat agttgagtcg atacttcggc   6900

gatcaccgct tccctcataa tgtttaactt tgttttaggg cgactgccct gctgcgtaac   6960

atcgttgctg ctccataaca tcaaacatcg acccacggcg taacgcgctt gctgcttgga   7020

tgcccgaggc atagactgta ccccaaaaaa acagtcataa caagccatga aaaccgccac   7080

tgcgccgtta ccaccgctgc gttcggtcaa ggttctggac cagttgcgtg agcgcatacg   7140
```

```
ctacttgcat tacagcttac gaaccgaaca ggcttatgtc cactgggttc gtgccttcat   7200
ccgtttccac ggtgtgcgtc acccggcaac cttgggtagc agcgaagtcg aggcatttct   7260
gtcctggctg gtcatgacca aaatccctta acgtgagtca gcctgccgcc ttgggccggg   7320
tgatgtcgta cttgcccgcc gcgaactcgg ttaccgtcca gcccagcgcg accagctccg   7380
gcaacgcctc gcgcacccgc ttgcggcgct tgcgcatggt cgaaccactg gcctctgacg   7440
gccagacata gccgcacaag gtatctatgg aagccttgcc ggttttgccg gggtcgatcc   7500
agccacacag ccgctggtgc agcaggcggg cggtttcgct gtccagcgcc cgcacctcgt   7560
ccatgctgat gcgcacatgc tggccgccac ccatgacggc ctgcgcgatc aaggggttca   7620
gggccacgta caggcgcccg tccgcctcgt cgctggcgta ctccgacagc agccgaaacc   7680
cctgccgctt gcggccattc tgggcgatga tggatacctt ccaaaggcgc tcgatgcagt   7740
cctgtatgtg cttgagcgcc ccaccactat cgacctctgc cccgatttcc tttgccagcg   7800
cccgatagct acctttgacc acatggcatt cagcggtgac ggcctcccac ttgggttcca   7860
ggaacagccg gagctgccgt ccgccttcgg tcttgggttc cgggccaagc actaggccat   7920
taggcccagc catggccacc agcccttgca ggatgcgcag atcatcagcg cccagcggct   7980
ccgggccgct gaactcgatc cgcttgccgt cgccgtagtc atacgtcacg tccagcttgc   8040
tgcgcttgcg ctcgccccgc ttgagggcac ggaacaggcc gggggccaga cagtgcgccg   8100
ggtcgtgccg gacgtggctg aggctgtgct tgttcttagg cttcaccacg gggcaccccc   8160
ttgctcttgc gctgcctctc cagcacggcg ggcttgagca ccccgccgtc atgccgcctg   8220
aaccaccgat cagcgaacgg tgcgccatag ttggccttgc tcacaccgaa gcggacgaag   8280
aaccggcgct ggtcgtcgtc cacaccccat tcctcggcct cggcgctggt catgctcgac   8340
aggtaggact gccagcggat gttatcgacc agtaccgagc tgccccggct ggcctgctgc   8400
tggtcgcctg cgcccatcat ggccgcgccc ttgctggcat ggtgcaggaa cacgatagag   8460
cacccggtat cggcggcgat ggcctccatg cgaccgatga cctgggccat ggggccgctg   8520
gcgttttctt cctcgatgtg gaaccggcgc agcgtgtcca gcaccatcag gcggcggccc   8580
tcggcggcgc gcttgaggcc gtcgaaccac tccggggcca tgatgttggg caggctgccg   8640
atcagcggct ggatcagcag gccgtcagcc acggcttgcc gttcctcggc gctgaggtgc   8700
gccccaaggg cgtgcaggcg gtgatgaatg gcggtgggcg ggtcttcggc gggcaggtag   8760
atcaccgggc cggtgggcag ttcgcccacc tccagcagat ccggcccgcc tgcaatctgt   8820
gcggccagtt gcagggccag catggattta ccggcaccac cgggcgacac cagcgccccg   8880
accgtaccgg ccaccatgtt gggcaaaacg tagtccagcg gtggcggcgc tgctgcgaac   8940
gcctccagaa tattgatagg cttatgggta gccattgatt gcctcctttg caggcagttg   9000
gtggttaggc gctggcgggg tcactacccc cgccctgcgc cgctctgagt tcttccaggc   9060
actcgcgcag cgcctcgtat tcgtcgtcgg tcagccagaa cttgcgctga cgcatccctt   9120
tggccttcat gcgctcggca tatcgcgctt ggcgtacagc gtcagggctg gccagcaggt   9180
cgccggtctg cttgtccttt tggtctttca tatcagtcac cgagaaactt gccggggccg   9240
aaaggcttgt cttcgcggaa caaggacaag gtgcagccgt caaggttaag gctggccata   9300
tcagcgactg aaaagcggcc agcctcggcc ttgtttgacg tataaccaaa gccaccgggc   9360
aaccaatagc ccttgtcact tttgatcagg tagaccgacc ctgaagcgct tttttcgtat   9420
tccataaaac cccccttctgt gcgtgagtac tcatagtata acaggcgtga gtaccaacgc   9480
aagcactaca tg                                                        9492
```

<210> SEQ ID NO 85
<211> LENGTH: 7787
<212> TYPE: DNA
<213> ORGANISM: Artificial Sequence
<220> FEATURE:
<223> OTHER INFORMATION: Chemically Synthesized, pBTK563

<400> SEQUENCE: 85

```
tcatgaccaa aatcccttaa cgtgagtcag cctgccgcct tgggccgggt gatgtcgtac     60
ttgcccgccg cgaactcggt taccgtccag cccagcgcga ccagctccgg caacgcctcg    120
cgcacccgct tgcggcgctt gcgcatggtc gaaccactgg cctctgacgg ccagacatag    180
ccgcacaagg tatctatgga agccttgccg gttttgccgg ggtcgatcca gccacacagc    240
cgctggtgca gcaggcgggc ggtttcgctg tccagcgccc gcacctcgtc catgctgatg    300
cgcacatgct ggccgccacc catgacggcc tgcgcgatca aggggttcag ggccacgtac    360
aggcgcccgt ccgcctcgtc gctggcgtac tccgacagca gccgaaaccc ctgccgcttg    420
cggccattct gggcgatgat ggataccttc caaaggcgct cgatgcagtc ctgtatgtgc    480
ttgagcgccc caccactatc gacctctgcc ccgatttcct ttgccagcgc ccgatagcta    540
cctttgacca catggcattc agcggtgacg gcctcccact tgggttccag gaacagccgg    600
agctgccgtc cgccttcggt cttgggttcc gggccaagca ctaggccatt aggcccagcc    660
atggccacca gcccttgcag gatgcgcaga tcatcagcgc ccagcggctc cgggccgctg    720
aactcgatcc gcttgccgtc gccgtagtca tacgtcacgt ccagcttgct gcgcttgcgc    780
tcgccccgct tgagggcacg gaacaggccg ggggccagac agtgcgccgg gtcgtgccgg    840
acgtggctga ggctgtgctt gttcttaggc ttcaccacgg ggcacccccct tgctcttgcg    900
ctgcctctcc agcacggcgg gcttgagcac cccgccgtca tgccgcctga accaccgatc    960
agcgaacggt gcgccatagt tggccttgct cacaccgaag cggacgaaga accggcgctg   1020
gtcgtcgtcc acaccccatt cctcggcctc ggcgctggtc atgctcgaca ggtaggactg   1080
ccagcggatg ttatcgacca gtaccgagct gccccggctg gcctgctgct ggtcgcctgc   1140
gcccatcatg gccgcgccct tgctggcatg gtgcaggaac acgatagagc acccggtatc   1200
ggcggcgatg gcctccatgc gaccgatgac ctgggccatg gggccgctgg cgttttcttc   1260
ctcgatgtgg aaccggcgca gcgtgtccag caccatcagg cggcggccct cggcggcgcg   1320
cttgaggccg tcgaaccact ccggggccat gatgttgggc aggctgccga tcagcggctg   1380
gatcagcagg ccgtcagcca cggcttgccg ttcctcggcg ctgaggtgcg ccccaagggc   1440
gtgcaggcgg tgatgaatgg cggtgggcgg gtcttcggcg ggcaggtaga tcaccgggcc   1500
ggtgggcagt tcgcccacct ccagcagatc cggcccgcct gcaatctgtg cggccagttg   1560
cagggccagc atggatttac cggcaccacc gggcgacacc agcgccccga ccgtaccggc   1620
caccatgttg ggcaaaacgt agtccagcgg tggcggcgct gctgcgaacg cctccagaat   1680
attgataggc ttatgggtag ccattgattg cctcctttgc aggcagttgg tggttaggcg   1740
ctggcggggt cactaccccc gccctgcgcc gctctgagtt cttccaggca ctcgcgcagc   1800
gcctcgtatt cgtcgtcggt cagccagaac ttgcgctgac gcatcccttt ggccttcatg   1860
cgctcggcat atcgcgcttg gcgtacagcg tcagggctgg ccagcaggtc gccggtctgc   1920
ttgtcctttt ggtctttcat atcagtcacc gagaaacttg ccggggccga aaggcttgtc   1980
ttcgcggaac aaggacaagg tgcagccgtc aaggttaagg ctggccatat cagcgactga   2040
```

-continued

```
aaagcggcca gcctcggcct tgtttgacgt ataaccaaag ccaccgggca accaatagcc   2100
cttgtcactt ttgatcaggt agaccgaccc tgaagcgctt ttttcgtatt ccataaaacc   2160
cccttctgtg cgtgagtact catagtataa caggcgtgag taccaacgca agcactacat   2220
gctgaaatct ggcccgcccc tgtccatgcc tcgctggcgg ggtgccggtg cccgtgccag   2280
ctcggcccgc gcaagctgga cgctgggcag acccatgacc ttgctgacgg tgcgctcgat   2340
gtaatccgct tcgtggccgg gcttgcgctc tgccagcgct gggctggcct cggccatggc   2400
cttgccgatt tcctcggcac tgcggccccg gctggccagc ttctgcgcgg cgataaagtc   2460
gcacttgctg aggtcatgac cgaagcgctt gaccagcccg gccatctcgc tgcggtactc   2520
gtccagcgcc gtgcgccggt ggcggctaag ctgccgctcg ggcagttcga ggctggccag   2580
cctgcgggcc ttctcctgct gccgctgggc ctgctcgatc tgctggccag cctgctgcac   2640
cagcgccggg ccagcggtgg cggtcttgcc cttggattca cgcagcagca cccacggctg   2700
ataaccggcg cgggtggtgt gcttgtcctt gcggttggtg aagcccgcca agcggccata   2760
gtggcggctg tcggcgctgg ccgggtcggc gtcgtactcg ctggccagcg tccgggcaat   2820
ctgcccccga agttcaccgc ctgcggcgtc ggccaccttg acccatgcct gatagttctt   2880
cgggctggtt tccactacca gggcaggctc ccggccctcg gctttcatgt catccaggtc   2940
aaactcgctg aggtcgtcca ccagcaccag accatgccgc tcctgctcgg cgggcctgat   3000
atacacgtca ttgccctggg cattcatccg cttgagccat ggcgtgttct ggagcacttc   3060
ggcggctgac cattcccggt tcatcatctg gccggtgggt gcgtccctga cgccgatatc   3120
gaagcgctca cagcccatgg ccttgagctg tcggcctatg gcctgcaaag tcctgtcgtt   3180
cttcatcggg ccaccaagcg cagccagatc gagccgtcct cggttgtcag tggcgtcagg   3240
tcgagcaaga gcaacgatgc gatcagcagc accaccgtag gcatcatgga agccagcatc   3300
acggttagcc atagcttcca gtgccacccc cgcgacgcgc tccgggcgct ctgcgcggcg   3360
ctgctcacct cggcggctac ctcccgcaac tctttggcca gctccaccca tgccgcccct   3420
gtctggcgct gggctttcag ccactccgcc gcctgcgcct cgctggcctg cttggtctgg   3480
ctcatgacct gccgggcttc gtcggccagt gtcgccatgc tctgggccag cggttcgatc   3540
tgctccgcta actcgttgat gcctctggat ttcttcactc tgtcgattgc gttcatggtc   3600
tattgcctcc cggtattcct gtaagtcgat gatctgggcg ttggcggtgt cgatgttcag   3660
ggccacgtct gcccggtcgg tgcggatgcc ccggccttcc atctccacca cgttcggccc   3720
caggtgaaca ccgggcaggc gctcgatgcc ctgcgcctca agtgttctgt ggtcaatgcg   3780
ggcgtcgtgg ccagcccgct ctaatgcccg gttggcatgg tcggcccatg cctcgcgggt   3840
ctgctcaagc catgccttgg gcttgagcgc ttcggtcttc tgtgccccgc ccttctccgg   3900
ggtcttgccg ttgtaccgct tgaaccactg agcggcgggc cgctcgatgc cgtcattgat   3960
ccgctcggag atcatcaggt ggcagtgcgg gttctcgccg ccaccggcat ggatggccag   4020
cgtatacggc aggcgctcgg caccggtcag gtgctgggcg aactcggacg ccagcgcctt   4080
ctgctggtcg agggtcagct cgaccggcag ggcaaattcg acctccttga acagccgccc   4140
attggcgcgt tcatacaggt cggcagcatc ccagtagtcg gcgggccgct cgacgaactc   4200
cggcatgtgc ccggattcgg cgtgcaagac ttcatccatg tcgcgggcat acttgccttc   4260
gcgctggatg tagtcggcct tggccctggc cgattggccg cccgacctgc tgccggtttt   4320
cgccgtaagg tgataaatcg ccatgctgcc tcgctgttgc ttttgctttt cggctccatg   4380
caatggccct cggagagcgc accgcccgaa gggtggccgt taggccagtt tctcgaagag   4440
```

```
aaaccggtaa gtgcgccctc ccctacaaag tagggtcggg attgccgccg ctgtgcctcc   4500
atgatagcct acgagacagc acattaacaa tggggtgtca agatggttaa ggggagcaac   4560
aaggcggcgg atcggctggc caagctcgaa gaacaacgag cgcgaatcaa tgccgaaatt   4620
cagcgggagc gggcaaggga acagcagcaa gagcgcaaga acgaaacaag gcgcaaggtg   4680
ctggtggggg ccatgatttt ggccaaggtg aacagcagcg agtggccgga ggatcggctc   4740
atggcggcaa tggatgcgta ccttgaacgc gaccacgacc gcgccttgtt cggtctgccg   4800
ccacgccaga aggatgagcc gggctgaatg atcgaccgag acaggccctg cggggctgca   4860
cacgcgcccc cacccttcgg gtagggggaa aggccgctaa agcggctaaa agcgctccag   4920
cgtatttctg cggggtttgg tgtggggttt agcgggcttt gcccgccttt ccccctgccg   4980
cgcagcggtg gggcggtgtg tagcctagcg cagcgaatag accagctatc cggcctctgg   5040
ccgggcatat tgggcaaggg cagcagcgcc ccacaagggc gctgataacc gcgcctagtg   5100
gattattctt agataatcat ggatggattt ttccaacacc ccgccagccc ccgcccctgc   5160
tgggtttgca ggtttggggg cgtgacagtt attgcagggg ttcgtgacag ttattgcagg   5220
ggggcgtgac agttattgca ggggttcgtg acagttagta cgggagtgac gggcactggc   5280
tggcaatgtc tagcaacggc aggcatttcg gctgagggta aaagaacttt ccgctaagcg   5340
atagactgta tgtaaacaca gtattgcaag gacgcggaac atgcctcatg tggcggccag   5400
gacggccagc cgggatcggg atactggtcg ttaccagagc caccgacccg agcaaaccct   5460
tctctatcag atcgttgacg agtattaccc ggcattcgct gcgcttatgg cagagcaggg   5520
aaaggaattg ccgggctatg tgcaacggga atttgaagaa tttctccaat gcgggcggct   5580
ggagcatggc tttctacggg ttcgctgcga gtcttgccac gccgagcacc tggtcgcttt   5640
cagaaatcaa tctaaagtat atatgagtaa acttggtctg acaggcccct gaattcgcat   5700
ctagatggta gagccacaaa cagccggtac aagcaacgat ctccaggacc atctgaatca   5760
tgcgcggatg acacgaactc acgacggcga tcacagacat taacccacag tacagacact   5820
gcgacaacgt ggcaattcgt cgcaataccg tctcactgaa ctggccgata attgcagacg   5880
aacgctttgg cagtttattc ttgacatgta gtgagggggc tggtataatc acatagtact   5940
gttatacaga aacagaggag atattacata tggtcttcac actcgaagat ttcgttgggg   6000
actggcgaca gacagccggc tacaacctgg accaagtcct tgaacaggga ggtgtgtcca   6060
gtttgtttca gaatctcggg gtgtccgtaa ctccgatcca aaggattgtc ctgagcggtg   6120
aaaatgggct gaagatcgac atccatgtca tcatcccgta tgaaggtctg agcggcgacc   6180
aaatgggcca gatcgaaaaa atttttaagg tggtgtaccc tgtggatgat catcacttta   6240
aggtgatcct gcactatggc acactggtaa tcgacggggt tacgccgaac atgatcgact   6300
atttcggacg gccgtatgaa ggcatcgccg tgttcgacgg caaaaagatc actgtaacag   6360
ggaccctgtg gaacggcaac aaaattatcg acgagcgcct gatcaacccc gacggctccc   6420
tgctgttccg agtaaccatc aacggagtga ccggctggcg gctgtgcgaa cgcattctgg   6480
cgtaaatccg taatcgttaa tccgcaaata acgtaaaaac ccgcttcggc gggttttttt   6540
atgggggggag tttagggaaa gagcatttgt cagctggatc agcagatggg aaccggatac   6600
tcctcagcct ccagagtagc caatgagacg ccgagcggcc gcttatttgc cgactacctt   6660
ggtgatctcg cctttcacgt agtggacaaa ttcttccaac tgatctgcgc gcgaggccaa   6720
gcgatcttct tcttgtccaa gataagcctg tctagcttca agtatgacgg gctgatactg   6780
```

ggccggcagg cgctccattg cccagtcggc agcgacatcc ttcggcgcga ttttgccggt 6840
tactgcgctg taccaaatgc gggacaacgt aagcactaca tttcgctcat cgccagccca 6900
gtcgggcggc gagttccata gcgttaaggt ttcatttagc gcctcaaata gatcctgttc 6960
aggaaccgga tcaaagagtt cctccgccgc tggacctacc aaggcaacgc tatgttctct 7020
tgcttttgtc agcaagatag ccagatcaat gtcgatcgtg gctggctcga agatacccgc 7080
aagaatgtca ttgcgctgcc attctccaaa ttgcagttcg cgcttagctg gataacgcca 7140
cggaatgatg tcgtcgtgca caacaatggt gacttctaca gcgcggagaa tctcgctctc 7200
tccaggggaa gccgaagttt ccaaaaggtc gttgatcaaa gctcgccgcg ttgtttcatc 7260
aagccttacg gtcaccgtaa ccagcaaatc aatatcactg tgtggcttca ggccgccatc 7320
cactgcggag ccgtacaaat gtacggccag caacgtcggt tcgagatggc gctcgatgac 7380
gccaactacc tctgatagtt gagtcgatac ttcggcgatc accgcttccc tcataatgtt 7440
taactttgtt ttagggcgac tgccctgctg cgtaacatcg ttgctgctcc ataacatcaa 7500
acatcgaccc acggcgtaac gcgcttgctg cttggatgcc cgaggcatag actgtacccc 7560
aaaaaaacag tcataacaag ccatgaaaac cgccactgcg ccgttaccac cgctgcgttc 7620
ggtcaaggtt ctggaccagt tgcgtgagcg catacgctac ttgcattaca gcttacgaac 7680
cgaacaggct tatgtccact gggttcgtgc cttcatccgt ttccacggtg tgcgtcaccc 7740
ggcaaccttg ggtagcagcg aagtcgaggc atttctgtcc tggctgg 7787

<210> SEQ ID NO 86
<211> LENGTH: 7798
<212> TYPE: DNA
<213> ORGANISM: Artificial Sequence
<220> FEATURE:
<223> OTHER INFORMATION: Chemically Synthesized, pBTK564

<400> SEQUENCE: 86
tcgatgtaat ccgcttcgtg gccgggcttg cgctctgcca gcgctgggct ggcctcggcc 60
atggccttgc cgatttcctc ggcactgcgg ccccggctgg ccagcttctg cgcggcgata 120
aagtcgcact tgctgaggtc atgaccgaag cgcttgacca gcccggccat ctcgctgcgg 180
tactcgtcca gcgccgtgcg ccggtggcgg ctaagctgcc gctcgggcag ttcgaggctg 240
gccagcctgc gggccttctc ctgctgccgc tgggcctgct cgatctgctg gccagcctgc 300
tgcaccagcg ccgggccagc ggtggcggtc ttgcccttgg attcacgcag cagcacccac 360
ggctgataac cggcgcgggt ggtgtgcttg tccttgcggt tggtgaagcc cgccaagcgg 420
ccatagtggc ggctgtcggc gctggccggg tcggcgtcgt actcgctggc cagcgtccgg 480
gcaatctgcc cccgaagttc accgcctgcg gcgtcggcca ccttgaccca tgcctgatag 540
ttcttcgggc tggtttccac taccagggca ggctcccggc cctcggcttt catgtcatcc 600
aggtcaaact cgctgaggtc gtccaccagc accagaccat gccgctcctg ctcggcgggc 660
ctgatataca cgtcattgcc ctgggcattc atccgcttga gccatggcgt gttctggagc 720
acttcggcgg ctgaccattc ccggttcatc atctggccgg tgggtgcgtc cctgacgccg 780
atatcgaagc gctcacagcc catggccttg agctgtcggc ctatggcctg caaagtcctg 840
tcgttcttca tcgggccacc aagcgcagcc agatcgagcc gtcctcggtt gtcagtggcg 900
tcaggtcgag caagagcaac gatgcgatca gcagcaccac cgtaggcatc atggaagcca 960
gcatcacggt tagccatagc ttccagtgcc acccccgcga cgcgctccgg gcgctctgcg 1020
cggcgctgct cacctcggcg gctacctccc gcaactcttt ggccagctcc acccatgccg 1080

```
ccccctgtctg gcgctgggct ttcagccact ccgccgcctg cgcctcgctg gcctgcttgg   1140

tctggctcat gacctgccgg gcttcgtcgg ccagtgtcgc catgctctgg gccagcggtt   1200

cgatctgctc cgctaactcg ttgatgcctc tggatttctt cactctgtcg attgcgttca   1260

tggtctattg cctcccggta ttcctgtaag tcgatgatct gggcgttggc ggtgtcgatg   1320

ttcagggcca cgtctgcccg gtcggtgcgg atgccccggc cttccatctc caccacgttc   1380

ggccccaggt gaacaccggg caggcgctcg atgccctgcg cctcaagtgt tctgtggtca   1440

atgcgggcgt cgtggccagc ccgctctaat gcccggttgg catggtcggc ccatgcctcg   1500

cgggtctgct caagccatgc cttgggcttg agcgcttcgg tcttctgtgc cccgcccttc   1560

tccggggtct tgccgttgta ccgcttgaac cactgagcgg cgggccgctc gatgccgtca   1620

ttgatccgct cggagatcat caggtggcag tgcgggttct cgccgccacc ggcatggatg   1680

gccagcgtat acggcaggcg ctcggcaccg gtcaggtgct gggcgaactc ggacgccagc   1740

gccttctgct ggtcgagggt cagctcgacc ggcagggcaa attcgacctc cttgaacagc   1800

cgcccattgg cgcgttcata caggtcggca gcatcccagt agtcggcggg ccgctcgacg   1860

aactccggca tgtgcccgga ttcggcgtgc aagacttcat ccatgtcgcg ggcatacttg   1920

ccttcgcgct ggatgtagtc ggccttggcc ctggccgatt ggccgcccga cctgctgccg   1980

gttttcgccg taaggtgata aatcgccatg ctgcctcgct gttgcttttg cttttcggct   2040

ccatgcaatg gccctcggag agcgcaccgc ccgaagggtg gccgttaggc cagtttctcg   2100

aagagaaacc ggtaagtgcg ccctccccta caaagtaggg tcgggattgc cgccgctgtg   2160

cctccatgat agcctacgag acagcacatt aacaatgggg tgtcaagatg gttaagggga   2220

gcaacaaggc ggcggatcgg ctggccaagc tcgaagaaca acgagcgcga atcaatgccg   2280

aaattcagcg ggagcgggca agggaacagc agcaagagcg caagaacgaa acaaggcgca   2340

aggtgctggt gggggccatg attttggcca aggtgaacag cagcgagtgg ccggaggatc   2400

ggctcatggc ggcaatggat gcgtaccttg aacgcgacca cgaccgcgcc ttgttcggtc   2460

tgccgccacg ccagaaggat gagccgggct gaatgatcga ccgagacagg ccctgcgggg   2520

ctgcacacgc gcccccaccc ttcgggtagg gggaaaggcc gctaaagcgg ctaaaagcgc   2580

tccagcgtat ttctgcgggg tttggtgtgg ggtttagcgg gctttgcccg cctttccccc   2640

tgccgcgcag cggtggggcg gtgtgtagcc tagcgcagcg aatagaccag ctatccggcc   2700

tctggccggg catattgggc aagggcagca gcgccccaca agggcgctga taaccgcgcc   2760

tagtggatta ttcttagata atcatggatg gatttttcca acaccccgcc agcccccgcc   2820

cctgctgggt ttgcaggttt gggggcgtga cagttattgc aggggttcgt gacagttatt   2880

gcaggggggc gtgacagtta ttgcaggggt tcgtgacagt tagtacggga gtgacgggca   2940

ctggctggca atgtctagca acggcaggca tttcggctga gggtaaaaga actttccgct   3000

aagcgataga ctgtatgtaa acacagtatt gcaaggacgc ggaacatgcc tcatgtggcg   3060

gccaggacgg ccagccggga tcgggatact ggtcgttacc agagccaccg acccgagcaa   3120

acccttctct atcagatcgt tgacgagtat tacccggcat tcgctgcgct tatggcagag   3180

cagggaaagg aattgccggg ctatgtgcaa cgggaatttg aagaatttct ccaatgcggg   3240

cggctggagc atggctttct acgggttcgc tgcgagtctt gccacgccga gcacctggtc   3300

gctttcagaa atcaatctaa agtatatatg agtaaacttg gtctgacagg cccctgaatt   3360

cgcatctaga tggtagagcc acaaacagcc ggtacaagca acgatctcca ggaccatctg   3420
```

```
aatcatgcgc ggatgacacg aactcacgac ggcgatcaca gacattaacc cacagtacag   3480
acactgcgac aacgtggcaa ttcgtcgcaa taccgtctca ctgaactggc cgataattgc   3540
agacgaacgg gtgaaacaaa acggttgaca acatgaagta aacacggtac gatgtaccac   3600
atgaaacgac agtgagtcaa tacagaaaca gaggagatat tacatatggt cttcacactc   3660
gaagatttcg ttggggactg gcgacagaca gccggctaca acctggacca agtccttgaa   3720
cagggaggtg tgtccagttt gtttcagaat ctcggggtgt ccgtaactcc gatccaaagg   3780
attgtcctga gcggtgaaaa tgggctgaag atcgacatcc atgtcatcat cccgtatgaa   3840
ggtctgagcg gcgaccaaat gggccagatc gaaaaaattt ttaaggtggt gtaccctgtg   3900
gatgatcatc actttaaggt gatcctgcac tatggcacac tggtaatcga cggggttacg   3960
ccgaacatga tcgactattt cggacggccg tatgaaggca tcgccgtgtt cgacggcaaa   4020
aagatcactg taacagggac cctgtggaac ggcaacaaaa ttatcgacga gcgcctgatc   4080
aaccccgacg gctccctgct gttccgagta accatcaacg gagtgaccgg ctggcggctg   4140
tgcgaacgca ttctggcgta aatccgtaat cgttaatccg caaataacgt aaaaacccgc   4200
ttcggcgggt ttttttatgg ggggagttta gggaaagagc atttgtcagc tggatcagca   4260
gatgggaacc ggatactcct cagcctccag agtagccaat gagacgccga gcggccgctt   4320
atttgccgac taccttggtg atctcgcctt tcacgtagtg gacaaattct tccaactgat   4380
ctgcgcgcga ggccaagcga tcttcttctt gtccaagata agcctgtcta gcttcaagta   4440
tgacgggctg atactgggcc ggcaggcgct ccattgccca gtcggcagcg acatccttcg   4500
gcgcgatttt gccggttact gcgctgtacc aaatgcggga caacgtaagc actacatttc   4560
gctcatcgcc agcccagtcg ggcggcgagt tccatagcgt taaggtttca tttagcgcct   4620
caaatagatc ctgttcagga accggatcaa agagttcctc cgccgctgga cctaccaagg   4680
caacgctatg ttctcttgct tttgtcagca agatagccag atcaatgtcg atcgtggctg   4740
gctcgaagat acccgcaaga atgtcattgc gctgccattc tccaaattgc agttcgcgct   4800
tagctggata acgccacgga atgatgtcgt cgtgcacaac aatggtgact tctacagcgc   4860
ggagaatctc gctctctcca ggggaagccg aagtttccaa aaggtcgttg atcaaagctc   4920
gccgcgttgt ttcatcaagc cttacggtca ccgtaaccag caaatcaata tcactgtgtg   4980
gcttcaggcc gccatccact gcggagccgt acaaatgtac ggccagcaac gtcggttcga   5040
gatggcgctc gatgacgcca actacctctg atagttgagt cgatacttcg gcgatcaccg   5100
cttccctcat aatgtttaac tttgttttag ggcgactgcc ctgctgcgta acatcgttgc   5160
tgctccataa catcaaacat cgacccacgg cgtaacgcgc ttgctgcttg gatgcccgag   5220
gcatagactg taccccaaaa aaacagtcat aacaagccat gaaaaccgcc actgcgccgt   5280
taccaccgct gcgttcggtc aaggttctgg accagttgcg tgagcgcata cgctacttgc   5340
attacagctt acgaaccgaa caggcttatg tccactgggt tcgtgccttc atccgtttcc   5400
acggtgtgcg tcacccggca accttgggta gcagcgaagt cgaggcattt ctgtcctggc   5460
tggtcatgac caaaatccct taacgtgagt cagcctgccg ccttgggccg ggtgatgtcg   5520
tacttgcccg ccgcgaactc ggttaccgtc cagcccagcg cgaccagctc cggcaacgcc   5580
tcgcgcaccc gcttgcggcg cttgcgcatg gtcgaaccac tggcctctga cggccagaca   5640
tagccgcaca aggtatctat ggaagccttg ccggttttgc cggggtcgat ccagccacac   5700
agccgctggt gcagcaggcg ggcggtttcg ctgtccagcg cccgcacctc gtccatgctg   5760
atgcgcacat gctggccgcc acccatgacg gcctgcgcga tcaaggggtt cagggccacg   5820
```

tacaggcgcc cgtccgcctc gtcgctggcg tactccgaca gcagccgaaa cccctgccgc 5880
ttgcggccat tctgggcgat gatggatacc ttccaaaggc gctcgatgca gtcctgtatg 5940
tgcttgagcg ccccaccact atcgacctct gccccgattt cctttgccag cgcccgatag 6000
ctacctttga ccacatggca ttcagcggtg acggcctccc acttgggttc caggaacagc 6060
cggagctgcc gtccgccttc ggtcttgggt tccgggccaa gcactaggcc attaggccca 6120
gccatggcca ccagcccttg caggatgcgc agatcatcag cgcccagcgg ctccgggccg 6180
ctgaactcga tccgcttgcc gtcgccgtag tcatacgtca cgtccagctt gctgcgcttg 6240
cgctcgcccc gcttgagggc acggaacagg ccgggggcca gacagtgcgc cgggtcgtgc 6300
cggacgtggc tgaggctgtg cttgttctta ggcttcacca cggggcaccc ccttgctctt 6360
gcgctgcctc tccagcacgg cgggcttgag caccccgccg tcatgccgcc tgaaccaccg 6420
atcagcgaac ggtgcgccat agttggcctt gctcacaccg aagcggacga agaaccggcg 6480
ctggtcgtcg tccacacccc attcctcggc ctcggcgctg gtcatgctcg acaggtagga 6540
ctgccagcgg atgttatcga ccagtaccga gctgccccgg ctggcctgct gctggtcgcc 6600
tgcgcccatc atggccgcgc ccttgctggc atggtgcagg aacacgatag agcacccggt 6660
atcggcggcg atggcctcca tgcgaccgat gacctgggcc atggggccgc tggcgttttc 6720
ttcctcgatg tggaaccggc gcagcgtgtc cagcaccatc aggcggcggc cctcggcggc 6780
gcgcttgagg ccgtcgaacc actccggggc catgatgttg ggcaggctgc cgatcagcgg 6840
ctggatcagc aggccgtcag ccacggcttg ccgttcctcg gcgctgaggt gcgccccaag 6900
ggcgtgcagg cggtgatgaa tggcggtggg cgggtcttcg gcgggcaggt agatcaccgg 6960
gccggtgggc agttcgccca cctccagcag atccggcccg cctgcaatct gtgcggccag 7020
ttgcagggcc agcatggatt taccggcacc accgggcgac accagcgccc cgaccgtacc 7080
ggccaccatg ttgggcaaaa cgtagtccag cggtggcggc gctgctgcga acgcctccag 7140
aatattgata ggcttatggg tagccattga ttgcctcctt tgcaggcagt tggtggttag 7200
gcgctggcgg ggtcactacc cccgccctgc gccgctctga gttcttccag gcactcgcgc 7260
agcgcctcgt attcgtcgtc ggtcagccag aacttgcgct gacgcatccc tttggccttc 7320
atgcgctcgg catatcgcgc ttggcgtaca gcgtcagggc tggccagcag gtcgccggtc 7380
tgcttgtcct tttggtcttt catatcagtc accgagaaac ttgccggggc cgaaaggctt 7440
gtcttcgcgg aacaaggaca aggtgcagcc gtcaaggtta aggctggcca tatcagcgac 7500
tgaaaagcgg ccagcctcgg ccttgtttga cgtataacca aagccaccgg gcaaccaata 7560
gcccttgtca cttttgatca ggtagaccga ccctgaagcg ctttttttcgt attccataaa 7620 accccttct gtgcgtgagt actcatagta taacaggcgt gagtaccaac gcaagcacta 7680
catgctgaaa tctggcccgc ccctgtccat gcctcgctgg cggggtgccg gtgcccgtgc 7740
cagctcggcc cgcgcaagct ggacgctggg cagacccatg accttgctga cggtgcgc 7798

<210> SEQ ID NO 87
<211> LENGTH: 7988
<212> TYPE: DNA
<213> ORGANISM: Artificial Sequence
<220> FEATURE:
<223> OTHER INFORMATION: Chemically Synthesized, pBTK569

<400> SEQUENCE: 87
tcgatgtaat ccgcttcgtg gccgggcttg cgctctgcca gcgctgggct ggcctcggcc 60

-continued

```
atggccttgc cgatttcctc ggcactgcgg ccccggctgg ccagcttctg cgcggcgata    120
aagtcgcact tgctgaggtc atgaccgaag cgcttgacca gcccggccat ctcgctgcgg    180
tactcgtcca gcgccgtgcg ccggtggcgg ctaagctgcc gctcgggcag ttcgaggctg    240
gccagcctgc gggccttctc ctgctgccgc tgggcctgct cgatctgctg gccagcctgc    300
tgcaccagcg ccgggccagc ggtggcggtc ttgcccttgg attcacgcag cagcacccac    360
ggctgataac cggcgcgggt ggtgtgcttg tccttgcggt tggtgaagcc cgccaagcgg    420
ccatagtggc ggctgtcggc gctggccggg tcggcgtcgt actcgctggc cagcgtccgg    480
gcaatctgcc cccgaagttc accgcctgcg gcgtcggcca ccttgaccca tgcctgatag    540
ttcttcgggc tggtttccac taccagggca ggctcccggc cctcggcttt catgtcatcc    600
aggtcaaact cgctgaggtc gtccaccagc accagaccat gccgctcctg ctcggcgggc    660
ctgatataca cgtcattgcc ctgggcattc atccgcttga gccatggcgt gttctggagc    720
acttcggcgg ctgaccattc ccggttcatc atctggccgg tgggtgcgtc cctgacgccg    780
atatcgaagc gctcacagcc catggccttg agctgtcggc ctatggcctg caaagtcctg    840
tcgttcttca tcgggccacc aagcgcagcc agatcgagcc gtcctcggtt gtcagtggcg    900
tcaggtcgag caagagcaac gatgcgatca gcagcaccac cgtaggcatc atggaagcca    960
gcatcacggt tagccatagc ttccagtgcc acccccgcga cgcgctccgg gcgctctgcg   1020
cggcgctgct cacctcggcg gctacctccc gcaactcttt ggccagctcc acccatgccg   1080
cccctgtctg gcgctgggct ttcagccact ccgccgcctg cgcctcgctg gcctgcttgg   1140
tctggctcat gacctgccgg gcttcgtcgg ccagtgtcgc catgctctgg gccagcggtt   1200
cgatctgctc cgctaactcg ttgatgcctc tggatttctt cactctgtcg attgcgttca   1260
tggtctattg cctcccggta ttcctgtaag tcgatgatct gggcgttggc ggtgtcgatg   1320
ttcagggcca cgtctgcccg gtcggtgcgg atgccccggc cttccatctc caccacgttc   1380
ggccccaggt gaacaccggg caggcgctcg atgccctgcg cctcaagtgt tctgtggtca   1440
atgcgggcgt cgtggccagc ccgctctaat gcccggttgg catggtcggc ccatgcctcg   1500
cgggtctgct caagccatgc cttgggcttg agcgcttcgg tcttctgtgc cccgcccttc   1560
tccggggtct tgccgttgta ccgcttgaac cactgagcgg cgggccgctc gatgccgtca   1620
ttgatccgct cggagatcat caggtggcag tgcgggttct cgccgccacc ggcatggatg   1680
gccagcgtat acggcaggcg ctcggcaccg gtcaggtgct gggcgaactc ggacgccagc   1740
gccttctgct ggtcgagggt cagctcgacc ggcagggcaa attcgacctc cttgaacagc   1800
cgcccattgg cgcgttcata caggtcggca gcatcccagt agtcggcggg ccgctcgacg   1860
aactccggca tgtgcccgga ttcggcgtgc aagacttcat ccatgtcgcg ggcatacttg   1920
ccttcgcgct ggatgtagtc ggccttggcc ctggccgatt ggccgcccga cctgctgccg   1980
gttttcgccg taaggtgata aatcgccatg ctgcctcgct gttgcttttg cttttcggct   2040
ccatgcaatg gccctcggag agcgcaccgc ccgaagggtg gccgttaggc cagtttctcg   2100
aagagaaacc ggtaagtgcg ccctccccta caaagtaggg tcgggattgc cgccgctgtg   2160
cctccatgat agcctacgag acagcacatt aacaatgggg tgtcaagatg gttaagggga   2220
gcaacaaggc ggcggatcgg ctggccaagc tcgaagaaca acgagcgcga atcaatgccg   2280
aaattcagcg ggagcgggca agggaacagc agcaagagcg caagaacgaa acaaggcgca   2340
aggtgctggt gggggccatg attttggcca aggtgaacag cagcgagtgg ccggaggatc   2400
ggctcatggc ggcaatggat gcgtaccttg aacgcgacca cgaccgcgcc ttgttcggtc   2460
```

```
tgccgccacg ccagaaggat gagccgggct gaatgatcga ccgagacagg ccctgcgggg   2520
ctgcacacgc gcccccaccc ttcgggtagg gggaaaggcc gctaaagcgg ctaaaagcgc   2580
tccagcgtat ttctgcgggg tttggtgtgg ggtttagcgg gctttgcccg cctttccccc   2640
tgccgcgcag cggtggggcg gtgtgtagcc tagcgcagcg aatagaccag ctatccggcc   2700
tctggccggg catattgggc aagggcagca gcgccccaca agggcgctga taaccgcgcc   2760
tagtggatta ttcttagata atcatggatg gatttttcca acaccccgcc agcccccgcc   2820
cctgctgggt ttgcaggttt gggggcgtga cagttattgc aggggttcgt gacagttatt   2880
gcagggggggc gtgacagtta ttgcaggggt tcgtgacagt tagtacggga gtgacgggca   2940
ctggctggca atgtctagca acggcaggca tttcggctga gggtaaaaga actttccgct   3000
aagcgataga ctgtatgtaa acacagtatt gcaaggacgc ggaacatgcc tcatgtggcg   3060
gccaggacgg ccagccggga tcgggatact ggtcgttacc agagccaccg acccgagcaa   3120
acccttctct atcagatcgt tgacgagtat tacccggcat tcgctgcgct tatggcagag   3180
cagggaaagg aattgccggg ctatgtgcaa cgggaatttg aagaatttct ccaatgcggg   3240
cggctggagc atggctttct acgggttcgc tgcgagtctt gccacgccga gcacctggtc   3300
gctttcagaa atcaatctaa agtatatatg agtaaacttg gtctgacagg cccctgaatt   3360
cgcatctaga tggtagagcc acaaacagcc ggtacaagca acgatctcca ggaccatctg   3420
aatcatgcgc ggatgacacg aactcacgac ggcgatcaca gacattaacc cacagtacag   3480
acactgcgac aacgtggcaa ttcgtcgcaa taccgtctca ctgaactggc cgataattgc   3540
agacgaacgc tttggcagtt tattcttgac atgtagtgag gggctggta taatcacata   3600
gtactgttat acagaaacag aggagatatt acatatggat agcactgaga acgtcatcaa   3660
gcccttcatg cgcttcaagg tgcacatgga gggctccgtg aacggccacg agttcgagat   3720
cgagggcgtg ggcgagggca agccctacga gggcacccag accgccaagc tgcaagtgac   3780
caagggcggc cccctgccct tcgcctggga catcctgtcc ccccagttct tctacggctc   3840
caaggcgtac atcaagcacc ccgccgacat ccccgactac ctcaagcagt ccttccccga   3900
gggcttcaag tgggagcgcg tgatgaactt cgaggacggc ggcgtggtga ccgtgaccca   3960
ggactcctcc ctgcaggacg gcaccctcat ctaccacgtg aagttcatcg gcgtgaactt   4020
cccctccgac ggccccgtaa tgcagaagaa gactctgggc tgggagccct ccactgagcg   4080
caactacccc cgcgacggcg tgctgaaggg cgagaaccac atggcgctga agctgaaggg   4140
cggcggccac tacctgtgtg agttcaagtc catctacatg gccaagaagc ccgtgaagct   4200
gcccggctac cactacgtgg actacaagct cgacatcacc tcccacaacg aggactacac   4260
cgtggtggag cagtacgagc gcgccgaggc ccgccaccac ctgttccaga ctcacggtat   4320
ggacgaattg tacaagcacg acgaattgta aatccgtaat cgttaatccg caaataacgt   4380
aaaaacccgc ttcggcgggt ttttttatgg ggggagttta gggaaagagc atttgtcagc   4440
tggatcagca gatgggaacc ggatactcct cagcctccag agtagccaat gagacgccga   4500
gcggccgctt atttgccgac taccttggtg atctcgcctt tcacgtagtg gacaaattct   4560
tccaactgat ctgcgcgcga ggccaagcga tcttcttctt gtccaagata agcctgtcta   4620
gcttcaagta tgacgggctg atactgggcc ggcaggcgct ccattgccca gtcggcagcg   4680
acatccttcg gcgcgatttt gccggttact gcgctgtacc aaatgcggga caacgtaagc   4740
actacatttc gctcatcgcc agcccagtcg ggcggcgagt tccatagcgt taaggtttca   4800
```

```
tttagcgcct caaatagatc ctgttcagga accggatcaa agagttcctc cgccgctgga   4860
cctaccaagg caacgctatg ttctcttgct tttgtcagca agatagccag atcaatgtcg   4920
atcgtggctg gctcgaagat acccgcaaga atgtcattgc gctgccattc tccaaattgc   4980
agttcgcgct tagctggata acgccacgga atgatgtcgt cgtgcacaac aatggtgact   5040
tctacagcgc ggagaatctc gctctctcca ggggaagccg aagtttccaa aaggtcgttg   5100
atcaaagctc gccgcgttgt ttcatcaagc cttacggtca ccgtaaccag caaatcaata   5160
tcactgtgtg gcttcaggcc gccatccact gcggagccgt acaaatgtac ggccagcaac   5220
gtcggttcga gatggcgctc gatgacgcca actacctctg atagttgagt cgatacttcg   5280
gcgatcaccg cttccctcat aatgtttaac tttgttttag ggcgactgcc ctgctgcgta   5340
acatcgttgc tgctccataa catcaaacat cgacccacgg cgtaacgcgc ttgctgcttg   5400
gatgcccgag gcatagactg taccccaaaa aaacagtcat aacaagccat gaaaaccgcc   5460
actgcgccgt taccaccgct gcgttcggtc aaggttctgg accagttgcg tgagcgcata   5520
cgctacttgc attacagctt acgaaccgaa caggcttatg tccactgggt tcgtgccttc   5580
atccgtttcc acggtgtgcg tcacccggca accttgggta gcagcgaagt cgaggcattt   5640
ctgtcctggc tggtcatgac caaaatccct taacgtgagt cagcctgccg ccttgggccg   5700
ggtgatgtcg tacttgcccg ccgcgaactc ggttaccgtc cagcccagcg cgaccagctc   5760
cggcaacgcc tcgcgcaccc gcttgcggcg cttgcgcatg gtcgaaccac tggcctctga   5820
cggccagaca tagccgcaca aggtatctat ggaagccttg ccggttttgc cggggtcgat   5880
ccagccacac agccgctggt gcagcaggcg ggcggtttcg ctgtccagcg cccgcacctc   5940
gtccatgctg atgcgcacat gctggccgcc acccatgacg gcctgcgcga tcaaggggtt   6000
cagggccacg tacaggcgcc cgtccgcctc gtcgctggcg tactccgaca gcagccgaaa   6060
cccctgccgc ttgcggccat tctgggcgat gatggatacc ttccaaaggc gctcgatgca   6120
gtcctgtatg tgcttgagcg ccccaccact atcgacctct gccccgattt cctttgccag   6180
cgcccgatag ctacctttga ccacatggca ttcagcggtg acggcctccc acttgggttc   6240
caggaacagc cggagctgcc gtccgccttc ggtcttgggt tccgggccaa gcactaggcc   6300
attaggccca gccatggcca ccagcccttg caggatgcgc agatcatcag cgcccagcgg   6360
ctccgggccg ctgaactcga tccgcttgcc gtcgccgtag tcatacgtca cgtccagctt   6420
gctgcgcttg cgctcgcccc gcttgagggc acggaacagg ccgggggcca gacagtgcgc   6480
cgggtcgtgc cggacgtggc tgaggctgtg cttgttctta ggcttcacca cggggcaccc   6540
ccttgctctt gcgctgcctc tccagcacgg cgggcttgag caccccgccg tcatgccgcc   6600
tgaaccaccg atcagcgaac ggtgcgccat agttggcctt gctcacaccg aagcggacga   6660
agaaccggcg ctggtcgtcg tccacacccc attcctcggc ctcggcgctg gtcatgctcg   6720
acaggtagga ctgccagcgg atgttatcga ccagtaccga gctgccccgg ctggcctgct   6780
gctggtcgcc tgcgcccatc atggccgcgc ccttgctggc atggtgcagg aacacgatag   6840
agcacccggt atcggcggcg atggcctcca tgcgaccgat gacctgggcc atggggccgc   6900
tggcgttttc ttcctcgatg tggaaccggc gcagcgtgtc cagcaccatc aggcggcggc   6960
cctcggcggc gcgcttgagg ccgtcgaacc actccggggc catgatgttg ggcaggctgc   7020
cgatcagcgg ctggatcagc aggccgtcag ccacggcttg ccgttcctcg gcgctgaggt   7080
gcgccccaag ggcgtgcagg cggtgatgaa tggcggtggg cgggtcttcg gcgggcaggt   7140
agatcaccgg gccggtgggc agttcgccca cctccagcag atccggcccg cctgcaatct   7200
```

```
gtgcggccag ttgcagggcc agcatggatt taccggcacc accgggcgac accagcgccc   7260
cgaccgtacc ggccaccatg ttgggcaaaa cgtagtccag cggtggcggc gctgctgcga   7320
acgcctccag aatattgata ggcttatggg tagccattga ttgcctcctt tgcaggcagt   7380
tggtggttag gcgctggcgg ggtcactacc cccgccctgc gccgctctga gttcttccag   7440
gcactcgcgc agcgcctcgt attcgtcgtc ggtcagccag aacttgcgct gacgcatccc   7500
tttggccttc atgcgctcgg catatcgcgc ttggcgtaca gcgtcagggc tggccagcag   7560
gtcgccggtc tgcttgtcct tttggtcttt catatcagtc accgagaaac ttgccggggc   7620
cgaaaggctt gtcttcgcgg aacaaggaca aggtgcagcc gtcaaggtta aggctggcca   7680
tatcagcgac tgaaaagcgg ccagcctcgg ccttgtttga cgtataacca aagccaccgg   7740
gcaaccaata gcccttgtca cttttgatca ggtagaccga ccctgaagcg ctttttttcgt   7800
attccataaa accccccttct gtgcgtgagt actcatagta taacaggcgt gagtaccaac   7860
gcaagcacta catgctgaaa tctggcccgc ccctgtccat gcctcgctgg cggggtgccg   7920
gtgcccgtgc cagctcggcc cgcgcaagct ggacgctggg cagacccatg accttgctga   7980
cggtgcgc                                                            7988
```

<210> SEQ ID NO 88
<211> LENGTH: 7999
<212> TYPE: DNA
<213> ORGANISM: Artificial Sequence
<220> FEATURE:
<223> OTHER INFORMATION: Chemically Synthesized, pBTK570

<400> SEQUENCE: 88

```
tccgcttcgt ggccgggctt gcgctctgcc agcgctgggc tggcctcggc catggccttg     60
ccgatttcct cggcactgcg gccccggctg gccagcttct gcgcggcgat aaagtcgcac    120
ttgctgaggt catgaccgaa gcgcttgacc agcccggcca tctcgctgcg gtactcgtcc    180
agcgccgtgc gccggtggcg gctaagctgc cgctcgggca gttcgaggct ggccagcctg    240
cgggccttct cctgctgccg ctgggcctgc tcgatctgct ggccagcctg ctgcaccagc    300
gccgggccag cggtggcggt cttgcccttg gattcacgca gcagcaccca cggctgataa    360
ccggcgcggg tggtgtgctt gtccttgcgg ttggtgaagc ccgccaagcg gccatagtgg    420
cggctgtcgg cgctggccgg gtcggcgtcg tactcgctgg ccagcgtccg ggcaatctgc    480
ccccgaagtt caccgcctgc ggcgtcggcc accttgaccc atgcctgata gttcttcggg    540
ctggtttcca ctaccagggc aggctcccgg ccctcggctt tcatgtcatc caggtcaaac    600
tcgctgaggt cgtccaccag caccagacca tgccgctcct gctcggcggg cctgatatac    660
acgtcattgc cctgggcatt catccgcttg agccatggcg tgttctggag cacttcggcg    720
gctgaccatt cccggttcat catctggccg gtgggtgcgt ccctgacgcc gatatcgaag    780
cgctcacagc ccatggcctt gagctgtcgg cctatggcct gcaaagtcct gtcgttcttc    840
atcgggccac caagcgcagc cagatcgagc cgtcctcggt tgtcagtggc gtcaggtcga    900
gcaagagcaa cgatgcgatc agcagcacca ccgtaggcat catggaagcc agcatcacgg    960
ttagccatag cttccagtgc cacccccgcg acgcgctccg ggcgctctgc gcggcgctgc   1020
tcacctcggc ggctacctcc cgcaactctt tggccagctc cacccatgcc gcccctgtct   1080
ggcgctgggc tttcagccac tccgccgcct gcgcctcgct ggcctgcttg gtctggctca   1140
tgacctgccg ggcttcgtcg gccagtgtcg ccatgctctg ggccagcggt tcgatctgct   1200
```

```
ccgctaactc gttgatgcct ctggatttct tcactctgtc gattgcgttc atggtctatt   1260
gcctcccggt attcctgtaa gtcgatgatc tgggcgttgg cggtgtcgat gttcagggcc   1320
acgtctgccc ggtcggtgcg gatgccccgg ccttccatct ccaccacgtt cggccccagg   1380
tgaacaccgg gcaggcgctc gatgccctgc gcctcaagtg ttctgtggtc aatgcgggcg   1440
tcgtggccag cccgctctaa tgcccggttg gcatggtcgg cccatgcctc gcgggtctgc   1500
tcaagccatg ccttgggctt gagcgcttcg gtcttctgtg ccccgccctt ctccggggtc   1560
ttgccgttgt accgcttgaa ccactgagcg gcgggccgct cgatgccgtc attgatccgc   1620
tcggagatca tcaggtggca gtgcgggttc tcgccgccac cggcatggat ggccagcgta   1680
tacggcaggc gctcggcacc ggtcaggtgc tgggcgaact cggacgccag cgccttctgc   1740
tggtcgaggg tcagctcgac cggcagggca aattcgacct ccttgaacag ccgcccattg   1800
gcgcgttcat acaggtcggc agcatcccag tagtcggcgg gccgctcgac gaactccggc   1860
atgtgcccgg attcggcgtg caagacttca tccatgtcgc gggcatactt gccttcgcgc   1920
tggatgtagt cggccttggc cctggccgat tggccgcccg acctgctgcc ggttttcgcc   1980
gtaaggtgat aaatcgccat gctgcctcgc tgttgctttt gcttttcggc tccatgcaat   2040
ggccctcgga gagcgcaccg cccgaagggt ggccgttagg ccagtttctc gaagagaaac   2100
cggtaagtgc gccctcccct acaaagtagg gtcgggattg ccgccgctgt gcctccatga   2160
tagcctacga gacagcacat taacaatggg gtgtcaagat ggttaagggg agcaacaagg   2220
cggcggatcg gctggccaag ctcgaagaac aacgagcgcg aatcaatgcc gaaattcagc   2280
gggagcgggc aagggaacag cagcaagagc gcaagaacga aacaaggcgc aaggtgctgg   2340
tgggggccat gattttggcc aaggtgaaca gcagcgagtg gccggaggat cggctcatgg   2400
cggcaatgga tgcgtacctt gaacgcgacc acgaccgcgc cttgttcggt ctgccgccac   2460
gccagaagga tgagccgggc tgaatgatcg accgagacag gccctgcggg gctgcacacg   2520
cgcccccacc cttcgggtag ggggaaaggc cgctaaagcg gctaaaagcg ctccagcgta   2580
tttctgcggg gtttggtgtg gggtttagcg ggctttgccc gcctttcccc ctgccgcgca   2640
gcggtggggc ggtgtgtagc ctagcgcagc gaatagacca gctatccggc ctctggccgg   2700
gcatattggg caagggcagc agcgccccac aagggcgctg ataaccgcgc ctagtggatt   2760
attcttagat aatcatggat ggatttttcc aacaccccgc cagcccccgc ccctgctggg   2820
tttgcaggtt tgggggcgtg acagttattg caggggttcg tgacagttat tgcagggggg   2880
cgtgacagtt attgcagggg ttcgtgacag ttagtacggg agtgacgggc actggctggc   2940
aatgtctagc aacggcaggc atttcggctg agggtaaaag aactttccgc taagcgatag   3000
actgtatgta aacacagtat tgcaaggacg cggaacatgc ctcatgtggc ggccaggacg   3060
gccagccggg atcgggatac tggtcgttac cagagccacc gacccgagca aacccttctc   3120
tatcagatcg ttgacgagta ttacccggca ttcgctgcgc ttatggcaga gcagggaaag   3180
gaattgccgg gctatgtgca acgggaattt gaagaatttc tccaatgcgg gcggctggag   3240
catggctttc tacgggttcg ctgcgagtct tgccacgccg agcacctggt cgctttcaga   3300
aatcaatcta aagtatatat gagtaaactt ggtctgacag gcccctgaat tcgcatctag   3360
atggtagagc cacaaacagc cggtacaagc aacgatctcc aggaccatct gaatcatgcg   3420
cggatgacac gaactcacga cggcgatcac agacattaac ccacagtaca gacactgcga   3480
caacgtggca attcgtcgca ataccgtctc actgaactgg ccgataattg cagacgaacg   3540
ggtgaaacaa aacggttgac aacatgaagt aaacacggta cgatgtacca catgaaacga   3600
```

```
cagtgagtca atacagaaac agaggagata ttacatatgg atagcactga gaacgtcatc   3660
aagcccttca tgcgcttcaa ggtgcacatg gagggctccg tgaacggcca cgagttcgag   3720
atcgagggcg tgggcgaggg caagccctac gagggcaccc agaccgccaa gctgcaagtg   3780
accaagggcg gccccctgcc cttcgcctgg gacatcctgt ccccccagtt cttctacggc   3840
tccaaggcgt acatcaagca ccccgccgac atccccgact acctcaagca gtccttcccc   3900
gagggcttca agtgggagcg cgtgatgaac ttcgaggacg gcggcgtggt gaccgtgacc   3960
caggactcct ccctgcagga cggcaccctc atctaccacg tgaagttcat cggcgtgaac   4020
ttcccctccg acggccccgt aatgcagaag aagactctgg gctgggagcc ctccactgag   4080
cgcaactacc cccgcgacgg cgtgctgaag ggcgagaacc acatggcgct gaagctgaag   4140
ggcggcggcc actacctgtg tgagttcaag tccatctaca tggccaagaa gcccgtgaag   4200
ctgcccggct accactacgt ggactacaag ctcgacatca cctcccacaa cgaggactac   4260
accgtggtgg agcagtacga gcgcgccgag gcccgccacc acctgttcca gactcacggt   4320
atggacgaat tgtacaagca cgacgaattg taaatccgta atcgttaatc cgcaaataac   4380
gtaaaaaccc gcttcggcgg gtttttttat ggggggagtt tagggaaaga gcatttgtca   4440
gctggatcag cagatgggaa ccggatactc ctcagcctcc agagtagcca atgagacgcc   4500
gagcggccgc ttatttgccg actaccttgg tgatctcgcc tttcacgtag tggacaaatt   4560
cttccaactg atctgcgcgc gaggccaagc gatcttcttc ttgtccaaga taagcctgtc   4620
tagcttcaag tatgacgggc tgatactggg ccggcaggcg ctccattgcc cagtcggcag   4680
cgacatcctt cggcgcgatt ttgccggtta ctgcgctgta ccaaatgcgg gacaacgtaa   4740
gcactacatt tcgctcatcg ccagcccagt cgggcggcga gttccatagc gttaaggttt   4800
catttagcgc ctcaaataga tcctgttcag gaaccggatc aaagagttcc tccgccgctg   4860
gacctaccaa ggcaacgcta tgttctcttg cttttgtcag caagatagcc agatcaatgt   4920
cgatcgtggc tggctcgaag atacccgcaa gaatgtcatt gcgctgccat tctccaaatt   4980
gcagttcgcg cttagctgga taacgccacg gaatgatgtc gtcgtgcaca acaatggtga   5040
cttctacagc gcggagaatc tcgctctctc caggggaagc cgaagtttcc aaaaggtcgt   5100
tgatcaaagc tcgccgcgtt gtttcatcaa gccttacggt caccgtaacc agcaaatcaa   5160
tatcactgtg tggcttcagg ccgccatcca ctgcggagcc gtacaaatgt acggccagca   5220
acgtcggttc gagatggcgc tcgatgacgc caactacctc tgatagttga gtcgatactt   5280
cggcgatcac cgcttccctc ataatgttta actttgtttt agggcgactg ccctgctgcg   5340
taacatcgtt gctgctccat aacatcaaac atcgacccac ggcgtaacgc gcttgctgct   5400
tggatgcccg aggcatagac tgtaccccaa aaaaacagtc ataacaagcc atgaaaaccg   5460
ccactgcgcc gttaccaccg ctgcgttcgg tcaaggttct ggaccagttg cgtgagcgca   5520
tacgctactt gcattacagc ttacgaaccg aacaggctta tgtccactgg gttcgtgcct   5580
tcatccgttt ccacggtgtg cgtcacccgg caaccttggg tagcagcgaa gtcgaggcat   5640
ttctgtcctg gctggtcatg accaaaatcc cttaacgtga gtcagcctgc cgccttgggc   5700
cgggtgatgt cgtacttgcc cgccgcgaac tcggttaccg tccagcccag cgcgaccagc   5760
tccggcaacg cctcgcgcac ccgcttgcgg cgcttgcgca tggtcgaacc actggcctct   5820
gacggccaga catagccgca caaggtatct atggaagcct tgccggtttt gccggggtcg   5880
atccagccac acagccgctg gtgcagcagg cgggcggttt cgctgtccag cgcccgcacc   5940
```

tcgtccatgc tgatgcgcac atgctggccg ccacccatga cggcctgcgc gatcaagggg 6000
ttcagggcca cgtacaggcg cccgtccgcc tcgtcgctgg cgtactccga cagcagccga 6060
aacccctgcc gcttgcggcc attctgggcg atgatggata ccttccaaag gcgctcgatg 6120
cagtcctgta tgtgcttgag cgccccacca ctatcgacct ctgccccgat ttcctttgcc 6180
agcgcccgat agctaccttt gaccacatgg cattcagcgg tgacggcctc ccacttgggt 6240
tccaggaaca gccggagctg ccgtccgcct tcggtcttgg gttccgggcc aagcactagg 6300
ccattaggcc cagccatggc caccagccct tgcaggatgc gcagatcatc agcgcccagc 6360
ggctccgggc cgctgaactc gatccgcttg ccgtcgccgt agtcatacgt cacgtccagc 6420
ttgctgcgct tgcgctcgcc ccgcttgagg gcacggaaca ggccgggggc cagacagtgc 6480
gccgggtcgt gccggacgtg gctgaggctg tgcttgttct taggcttcac cacggggcac 6540 cccttgctc ttgcgctgcc tctccagcac ggcgggcttg agcaccccgc cgtcatgccg 6600
cctgaaccac cgatcagcga acggtgcgcc atagttggcc ttgctcacac cgaagcggac 6660
gaagaaccgg cgctggtcgt cgtccacacc ccattcctcg gcctcggcgc tggtcatgct 6720
cgacaggtag gactgccagc ggatgttatc gaccagtacc gagctgcccc ggctggcctg 6780
ctgctggtcg cctgcgccca tcatggccgc gcccttgctg gcatggtgca ggaacacgat 6840
agagcacccg gtatcggcgg cgatggcctc catgcgaccg atgacctggg ccatggggcc 6900
gctggcgttt tcttcctcga tgtggaaccg gcgcagcgtg tccagcacca tcaggcggcg 6960
gccctcggcg gcgcgcttga ggccgtcgaa ccactccggg gccatgatgt tgggcaggct 7020
gccgatcagc ggctggatca gcaggccgtc agccacggct tgccgttcct cggcgctgag 7080
gtgcgcccca agggcgtgca ggcggtgatg aatggcggtg ggcgggtctt cggcgggcag 7140
gtagatcacc gggccggtgg gcagttcgcc cacctccagc agatccggcc cgcctgcaat 7200
ctgtgcggcc agttgcaggg ccagcatgga tttaccggca ccaccgggcg acaccagcgc 7260
cccgaccgta ccggccacca tgttgggcaa aacgtagtcc agcggtggcg gcgctgctgc 7320
gaacgcctcc agaatattga taggcttatg ggtagccatt gattgcctcc tttgcaggca 7380
gttggtggtt aggcgctggc ggggtcacta cccccgccct gcgccgctct gagttcttcc 7440
aggcactcgc gcagcgcctc gtattcgtcg tcggtcagcc agaacttgcg ctgacgcatc 7500
cctttggcct tcatgcgctc ggcatatcgc gcttggcgta cagcgtcagg gctggccagc 7560
aggtcgccgg tctgcttgtc cttttggtct ttcatatcag tcaccgagaa acttgccggg 7620
gccgaaaggc ttgtcttcgc ggaacaagga caaggtgcag ccgtcaaggt taaggctggc 7680
catatcagcg actgaaaagc ggccagcctc ggccttgttt gacgtataac caaagccacc 7740
gggcaaccaa tagcccttgt cacttttgat caggtagacc gaccctgaag cgcttttttc 7800
gtattccata aaaccccctt ctgtgcgtga gtactcatag tataacaggc gtgagtacca 7860
acgcaagcac tacatgctga aatctggccc gcccctgtcc atgcctcgct ggcggggtgc 7920
cggtgcccgt gccagctcgg cccgcgcaag ctggacgctg ggcagaccca tgaccttgct 7980
gacggtgcgc tcgatgtaa 7999

<210> SEQ ID NO 89
<211> LENGTH: 12160
<212> TYPE: DNA
<213> ORGANISM: Artificial Sequence
<220> FEATURE:
<223> OTHER INFORMATION: Chemically Synthesized, pBTK601

<400> SEQUENCE: 89

```
gggccgaaa ggcttgtctt cgcggaacaa ggacaaggtg cagccgtcaa ggttaaggct     60
ggccatatca gcgactgaaa agcggccagc ctcggccttg tttgacgtat aaccaaagcc    120
accgggcaac caatagccct tgtcactttt gatcaggtag accgaccctg aagcgctttt    180
ttcgtattcc ataaaacccc cttctgtgcg tgagtactca tagtataaca ggcgtgagta    240
ccaacgcaag cactacatgc tgaaatctgg cccgcccctg tccatgcctc gctggcgggg    300
tgccggtgcc cgtgccagct cggcccgcgc aagctggacg ctgggcagac ccatgacctt    360
gctgacggtg cgctcgatgt aatccgcttc gtggccgggc ttgcgctctg ccagcgctgg    420
gctggcctcg gccatggcct tgccgatttc ctcggcactg cggcccccggc tggccagctt    480
ctgcgcggcg ataaagtcgc acttgctgag gtcatgaccg aagcgcttga ccagcccggc    540
catctcgctg cggtactcgt ccagcgccgt gcgccggtgg cggctaagct gccgctcggg    600
cagttcgagg ctggccagcc tgcgggcctt ctcctgctgc cgctgggcct gctcgatctg    660
ctggccagcc tgctgcacca gcgccgggcc agcggtggcg gtcttgccct tggattcacg    720
cagcagcacc cacggctgat aaccggcgcg ggtggtgtgc ttgtccttgc ggttggtgaa    780
gcccgccaag cggccatagt ggcggctgtc ggcgctggcc gggtcggcgt cgtactcgct    840
ggccagcgtc cgggcaatct gcccccgaag ttcaccgcct gcggcgtcgg ccaccttgac    900
ccatgcctga tagttcttcg ggctggtttc cactaccagg gcaggctccc ggccctcggc    960
tttcatgtca tccaggtcaa actcgctgag gtcgtccacc agcaccagac catgccgctc   1020
ctgctcggcg ggcctgatat acacgtcatt gccctgggca ttcatccgct tgagccatgg   1080
cgtgttctgg agcacttcgg cggctgacca ttcccggttc atcatctggc cggtgggtgc   1140
gtccctgacg ccgatatcga agcgctcaca gcccatggcc ttgagctgtc ggcctatggc   1200
ctgcaaagtc ctgtcgttct tcatcgggcc accaagcgca gccagatcga gccgtcctcg   1260
gttgtcagtg gcgtcaggtc gagcaagagc aacgatgcga tcagcagcac caccgtaggc   1320
atcatggaag ccagcatcac ggttagccat agcttccagt gccacccccg cgacgcgctc   1380
cgggcgctct gcgcggcgct gctcacctcg gcggctacct cccgcaactc tttggccagc   1440
tccacccatg ccgcccctgt ctggcgctgg gctttcagcc actccgccgc ctgcgcctcg   1500
ctggcctgct tggtctggct catgacctgc cgggcttcgt cggccagtgt cgccatgctc   1560
tgggccagcg gttcgatctg ctccgctaac tcgttgatgc ctctggattt cttcactctg   1620
tcgattgcgt tcatggtcta ttgcctcccg gtattcctgt aagtcgatga tctgggcgtt   1680
ggcggtgtcg atgttcaggg ccacgtctgc ccggtcggtg cggatgcccc ggccttccat   1740
ctccaccacg ttcggcccca ggtgaacacc gggcaggcgc tcgatgccct gcgcctcaag   1800
tgttctgtgg tcaatgcggg cgtcgtggcc agcccgctct aatgcccggt tggcatggtc   1860
ggcccatgcc tcgcgggtct gctcaagcca tgccttgggc ttgagcgctt cggtcttctg   1920
tgccccgccc ttctccgggg tcttgccgtt gtaccgcttg aaccactgag cggcgggccg   1980
ctcgatgccg tcattgatcc gctcggagat catcaggtgg cagtgcgggt tctcgccgcc   2040
accggcatgg atggccagcg tatacggcag gcgctcggca ccggtcaggt gctgggcgaa   2100
ctcggacgcc agcgccttct gctggtcgag ggtcagctcg accggcaggg caaattcgac   2160
ctccttgaac agccgcccat tggcgcgttc atacaggtcg gcagcatccc agtagtcggc   2220
gggccgctcg acgaactccg gcatgtgccc ggattcggcg tgcaagactt catccatgtc   2280
gcgggcatac ttgccttcgc gctggatgta gtcggccttg gccctggccg attggccgcc   2340
```

-continued

```
cgacctgctg ccggttttcg ccgtaaggtg ataaatcgcc atgctgcctc gctgttgctt   2400
ttgcttttcg gctccatgca atggccctcg gagagcgcac cgcccgaagg gtggccgtta   2460
ggccagtttc tcgaagagaa accggtaagt gcgccctccc ctacaaagta gggtcgggat   2520
tgccgccgct gtgcctccat gatagcctac gagacagcac attaacaatg gggtgtcaag   2580
atggttaagg ggagcaacaa ggcggcggat cggctggcca agctcgaaga acaacgagcg   2640
cgaatcaatg ccgaaattca gcgggagcgg gcaagggaac agcagcaaga gcgcaagaac   2700
gaaacaaggc gcaaggtgct ggtgggggcc atgattttgg ccaaggtgaa cagcagcgag   2760
tggccggagg atcggctcat ggcggcaatg gatgcgtacc ttgaacgcga ccacgaccgc   2820
gccttgttcg gtctgccgcc acgccagaag gatgagccgg gctgaatgat cgaccgagac   2880
aggccctgcg gggctgcaca cgcgccccca cccttcgggt agggggaaag gccgctaaag   2940
cggctaaaag cgctccagcg tatttctgcg gggtttggtg tggggtttag cgggctttgc   3000
ccgcctttcc ccctgccgcg cagcggtggg gcggtgtgta gcctagcgca gcgaatagac   3060
cagctatccg gcctctggcc gggcatattg ggcaagggca gcagcgcccc acaagggcgc   3120
tgataaccgc gcctagtgga ttattcttag ataatcatgg atggattttt ccaacacccc   3180
gccagccccc gcccctgctg ggtttgcagg tttgggggcg tgacagttat tgcaggggtt   3240
cgtgacagtt attgcagggg ggcgtgacag ttattgcagg ggttcgtgac agttagtacg   3300
ggagtgacgg gcactggctg gcaatgtcta gcaacggcag gcatttcggc tgagggtaaa   3360
agaactttcc gctaagcgat agactgtatg taaacacagt attgcaagga cgcggaacat   3420
gcctcatgtg gcggccagga cggccagccg ggatcgggat actggtcgtt accagagcca   3480
ccgacccgag caaacccttc tctatcagat cgttgacgag tattacccgg cattcgctgc   3540
gcttatggca gagcagggaa aggaattgcc gggctatgtg caacgggaat ttgaagaatt   3600
tctccaatgc gggcggctgg agcatggctt tctacgggtt cgctgcgagt cttgccacgc   3660
cgagcacctg gtcgctttca gaaatcaatc taaagtatat atgagtaaac ttggtctgac   3720
aggcccctga attcgcatct agactgaact ggccgataat tgcagacgaa cggacagtca   3780
ttcatctttc tgcccctcca aaagcaaaaa cccgccgaag cgggttttta cgtaaatcag   3840
gtgaaactga ccgataatac gactcactat aggaactaat ttagtaccct atccaagaat   3900
tcatttccca ttggttacct atgcgccagt catttccgct gaaaaagcgt atcacgaaca   3960
actttctgta gcggaaatca cgaatgcttg cttcgaaccg gctaatcaga tggtaaaatg   4020
cgatcctcgt catggaaaat atatggcgtg ttgtatgctg tacagaggag atgttgtacc   4080
taaggatgtt aatgcagcca ttgcaactat caagactaag cgcaccattc aatttgtcga   4140
ttggtgccca actggattca aagttggcat taattatcaa ccacctactg ttgtaccagg   4200
tggtgatctt gctaaagtac aacgagctgt ttgcatgtta tccaatacta ctgctatcgc   4260
agaagcttgg gccagacttg accataaatt tgatttaatg tacgctaaga gagcatttgt   4320
acactggtac gtcggtgagg gtatggagga aggtgagttc tccgaagcac gatcccctat   4380
agtgagtcgt attagtaatc gttaatccgc aaataacgta aaaacccgct tcggcgggtt   4440
tttttatggg gggagtttag ggaaagagca tttgtcagct ggctgccaac caaaccagat   4500
gtcaacacag ctacaacgct gatccttcaa ctcagcaaaa gttcgattta ttcaacaaag   4560
ccacgttgtg tctcaaaatc tctgatgtta cattgcacaa gataaaaata tatcatcatg   4620
aacaataaaa ctgtctgctt acataaacag taatacaagg ggtgttatgg ataagaaata   4680
ctcaatagge ttagctatcg gcacaaatag cgtcggatgg gcggtgatca ctgatgaata   4740
```

```
taaggttccg tctaaaaagt tcaaggttct gggaaataca gaccgccaca gtatcaaaaa   4800
aaatcttata ggggctcttt tatttgacag tggagagaca gcggaagcga ctcgtctaaa   4860
acggacagct cgtagaaggt atacacgtcg gaagaatcgt atttgttatc tacaggagat   4920
tttttcaaat gagatggcga aagtagatga tagtttcttt catcgacttg aagagtcttt   4980
tttggtggaa gaagacaaga agcatgaacg tcatcctatt tttggaaata tagtagatga   5040
agttgcttat catgagaaat atccaactat ctatcatctg cgaaaaaaat tggtagattc   5100
tactgataaa gcggatttgc gcttaatcta tttggcctta gcgcatatga ttaagtttcg   5160
tggtcatttt ttgattgagg gagatttaaa tcctgataat agtgatgtgg acaaactatt   5220
tatccagttg gtacaaacct acaatcaatt atttgaagaa aaccctatta acgcaagtgg   5280
agtagatgct aaagcgattc tttctgcacg attgagtaaa tcaagacgat tagaaaatct   5340
cattgctcag ctccccggtg agaagaaaaa tggcttattt gggaatctca ttgctttgtc   5400
attgggtttg acccctaatt ttaaatcaaa ttttgatttg gcagaagatg ctaaattaca   5460
gctttcaaaa gatacttacg atgatgattt agataattta ttggcgcaaa ttggagatca   5520
atatgctgat ttgtttttgg cagctaagaa tttatcagat gctattttac tttcagatat   5580
cctaagagta aatactgaaa taactaaggc tcccctatca gcttcaatga ttaaacgcta   5640
cgatgaacat catcaagact tgactctttt aaaagcttta gttcgacaac aacttccaga   5700
aaagtataaa gaaatctttt ttgatcaatc aaaaaacgga tatgcaggtt atattgatgg   5760
gggagctagc caagaagaat tttataaatt tatcaaacca attttagaaa aaatggatgg   5820
tactgaggaa ttattggtga aactaaatcg tgaagatttg ctgcgcaagc aacggacctt   5880
tgacaacggc tctattcccc atcaaattca cttgggtgag ctgcatgcta ttttgagaag   5940
acaagaagac ttttatccat ttttaaaaga caatcgtgag aagattgaaa aaatcttgac   6000
ttttcgaatt ccttattatg ttggtccatt ggcgcgtggc aatagtcgtt ttgcatggat   6060
gactcggaag tctgaagaaa caattacccc atggaatttt gaagaagttg tcgataaagg   6120
tgcttcagct caatcattta ttgaacgcat gacaaacttt gataaaaatc ttccaaatga   6180
aaaagtacta ccaaaacata gtttgcttta tgagtatttt acggtttata acgaattgac   6240
aaaggtcaaa tatgttactg aaggaatgcg aaaaccagca tttctttcag gtgaacagaa   6300
gaaagccatt gttgatttac tcttcaaaac aaatcgaaaa gtaaccgtta agcaattaaa   6360
agaagattat ttcaaaaaaa tagaatgttt tgatagtgtt gaaatttcag gagttgaaga   6420
tagatttaat gcttcattag gtacctacca tgatttgcta aaaattatta aagataaaga   6480
tttttttggat aatgaagaaa atgaagatat cttagaggat attgttttaa cattgacctt   6540
atttgaagat agggagatga ttgaggaaag acttaaaaca tatgctcacc tctttgatga   6600
taaggtgatg aaacagctta aacgtcgccg ttatactggt tggggacgtt tgtctcgaaa   6660
attgattaat ggtattaggg ataagcaatc tggcaaaaca atattagatt ttttgaaatc   6720
agatggtttt gccaatcgca attttatgca gctgatccat gatgatagtt tgacatttaa   6780
agaagacatt caaaaagcac aagtgtctgg acaaggcgat agtttacatg aacatattgc   6840
aaatttagct ggtagccctg ctattaaaaa aggtatttta cagactgtaa aagttgttga   6900
tgaattggtc aaagtaatgg ggcggcataa gccagaaaat atcgttattg aaatggcacg   6960
tgaaaatcag acaactcaaa agggccagaa aaattcgcga gagcgtatga aacgaatcga   7020
agaaggtatc aaagaattag gaagtcagat tcttaaagag catcctgttg aaaatactca   7080
```

```
attgcaaaat gaaaagctct atctctatta tctccaaaat ggaagagaca tgtatgtgga   7140
ccaagaatta gatattaatc gtttaagtga ttatgatgtc gatcacattg ttccacaaag   7200
tttccttaaa gacgattcaa tagacaataa ggtcttaacg cgttctgata aaaatcgtgg   7260
taaatcggat aacgttccaa gtgaagaagt agtcaaaaag atgaaaaact attggagaca   7320
acttctaaac gccaagttaa tcactcaacg taagtttgat aatttaacga aagctgaacg   7380
tggaggtttg agtgaacttg ataaagctgg ttttatcaaa cgccaattgg ttgaaactcg   7440
ccaaatcact aagcatgtgg cacaaatttt ggatagtcgc atgaatacta aatacgatga   7500
aaatgataaa cttattcgag aggttaaagt gattacctta aaatctaaat tagtttctga   7560
cttccgaaaa gatttccaat tctataaagt acgtgagatt aacaattacc atcatgccca   7620
tgatgcgtat ctaaatgccg tcgttggaac tgctttgatt aagaaatatc caaaacttga   7680
atcggagttt gtctatggtg attataaagt ttatgatgtt cgtaaaatga ttgctaagtc   7740
tgagcaagaa ataggcaaag caaccgcaaa atatttcttt tactctaata tcatgaactt   7800
cttcaaaaca gaaattacac ttgcaaatgg agagattcgc aaacgccctc taatcgaaac   7860
taatggggaa actggagaaa ttgtctggga taaagggcga gattttgcca cagtgcgcaa   7920
agtattgtcc atgccccaag tcaatattgt caagaaaaca gaagtacaga caggcggatt   7980
ctccaaggag tcaattttac caaaaagaaa ttcggacaag cttattgctc gtaaaaaaga   8040
ctgggatcca aaaaaatatg gtggttttga tagtccaacg gtagcttatt cagtcctagt   8100
ggttgctaag gtggaaaaag ggaaatcgaa gaagttaaaa tccgttaaag agttactagg   8160
gatcacaatt atggaaagaa gttcctttga aaaaaatccg attgactttt tagaagctaa   8220
aggatataag gaagttaaaa aagacttaat cattaaacta cctaaatata gtctttttga   8280
gttagaaaac ggtcgtaaac ggatgctggc tagtgccgga gaattacaaa aaggaaatga   8340
gctggctctg ccaagcaaat atgtgaattt tttatattta gctagtcatt atgaaaagtt   8400
gaagggtagt ccagaagata acgaacaaaa acaattgttt gtggagcagc ataagcatta   8460
tttagatgag attattgagc aaatcagtga attttctaag cgtgttattt tagcagatgc   8520
caatttagat aaagttctta gtgcatataa caaacataga gacaaaccaa tacgtgaaca   8580
agcagaaaat attattcatt tatttacgtt gacgaatctt ggagctcccg ctgcttttaa   8640
atattttgat acaacaattg atcgtaaacg atatacgtct acaaaagaag ttttagatgc   8700
cactcttatc catcaatcca tcactggtct ttatgaaaca cgcattgatt tgagtcagct   8760
aggaggtgac tgaatccaaa gcaagctgat aaaccgatac aattaaaggc tccttttgga   8820
gcctttttttt ttggagattt tcaacatgaa gaaattatta tttgatgatc agatagcggc   8880
ggggaactgc cagacatcaa ataaaacaaa aggctcagtc ggaagactgg gccttttgtt   8940
ttatctgttg tttgtcggtg aacactctcc cggctgagca gttacagaga tgttacgaac   9000
ccccaggaca tccgagaatg cgaggcgatg gagggtacaa cccgagcggc cgcttatttg   9060
ccgactacct tggtgatctc gcctttcacg tagtggacaa attcttccaa ctgatctgcg   9120
cgcgaggcca agcgatcttc ttcttgtcca agataagcct gtctagcttc aagtatgacg   9180
ggctgatact gggccggcag gcgctccatt gcccagtcgg cagcgacatc cttcggcgcg   9240
attttgccgg ttactgcgct gtaccaaatg cgggacaacg taagcactac atttcgctca   9300
tcgccagccc agtcgggcgg cgagttccat agcgttaagg tttcatttag cgcctcaaat   9360
agatcctgtt caggaaccgg atcaaagagt tcctccgccg ctggacctac caaggcaacg   9420
ctatgttctc ttgcttttgt cagcaagata gccagatcaa tgtcgatcgt ggctggctcg   9480
```

```
aagatacccg caagaatgtc attgcgctgc cattctccaa attgcagttc gcgcttagct   9540
ggataacgcc acggaatgat gtcgtcgtgc acaacaatgg tgacttctac agcgcggaga   9600
atctcgctct ctccagggga agccgaagtt tccaaaaggt cgttgatcaa agctcgccgc   9660
gttgtttcat caagccttac ggtcaccgta accagcaaat caatatcact gtgtggcttc   9720
aggccgccat ccactgcgga gccgtacaaa tgtacggcca gcaacgtcgg ttcgagatgg   9780
cgctcgatga cgccaactac ctctgatagt tgagtcgata cttcggcgat caccgcttcc   9840
ctcataatgt ttaactttgt tttagggcga ctgccctgct gcgtaacatc gttgctgctc   9900
cataacatca aacatcgacc cacggcgtaa cgcgcttgct gcttggatgc ccgaggcata   9960
gactgtaccc caaaaaaaca gtcataacaa gccatgaaaa ccgccactgc gccgttacca  10020
ccgctgcgtt cggtcaaggt tctggaccag ttgcgtgagc gcatacgcta cttgcattac  10080
agcttacgaa ccgaacaggc ttatgtccac tgggttcgtg ccttcatccg tttccacggt  10140
gtgcgtcacc cggcaacctt gggtagcagc gaagtcgagg catttctgtc ctggctggtc  10200
atgaccaaaa tcccttaacg tgagtcagcc tgccgccttg ggccgggtga tgtcgtactt  10260
gcccgccgcg aactcggtta ccgtccagcc cagcgcgacc agctccggca acgcctcgcg  10320
cacccgcttg cggcgcttgc gcatggtcga accactggcc tctgacggcc agacatagcc  10380
gcacaaggta tctatggaag ccttgccggt tttgccgggg tcgatccagc cacacagccg  10440
ctggtgcagc aggcgggcgg tttcgctgtc cagcgcccgc acctcgtcca tgctgatgcg  10500
cacatgctgg ccgccaccca tgacggcctg cgcgatcaag ggttcaggg ccacgtacag  10560
gcgcccgtcc gcctcgtcgc tggcgtactc cgacagcagc cgaaacccct gccgcttgcg  10620
gccattctgg gcgatgatgg ataccttcca aaggcgctcg atgcagtcct gtatgtgctt  10680
gagcgcccca ccactatcga cctctgcccc gatttccttt gccagcgccc gatagctacc  10740
tttgaccaca tggcattcag cggtgacggc ctcccacttg ggttccagga acagccggag  10800
ctgccgtccg ccttcggtct tgggttccgg gccaagcact aggccattag gcccagccat  10860
ggccaccagc ccttgcagga tgcgcagatc atcagcgccc agcggctccg ggccgctgaa  10920
ctcgatccgc ttgccgtcgc cgtagtcata cgtcacgtcc agcttgctgc gcttgcgctc  10980
gccccgcttg agggcacgga acaggccggg ggccagacag tgcgccgggt cgtgccggac  11040
gtggctgagg ctgtgcttgt tcttaggctt caccacgggg cacccccttg ctcttgcgct  11100
gcctctccag cacggcgggc ttgagcaccc cgccgtcatg ccgcctgaac caccgatcag  11160
cgaacggtgc gccatagttg gccttgctca caccgaagcg gacgaagaac cggcgctggt  11220
cgtcgtccac accccattcc tcggcctcgg cgctggtcat gctcgacagg taggactgcc  11280
agcggatgtt atcgaccagt accgagctgc cccggctggc ctgctgctgg tcgcctgcgc  11340
ccatcatggc cgcgcccttg ctggcatggt gcaggaacac gatagagcac ccggtatcgg  11400
cggcgatggc ctccatgcga ccgatgacct gggccatggg gccgctggcg ttttcttcct  11460
cgatgtggaa ccggcgcagc gtgtccagca ccatcaggcg gcggccctcg gcggcgcgct  11520
tgaggccgtc gaaccactcc ggggccatga tgttgggcag gctgccgatc agcggctgga  11580
tcagcaggcc gtcagccacg gcttgccgtt cctcggcgct gaggtgcgcc ccaagggcgt  11640
gcaggcggtg atgaatggcg gtgggcgggt cttcggcggg caggtagatc accgggccgg  11700
tgggcagttc gcccacctcc agcagatccg gcccgcctgc aatctgtgcg gccagttgca  11760
gggccagcat ggatttaccg gcaccaccgg gcgacaccag cgccccgacc gtaccggcca  11820
```

```
ccatgttggg caaaacgtag tccagcggtg gcggcgctgc tgcgaacgcc tccagaatat  11880

tgataggctt atgggtagcc attgattgcc tcctttgcag gcagttggtg gttaggcgct  11940

ggcggggtca ctacccccgc cctgcgccgc tctgagttct tccaggcact cgcgcagcgc  12000

ctcgtattcg tcgtcggtca gccagaactt gcgctgacgc atccctttgg ccttcatgcg  12060

ctcggcatat cgcgcttggc gtacagcgtc agggctggcc agcaggtcgc cggtctgctt  12120

gtccttttgg tctttcatat cagtcaccga gaaacttgcc                        12160
```

<210> SEQ ID NO 90
<211> LENGTH: 6699
<212> TYPE: DNA
<213> ORGANISM: Artificial Sequence
<220> FEATURE:
<223> OTHER INFORMATION: Chemically Synthesized, pBTK614

<400> SEQUENCE: 90

```
gaattcgcat ctagaacggg gtcatcacgg ctcatcatgc gccaaacaaa tgtgtgcaat    60

acacgctcgg atgactgcat gatgaccgca ctgactgggg acagcagatc cacctaagcc   120

tgtgagagaa gcagacaccc gacagatcaa ggcagttacg tctcaccaac caaaccagat   180

gtcaacacag ctacaacgct gatccttcaa ctcagcaaaa gttcgattta ttcaacaaag   240

ccacgttgtg tctcaaaatc tctgatgtta cattgcacaa gataaaaata tatcatcatg   300

aacaataaaa ctgtctgctt acataaacag taatacaagg ggtgttatgg ataagaaata   360

ctcaataggc ttagctatcg gcacaaatag cgtcggatgg gcggtgatca ctgatgaata   420

taaggttccg tctaaaaagt tcaaggttct gggaaataca gaccgccaca gtatcaaaaa   480

aaatcttata ggggctcttt tatttgacag tggagagaca gcggaagcga ctcgtctcaaa   540

acggacagct cgtagaaggt atacacgtcg gaagaatcgt atttgttatc tacaggagat   600

tttttcaaat gagatggcga aagtagatga tagtttcttt catcgacttg aagagtcttt   660

tttggtggaa gaagacaaga agcatgaacg tcatcctatt tttggaaata tagtagatga   720

agttgcttat catgagaaat atccaactat ctatcatctg cgaaaaaaat tggtagattc   780

tactgataaa gcggatttgc gcttaatcta tttggcctta gcgcatatga ttaagtttcg   840

tggtcatttt ttgattgagg gagatttaaa tcctgataat agtgatgtgg acaaactatt   900

tatccagttg gtacaaacct acaatcaatt atttgaagaa aaccctatta acgcaagtgg   960

agtagatgct aaagcgattc tttctgcacg attgagtaaa tcaagacgat tagaaaatct  1020

cattgctcag ctccccggtg agaagaaaaa tggcttattt gggaatctca ttgctttgtc  1080

attgggtttg acccctaatt ttaaatcaaa ttttgatttg gcagaagatg ctaaattaca  1140

gctttcaaaa gatacttacg atgatgattt agataattta ttggcgcaaa ttggagatca  1200

atatgctgat ttgtttttgg cagctaagaa tttatcagat gctattttac tttcagatat  1260

cctaagagta aatactgaaa taactaaggc tcccctatca gcttcaatga ttaaacgcta  1320

cgatgaacat catcaagact tgactctttt aaaagcttta gttcgacaac aacttccaga  1380

aaagtataaa gaaatctttt ttgatcaatc aaaaaacgga tatgcaggtt atattgatgg  1440

gggagctagc caagaagaat tttataaatt tatcaaacca attttagaaa aaatggatgg  1500

tactgaggaa ttattggtga aactaaatcg tgaagatttg ctgcgcaagc aacggacctt  1560

tgacaacggc tctattcccc atcaaattca cttgggtgag ctgcatgcta ttttgagaag  1620

acaagaagac ttttatccat ttttaaaaga caatcgtgag aagattgaaa aaatcttgac  1680

ttttcgaatt ccttattatg ttggtccatt ggcgcgtggc aatagtcgtt ttgcatggat  1740
```

```
gactcggaag tctgaagaaa caattacccc atggaatttt gaagaagttg tcgataaagg   1800
tgcttcagct caatcattta ttgaacgcat gacaaacttt gataaaaatc ttccaaatga   1860
aaaagtacta ccaaaacata gtttgcttta tgagtatttt acggtttata acgaattgac   1920
aaaggtcaaa tatgttactg aaggaatgcg aaaaccagca tttctttcag gtgaacagaa   1980
gaaagccatt gttgatttac tcttcaaaac aaatcgaaaa gtaaccgtta agcaattaaa   2040
agaagattat ttcaaaaaaa tagaatgttt tgatagtgtt gaaatttcag gagttgaaga   2100
tagatttaat gcttcattag gtacctacca tgatttgcta aaaattatta aagataaaga   2160
tttttggat aatgaagaaa atgaagatat cttagaggat attgttttaa cattgacctt   2220
atttgaagat agggagatga ttgaggaaag acttaaaaca tatgctcacc tctttgatga   2280
taaggtgatg aaacagctta aacgtcgccg ttatactggt tggggacgtt tgtctcgaaa   2340
attgattaat ggtattaggg ataagcaatc tggcaaaaca atattagatt ttttgaaatc   2400
agatggtttt gccaatcgca attttatgca gctgatccat gatgatagtt tgacatttaa   2460
agaagacatt caaaaagcac aagtgtctgg acaaggcgat agtttacatg aacatattgc   2520
aaatttagct ggtagccctg ctattaaaaa aggtatttta cagactgtaa aagttgttga   2580
tgaattggtc aaagtaatgg ggcggcataa gccagaaaat atcgttattg aaatggcacg   2640
tgaaaatcag acaactcaaa agggccagaa aaattcgcga gagcgtatga aacgaatcga   2700
agaaggtatc aaagaattag gaagtcagat tcttaaagag catcctgttg aaaatactca   2760
attgcaaaat gaaaagctct atctctatta tctccaaaat ggaagagaca tgtatgtgga   2820
ccaagaatta gatattaatc gtttaagtga ttatgatgtc gatcacattg ttccacaaag   2880
tttccttaaa gacgattcaa tagacaataa ggtcttaacg cgttctgata aaaatcgtgg   2940
taaatcggat aacgttccaa gtgaagaagt agtcaaaaag atgaaaaact attggagaca   3000
acttctaaac gccaagttaa tcactcaacg taagtttgat aatttaacga aagctgaacg   3060
tggaggtttg agtgaacttg ataaagctgg ttttatcaaa cgccaattgg ttgaaactcg   3120
ccaaatcact aagcatgtgg cacaaatttt ggatagtcgc atgaatacta aatacgatga   3180
aaatgataaa cttattcgag aggttaaagt gattacctta aaatctaaat tagtttctga   3240
cttccgaaaa gatttccaat tctataaagt acgtgagatt aacaattacc atcatgccca   3300
tgatgcgtat ctaaatgccg tcgttggaac tgctttgatt aagaaatatc caaaacttga   3360
atcggagttt gtctatggtg attataaagt ttatgatgtt cgtaaaatga ttgctaagtc   3420
tgagcaagaa ataggcaaag caaccgcaaa atatttcttt tactctaata tcatgaactt   3480
cttcaaaaca gaaattacac ttgcaaatgg agagattcgc aaacgccctc taatcgaaac   3540
taatggggaa actggagaaa ttgtctggga taaagggcga gattttgcca cagtgcgcaa   3600
agtattgtcc atgccccaag tcaatattgt caagaaaaca gaagtacaga caggcggatt   3660
ctccaaggag tcaattttac caaaaagaaa ttcggacaag cttattgctc gtaaaaaaga   3720
ctgggatcca aaaaaatatg gtggttttga tagtccaacg gtagcttatt cagtcctagt   3780
ggttgctaag gtggaaaaag ggaaatcgaa gaagttaaaa tccgttaaag agttactagg   3840
gatcacaatt atggaaagaa gttcctttga aaaaaatccg attgactttt tagaagctaa   3900
aggatataag gaagttaaaa aagacttaat cattaaacta cctaaatata gtctttttga   3960
gttagaaaac ggtcgtaaac ggatgctggc tagtgccgga gaattacaaa aaggaaatga   4020
gctggctctg ccaagcaaat atgtgaattt tttatattta gctagtcatt atgaaaagtt   4080
```

```
gaagggtagt ccagaagata acgaacaaaa acaattgttt gtggagcagc ataagcatta   4140
tttagatgag attattgagc aaatcagtga attttctaag cgtgttattt tagcagatgc   4200
caatttagat aaagttctta gtgcatataa caaacataga gacaaaccaa tacgtgaaca   4260
agcagaaaat attattcatt tatttacgtt gacgaatctt ggagctcccg ctgcttttaa   4320
atattttgat acaacaattg atcgtaaacg atatacgtct acaaaagaag ttttagatgc   4380
cactcttatc catcaatcca tcactggtct ttatgaaaca cgcattgatt tgagtcagct   4440
aggaggtgac tgaatccaaa gcaagctgat aaaccgatac aattaaaggc tccttttgga   4500
gcctttttttt ttggagattt tcaacatgaa gaaattatta tttgatgatc agatagcggc   4560
ggggaactgc cagacatcaa ataaaacaaa aggctcagtc ggaagactgg gccttttgtt   4620
ttatctgttg tttgtcggtg aacactctcc cggctgagca tgagacggaa atctgctcgt   4680
cagtggtgct cacactgacg aatcatgtac agatcatacc gatgactgcc tggcgactca   4740
caactaagca agacagccgg aaccagcgcc ggcgaacacc actgcatata tggcatatca   4800
caacagtcca actagtgcac tgcagtacag cggccgcgat tatcaaaaag gatcttcacc   4860
tagatccttt taaattaaaa atgaagtttt aaatcaatct aaagtatata tgagtaaact   4920
tggtctgaca gttaccaatg cttaatcagt gaggcaccta tctcagcgat ctgtctattt   4980
cgttcatcca tagttgcctg actccccgtc gtgtagataa ctacgatacg ggagggctta   5040
ccatctggcc ccagtgctgc aatgataccg cgggacccac gctcaccggc tccagattta   5100
tcagcaataa accagccagc cggaagggcc gagcgcagaa gtggtcctgc aactttatcc   5160
gcctccatcc agtctattaa ttgttgccgg gaagctagag taagtagttc gccagttaat   5220
agtttgcgca acgttgttgc cattgctaca ggcatcgtgg tgtcacgctc gtcgtttggt   5280
atggcttcat tcagctccgg ttcccaacga tcaaggcgag ttacatgatc ccccatgttg   5340
tgcaaaaaag cggttagctc cttcggtcct ccgatcgttg tcagaagtaa gttggccgca   5400
gtgttatcac tcatggttat ggcagcactg cataattctc ttactgtcat gccatccgta   5460
agatgctttt ctgtgactgg tgagtactca accaagtcat tctgagaata gtgtatgcgg   5520
cgaccgagtt gctcttgccc ggcgtcaata cgggataata ccgcgccaca tagcagaact   5580
ttaaaagtgc tcatcattgg aaaacgttct tcggggcgaa aactctcaag gatcttaccg   5640
ctgttgagat ccagttcgat gtaacccact cgtgcaccca actgatcttc agcatctttt   5700
actttcacca gcgtttctgg gtgagcaaaa acaggaaggc aaaatgccgc aaaaaaggga   5760
ataagggcga cacggaaatg ttgaatactc atactcttcc tttttcaata ttattgaagc   5820
atttatcagg gttattgtct catgagcgga tacatatttg aatgtattta gaaaaataaa   5880
caaatagggg ttccgcgcac atttccccga aaagtgccac ctgtcatgac caaaatccct   5940
taacgtgagt tttcgttcca ctgagcgtca gaccccgtag aaaagatcaa aggatcttct   6000
tgagatcctt tttttctgcg cgtaatctgc tgcttgcaaa caaaaaaacc accgctacca   6060
gcggtggttt gtttgccgga tcaagagcta ccaactcttt ttccgaaggt aactggcttc   6120
agcagagcgc agataccaaa tactgttctt ctagtgtagc cgtagttagg ccaccacttc   6180
aagaactctg tagcaccgcc tacatacctc gctctgctaa tcctgttacc agtggctgct   6240
gccagtggcg ataagtcgtg tcttaccggg ttggactcaa gacgatagtt accggataag   6300
gcgcagcggt cgggctgaac ggggggttcg tgcacacagc ccagcttgga gcgaacgacc   6360
tacaccgaac tgagatacct acagcgtgag ctatgagaaa gcgccacgct tcccgaaggg   6420
agaaaggcgg acaggtatcc ggtaagcggc agggtcggaa caggagagcg cacgagggag   6480
```

```
cttccagggg gaaacgcctg gtatctttat agtcctgtcg ggtttcgcca cctctgactt   6540

gagcgtcgat ttttgtgatg ctcgtcaggg gggcggagcc tatggaaaaa cgccagcaac   6600

gcggcctttt tacggttcct ggccttttgc tggccttttg ctcacatgtt ctttcctgcg   6660

ttatcccctg attctgtgga taaccgtgcg gccgcccct                          6699
```

<210> SEQ ID NO 91
<211> LENGTH: 2567
<212> TYPE: DNA
<213> ORGANISM: Artificial Sequence
<220> FEATURE:
<223> OTHER INFORMATION: Chemically Synthesized, pBTK615

<400> SEQUENCE: 91

```
gaattcgcat ctagatggta gagccacaaa cagccggtac aagcaacgat ctccaggacc     60

atctgaatca tgcgcggatg acacgaactc acgacggcga tcacagacat taacccacag    120

tacagacact gcgacaacgt ggcaattcgt cgcaataccg tctcactgaa ctggccgata    180

attgcagacg aacgctttgg cagtttattc ttgacatgta gtgagggggc tggtataatc    240

acatacgtct aattccacga ggattgtttt agagctagaa atagcaagtt aaaataaggc    300

tagtccgtta tcaacttgaa aaagtggcac cgagtcggtg cttttttga attctctaga     360

gtcgacctgc agaagcttag atctattacc ctgttatccc tactcgagtt catgtgcagc    420

tccatcagca tccgtaatcg ttaatccgca aataacgtaa aaacccgctt cggcgggttt    480

ttttatgggg ggagtttagg gaaagagcat ttgtcagctg gctgccaatg agacgacggg    540

gtcatcacgg ctcatcatgc gccaaacaaa tgtgtgcaat acacgctcgg atgactgcat    600

gatgaccgca ctgactgggg acagcagatc cacctaagcc tgtgagagaa gcagacaccc    660

gacagatcaa ggcagttaac tagtgcactg cagtacagcg gccgcgatta tcaaaaagga    720

tcttcaccta gatcctttta aattaaaaat gaagttttaa atcaatctaa agtatatatg    780

agtaaacttg gtctgacagt taccaatgct taatcagtga ggcacctatc tcagcgatct    840

gtctatttcg ttcatccata gttgcctgac tccccgtcgt gtagataact acgatacggg    900

agggcttacc atctggcccc agtgctgcaa tgataccgcg ggacccacgc tcaccggctc    960

cagatttatc agcaataaac cagccagccg gaagggccga gcgcagaagt ggtcctgcaa   1020

ctttatccgc ctccatccag tctattaatt gttgccggga agctagagta agtagttcgc   1080

cagttaatag tttgcgcaac gttgttgcca ttgctacagg catcgtggtg tcacgctcgt   1140

cgtttggtat ggcttcattc agctccggtt cccaacgatc aaggcgagtt acatgatccc   1200

ccatgttgtg caaaaaagcg gttagctcct tcggtcctcc gatcgttgtc agaagtaagt   1260

tggccgcagt gttatcactc atggttatgg cagcactgca taattctctt actgtcatgc   1320

catccgtaag atgcttttct gtgactggtg agtactcaac caagtcattc tgagaatagt   1380

gtatgcggcg accgagttgc tcttgcccgg cgtcaatacg ggataatacc gcgccacata   1440

gcagaacttt aaaagtgctc atcattggaa aacgttcttc ggggcgaaaa ctctcaagga   1500

tcttaccgct gttgagatcc agttcgatgt aacccactcg tgcacccaac tgatcttcag   1560

catcttttac tttcaccagc gtttctgggt gagcaaaaac aggaaggcaa aatgccgcaa   1620

aaaagggaat aagggcgaca cggaaatgtt gaatactcat actcttcctt tttcaatatt   1680

attgaagcat ttatcagggt tattgtctca tgagcggata catatttgaa tgtatttaga   1740

aaaataaaca aataggggtt ccgcgcacat ttccccgaaa agtgccacct gtcatgacca   1800
```

```
aaatccctta acgtgagttt tcgttccact gagcgtcaga ccccgtagaa aagatcaaag   1860

gatcttcttg agatcctttt tttctgcgcg taatctgctg cttgcaaaca aaaaaaccac   1920

cgctaccagc ggtggtttgt ttgccggatc aagagctacc aactcttttt ccgaaggtaa   1980

ctggcttcag cagagcgcag ataccaaata ctgttcttct agtgtagccg tagttaggcc   2040

accacttcaa gaactctgta gcaccgccta catacctcgc tctgctaatc ctgttaccag   2100

tggctgctgc cagtggcgat aagtcgtgtc ttaccgggtt ggactcaaga cgatagttac   2160

cggataaggc gcagcggtcg ggctgaacgg ggggttcgtg cacacagccc agcttggagc   2220

gaacgaccta caccgaactg agatacctac agcgtgagct atgagaaagc gccacgcttc   2280

ccgaagggag aaaggcggac aggtatccgg taagcggcag ggtcggaaca ggagagcgca   2340

cgagggagct tccaggggga aacgcctggt atctttatag tcctgtcggg tttcgccacc   2400

tctgacttga gcgtcgattt ttgtgatgct cgtcaggggg gcggagccta tggaaaaacg   2460

ccagcaacgc ggccttttta cggttcctgg ccttttgctg gccttttgct cacatgttct   2520

ttcctgcgtt atcccctgat tctgtggata accgtgcggc cgcccct                 2567
```

```
<210> SEQ ID NO 92
<211> LENGTH: 8054
<212> TYPE: DNA
<213> ORGANISM: Artificial Sequence
<220> FEATURE:
<223> OTHER INFORMATION: Chemically Synthesized, pBTK619

<400> SEQUENCE: 92

acagatcata ccgatgactg cctggcgact cacaactaag caagacagcc ggaaccagcg     60

ccggcgaaca ccactgcata tatggcatat cacaacagtc caactagtgc actgcagtac    120

accaggcatc aaataaaacg aaaggctcag tcgaaagact gggcctttcg ttttatctgt    180

tgtttgtcgg tgaacgctct ctactagagt cacactggct caccttcggg tgggcctttc    240

tgcgtttata ccgagcggcc gcgtgttaca accaattaac caattctgat tagaaaaact    300

catcgagcat caaatgaaac tgcaatttat tcatatcagg attatcaata ccatattttt    360

gaaaaagccg tttctgtaat gaaggagaaa actcaccgag gcagttccat aggatggcaa    420

gatcctggta tcggtctgcg attccgactc gtccaacatc aatacaacct attaatttcc    480

cctcgtcaaa aataaggtta tcaagtgaga aatcaccatg agtgacgact gaatccggtg    540

agaatggcaa aagcttatgc atttctttcc agacttgttc aacaggccag ccattacgct    600

cgtcatcaaa atcactcgca tcaaccaaac cgttattcat tcgtgattgc gcctgagcga    660

ggcgaaatac gcgatcgctg ttaaaaggac aattacaaac aggaatcgaa tgcaaccggc    720

gcaggaacac tgccagcgca tcaacaatat tttcacctga atcaggatat tcttctaata    780

cctggaatgc tgttttcccg gggatcgcag tggtgagtaa ccatgcatca tcaggagtac    840

ggataaaatg cttgatggtc ggaagaggca taaattccgt cagccagttt agtctgacca    900

tctcatctgt aacatcattg gcaacgctac ctttgccatg tttcagaaac aactctggcg    960

catcgggctt cccatacaat cgatagattg tcgcacctga ttgcccgaca ttatcgcgag   1020

cccatttata cccatataaa tcagcatcca tgttggaatt taatcgcggc ctggagcaag   1080

acgtttcccg ttgaatatgg ctcataacac cccttgtatt actgtttatg taagcagaca   1140

gttttattgt tcatgatgat atatttttat cttgtgcaat gtaacatcag agattttgag   1200

acacaacgtg gctttgttga ataaatcgaa cttttgctga gttgaaggat cagtcatgac   1260

caaaatccct taacgtgagt cagcctgccg ccttgggccg ggtgatgtcg tacttgcccg   1320
```

```
ccgcgaactc ggttaccgtc cagcccagcg cgaccagctc cggcaacgcc tcgcgcaccc   1380
gcttgcggcg cttgcgcatg gtcgaaccac tggcctctga cggccagaca tagccgcaca   1440
aggtatctat ggaagccttg ccggttttgc cggggtcgat ccagccacac agccgctggt   1500
gcagcaggcg ggcggtttcg ctgtccagcg cccgcacctc gtccatgctg atgcgcacat   1560
gctggccgcc acccatgacg gcctgcgcga tcaaggggtt cagggccacg tacaggcgcc   1620
cgtccgcctc gtcgctggcg tactccgaca gcagccgaaa cccctgccgc ttgcggccat   1680
tctgggcgat gatggatacc ttccaaaggc gctcgatgca gtcctgtatg tgcttgagcg   1740
ccccaccact atcgacctct gccccgattt cctttgccag cgcccgatag ctacctttga   1800
ccacatggca ttcagcggtg acggcctccc acttgggttc caggaacagc cggagctgcc   1860
gtccgccttc ggtcttgggt tccgggccaa gcactaggcc attaggccca gccatggcca   1920
ccagcccttg caggatgcgc agatcatcag cgcccagcgg ctccgggccg ctgaactcga   1980
tccgcttgcc gtcgccgtag tcatacgtca cgtccagctt gctgcgcttg cgctcgcccc   2040
gcttgagggc acggaacagg ccgggggcca gacagtgcgc cgggtcgtgc cggacgtggc   2100
tgaggctgtg cttgttctta ggcttcacca cggggcaccc ccttgctctt gcgctgcctc   2160
tccagcacgg cgggcttgag caccccgccg tcatgccgcc tgaaccaccg atcagcgaac   2220
ggtgcgccat agttggcctt gctcacaccg aagcggacga agaaccggcg ctggtcgtcg   2280
tccacacccc attcctcggc ctcggcgctg gtcatgctcg acaggtagga ctgccagcgg   2340
atgttatcga ccagtaccga gctgccccgg ctggcctgct gctggtcgcc tgcgcccatc   2400
atggccgcgc ccttgctggc atggtgcagg aacacgatag agcacccggt atcggcggcg   2460
atggcctcca tgcgaccgat gacctgggcc atggggccgc tggcgttttc ttcctcgatg   2520
tggaaccggc gcagcgtgtc cagcaccatc aggcggcggc cctcggcggc gcgcttgagg   2580
ccgtcgaacc actccggggc catgatgttg ggcaggctgc cgatcagcgg ctggatcagc   2640
aggccgtcag ccacggcttg ccgttcctcg gcgctgaggt gcgccccaag ggcgtgcagg   2700
cggtgatgaa tggcggtggg cgggtcttcg gcgggcaggt agatcaccgg gccggtgggc   2760
agttcgccca cctccagcag atccggcccg cctgcaatct gtgcggccag ttgcagggcc   2820
agcatggatt taccggcacc accgggcgac accagcgccc cgaccgtacc ggccaccatg   2880
ttgggcaaaa cgtagtccag cggtggcggc gctgctgcga acgcctccag aatattgata   2940
ggcttatggg tagccattga ttgcctcctt tgcaggcagt tggtggttag gcgctggcgg   3000
ggtcactacc cccgccctgc gccgctctga gttcttccag gcactcgcgc agcgcctcgt   3060
attcgtcgtc ggtcagccag aacttgcgct gacgcatccc tttggccttc atgcgctcgg   3120
catatcgcgc ttggcgtaca gcgtcagggc tggccagcag gtcgccggtc tgcttgtcct   3180
tttggtcttt catatcagtc accgagaaac ttgccggggc cgaaaggctt gtcttcgcgg   3240
aacaaggaca aggtgcagcc gtcaaggtta aggctggcca tatcagcgac tgaaaagcgg   3300
ccagcctcgg ccttgtttga cgtataacca aagccaccgg gcaaccaata gcccttgtca   3360
cttttgatca ggtagaccga ccctgaagcg ctttttttcgt attccataaa accccccttct   3420
gtgcgtgagt actcatagta taacaggcgt gagtaccaac gcaagcacta catgctgaaa   3480
tctggcccgc ccctgtccat gcctcgctgg cggggtgccg gtgcccgtgc cagctcggcc   3540
cgcgcaagct ggacgctggg cagacccatg accttgctga cggtgcgctc gatgtaatcc   3600
gcttcgtggc cgggcttgcg ctctgccagc gctgggctgg cctcggccat ggccttgccg   3660
```

```
atttcctcgg cactgcggcc ccggctggcc agcttctgcg cggcgataaa gtcgcacttg   3720
ctgaggtcat gaccgaagcg cttgaccagc ccggccatct cgctgcggta ctcgtccagc   3780
gccgtgcgcc ggtggcggct aagctgccgc tcgggcagtt cgaggctggc cagcctgcgg   3840
gccttctcct gctgccgctg ggcctgctcg atctgctggc cagcctgctg caccagcgcc   3900
gggccagcgg tggcggtctt gcccttggat tcacgcagca gcacccacgg ctgataaccg   3960
gcgcgggtgg tgtgcttgtc cttgcggttg gtgaagcccg ccaagcggcc atagtggcgg   4020
ctgtcggcgc tggccgggtc ggcgtcgtac tcgctggcca gcgtccgggc aatctgcccc   4080
cgaagttcac cgcctgcggc gtcggccacc ttgacccatg cctgatagtt cttcgggctg   4140
gtttccacta ccagggcagg ctcccggccc tcggctttca tgtcatccag gtcaaactcg   4200
ctgaggtcgt ccaccagcac cagaccatgc cgctcctgct cggcgggcct gatatacacg   4260
tcattgccct gggcattcat ccgcttgagc catggcgtgt tctggagcac ttcggcggct   4320
gaccattccc ggttcatcat ctggccggtg ggtgcgtccc tgacgccgat atcgaagcgc   4380
tcacagccca tggccttgag ctgtcggcct atggcctgca aagtcctgtc gttcttcatc   4440
gggccaccaa gcgcagccag atcgagccgt cctcggttgt cagtggcgtc aggtcgagca   4500
agagcaacga tgcgatcagc agcaccaccg taggcatcat ggaagccagc atcacggtta   4560
gccatagctt ccagtgccac ccccgcgacg cgctccgggc gctctgcgcg gcgctgctca   4620
cctcggcggc tacctcccgc aactctttgg ccagctccac ccatgccgcc cctgtctggc   4680
gctgggcttt cagccactcc gccgcctgcg cctcgctggc ctgcttggtc tggctcatga   4740
cctgccgggc ttcgtcggcc agtgtcgcca tgctctgggc cagcggttcg atctgctccg   4800
ctaactcgtt gatgcctctg gatttcttca ctctgtcgat tgcgttcatg gtctattgcc   4860
tcccggtatt cctgtaagtc gatgatctgg gcgttggcgg tgtcgatgtt cagggccacg   4920
tctgcccggt cggtgcggat gccccggcct tccatctcca ccacgttcgg ccccaggtga   4980
acaccgggca ggcgctcgat gccctgcgcc tcaagtgttc tgtggtcaat gcgggcgtcg   5040
tggccagccc gctctaatgc ccggttggca tggtcggccc atgcctcgcg ggtctgctca   5100
agccatgcct tgggcttgag cgcttcggtc ttctgtgccc cgcccttctc cggggtcttg   5160
ccgttgtacc gcttgaacca ctgagcggcg ggccgctcga tgccgtcatt gatccgctcg   5220
gagatcatca ggtggcagtg cgggttctcg ccgccaccgg catggatggc cagcgtatac   5280
ggcaggcgct cggcaccggt caggtgctgg gcgaactcgg acgccagcgc cttctgctgg   5340
tcgagggtca gctcgaccgg cagggcaaat tcgacctcct tgaacagccg cccattggcg   5400
cgttcataca ggtcggcagc atcccagtag tcggcgggcc gctcgacgaa ctccggcatg   5460
tgcccggatt cggcgtgcaa gacttcatcc atgtcgcggg catacttgcc ttcgcgctgg   5520
atgtagtcgg ccttggccct ggccgattgg ccgcccgacc tgctgccggt tttcgccgta   5580
aggtgataaa tcgccatgct gcctcgctgt tgcttttgct tttcggctcc atgcaatggc   5640
cctcggagag cgcaccgccc gaagggtggc cgttaggcca gtttctcgaa gagaaaccgg   5700
taagtgcgcc ctcccctaca aagtagggtc gggattgccg ccgctgtgcc tccatgatag   5760
cctacgagac agcacattaa caatggggtg tcaagatggt taaggggagc aacaaggcgg   5820
cggatcggct ggccaagctc gaagaacaac gagcgcgaat caatgccgaa attcagcggg   5880
agcgggcaag ggaacagcag caagagcgca agaacgaaac aaggcgcaag gtgctggtgg   5940
gggccatgat tttggccaag gtgaacagca gcgagtggcc ggaggatcgg ctcatggcgg   6000
caatggatgc gtaccttgaa cgcgaccacg accgcgcctt gttcggtctg ccgccacgcc   6060
```

```
agaaggatga gccgggctga atgatcgacc gagacaggcc ctgcggggct gcacacgcgc   6120
ccccaccctt cgggtagggg gaaaggccgc taaagcggct aaaagcgctc cagcgtattt   6180
ctgcggggtt tggtgtgggg tttagcgggc tttgcccgcc tttccccctg ccgcgcagcg   6240
gtggggcggt gtgtagccta gcgcagcgaa tagaccagct atccggcctc tggccgggca   6300
tattgggcaa gggcagcagc gccccacaag ggcgctgata accgcgccta gtggattatt   6360
cttagataat catggatgga tttttccaac accccgccag cccccgcccc tgctgggttt   6420
gcaggtttgg gggcgtgaca gttattgcag ggggttcgtga cagttattgc aggggggcgt  6480
gacagttatt gcaggggttc gtgacagtta gtacgggagt gacgggcact ggctggcaat   6540
gtctagcaac ggcaggcatt tcggctgagg gtaaaagaac tttccgctaa gcgatagact   6600
gtatgtaaac acagtattgc aaggacgcgg aacatgcctc atgtggcggc caggacggcc   6660
agccgggatc gggatactgg tcgttaccag agccaccgac ccgagcaaac ccttctctat   6720
cagatcgttg acgagtatta cccggcattc gctgcgctta tggcagagca gggaaaggaa   6780
ttgccgggct atgtgcaacg ggaatttgaa gaatttctcc aatgcgggcg gctggagcat   6840
ggctttctac gggttcgctg cgagtcttgc cacgccgagc acctggtcgc tttcagaaat   6900
caatctaaag tatatatgag taaacttggt ctgacaggcc cctgaattcg catctagatg   6960
gtagagccac aaacagccgg tacaagcaac gatctccagg accatctgaa tcatgcgcgg   7020
atgacacgaa ctcacgacgg cgatcacaga cattaaccca cagtacagac actgcgacaa   7080
cgtggcaatt cgtcgcaata ccgtctcact gaactggccg ataattgcag acgaacgcat   7140
atacaagttt attcttgaca ctagtcggcc aaaatgatat aatacctgag tactgttata   7200
cagaaacaga ggagatatta catatgagta aaggagaaga gcttttcaca ggagttgtcc   7260
caatcctcgt ggaattagac ggtgatgtta atgggcacaa gttctctgtc agtggagagg   7320
gtgaaggcga cgcaacatat ggcaagctga cccttaaatt tatttgcacc acgggtaaac   7380
tacctgttcc atggccaaca ctggtcacta cgttcgggta tggggttcag tgctttgcgc   7440
gctacccaga tcacatgaaa cagcacgact tttcaagag tgcaatgccc gaaggctatg    7500
tacaggagag aaccatcttt tttaaggatg acggcaacta taagacacgc gccgaagtga   7560
agttcgaggg tgataccctt gttaatagaa tcgagttaaa gggtattgac tttaaggaag   7620
atggaaatat tttaggccac aaactggaat ataactataa ctcccataat gtgtacatta   7680
tggccgacaa gcaaaagaac ggtatcaagg ttaacttcaa gatcagacac aacattgagg   7740
atggaagcgt tcaactagcc gaccattacc aacaaaacac cccaattggc gatgggcctg   7800
tgctgttacc agacaaccat tacctgtcca ctcaatctgc cctttcgaaa gatcccaacg   7860
aaaagcgcga ccacatggtc cttcttgagt ttgtcacggc tgctgggatt acacacggca   7920
tggatgaact atacaaataa atcctaacta gcataacccc ttggggcctc taaacgggtc   7980
ttgaggggtt ttttgctggc tgagcatgag acggaaatct gctcgtcagt ggtgctcaca   8040
ctgacgaatc atgt                                                     8054
```

<210> SEQ ID NO 93
<211> LENGTH: 8054
<212> TYPE: DNA
<213> ORGANISM: Artificial Sequence
<220> FEATURE:
<223> OTHER INFORMATION: Chemically Synthesized, pBTK620

<400> SEQUENCE: 93

```
actgcctggc gactcacaac taagcaagac agccggaacc agcgccggcg aacaccactg      60
catatatggc atatcacaac agtccaacta gtgcactgca gtacaccagg catcaaataa     120
aacgaaaggc tcagtcgaaa gactgggcct ttcgttttat ctgttgtttg tcggtgaacg     180
ctctctacta gagtcacact ggctcacctt cgggtgggcc tttctgcgtt tataccgagc     240
ggccgcgtgt tacaaccaat taaccaattc tgattagaaa aactcatcga gcatcaaatg     300
aaactgcaat ttattcatat caggattatc aataccatat ttttgaaaaa gccgtttctg     360
taatgaagga gaaaactcac cgaggcagtt ccataggatg gcaagatcct ggtatcggtc     420
tgcgattccg actcgtccaa catcaataca acctattaat ttcccctcgt caaaaataag     480
gttatcaagt gagaaatcac catgagtgac gactgaatcc ggtgagaatg gcaaaagctt     540
atgcatttct ttccagactt gttcaacagg ccagccatta cgctcgtcat caaaatcact     600
cgcatcaacc aaaccgttat tcattcgtga ttgcgcctga gcgaggcgaa atacgcgatc     660
gctgttaaaa ggacaattac aaacaggaat cgaatgcaac cggcgcagga acactgccag     720
cgcatcaaca atattttcac ctgaatcagg atattcttct aatacctgga atgctgtttt     780
cccggggatc gcagtggtga gtaaccatgc atcatcagga gtacggataa aatgcttgat     840
ggtcggaaga ggcataaatt ccgtcagcca gtttagtctg accatctcat ctgtaacatc     900
attggcaacg ctacctttgc catgtttcag aaacaactct ggcgcatcgg gcttcccata     960
caatcgatag attgtcgcac ctgattgccc gacattatcg cgagcccatt tatacccata    1020
taaatcagca tccatgttgg aatttaatcg cggcctggag caagacgttt cccgttgaat    1080
atggctcata acaccccttg tattactgtt tatgtaagca gacagtttta ttgttcatga    1140
tgatatattt ttatcttgtg caatgtaaca tcagagattt tgagacacaa cgtggctttg    1200
ttgaataaat cgaacttttg ctgagttgaa ggatcagtca tgaccaaaat cccttaacgt    1260
gagtcagcct gccgccttgg gccgggtgat gtcgtacttg cccgccgcga actcggttac    1320
cgtccagccc agcgcgacca gctccggcaa cgcctcgcgc acccgcttgc ggcgcttgcg    1380
catggtcgaa ccactggcct ctgacggcca gacatagccg cacaaggtat ctatggaagc    1440
cttgccggtt ttgccggggt cgatccagcc acacagccgc tggtgcagca ggcgggcggt    1500
ttcgctgtcc agcgcccgca cctcgtccat gctgatgcgc acatgctggc cgccacccat    1560
gacggcctgc gcgatcaagg ggttcagggc cacgtacagg cgcccgtccg cctcgtcgct    1620
ggcgtactcc gacagcagcc gaaacccctg ccgcttgcgg ccattctggg cgatgatgga    1680
taccttccaa aggcgctcga tgcagtcctg tatgtgcttg agcgccccac cactatcgac    1740
ctctgccccg atttcctttg ccagcgcccg atagctacct ttgaccacat ggcattcagc    1800
ggtgacggcc tcccacttgg gttccaggaa cagccggagc tgccgtccgc cttcggtctt    1860
gggttccggg ccaagcacta ggccattagg cccagccatg gccaccagcc cttgcaggat    1920
gcgcagatca tcagcgccca gcggctccgg gccgctgaac tcgatccgct tgccgtcgcc    1980
gtagtcatac gtcacgtcca gcttgctgcg cttgcgctcg ccccgcttga gggcacggaa    2040
caggccgggg gccagacagt gcgccgggtc gtgccggacg tggctgaggc tgtgcttgtt    2100
cttaggcttc accacggggc accccccttgc tcttgcgctg cctctccagc acggcgggct    2160
tgagcacccc gccgtcatgc cgcctgaacc accgatcagc gaacggtgcg ccatagttgg    2220
ccttgctcac accgaagcgg acgaagaacc ggcgctggtc gtcgtccaca ccccattcct    2280
cggcctcggc gctggtcatg ctcgacaggt aggactgcca gcggatgtta tcgaccagta    2340
ccgagctgcc ccggctggcc tgctgctggt cgcctgcgcc catcatggcc gcgcccttgc    2400
```

```
tggcatggtg caggaacacg atagagcacc cggtatcggc ggcgatggcc tccatgcgac   2460
cgatgacctg ggccatgggg ccgctggcgt tttcttcctc gatgtggaac cggcgcagcg   2520
tgtccagcac catcaggcgg cggccctcgg cggcgcgctt gaggccgtcg aaccactccg   2580
gggccatgat gttgggcagg ctgccgatca gcggctggat cagcaggccg tcagccacgg   2640
cttgccgttc ctcggcgctg aggtgcgccc caagggcgtg caggcggtga tgaatggcgg   2700
tgggcgggtc ttcggcgggc aggtagatca ccgggccggt gggcagttcg cccacctcca   2760
gcagatccgg cccgcctgca atctgtgcgg ccagttgcag ggccagcatg gatttaccgg   2820
caccaccggg cgacaccagc gccccgaccg taccggccac catgttgggc aaaacgtagt   2880
ccagcggtgg cggcgctgct gcgaacgcct ccagaatatt gataggctta tgggtagcca   2940
ttgattgcct cctttgcagg cagttggtgg ttaggcgctg gcggggtcac tacccccgcc   3000
ctgcgccgct ctgagttctt ccaggcactc gcgcagcgcc tcgtattcgt cgtcggtcag   3060
ccagaacttg cgctgacgca tccctttggc cttcatgcgc tcggcatatc gcgcttggcg   3120
tacagcgtca gggctggcca gcaggtcgcc ggtctgcttg tccttttggt ctttcatatc   3180
agtcaccgag aaacttgccg gggccgaaag gcttgtcttc gcggaacaag gacaaggtgc   3240
agccgtcaag gttaaggctg gccatatcag cgactgaaaa gcggccagcc tcggccttgt   3300
ttgacgtata accaaagcca ccgggcaacc aatagccctt gtcacttttg atcaggtaga   3360
ccgaccctga agcgcttttt tcgtattcca taaaaccccc ttctgtgcgt gagtactcat   3420
agtataacag gcgtgagtac caacgcaagc actacatgct gaaatctggc ccgcccctgt   3480
ccatgcctcg ctggcggggt gccggtgccc gtgccagctc ggcccgcgca agctggacgc   3540
tgggcagacc catgaccttg ctgacggtgc gctcgatgta atccgcttcg tggccgggct   3600
tgcgctctgc cagcgctggg ctggcctcgg ccatggcctt gccgatttcc tcggcactgc   3660
ggccccggct ggccagcttc tgcgcggcga taaagtcgca cttgctgagg tcatgaccga   3720
agcgcttgac cagcccggcc atctcgctgc ggtactcgtc cagcgccgtg cgccggtggc   3780
ggctaagctg ccgctcgggc agttcgaggc tggccagcct gcgggccttc tcctgctgcc   3840
gctgggcctg ctcgatctgc tggccagcct gctgcaccag cgccgggcca gcggtggcgg   3900
tcttgccctt ggattcacgc agcagcaccc acggctgata accggcgcgg gtggtgtgct   3960
tgtccttgcg gttggtgaag cccgccaagc ggccatagtg gcggctgtcg gcgctggccg   4020
ggtcggcgtc gtactcgctg gccagcgtcc gggcaatctg cccccgaagt tcaccgcctg   4080
cggcgtcggc caccttgacc catgcctgat agttcttcgg gctggtttcc actaccaggg   4140
caggctcccg gccctcggct ttcatgtcat ccaggtcaaa ctcgctgagg tcgtccacca   4200
gcaccagacc atgccgctcc tgctcggcgg gcctgatata cacgtcattg ccctgggcat   4260
tcatccgctt gagccatggc gtgttctgga gcacttcggc ggctgaccat tcccggttca   4320
tcatctggcc ggtgggtgcg tccctgacgc cgatatcgaa gcgctcacag cccatggcct   4380
tgagctgtcg gcctatggcc tgcaaagtcc tgtcgttctt catcgggcca ccaagcgcag   4440
ccagatcgag ccgtcctcgg ttgtcagtgg cgtcaggtcg agcaagagca acgatgcgat   4500
cagcagcacc accgtaggca tcatggaagc cagcatcacg gttagccata gcttccagtg   4560
ccacccccgc gacgcgctcc gggcgctctg cgcggcgctg ctcacctcgg cggctacctc   4620
ccgcaactct ttggccagct ccacccatgc cgcccctgtc tggcgctggg ctttcagcca   4680
ctccgccgcc tgcgcctcgc tggcctgctt ggtctggctc atgacctgcc gggcttcgtc   4740
```

```
ggccagtgtc gccatgctct gggccagcgg ttcgatctgc tccgctaact cgttgatgcc   4800
tctggatttc ttcactctgt cgattgcgtt catggtctat tgcctcccgg tattcctgta   4860
agtcgatgat ctgggcgttg gcggtgtcga tgttcagggc cacgtctgcc cggtcggtgc   4920
ggatgccccg gccttccatc tccaccacgt tcggccccag gtgaacaccg ggcaggcgct   4980
cgatgccctg cgcctcaagt gttctgtggt caatgcgggc gtcgtggcca gcccgctcta   5040
atgcccggtt ggcatggtcg gcccatgcct cgcgggtctg ctcaagccat gccttgggct   5100
tgagcgcttc ggtcttctgt gccccgccct tctccggggt cttgccgttg taccgcttga   5160
accactgagc ggcgggccgc tcgatgccgt cattgatccg ctcggagatc atcaggtggc   5220
agtgcgggtt ctcgccgcca ccggcatgga tggccagcgt atacggcagg cgctcggcac   5280
cggtcaggtg ctgggcgaac tcggacgcca gcgccttctg ctggtcgagg gtcagctcga   5340
ccggcagggc aaattcgacc tccttgaaca gccgcccatt ggcgcgttca tacaggtcgg   5400
cagcatccca gtagtcggcg ggccgctcga cgaactccgg catgtgcccg gattcggcgt   5460
gcaagacttc atccatgtcg cgggcatact tgccttcgcg ctggatgtag tcggccttgg   5520
ccctggccga ttggccgccc gacctgctgc cggttttcgc cgtaaggtga taaatcgcca   5580
tgctgcctcg ctgttgcttt tgcttttcgg ctccatgcaa tggccctcgg agagcgcacc   5640
gcccgaaggg tggccgttag gccagtttct cgaagagaaa ccggtaagtg cgccctcccc   5700
tacaaagtag ggtcgggatt gccgccgctg tgcctccatg atagcctacg agacagcaca   5760
ttaacaatgg ggtgtcaaga tggttaaggg gagcaacaag gcggcggatc ggctggccaa   5820
gctcgaagaa caacgagcgc gaatcaatgc cgaaattcag cgggagcggg caagggaaca   5880
gcagcaagag cgcaagaacg aaacaaggcg caaggtgctg gtgggggcca tgattttggc   5940
caaggtgaac agcagcgagt ggccggagga tcggctcatg gcggcaatgg atgcgtacct   6000
tgaacgcgac cacgaccgcg ccttgttcgg tctgccgcca cgccagaagg atgagccggg   6060
ctgaatgatc gaccgagaca ggccctgcgg ggctgcacac gcgcccccac ccttcgggta   6120
gggggaaagg ccgctaaagc ggctaaaagc gctccagcgt atttctgcgg ggtttggtgt   6180
ggggtttagc gggctttgcc cgcctttccc cctgccgcgc agcggtgggg cggtgtgtag   6240
cctagcgcag cgaatagacc agctatccgg cctctggccg ggcatattgg gcaagggcag   6300
cagcgcccca caagggcgct gataaccgcg cctagtggat tattcttaga taatcatgga   6360
tggatttttc caacaccccg ccagcccccg cccctgctgg gtttgcaggt ttgggggcgt   6420
gacagttatt gcaggggttc gtgacagtta ttgcaggggg gcgtgacagt tattgcaggg   6480
gttcgtgaca gttagtacgg gagtgacggg cactggctgg caatgtctag caacggcagg   6540
catttcggct gagggtaaaa gaactttccg ctaagcgata gactgtatgt aaacacagta   6600
ttgcaaggac gcggaacatg cctcatgtgg cggccaggac ggccagccgg gatcgggata   6660
ctggtcgtta ccagagccac cgacccgagc aaacccttct ctatcagatc gttgacgagt   6720
attacccggc attcgctgcg cttatggcag agcagggaaa ggaattgccg ggctatgtgc   6780
aacgggaatt tgaagaattt ctccaatgcg ggcggctgga gcatggcttt ctacgggttc   6840
gctgcgagtc ttgccacgcc gagcacctgg tcgctttcag aaatcaatct aaagtatata   6900
tgagtaaact tggtctgaca ggcccctgaa ttcgcatcta gatggtagag ccacaaacag   6960
ccggtacaag caacgatctc caggaccatc tgaatcatgc gcggatgaca cgaactcacg   7020
acggcgatca cagacattaa cccacagtac agacactgcg acaacgtggc aattcgtcgc   7080
aataccgtct cactgaactg gccgataatt gcagacgaac gcatacggga gtttattctt   7140
```

```
gacatattgc cggtgtgttg gtataataac ttagtactgt tatacagaaa cagaggagat   7200
attacatatg agtaaaggag aagagctttt cacaggagtt gtcccaatcc tcgtggaatt   7260
agacggtgat gttaatgggc acaagttctc tgtcagtgga gagggtgaag gcgacgcaac   7320
atatggcaag ctgaccctta aatttatttg caccacgggt aaactacctg ttccatggcc   7380
aacactggtc actacgttcg ggtatggggt tcagtgcttt gcgcgctacc cagatcacat   7440
gaaacagcac gactttttca agagtgcaat gcccgaaggc tatgtacagg agagaaccat   7500
ctttttaag gatgacggca actataagac acgcgccgaa gtgaagttcg agggtgatac   7560
ccttgttaat agaatcgagt taaagggtat tgactttaag gaagatggaa atattttagg   7620
ccacaaactg gaatataact ataactccca taatgtgtac attatggccg acaagcaaaa   7680
gaacggtatc aaggttaact tcaagatcag acacaacatt gaggatggaa gcgttcaact   7740
agccgaccat taccaacaaa acaccccaat tggcgatggg cctgtgctgt taccagacaa   7800
ccattacctg tccactcaat ctgccctttc gaaagatccc aacgaaaagc gcgaccacat   7860
ggtccttctt gagtttgtca cggctgctgg gattacacac ggcatggatg aactatacaa   7920
ataaatccta actagcataa ccccttgggg cctctaaacg ggtcttgagg ggttttttgc   7980
tggctgagca tgagacggaa atctgctcgt cagtggtgct cacactgacg aatcatgtac   8040
agatcatacc gatg                                                      8054
```

<210> SEQ ID NO 94
<211> LENGTH: 8054
<212> TYPE: DNA
<213> ORGANISM: Artificial Sequence
<220> FEATURE:
<223> OTHER INFORMATION: Chemically Synthesized, pBTK621

<400> SEQUENCE: 94

```
gcggccgcgt gttacaacca attaaccaat tctgattaga aaaactcatc gagcatcaaa     60
tgaaactgca atttattcat atcaggatta tcaataccat atttttgaaa aagccgtttc    120
tgtaatgaag gagaaaactc accgaggcag ttccatagga tggcaagatc ctggtatcgg    180
tctgcgattc cgactcgtcc aacatcaata caacctatta atttcccctc gtcaaaaata    240
aggttatcaa gtgagaaatc accatgagtg acgactgaat ccggtgagaa tggcaaaagc    300
ttatgcattt ctttccagac ttgttcaaca ggccagccat tacgctcgtc atcaaaatca    360
ctcgcatcaa ccaaaccgtt attcattcgt gattgcgcct gagcgaggcg aaatacgcga    420
tcgctgttaa aaggacaatt acaaacagga atcgaatgca accggcgcag gaacactgcc    480
agcgcatcaa caatattttc acctgaatca ggatattctt ctaatacctg gaatgctgtt    540
ttcccgggga tcgcagtggt gagtaaccat gcatcatcag gagtacggat aaaatgcttg    600
atggtcggaa gaggcataaa ttccgtcagc cagtttagtc tgaccatctc atctgtaaca    660
tcattggcaa cgctaccttt gccatgtttc agaaacaact ctggcgcatc gggcttccca    720
tacaatcgat agattgtcgc acctgattgc ccgacattat cgcgagccca tttataccca    780
tataaatcag catccatgtt ggaatttaat cgcggcctgg agcaagacgt ttcccgttga    840
atatggctca taacacccct tgtattactg tttatgtaag cagacagttt tattgttcat    900
gatgatatat ttttatcttg tgcaatgtaa catcagagat tttgagacac aacgtggctt    960
tgttgaataa atcgaacttt tgctgagttg aaggatcagt catgaccaaa atcccttaac   1020
gtgagtcagc ctgccgcctt gggccgggtg atgtcgtact tgcccgccgc gaactcggtt   1080
```

```
accgtccagc ccagcgcgac cagctccggc aacgcctcgc gcacccgctt gcggcgcttg   1140
cgcatggtcg aaccactggc ctctgacggc cagacatagc cgcacaaggt atctatggaa   1200
gccttgccgg ttttgccggg gtcgatccag ccacacagcc gctggtgcag caggcgggcg   1260
gtttcgctgt ccagcgcccg cacctcgtcc atgctgatgc gcacatgctg gccgccaccc   1320
atgacggcct gcgcgatcaa ggggttcagg gccacgtaca ggcgcccgtc cgcctcgtcg   1380
ctggcgtact ccgacagcag ccgaaacccc tgccgcttgc ggccattctg ggcgatgatg   1440
gataccttcc aaaggcgctc gatgcagtcc tgtatgtgct tgagcgcccc accactatcg   1500
acctctgccc cgatttcctt tgccagcgcc cgatagctac ctttgaccac atggcattca   1560
gcggtgacgg cctcccactt gggttccagg aacagccgga gctgccgtcc gccttcggtc   1620
ttgggttccg ggccaagcac taggccatta ggcccagcca tggccaccag cccttgcagg   1680
atgcgcagat catcagcgcc cagcggctcc gggccgctga actcgatccg cttgccgtcg   1740
ccgtagtcat acgtcacgtc cagcttgctg cgcttgcgct cgccccgctt gagggcacgg   1800
aacaggccgg gggccagaca gtgcgccggg tcgtgccgga cgtggctgag gctgtgcttg   1860
ttcttaggct tcaccacggg gcaccccctt gctcttgcgc tgcctctcca gcacggcggg   1920
cttgagcacc ccgccgtcat gccgcctgaa ccaccgatca gcgaacggtg cgccatagtt   1980
ggccttgctc acaccgaagc ggacgaagaa ccggcgctgg tcgtcgtcca caccccattc   2040
ctcggcctcg gcgctggtca tgctcgacag gtaggactgc cagcggatgt tatcgaccag   2100
taccgagctg ccccggctgg cctgctgctg gtcgcctgcg cccatcatgg ccgcgccctt   2160
gctggcatgg tgcaggaaca cgatagagca cccggtatcg gcggcgatgg cctccatgcg   2220
accgatgacc tgggccatgg ggccgctggc gttttcttcc tcgatgtgga accggcgcag   2280
cgtgtccagc accatcaggc ggcggccctc ggcggcgcgc ttgaggccgt cgaaccactc   2340
cggggccatg atgttgggca ggctgccgat cagcggctgg atcagcaggc cgtcagccac   2400
ggcttgccgt tcctcggcgc tgaggtgcgc cccaagggcg tgcaggcggt gatgaatggc   2460
ggtgggcggg tcttcggcgg gcaggtagat caccgggccg gtgggcagtt cgcccacctc   2520
cagcagatcc ggcccgcctg caatctgtgc ggccagttgc agggccagca tggatttacc   2580
ggcaccaccg ggcgacacca gcgccccgac cgtaccggcc accatgttgg gcaaaacgta   2640
gtccagcggt ggcggcgctg ctgcgaacgc ctccagaata ttgataggct tatgggtagc   2700
cattgattgc ctcctttgca ggcagttggt ggttaggcgc tggcggggtc actacccccg   2760
ccctgcgccg ctctgagttc ttccaggcac tcgcgcagcg cctcgtattc gtcgtcggtc   2820
agccagaact tgcgctgacg catccctttg gccttcatgc gctcggcata tcgcgcttgg   2880
cgtacagcgt cagggctggc cagcaggtcg ccggtctgct tgtccttttg gtctttcata   2940
tcagtcaccg agaaacttgc cggggccgaa aggcttgtct tcgcggaaca aggacaaggt   3000
gcagccgtca aggttaaggc tggccatatc agcgactgaa aagcggccag cctcggcctt   3060
gtttgacgta taaccaaagc caccgggcaa ccaatagccc ttgtcacttt tgatcaggta   3120
gaccgaccct gaagcgcttt tttcgtattc cataaaaccc ccttctgtgc gtgagtactc   3180
atagtataac aggcgtgagt accaacgcaa gcactacatg ctgaaatctg gcccgcccct   3240
gtccatgcct cgctggcggg gtgccggtgc ccgtgccagc tcggcccgcg caagctggac   3300
gctgggcaga cccatgacct tgctgacggt gcgctcgatg taatccgctt cgtggccggg   3360
cttgcgctct gccagcgctg ggctggcctc ggccatggcc ttgccgattt cctcggcact   3420
gcggccccgg ctggccagct tctgcgcggc gataaagtcg cacttgctga ggtcatgacc   3480
```

```
gaagcgcttg accagcccgg ccatctcgct gcggtactcg tccagcgccg tgcgccggtg 3540
gcggctaagc tgccgctcgg gcagttcgag gctggccagc ctgcgggcct tctcctgctg 3600
ccgctgggcc tgctcgatct gctggccagc ctgctgcacc agcgccgggc cagcggtggc 3660
ggtcttgccc ttggattcac gcagcagcac ccacggctga taaccggcgc gggtggtgtg 3720
cttgtccttg cggttggtga agcccgccaa gcggccatag tggcggctgt cggcgctggc 3780
cgggtcggcg tcgtactcgc tggccagcgt ccgggcaatc tgcccccgaa gttcaccgcc 3840
tgcggcgtcg gccaccttga cccatgcctg atagttcttc gggctggttt ccactaccag 3900
ggcaggctcc cggccctcgg ctttcatgtc atccaggtca aactcgctga ggtcgtccac 3960
cagcaccaga ccatgccgct cctgctcggc gggcctgata tacacgtcat tgccctgggc 4020
attcatccgc ttgagccatg gcgtgttctg gagcacttcg gcggctgacc attcccggtt 4080
catcatctgg ccggtgggtg cgtccctgac gccgatatcg aagcgctcac agcccatggc 4140
cttgagctgt cggcctatgg cctgcaaagt cctgtcgttc ttcatcgggc caccaagcgc 4200
agccagatcg agccgtcctc ggttgtcagt ggcgtcaggt cgagcaagag caacgatgcg 4260
atcagcagca ccaccgtagg catcatggaa gccagcatca cggttagcca tagcttccag 4320
tgccaccccc gcgacgcgct ccgggcgctc tgcgcggcgc tgctcacctc ggcggctacc 4380
tcccgcaact ctttggccag ctccacccat gccgcccctg tctggcgctg ggctttcagc 4440
cactccgccg cctgcgcctc gctggcctgc ttggtctggc tcatgacctg ccgggcttcg 4500
tcggccagtg tcgccatgct ctgggccagc ggttcgatct gctccgctaa ctcgttgatg 4560
cctctggatt tcttcactct gtcgattgcg ttcatggtct attgcctccc ggtattcctg 4620
taagtcgatg atctgggcgt tggcggtgtc gatgttcagg gccacgtctg cccggtcggt 4680
gcggatgccc cggccttcca tctccaccac gttcggcccc aggtgaacac cgggcaggcg 4740
ctcgatgccc tgcgcctcaa gtgttctgtg gtcaatgcgg gcgtcgtggc cagcccgctc 4800
taatgcccgg ttggcatggt cggcccatgc ctcgcgggtc tgctcaagcc atgccttggg 4860
cttgagcgct tcggtcttct gtgccccgcc cttctccggg gtcttgccgt tgtaccgctt 4920
gaaccactga gcggcgggcc gctcgatgcc gtcattgatc cgctcggaga tcatcaggtg 4980
gcagtgcggg ttctcgccgc caccggcatg gatggccagc gtatacggca ggcgctcggc 5040
accggtcagg tgctgggcga actcggacgc cagcgccttc tgctggtcga gggtcagctc 5100
gaccggcagg gcaaattcga cctccttgaa cagccgccca ttggcgcgtt catacaggtc 5160
ggcagcatcc cagtagtcgg cgggccgctc gacgaactcc ggcatgtgcc cggattcggc 5220
gtgcaagact tcatccatgt cgcgggcata cttgccttcg cgctggatgt agtcggcctt 5280
ggccctggcc gattggccgc ccgacctgct gccggttttc gccgtaaggt gataaatcgc 5340
catgctgcct cgctgttgct tttgcttttc ggctccatgc aatggccctc ggagagcgca 5400
ccgcccgaag ggtggccgtt aggccagttt ctcgaagaga aaccggtaag tgcgccctcc 5460
cctacaaagt agggtcggga ttgccgccgc tgtgcctcca tgatagccta cgagacagca 5520
cattaacaat ggggtgtcaa gatggttaag gggagcaaca aggcggcgga tcggctggcc 5580
aagctcgaag aacaacgagc gcgaatcaat gccgaaattc agcgggagcg ggcaagggaa 5640
cagcagcaag agcgcaagaa cgaaacaagg cgcaaggtgc tggtgggggc catgattttg 5700
gccaaggtga acagcagcga gtggccggag gatcggctca tggcggcaat ggatgcgtac 5760
cttgaacgcg accacgaccg cgccttgttc ggtctgccgc cacgccagaa ggatgagccg 5820
```

```
ggctgaatga tcgaccgaga caggccctgc ggggctgcac acgcgccccc acccttcggg   5880

tagggggaaa ggccgctaaa gcggctaaaa gcgctccagc gtatttctgc ggggtttggt   5940

gtggggttta gcgggctttg cccgcctttc cccctgccgc gcagcggtgg ggcggtgtgt   6000

agcctagcgc agcgaataga ccagctatcc ggcctctggc cgggcatatt gggcaagggc   6060

agcagcgccc cacaagggcg ctgataaccg cgcctagtgg attattctta gataatcatg   6120

gatggatttt tccaacaccc cgccagcccc cgcccctgct gggtttgcag gtttgggggc   6180

gtgacagtta ttgcaggggt tcgtgacagt tattgcaggg gggcgtgaca gttattgcag   6240

gggttcgtga cagttagtac gggagtgacg ggcactggct ggcaatgtct agcaacggca   6300

ggcatttcgg ctgagggtaa aagaactttc cgctaagcga tagactgtat gtaaacacag   6360

tattgcaagg acgcggaaca tgcctcatgt ggcggccagg acggccagcc gggatcggga   6420

tactggtcgt taccagagcc accgacccga gcaaaccctt ctctatcaga tcgttgacga   6480

gtattacccg gcattcgctg cgcttatggc agagcaggga aaggaattgc cgggctatgt   6540

gcaacgggaa tttgaagaat ttctccaatg cgggcggctg gagcatggct ttctacgggt   6600

tcgctgcgag tcttgccacg ccgagcacct ggtcgctttc agaaatcaat ctaaagtata   6660

tatgagtaaa cttggtctga caggcccctg aattcgcatc tagatggtag agccacaaac   6720

agccggtaca agcaacgatc tccaggacca tctgaatcat gcgcggatga cacgaactca   6780

cgacggcgat cacagacatt aacccacagt acagacactg cgacaacgtg gcaattcgtc   6840

gcaataccgt ctcactgaac tggccgataa ttgcagacga acgcatgtgg gagtttattc   6900

ttgacacaga tatttccgga tgatataata actgagtact gttatacaga aacagaggag   6960

atattacata tgagtaaagg agaagagctt ttcacaggag ttgtcccaat cctcgtggaa   7020

ttagacggtg atgttaatgg gcacaagttc tctgtcagtg gagagggtga aggcgacgca   7080

acatatggca agctgaccct taaatttatt tgcaccacgg gtaaactacc tgttccatgg   7140

ccaacactgg tcactacgtt cgggtatggg gttcagtgct ttgcgcgcta cccagatcac   7200

atgaaacagc acgacttttt caagagtgca atgcccgaag gctatgtaca ggagagaacc   7260

atctttttta aggatgacgg caactataag acacgcgccg aagtgaagtt cgagggtgat   7320

acccttgtta atagaatcga gttaaagggt attgacttta aggaagatgg aaatatttta   7380

ggccacaaac tggaatataa ctataactcc cataatgtgt acattatggc cgacaagcaa   7440

aagaacggta tcaaggttaa cttcaagatc agacacaaca ttgaggatgg aagcgttcaa   7500

ctagccgacc attaccaaca aaacacccca attggcgatg ggcctgtgct gttaccagac   7560

aaccattacc tgtccactca atctgccctt tcgaaagatc ccaacgaaaa gcgcgaccac   7620

atggtccttc ttgagtttgt cacggctgct gggattacac acggcatgga tgaactatac   7680

aaataaatcc taactagcat aaccccttgg ggcctctaaa cgggtcttga ggggtttttt   7740

gctggctgag catgagacgg aaatctgctc gtcagtggtg ctcacactga cgaatcatgt   7800

acagatcata ccgatgactg cctggcgact cacaactaag caagacagcc ggaaccagcg   7860

ccggcgaaca ccactgcata tatggcatat cacaacagtc caactagtgc actgcagtac   7920

accaggcatc aaataaaacg aaaggctcag tcgaaagact gggcctttcg ttttatctgt   7980

tgtttgtcgg tgaacgctct ctactagagt cacactggct caccttcggg tgggcctttc   8040

tgcgtttata ccga                                                      8054
```